US012606533B2

(12) United States Patent
Kageji et al.

(10) Patent No.: US 12,606,533 B2
(45) Date of Patent: *Apr. 21, 2026

(54) 3-PHENYLPROPYLAMINE DERIVATIVE

(71) Applicant: DAIICHI SANKYO COMPANY, LIMITED, Tokyo (JP)

(72) Inventors: Hideaki Kageji, Tokyo (JP); Tomoharu Tsukada, Tokyo (JP); Takashi Tsuji, Tokyo (JP); Masaya Fujii, Tokyo (JP); Yuuichi Sugimoto, Tokyo (JP); Yuto Tsuchiya, Tokyo (JP); Keigo Murakami, Tokyo (JP); Hidekazu Inoue, Tokyo (JP); Masayuki Ebisawa, Tokyo (JP); Naoki Kuki, Tokyo (JP); Noriyuki Hayashi, Tokyo (JP); Tetsuyoshi Matsufuji, Tokyo (JP); Takashi Asahi, Tokyo (JP); Saki Banjo, Tokyo (JP); Shinji Tsutsumi, Tokyo (JP); Mariko Shimonaga, Tokyo (JP); Takuya Igarashi, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/177,410

(22) Filed: Apr. 11, 2025

(65) Prior Publication Data

US 2025/0353824 A1 Nov. 20, 2025

Related U.S. Application Data

(63) Continuation of application No. 19/117,009, filed as application No. PCT/JP2024/034567 on Sep. 27, 2024.

(30) Foreign Application Priority Data

Sep. 29, 2023 (JP) ................................ 2023-169833

(51) Int. Cl.

| | |
|---|---|
| ***C07D 309/04*** | (2006.01) |
| ***A61K 31/216*** | (2006.01) |
| ***A61K 31/351*** | (2006.01) |
| ***A61K 31/404*** | (2006.01) |
| ***A61K 31/4166*** | (2006.01) |

(Continued)

(52) U.S. Cl.

CPC .......... *C07D 309/04* (2013.01); *A61K 31/216* (2013.01); *A61K 31/351* (2013.01); *A61K 31/404* (2013.01); *A61K 31/4166* (2013.01); *A61K 31/4433* (2013.01); *A61K 31/4745* (2013.01); *A61K 31/5513* (2013.01); *A61K 31/695* (2013.01); *C07C 69/22* (2013.01); *C07C 69/78* (2013.01); *C07D 209/04* (2013.01); *C07D 211/14* (2013.01); *C07D 211/22* (2013.01); *C07D 217/04* (2013.01); *C07D 235/02* (2013.01); *C07D 241/38* (2013.01); *C07D 243/14* (2013.01); *C07D 307/14* (2013.01); *C07D 401/04* (2013.01); *C07D 401/14* (2013.01); *C07D 405/12* (2013.01); *C07D 405/14* (2013.01); *C07D 471/04* (2013.01); *C07D 487/04* (2013.01); *C07D 498/04* (2013.01); *C07F 7/0834* (2013.01)

(58) Field of Classification Search

CPC .................................................... C07D 309/04

See application file for complete search history.

(56) References Cited

U.S. PATENT DOCUMENTS

| | | | |
|---|---|---|---|
| 2020/0199106 | A1 | 6/2020 | Shu |
| 2020/0306273 | A1 | 10/2020 | Yang |
| 2022/0041578 | A1 | 2/2022 | Chen |

FOREIGN PATENT DOCUMENTS

| | | |
|---|---|---|
| CN | 110684015 | 1/2020 |
| CN | 111285849 | 6/2020 |

(Continued)

OTHER PUBLICATIONS

Judd "Discovery and SAR of Methylated Tetrahydropyranyl Derivatives as Inhibitors of Isoprenylcysteine Carboxyl Methyltransferase (ICMT)." Journal of Medicinal Chemistry, 54(14), 5031-5047, 2011.*

(Continued)

*Primary Examiner* — David K O'Dell

(74) *Attorney, Agent, or Firm* — Christensen O'Connor Johnson Kindness PLLC

(57) ABSTRACT

The present invention aims to provide a novel compound having SF-1 antagonist activity and a polyfunctional molecule containing a moiety corresponding to the compound, particularly an SF-1 degrader. The present invention relates to a 3-phenylpropylamine derivative compound represented by the formula (1) and the like, and a polyfunctional molecule containing a moiety corresponding to the compound represented by the formula (1) and the like.

(1)

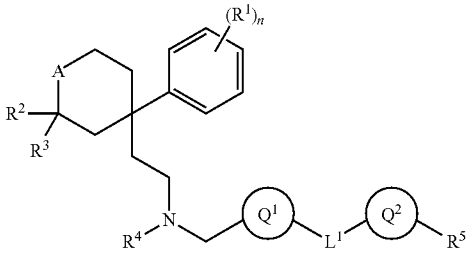

29 Claims, 4 Drawing Sheets

(51) Int. Cl.

| | |
|---|---|
| ***A61K 31/4433*** | (2006.01) |
| ***A61K 31/4745*** | (2006.01) |
| ***A61K 31/5513*** | (2006.01) |
| ***A61K 31/695*** | (2006.01) |
| ***C07C 69/22*** | (2006.01) |
| ***C07C 69/78*** | (2006.01) |
| ***C07D 209/04*** | (2006.01) |
| ***C07D 211/14*** | (2006.01) |
| ***C07D 211/22*** | (2006.01) |
| ***C07D 217/04*** | (2006.01) |
| ***C07D 235/02*** | (2006.01) |
| ***C07D 241/38*** | (2006.01) |
| ***C07D 243/14*** | (2006.01) |
| ***C07D 307/14*** | (2006.01) |
| ***C07D 401/04*** | (2006.01) |
| ***C07D 401/14*** | (2006.01) |
| ***C07D 405/12*** | (2006.01) |
| ***C07D 405/14*** | (2006.01) |
| ***C07D 471/04*** | (2006.01) |
| ***C07D 487/04*** | (2006.01) |
| ***C07D 498/04*** | (2006.01) |
| ***C07F 7/08*** | (2006.01) |

(56) References Cited

FOREIGN PATENT DOCUMENTS

| | | | |
|---|---|---|---|
| WO | 2000047220 | 8/2000 | |
| WO | 2002020740 | 3/2002 | |
| WO | 2007041341 | 4/2007 | |
| WO | WO-2007041341 A2 * | 4/2007 | .............. A61P 35/04 |
| WO | 2012129495 | 9/2012 | |
| WO | 2013106643 | 7/2013 | |
| WO | 2014063061 | 4/2014 | |
| WO | 2015160845 | 10/2015 | |
| WO | 2016105518 | 6/2016 | |
| WO | 2016146985 | 9/2016 | |
| WO | 2016149668 | 9/2016 | |
| WO | 2016169989 | 10/2016 | |
| WO | 2017007612 | 1/2017 | |
| WO | 2017011371 | 1/2017 | |
| WO | 2017011590 | 1/2017 | |
| WO | 2017079267 | 5/2017 | |
| WO | 2017197036 | 11/2017 | |
| WO | 2017197046 | 11/2017 | |
| WO | 2017197051 | 11/2017 | |
| WO | 2017197055 | 11/2017 | |
| WO | 2017204445 | 11/2017 | |
| WO | 2017211924 | 12/2017 | |
| WO | 2018033556 | 2/2018 | |
| WO | 2018051107 | 3/2018 | |
| WO | 2018098280 | 5/2018 | |
| WO | 2018118598 | 6/2018 | |
| WO | 2018119441 | 6/2018 | |
| WO | 2018144649 | 8/2018 | |
| WO | 2018237026 | 12/2018 | |
| WO | 2019042444 | 3/2019 | |
| WO | 2019060693 | 3/2019 | |
| WO | 2019060742 | 3/2019 | |
| WO | 2019099868 | 5/2019 | |
| WO | 2019113071 | 6/2019 | |
| WO | 2019114770 | 6/2019 | |
| WO | 2019118893 | 6/2019 | |
| WO | 2019133531 | 7/2019 | |
| WO | 2019148055 | 8/2019 | |
| WO | 2019199816 | 10/2019 | |
| WO | 2020010177 | 1/2020 | |
| WO | 2020010227 | 1/2020 | |
| WO | 2020069106 | 4/2020 | |
| WO | 2020114482 | 6/2020 | |
| WO | 2020210630 | 10/2020 | |
| WO | 2022081927 | 4/2022 | |
| WO | 2022081928 | 4/2022 | |
| WO | 2022125725 | 6/2022 | |

OTHER PUBLICATIONS

International Search Report mailed on Nov. 26, 2024, issued in PCT/JP2024/034567; 3 pages.

Parker, K. L. et al., "Steroidogenic Factor 1: A Key Determinant of Endocrine Development and Function," Endocrine Reviews, vol. 18, No. 3, pp. 361-377.

Doghman, M. et al., "Increased Steroidogenic Factor-1 Dosage Triggers Adrenocortical Cell Proliferation and Cancer," Molecular Endocrinology 21(12):2968-2987.

Sbiera, S. et al., "High Diagnostic and Prognostic Value of Steroidogenic Factor-1 Expression in Adrenal Tumors," J Clin Endocrinol Metab, Oct. 2010, 95(10):E161-E171.

Relav, L. et al., "Steroidogenic Factor 1, a Goldilocks Transcription Factor from Adrenocortical Organogenesis to Malignancy," Int. J. Mol. Sci. 2023, 24, 3585. https://doi.org/10.3390/ijms24043585.

Lin, L. and J.C. Achermann, "Steroidogenic Factor-1 (SF-1, Ad4BP, NR5A1) and Disorders of Testis Development," Sex Dev 2008;2:200-209. DOI: 10.1159/000152036.

Attard, G. et al., "Improving the outcome of patients with castration-resistant prostate cancer through rational drug development," British Journal of Cancer (2006) 95, 767-774.

Hua, L. et al., "Beyond Proteolysis-Targeting Chimeric Molecules: Designing Heterobifunctional Molecules Based on Functional Effectors," J. Med. Chem. 2022, 65, 8091-8112.

Cao, C. et al., "Chemistries of bifunctional PROTAC degraders," Chem. Soc. Rev., 2022, 51, 7066-7144.

Kazantsev, A. and M. Krasavin, "Ligands for cereblon: 2017-2021 patent overview," Expert Opinion on Therapeutic Patents, 32:2, 171-190, DOI: 10.1080/13543776.2022.1999415.

Bondeson, D.P. et al., "Catalytic in vivo protein knockdown by small-molecule PROTACs," Nature Chemical Biology, vol. 11, Aug. 2015, pp. 611-619.

Notice of Reasons for Refusal mailed Jan. 10, 2026, issued in Japanese Application No. 2025-085463, filed Sep. 27, 2024, 9 pages.

* cited by examiner

[Fig. 1]
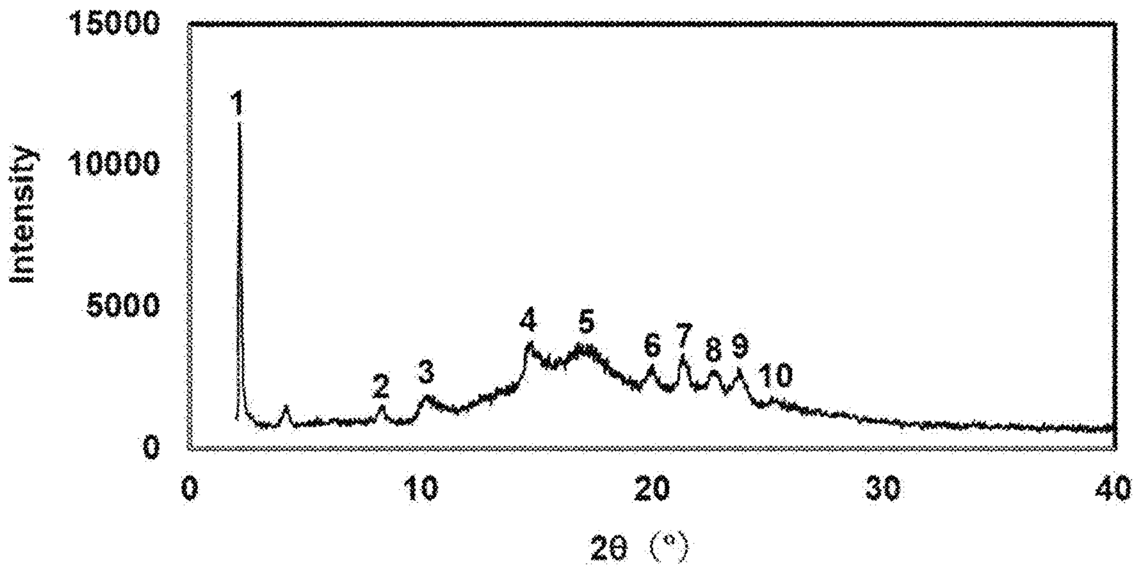
[Fig. 2]
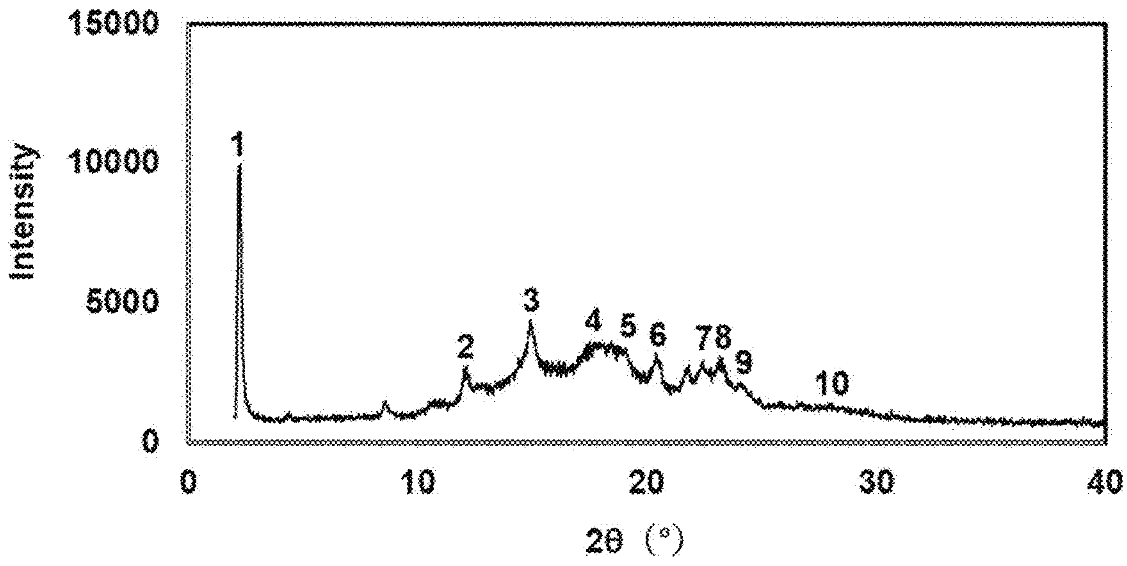

[Fig. 3]
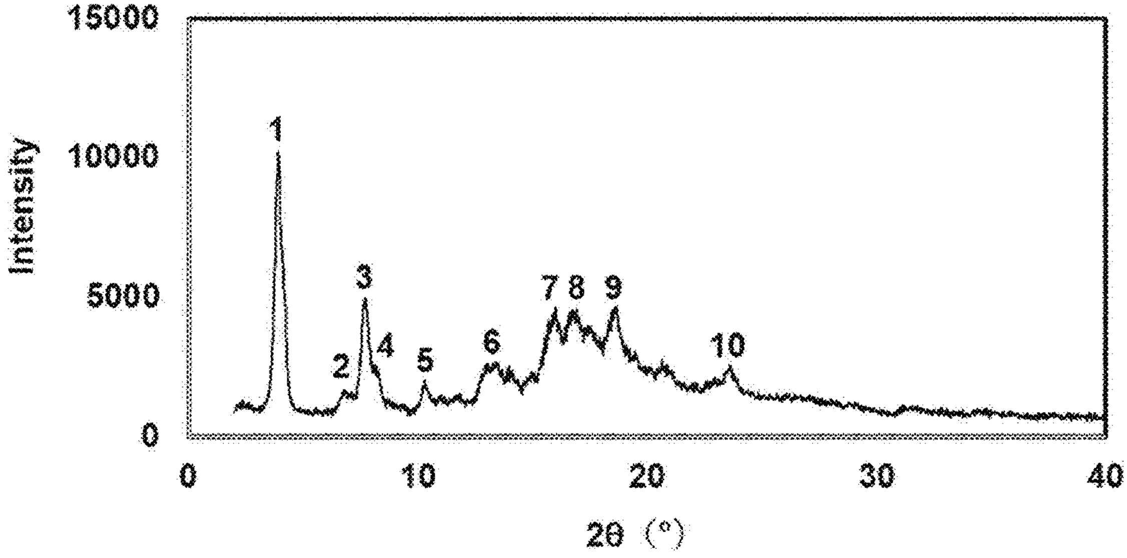
[Fig. 4]
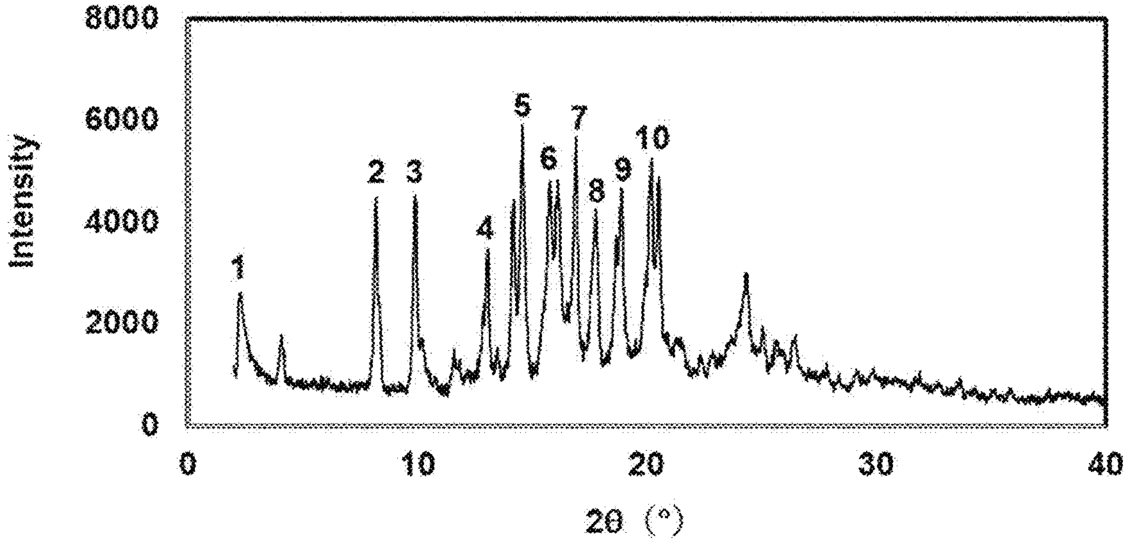

[Fig. 5]
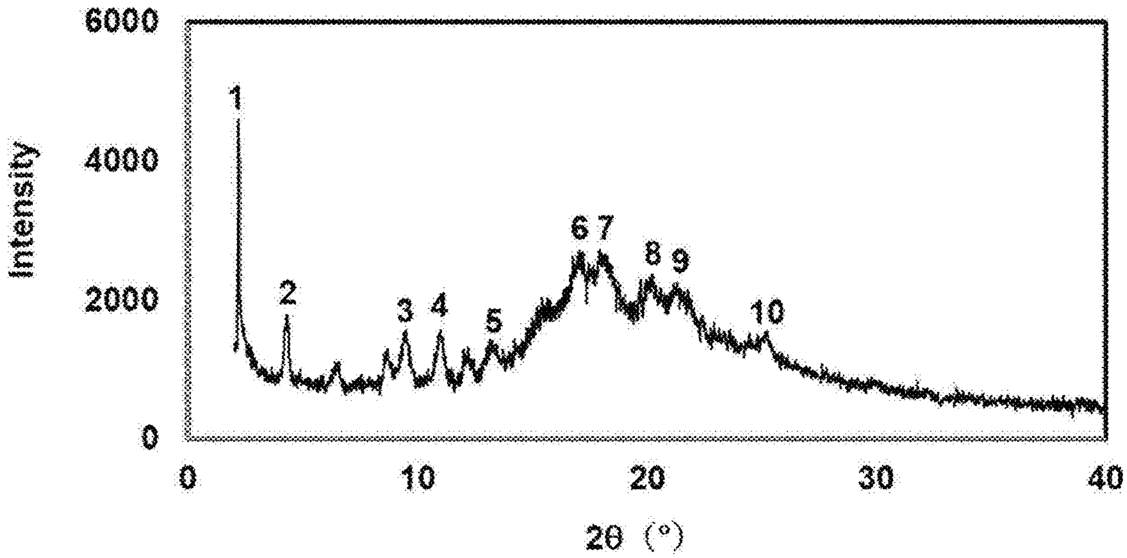
[Fig. 6]
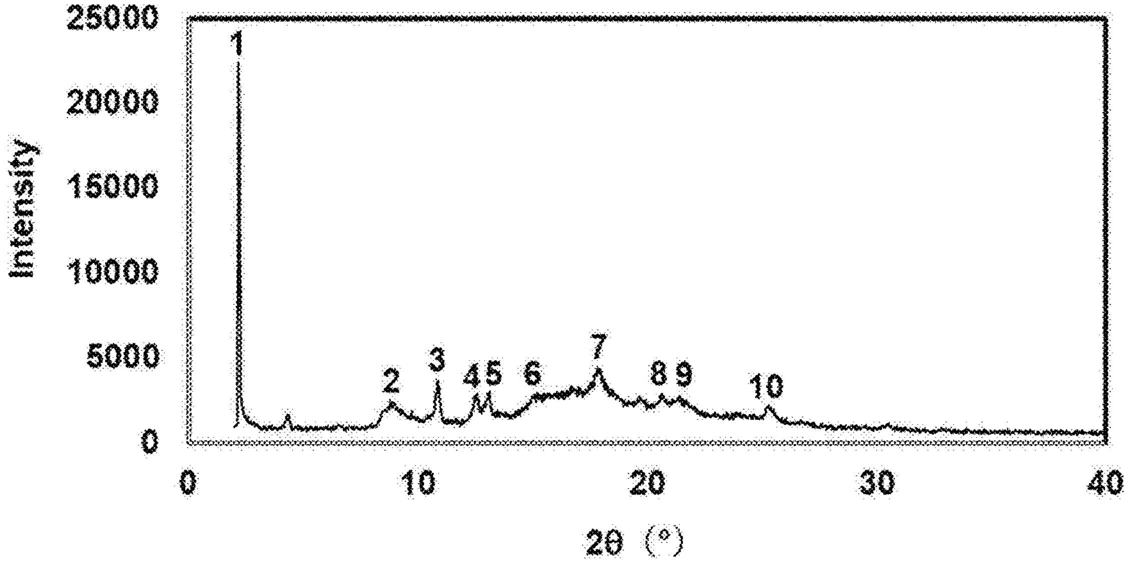

[Fig. 7]
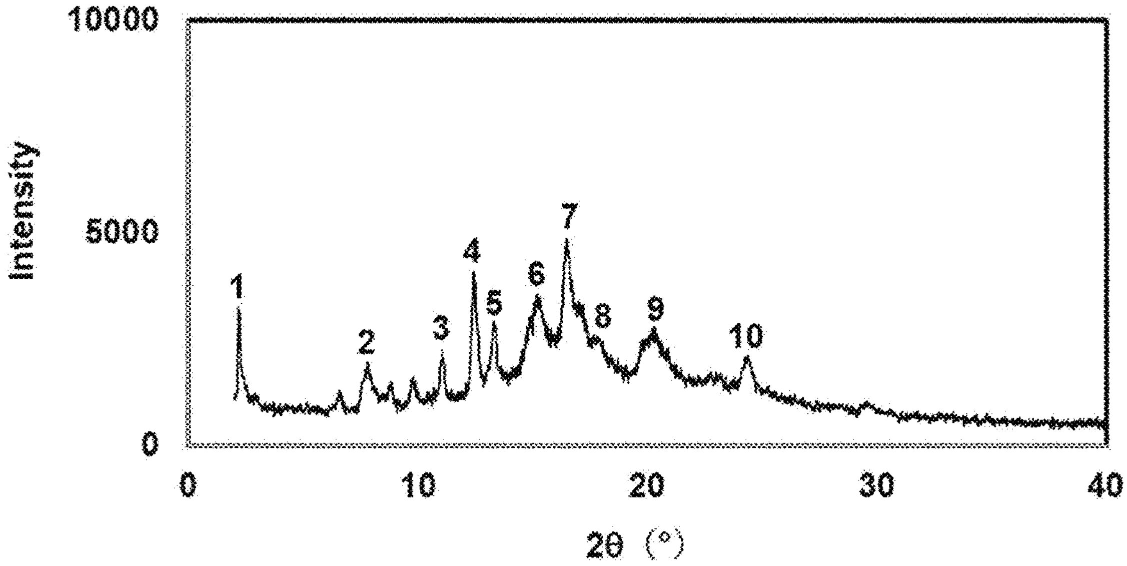

3-PHENYLPROPYLAMINE DERIVATIVE

CROSS-REFERENCE TO RELATED APPLICATIONS

This application is a Continuation of U.S. patent application Ser. No. 19/117,009, filed Mar. 28, 2025, which is a National Stage of International Application No. PCT/JP2024/034567, filed Sep. 27, 2024, which claims priority to Japanese Patent Application No. 2023-169833, filed Sep. 29, 2023, each of which is incorporated herein by reference in its entirety.

TECHNICAL FIELD

The present invention relates to a novel compound having SF-1 antagonist activity, a polyfunctional molecule containing a moiety corresponding to the compound, particularly an SF-1 degrader, and a pharmaceutical composition etc. containing same.

BACKGROUND ART

Steroidogenic factor 1 (also to be referred to as "SF1" or "SF-1") is a nuclear receptor expressed in adrenal cortex, gonad, hypothalamus, and pituitary gland, and is a molecule important for the development of adrenal gland and gonad (Non Patent Literature 1). Since adrenal tumor develops in mice overexpressing SF-1 (Non-Patent Literature 2) and there have been reports of overexpression of SF-1 protein in adrenocortical carcinoma tissue (Non-Patent Literature 3), it is believed that SF-1 contributes to the development and progression of adrenal tumors. On the other hand, it has been shown that SF-1 controls the expression of steroid hormone synthases such as CYP11A1 and CYP17A1 in the adrenal cortex and testis, and induces the production of steroid hormones such as androgen and the like (Non Patent Literatures 4, 5). Androgen is important for the development and growth of prostate cancer. Although the progression of prostate cancer can be suppressed by hormonal therapy such as castration and the like in the early stages of treatment, it progresses to castration-resistant prostate cancer, which is resistant to hormonal therapy. The growth of castration-resistant prostate cancer is known to depend on androgens derived from the adrenal gland (Non Patent Literature 6).

On the other hand, in recent years, the usefulness of a heterobifunctional molecule, which binds a part that binds to a target protein and a part that recruits an endogenous effector molecule via a linker, has been reported. Heterobifunctional molecules bring a target protein and an endogenous effector molecule into physical proximity, thereby causing a change in the target protein and exerting a desired effect (Non Patent Literature 7).

As one of the techniques that utilize such heterobifunctional molecules, Targeted Protein Degradation (TPD) is known. TPD is a technology that induces the degradation of a target protein. It uses a heterobifunctional molecule in which a binder portion that binds to a target protein and a binder portion that binds to an E3 ligase are linked by a linker to induce formation of a complex between the target protein and E3 ligase in cells, and induces ubiquitination and degradation of the target protein, thereby exhibiting strong physiological activity. More than 600 types of E3 ligases have been identified, but only a limited number of them are used in TPD and, in particular, cereblon (CRBN) and Von Hippel-Lindau (VHL) can be mentioned (Non Patent Literature 8). Particularly, binder moieties that bind to CRBN (also called "CRBN ligand") are widely used in TPD, and the diverse structures and usefulness thereof have been reported (Patent Literatures 1-9, Non Patent Literature 9). Although various proteins have been reported as targets in TPD, a targeted protein degrader targeting SF-1 has not been reported so far.

CITATION LIST

Patent Literature

[Patent Literature 1]
WO 2017/197051
[Patent Literature 2]
WO 2018/237026
[Patent Literature 3]
WO 2019/060693
[Patent Literature 4]
WO 2019/060742
[Patent Literature 5]
WO 2019/099868
[Patent Literature 6]
WO 2019/199816
[Patent Literature 7]
WO 2020/210630
[Patent Literature 8]
WO 2022/081927
[Patent Literature 9]
WO 2022/081928

Non Patent Literature

[Non Patent Literature 1]
Parker K L, Schimmer B P, Steroidogenic factor 1: a key determinant of endocrine development and function. Endocr Rev., 1997; 18: 361-77.
[Non Patent Literature 2]
Doghman M, Karpova T, Rodrigues G A, et al., Increased steroidogenic factor-1 dosage triggers adrenocortical cell proliferation and cancer. Mol Endocrinol., 2007; 21: 2968-87.
[Non Patent Literature 3]
Sbiera S, Schmull S, Assie G, et al., High Diagnostic and Prognostic Value of Steroidogenic Factor-1 Expression in Adrenal Tumors. J Clin Endocrinol Metab., 2010; 95: E161-71.
[Non Patent Literature 4]
Relav L, Doghman-Bouguerra M, Ruggiero C, Muzzi J C D, Figueiredo B C, Lalli E, Steroidogenic Factor 1, a Goldilocks Transcription Factor from Adrenocortical Organogenesis to Malignancy. Int J Mol Sci., 2023; 24: 3585.
[Non Patent Literature 5]
Lin L, Achermann J, C: Steroidogenic Factor-1 (SF-1, Ad4BP, NR5A1) and Disorders of Testis Development. Sex Dev., 2008; 2: 200-209.
[Non Patent Literature 6]
Attard G, Sarker D, Reid A, Molife R, Parker C, de Bono J S, Improving the outcome of patients with castration-resistant prostate cancer through rational drug development. Br J Cancer., 2006 9; 95: 767-74.
[Non Patent Literature 7]
Liwen Hua, et al., Beyond Proteolysis-Targeting Chimeric Molecules: Designing Heterobifunctional Molecules Based on Functional Effectors. J. Med. Chem., 2022; 65: 8091-8112.

[Non Patent Literature 8]

Chaoguo Cao, et al. Chemistries of bifunctional PROTAC degraders. Chem. Soc. Rev., 2022: 51: 7066-7114.

[Non Patent Literature 9]

Alexander Kazantsev and Mikhail Krasavin, Ligands for cereblon: 2017-2021 patent overview. Expert Opinion on Therapeutic Patents. 2022; 32: 2: 171-190.

SUMMARY OF INVENTION

Technical Problem

A problem of the present invention is to provide a novel compound having SF-1 antagonist activity, and a polyfunctional molecule containing a moiety corresponding to the compound, particularly SF-1 degrader. A further problem of the present invention is to provide a composition for inhibiting SF-1, a composition for inducing degradation of SF-1, or a pharmaceutical composition containing the compound or polyfunctional molecule. Another problem of the present invention is to provide a method for treating diseases (particularly, cancers such as castration-resistant prostate cancer, adrenocortical carcinoma, Leydig cell tumor, hormone-sensitive prostate cancer, breast cancer and the like, Cushing's syndrome or primary aldosteronism) including administering the compound or polyfunctional molecule. A still another problem of the present invention is to provide an intermediate that can be used in the production of the compound or polyfunctional molecule.

Solution to Problem

The present inventors have conducted intensive studies and found that 3-phenylpropylamine derivative compounds represented by the following formula (1) and the like have SF-1 antagonist activity, and that polyfunctional molecules containing a moiety corresponding to the compound represented by the formula (1) or the like can degrade SF-1 protein, and can inhibit proliferation of tumor cells, which resulted in the completion of the present invention.

That is, the present invention relates to the following.

[1]

A compound represented by the following formula (1):

[Chem. 1]

(1)

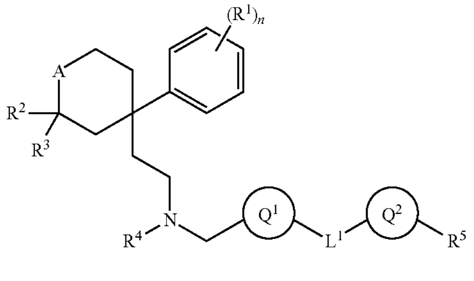

wherein

A is —O—, —S—, —$NR^a$—, or —$CR^bR^c$—, wherein $R^a$ is hydrogen or $C_{1-3}$ alkyl, $R^b$ and $R^c$ are each independently hydrogen, halogen, or $C_{1-3}$ alkyl, and the aforementioned alkyl is unsubstituted or substituted by 1 to 3 halogens, each $R^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(═O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl, and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, and heterocycloalkene ring have 1 or 2 hetero atoms selected from oxygen, nitrogen, and sulfur as ring member atoms, $L^1$ is a single bond, —O—, —S—, —NH—, $C_{1-3}$ alkylene, $C_{2-3}$ alkenylene, —C(═O)—, —C(═O)NH—, —NHC(═O)—, —C(═O)O—, or —OC(═O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring have 1 or 2 hetero atoms selected from oxygen, nitrogen, and sulfur as ring member atoms, $R^5$ is $C_{1-6}$ alkyl, carboxy, hydroxy, or a group represented by the following formula:

[Chem. 2]

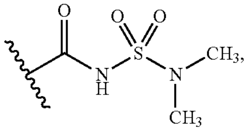
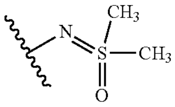
or
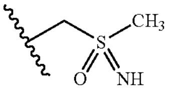

wherein the aforementioned $C_{1-6}$ alkyl is unsubstituted or substituted by 1 or 2 groups selected from the group consisting of carboxy, hydroxy, and —O—$C_{1-6}$ alkyl, and n is an integer of 0 to 3, or a pharmaceutically acceptable salt thereof.

[2]

The compound according to [1] or a pharmaceutically acceptable salt thereof, wherein A is —O— or —$CR^bR^c$—.

[3]

The compound according to [1] or [2] or a pharmaceutically acceptable salt thereof, wherein each $R^1$ in the number of n is independently halogen, —O—$C_{1-6}$ alkyl, —N(H)—$C_{1-3}$ alkyl, —N($C_{1-3}$ alkyl$)_2$, or 3- to 7-membered heterocycloalkyl, wherein the aforementioned heterocycloalkyl has 1 or 2 nitrogen atoms as ring member atoms.

[4]

The compound according to any one of [1] to [3] or a pharmaceutically acceptable salt thereof, wherein $R^2$ and $R^3$ are each independently hydrogen or $C_{1-6}$ alkyl.

[5]

The compound according to any one of [1] to [4] or a pharmaceutically acceptable salt thereof, wherein $R^4$ is $C_{1-6}$ alkyl, —C(═O)—$R^d$, or 6- to 12-membered heteroaryl, wherein the aforementioned $R^d$ is $C_{1-6}$ alkyl, the aforementioned $C_{1-6}$ alkyl is unsubstituted or substituted by 1 to 3 halogens or $C_{3-7}$ cycloalkyl, and the aforementioned heteroaryl has 1 or 2 nitrogen atoms as ring member atoms.

[6]

The compound according to any one of [1] to [5] or a pharmaceutically acceptable salt thereof, wherein ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, or a $C_{3-7}$ cycloalkene ring, and the aforementioned aromatic heterocycle has 1 or 2 nitrogen atoms as ring member atoms.

[7]

The compound according to any one of [1] to [6] or a pharmaceutically acceptable salt thereof, wherein $L^1$ is a single bond, —O—, $C_{1-3}$ alkylene, or —C(═O)—.

[8]

The compound according to any one of [1] to [7] or a pharmaceutically acceptable salt thereof, wherein ring $Q^2$ is a $C_{6-12}$ monocyclic or bicyclic aromatic hydrocarbocycle, a $C_{3-7}$ cycloalkane ring, a 3- to 7-membered heterocycloalkane ring, a $C_{3-7}$ cycloalkene ring, or a 5- to 12-membered spiroheterocycloalkane ring, and the aforementioned heterocycloalkane ring and spiroheterocycloalkane ring have 1 or 2 nitrogen atoms as ring member atoms.

[9]

A compound represented by the following formula (1'):

[Chem. 3]

(1')

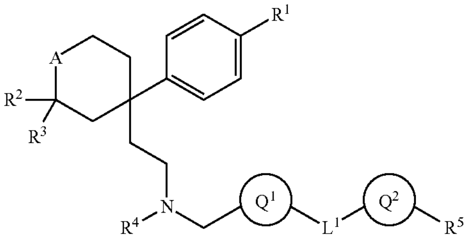

wherein

A is —O— or —$CF_2$—, $R^1$ is halogen, —O—$C_{1-6}$ alkyl optionally substituted by 1 to 3 halogens, —N(H)—$C_{1-3}$ alkyl, —N($C_{1-3}$ alkyl$)_2$ or 4- to 6-membered heterocycloalkyl having one nitrogen atom as a ring member atom, $R^2$ and $R^3$ are each independently hydrogen or $C_{1-6}$ alkyl, $R^4$ is $C_{1-6}$ alkyl optionally substituted by 1 to 3 halogens, —C(═O)—$C_{1-6}$ alkyl optionally substituted by 1 to 3 halogens, $C_{3-6}$ cycloalkylmethyl optionally substituted by one trifluoromethyl or 6-membered heteroaryl having 1 or 2 nitrogen atoms as ring member atoms (the heteroaryl is optionally substituted by one halogen), ring $Q^1$ is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, $L^1$ is a single bond, —O—, —$CH_2$—, or —C(═O)—, ring $Q^2$ is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, and $R^5$ is $C_{1-6}$ alkyl optionally having 1 or 2 groups selected from the group consisting of carboxy, hydroxy, and —O—$C_{1-6}$ alkyl, carboxy, hydroxy, or a group represented by the following formula:

[Chem. 4]

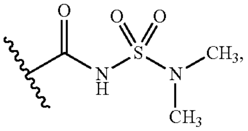
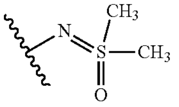
or

-continued

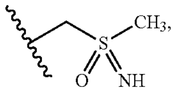

or a pharmaceutically acceptable salt thereof.

[10]

The compound according to [9] or a pharmaceutically acceptable salt thereof, wherein A is —O—, $R^2$ is methyl, $R^3$ is methyl, $R^4$ is $C_{1-6}$ alkyl optionally substituted by 1 to 3 halogens, —C(═O)—$C_{1-6}$ alkyl optionally substituted by 1 to 3 halogens, or 6-membered heteroaryl having 1 or 2 nitrogen atoms as ring member atoms (the heteroaryl is optionally substituted by one halogen), ring $Q^1$ is a benzene ring optionally having one group selected from the group consisting of halogen and $C_{1-3}$ alkyl, or a pyridine ring, $L^1$ is a single bond, —O—, or —C(═O)—, and ring $Q^2$ is a benzene ring, a $C_{4-7}$ cycloalkane ring, or a $C_{4-7}$ cycloalkene ring.

[11]

The compound according to [9] or [10] or a pharmaceutically acceptable salt thereof, wherein $R^1$ is methoxy, and $R^4$ is 3,3,3-trifluoro-2,2-dimethylpropyl.

[12]

Any one compound selected from the following group:

trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexanecarboxylic acid, 2-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)phenyl]propanoic acid, {trans-4-[(5-{[{2-[(4R)-4-(4-methoxyphenyl)-2,2-dimethyltetrahydro-2H-pyran-4-yl]ethyl) (3,3,3-trifluoro-2,2-dimethylpropyl)amino]methyl}pyridin-2-yl)oxy] cyclohexyl}acetic acid,

[trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexyl]acetic acid, (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid,

[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methanol, and tert-butyl 4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro [biphenyl]-4-yl]methyl}piperazine-1-carboxylate, or a pharmaceutically acceptable salt thereof.

[13]

A polyfunctional molecule comprising a moiety corresponding to the compound or a pharmaceutically acceptable salt thereof according to any one of [1] to [12].

[14]

The polyfunctional molecule according to [13], further comprising another functional moiety, wherein the moiety corresponding to the aforementioned compound or a pharmaceutically acceptable salt thereof is linked to the other functional moiety directly or is linked via a linker at any position in $R^5$.

[15]

The polyfunctional molecule according to [14], wherein said other functional moiety is an E3 ligase-binding moiety, an autophagy-recruiting moiety, a lysosome-recruiting moiety, a kinase-recruiting moiety, a phosphatase-recruiting moiety, a glycosyltransferase-recruiting moiety, an acetyltransferase-recruiting moiety, or ADC.

[16]

The polyfunctional molecule according to [14], wherein said other functional moiety is an E3 ligase-binding moiety.

[17]

The polyfunctional molecule according to [16], wherein the E3 ligase-binding moiety is a cereblon (CRBN)-binding moiety.

[18]

A compound represented by the following formula (2):

[Chem. 5]

(2)

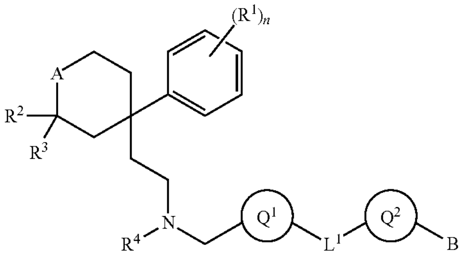

wherein

A is —O—, —S—, —$NR^a$—, or —$CR^bR^c$—, wherein $R^a$ is hydrogen or $C_{1-3}$ alkyl, $R^b$ and $R^c$ are each independently hydrogen, halogen, or $C_{1-3}$ alkyl, and the aforementioned alkyl is unsubstituted or substituted by 1 to 3 halogens, each $R^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(═O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl, and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, and heterocycloalkene ring have 1 or 2 hetero atoms selected from oxygen, nitrogen, and sulfur as ring member atoms, $L^1$ is a single bond, —O—, —S—, —NH—, $C_{1-3}$ alkylene, $C_{2-3}$ alkenylene, —C(═O)—, —C(═O)NH—, —NHC(═O)—, —C(═O)O—, or —OC(═O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring have 1 or 2 hetero atoms selected from oxygen, nitrogen, and sulfur as ring member atoms, B is $-L^2-L^3-L^4-R^6$, $L^2$ is a single bond, $C_{1-6}$ alkylene, —C(═O)—, —C(═O)NH—, $-(CH_2)_k-$C(═O)NH— (k indicates an integer of 1 to 3), or —NHC(═O)—, $L^3$ is a single bond, $C_{1-6}$ alkylene, $C_{3-6}$ cycloalkylene, piperazinediyl, piperazin-2-onediyl, piperidinediyl, pyrrolidinediyl, azetidinediyl, or 3-oxa-9-azabicyclo[3.3.1]nonanediyl, $L^4$ is a single bond, —NH—, —N(—$R^7$)— ($R^7$ indicates $C_{1-6}$ alkyl), $-CH_2-$, or —C(═O)—, and $R^6$ is an E3 ligase-binding moiety, an autophagy-recruiting moiety, a lysosome-recruiting moiety, a kinase-recruiting moiety, a phosphatase-recruiting moiety, a glycosyltransferase-recruiting moiety, an acetyltransferase-recruiting moiety, or ADC, and n is an integer of 0 to 3, or a pharmaceutically acceptable salt thereof.

[19]

The compound according to [18] or a pharmaceutically acceptable salt thereof, wherein A is —O— or —$CR^bR^c$—.

[20]

The compound according to [18] or [19] or a pharmaceutically acceptable salt thereof, wherein each $R^1$ in the number of n is independently halogen, —O—$C_{1-6}$ alkyl, —N(H)—$C_{1-3}$ alkyl, —N($C_{1-3}$ alkyl)$_2$, or 3- to 7-membered heterocycloalkyl, and the aforementioned heterocycloalkyl has 1 or 2 nitrogen atoms as ring member atoms.

[21]

The compound according to any one of [18] to [20] or a pharmaceutically acceptable salt thereof, wherein $R^2$ and $R^3$ are each independently hydrogen or $C_{1-6}$ alkyl.

[22]

The compound according to any one of [18] to [21] or a pharmaceutically acceptable salt thereof, wherein $R^4$ is $C_{1-6}$ alkyl, —C(═O)—$R^d$, or 6- to 12-membered heteroaryl, wherein the aforementioned $R^d$ is $C_{1-6}$ alkyl, the aforementioned $C_{1-6}$ alkyl is unsubstituted or substituted by 1 to 3 halogens or $C_{3-7}$ cycloalkyl, and the aforementioned heteroaryl has 1 or 2 nitrogen atoms as ring member atoms.

[23]

The compound according to any one of [18] to [22] or a pharmaceutically acceptable salt thereof, wherein ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, or a $C_{3}$_7 cycloalkene ring, and the aforementioned aromatic heterocycle has 1 or 2 nitrogen atoms as ring member atoms.

[24]

The compound according to any one of [18] to [23] or a pharmaceutically acceptable salt thereof, wherein $L^1$ is a single bond, —O—, $C_{1-3}$ alkylene, or —C(═O)—.

[25]

The compound according to any one of [18] to [24] or a pharmaceutically acceptable salt thereof, wherein ring $Q^2$ is a $C_{6-12}$ monocyclic or bicyclic aromatic hydrocarbocycle, a $C_{3-7}$ cycloalkane ring, a 3- to 7-membered heterocycloalkane ring, a $C_{3-7}$ cycloalkene ring, or a 5- to 12-membered spiroheterocycloalkane ring, and the aforementioned heterocycloalkane ring and spiroheterocycloalkane ring have 1 or 2 nitrogen atoms as ring member atoms.

[26]

A compound represented by the following formula (2'):

[Chem. 6]

(2')

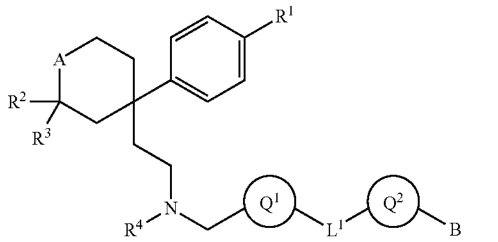

wherein

A is —O— or —$CF_2$—, $R^1$ is halogen, —O—$C_{1-6}$ alkyl optionally substituted by 1 to 3 halogens, —N(H)—$C_{1-3}$ alkyl, —N($C_{1-3}$ alkyl)$_2$ or 4- to 6-membered heterocycloalkyl having one nitrogen atom as a ring member atom, $R^2$ and $R^3$ are each independently hydrogen or $C_{1-6}$ alkyl, $R^4$ is $C_{1-6}$ alkyl optionally substituted by 1 to 3 halogens, —C(═O)—$C_{1-6}$ alkyl optionally substituted by 1 to 3 halogens, $C_{3-6}$ cycloalkylmethyl optionally substituted by one trifluoromethyl, or 6-membered heteroaryl having 1 or 2 nitrogen atoms as ring member atoms (the heteroaryl is optionally substituted by one halogen), ring $Q^1$ is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, $L^1$ is a single bond, —O—, —$CH_2$—, or —C(═O)—, ring $Q^2$ is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, B is -$L^2$-$L^3$-$L^4$-$R^6$, $L^2$ is a single bond, $C_{1-6}$ alkylene, —C(═O)—, —C(═O)NH—, —$(CH_2)_k$—C(═O)NH— (k indicates an integer of 1 to 3), or —NHC(═O)—, $L^3$ is a single bond, $C_{1-6}$ alkylene, $C_{3-6}$ cycloalkylene, piperazinediyl, piperazin-2-onediyl, piperidinediyl, pyrrolidinediyl, azetidinediyl, or 3-oxa-9-azabicyclo[3.3.1]nonanediyl, $L^4$ is a single bond, —NH—, —N(—$R^7$)— ($R^7$ indicates $C_{1-6}$ alkyl), —$CH_2$—, or —C(═O)—, and $R^6$ is an E3 ligase-binding moiety, an autophagy-recruiting moiety, a lysosome-recruiting moiety, a kinase-recruiting moiety, a phosphatase-recruiting moiety, a glycosyltransferase-recruiting moiety, an acetyltransferase-recruiting moiety, or ADC, or a pharmaceutically acceptable salt thereof.

[27]

The compound according to any one of [18] to [26] or a pharmaceutically acceptable salt thereof, wherein $R^6$ is an E3 ligase-binding moiety.

[28]

The compound according to [27] or a pharmaceutically acceptable salt thereof, wherein the E3 ligase-binding moiety is a cereblon (CRBN)-binding moiety.

[29]

The compound according to any one of [18] to [28] or a pharmaceutically acceptable salt thereof, wherein $R^6$ is any group selected from the following formulas:

[Chem. 7]

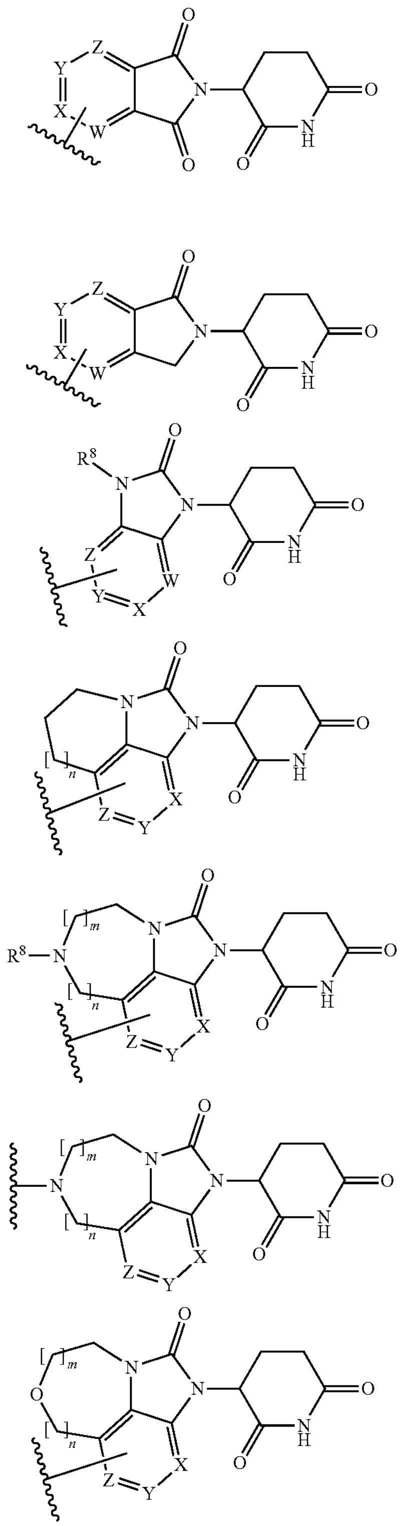

-continued

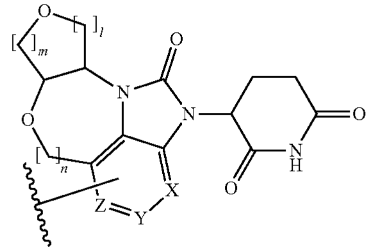

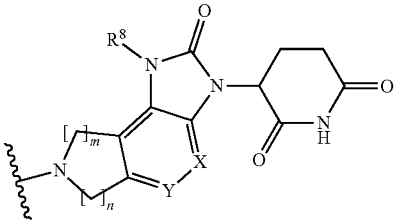

wherein, $R^8$ is hydrogen or $C_{1-6}$ alkyl,

W, X, Y, and Z indicate each independently a nitrogen atom or a carbon atom optionally having one group selected from the group consisting of halogen, $C_{1-6}$ alkyl, and —O—$C_{1-6}$ alkyl, l, m, and n are each independently an integer of 0 to 3, and a wavy line indicates the bonding position with $L^4$.

[30]

The compound according to [29] or a pharmaceutically acceptable salt thereof, wherein $R^6$ is any group selected from the following formulas:

[Chem. 8]

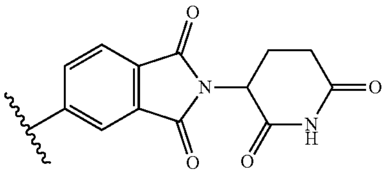

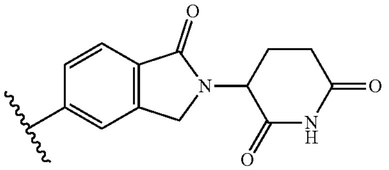

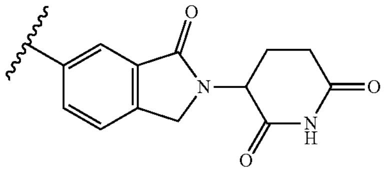

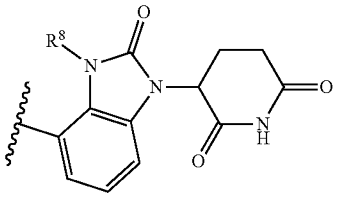

-continued

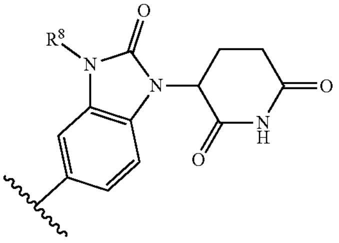

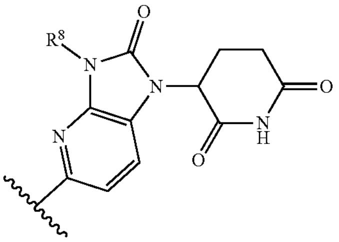

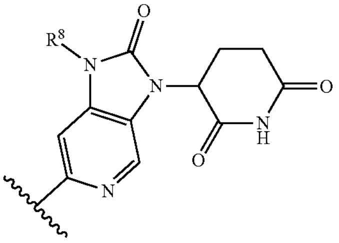

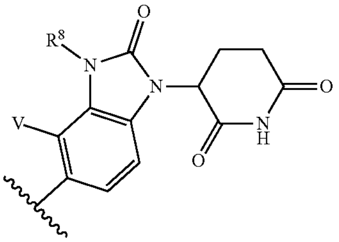

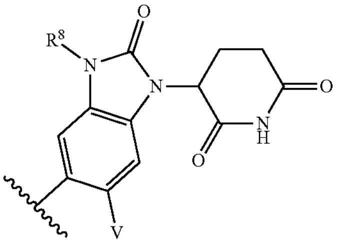

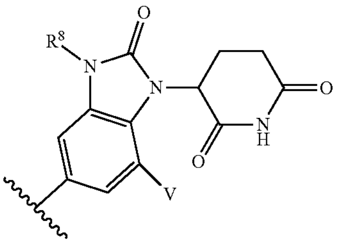

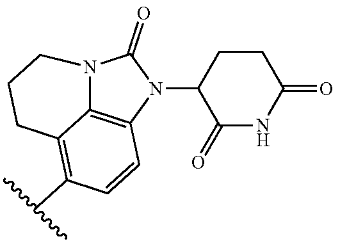

-continued

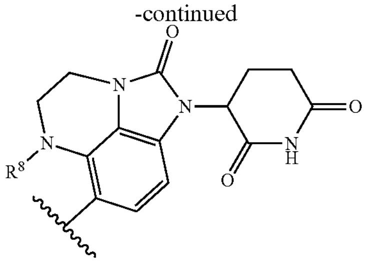

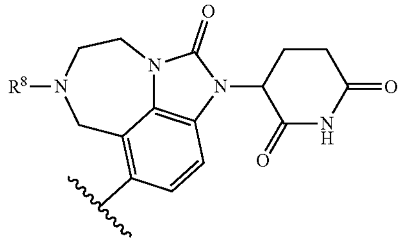

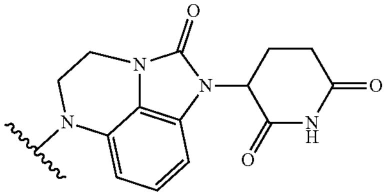

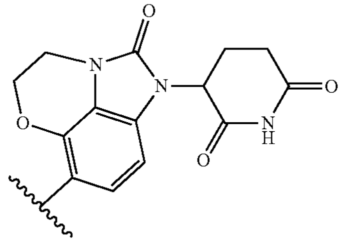

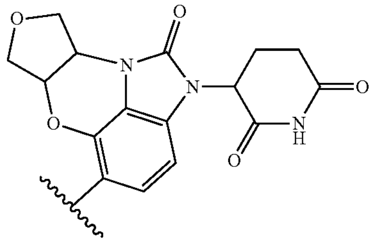

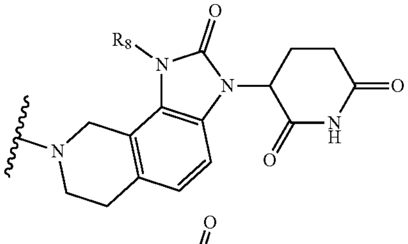

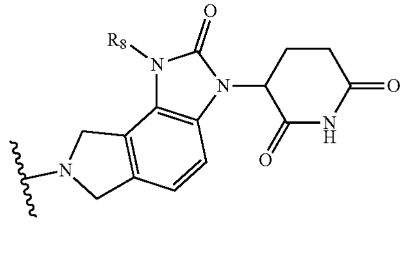

wherein $R^8$ is hydrogen or $C_{1-6}$ alkyl,

V is halogen, and a wavy line indicates the bonding position with $L^4$.

[31]

The compound according to any one of [18] to [30] or a pharmaceutically acceptable salt thereof, wherein $R^1$ is —O—$C_{1-6}$ alkyl optionally substituted by 1 to 3 halogens, $R^4$ is $C_{1-6}$ alkyl optionally substituted by 1 to 3 halogens or $C_{3-6}$ cycloalkylmethyl optionally substituted by one trifluoromethyl, ring $Q^1$ is a benzene ring optionally having 1 or 2 groups selected from the group consisting of halogen and $C_{1-6}$ alkyl, a 9- to 10-membered bicyclic aromatic heterocycle having 1 or 2 nitrogen atoms as ring member atoms, a $C_{4-7}$ cycloalkane ring, or a $C_{4-7}$ cycloalkene ring, and $L^1$ is a single bond or —O—.

[32]

The compound according to any one of [18] to [31] or a pharmaceutically acceptable salt thereof, wherein A is —O—, $R^2$ is methyl, and $R^3$ is methyl.

[33]

The compound according to any one of [18] to [32] or a pharmaceutically acceptable salt thereof, wherein $R^1$ is methoxy, and $R^4$ is 3,3,3-trifluoro-2,2-dimethylpropyl.

[34]

The compound according to any one of [18] to [33] or a pharmaceutically acceptable salt thereof, wherein ring $Q^1$ is a benzene ring optionally having one halogen, $L^1$ is a single bond, and ring $Q^2$ is a cyclohexene ring.

[35]

Any one compound selected from the following group:

3-{5-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, (3R)-3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, (3S)-3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione, (3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione, (3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione, 3-{7-[(1-{[(4R)-2'-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, (3R)-3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, (3S)-3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione, (3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione, and (3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione, or a pharmaceutically acceptable salt thereof.

[35-2]

Any one compound selected from the following group:

(3RS)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3R)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3S)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3R)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3S)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3RS)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3R)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3S)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, (3R)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, and (3S)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, or a pharmaceutically acceptable salt thereof.

[36]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione benzenesulfonate.

[36-2]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione monobenzenesulfonate.

[36-3]

(3RS)-3-[7-(4-{[(4R)-4'-{([{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate.

[36-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl)piperazine-1-carbonyl)-2-oxo-5,6-dihydro-4H-imidazo[4,5,1-ij]quinolin-1(2H)-yl]piperidine-2,6-dione monobenzenesulfonate.

[36-5]

A crystal of 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione benzenesulfonate, the crystal having peaks at diffraction angles (2θ) of 2.15±0.2, 8.30±0.2, 10.29±0.2, 14.75±0.2, 17.19±0.2, 20.00±0.2, 21.34±0.2, 22.68±0.2, 23.77±0.2, and 25.23±0.2 in a powder X-ray diffraction pattern obtained by irradiation with copper Kα ray (λ=1.54 angstroms).

[36-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate, the crystal having peaks at diffraction angles (2θ) of 2.15±0.2, 8.30±0.2, 10.29±0.2, 14.75±0.2, 17.19±0.2, 20.00±0.2, 21.34±0.2, 22.68±0.2, 23.77±0.2, and 25.23±0.2 in a powder X-ray diffraction pattern obtained by irradiation with copper Kα ray (λ=1.54 angstroms).

[37]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione ethanesulfonate.

[37-2]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione monoethanesulfonate.

[37-3]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate.

[37-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione monoethanesulfonate.

[37-5]

A crystal of 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl)piperidine-2,6-dione ethanesulfonate, the crystal having peaks at diffraction angles (2θ) of 2.21±0.2, 12.04±0.2, 14.87±0.2, 17.69±0.2, 18.93±0.2, 20.41±0.2, 22.42±0.2, 23.19±0.2, 24.13±0.2, and 27.98±0.2 in a powder X-ray diffraction pattern obtained by irradiation with copper Kα ray (λ=1.54 angstroms).

[37-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate, the crystal having peaks at diffraction angles (2θ) of 2.21±0.2, 12.04±0.2, 14.87±0.2, 17.69±0.2, 18.93±0.2, 20.41±0.2, 22.42±0.2, 23.19±0.2, 24.13±0.2, and 27.98±0.2 in a powder X-ray diffraction pattern obtained by irradiation with copper Kα ray (λ=1.54 angstroms).

[38]

3-{7-[(1-{[(4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione 10-camphorsulfonate.

[38-2]

3-{7-[(1-{[(4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione mono-10-camphorsulfonate.

[38-3]

(3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate.

[38-4]

(3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione mono-10-camphorsulfonate.

[38-5]

A crystal of 3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione 10-camphorsulfonate, the crystal having peaks at diffraction angles (2θ) of 3.89±0.2, 6.81±0.2, 7.68±0.2, 8.20±0.2, 10.28±0.2, 13.15±0.2, 15.97±0.2, 16.81±0.2, 18.58±0.2, and 23.56±0.2 in a powder X-ray diffraction pattern obtained by irradiation with copper Kα ray (λ=1.54 angstroms).

[38-6]

A crystal of (3RS)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate, the crystal having peaks at diffraction angles (2θ) of 3.89±0.2, 6.81±0.2, 7.68±0.2, 8.20±0.2, 10.28±0.2, 13.15±0.2, 15.97±0.2, 16.81±0.2, 18.58±0.2, and 23.56±0.2 in a powder X-ray diffraction pattern obtained by irradiation with copper Kα ray (λ=1.54 angstroms).

[39]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione ethanesulfonate.

[39-2]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monoethanesulfonate.

[39-3]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl] piperidine-2,6-dione ethanesulfonate.

[39-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl] piperidine-2,6-dione monoethanesulfonate.

[39-5]

A crystal of 3-{7-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione ethanesulfonate, the crystal having peaks at diffraction angles (2θ) of 2.27±0.2, 8.18±0.2, 9.88±0.2, 13.09±0.2, 14.57±0.2, 15.80±0.2, 16.91±0.2, 17.77±0.2, 18.87±0.2, and 20.14±0.2 in a powder X-ray diffraction pattern obtained by irradiation with copper Kα ray (λ=1.54 angstroms).

[39-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione ethanesulfonate, the crystal having peaks at diffraction angles (2θ) of 2.27±0.2, 8.18±0.2, 9.88±0.2, 13.09±0.2, 14.57±0.2, 15.80±0.2, 16.91±0.2, 17.77±0.2, 18.87±0.2, and 20.14±0.2 in a powder X-ray diffraction pattern obtained by irradiation with copper Kα ray (λ=1.54 angstroms).

[40]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione salicylate.

[40-2]

3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monosalicylate.

[40-3]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl] piperidine-2,6-dione salicylate.

[40-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl] piperidine-2,6-dione monosalicylate.

[40-5]

A crystal of 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione salicylate, the crystal having peaks at diffraction angles (2θ) of 2.20±0.2, 4.34±0.2, 9.45±0.2, 10.97±0.2, 13.23±0.2, 16.98±0.2, 18.09±0.2, 20.20±0.2, 21.32±0.2, and 25.19±0.2 in a powder X-ray diffraction pattern obtained by irradiation with copper Kα ray (λ=1.54 angstroms).

[40-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione salicylate, the crystal having peaks at diffraction angles (2θ) of 2.20±0.2, 4.34±0.2, 9.45±0.2, 10.97±0.2, 13.23±0.2, 16.98±0.2, 18.09±0.2, 20.20±0.2, 21.32±0.2, and 25.19±0.2 in a powder X-ray diffraction pattern obtained by irradiation with copper Kα ray (λ=1.54 angstroms).

[41]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione benzenesulfonate.

[41-2]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monobenzenesulfonate.

[41-3]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl] piperidine-2,6-dione benzenesulfonate.

[41-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6- dihydro-4H-imidazo[1,5,4-de]quinoxalin-1(2H)-yl]piperidine-2,6-dione monobenzenesulfonate.

[41-5]

A crystal of 3-{7-[(4-{[(4R)-4'-{[{2-[(4R)-4-(4-methoxyphenyl)-2,2-dimethyltetrahydro-2H-pyran-4-yl]ethyl) (3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione benzenesulfonate, the crystal having peaks at diffraction angles (2θ) of 2.19±0.2, 8.87±0.2, 10.86±0.2, 12.55±0.2, 13.05±0.2, 14.99±0.2, 17.84±0.2, 20.62±0.2, 21.43±0.2, and 25.27±0.2 in a powder X-ray diffraction pattern obtained by irradiation with copper Kα ray (λ=1.54 angstroms).

[41-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione benzenesulfonate, having peaks at diffraction angles (2θ) of 2.19±0.2, 8.87±0.2, 10.86±0.2, 12.55±0.2, 13.05±0.2, 14.99±0.2, 17.84±0.2, 20.62±0.2, 21.43±0.2, and 25.27±0.2 in a powder X-ray diffraction pattern obtained by irradiation with copper Kα ray (λ=1.54 angstroms).

[42]

3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione 10-camphorsulfonate.

[42-2]

3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione mono-10-camphorsulfonate.

[42-3](3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate.

[42-4]

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione mono-10-camphorsulfonate.

[42-5]

A crystal of 3-{7-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione 10-camphorsulfonate, having peaks at diffraction angles (2θ) of 2.20±0.2, 7.82±0.2, 11.05±0.2, 12.42±0.2, 13.34±0.2, 15.23±0.2, 16.49±0.2, 17.86±0.2, 20.15±0.2, and 24.36±0.2 in a powder X-ray diffraction pattern obtained by irradiation with copper Kα ray (λ=1.54 angstroms) crystal.

[42-6]

A crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro(1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate, having peaks at diffraction angles (2θ) of 2.20±0.2, 7.82±0.2, 11.05±0.2, 12.42±0.2, 13.34±0.2, 15.23±0.2, 16.49±0.2, 17.86±0.2, 20.15±0.2, and 24.36±0.2 in a powder X-ray diffraction pattern obtained by irradiation with copper Kα ray (λ=1.54 angstroms) crystal.

[43]

A composition for inhibiting Steroidogenic Factor 1, comprising the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6].

[44]

A composition for inducing degradation of Steroidogenic Factor 1, comprising the polyfunctional molecule according to any one of [13] to [17] or the compound or a pharmaceutically acceptable salt thereof, or the crystal thereof according to any one of [18] to [42-6].

[45]

A pharmaceutical composition comprising the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6].

[46]

The pharmaceutical composition according to [45], which is for the treatment of castration-resistant prostate cancer, adrenocortical carcinoma, Leydig cell tumor, hormone-sensitive prostate cancer, breast cancer, Cushing's syndrome, or primary aldosteronism.

[46-2]

The pharmaceutical composition according to [45], which is for the treatment of castration-resistant prostate cancer, adrenocortical carcinoma, Leydig cell tumor, hormone-sensitive prostate cancer, Cushing's syndrome, or primary aldosteronism.

[47]

A method for treating castration-resistant prostate cancer, adrenocortical carcinoma, Leydig cell tumor, hormone-sensitive prostate cancer, breast cancer, Cushing's syndrome, or primary aldosteronism, comprising administering an effective amount of the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6] to a subject in need of a treatment of castration-resistant prostate cancer, adrenocortical carcinoma, Leydig cell tumor, hormone-sensitive prostate cancer, breast cancer, Cushing's syndrome, or primary aldosteronism.

[47-2]

A method for treating castration-resistant prostate cancer, adrenocortical carcinoma, Leydig cell tumor, hormone-sensitive prostate cancer, Cushing's syndrome, or primary aldosteronism, comprising administering an effective amount of the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6] to a subject in need of a treatment of castration-resistant prostate cancer, adrenocortical carcinoma, Leydig cell tumor, hormone-sensitive prostate cancer, Cushing's syndrome, or primary aldosteronism.

[48]

The compound or a pharmaceutically acceptable salt thereof according to any one of [1] to [12], the polyfunctional molecule according to any one of [13] to [17] or the compound or a pharmaceutically acceptable salt thereof, or the crystal thereof according to any one of [18] to [42-6], which is for use in the treatment of castration-resistant prostate cancer, adrenocortical carcinoma, Leydig cell tumor, hormone-sensitive prostate cancer, breast cancer, Cushing's syndrome, or primary aldosteronism.

[48-2]

The compound or a pharmaceutically acceptable salt thereof according to any one of [1] to [12], the polyfunctional molecule according to any one of [13] to [17] or the compound or a pharmaceutically acceptable salt thereof, or the crystal thereof according to any one of [18] to [42-6], which is for use in the treatment of castration-resistant prostate cancer, adrenocortical carcinoma, Leydig cell tumor, hormone-sensitive prostate cancer, Cushing's syndrome, or primary aldosteronism.

[49]

Use of the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6] in the production of a medicament for the treatment of castration-resistant prostate cancer, adrenocortical carcinoma, Leydig cell tumor, hormone-sensitive prostate cancer, breast cancer, Cushing's syndrome, or primary aldosteronism.

[49-2]

Use of the compound or a pharmaceutically acceptable salt thereof according to any one of [1] to [12], the polyfunctional molecule according to any one of [13] to [17], or the compound or a pharmaceutically acceptable salt thereof, or the crystal thereof according to any one of [18] to [42-6] in the production of a medicament for the treatment of castration-resistant prostate cancer, adrenocortical carcinoma, Leydig cell tumor, hormone-sensitive prostate cancer, Cushing's syndrome, or primary aldosteronism.

[50]

A compound represented by the following formula (10):

[Chem. 9]

(10)

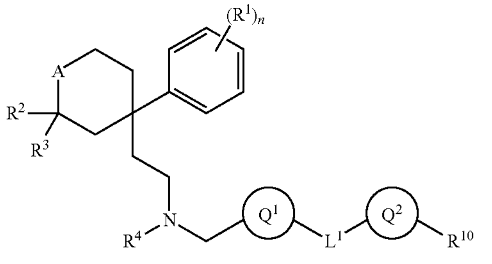

wherein

A is —O—, —S—, —$NR^a$—, or —$CR^bR^c$—, wherein $R^a$ is hydrogen or $C_{1-3}$ alkyl, $R^b$ and $R^c$ are each independently hydrogen, halogen, or $C_{1-3}$ alkyl, and the aforementioned alkyl is unsubstituted or substituted by 1 to 3 halogens, each $R^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(═O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl, and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring and heterocycloalkene ring have 1 or 2 hetero atoms selected from oxygen, nitrogen, and sulfur as ring member atoms, $L^1$ is a single bond, —O—, —S—, —NH—, $C_{1-3}$ alkylene, $C_{2-3}$ alkenylene, —C(═O)—, —C(═O)NH—, —NHC(═O)—, —C(═O)O—, or —OC(═O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring have 1 or 2 hetero atoms selected from oxygen, nitrogen, and sulfur as ring member atoms, $R^{10}$ is $C_{1-6}$ alkyl, wherein the aforementioned $C_{1-6}$ alkyl is substituted by one or two 3- to 7-membered heterocycloalkyls, the aforementioned heterocycloalkyl has 1 or 2 hetero atoms selected from oxygen, nitrogen, and sulfur as ring member atoms, and the aforementioned heterocycloalkyl is unsubstituted or substituted by an amino-protecting group, and n is an integer of 0 to 3, or a pharmaceutically acceptable salt thereof.

For example, when item numbers are indicated as a range, such as "[18] to [42-6]", and the range includes an item including a sub-number such as [36-3] or [42-4], the item including the sub-number is also included in the range.

Advantageous Effects of Invention

Since a compound represented by the formula (1) or a pharmaceutically acceptable salt thereof of the present invention has SF-1 antagonist activity, it can be used as an SF-1 antagonist or an SF-1 inhibitor. In addition, since SF-1 is known to be involved in the development or progression of various diseases such as adrenocortical carcinoma and castration-resistant prostate cancer, the compound represented by the formula (1) or a pharmaceutically acceptable salt thereof of the present invention can be used in the treatment of such diseases. In addition, since the compound represented by the formula (1) or a pharmaceutically acceptable salt thereof of the present invention has SF-1 antagonist activity, it can be used as a partial structure in a larger molecule (e.g., polyfunctional molecule) by combining with other functional moieties.

In addition, since the compound represented by the formula (1) or a pharmaceutically acceptable salt thereof of the present invention specifically binds to SF-1, it can also be used as an SF-1 binder, and further can be used as an SF-1 binding moiety in a larger molecule (e.g., polyfunctional molecule) by combining a moiety corresponding to the compound represented by the formula (1) or a pharmaceutically acceptable salt thereof of the present invention with other functional moieties. Among these, a polyfunctional molecule containing a moiety corresponding to the compound represented by the formula (1) or a pharmaceutically acceptable salt thereof of the present invention and an E3 ligase-binding moiety, particularly, a compound represented by the formula (2) or a pharmaceutically acceptable salt thereof, or the crystal of the present invention can degrade SF-1 protein and inhibit the proliferation of tumor cells, and thus can be used as an SF-1 inhibitor and an SF-1 degrader, as well as for the treatment of SF-1-related diseases such as adrenocortical carcinoma, castration-resistant prostate cancer, and the like.

BRIEF DESCRIPTION OF DRAWINGS

FIG. 1

A powder X-ray diffraction pattern of the crystal obtained in Example CI1, in which the vertical axis indicates the diffraction intensity in counts/second (cps) and the horizontal axis indicates the value of the diffraction angle 2e.

FIG. 2

A powder X-ray diffraction pattern of the crystal obtained in Example CJ1, in which the vertical axis indicates the diffraction intensity in counts/second (cps) and the horizontal axis indicates the value of the diffraction angle 2θ.

FIG. 3

A powder X-ray diffraction pattern of the crystal obtained in Example CK1, in which the vertical axis indicates the diffraction intensity in counts/second (cps) and the horizontal axis indicates the value of the diffraction angle 2θ.

FIG. 4

A powder X-ray diffraction pattern of the crystal obtained in Example CL1, in which the vertical axis indicates the diffraction intensity in counts/second (cps) and the horizontal axis indicates the value of the diffraction angle 2θ.

FIG. 5

A powder X-ray diffraction pattern of the crystal obtained in Example CM1, in which the vertical axis indicates the diffraction intensity in counts/second (cps) and the horizontal axis indicates the value of the diffraction angle 2θ.

FIG. 6

A powder X-ray diffraction pattern of the crystal obtained in Example CN1, in which the vertical axis indicates the diffraction intensity in counts/second (cps) and the horizontal axis indicates the value of the diffraction angle 2θ.

FIG. 7

A powder X-ray diffraction pattern of the crystal obtained in Example CO1, in which the vertical axis indicates the diffraction intensity in counts/second (cps) and the horizontal axis indicates the value of the diffraction angle 2θ.

DESCRIPTION OF EMBODIMENTS

1. Definitions

Unless otherwise defined, all technical terms and scientific terms used in the present specification have the same meaning as generally understood by those of ordinary skill in the art. If there is any discrepancy between the meaning of a term defined in the present specification and the meaning generally understood by those of ordinary skill in the art, the meaning defined in the present specification shall prevail. Preferred methods and materials are described below; however, methods and materials similar or equivalent to those described in the present specification may be used for practicing or testing the present invention. All references cited in the present specification (including patent literatures and non-patent literatures) are incorporated herein in their entirety by reference. The materials, methods, and examples disclosed in the present specification are merely illustrative and are not intended for limitation.

In the present specification, Steroidogenic factor 1 means the protein encoded by the NR5A1 gene, and may be sometimes abbreviated or synonymously referred to as SF-1, hSF-1, SF1, Ad4BP, AD4BP, ELP, FTZ1, TZF1, POF7, SPGF8, SRXX4, or SRXY3.

In the present specification, “antagonist” means a substance that reduces, interferes with, or neutralizes the action, activity, or effect of another substance. Thus, in the present specification, “SF-1 antagonist” means a substance that reduces, interferes with, or neutralizes the action, activity, or effect of SF-1.

In the present specification, “halogen” means fluorine atom (F), chlorine atom (Cl), bromine atom (Br), or iodine atom (I).

In the present specification, “alkyl” means linear or branched alkyl. In the present specification, “$C_{1-6}$ alkyl” means alkyl having 1 to 6 carbon atoms, and “$C_{1-3}$ alkyl” means alkyl having 1 to 3 carbon atoms. Examples of the “alkyl” include, but are not limited to, methyl, ethyl, n-propyl, i-propyl, n-butyl, i-butyl, s-butyl, t-butyl, n-pentyl, n-hexyl, and the like.

In the present specification, “alkylene” means linear or branched alkylene. In the present specification, “$C_{1-6}$ alkylene” means alkylene having 1 to 6 carbon atoms, and “$C_{1-3}$ alkylene” means alkylene having 1 to 3 carbon atoms. Examples of the “alkylene” include, but are not limited to, methylene, ethylene, n-propylene, i-propylene, n-butylene, i-butylene, s-butylene, t-butylene, n-pentylene, n-hexylene, and the like.

In the present specification, “alkenyl” means linear or branched alkenyl. In the present specification, “$C_{2-6}$ alkenyl” means alkenyl having 2 to 6 carbon atoms, and “$C_{2-5}$ alkenyl” means alkenyl having 2 to 5 carbon atoms. Examples of the “alkenyl” include, but are not limited to, ethenyl (vinyl), 1-propenyl, 2-propenyl, 1-butenyl, 2-butenyl, 3-butenyl, buta-2,3-dienyl, pentenyl, hexenyl, and the like.

In the present specification, “alkenylene” means linear or branched alkenylene. In the present specification, “$C_{2-3}$ alkenylene” means alkenylene having 2 or 3 carbon atoms. Examples of the “alkenylene” include, but are not limited to, ethenylene (vinylene), 1-propenylene, 2-propenylene, 1-butenylene, 2-butenylene, 3-butenylene, buta-2,3-dienylene, pentenylene, hexenylene, and the like.

In the present specification, “haloalkyl” means alkyl substituted by one or more halogens, and “$C_{1-3}$ haloalkyl” means $C_{1-3}$ alkyl substituted by one or more halogens. Examples of the “haloalkyl” include, but are not limited to, trifluoromethyl, difluoromethyl, monofluoromethyl, pentafluoroethyl, tetrafluoroethyl, monofluoroethyl, trifluoroethyl, trichloromethyl, and the like.

In the present specification, “aromatic hydrocarbocycle” means a monocyclic or polycyclic hydrocarbocycle where at least one of the rings is an aromatic ring. In the present specification, “aryl” means a group derived from an aromatic hydrocarbocycle. “$C_{6-12}$ aryl” means aryl containing 6 to 12 carbon atoms as ring member atoms, “$C_{6-12}$ monocyclic or bicyclic aromatic hydrocarbocycle” means monocyclic or bicyclic aromatic hydrocarbocycle containing 6 to 12 carbon atoms as ring member atoms. Examples of the “aromatic hydrocarbocycle” include, but are not limited to, benzene, indene, naphthalene, anthracene, and the like. Examples of the “aryl” include, but are not limited to, phenyl, indenyl, naphthyl, anthryl, and the like.

In the present specification, “aromatic heterocycle” means a monocyclic or polycyclic ring where at least one of the rings is an aromatic ring, which contains one or more heteroatoms selected from atoms other than carbon, such as nitrogen, oxygen, and sulfur, as ring member atoms. In the present specification, “heteroaryl” means a group derived from an aromatic heterocycle. The “6- to 12-membered heteroaryl” means heteroaryl consisting of 6 to 12 ring member atoms, and “6- to 12-membered monocyclic or bicyclic aromatic heterocycle” means a monocyclic or bicyclic aromatic heterocycle consisting of 6 to 12 ring member atoms. Examples of the “aromatic heterocycle” include, but are not limited to, thiophene, pyrrole, pyrazole, triazole, oxazole, oxadiazole, thiazole, pyridine, pyrimidine, pyridazine, pyrazine, quinoline, quinoxaline, benzothiophene, benzimidazole, benzotriazole, benzofuran, and the like. Examples of the “heteroaryl” include, but are not limited to, thienyl, pyrrolyl, pyrazolyl, triazolyl, oxazolyl, oxadiazolyl, thiazolyl, pyridyl, pyrimidyl, pyridazyl, pyrazinyl, quinolyl, quinoxalyl, benzothiophenyl, benzimidazolyl, benzotriazolyl, benzofuranyl, and the like.

In the present specification, examples of the “6-membered heteroaryl having 1 or 2 nitrogen atoms as ring member atoms” include pyridinyl, pyrazinyl, pyrimidinyl, pyridazinyl, and the like.

In the present specification, examples of the “6- to 12-membered monocyclic or bicyclic aromatic heterocycle having 1 or 2 nitrogen atoms as ring member atoms” include, but are not limited to, 6-membered rings such as pyridine, pyrazine, pyrimidine, and pyridazine; 7-membered rings such as azepine, 1,2-diazepine, 1,3-diazepine, and 1,4-diazepine; 8-membered rings such as azocine; 9-membered rings such as azonine; 6/5-membered fused rings such as indole, isoindole, indazole, benzimidazole, and imidazopyridine (including imidazo[1,2-a]pyridine); and 6/6-membered fused rings such as quinoline, isoquinoline, quinazoline, quinoxaline, and cinnoline. In the present specification, examples of the “9- or 10-membered bicyclic aromatic heterocycle having 1 or 2 nitrogen atoms as ring member atoms” include, but are not limited to, 6/5-membered fused rings such as indole, isoindole, indazole, benzimidazole, and imidazopyridine (including imidazo[1,2-a]pyridine); and 6/6-membered fused rings such as quinoline, isoquinoline, quinazoline, quinoxaline, and cinnoline.

In the present specification, “cycloalkane ring” means a hydrocarbon ring that does not contain an unsaturated bond. In the present specification, “cycloalkyl” means a monovalent group derived from a cycloalkane ring. The “cycloalkane ring” may be a monocyclic cycloalkane, a fused bicyclic cycloalkane, a spiro ring, or a bridged cycloalkane in which two non-adjacent atoms of the ring are connected by an alkylene bridge of 1, 2, 3, or 4 carbon atoms. In the present specification, “$C_{3-7}$ cycloalkane ring” and “$C_{4-7}$ cycloalkane ring” mean cycloalkane rings having 3 to 7 and 4 to 7 carbon atoms, respectively, “$C_{3-7}$ cycloalkyl” and “$C_{3-6}$ cycloalkyl” mean cycloalkyls having 3 to 7 and 3 to 6 carbon atoms, respectively, and “$C_{5-12}$ spirocycloalkane ring” means a spirocycloalkane ring having 5 to 12 carbon atoms. Examples of the “cycloalkane ring” include cyclobutane, cyclopentane, cyclohexane, cycloheptane, and the like.

In the present specification, “cycloalkylene” means a divalent group derived from a cycloalkane ring. In the present specification, “$C_{3-6}$ cycloalkylene” means cycloalkylene having 3 to 6 carbon atoms. Examples of the “cycloalkylene” include, but are not limited to, cyclobutylene, cyclopentylene, cyclohexylene, and the like.

In the present specification, “cycloalkene ring” means a hydrocarbocycle containing at least one carbon-carbon double bond. In the present specification, the “cycloalkene ring” may be a monocyclic cycloalkene, a fused bicyclic cycloalkene, or a bridged cycloalkene in which two non-adjacent atoms of the ring are connected by an alkylene bridge of 1, 2, 3, or 4 carbon atoms. In the present specification, the “$C_{3-7}$ cycloalkene ring” means a cycloalkene ring having 3 to 7 carbon atoms, and the “$C_{4-7}$ cycloalkene ring”

means a cycloalkene ring having 4 to 7 carbon atoms. "Examples of the "cycloalkene ring" include, but are not limited to, cyclobutene, cyclobutadiene, cyclopentene, cyclopentadiene, cyclohexene, 1,3-cyclohexadiene, 1,4-cyclohexadiene, cycloheptene, 1,3-cycloheptadiene, 1,4-cycloheptadiene, cycloheptatriene, and the like.

In the present specification, "heterocycloalkane ring" means a saturated ring containing one or more heteroatoms selected from atoms other than carbon, such as nitrogen, oxygen, and sulfur, as ring member atoms. In the present specification, "heterocycloalkyl" means a monovalent group derived from a heterocycloalkane ring. The "heterocycloalkane ring" may be a monocyclic heterocycloalkane, a fused bicyclic heterocycloalkane, a spiro ring, or a bridged heterocycloalkane in which two non-adjacent atoms of the ring are connected by an alkylene bridge of 1, 2, 3, or 4 carbon atoms. In the present specification, "3- to 7-membered heterocycloalkane ring" means a heterocycloalkane ring having 3 to 7 carbon atoms and heteroatoms in total as ring member atoms, "5- to 12-membered spiroheterocycloalkane ring" means a spiroheterocycloalkane ring having 5 to 12 carbon atoms and heteroatoms in total as ring member atoms, and "3- to 7-membered heterocycloalkyl" means a heterocycloalkyl having 3 to 7 carbon atoms and heteroatoms in total as ring member atoms. Examples of the "heterocycloalkyl" include oxiranyl, thiiranyl, aziridinyl, oxetanyl, thietanyl, azetidinyl, tetrahydrofuranyl, tetrahydrothiophenyl, pyrrolidinyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxazepanyl, 1,4-dithiepanyl, 1,4-thiazepanyl, 1,4-azaphosphinanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4,4]nonanyl, 3-azabicyclo[3.1.0]hexanyl, indolinyl, dihydroindolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, 1,2,5,6-tetrahydropyridinyl, tetrahydro-1H-benzo[d]azepinyl and the like.

In the present specification, "heterocycloalkene ring" means a ring containing one or more heteroatoms selected from atoms other than carbon, such as nitrogen, oxygen, and sulfur, and at least one double bond. The "heterocycloalkene ring" may be a monocyclic heterocycloalkene, a fused bicyclic heterocycloalkene, a spiro ring, or a bridged heterocycloalkene in which two non-adjacent atoms of the ring are connected by an alkylene bridge of 1, 2, 3, or 4 carbon atoms. In the present specification, "3- to 7-membered heterocycloalkene ring" means a heterocycloalkene ring having 3 to 7 carbon atoms and heteroatoms in total as ring member atoms. Examples of the "heterocycloalkene ring" include, but are not limited to, imidazoline, tetrahydropyridine, dihydropyridine, pyran, thiopyran, dihydropyran, dihydrofuran, dihydropyrazine, octahydroquinoline, octahydroisoquinoline, dihydrothiophene, dihydropyrroline, and the like.

In the present specification, unless otherwise specified, as is clear to those of ordinary skill in the art, the symbol:

[Chem. 10]

 means that it is bonded to the other side of the paper (α-configuration), and the symbol:

[Chem. 11]

means that it is bonded to the front side of the paper (β-configuration).

In addition, stereo symbols with an * (e.g. R*, S*, etc.) indicate the relative steric configuration of the asymmetric center. The relative steric configuration is structurally represented by the symbols:

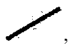, 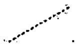.

[Chem. 12]

In the present specification, "pharmaceutically acceptable" means that it has no significant toxicity and can be used as a pharmaceutical composition. Therefore, in the present specification, "pharmaceutically acceptable salt" means a salt that does not have significant toxicity and can be used as a pharmaceutical composition.

In the present invention, "(3RS)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione" means the same compound as "3-{5-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione".

In the present invention, "(3R)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione" means the same compound as "(3R)-3-{5-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione".

In the present invention, "(3S)-3-[5-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione" means the same compound as "(3S)-3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione".

In the present invention, "(3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione" means the same compound as "3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione".

In the present invention, "(3R)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5- tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione" means the same compound as "(3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione".

In the present invention, "(3S)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione" means the same compound as "(3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl)piperidine-2,6-dione".

In the present invention, "(3RS)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione" means the same compound as "3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione".

In the present invention, "(3R)-3-[7-({1-[(4R)-2'-fluoro-4'-{[{2-[(4R)-4-(4-methoxyphenyl)-2,2-dimethyloxan-4-yl]ethyl)(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione" means the same compound as "(3R)-3-{7-[(1-{[(4R)-2'-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione".

In the present invention, "(3S)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl)-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione" means the same compound as "(3S)-3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione".

In the present invention, "(3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione" means the same compound as "3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione".

In the present invention, "(3R)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione" means the same compound as "(3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione".

In the present invention, "(3S)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione" means the same compound as "(3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione".

2. SF-1 Antagonist

In one embodiment of the present invention, a compound represented by the following formula (1):

[Chem. 13]

(1)

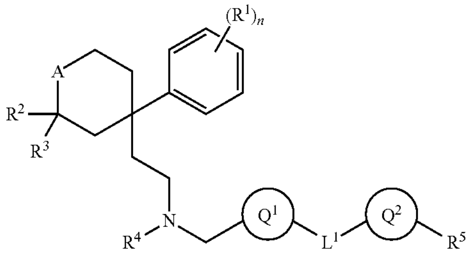

wherein

A is —O—, —S—, —NR$^a$—, or —CR$^b$R$^c$—, wherein

R$^a$ is hydrogen or $C_{1-3}$ alkyl,

R$^b$ and R$^c$ are each independently hydrogen, halogen, or $C_{1-3}$ alkyl, and the aforementioned alkyl is unsubstituted or substituted by 1 to 3 halogens, each R$^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(=O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, and heterocycloalkene ring has 1 or 2 hetero atoms selected from oxygen, nitrogen, and sulfur as ring member atoms, $L^1$ is a single bond, —O—, —S—, —NH—, $C_{1-3}$ alkylene, $C_{2-3}$ alkenylene, —C(=O)—, —C(=O)NH—, —NHC(=O)—, —C(=O)O—, or —OC(=O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring have 1 or 2 hetero atoms selected from oxygen, nitrogen, and sulfur as ring member atoms, $R^5$ is $C_{1-6}$ alkyl, carboxy, hydroxy, or a group represented by the following formula:

[Chem. 14]

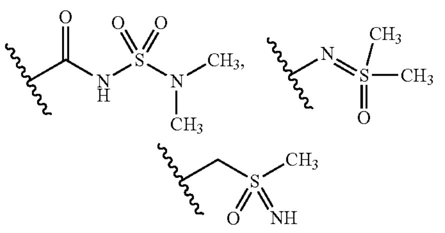

or wherein the aforementioned $C_{1-6}$ alkyl is unsubstituted or substituted by 1 or 2 groups selected from the group consisting of carboxy, hydroxy, and —O—$C_{1-6}$ alkyl, and n is an integer of 0 to 3, or a pharmaceutically acceptable salt thereof is provided.

In one embodiment of the present invention, A in the above-mentioned formula (1) is —O—, —S—, or —$CR^bR^c$—, preferably —O— or —$CR^bR^c$—, more preferably —O— or —$CF_2$—, particularly preferably —O—.

In one embodiment of the present invention, $R^a$ in the above-mentioned formula (1) is hydrogen or $C_{1-2}$ alkyl, preferably hydrogen or methyl, more preferably hydrogen.

In one embodiment of the present invention, $R^b$ and $R^c$ in the above-mentioned formula (1) are each independently hydrogen or halogen, preferably halogen, more preferably F.

In one embodiment of the present invention, each $R^1$ in the number of n in the above-mentioned formula (1) is independently halogen, —O—$C_{1-6}$ alkyl, —N(H)—$C_{1-3}$ alkyl, —N($C_{1-3}$ alkyl$)_2$ or 3- to 7-membered heterocycloalkyl (the aforementioned heterocycloalkyl has 1 or 2 nitrogen atoms as ring member atoms). In another embodiment of the present invention, each $R^1$ in the number of n in the above-mentioned formula (1) is independently halogen, —O—$C_{1-6}$ alkyl optionally substituted by 1 to 3 halogens, —N(H)—$C_{1-3}$ alkyl, —N($C_{1-3}$ alkyl$)_2$ or 4- to 6-membered heterocycloalkyl having one nitrogen atom as a ring member atom, preferably —O—$C_{1-6}$ alkyl optionally substituted by 1 to 3 halogens, —N($C_{1-3}$ alkyl$)_2$ or 4- to 6-membered heterocycloalkyl having one nitrogen atom as a ring member atom, more preferably —O—$C_{1-6}$ alkyl optionally substituted by 1 to 3 halogens, further preferably —O—$C_{1-3}$ alkyl, most preferably methoxy.

In one embodiment of the present invention, $R^2$ in the above-mentioned formula (1) is hydrogen or $C_{1-6}$ alkyl, preferably $C_{1-3}$ alkyl, more preferably methyl or ethyl, further preferably methyl.

In one embodiment of the present invention, $R^3$ in the above-mentioned formula (1) is hydrogen or $C_{1-6}$ alkyl, preferably $C_{1-3}$ alkyl, more preferably methyl or ethyl, further preferably methyl.

In one embodiment of the present invention, $R^4$ in the above-mentioned formula (1) is $C_{1-6}$ alkyl which is unsubstituted or substituted by $C_{3-7}$ cycloalkyl, —C(=O)—$C_{1-6}$ alkyl, or 6- to 12-membered heteroaryl (the aforementioned heteroaryl has 1 or 2 nitrogen atoms as ring member atoms). In another embodiment of the present invention, $R^4$ in the above-mentioned formula (1) is $C_{1-6}$ alkyl optionally substituted by 1 to 3 halogens, —C(=O)—$C_{1-6}$ alkyl optionally substituted by 1 to 3 halogens, $C_{3-6}$ cycloalkylmethyl optionally substituted by one trifluoromethyl, or 6-membered heteroaryl having 1 or 2 nitrogen atoms as ring member atoms (the heteroaryl is optionally substituted by one halogen), preferably $C_{1-6}$ alkyl optionally substituted by 1 to 3 halogens, —C(═O)—$C_{1-6}$ alkyl optionally substituted by 1 to 3 halogens, or 6-membered heteroaryl having 1 or 2 nitrogen atoms as ring member atoms (the heteroaryl is optionally substituted by one halogen), more preferably 3,3,3-trifluoro-2,2-dimethylpropyl, or —C(═O)—$C_{1-6}$ alkyl optionally substituted by 1 to 3 halogens, most preferably 3,3,3-trifluoro-2,2-dimethylpropyl.

In one embodiment of the present invention, ring $Q^1$ in the above-mentioned formula (1) is a $C_{6-12}$ monocyclic or bicyclic aromatic hydrocarbocycle, a 6- to 12-membered monocyclic or bicyclic aromatic heterocycle (the aromatic heterocycle has 1 or 2 nitrogen atoms as ring member atoms), a $C_{3-7}$ cycloalkane ring, or a $C_{3-7}$ cycloalkene ring. In another embodiment of the present invention, ring $Q^1$ in the above-mentioned formula (1) is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, preferably a benzene ring optionally having one substituent selected from the group consisting of halogen and $C_{1-3}$ alkyl, or a pyridine ring, more preferably a benzene ring optionally having one substituent selected from the group consisting of halogen and $C_{1-3}$ alkyl, particularly preferably a benzene ring.

In one embodiment of the present invention, $L^1$ in the above-mentioned formula (1) is preferably a single bond, —O—, $C_{1-3}$ alkylene-, or —C(═O)—, more preferably a single bond, —O—, —$CH_2$— or —C(═O)—, further preferably a single bond, —O—, or —C(═O)—, particularly preferably a single bond.

In one embodiment of the present invention, ring $Q^2$ in the above-mentioned formula (1) is a $C_{6-12}$ monocyclic or bicyclic aromatic hydrocarbocycle, a $C_{3-7}$ cycloalkane ring, a 3- to 7-membered heterocycloalkane ring (the aforementioned heterocycloalkane ring has 1 or 2 nitrogen atoms as ring member atoms), a $C_{3-7}$ cycloalkene ring, or a 5- to 12-membered spiroheterocycloalkane ring (the aforementioned spiroheterocycloalkane ring has 1 or 2 nitrogen atoms as ring member atoms). In another embodiment of the present invention, ring $Q^2$ in the above-mentioned formula (1) is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, preferably a benzene ring, a $C_{4-7}$ cycloalkane ring, or a $C_{4-7}$ cycloalkene ring, further preferably a $C_{4-7}$ cycloalkene ring.

In one embodiment of the present invention, $R^5$ in the above-mentioned formula (1) is preferably carboxy or $C_{1-6}$ alkyl optionally substituted by one or two groups selected from the group consisting of carboxy, hydroxy and —O—$C_{1-6}$ alkyl, more preferably carboxy or $C_{1-6}$ alkyl optionally substituted by one group selected from the group consisting of carboxy and hydroxy, further preferably $C_{1-6}$ alkyl optionally substituted by one group selected from the group consisting of carboxy and hydroxy.

In one embodiment of the present invention, a compound of the above-mentioned formula (1) or a pharmaceutically acceptable salt thereof, wherein A is —O—, $R^2$ is methyl, $R^3$ is methyl, $R^4$ is $C_{1-6}$ alkyl optionally substituted by 1 to 3 halogens, —C(═O)—$C_{1-6}$ alkyl optionally substituted by 1 to 3 halogens or 6-membered heteroaryl having 1 or 2 nitrogen atoms as ring member atoms (the heteroaryl is optionally substituted by one halogen), ring $Q^1$ is a benzene ring optionally having one substituent selected from the group consisting of halogen and $C_{1-3}$ alkyl or a pyridine ring, $L^1$ is a single bond, —O— or —C(═O)—, and ring $Q^2$ is a benzene ring, a $C_{4-7}$ cycloalkane ring, or a $C_{4-7}$ cycloalkene ring, is provided.

In another embodiment of the present invention, a compound of the above-mentioned formula (1), wherein $R^1$ is methoxy, and $R^4$ is 3,3,3-trifluoro-2,2-dimethylpropyl, or a pharmaceutically acceptable salt thereof is provided.

In another embodiment of the present invention, a compound represented by the formula (1) or a pharmaceutically acceptable salt thereof is a compound represented by the following formula (1') or a pharmaceutically acceptable salt thereof. Therefore, in one embodiment of the present invention, a compound of the following formula (1'):

[Chem. 15]

(1')

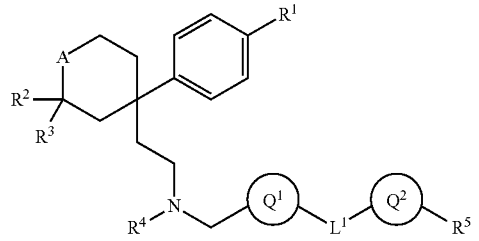

wherein

A is —O— or —$CF_2$—, $R^1$ is halogen, —O—$C_{1-6}$ alkyl optionally substituted by 1 to 3 halogens, —N(H)—$C_{1-3}$ alkyl, —N($C_{1-3}$ alkyl)$_2$ or 4- to 6-membered heterocycloalkyl having one nitrogen atom as a ring member atom, $R^2$ and $R^3$ are each independently hydrogen or $C_{1-6}$ alkyl, $R^4$ is $C_{1-6}$ alkyl optionally substituted by 1 to 3 halogens, —C(═O)—$C_{1-6}$ alkyl optionally substituted by 1 to 3 halogens, $C_{3-6}$ cycloalkylmethyl optionally substituted by one trifluoromethyl or 6-membered heteroaryl having 1 or 2 nitrogen atoms as ring member atoms (the heteroaryl is optionally substituted by one halogen), ring $Q^1$ is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, $L^1$ is a single bond, —O—, —$CH_2$—, or —C(═O)—, ring $Q^2$ is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, and $R^5$ is $C_{1-6}$ alkyl optionally having 1 or 2 groups selected from the group consisting of carboxy, hydroxy and —O—$C_{1-6}$ alkyl, carboxy, hydroxy, or a group represented by the following formula:

[Chem. 16]

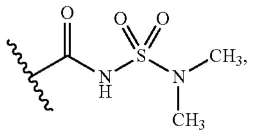

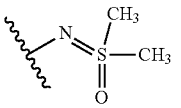

or

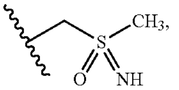

or a pharmaceutically acceptable salt thereof is provided.

Since the formula (1') corresponds to a lower concept of the formula (1), the definitions, explanations, preferred embodiments, and the like of each group in the formula (1) in the above all apply to each group in the formula (1'). Also, in the present specification, when "a compound represented by the formula (1)" is mentioned without any particular reservation, this means a concept also including "a compound represented by the formula (1')", in other words, "compounds represented by the formula (1) and the formula (1')".

In another embodiment of the present invention, a compound of the above-mentioned formula (1') or a pharmaceutically acceptable salt thereof, wherein A is —O—, $R^2$ is methyl, $R^3$ is methyl, $R^4$ is $C_{1-6}$ alkyl optionally substituted by 1 to 3 halogens, —C(═O)—$C_{1-6}$ alkyl optionally substituted by 1 to 3 halogens or 6-membered heteroaryl having 1 or 2 nitrogen atoms as ring member atoms (the heteroaryl is optionally substituted by one halogen), ring $Q^1$ is a benzene ring optionally having one substituent selected from the group consisting of halogen and $C_{1-3}$ alkyl or a pyridine ring, $L^1$ is a single bond, —O— or —C(═O)—, and ring $Q^2$ is a benzene ring, a $C_{4-7}$ cycloalkane ring, or a $C_{4-7}$ cycloalkene ring, is provided.

In yet another embodiment of the present invention, a compound of the above-mentioned formula (1') or a pharmaceutically acceptable salt thereof, wherein $R^1$ is methoxy, and $R^4$ is 3,3,3-trifluoro-2,2-dimethylpropyl, is provided.

In yet another embodiment of the present invention, any one compound selected from the following group:

trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexanecarboxylic acid, 2-[4-(4-{[{2-[(4R)-4-(4-methoxyphenyl)-2,2-dimethyltetrahydro-2H-pyran-4-yl]ethyl](3,3,3-trifluoro-2,2-dimethylpropyl)amino]methyl}phenoxy)phenyl]propanoic acid, {trans-4-[(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}pyridin-2-yl)oxy]cyclohexyl}acetic acid,

[trans-4-(4-{[{2-[(4R)-4-(4-methoxyphenyl)-2,2-dimethyltetrahydro-2H-pyran-4-yl]ethyl) (3,3,3-trifluoro-2,2-dimethylpropyl)amino]methyl}phenoxy)cyclohexyl]acetic acid, (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid,

[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methanol, and tert-butyl 4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazine-1-carboxylate, or a pharmaceutically acceptable salt thereof is provided. All of these compounds correspond to the compounds represented by the aforementioned formula (1) and the formula (1') or pharmaceutical acceptable salts thereof.

3. Polyfunctional Molecule

As described above, since the compound represented by the formula (1) or a pharmaceutically acceptable salt thereof of the present invention has SF-1 antagonist activity, it can be used as a partial structure in a larger molecule (e.g., polyfunctional molecule) by combining with other functional moieties. In particular, since the compound represented by the formula (1) or a pharmaceutically acceptable salt thereof of the present invention specifically binds to SF-1, it can also be used as an SF-1-binding moiety in a larger molecule (e.g., polyfunctional molecule) by combining with other functional moieties.

Therefore, in one embodiment of the present invention, a polyfunctional molecule containing the moiety corresponding to a compound represented by the above-mentioned formula (1) or a pharmaceutically acceptable salt thereof is provided.

Since a compound represented by the formula (1) itself is a complete structure, when linking to other partial structure, it is necessary to remove a specific atom or atomic group from any position in the compound. For example, when a carboxy group present at the end of the compound represented by the formula (1) is linked to an amino group in other partial structure by dehydration condensation, the "part corresponding to the compound represented by the formula (1)" in the molecule after linking is structurally different from the compound represented by the formula (1) in that the "—OH" part of the carboxy group has been removed. In the present specification, a compound represented by the formula (1) or a pharmaceutically acceptable salt thereof from which a specific atom or atomic group has been removed due to the linking reaction is referred to as a "moiety corresponding to a compound represented by the formula (1) or a pharmaceutically acceptable salt thereof".

The linking point when linking the compound represented by the formula (1) to other partial structure (e.g., E3 ligase-binding moiety or a linker portion for linking to the E3 ligase-binding moiety) is not particularly limited as long as it maintains the function of the compound represented by the formula (1), particularly SF-1 inhibitory activity and SF-1 binding activity, and preferably any position in $R^5$. Therefore, in one embodiment of the present invention, the polyfunctional molecule of the present invention has a moiety corresponding to a compound represented by the formula (1) or a pharmaceutically acceptable salt thereof linked directly to other functional moiety at any position in $R^5$ or linked via a linker. The any position in $R^5$ is preferably a carboxy moiety or an amine moiety in $R^5$.

In the present invention, "polyfunctional molecule" means a molecule that includes a moiety having two or more specific functions (functionalities). As described above, since the moiety corresponding to the compound represented by the formula (1) or a pharmaceutically acceptable salt thereof of the present invention has SF-1 antagonist activity and SF-1 binding activity, the polyfunctional molecule of the present invention includes at least one other functional moiety having a specific function. When one other functional moiety is involved, the polyfunctional molecule of the present invention is "a bifunctional molecule", and when 2, 3, or 4 other functional moieties are involved, the polyfunctional molecule of the present invention is a "trifunctional molecule", "tetrafunctional molecule", or "pentafunctional molecule", respectively. In one embodiment of the present invention, the polyfunctional molecule of the present invention is a bifunctional molecule, a trifunctional molecule, a tetrafunctional molecule, or a pentafunctional molecule, preferably a bifunctional molecule, a trifunctional molecule, or a tetrafunctional molecule, more preferably a bifunctional molecule or a trifunctional molecule, particularly preferably a bifunctional molecule. The other functional moiety may be a moiety having the same function as the moiety corresponding to the compound represented by the formula (1) or a pharmaceutically acceptable salt thereof, or may be a moiety having a different function. Therefore, in one embodiment of the present invention, the polyfunctional molecule is a homopolyfunctional molecule, and in another embodiment, the polyfunctional molecule is a heteropolyfunctional molecule. In one embodiment of the present invention, the polyfunctional molecule of the present invention is preferably a heterobifunctional molecule or a heterotrifunctional molecule, more preferably a heterobifunctional molecule.

The other functional moiety contained in the polyfunctional molecule of the present invention is not particularly limited, and is preferably one that is reasonably expected to have a beneficial effect when linked to a moiety having SF-1 inhibitory/binding activity, such as enhancing or complementing the activity thereof. Examples of such other functional moiety include, but are not limited to, an E3 ligase-binding moiety (or E3 ligase-recruiting moiety), an autophagy-recruiting moiety, a lysosome-recruiting moiety, a kinase-recruiting moiety, a phosphatase-recruiting moiety, a glycosyltransferase-recruiting moiety, acetyltransferase-recruiting moiety, ADC, and the like. In addition, such other functional moiety may be, for example, a substance that is useful exclusively in research applications, such as specific molecular markers and radioactive labels, or a functional substituent for making the compound of formula (1) into a prodrug.

In the present invention, "binding moiety" (e.g., "E3 ligase-binding moiety") means a moiety that binds to a target (e.g., "E3 ligase"), and "recruitment moiety" (e.g., "E3 ligase-recruiting moiety") means a moiety that allows for the recruitment of a target (e.g., "E3 ligase"). Since a moiety that binds to a target can be used to recruit the target, in one aspect of the present invention, "binding moiety" and "recruitment moiety" are used interchangeably.

4. E3 Ligase-Binding Moiety

In the present invention, "E3 ligase" (or "E3 ubiquitin ligase") means a protein that recruits a ubiquitin-loaded E2 ubiquitin-binding enzyme, recognizes a protein substrate, and assists or directly catalyzes the transfer of ubiquitin from the E2 protein to the substrate. A polyfunctional molecule in which a moiety corresponding to the compound represented by the formula (1) or a pharmaceutically acceptable salt thereof of the present invention is linked to an E3 ligase-binding moiety can induce degradation of SF-1. Therefore, in one embodiment of the present invention, a polyfunctional molecule containing a moiety corresponding to the compound represented by the formula (1) or a pharmaceutically acceptable salt thereof of the present invention, and other functional moiety, wherein the moiety corresponding to the aforementioned compound or a pharmaceutically acceptable salt thereof is linked directly to other functional moiety at any position in $R^5$ or linked via a linker, and said other functional moiety is an E3 ligase-binding moiety, is provided. Without intending to be bound by theory, it is believed that when a polyfunctional molecule in which a moiety corresponding to the compound represented by the formula (1) or a pharmaceutically acceptable salt thereof of the present invention is linked to an E3 ligase-binding moiety is administered to a living body, the polyfunctional molecule recruits both SF-1 and E3 ligase to form a ternary complex consisting of SF-1, E3 ligase, and the polyfunctional molecule, and places SF-1 and E3 ligase in close proximity to each other to ubiquitinate SF-1. Since ubiquitinated SF-1 is degraded by the endogenous proteasome system, the polyfunctional molecule of the present invention containing an E3 ligase-binding moiety is considered to be able to induce specific degradation of SF-1.

The technology of inducing degradation of a target protein using a heterobifunctional molecule in which a binder portion that binds to a target protein (also called a Protein of Interest (POI)) and a binder portion that binds to an E3 ligase are linked via an appropriate linker is collectively called Targeted Protein Degradation (TPD). Many reports have been published regarding this technology as to the type of E3 ligase to be targeted, various E3 ligase-binding moieties suitable for recruiting the E3 ligase, linker structures suitable for linking the POI and the E3 ligase-binding moiety, technical theories for designing such linker structures, and the like (e.g., Patent Literatures 1-9, Non Patent Literatures 7-9). The present invention reports for the first time that such TPD platform can target SF-1 and actually induce degradation, and in particular presents a novel POI-binding moiety in such a TPD platform.

In the TPD platform, the POI-binding moiety and the E3 ligase-binding moiety each play a nearly independent and separate role, and therefore, when each block (part) that has been proven to function is combined, there is a high probability that the desired effect will be obtained. Therefore, as the E3 ligase-binding moiety (or combination of ligase-binding moiety and linker portion) in the polyfunctional molecule of the present invention, any E3 ligase-binding moiety (or combination of ligase-binding moiety and linker portion) of any targeted protein degrader that has been confirmed to be useful, for example, the E3 ligase-binding moiety (or combination of ligase-binding moiety and linker portion) disclosed in Patent Literatures 1-9, Non Patent Literatures 7-9 can be applied. In addition, the E3 ligase-binding moiety (or combination of ligase-binding moiety and linker portion) in a heterobifunctional molecule such as ARV-471, ARV-110, CFT8634, CFT7455, CFT1946, ARV-766, AR-LDD, GT20029, NX-2127, HSK29116, BGB-16673, DT-2216, FHD-609, LNK01002, KT-474, KT-413, NX-5948, KT-333, CG001419, CFT8919 and the like, which has been reported to have been subjected to clinical trials or preclinical trials can also be applied. In other words, when a moiety corresponding to the compound represented by the formula (1) or a pharmaceutically acceptable salt thereof of the present invention is linked to an E3 ligase-binding moiety (or combination of ligase-binding moiety and linker portion) of any targeted protein degrader that has heretofore been confirmed to be useful, for example, E3 ligase-binding moieties (or combinations of ligase-binding moiety and linker portion) disclosed in Patent Literatures 1-8, Non Patent Literatures 7-9 and the like or the E3 ligase-binding moiety (or combination of ligase-binding moiety and linker portion) in a heterobifunctional molecule such as ARV-471, ARV-110, CFT8634, CFT7455, CFT1946, ARV-766, AR-LDD, GT20029, NX-2127, HSK29116, BGB-16673, DT-2216, FHD-609, LNK01002, KT-474, KT-413, NX-5948, KT-333, CG001419, CFT8919 and the like, it can be reasonably expected that a polyfunctional molecule (particularly heterobifunctional molecule) having the desired SF-1 degradation activity can be obtained, although the degree of activity may differ.

600 or more kinds of E3 ligases have been identified to date, but only a limited number have been used in TPD platforms. The E3 ligase targeted by the polyfunctional molecule of the present invention is not particularly limited. In one embodiment of the present invention, the E3 ligase targeted by the polyfunctional molecule of the present invention includes cereblon (CRBN), Von Hippel-Lindau (VHL), cellular inhibitor of apoptosis protein (cIAP), DDB1 and CUL4 associated factor 11 (DCAF11), DDB1 and CUL4 associated factor (DCAF15), DDB1 and CUL4 associated factor 16 (DCAF16), Mouse double minute 2 homolog (MDM2), Kelch-like ECH-associated protein 1 (KEAP1), RING finger protein 4 (RNF4), RING finger protein 114 (RNF114), Aryl hydrocarbon receptor (AhR), and Fem-1 homolog B (FEM1B), preferably CRBN, VHL, or cIAP, more preferably CRBN or VHL, further preferably CRBN. Therefore, in one embodiment of the present invention, the E3 ligase-binding moiety is CRBN-binding moiety, VHL-binding moiety, cIAP-binding moiety, DCAF11-binding moiety, DCAF15-binding moiety, DCAF16-binding moiety, MDM2-binding moiety, KEAP1-binding moiety, RNF4-binding moiety, RNF114-binding moiety, AhR-binding moiety, or FEM1B-binding moiety, preferably CRBN-binding moiety, VHL-binding moiety, or cIAP-binding moiety, more preferably CRBN-binding moiety or VHL-binding moiety, further preferably CRBN-binding moiety.

As the "CRBN-binding moiety" in the present invention, any compound moiety having any structure can be used without limitation as long as it exhibits the desired binding ability to CRBN. For example, the CRBN binding moieties disclosed in Patent Literatures 1-9 and Non Patent Literatures 7-9 can be exemplified. For example, thalidomide, and lenalidomide and pomalidomide which are derivatives thereof are known to exhibit binding ability to CRBN. Therefore, in one embodiment of the present invention, the CRBN-binding moiety is selected from thalidomide, lenalidomide, pomalidomide, thalidomide derivatives, lenalidomide derivatives, and pomalidomide derivatives. In the present invention, the "derivative" in the context of an E3 ligand-binding moiety means a molecule that has a structural difference from the parent molecule (E3 ligand-binding molecule), but maintains the intended binding activity to the target E3 ligase or has a higher binding activity to the target E3 ligase. As the targeted protein degrader containing a CRBN-binding moiety or proteolysis targeting chimera (PROTAC), compounds called ARV-471, ARV-110, CFT8634, CFT7455, CFT1946, AR-LDD, NX-2127, KT-413, NX-5948, CG001419, and CFT8919 have been subjected to clinical trials or preclinical trials. Therefore, in one embodiment of the present invention, the CRBN-binding moiety may be the CRBN-binding moiety in these compounds.

In one embodiment of the present invention, the E3 ligase-binding moiety (CRBN-binding moiety) in the present invention may be that referred to in Non Patent Literature 9.

In one embodiment of the present invention, the VHL-binding moiety includes VH032 (J. D. Sander and J. K. Joung, Nat. Biotechnol., 2014, 32, 347-355), VH101 (M. Toure and C. M. Crews, Angew. Chem., Int. Ed., 2016, 55, 1966-1973), VH298 (S. L. Schreiber, Cell, 2021, 184, 3-9), and derivatives of these.

In one embodiment of the present invention, the cIAP-binding moiety includes MeBS (J. A. Doudna and E. Charpentier, Science, 2014, 346, 1258096), MV1 (Y. Fedorov, et al., RNA, 2006, 12, 1188-1196), LCL161 (A. L. Jackson, et al., J. Burchard, M. Mao, B. Li, G. Cavet and P. S. Linsley, Nat. Biotechnol., 2003, 21, 635-637), and derivatives of these.

In one embodiment of the present invention, the DCAF11-binding moiety includes the ligands disclosed in S. Khan, X. et al., Nat. Med., 2019, 25, 1938-1947, and derivatives thereof.

In one embodiment of the present invention, the DCAF15-binding moiety includes E7820 (L. Snyder, American Association for Cancer Research Annual Meeting, April 2021) and a derivative thereof.

In one embodiment of the present invention, the DCAF16-binding moiety includes KB02 (G. Weng, et al., Nucleic Acids Res., 2021, 49, D1381-D1387) and a derivative thereof.

In one embodiment of the present invention, the MDM2-binding moiety includes Nutlin-3a (J. S. Lazo and E. R. Sharlow, Annu. Rev. Pharmacol. Toxicol., 2016, 56, 23-40), Idasanutlin (L. Jin, W. Wang and G. Fang, Annu. Rev. Pharmacol. Toxicol., 2014, 54, 435-456), and derivatives of these.

In one embodiment of the present invention, the KEAP1-binding moiety includes CDDO (R. G. Guenette, et al., Chem. Soc. Rev., 2022, 51, 5740-5756), the ligands disclosed in L. Snyder, American Association for Cancer Research Annual Meeting, April 2021, and derivatives of these.

In one embodiment of the present invention, the RNF4-binding moiety includes CCW-16 (I. Sosic, et al., Chem. Soc. Rev., 2022, 51, 3487-3534) and a derivative thereof.

In one embodiment of the present invention, the RNF114-binding moiety includes Nimbolide (M. Bekes, et al., Nat. Rev. Drug Discovery, 2022, 21, 181-200), EN219 (M. He, et al., Signal Transduction Targeted Ther., 2022, 7, 181), and derivatives of these.

In one embodiment of the present invention, the AhR-binding moiety includes beta-NF (K. Li and C. M. Crews, Chem. Soc. Rev., 2022, 51, 5214-5236), and a derivative thereof.

In one embodiment of the present invention, the FEM1B-binding moiety includes EN106 (M. He, et al., Front. Cell Dev. Biol., 2021, 9, 685106), and a derivative thereof.

As the E3 ligase-binding moiety in the present invention, any of the structures defined as "$R^6$" in a formula represented by the below-mentioned formula (2) may be adopted.

5. Linker

In the polyfunctional molecule of the present invention, the moiety corresponding to a compound represented by the formula (1) or a pharmaceutically acceptable salt thereof may be directly linked to other functional moiety as long as the desired function (e.g., SF-1 inhibitory activity or SF-1 degradation activity) is exhibited, but is preferably linked via a linker. Therefore, in one embodiment of the present invention, a polyfunctional molecule in which the moiety corresponding to a compound represented by the formula (1)

or a pharmaceutically acceptable salt thereof and other functional moiety (e.g., E3 ligase-binding moiety) are directly linked or linked via a linker, preferably linked via a linker, is provided. The linker used in the polyfunctional molecule of the present invention is not particularly limited as long as it does not impair the desired function (e.g., SF-1 inhibitory activity or SF-1 degradation activity). Therefore, any linker having a structure that is reasonably expected not to impair the desired function (e.g., SF-1 inhibitory activity or SF-1 degradation activity) can be used.

As described above, in the TPD platform, it is known that the composition and length of the linker can affect the formation of a ternary complex of POI/heterobifunctional molecule/E3 ligase, the degradation induction activity of POI, and the target selectivity. There have been many reports on linker structures used in targeted protein degraders and technical theories for designing and optimizing them (e.g., Patent Literatures 1-8, Non Patent Literatures 7-9). As described above, the present invention presents a novel POI-binding moiety that can be used in such TPD platform. Therefore, when a linker whose effectiveness has already been proven is adopted, there is a high probability that the desired effect will be obtained. Therefore, in one embodiment of the present invention, as the linker portion in the polyfunctional molecule of the present invention, any of the linker portions of targeted protein degraders that have been confirmed to be useful, for example, the linker portions disclosed in Patent Literatures 1-8, Non Patent Literatures 7-9 or the linker portions of ARV-471, ARV-110, CFT8634, ARV-766, AR-LDD, GT20029, NX-2127, HSK29116, BGB-16673, DT-2216, FHD-609, LNK01002, KT-474, KT-413, NX-5948, KT-333, CG001419, CFT7455, CFT1946, or CFT8919 that have been reported to have been subjected to clinical trials or preclinical trials can be applied. In one embodiment of the present invention, for example, the linker may be selected from the linker structures shown in Non Patent Literature 8, Table 2, specifically, those having any structural motif represented by the following formula:

[Chem. 17]

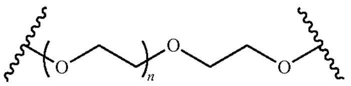

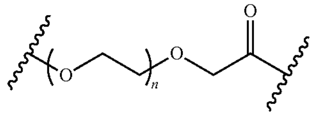

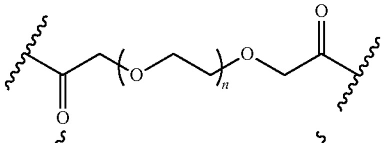

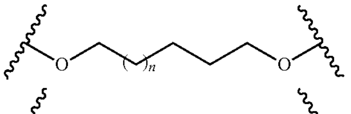

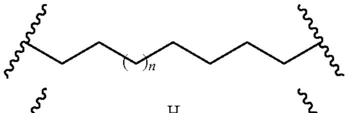

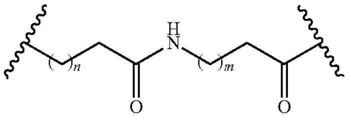

-continued

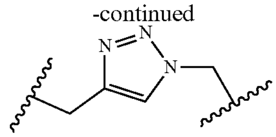

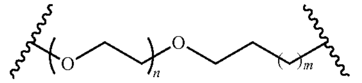

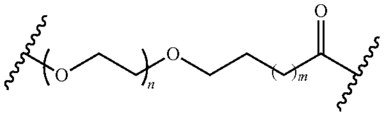

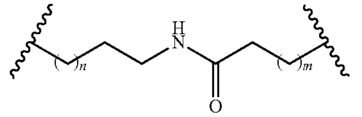

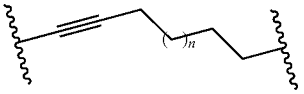

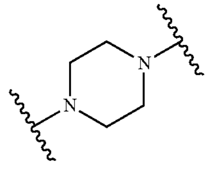

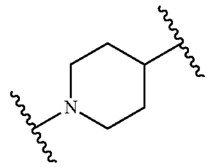

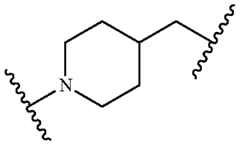

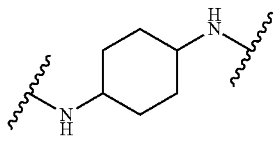

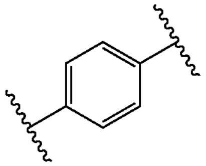

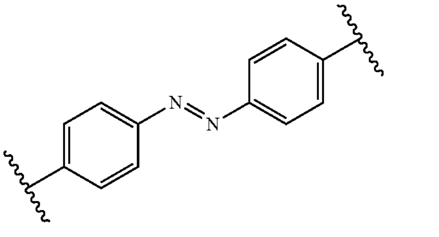

wherein n and m indicate each independently an integer of 1 to 10. Generally, it is known that use of a too short linker tends to decrease the efficiency of formation of a ternary complex (POI/heterobifunctional molecule/E3 ligase), and instead, increase the directivity of formation of a binary complex (POI/heterobifunctional molecule or heterobifunctional molecule/E3 ligase). On the other hand, it is known that use of a too long linker tends to increase the spatial degree of freedom, decrease the efficiency of formation of a ternary complex, and also decrease the stability of the entire molecule. Therefore, it is preferable to adopt a linker of an appropriate length in the present invention. From the above-mentioned aspects, in one embodiment of the present invention, n and m in the above-mentioned formula are each independently an integer of 1 to 5; in another embodiment of the present invention, n and m in the above-mentioned formula are each independently an integer of 1 to 4; in yet another embodiment of the present invention, n and m in the above-mentioned formula are each independently an integer of 1 to 3; in yet another embodiment of the present invention, n and m in the above-mentioned formula are each independently an integer of 1 or 2.

In the TPD platform, it is known that the binding position between the linker and the POI, or the linker and the E3 ligase can also affect the formation of a ternary complex of POI/heterobifunctional molecule/E3 ligase, the degradation induction activity of the POI, and the target selectivity. Regarding the binding position of the linker, it is generally considered to be essential that the linker is not linked to the main active site in the POI-binding moiety and E3 ligase-binding moiety, and that the linker is linked to a solvent-exposed site in the POI-binding moiety and E3 ligase-binding moiety. From such aspects, in the polyfunctional molecule of the present invention, the moiety corresponding to a compound represented by the formula (1) or a pharmaceutically acceptable salt thereof is preferably linked to the linker at any position in $R^5$, and is particularly preferably linked to the linker at the carboxy or amine moiety in $R^5$. Furthermore, the binding moiety of the linker and the E3 ligase-binding moiety is preferably selected as appropriate from the above-mentioned aspects, with reference to known reports.

In one embodiment of the present invention, the linker of the present invention may be "-$L^2$-$L^3$-$L^4$-" defined in the below-mentioned formula (2).

6. SF-1 Degrader

In one embodiment of the present invention, a compound represented by the following formula (2):

[Chem. 18]

(2)

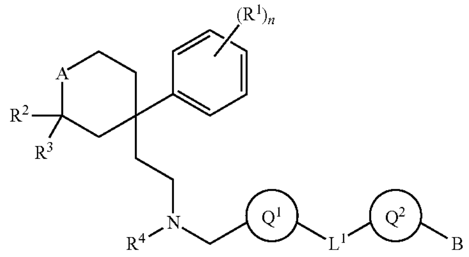

wherein

A is —O—, —S—, —$NR^a$— or —$CR^bR^c$—, wherein $R^a$ is hydrogen or $C_{1-3}$ alkyl, $R^b$ and $R^c$ are each independently hydrogen, halogen, or $C_{1-3}$ alkyl, and the aforementioned alkyl is unsubstituted or substituted by 1 to 3 halogens, each $R^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(═O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl, and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring and heterocycloalkene ring have 1 or 2 hetero atoms selected from oxygen, nitrogen, and sulfur as ring member atoms, $L^1$ is a single bond, —O—, —S—, —NH—, $C_{1-3}$ alkylene, $C_{2-3}$ alkenylene, —C(═O)—, —C(═O)NH—, —NHC(═O)—, —C(═O)O—, or —OC(═O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring have 1 or 2 hetero atoms selected from oxygen, nitrogen, and sulfur as ring member atoms, B is -$L^2$-$L^3$-$L^4$-$R^6$, $L^2$ is a single bond, $C_{1-6}$ alkylene, —C(═O)—, —C(═O)NH—, —$(CH_2)_k$—C(═O)NH— (k indicates an integer of 1 to 3), or —NHC(═O)—, $L^3$ is a single bond, $C_{1-6}$ alkylene, $C_{3-6}$ cycloalkylene, piperazinediyl, piperazin-2-onediyl, piperidinediyl, pyrrolidinediyl, azetidinediyl, or 3-oxa-9-azabicyclo[3.3.1]nonanediyl, $L^4$ is a single bond, —NH—, —N(—$R^7$)— ($R^7$ indicates $C_{1-6}$ alkyl), —$CH_2$—, or —C(═O)—, $R^6$ is an E3 ligase-binding moiety, an autophagy-recruiting moiety, a lysosome-recruiting moiety, a kinase-recruiting moiety, a phosphatase-recruiting moiety, a glycosyltransferase-recruiting moiety, an acetyltransferase-recruiting moiety, or ADC, and n is an integer of 0 to 3, or a pharmaceutically acceptable salt thereof is provided.

In one embodiment of the present invention, A in the above-mentioned formula (2) is —O—, —S—, or —$CR^bR^c$—, preferably —O— or —$CR^bR^c$—, more preferably —O— or —$CF_2$—, particularly preferably —O—.

In one embodiment of the present invention, $R^a$ in the above-mentioned formula (2) is hydrogen or $C_{12}$ alkyl, preferably hydrogen or methyl, more preferably hydrogen.

In one embodiment of the present invention, $R^b$ and $R^c$ in the above-mentioned formula (2) are each independently hydrogen or halogen, preferably halogen, more preferably F.

In one embodiment of the present invention, each $R^1$ in the number of n in the above-mentioned formula (2) is independently halogen, —O—$C_{1-6}$ alkyl, —N(H)—$C_{1-3}$ alkyl, —N($C_{1-3}$ alkyl)$_2$, or 3- to 7-membered heterocycloalkyl (the aforementioned heterocycloalkyl has 1 or 2 nitrogen atoms as ring member atoms). In another embodiment of the present invention, each $R^1$ in the number of n in the above-mentioned formula (1) is independently halogen, —O—$C_{1-6}$ alkyl optionally substituted by 1 to 3 halogens, —N(H)—$C_{1-3}$ alkyl, —N($C_{1-3}$ alkyl)$_2$ or 4- to 6-membered heterocycloalkyl having one nitrogen atom as a ring member atom, preferably —O—$C_{1-6}$ alkyl optionally substituted by 1 to 3 halogens, —N($C_{1-3}$ alkyl)$_2$ or 4- to 6-membered heterocycloalkyl having one nitrogen atom as a ring member atom, more preferably —O—$C_{1-6}$ alkyl optionally substituted by 1 to 3 halogens, further preferably —O—$C_{1-3}$ alkyl, most preferably methoxy.

In one embodiment of the present invention, $R^2$ in the above-mentioned formula (2) is hydrogen or $C_{1-6}$ alkyl, preferably $C_{1-3}$ alkyl, more preferably methyl or ethyl, further preferably methyl.

In one embodiment of the present invention, $R^3$ in the above-mentioned formula (2) is hydrogen or $C_{1-6}$ alkyl, preferably $C_{1-3}$ alkyl, more preferably methyl or ethyl, further preferably methyl.

In one embodiment of the present invention, each $R^4$ in the above-mentioned formula (2) is $C_{1-6}$ alkyl, —C(═O)—$C_{1-6}$ alkyl, or 6- to 12-membered heteroaryl (the aforementioned heteroaryl has 1 or 2 nitrogen atoms as ring member atoms), each of which is unsubstituted or substituted by $C_{3-7}$ cycloalkyl. In another embodiment of the present invention, $R^4$ in the above-mentioned formula (2) is $C_{1-6}$ alkyl optionally substituted by 1 to 3 halogens, —C(═O)—$C_{1-6}$ alkyl optionally substituted by 1 to 3 halogens, $C_{3-6}$ cycloalkylmethyl optionally substituted by one trifluoromethyl or 6-membered heteroaryl having 1 or 2 nitrogen atoms as ring member atoms (the heteroaryl is optionally substituted by one halogen), preferably $C_{1-6}$ alkyl optionally substituted by 1 to 3 halogens, —C(═O)—$C_{1-6}$ alkyl optionally substituted by 1 to 3 halogens or 6-membered heteroaryl having 1 or 2 nitrogen atoms as ring member atoms (the heteroaryl is optionally substituted by one halogen), more preferably 3,3,3-trifluoro-2,2-dimethylpropyl or —C(═O)—$C_{1-6}$ alkyl optionally substituted by 1 to 3 halogens, most preferably 3,3,3-trifluoro-2,2-dimethylpropyl.

In one embodiment of the present invention, ring $Q^1$ in the above-mentioned formula (2) is $C_{6-12}$ monocyclic or bicyclic aromatic hydrocarbocycle, a 6- to 12-membered monocyclic or bicyclic aromatic heterocycle (the aromatic heterocycle has 1 or 2 nitrogen atoms as ring member atoms), a $C_{3-7}$ cycloalkane ring, or a $C_{3-7}$ cycloalkene ring. In another embodiment of the present invention, ring $Q^1$ in the above-mentioned formula (1) is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, preferably a benzene ring optionally having one substituent selected from the group consisting of halogen and $C_{1-3}$ alkyl, or a pyridine ring, more preferably a benzene ring optionally having one substituent selected from the group consisting of halogen and $C_{1-3}$ alkyl, particularly preferably a benzene ring.

In one embodiment of the present invention, $L^1$ in the above-mentioned formula (2) is preferably a single bond, —O—, $C_{1-3}$ alkylene, or —C(═O)—, more preferably a single bond, —O—, —$CH_2$—, or —C(═O)—, further preferably a single bond, —O—, or —C(═O)—, particularly preferably a single bond.

In one embodiment of the present invention, ring $Q^2$ in the above-mentioned formula (2) is a $C_{6-12}$ monocyclic or bicyclic aromatic hydrocarbocycle, a $C_{3-7}$ cycloalkane ring, a 3- to 7-membered heterocycloalkane ring (the aforementioned heterocycloalkane ring has 1 or 2 nitrogen atoms as ring member atoms), a $C_{3-7}$ cycloalkene ring, or a 5- to 12-membered spiroheterocycloalkane ring (the aforementioned spiroheterocycloalkane ring has 1 or 2 nitrogen atoms as ring member atoms). In another embodiment of the present invention, ring $Q^2$ in the above-mentioned formula (1) is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, preferably a benzene ring, a $C_{4-7}$ cycloalkane ring, or a $C_{4-7}$ cycloalkene ring, further preferably a $C_{4-7}$ cycloalkene ring.

In one embodiment of the present invention, $L^2$ in the above-mentioned formula (2) is preferably $C_{1-6}$ alkylene, —C(═O)—, or —C(═O)NH—, more preferably $C_{1-6}$ alkylene or —C(═O)—, further preferably $C_{1-6}$ alkylene.

In one embodiment of the present invention, $L^3$ in the above-mentioned formula (2) is preferably piperazinediyl, piperazin-2-onediyl, piperidinediyl, pyrrolidinediyl, azetidinediyl, or 3-oxa-9-azabicyclo[3.3.1]nonanediyl, more preferably piperazinediyl, piperazin-2-onediyl, piperidinediyl, or 3-oxa-9-azabicyclo[3.3.1]nonanediyl, further preferably piperazinediyl or piperidinediyl, particularly preferably piperazinediyl.

In one embodiment of the present invention, $L^4$ in the above-mentioned formula (2) is preferably —NH—, —$CH_2$—, or —C(═O)—, more preferably —NH— or —C(═O)—, further preferably —C(═O)—.

In one embodiment of the present invention, "-$L^2$-$L^3$-$L^4$-" in the above-mentioned formula (2) indicates any structure selected from the groups represented by the following formulas:

[Chem. 19]

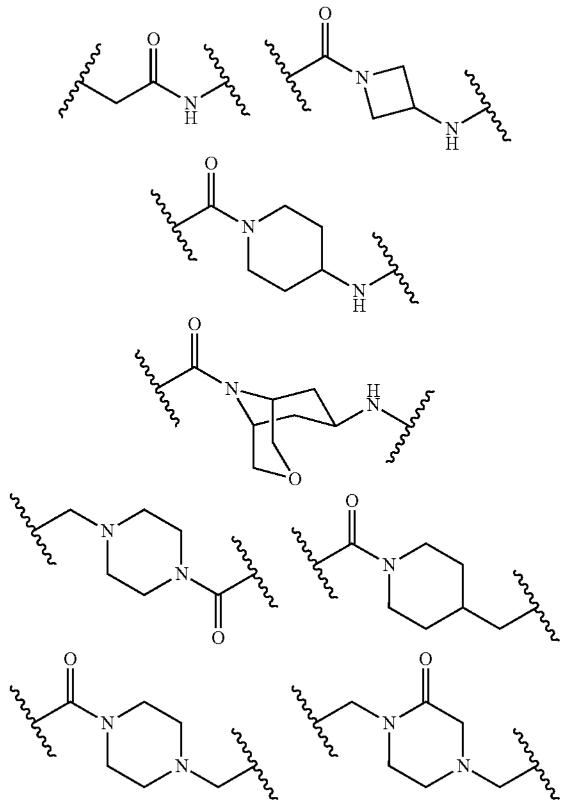

wherein a wavy line indicates the bonding position with $Q^2$ and $R^6$.

In one embodiment of the present invention, a compound of the above-mentioned formula (2), wherein A is —O—, $R^2$ is methyl, $R^3$ is methyl, $R^4$ is $C_{1-6}$ alkyl optionally substituted by 1 to 3 halogens, —C(═O)—$C_{1-6}$ alkyl optionally substituted by 1 to 3 halogens, or 6-membered heteroaryl having 1 or 2 nitrogen atoms as ring member atoms (the heteroaryl is optionally substituted by one halogen), ring $Q^1$ is a benzene ring optionally having one substituent selected from the group consisting of halogen and $C_{1-3}$ alkyl, or a pyridine ring, $L^1$ is a single bond, —O—, or —C(═O)—, and ring $Q^2$ is a benzene ring, a $C_{4-7}$ cycloalkane ring, or a $C_{4-7}$ cycloalkene ring, or a pharmaceutically acceptable salt thereof is provided.

In another embodiment of the present invention, a compound of the above-mentioned formula (2), wherein each $R^1$ in the number of n is methoxy, and $R^4$ is 3,3,3-trifluoro-2,2-dimethylpropyl, or a pharmaceutically acceptable salt thereof is provided.

In another embodiment of the present invention, a compound represented by the formula (2) or a pharmaceutically acceptable salt thereof is a compound represented by the following formula (2') or a pharmaceutically acceptable salt thereof. Therefore, in one embodiment of the present invention, a compound represented by the following formula (2'):

[Chem. 20]

(2')

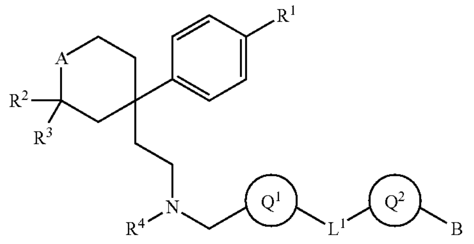

wherein

A is —O— or —$CF_2$—, $R^1$ is halogen, —O—$C_{1-6}$ alkyl optionally substituted by 1 to 3 halogens, —N(H)—$C_{1-3}$ alkyl, —N($C_{1-3}$ alkyl)$_2$ or 4- to 6-membered heterocycloalkyl having one nitrogen atom as a ring member atom, $R^2$ and $R^3$ are each independently hydrogen or $C_{1-6}$ alkyl, $R^4$ is $C_{1-6}$ alkyl optionally substituted by 1 to 3 halogens, —C(═O)—$C_{1-6}$ alkyl optionally substituted by 1 to 3 halogens, $C_{3-6}$ cycloalkylmethyl optionally substituted by one trifluoromethyl, or 6-membered heteroaryl having 1 or 2 nitrogen atoms as ring member atoms (the heteroaryl is optionally substituted by one halogen), ring $Q^1$ is a benzene ring optionally having 1 or 2 groups selected from the group consisting of halogen and $C_{1-3}$ alkyl, a 6- to 12-membered monocyclic or bicyclic aromatic heterocycle having 1 or 2 nitrogen atoms as ring member atoms, a $C_{4-7}$ cycloalkane ring, or a $C_{4-7}$ cycloalkene ring, $L^1$ is a single bond, —O—, —$CH_2$—, or —C(═O)—, ring $Q^2$ is a benzene ring optionally substituted by one halogen, a $C_{4-7}$ cycloalkane ring, a $C_{4-7}$ cycloalkene ring optionally substituted by one halogen, a piperidine ring, or a 7-azaspiro[3.5]nonane ring, B is -$L^2$-$L^3$-$L^4$-$R^6$, $L^2$ is a single bond, $C_{1-6}$ alkylene, —C(═O)—, —C(═O)NH—, —$(CH_2)_k$—C(═O)NH— (k indicates an integer of 1 to 3), or —NHC(═O)—, $L^3$ is a single bond, $C_{1-6}$ alkylene, $C_{3-6}$ cycloalkylene, piperazinediyl, piperazin-2-onediyl, piperidinediyl, pyrrolidinediyl, azetidinediyl, or 3-oxa-9-azabicyclo[3.3.1]nonanediyl, $L^4$ is a single bond, —NH—, —N(—$R^7$)— ($R^7$ indicates $C_{1-6}$ alkyl), —$CH_2$—, or —C(═O)—, and $R^6$ is an E3 ligase-binding moiety, an autophagy-recruiting moiety, a lysosome-recruiting moiety, a kinase-recruiting moiety, a phosphatase-recruiting moiety, a glycosyltransferase-recruiting moiety, an acetyltransferase-recruiting moiety, or ADC, or a pharmaceutically acceptable salt thereof is provided.

Since the formula (2') corresponds to a lower concept of the formula (2), the definitions, explanations, preferred embodiments, and the like of each group in the formula (2) in the above all apply to each group in the formula (2'). Also, in the present specification, when "a compound represented by the formula (2)" is mentioned without any particular reservation, this means a concept also including "a compound represented by the formula (2')", in other words, "compounds represented by the formula (2) and the formula (2')".

In one embodiment of the present invention, $R^6$ in the above-mentioned formula (2) and the formula (2') is an E3 ligase-binding moiety. In another embodiment of the present invention, $R^6$ in the above-mentioned formula (2) and the formula (2') is a CRBN-binding moiety. For the E3 ligase-binding moiety or CRBN-binding moiety that can be utilized as $R^6$, the same references as in the above-mentioned <3. E3 ligase-binding moiety> can be directly applied.

In another embodiment of the present invention, $R^6$ in the above-mentioned formula (2) and the formula (2') is any group selected from the following formulas:

[Chem. 21]

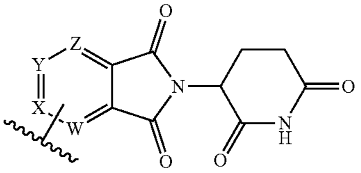

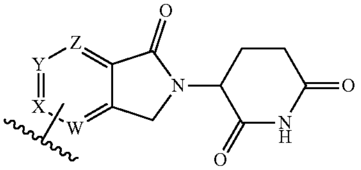

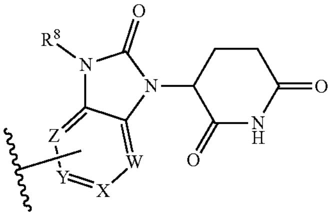

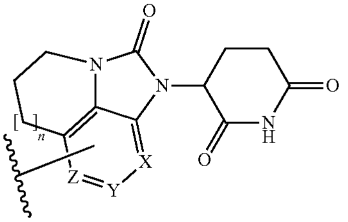

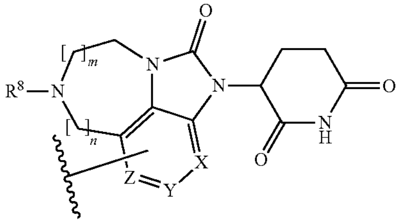

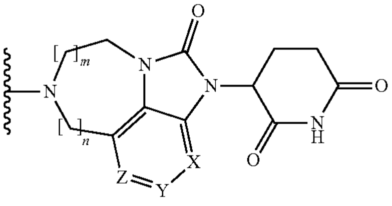

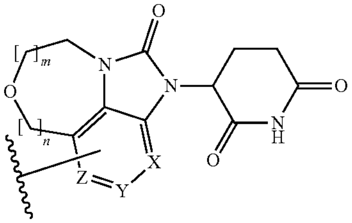

-continued

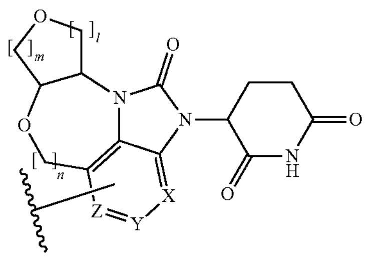

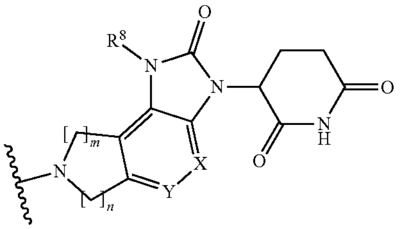

wherein $R^8$ is hydrogen or $C_{1-6}$ alkyl,

W, X, Y, and Z are each independently a nitrogen atom or a carbon atom optionally having one group selected from the group consisting of halogen, $C_{1-6}$ alkyl and $-O-C_{1-6}$ alkyl, l, m, and n indicate each independently an integer of 0 to 3, and a wavy line indicates the bonding position with $L^4$.

In yet another embodiment of the present invention, $R^6$ in the above-mentioned formula (2) and the formula (2') is any group selected from the following formulas:

[Chem. 22]

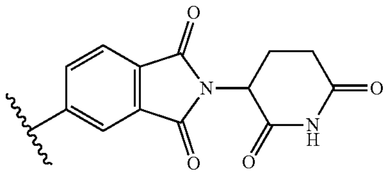

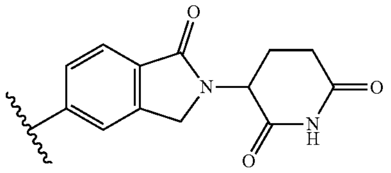

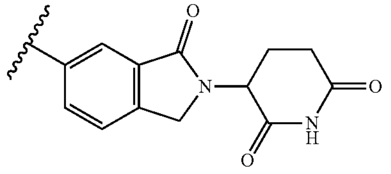

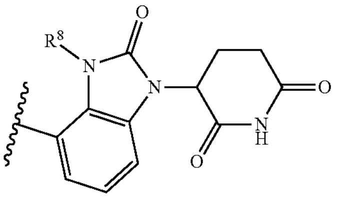

-continued
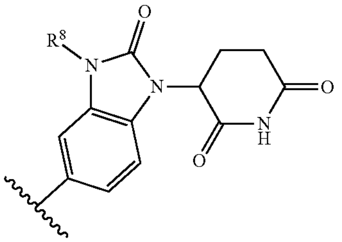
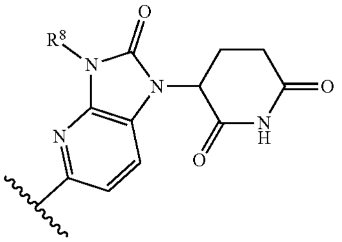
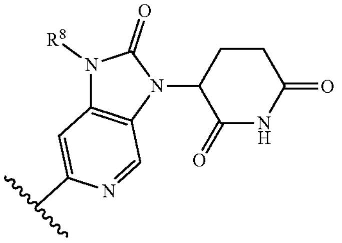
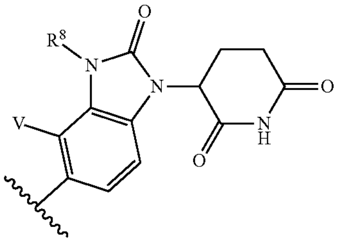
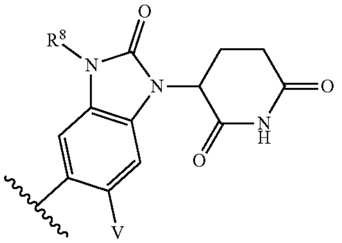
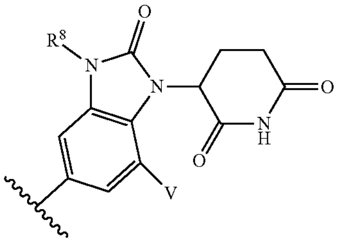
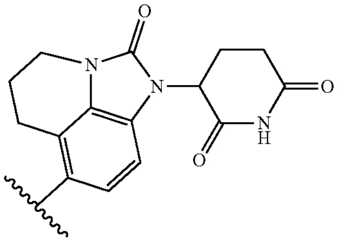
-continued
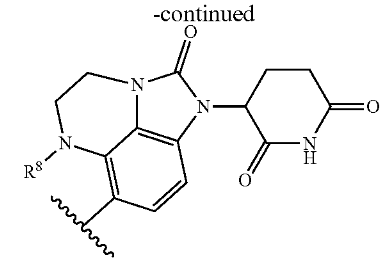
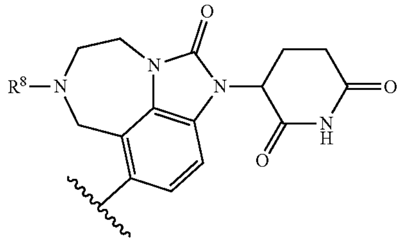
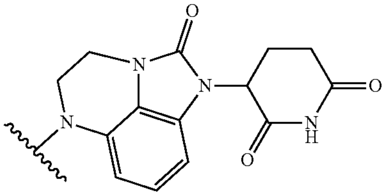
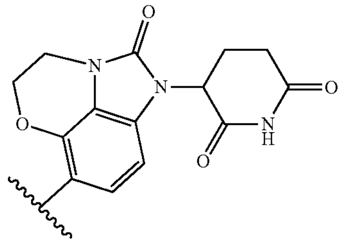
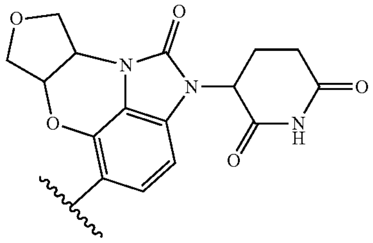
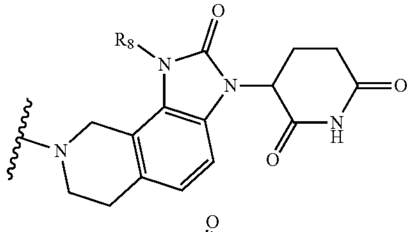
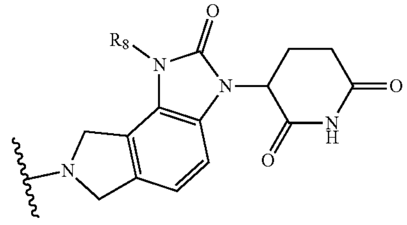
wherein
$R^8$ is hydrogen or $C_6$ alkyl,
V is halogen, and
a wavy line indicates the bonding position with $L^4$.

In one embodiment of the present invention, a compound of the above-mentioned formula (2) or the formula (2'), wherein $R^4$ is —O—$C_{1-6}$ alkyl optionally substituted by 1 to 3 halogens, $R^4$ is $C_{1-6}$ alkyl optionally substituted by 1 to 3 halogens, or $C_{3-6}$ cycloalkylmethyl optionally substituted by one trifluoromethyl, ring $Q^1$ is a benzene ring optionally having 1 or 2 groups selected from the group consisting of halogen and $C_{1-6}$ alkyl, a 9- to 10-membered bicyclic aromatic heterocycle having 1 or 2 nitrogen atoms as ring member atoms, a $C_{4-7}$ cycloalkane ring, or a $C_{4-7}$ cycloalkene ring, and $L^1$ is a single bond or —O—, or a pharmaceutically acceptable salt thereof is provided.

In one embodiment of the present invention, a compound of the above-mentioned formula (2) or the formula (2'), wherein A is —O—, $R^2$ is methyl, and $R^3$ is methyl, or a pharmaceutically acceptable salt thereof is provided.

In one embodiment of the present invention, a compound of the above-mentioned formula (2) or the formula (2'), wherein $R^1$ is methoxy, and $R^4$ is 3,3,3-trifluoro-2,2-dimethylpropyl, or a pharmaceutically acceptable salt thereof is provided.

In one embodiment of the present invention, a compound of the above-mentioned formula (2) or the formula (2'), wherein ring $Q^1$ is a benzene ring optionally having one halogen, $L^1$ is a single bond, and ring $Q^2$ is a cyclohexene ring, or a pharmaceutically acceptable salt thereof is provided.

In another embodiment of the present invention, any one compound selected from the following group:

3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, (3R)-3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, (3S)-3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione, 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione, (3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo(4,5,1-ij]quinolin-1(2H)-yl}piperidine-2,6-dione, (3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione, 3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, (3R)-3-{7-[(1-{[(4R)-2'-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, (3S)-3-{7-[(1-{[(4R)-2'-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione, 3-{7-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione, (3R)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione, and (3S)-3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione or a pharmaceutically acceptable salt thereof is provided. All of these compounds correspond to a compound represented by the aforementioned formula (2) or a pharmaceutically acceptable salt thereof.

In another embodiment of the present invention, a compound represented by the formula (2) or a pharmaceutically acceptable salt thereof may be a crystal thereof. Therefore, in one embodiment of the present invention, a crystal of a compound represented by the formula (2) or a pharmaceutically acceptable salt thereof is provided. The crystal can be produced by a method known per se, or the method described in the below-mentioned Example, or a method analogous thereto.

The powder X-ray diffraction measurement of crystals may be performed by a method generally used in the pertinent field, for example, by the method described in the below-mentioned Examples. Generally, the diffraction angle (2θ) in powder X-ray diffraction may vary within a range of about ±0.2° 2θ. For example, the lattice constant of a hydrate or dehydrate may change due to the attachment and detachment of water of crystallization, which may cause a change in the diffraction angle (2θ) in powder X-ray diffraction. The intensity of the diffraction peak may vary depending on the difference in the crystal growth plane (crystal habit), and the like. Therefore, when the crystal of the present invention is expressed based on the data of powder X-ray diffraction, crystals having the same diffraction angles of peaks and X-ray diffraction patterns in powder X-ray diffraction, as well as hydrates and dehydrates obtained therefrom are included in the scope of the present invention.

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate, the crystal having peaks at diffraction angles (2θ) of 2.15±0.2, 8.30±0.2, 10.29±0.2, 14.75±0.2, 17.19±0.2, 20.00±0.2, 21.34±0.2, 22.68±0.2, 23.77±0.2, and 25.23±0.2 in a powder X-ray diffraction pattern obtained by irradiation with copper Kα ray (λ=1.54 angstroms).

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate, the crystal having peaks at diffraction angles (2θ) of 2.21±0.2, 12.04±0.2, 14.87±0.2, 17.69±0.2, 18.93±0.2, 20.41±0.2, 22.42±0.2, 23.19±0.2, 24.13±0.2, and 27.98±0.2 in a powder X-ray diffraction pattern obtained by irradiation with copper Kα ray (λ=1.54 angstroms).

In one embodiment of the present invention, the crystal is a crystal of (3RS)-3-[7-({1-[(4R)-2'-fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate, the crystal having peaks at diffraction angles (2θ) of 3.89±0.2, 6.81±0.2, 7.68±0.2, 8.20±0.2, 10.28±0.2, 13.15±0.2, 15.97±0.2, 16.81±0.2, 18.58±0.2, and 23.56±0.2 in a powder X-ray diffraction pattern obtained by irradiation with copper Kα ray (λ=1.54 angstroms).

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione ethanesulfonate, the crystal having peaks at diffraction angles (29) of 2.27±0.2, 8.18±0.2, 9.88±0.2, 13.09±0.2, 14.57±0.2, 15.80±0.2, 16.91±0.2, 17.77±0.2, 18.87±0.2, and 20.14±0.2 in a powder X-ray diffraction pattern obtained by irradiation with copper Kα ray (λ=1.54 angstroms).

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione salicylate, the crystal having peaks at diffraction angles (2θ) of 2.20±0.2, 4.34±0.2, 9.45±0.2, 10.97±0.2, 13.23±0.2, 16.98±0.2, 18.09±0.2, 20.20±0.2, 21.32±0.2, and 25.19±0.2 in a powder X-ray diffraction pattern obtained by irradiation with copper Kα ray (λ=1.54 angstroms).

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione benzenesulfonate, the crystal having peaks at diffraction angles (2θ) of 2.19±0.2, 8.87±0.2, 10.86±0.2, 12.55±0.2, 13.05±0.2, 14.99±0.2, 17.84±0.2, 20.62±0.2, 21.43±0.2, and 25.27±0.2 in a powder X-ray diffraction pattern obtained by irradiation with copper Kα ray (λ=1.54 angstroms).

In one embodiment of the present invention, the crystal is a crystal of (3RS)-3-[7-(4-{[(4R)-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate, the crystal having peaks at diffraction angles (2θ) of 2.20±0.2, 7.82±0.2, 11.05±0.2, 12.42±0.2, 13.34±0.2, 15.23±0.2, 16.49±0.2, 17.86±0.2, 20.15±0.2, and 24.36±0.2 in a powder X-ray diffraction pattern obtained by irradiation with copper Kα ray (λ=1.54 angstroms).

7. Salt, Isomer, Prodrug and the Like

The "pharmaceutically acceptable salt" in the present invention means a salt that can be used as a medicament. When the compound or polyfunctional molecule of the present invention has an acidic group, it can be reacted with a base to form a basic salt (also referred to as a "base addition salt"), and when it has a basic group, it can be reacted with an acid to form an acidic salt (also referred to as an "acid addition salt"). Therefore, in one embodiment of the present invention, a pharmaceutically acceptable salt of a compound represented by the formula (1) or a compound represented by the formula (2) is a basic salt, and in another embodiment of the present invention, a pharmaceutically acceptable salt of a compound represented by the formula (1) or a compound represented by the formula (2) is an acidic salt.

Preferred examples of the "basic salt" in the present invention include alkali metal salts such as sodium salt, potassium salt, and lithium salt; alkaline earth metal salts such as magnesium salt and calcium salt; organic base salts such as N-methylmorpholine salt, triethylamine salt, tributylamine salt, diisopropylethylamine salt, dicyclohexylamine salt, N-methylpiperidine salt, pyridine salt, 4-pyrrolidinopyridine salt, and picoline salt; and amino acid salts such as glycine salt, lysine salt, arginine salt, ornithine salt, glutamic acid salt, and aspartic acid salt.

Preferred examples of the "acidic salt" in the present invention include inorganic acid salts such as hydrohalide (e.g., hydrofluoride, hydrochloride, hydrobromide, hydroiodide), nitrate, perchlorate, sulfate, and phosphate; lower alkanesulfonate (e.g., methanesulfonate, trifluoromethanesulfonate, ethanesulfonate), arylsulfonate (e.g., benzenesulfonate, p-toluenesulfonate), organic acid salts such as acetate, malate, fumarate, succinate, citrate, ascorbate, tartrate, oxalate, and maleate; and amino acid salts such as glycinate, lysinate, argininate, ornithinate, glutamate, and aspartate.

The compound or a pharmaceutically acceptable salt thereof of the present invention may become a hydrate by incorporating water molecules when left in the air or when recrystallized, and such hydrates are also included in the present invention. The compound or a pharmaceutically acceptable salt thereof of the present invention may absorb a certain type of solvent when left in a solvent or recrystallized, and become a solvate, and such solvates are also included in the present invention. Furthermore, the compound of the present invention or a pharmaceutically acceptable salt thereof can also exist in amorphous or crystalline form.

The compound or a pharmaceutically acceptable salt thereof of the present invention may be labeled with pharmaceutically acceptable one or more radioactive or non-radioactive isotopes. Examples of the isotopes that can be incorporated into the compound of the present invention or a pharmaceutically acceptable salt thereof include, but are not limited to, isotopes of hydrogen, carbon, nitrogen, oxygen, and fluorine, for example, $^{2}H$, $^{3}H$, $^{11}C$, $^{13}C$, $^{14}C$, $^{13}N$, $^{15}N$, $^{15}O$, $^{17}O$, $^{18}O$, and $^{18}F$, respectively. The radioactive or non-radioactive labeled compound can be useful to help determine or measure the effectiveness of the compound of the present invention, for example, by characterizing the site of action or mode of action, or binding affinity to a pharmacologically important site of action. Such isotopically labeled compounds can generally be prepared by conventional techniques known to those skilled in the art.

In the compound, pharmaceutically acceptable salt thereof or solvate thereof of the present invention, various isomers such as geometric isomers such as cis-forms and trans-forms, tautomers, rotamers, optical isomers such as d-form and l-form (including enantiomers and diastereomers) and the like can be present depending on the type and combination of substituents. The compound of the present invention includes all of these isomers and stereoisomers, and mixtures of these isomers and stereoisomers in any ratio, unless otherwise specified.

The present invention also includes prodrugs of the compounds represented by the formula (1) or the formula (2). A prodrug is a compound having a group that can be converted to an amino group, a hydroxy group, a carboxy group, or the like of a compound by hydrolysis or under physiological conditions. Examples of groups that form such prodrugs include the groups described in Prog. Med., Vol. 5, pp. 2157-2161, 1985, and the like. More specifically, examples of the prodrug include:

(1) compounds in which, when an amino group is present in the compound, the amino group is acylated, alkylated, or phosphorylated (e.g., compounds in which the amino group is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated, or tert-butylated, etc.), (2) compounds in which, when a hydroxy group is present in the compound, the hydroxy group is acylated, alkylated, phosphorylated, or borated (e.g., compounds in which the hydroxy group is acetylated, palmitoylated, propanoylated, pivaloylated, succinylated, fumarylated, alanylated, or dimethylaminomethylcarbonylated, etc.), (3) compounds in which, when a carboxy group is present in the compound, the carboxy group is esterified or amidated (e.g., compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated, etc.), and the like.

8. Composition and Pharmaceutical Use

In one embodiment of the present invention, a composition for inhibiting SF-1, a composition for inducing degradation of SF-1, or a pharmaceutical composition containing a compound represented by the aforementioned formula (1) or a pharmaceutically acceptable salt thereof, a polyfunctional molecule containing the moiety corresponding to the compound or a pharmaceutically acceptable salt thereof, or a compound represented by the aforementioned formula (2) or a pharmaceutically acceptable salt thereof, or a crystal thereof is provided. In another embodiment of the present invention, a method for treating a disease, including administering an effective amount of a compound represented by the aforementioned formula (1) or a pharmaceutically acceptable salt thereof, a polyfunctional molecule containing the moiety corresponding to the compound or a pharmaceutically acceptable salt thereof, or a compound represented by the aforementioned formula (2) or a pharmaceutically acceptable salt thereof, or a crystal thereof to a subject in need of a treatment of the disease is provided. In a yet another embodiment of the present invention, a compound represented by the aforementioned formula (1) or a pharmaceutically acceptable salt thereof, a polyfunctional molecule containing the moiety corresponding to the compound or a pharmaceutically acceptable salt thereof, or a compound represented by the aforementioned formula (2) or a pharmaceutically acceptable salt thereof, or a crystal thereof for use in the treatment of a disease is provided. In addition, in yet another embodiment of the present invention, a compound represented by the aforementioned formula (1) or a pharmaceutically acceptable salt thereof, a polyfunctional molecule containing the moiety corresponding to the compound or a pharmaceutically acceptable salt thereof, or a compound represented by the aforementioned formula (2) or a pharmaceutically acceptable salt thereof, or a crystal thereof for use in the production of a medicament for the treatment of a disease is provided.

In the present invention, the "composition for inhibiting SF-1" refers to a composition intended to inhibit SF-1. Inhibition of SF-1 typically means inhibiting the physiological activity of SF-1, particularly blocking or attenuating the expression of a gene transcriptionaily controlled by SF-1. The embodiment of inhibiting SF-1 includes an embodiment in which the transcription induction activity of downstream genes by SF-1 is blocked or attenuated by binding directly to SF-1, but also includes an embodiment in which the physiological activity of SF-1 is consequently blocked or attenuated by acting on a protein upstream of SF-1 without directly binding to SF-1. The "composition for inhibiting SF-1" includes not only a composition intended solely for the inhibition of SF-1, but also one having the inhibition of SF-1 as one of its purposes. The "composition for inhibiting SF-1" typically includes a composition indicating inhibition of SF-1 as one of its intended uses in the package insert, package, promotional materials, etc., but also includes a composition that substantially includes inhibition of SF-1 as one of its intended uses even if there is no such explicit indication.

In the present invention, "composition for inducing degradation of SF-1" means a composition intended to induce degradation of SF-1. The "composition for inducing degradation of SF-1" includes not only a composition intended solely for inducing the degradation of SF-1, but also one having induction of the degradation of SF-1 as one of its purposes. The "composition for inducing degradation of SF-1" typically includes a composition indicating induction of the degradation of SF-1 as one of its intended uses in the package insert, package, promotional materials, etc., but also includes a composition that substantially includes induction of the degradation of SF-1 as one of its intended uses even if there is no such explicit indication.

In the present invention, the "pharmaceutical composition" means a composition used for the treatment/prevention of any disease. Since the compound or polyfunctional molecule of the present invention has SF-1 antagonist activity, it can be used as a composition for the treatment and/or prevention of a disease in which SF-1 is involved in the development or progression. Such diseases include, but are not limited to, cancer such as castration-resistant prostate cancer, adrenocortical carcinoma, Leydig cell tumor, hormone-sensitive prostate cancer, breast cancer and the like, Cushing's syndrome, and primary aldosteronism. Thus, in one embodiment of the present invention, the pharmaceutical composition of the present invention is for treating cancer such as castration-resistant prostate cancer, adrenocortical carcinoma, Leydig cell tumor, hormone-sensitive prostate cancer, breast cancer and the like, Cushing's syndrome or primary aldosteronism. In a further embodiment of the present invention, the pharmaceutical composition of the present invention is for treating castration-resistant prostate cancer or adrenocortical carcinoma, in another embodiment of the present invention, the pharmaceutical composition of the present invention is for treating castration-resistant prostate cancer, and in yet another embodiment of the present invention, the pharmaceutical composition of the present invention is for treating adrenocortical carcinoma.

The route of administration of such compositions to humans or other animals may be oral administration using tablet, pill, capsule, granule, powder, liquid, and the like, or parenteral administration using intra-articular, intravenous, or intramuscular injection, etc., suppository, eye drop, eye ointment, transdermal liquid, ointment, transdermal adhesive preparation, transmucosal liquid, transmucosal adhesive preparation, inhalant, and the like. Considering that the molecular weight of the compound or polyfunctional molecule of the present invention is not extremely large, oral administration is preferred from the viewpoint of reducing the burden of taking drugs.

Solid composition for oral administration includes tablet, powder, granule, and the like. Such solid composition contains at least one inactive excipient, such as lactose, mannitol, glucose, hydroxypropylcellulose, microcrystalline cellulose, starch, polyvinylpyrrolidone, magnesium aluminometasilicate, etc., in addition to the compound or polyfunctional molecule of the present invention. Such solid composition may contain inactive additives, such as lubricants such as magnesium stearate, disintegrants such as sodium carboxymethyl starch, stabilizer, solubilizing agent, and the like, according to conventional methods. Tablets or pills may be coated with sugar coatings or films of gastric or enteric soluble substances, as necessary.

Liquid compositions for oral administration include pharmaceutically acceptable emulsion, solution, suspension, syrup, elixir, and the like. To such liquid compositions, it is possible to add generally used inert diluents, such as purified water or ethanol. In addition to the inert diluents, such liquid compositions may contain auxiliary agents such as solubilizer and wetting agent, sweetener, flavoring, fragrance, preservative, and the like.

Examples of the injections for parenteral administration includes sterile aqueous or non-aqueous solution, suspension, emulsion, and the like. Aqueous solvents include, for example, distilled water for injection, physiological saline, and the like. Non-aqueous solvents include, for example, propylene glycol, polyethylene glycol, vegetable oils such as olive oil, alcohols such as ethanol, polysorbate 80, and the like. Such injection compositions may further contain isotonic agent, preservative, wetting agent, emulsifier, dispersant, stabilizer, solubilizing agent, and the like. These injection compositions may be sterilized, for example, by filtration through a bacteria-retaining filter, by blending with a 1 bactericide, or by irradiation. In addition, these injection compositions may be prepared as sterile solid compositions, which may be dissolved or suspended in sterile water or a sterile solvent for injection before use.

Examples of the external preparation include ointment, plaster, cream, jelly, cataplasm, spray, lotion, eye drop, eye ointment and the like. These external preparations may contain generally used ointment base, lotion base, aqueous or non-aqueous liquid, suspension, emulsion and the like. For example, ointment or lotion base includes polyethylene glycol, propylene glycol, white petrolatum, white beeswax, polyoxyethylene hydrogenated castor oil, glycerin monostearate, stearyl alcohol, cetyl alcohol, lauromacrogol, sorbitan sesquioleate, and the like.

Transmucosal agents such as inhalants and nasal agents may be solid, liquid, or semisolid, and can be produced according to a conventional known method. For example, known excipients and further pH adjusters, preservatives, surfactants, lubricants, stabilizers, thickeners, and the like may be appropriately added. For these transmucosal agents, a suitable device for inhalation or insufflation may be used as a method of administration. For example, the compound or polyfunctional molecule can be administered as a powder, either alone or in a formulated mixture powder, or in a solution or suspension in combination with a pharmaceutically acceptable carrier, using known devices and nebulizers, such as metered dose inhalation device and the like. Dry powder inhalers and the like may be for single or multiple dose administration, and dry powder or powder-containing capsule can be used. Alternatively, a suitable propellant can also be used. The compositions may be in the form of a pressurized aerosol spray using, for example, a suitable gas such as chlorofluoroalkane, hydrofluoroalkane, carbon dioxide, or the like.

The composition of the present invention may contain other active ingredients, or may be used in combination with another composition containing other active ingredients. The combined use may be simultaneous administration, or separate consecutive administration or administration at a desired time interval. The simultaneous administration preparation may be a combination drug or separate formulations.

The amount of the compound or polyfunctional molecule of the present invention loaded into a composition or the amount administered to a subject is not particularly limited as long as it is an amount effective for achieving the purpose, and can be appropriately selected depending on the purpose of use, and the age, weight, symptoms, health condition, disease progression and the like of the subject. The frequency of administration is not particularly limited, and it can be appropriately selected depending on the purpose. For example, the daily dosage may be administered once a day or may be administered in multiple doses.

In the present invention, the "effective amount" or "therapeutically effective amount" means an amount effective for treating, preventing the progression of, or alleviating existing symptoms in the subject being treated. The effective amount can be appropriately determined according to conventional methods, taking into account the desired therapeutic effect and side effects.

9. Combined Use

The compound or pharmacologically acceptable salt thereof, polyfunctional molecule, composition for inhibiting SF-1, composition for inducing degradation of SF-1, or pharmaceutical composition of the present invention can be used in combination with other antitumor agents. Examples of other antitumor agents include alkylating agents, antimetabolites, antitumor antibiotics, microtubule inhibitors, topoisomerase inhibitors, BRMs (biological response modifiers), hormonal agents, vitamins, antitumor antibodies, molecular target drugs, other antitumor agents and the like.

More specifically, examples of the alkylating agents include alkylating agents such as nitrogen mustard, nitrogen mustard-N-oxide, chlorambucil and the like; aziridine-based alkylating agents such as carboquone, thiotepa and the like; epoxide-based alkylating agents such as dibromomannitol, dibromodulcitol and the like; nitrosourea-based alkylating agents such as carmustine, lomustine, semustine, nimustine hydrochloride, streptozocin, chlorozotocin, ranimustine and the like; busulfan; improsulfan tosylate; dacarbazine and the like.

Examples of various antimetabolites include purine antimetabolites such as 6-mercaptopurine, 6-thioguanine, thioinosine, and the like; pyrimidine antimetabolites such as fluorouracil, tegafur, tegafur-uracil, carmofur, doxifluridine, broxuridine, cytarabine, enocitabine, capecitabine and the like; folic acid antimetabolites such as methotrexate, trimetrexate, pemetrexed and the like; activated folic acid agents such as levofolinate; and the like.

Examples of the antitumor antibiotics include anthracycline antibiotic antitumor agents such as daunorubicin, aclarbicin, doxorubicin, pirarubicin, THP-adriamycin, 4'-epidoxorubicin, epirubicin, amrubicin and the like; mitomycin C; bleomycin; peplomycin; chromomycin A3, actinomycin D and the like.

Examples of the microtubule inhibitors include *vinca* alkaloids such as vindesine, vincristine, vinblastine, vinorelbine, and the like; taxanes such as paclitaxel, docetaxel, cabazitaxel, and the like; eribulin, and the like.

Examples of the topoisomerase inhibitors include epipodophyllotoxins such as etoposide, teniposide and the like; camptothecin derivatives such as irinotecan and the like, and the like.

Examples of the BRMs include tumor necrosis factor, indomethacin and the like.

Examples of the hormonal agents include hydrocortisone, cortisone acetate, fludrocortisone, fludrocortisone acetate, dexamethasone, methylprednisolone, prednisolone, prasterone, betamethasone, triamcinolone, oxymetholone, nandrolone, methenolone, fosfestrol, ethinylestradiol, chlormadinone, glucocorticoids, medroxyprogesterone, bicalutamide, enzalutamide, apalutamide, darolutamide, flutamide, anastrozole, exemestane, letrozole, abiraterone, goserelin, leuprorelin, toremifene, degarelix, mitotane, tamoxifen, and the like.

Examples of the vitamin include vitamin C, vitamin A and the like.

Examples of the antitumor antibodies, molecular target drugs include antitumor antibodies such as trastuzumab, rituximab, cetuximab, pertuzumab, nimotuzumab, pembrolizumab, camrelizumab, denosumab, bevacizumab, infliximab, ramucirumab and the like (including their modified forms); kinase inhibitors such as imatinib, gefitinib, erlotinib, sunitinib, lapatinib, eganelisib, sorafenib, dasatinib, nilotinib, vemurafenib, osimertinib, apatinib, cabozantinib and the like; PARP inhibitors such as olaparib, rucaparib, velparib, niraparib and the like; and molecular target drugs such as OR-449 and the like.

Examples of other antitumor agents include platinum compounds such as cisplatin, carboplatin, oxaliplatin and the like, ifosfamide, cyclophosphamide, melphalan, L-asparaginase, aceglatone, sizofiran, picibanil, procarbazine, pipobroman, neocarzinostatin, hydroxyurea, ubenimex, krestin, and the like.

The compound of or a pharmaceutically acceptable salt thereof, polyfunctional molecule, composition for inhibiting SF-1, composition for inducing degradation of SF-1, or pharmaceutical composition of the present invention may be used in combination with an antibody-drug conjugate (ADC) containing the above-mentioned other antitumor agent as a payload, or a targeted protein degrader having the above-mentioned other antitumor agent as a POI ligand.

The compound of or a pharmaceutically acceptable salt thereof, polyfunctional molecule, composition for inhibiting SF-1, composition for inducing degradation of SF-1, or pharmaceutical composition of the present invention may be administered simultaneously or separately at the same time or at different times with the above-mentioned drugs to be used in combination, and may be prepared as a combination drug or a kit formulation.

In the treatment of adrenocortical carcinoma, antitumor agents that are preferably used in combination with the compound of or a pharmaceutically acceptable salt thereof, polyfunctional molecule, composition for inhibiting SF-1, composition for inducing degradation of SF-1, or pharmaceutical composition of the present invention include, for example, one or more selected from anthracycline compounds such as doxorubicin; platinum compounds such as cisplatin and carboplatin; antitumor antibodies such as nivolumab, pembrolizumab, and camrelizumab; molecular target drugs such as eganelisib, apatinib, cabozantinib, and OR-449; mitotane; and etoposide.

In the treatment of castration-resistant prostate cancer, antitumor agents that are preferably used in combination with the compound of or a pharmaceutically acceptable salt thereof, polyfunctional molecule, composition for inhibiting SF-1, composition for inducing degradation of SF-1, or pharmaceutical composition of the present invention include, for example, one or more selected from hormonal agents such as abiraterone, enzalutamide, darolutamide, apalutamide, and the like; microtubule inhibitors such as docetaxel, cabazitaxel, and the like; PARP inhibitors such as olaparib, rucaparib, and the like; androgen receptor degraders such as ARV-110, ARV-766, CC-94676, and the like; CYP11A1 enzyme inhibitors such as ODM-208, and the like; and anti-tumor antibodies such as nivolumab, pembrolizumab, camrelizumab, and the like.

10. Novel Intermediate

In one embodiment of the present invention, a compound represented by the following formula (10):

[Chem. 23]

(10)

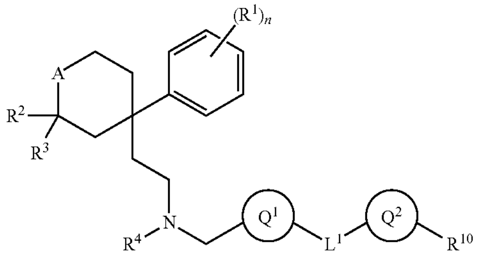

wherein

A is —O—, —S—, —$NR^a$—, or —$CR^bR^c$—, wherein $R^a$ is hydrogen or $C_{1-3}$ alkyl, $R^b$ and $R^c$ are each independently hydrogen, halogen, or $C_{1-3}$ alkyl, and the aforementioned alkyl is unsubstituted or substituted by 1 to 3 halogens, each $R^1$ in the number of n is independently halogen, hydroxy, —CN, $C_{1-6}$ alkyl, $C_{2-6}$ alkenyl, —O—$C_{1-6}$ alkyl, —N(H)—$C_{1-3}$ alkyl, —N($C_{1-3}$ alkyl)$_2$, $C_{3-7}$ cycloalkyl, or 3- to 7-membered heterocycloalkyl, wherein the aforementioned alkyl and alkenyl are each independently unsubstituted or substituted by 1 to 3 halogens, the aforementioned cycloalkyl and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heterocycloalkyl has 1 or 2 hetero atoms selected from oxygen, nitrogen, and sulfur as ring member atoms, $R^2$ and $R^3$ are each independently hydrogen, halogen, $C_{1-6}$ alkyl, or $C_{2-6}$ alkenyl, wherein the aforementioned alkyl and alkenyl are each independently unsubstituted or substituted by 1 to 3 halogens, $R^4$ is $C_{1-6}$ alkyl, —C(═O)—$R^d$ ($R^d$ indicates $C_{1-6}$ alkyl, $C_{2-5}$ alkenyl, $C_{3-7}$ cycloalkyl, or 3- to 7-membered heterocycloalkyl), $C_{6-12}$ aryl, or 6- to 12-membered heteroaryl, wherein the aforementioned $C_{1-6}$ alkyl is unsubstituted or substituted by 1 to 3 halogens, $C_{3-7}$ cycloalkyl, or 3- to 7-membered heterocycloalkyl, the aforementioned aryl, heteroaryl, cycloalkyl, and heterocycloalkyl are each independently unsubstituted or substituted by 1 to 3 groups selected from the group consisting of halogen, unsubstituted $C_{1-3}$ alkyl, and $C_{1-3}$ haloalkyl, and the aforementioned heteroaryl and heterocycloalkyl have 1 or 2 hetero atoms selected from oxygen, nitrogen, and sulfur as ring member atoms, ring $Q^1$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, or a 3- to 7-membered heterocycloalkene ring, wherein the aforementioned aromatic hydrocarbocycle, aromatic heterocycle, cycloalkane ring, heterocycloalkane ring, cycloalkene ring, and heterocycloalkene ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring and heterocycloalkene ring have 1 or 2 hetero atoms selected from oxygen, nitrogen, and sulfur as ring so member atoms, $L^1$ is a single bond, —O—, —S—, —NH—, $C_{1-3}$ alkylene, $C_{2-3}$ alkenylene, —C(═O)—, —C(═O)NH—, —NHC(═O)—, —C(═O)O—, or —OC(═O)—, wherein the aforementioned alkylene and alkenylene are each independently unsubstituted or substituted by 1 to 3 halogens, ring $Q^2$ is a $C_{6-12}$ monocyclic or bicyclic aromatic hydrocarbocycle, a 6- to 12-membered monocyclic or bicyclic aromatic heterocycle, a $C_{3-7}$ cycloalkane ring, a 3- to 7-membered heterocycloalkane ring, a $C_{3-7}$ cycloalkene ring, a 3- to 7-membered heterocycloalkene ring, a $C_{5-12}$ spirocycloalkane ring, or a 5- to 12-membered spiroheterocycloalkane ring, wherein the aforementioned aromatic hydrocarbocycle, aromatic heterocycle, cycloalkane ring, heterocycloalkane ring, cycloalkene ring, heterocycloalkene ring, spirocycloalkane ring, and spiroheterocycloalkane ring are each independently unsubstituted or substituted by 1 to 3 groups selected from the group consisting of halogen, unsubstituted $C_{1-3}$ alkyl, and $C_{1-3}$ haloalkyl, and the aforementioned aromatic heterocycle, heterocycloalkane ring, heterocycloalkene ring, and spiroheterocycloalkane ring has 1 or 2 hetero atoms selected from oxygen, nitrogen, and sulfur as ring member atoms, $R^{10}$ is $C_{1-6}$ alkyl, wherein the aforementioned $C_{1-6}$ alkyl is substituted by one or two 3- to 7-membered heterocycloalkyls, the aforementioned heterocycloalkyl has 1 or 2 hetero atoms selected from oxygen, nitrogen, and sulfur as ring member atoms, and the aforementioned heterocycloalkyl is unsubstituted, or substituted by an amino-protecting group, and n is an integer of 0 to 3, or a pharmaceutically acceptable salt thereof is provided.

The compound of the formula (10) of the present invention can be used as a production intermediate for the compound of the formula (2) or the formula (2') of the present invention, or is useful as a production intermediate, as described in detail in the following general production method and examples. The compound of the formula (10) of the present invention is the same as the compound of the formula (1), except that the definition of $R^{10}$ is different from that of the compound of the formula (1). Therefore, the definitions, explanations, preferred embodiments, and the like of each group in the above-mentioned formula (1), except for those relating to $R^5$, also apply to each group in the formula (10).

In one embodiment of the present invention, $R^{10}$ in the above-mentioned formula (10) is $C_{1-6}$ alkyl substituted by one 3- to 7-membered heterocycloalkyl (the aforementioned heterocycloalkyl is unsubstituted or substituted by an amino-protecting group), preferably $C_{1-6}$ alkyl substituted by one 4- to 6-membered heterocycloalkyl (the aforementioned heterocycloalkyl is unsubstituted or substituted by an amino-protecting group), further preferably $C_{1-6}$ alkyl substituted by one 6-membered heterocycloalkyl (the aforementioned heterocycloalkyl is unsubstituted or substituted by an amino-protecting group), particularly preferably $C_{1-6}$ alkyl substituted by piperazine (the aforementioned piperazine is unsubstituted or substituted by an amino-protecting group).

In one embodiment of the present invention, the "amino-protecting group" means a protecting group used as a protecting group for an amino group in the synthesis of an organic compound, and examples thereof include alkoxycarbonyl groups such as tert-butoxycarbonyl group, methoxycarbonyl group, ethoxycarbonyl group, 2,2,2-trichloroethoxycarbonyl group, 2-trimethylsilylethoxycarbonyl group and the like; allyloxycarbonyl group; arylmethoxycarbonyl groups such as benzyloxycarbonyl group, 4-methoxybenzyloxycarbonyl group, 4-nitrobenzyloxycarbonyl group, 2-nitrobenzyloxycarbonyl group and the like; 9-fluorenylmethyloxycarbonyl group; arylmethyl groups such as benzyl group, 4-methoxybenzyl group, 2,3-dimethoxybenzyl group, 3,4-dimethoxybenzyl group, diphenylmethyl group, triphenylmethyl group and the like; alkanoyl groups such as formyl group, acetyl group, trimethylacetyl group, trichloroacetyl group, trifluoroacetyl group and the like; aroyl groups such as benzoyl group and the like; arylsulfonyl groups such as benzenesulfonyl group, p-toluenesulfonyl group, 2-nitrobenzenesulfonyl group, 4-nitrobenzenesulfonyl group, 2,4-di-nitrobenzenesulfonyl group and the like, and the like. These amino-protecting groups can be selected depending on the properties of the compound that protects the amino group, and the removal of the protecting groups can be performed by selecting reagents and conditions according to the protecting group.

11. General Production Method

Representative methods for producing the compound of the present invention or a pharmaceutically acceptable salt thereof are described below.

The compound of the present invention can be produced by various production methods, and the production methods shown below and Reference Examples and Examples described below are only examples, and the present invention should not be interpreted as being limited to these.

Each raw material compound may form a salt as long as it does not inhibit the reaction, and examples of such salts include the same as the pharmaceutically acceptable salts of the compound described above.

When no specific production method is described, the raw material compounds can be easily obtained from commercial sources and used, or can be produced according to a method known per se or a method equivalent thereto. In addition, the production intermediates generated in the following production methods may be isolated and purified by a method such as column chromatography (including normal phase and reverse phase) using silica gel or alumina, recrystallization, reprecipitation, distillation, and the like, or may be used directly in the next reaction without isolation and purification.

In the present specification, all patent literatures, non-patent literatures, or references expressly cited herein may all be cited herein as a part of the present specification. The compound, a pharmaceutically acceptable salt thereof, and a production intermediate therefor can be produced by utilizing the characteristics based on the kind of the basic skeleton or substituent, and applying various known production methods. Examples of the known methods include the methods described in "ORGANIC FUNCTIONAL GROUP PREPARATIONS", 2nd edition, ACADEMIC PRESS, INC., 1989, "Comprehensive Organic Transformations", 2nd edition, VCH Publishers Inc., 1999, and the like.

In such cases, depending on the type of functional group present in the compound, it may be effective in terms of manufacturing technology to protect the functional group with an appropriate protecting group at the starting material or intermediate stage, or to replace the functional group with a group that can be easily converted to the functional group concerned.

Examples of the functional group include amino group, hydroxy group, formyl group, carbonyl group, carboxy group, and the like, and examples of the protecting group thereof include the protecting groups described in P. G. Wuts, "Protective Groups in Organic Synthesis", 5th edition, Wiley, 2014.

The protecting group or the group that can be easily converted into the functional group may be appropriately selected depending on the reaction conditions of the production method for producing the compound.

According to such a method, a desired compound can be obtained by introducing the group and performing a reaction, and then removing the protecting group as necessary or converting same into a desired group.

A prodrug of the compound can be produced by, similar to the above-mentioned protecting groups, introducing a particular group in the stage of a starting material or intermediate, or by a reaction using the obtained compound. The reaction for producing a prodrug can be performed by those of ordinary skill in the art, by applying a known method such as general esterification, amidation, dehydration, hydrogenation and the like.

Furthermore, functional group conversion and use of protecting groups in the production intermediates used in each step of the following methods can be performed by known methods or methods analogous thereto, or the methods described in the below-mentioned examples or methods analogous thereto.

In the following description of the general production methods, symbols used in the formulas without a definition have the same meaning as defined above.

A general production method of the compound of the formula (1) of the present invention is described below. In the following description, the abbreviations shown here may be used.

THF: tetrahydrofuran

DMF: N,N-dimethylformamide

DMA: N,N-dimethylacetamide

HATU: 1-[bis(dimethylamino)methylene]-1H-1,2,3-triazolo[4,5-b]pyridinium 3-oxide hexafluorophosphate DIPEA: N,N-diisopropylethylamine RuPhos Pd G3: (2-dicyclohexylphosphino-2',6'-diisopropyloxy-1,1'-biphenyl) [2-(2'-amino-1,1'-biphenyl)]palladium(II) methanesulfonate (CAS Registry Number: 1445085-77-7)

BrettPhos Pd G3: [(2-dicyclohexylphosphino-3,6-dimethoxy-2',4',6'-triisopropyl-1,1'-biphenyl)-2-(2'-amino-1,1'-biphenyl)]palladium(II) methanesulfonate (CAS Registry Number: 1470372-59-8)

Tf: trifluoromethanesulfonyl group

SEM: 2-(trimethylsilyl) ethoxymethyl group

XantPhos: 4,5-bis(diphenylphosphino)-9,9-dimethylxanthene (CAS Registry Number: 161265-03-8)

tBuXPhos: 2-di-tert-butylphosphino-2',4',6'-triisopropyl-biphenyl (CAS Registry Number: 564483-19-8)

(Method A)

Among the compounds represented by the formula (1), compound a12 wherein $R^4$ is a $C_{1-6}$ alkyl group optionally substituted by 1 to 3 halogen atoms, or a $C_{3-6}$ cycloalkyl-methyl group optionally substituted by one trifluoromethyl group, compound all wherein $R^4$ is a $C_{1-6}$ alkylcarbonyl group optionally substituted by 1 to 3 halogen atoms, and compound a14 wherein $R^4$ is 6-membered heteroaryl having 1 or 2 nitrogen atoms as ring member atoms (the heteroaryl group is optionally substituted by one halogen atom) can be produced according to the following method. A general production method for each reaction site is shown in order, but it is not necessary to perform each step in the order shown below as long as it does not affect the reaction substrate and reaction product.

[Chem. 24]

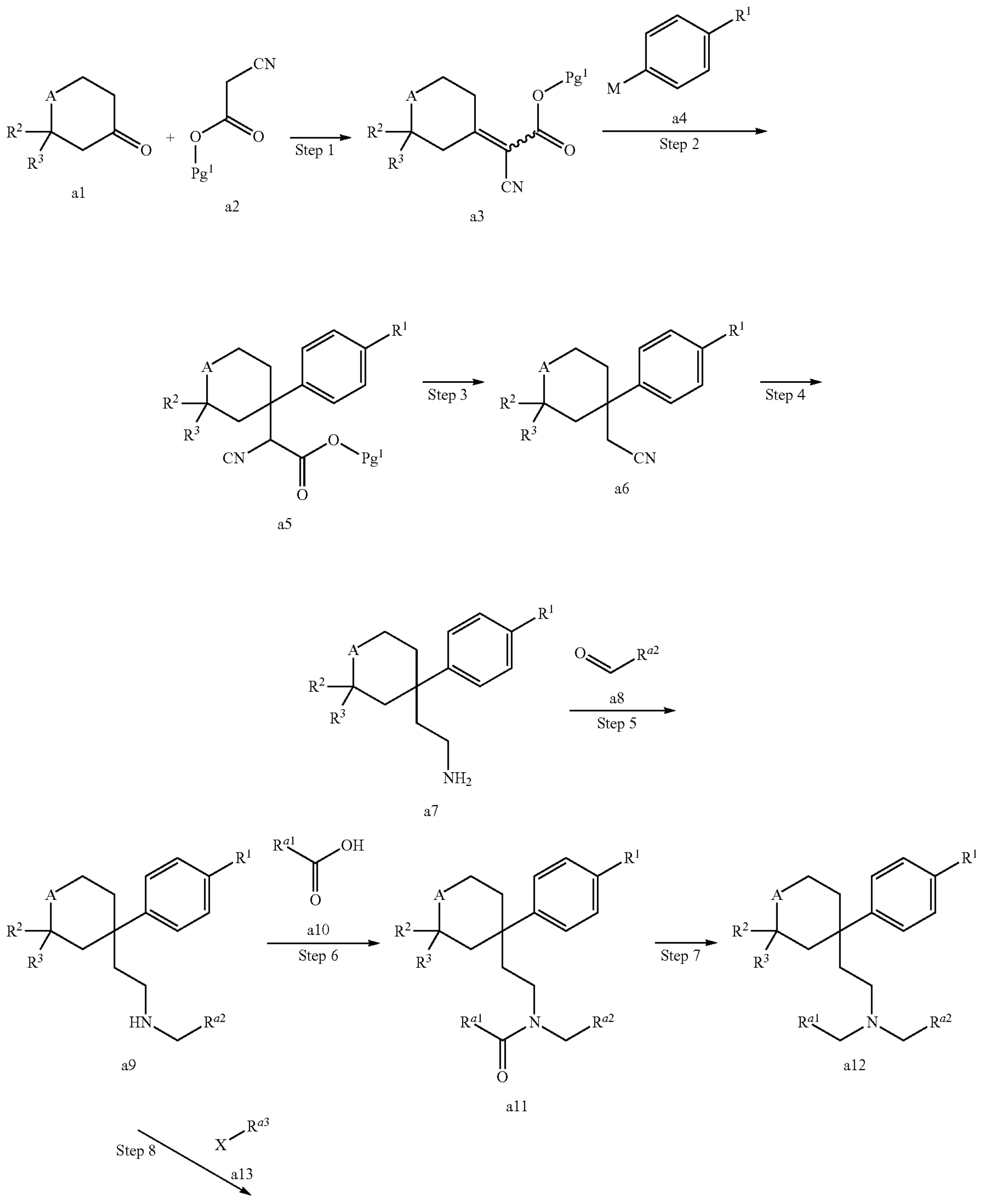

-continued

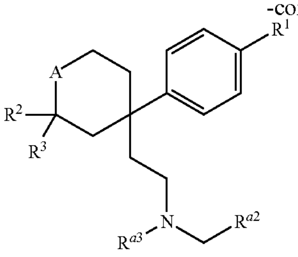

a14 wherein $Pg^1$ is a carboxy-protecting group (e.g., methyl group, ethyl group, benzyl group, or tert-butyl group, etc.), M is metal or halogenated metal (e.g., magnesium halide, lithium or zinc halide, etc.), $R^{a1}$ is a $C_{1-6}$ alkyl group optionally substituted by 1 to 3 halogen atoms, or $C_{3-6}$ cycloalkyl group optionally substituted by one trifluoromethyl group, $R^{a2}$ is a substituent represented by the following formula:

[Chem. 25]

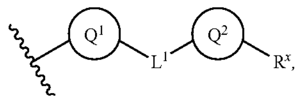

$R^X$ is $R^5$ or a group that can be converted to $R^5$, $R^{a3}$ is a 6-membered heteroaryl group having 1 or 2 nitrogen atoms as ring member atoms (the heteroaryl group is optionally substituted by one halogen atom.

In the first step, compound a3 is obtained by aldol condensation reaction of compound a1 and compound a2. The aldol condensation reaction in this step can be performed by reacting compound a1 with compound a2 using, for example, acetic acid and piperidine as catalysts.

In the second step, compound a5 is obtained by 1,4-nucleophilic addition of compound a4 to the α,β-unsaturated ester of compound a3. The 1,4-nucleophilic addition reaction in this step can be performed, for example, by reacting compound a3 with compound a4 in a solvent such as THF and the like in the presence of a copper reagent such as copper(II) bromide and the like. The reaction temperature is preferably from −78° C. to room temperature.

In the third step, compound a6 is obtained by hydrolysis of the ester of compound a5 and decarboxylation of the resulting carboxy group. The hydrolysis and decarboxylation reaction in this step can be performed, for example, by reacting compound a5 with a base such as sodium hydroxide and the like under heating in a solvent such as ethylene glycol and the like.

In the fourth step, compound a7 is obtained by reducing the cyano group of compound a6. The reduction reaction in this step can be performed, for example, by reacting compound a6 with a reducing agent such as lithium aluminum hydride and the like under heating in a solvent such as THF and the like.

In the fifth step, compound a9 is obtained from compound a7 and compound a8 by reductive amination reaction. The reductive amination reaction in this step can be performed, for example, by reacting compound a7 and compound a8 with a reducing agent such as sodium triacetoxyborohydride, sodium cyanoborohydride and the like in a solvent such as dichloromethane, methanol and the like. In this reaction, it may be preferable to add an acid such as acetic acid and the like. The reductive amination reaction in this step can also be performed, for example, by reacting a reducing agent such as sodium borohydride in a solvent such as methanol with the imine obtained by reacting compound a7 with compound a8 in a solvent such as toluene and then heating same, using a Dean-Stark apparatus.

In the sixth step, compound all is obtained by condensing compound a9 and compound a10. The condensation reaction in this step can be performed, for example, by reacting compound a9 and compound a10 with a condensing agent such as HATU and the like in a solvent such as DMF and the like. The condensation reaction in this step can also be performed, for example, by reacting acid chloride obtained by reacting oxalyl chloride and the like with compound a10 in a solvent such as dichloromethane and the like, with compound a9 in a solvent such as dichloromethane and the like, in the presence of a base such as DIPEA and the like.

In the seventh step, compound a12 is obtained by reducing carbonyl group of compound all. The reduction reaction in this step can be performed, for example, by reacting compound all with a reducing agent such as borane-THF complex and the like under heating in a solvent such as THE and the like.

In the eighth step, compound a14 is obtained from compound a9 and compound a13 by Buchwald amination reaction or aromatic nucleophilic substitution reaction. The Buchwald amination reaction in this step can be performed, for example, by reacting compound a9 with compound a13 under heating in a solvent such as 1,4-dioxane and the like, in the presence of a base such as cesium carbonate and the like and a metal catalyst such as RuPhos Pd G3 or BrettPhos Pd G3 and the like. The aromatic nucleophilic substitution reaction in this step can be performed, for example, by reacting compound a9 with compound a13 under heating in a solvent such as 2-butanol, N,N-dimethylacetamide and the like, in the presence of a base such as 1,8-diazabicyclo [5.4.0]-7-undecene, potassium carbonate and the like.

When $R^5$ is a group represented by the following formula:

[Chem. 26]

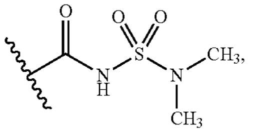

$R^5$ moiety can be introduced according to a known method. Examples of literature on the known method include, but are not limited to, WO 2013088315 A1, WO 2020192588 A1 and the like.

When $R^5$ is a group represented by the following formula:

[Chem. 27]

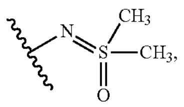

$R^5$ moiety can be introduced according to a known method. Examples of literature on the known method include, but are not limited to, J. Org. Chem., 2000, 65, 1, 169-175, Tetrahedron Lett., 1998, 39, 5731-5734 and the like.

When $R^5$ is a group represented by the following formula:

[Chem. 28]

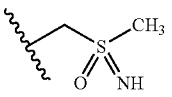

$R^5$ moiety can be introduced according to a known method. Examples of literature on the known method include, but are not limited to, J. Org. Chem., 2015, 80, 6391-6399, WO 2019148132 A1 and the like.

(Method B)

Among the compounds represented by the formula (1), a compound represented by the following formula b2 can be produced according to the following method.

[Chem. 29]

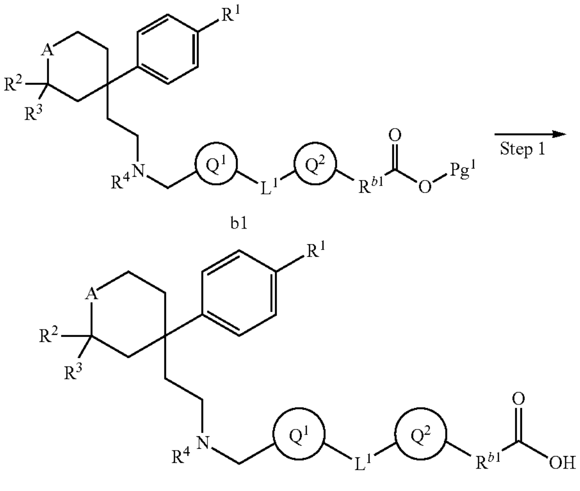

b1 b2 wherein $R^{b1}$ is a single bond or a $C_{1-6}$ alkylene group optionally having a group selected from the group consisting of a hydroxy group, a $C_{1-6}$ alkoxy group, a piperazinyl group and a 1-tert-butoxy carbonylpiperazinyl group, and $Pg^1$ is a carboxy-protecting group.

In the first step, compound b2 is obtained from compound b1 by a deprotection reaction of the carboxy-protecting group $Pg^1$. The deprotection reaction in this reaction can be performed by a method generally used for deprotecting a carboxy-protecting group. For example, when $Pg^1$ is a methyl group or an ethyl group, the deprotection reaction can be performed by reacting compound b1 with a base such as an aqueous sodium hydroxide solution in a solvent such as methanol.

(Method C)

Among the compounds represented by the formula (1), compounds represented by the following formulas c2 and c5 can be produced according to the following methods.

[Chem. 30]

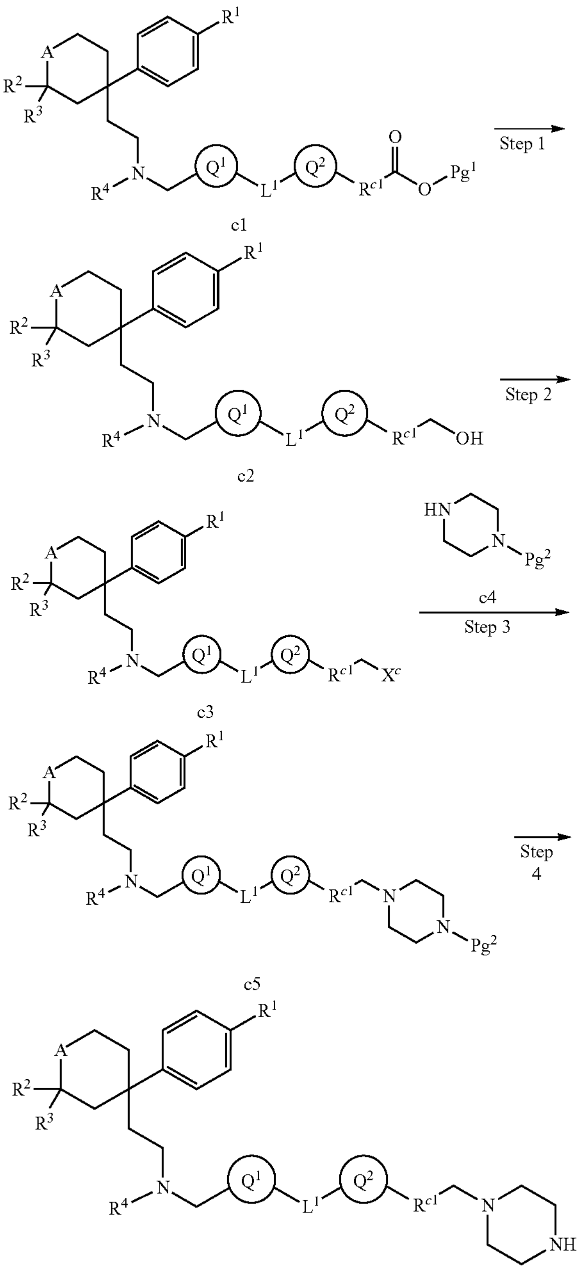

c1 c2 c4 c3 c5 c6 wherein Rei is a single bond or a $C_{1-6}$ alkylene group optionally having substituent(s) selected from the group consisting of a carboxy group, a hydroxy group and a $C_{1-6}$ alkoxy group, $Pg^1$ is a carboxy-protecting group, $Pg^2$ is an amino-protecting group, and $X^c$ is a leaving group.

In the first step, compound c2 is obtained by reducing the ester of compound c1. The reduction reaction in this step can be performed, for example, by reacting compound c1 with a reducing agent such as lithium aluminum hydride, diisobutylaluminum hydride and the like in a solvent such as THE and the like.

In the second step, compound c3 is obtained by converting the hydroxy group of compound c2 into a leaving group. Examples of the leaving group in this step include a methanesulfonyloxy group, a para-toluenesulfonyloxy group, and the like and the group can be converted by a generally used method (reagent, solvent, reaction conditions, etc.).

In the third step, compound c5 is obtained from compound c3 and compound c4 by nucleophilic substitution reaction. The nucleophilic substitution reaction in this step can be performed by reacting compound c3 with compound c4 under heating in a solvent such as DMF, acetonitrile and the like, and/or can also be performed in the presence of a base such as N,N-diisopropylethylamine and the like.

In the fourth step, compound c6 is obtained by deprotecting the amino-protecting group $Pg^2$ of compound c5. The deprotection reaction in this step can be performed by a method generally used for deprotecting an amino-protecting group. For example, when $Pg^2$ is a tert-butoxy carbonyl group, the deprotection reaction can be performed by reacting compound c5 with an acid such as hydrogen chloride, trifluoroacetic acid and the like in a solvent such as dichloromethane.

(Method D)

Among the compounds represented by the formula (1), a compound represented by the following formula d5 or d7 can be produced according to the following production method.

[Chem. 31]

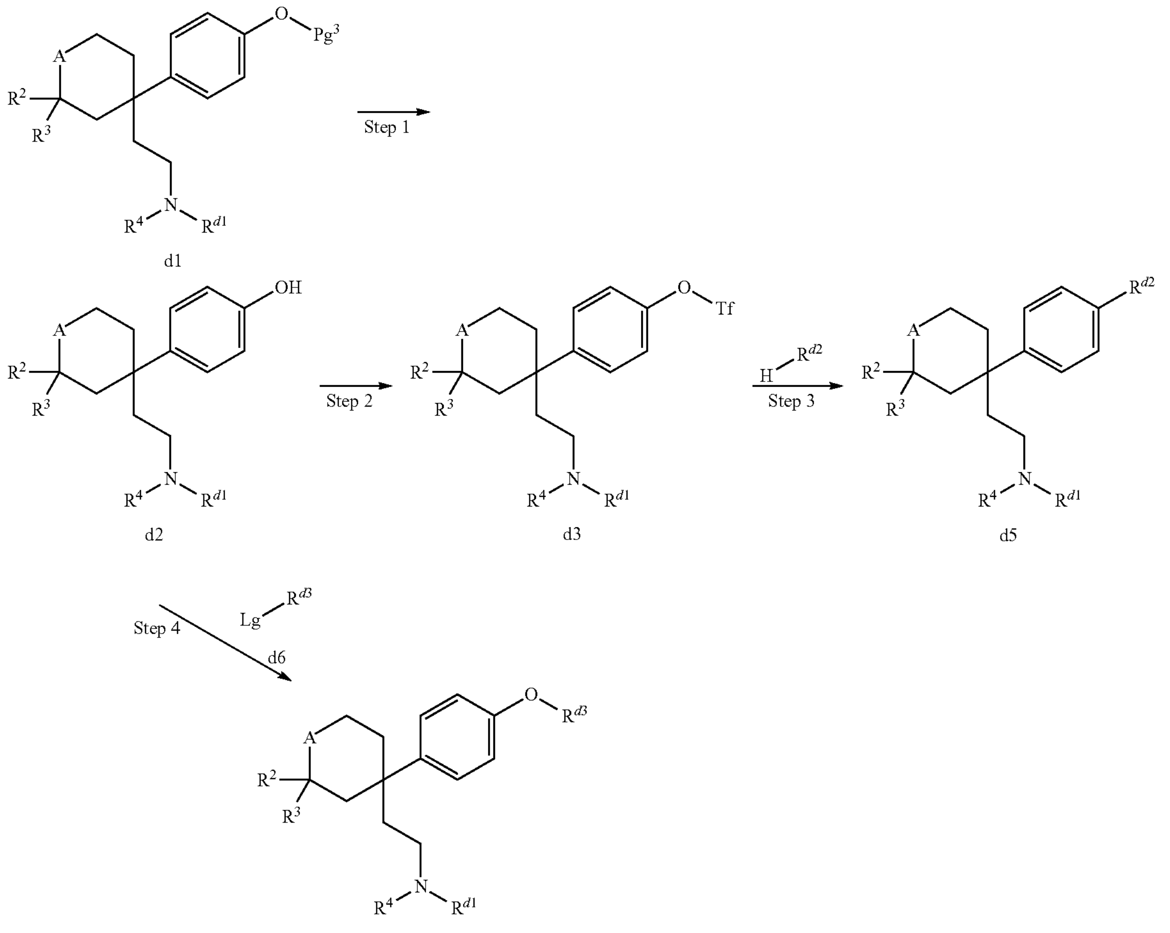

d1 d2 d3 d5 d7 wherein $Pg^3$ is a hydroxy-protecting group (e.g., methyl group, benzyl group, methoxymethyl group, etc.), Lg is a leaving group, $R^{d1}$ is a group represented by the following formula:

[Chem. 32]

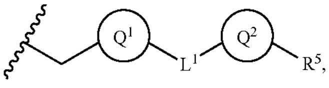

or a group that can be converted to the group, $R^{d2}$ is a $C_{1-3}$ alkylamino group, a di-$C_{1-3}$ alkylamino group, or a 4- to 6-membered saturated heterocyclic group having one nitrogen atom as a ring member atom, and $R^{d3}$ is a $C_{1-6}$ alkyl group optionally substituted by 1 to 3 halogen atoms.

In the first step, compound d2 is obtained from compound d1 by a deprotection reaction of a hydroxy-protecting group $Pg^3$. The deprotection reaction in this step can be performed by a method generally used for deprotection of a hydroxy-protecting group. For example, when $Pg^3$ is a methyl group, the deprotection reaction can be performed by reacting compound d1 with sodium thiomethoxide under heating in a solvent such as DMF and the like. This reaction can also be performed under microwave irradiation. The reaction temperature is preferably 80° C. to 160° C.

In the second step, compound d3 is obtained from compound d2 by triflation of a hydroxy group. The triflation reaction in this step can be performed, for example, by reacting a triflation agent such as trifluoromethanesulfonic anhydride and the like and compound d2 in a solvent such as dichloromethane and the like, in the presence of a base such as pyridine and the like.

In the third step, compound d5 is obtained from compound d3 and amine d4 by Buchwald amination reaction. The Buchwald amination reaction in this step can be performed by reacting compound d3 and amine d4 under heating in a solvent such as 1,4-dioxane and the like, in the presence of a ligand such as 2-(di-tert-butylphosphino) biphenyl and the like, and a metal catalyst such as tris (dibenzylideneacetone)dipalladium(0) and the like.

In the fourth step, compound d7 is obtained by alkylation reaction of compound d2 with an alkylating agent d6. The alkylation reaction in this step can be performed, for example, by reacting alkylating agent d6 and compound d2 under heating in a solvent such as DMF and the like, in the presence of a base such as potassium carbonate and the like. The reaction temperature is preferably from room temperature to 150° C.

(Method E)

Compound e4, which is a compound represented by the formula (1) wherein $L^1$ is —C(═O)—, can be produced according to the following method.

[Chem. 33]

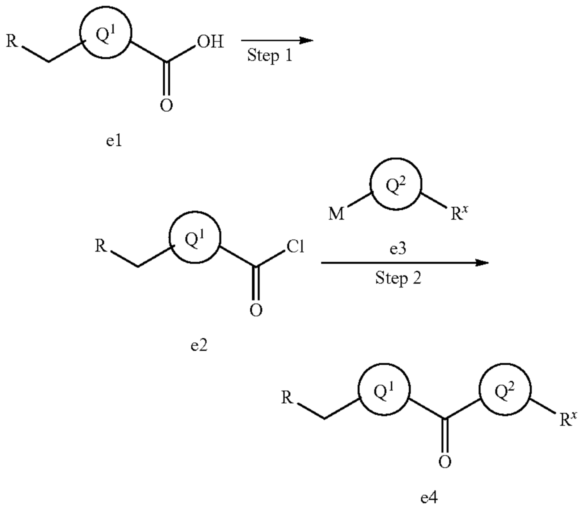

wherein R is a group represented by the following formula:

[Chem. 34]

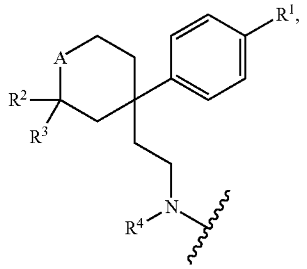

M is a dihydroxyboryl group, a pinacolatoboryl group and the like, $R^X$ is $R^5$ or a group that can be converted to $R^5$.

In the first step, carboxylic acid e1 is converted to acid chloride e2. Chlorination reaction in this step can be performed, for example, by reacting compound e1 and a chlorinating agent such as oxalyl chloride, thionyl chloride and the like in a solvent such as dichloromethane and the like, in the presence of a catalytic amount of DMF.

In the second step, compound e4 is obtained by coupling reaction of compound e2 and compound e3. The coupling reaction in this step can be performed, for example, by reacting compound e2 and compound e3 under heating in a solvent such as toluene and the like in the presence of a base such as cesium carbonate and the like and a metal catalyst such as tetrakis(triphenylphosphine)palladium(0) and the like. Examples of literature on the coupling reaction of this step include Catalysts, 2019, 9(1), 53.

A production method of a starting compound represented by the formula (3):

[Chem. 35]

(3)

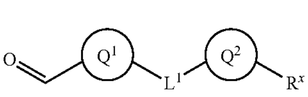

wherein $R^X$ is $R^5$ or a group that can be converted to $R^5$ is shown below.

(Method F)

Among starting compounds (3), compound f3 wherein $L^1$ is oxygen atom, compound f6 wherein $L^1$ is a single bond, and compounds f12 and f13 wherein $Q^1$ is a 7-azaspiro[3.5] nonane ring can be produced according to the following methods.

[Chem. 36]

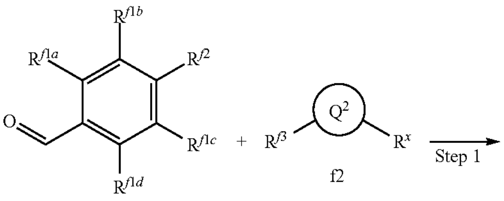

f1

-continued

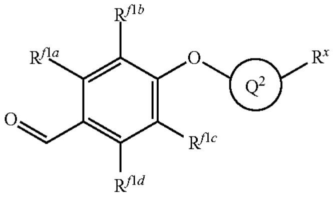

f3

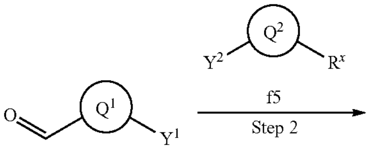

f4

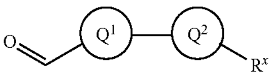

f6

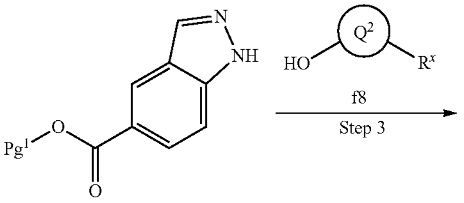

f7

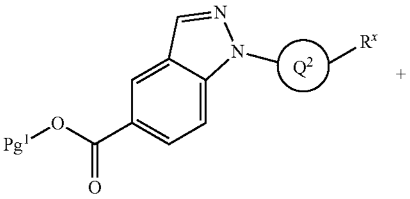

f9

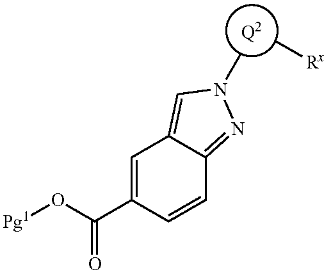

f10

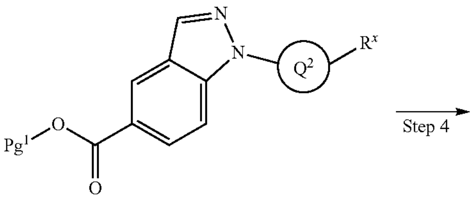

f9

-continued

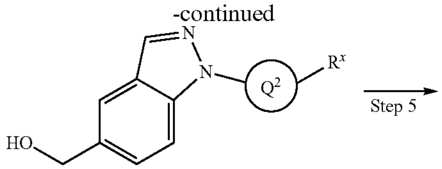

f11

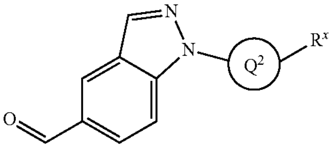

f12

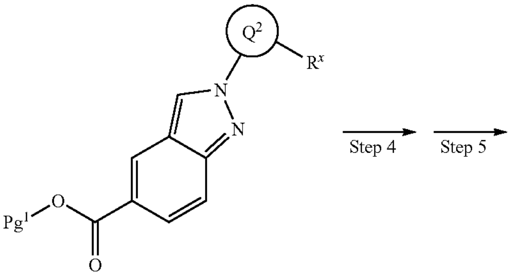

f10

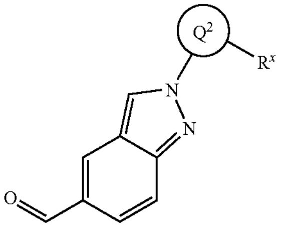

f13 wherein $R^{f1a}$, $R^{f1b}$, $R^{f1c}$, and $R^{f1d}$ are each independently a hydrogen atom, a halogen atom, or a $C_{1-6}$ alkyl group, $R^{f2}$ is OH or a leaving group, wherein when $R^{f2}$ is OH, then $R^{f3}$ is OH or a leaving group and when $R^{f2}$ is a leaving group, then $R^{f3}$ is OH, $Y^1$ is a halogen atom, a trifluoromethanesulfonyloxy group, a pinacolatoboryl group, or a dihydroxyboryl group, wherein when $Y^1$ is a halogen atom or a trifluoromethanesulfonyloxy group, then $Y^2$ is a pinacolatoboryl group or a dihydroxyboryl group or when $Y^1$ is a pinacolatoboryl group or a dihydroxyboryl group, then $Y^2$ is a halogen atom or a trifluoromethanesulfonyloxy group, $Pg^1$ is a carboxy-protecting group, and $R^X$ is $R^5$ or a group that can be converted to $R^5$.

In the first step, compound f3 is obtained from compound f1 and compound f2. When $R^{f2}$ is OH and $R^{f3}$ is OH, this reaction can be performed by Mitsunobu reaction. The Mitsunobu reaction in this step can be performed, for example, by reacting compound f1 and compound f2 with phosphine such as triphenylphosphine and the like and azodicarboxylic acid ester such as diisopropyl azodicarboxylate and the like in a solvent such as THF and the like. When $R^{f2}$ or $R^{f3}$ is a leaving group, this reaction can be performed by a nucleophilic substitution reaction. The nucleophilic substitution reaction in this step can be performed, for example, by reacting compound f1 and compound f2 with a base such as potassium carbonate, cesium carbonate and the like under heating in a solvent such as DMF, N,N-dimethylacetamide and the like.

In the second step, compound f6 is obtained by coupling reaction of compound f4 and compound f5. The coupling reaction in this step can be performed, for example, by heating compound f4 and compound f5 in a solvent such as aqueous 1,4-dioxane and the like, in the presence of a base such as potassium carbonate and the like and a metal catalyst such as [1,1'-bis(diphenylphosphino)ferrocene]palladium (II) dichloride dichloromethane adduct and the like.

In the third step, compound f9 and compound f10 are obtained by Mitsunobu reaction of compound f7 and compound f8. The Mitsunobu reaction in this step can be performed, for example, by reacting compound f7 and compound f8 with a phosphorane reagent such as cyanomethylenetributylphosphorane and the like under heating in a solvent such as toluene and the like.

In the fourth step, compound f11 is obtained by reduction reaction of compound f9. The reduction reaction in this step can be performed under the same conditions as in the first step of Method C.

In the fifth step, compound f12 is obtained from compound f11 by oxidation reaction. The oxidation reaction in this step can be performed, for example, by reacting compound f11 with an oxidizing agent such as 1,1,1-triacetoxy-1,1-dihydro-1,2-benzoiodoxol-3-(1H)-one, manganese(IV) oxide and the like in a solvent such as dichloromethane and the like.

Compound f13 can be obtained by subjecting compound f10 to the same steps as the fourth step and the fifth step of this method.

In the following, a general production method of a compound of the formula (2) of the present invention is described.

(Method G)

Method G is a production method of a compound represented by the formula (2).

[Chem. 37]

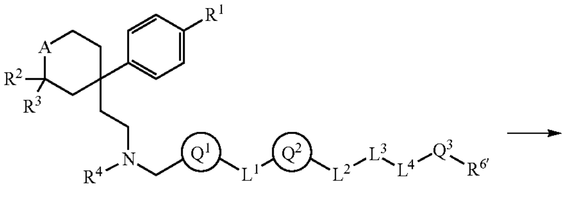

(4)

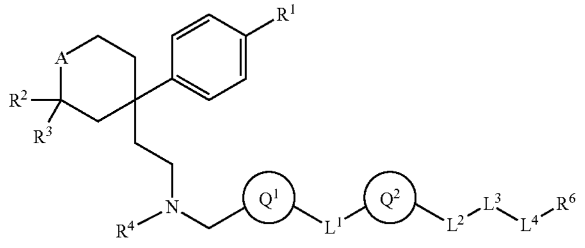

(2)

wherein $R^{6'}$ is any group selected from the groups represented by the following formulas:

[Chem. 38]

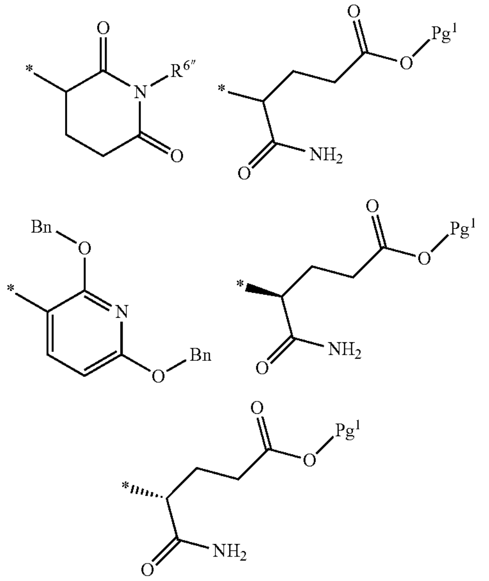

$R^{6''}$ is an imide-protecting group (e.g., (2-trimethylsilylethoxy)methyl group, tert-butoxycarbonyl group, benzyloxymethyl group, etc.), $Q^3$ is any group selected from the following formulas:

[Chem. 39]

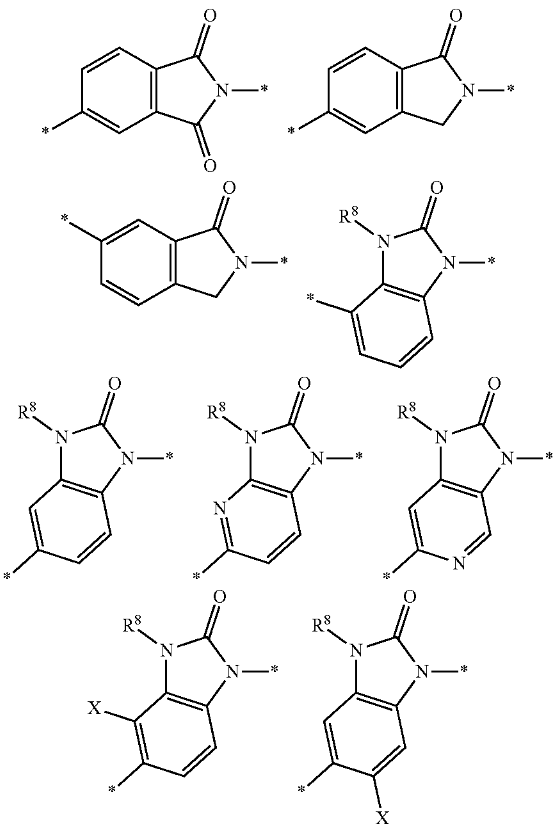

-continued

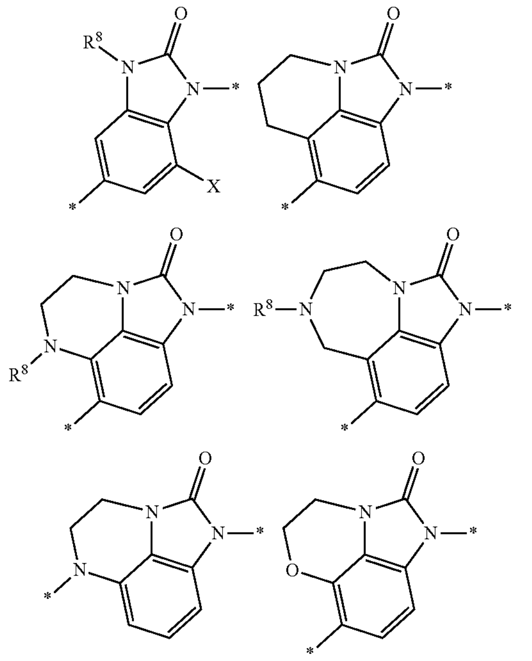

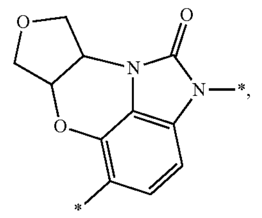

and

Pg¹ is a carboxy-protecting group (e.g., methyl group, ethyl group, tert-butyl group, etc.).

When $R^{6'}$ is a group represented by the following formula:

[Chem. 40]

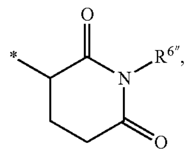

this step can be performed by deprotecting the protecting group of compound (4).

The deprotection reaction in this step can be performed by a method generally used for deprotecting a protecting group for the nitrogen atom of imide. For example, when the protecting group is an SEM group, the deprotection reaction in this step can be performed by reacting compound (4) with an acid such as trifluoroacetic acid and the like in a dichloromethane solvent to remove trimethylsilyl ethyl group, followed by reaction with a base such as N,N'-dimethylethylenediamine and the like in a solvent such as ethyl acetate and the like.

When $R^{6'}$ is any group selected from the following formulas:

[Chem. 41]

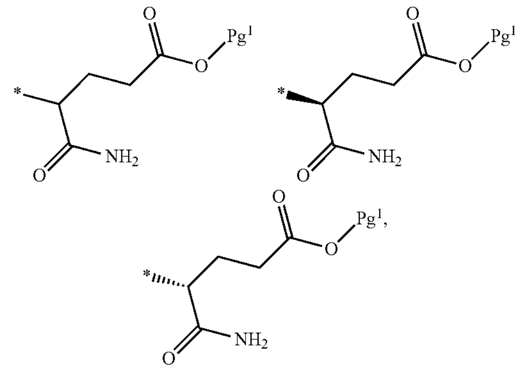

this step can be performed by a cyclization reaction.

When $Pg^1$ is a tert-butyl group, the cyclization reaction in this step can be performed, for example, by reacting compound (4) and an acid such as benzenesulfonic acid and the like under heating in a solvent such as acetonitrile and the like. When $Pg^1$ is a methyl group or an ethyl group, the cyclization reaction in this step can be performed, for example, by reacting compound (4) with a base such as potassium tert-butoxide and the like in a solvent such as THF and the like.

When $R^{6'}$ is a group represented by the following formula:

[Chem. 42]

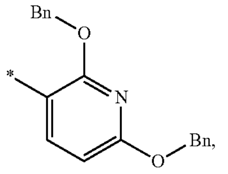

this step can be performed by a catalytic hydrogenation reaction.

The catalytic hydrogenation reaction in this step can be performed, for example, by reacting compound (4) with a metal catalyst such as palladium carbon and the like under a hydrogen atmosphere in a solvent such as ethyl acetate, ethanol and the like.

A production method of a starting compound represented by the formula (4):

[Chem. 43]

(4)

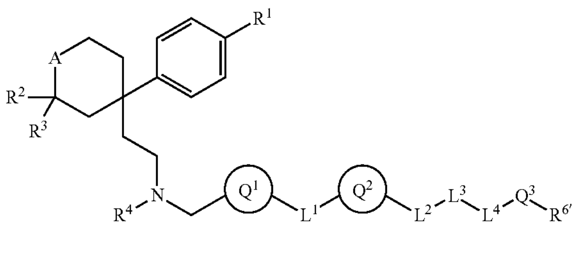

is shown below.

(Method H)

Compound h4, which is a starting compound (4) wherein $L^4$ is —C(=O)— can be produced according to the following method.

[Chem. 44]

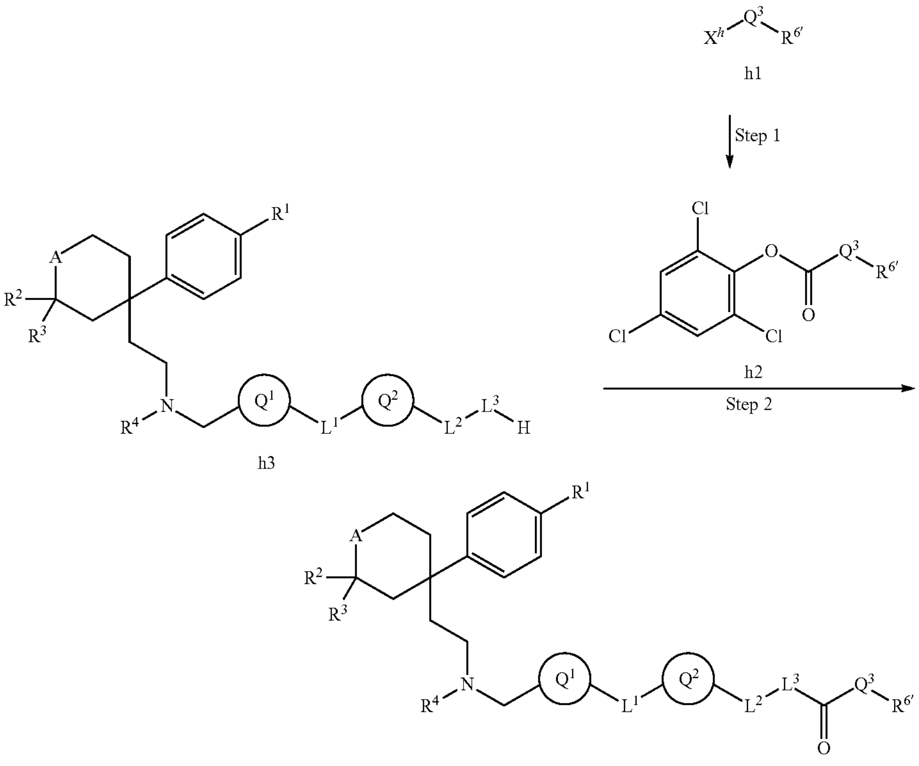

h4 wherein $R^1$, $R^2$, $R^3$, $R^4$, $R^{6\prime}$, ring $Q^1$, ring $Q^2$, ring $Q^3$, $L^1$, and $L^2$ are as defined above, $L^3$ is a piperazinediyl group, a piperazin-2-onediyl group, a piperidinediyl group, a pyrrolidinediyl group, an azetidinediyl group, or a 3-oxa-9-azabicyclo[3.3.1]nonanediyl group, and $X^h$ is a halogen atom.

In the first step, compound h1 is converted to compound h2 by a carbonylation reaction. The carbonylation reaction in this step can be performed, for example, by reacting compound h1 and 2,4,6-trichlorophenyl formate (CAS Registry Number: 4525-65-9) under heating in a solvent such as toluene and the like, in the presence of a base such as triethylamine and the like, a ligand such as XantPhos and the like, and a metal catalyst such as palladium(II) acetate and the like in a carbon monoxide atmosphere.

In the second step, compound h4 is obtained from compound h2 and compound h3 by an amidation reaction. The amidation reaction in this step can be performed, for example, by reacting compound h2 and compound h3 under heating in a solvent such as acetonitrile and the like, in the presence of a base such as DIPEA and the like, and a catalyst such as 4-dimethylaminopyridine and the like.

(Method I)

Compound i4, which is a starting compound (4) wherein $L^4$ is —$CH_2$—, can be produced according to the following method.

[Chem. 45]

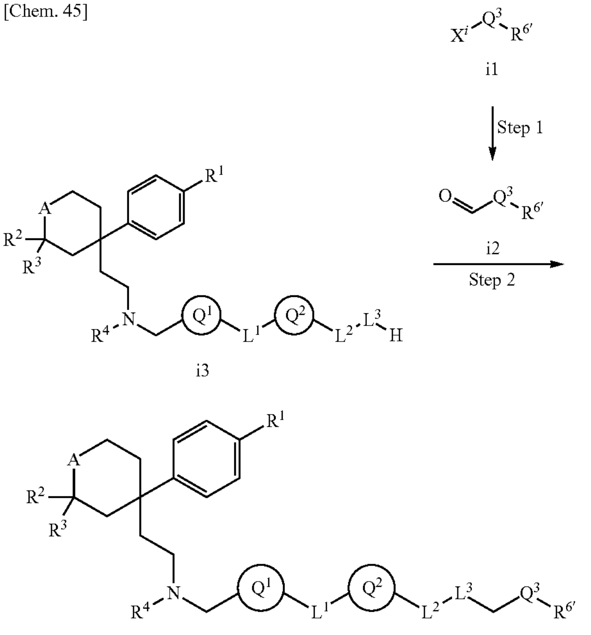

i4 wherein $R^1$, $R^2$, $R^3$, $R^4$, $R^{6\prime}$, ring $Q^1$, ring $Q^2$, ring $Q^3$, $L^1$, and $L^2$ are as defined above, $L^3$ is a piperazinediyl group, a piperazin-2-onediyl group, a piperidinediyl group, a pyrrolidinediyl group, an azetidinediyl group, or a 3-oxa-9-azabicyclo[3.3.1]nonanediyl group, and $X^i$ is a halogen atom.

In the first step, compound i1 is converted to compound i2 by a formylation reaction. The formylation reaction in this step can be performed, for example, by reacting compound i1 with a reducing agent such as triethylsilane and the like under heating in a solvent such as toluene and the like, in the presence of a base such as triethylamine and the like, a ligand such as XantPhos and the like, and a metal catalyst such as palladium(II) acetate and the like in a carbon monoxide atmosphere. In this reaction, it may be preferable to add saccharin.

In the second step, compound i4 is obtained from compound i2 and compound i3 by a reductive amination reaction. The reductive amination reaction in this step can be performed, for example, by reacting compound i2 and compound i3 with a reducing agent such as sodium triacetoxyborohydride, sodium cyanoborohydride and the like in a solvent such as dichloromethane, methanol and the like. In this reaction, it may be preferable to add an acid such as acetic acid and the like. The reductive amination reaction in this step can also be performed, for example, by reacting a reducing agent such as sodium borohydride in a solvent such as methanol with the imine obtained by reacting compound i3 with compound i2 under heating in a solvent such as toluene, using a Dean-Stark apparatus.

(Method J)

Compound j3, which is a starting compound (4) wherein $L^2$ is C═O, can be produced according to the following method.

[Chem. 46]

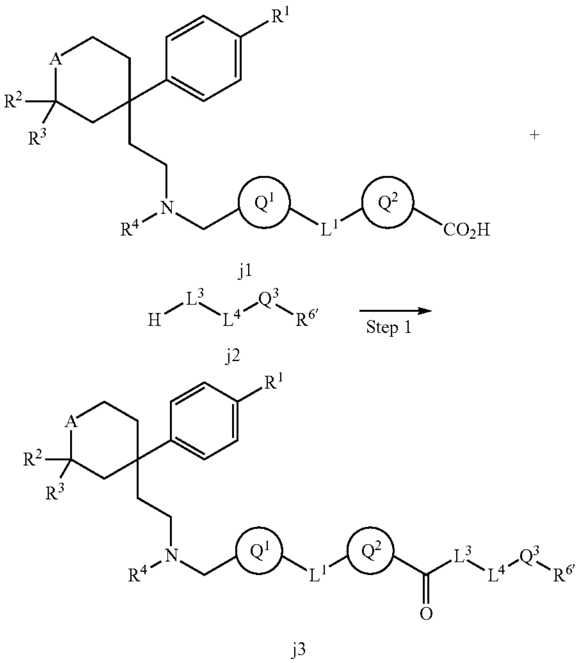

j1 j2 j3 wherein $R^1$, $R^2$, $R^3$, $R^4$, $R^{6\prime}$, ring $Q^1$, ring $Q^2$, ring $Q^3$, $L^1$, and $L^4$ are as defined above, $L^3$ is a piperazinediyl group, a piperazin-2-onediyl group, a piperidinediyl group, a pyrrolidinediyl group, an azetidinediyl group, or a 3-oxa-9-azabicyclo[3.3.1]nonanediyl group.

In the first step, compound j3 is obtained by condensing compound j1 and compound j2. The condensation reaction in this step can be performed, for example, by reacting compound j1 and compound j2 with a condensing agent such as HATU and the like in a solvent such as DMF and the like. The condensation reaction in this step can also be performed, for example, by reacting acid chloride obtained by reacting a chlorinating agent such as oxalyl chloride and the like with compound j1 in a solvent such as dichloromethane and the like, in the presence of a catalytic amount of DMF, with compound j1 in a solvent such as dichloromethane and the like, in the presence of a base such as DIPEA and the like.

A compound wherein $L^2$ is CONH or $(CH_2)_n$CONH (n indicates an integer of 1 to 3) can be obtained under similar conditions by changing compound j1 and compound j2 to the corresponding carboxylic acid and amine, respectively.

A compound wherein $L^2$ is NHCO can be obtained under similar conditions by changing compound j1 and compound j2 to the corresponding amine and carboxylic acid, respectively.

(Method K)

Compound k3, which is a starting compound (4) wherein $L^2$ is $—CH_2—$, can be produced according to the following method.

[Chem. 47]

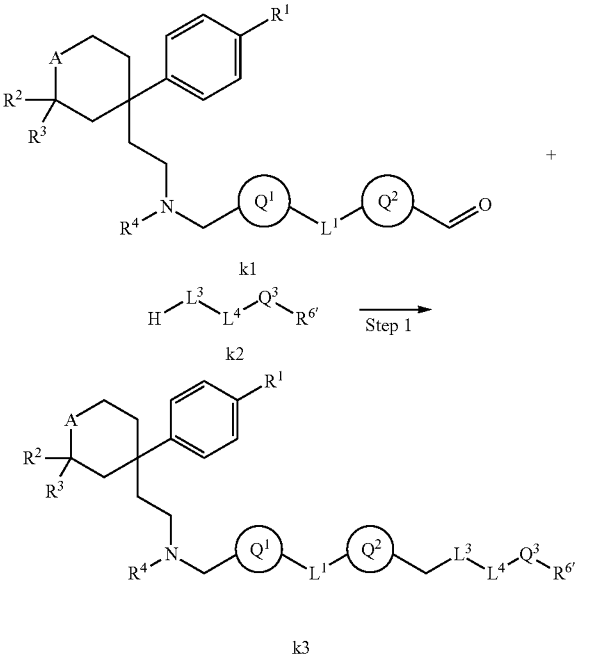

k1 k2 k3 wherein $R^1$, $R^2$, $R^3$, $R^4$, $R^{6\prime}$, ring $Q^1$, ring $Q^2$, ring $Q^3$, $L^1$, and $L^4$ are as defined above, $L^3$ is a piperazinediyl group, a piperazin-2-onediyl group, a piperidinediyl group, a pyrrolidinediyl group, an azetidinediyl group, or a 3-oxa-9-azabicyclo[3.3.1]nonanediyl group.

In the first step, compound k3 is obtained from compound k1 and compound k2 by a reductive amination reaction. The reductive amination reaction in this step can be performed as in the second step of Method I.

A compound wherein $L^2$ is a $C_{2-6}$ alkylene group can also be obtained under the same conditions by changing compound k1 to the corresponding aldehyde.

(Method L)

Compound 16, which is a starting compound (4) wherein $Q^2$ is a benzene ring optionally substituted by one halogen atom and $L^2$ is —NHCO— can be produced according to the following method.

[Chem. 48]

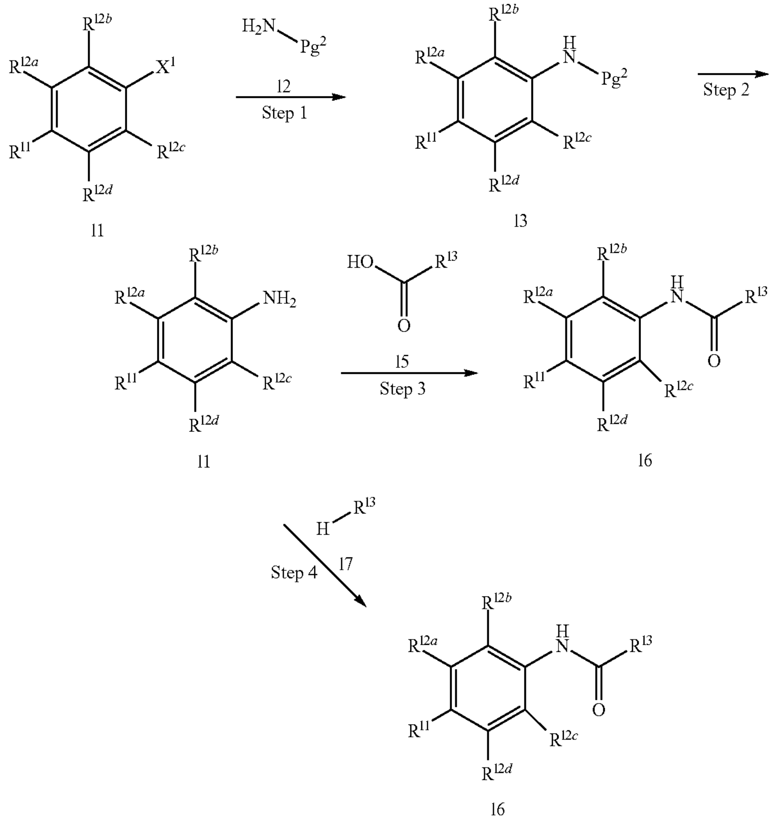

wherein $X^1$ is a halogen atom, $Pg^2$ is an amino-protecting group, $R^{11}$ is a group represented by the following formula:

[Chem. 49]

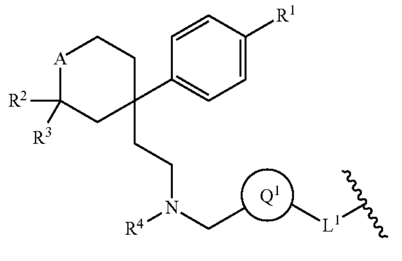

$R^{12a}$, $R^{12b}$, $R^{12c}$, and $R^{12d}$ are each independently a hydrogen atom or a halogen atom, and $R^{13}$ is a group represented by the following formula:

[Chem. 50]

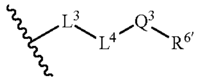

or a group that can be converted to the group.

In the first step, compound 13 is obtained from compound 11 and compound 12 by a Buchwald amination reaction. The amination reaction in this step can be performed, for example, by reacting compound 11 and compound 12 under heating in a solvent such as tert-butyl alcohol, DMSO and the like, in the presence of a ligand such as 1,2,3,4,5-pentaphenyl-1'-(di-tert-butylphosphino)ferrocene, tBuXPhos and the like; a metal catalyst such as tris(dibenzylideneacetone)dipalladium(0) and the like; and a base such as cesium carbonate, 7-methyl-1,5,7-triazabicyclo[4.4.0]dec-5-ene and the like.

In the second step, compound 13 is converted to compound 14 by a deprotection reaction of an amino-protecting group $Pg^2$. The deprotection reaction in this step can be performed by a method generally used for the deprotection of an amino-protecting group. For example, when $Pg^2$ is a tert-butoxy carbonyl group, it can be performed by reacting compound 13 with an acid such as hydrochloric acid and the like in a solvent such as dichloromethane and the like.

In the third step, compound 16 is obtained by a condensation reaction of compound 14 and compound 15. The condensation reaction in this step can be performed under the same conditions as in the first step of Method J.

In the fourth step, compound 16 is obtained from compound 14 and compound 17 by a ureation reaction. The ureation reaction in this step can be performed by reacting carbamoyl chloride obtained by reacting compound 14 with triphosgene in a solvent such as dichloromethane and the like, in the presence of a base such as triethylamine, pyridine and the like, with compound 17 in a solvent such as dichloromethane and the like, in the presence of a base such as triethylamine and the like.

A production method of the starting compound represented by the formula (5)

[Chem. 51]

(5)

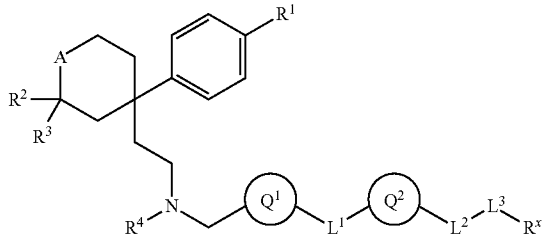

wherein $R^X$ is a group that can be converted to a group represented by the following formula:

[Chem. 52]

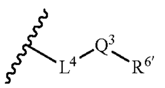

is shown.

Among the starting compounds (5), a compound wherein $L^2$ is C═O, CONH, $(CH_2)_nCONH$ (n indicates an integer of 1 to 3), or NHCO can be produced according to a method similar to that of Method J. Among the starting compounds (5), a compound wherein $L^2$ is a $C_{1-6}$ alkylene group can be produced according to a method similar to that of Method K.

(Method M)

Compound m5, which is a starting compound (5) wherein $L^2$ is a $C_{1-6}$ alkylene group, can be produced according to the following method.

[Chem. 53]

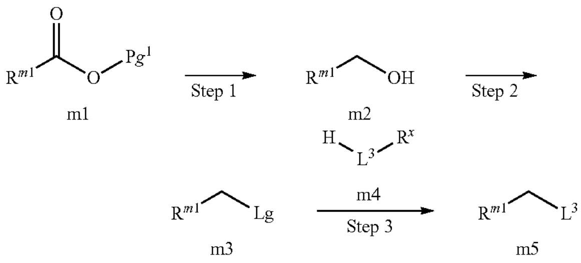

wherein $L^3$ is a piperazinediyl group, a piperazin-2-onediyl group, a piperidinediyl group, a pyrrolidinediyl group, an azetidinediyl group, or a 3-oxa-9-azabicyclo[3.3.1]nonanediyl group, Lg is a leaving group (e.g., bromine atom, iodine atom, chlorine atom, methanesulfonyloxy group, para-toluenesulfonyloxy group, trifluoromethanesulfonyloxy group, etc.), $R^{m1}$ is a group represented by the following formula:

[Chem. 54]

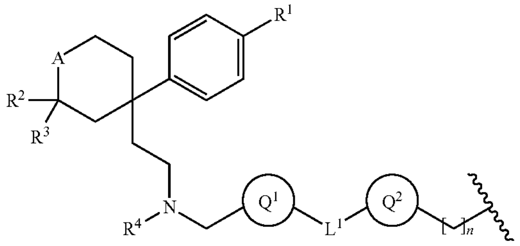

wherein n is an integer of 0 to 5, $Pg^1$ is a carboxy-protecting group, $R^X$ is a group that can be converted to a group represented by the following formula:

[Chem. 55]

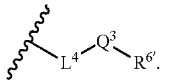

In the first step, compound m2 is obtained by reducing the ester group of compound m1. The reduction reaction in this step can be performed, for example, by reacting compound m1 with a reducing agent such as lithium aluminum hydride, diisobutylaluminum hydride and the like in a solvent such as tetrahydrofuran and the like.

In the second step, compound m3 is obtained by converting the hydroxy group of compound m2 to a leaving group. Examples of the leaving group in this step include bromine atom, iodine atom, chlorine atom, methanesulfonyloxy group, para-toluenesulfonyloxy group, trifluoromethanesulfonyloxy group and the like, and conversion to a leaving group can be performed by a method used generally (reagent, solvent, reaction conditions, etc.).

In the third step, compound m5 is obtained from compound m3 and compound m4 by a nucleophilic substitution reaction. The nucleophilic substitution reaction in this step can be performed by reacting compound m3 and compound m4 under heating, in a solvent such as DMF, acetonitrile and the like. In this reaction, it may be preferable to add a base such as N,N-diisopropylethylamine and the like.

A production method of a starting compound represented by the formula (6):

[Chem. 56]

(6)

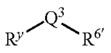

wherein $R^y$ is a group that can be converted to a group represented by the following formula:

[Chem. 57]

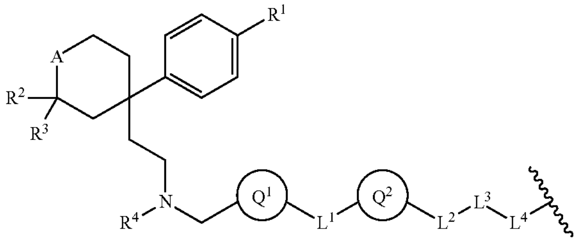

is shown below.

The starting compound (6) is either known or is produced according to a known or similar method using a known compound as a starting material. Known compounds can be purchased from commercial suppliers or can be readily synthesized by methods described in literatures or similar methods thereto. Examples of the known literatures include, but are not limited to, WO2022081928 A1, WO2022081927 A1, WO2019060693 A1, WO2019038717 A1, ACS Med. Chem. Lett., 2021, 12, 1733, WO2021170109 A1 and the like.

As examples of the production methods of the starting compound (6), Method N to Method P are described below, but the synthetic method of the starting compound (6) is not limited to these.

(Method N)

Compound n8, which is a starting compound (6) wherein $Q^3$ is a group selected from the following formulas:

[Chem. 58]

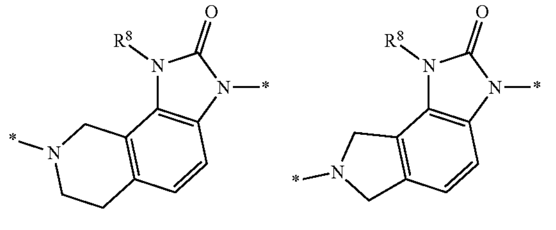

can be produced according to the following method.

[Chem. 59]

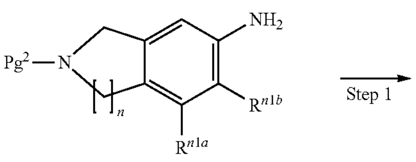

n1

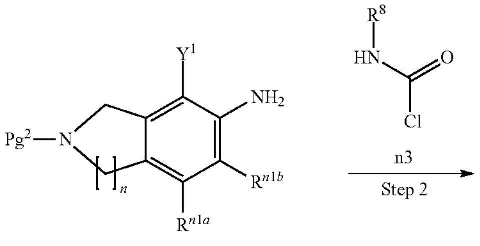

n2

-continued

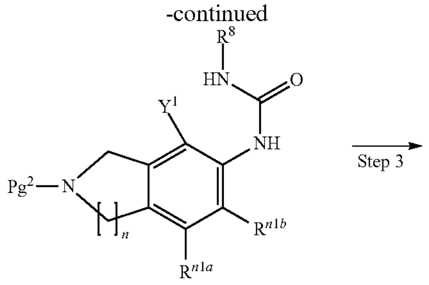

n4

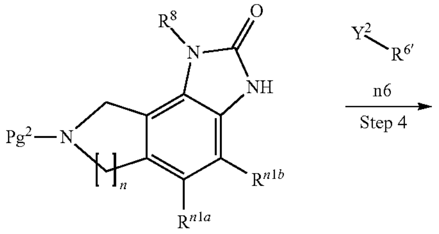

n5

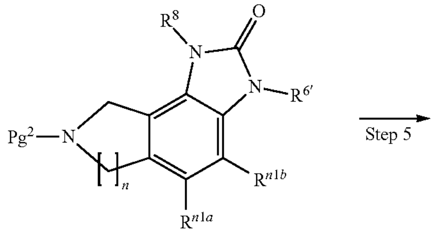

n7

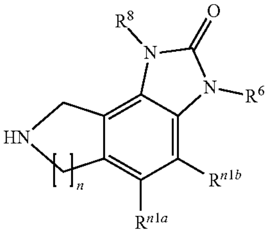

n8 wherein $Y^1$ is a halogen atom, $Y^2$ is a halogen atom, a dihydroxyboryl group or a pinacolatoboryl group and the like, $R^{n1a}$ and $R^{n1b}$ are each independently a hydrogen atom or a halogen atom, $Pg^2$ is an amino-protecting group, and n is an integer of 1 or 2.

In the first step, compound n1 is converted to compound n2 by a halogenation reaction. The halogenation in this step can be performed, for example, in a solvent such as DMF and the like, by reacting compound n1 with a halogenating agent such as N-bromosuccinimide, benzyltrimethylammonium tribromide, N-iodosuccinimide and the like.

In the second step, compound n4 is obtained by ureation of compound n2 using compound n3. The ureation reaction in this step can be performed, for example, by reacting compound n2 with compound n3 in a solvent such as dichloromethane and the like, in the presence of a base such as DIPEA and the like.

In the third step, compound n5 is obtained by a cyclization reaction of compound n4. The cyclization reaction in this step can be performed, for example, by reacting compound n4 with a copper catalyst such as copper(I) iodide and the like under heating in a solvent such as DMSO and the like, in the presence of a copper ligand such as trans-4-hydroxy-L-proline and the like and a base such as tripotassium phosphate and the like. The reaction temperature is preferably 80° C. to 160° C.

In the fourth step, compound n7 is obtained from compound n5 and compound n6. When $Y^2$ is a halogen atom, this step can be performed by an alkylation reaction. The alkylation reaction in this step can be performed, for example, by reacting compound n5 with compound n6 in a solvent such as DMF and the like, in the presence of a base such as potassium carbonate, cesium carbonate and the like. When $Y^2$ is a pinacolatoboryl group, this step can be performed by Chan-Lam-Evans coupling reaction. The Chan-Lam-Evans coupling reaction in this step can be performed, for example, by reacting compound n5 with compound n6 under heating in an organic solvent such as acetonitrile and the like, in the presence of a base such as triethylamine and the like and a metal catalyst such as copper(II) acetate and the like.

In the fifth step, compound n7 is converted to compound n8 by a deprotection reaction of an amino-protecting group $Pg^2$. The deprotection reaction in this step can be performed by a method generally used for the deprotection of an amino-protecting group.

(Method O)

Compound o4, which is a starting compound (6) wherein $Q^3$ is any group selected from the following formulas:

[Chem. 60]

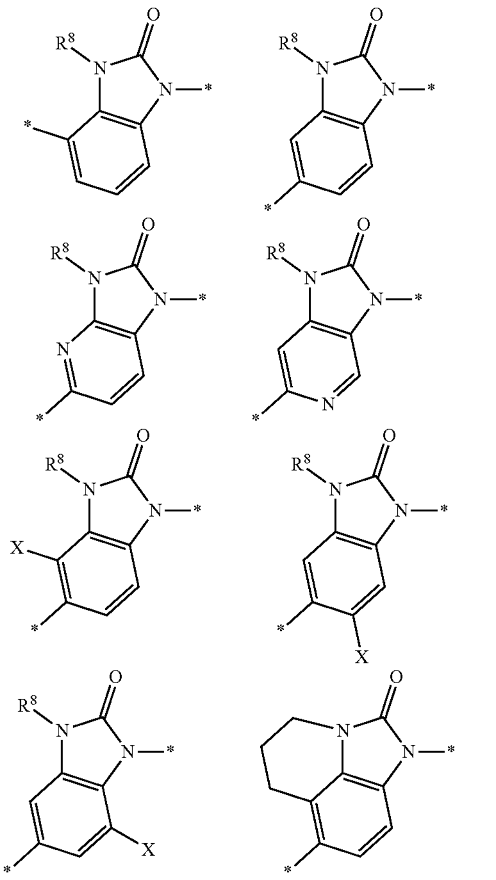

-continued

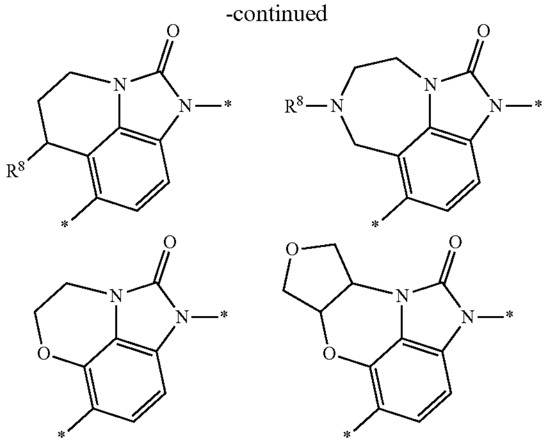

can be produced according to the following method.

[Chem. 61]

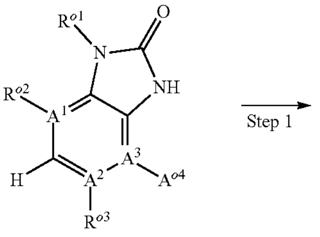

o1

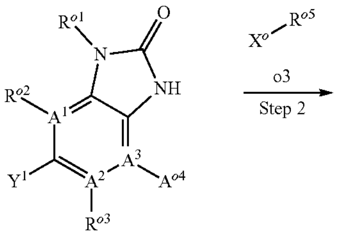

o2

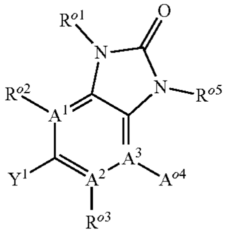

o4 wherein $A^1$, $A^2$, and $A^3$ are each independently a carbon atom or a nitrogen atom,

- $X^o$ is a halogen atom or a pinacolatoboryl group and the like,
- $Y^1$ is a nitro group or a halogen atom,
- $R^{o1}$ is $R^8$ or $R^{6'}$,
- $R^{o4}$ is $R^8$ or $R^{6'}$,
- when A1 is a nitrogen atom, $R^{o2}$ is absent,
- when A1 is a carbon atom, $R^{o2}$ is a hydrogen atom or a halogen atom, or $R^{o1}$ and $R^{o2}$ are bonded to each other to optionally form any partial structure selected from the group represented by the following formulas:

[Chem. 62]

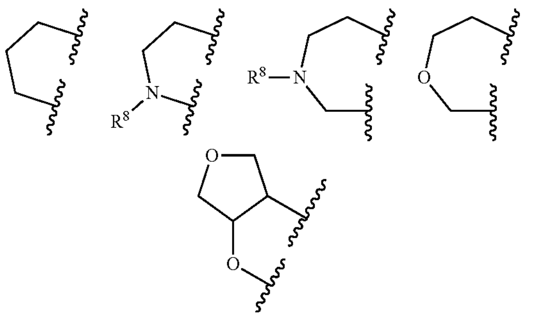

wherein the lower end of the partial structure is a bond of $R^{o2}$, and the upper end of the partial structure is a bond of $R^{o1}$, when $A^2$ is a nitrogen atom, $R^{o3}$ is absent, when $A^2$ is a carbon atom, $R^{o3}$ is a hydrogen atom or a halogen atom, when $A^3$ is a nitrogen atom, $R^{o4}$ is absent, and when $A^3$ is a carbon atom, $R^{o4}$ is a hydrogen atom or a halogen atom.

Compound o1 and compound o2 are either known or can be produced according to a known method or by appropriately combining similar methods using a known compound as a starting material. Examples of literatures on the above-mentioned known method include, but are not limited to, Bioorg. Med. Chem., 2013, 21, 125, J. Med. Chem., 1995, 38, 5, 771-793, WO2011163355 A1, WO2005044793 A2, WO2007015877 A2, WO2021213929 A1, WO2018039384 A1, WO2016097749 A1 and the like.

In the first step, compound o2 is obtained by nitration or halogenation of compound o1. The nitration reaction in this step can be performed, for example, by reacting compound o1 with a nitrating agent such as potassium nitrite and the like in an acid solvent such as trifluoroacetic acid and the like. The halogenation in this step can be performed under the same conditions as in the first step of Method N.

In the second step, compound o4 is obtained from compound o2 and compound o3 by an alkylation reaction or Chan-Lam-Evans coupling reaction. The alkylation or Chan-Lam-Evans coupling reaction in this step can be performed under the same conditions as in the fourth step of Method N.

(Method P)

Compound p5, which is a starting compound (6) wherein $Q^3$ is any group selected from the following formulas:

[Chem. 63]

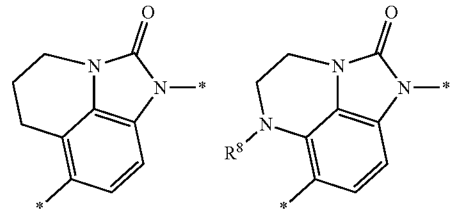

-continued

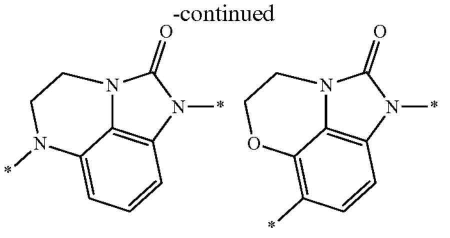

can be produced according to the following method.

[Chem. 64]

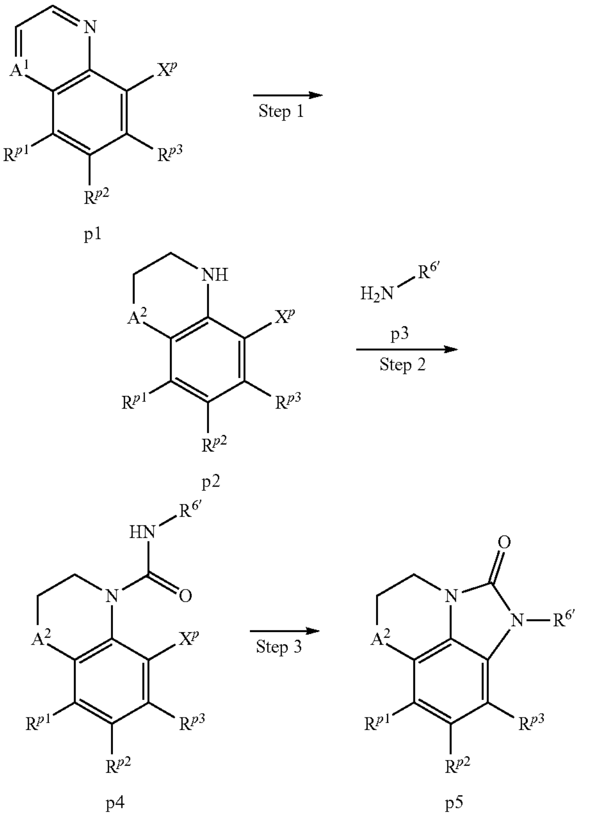

wherein A1 is CH or a nitrogen atom, $A^2$ is $CH_2$ or NH, $X^p$ is a halogen atom, $R^{p1}$, $R^{p2}$, and $R^{p3}$ are each independently a hydrogen atom or a halogen atom.

In the first step, compound p2 is obtained by a nuclear hydrogenation of compound p1. The nuclear hydrogenation reaction in this step can be performed, for example, by reacting compound p1 with a reducing agent such as diethyl 1,4-dihydro-2,6-dimethyl-3,5-pyridinedicarboxylate and the like under heating in a solvent such as dichloroethane and the like, in the presence of an acid such as boronic acid, para-toluenesulfonic acid and the like.

In the second step, compound p4 is obtained from compound p2 and compound p3 by ureation. The ureation reaction in this step can be performed under the same conditions as in the fourth step of Method L.

In the third step, compound p5 is obtained by cyclization reaction of compound p4. The cyclization reaction in this step can be performed under the same conditions as in the third step of Method N. The reaction temperature is preferably from room temperature to 100° C.

A production method of a starting compound represented by the formula (7):

[Chem. 65]

(7)

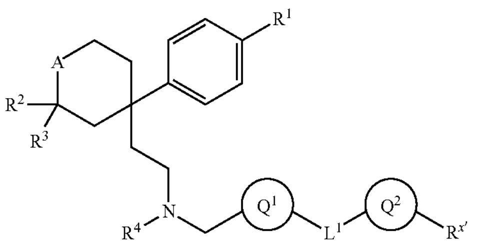

wherein $R^{x\prime}$ is a group that can be converted to a group represented by the following formula:

[Chem. 66]

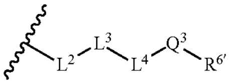

is shown below.

(Method Q)

Among the starting compounds (7), compound q12 wherein $R^4$ is a $C_{1-6}$ alkyl group optionally substituted by 1 to 3 halogen atoms or a $C_{3-6}$ cycloalkylmethyl group optionally substituted by one trifluoromethyl group, compound q11 wherein $R^4$ is a $C_{1-6}$ alkylcarbonyl group optionally substituted by 1 to 3 halogen atoms, and compound q14 wherein $R^4$ is a 6-membered heteroaryl group having 1 or 2 nitrogen atoms as ring member atoms (the heteroaryl group is optionally substituted by one halogen atom) can be produced according to the following method. A general production method for each reaction site is shown in order, but it is not necessary to perform each step in the order shown below as long as it does not affect the reaction substrate and reaction product.

[Chem. 67]

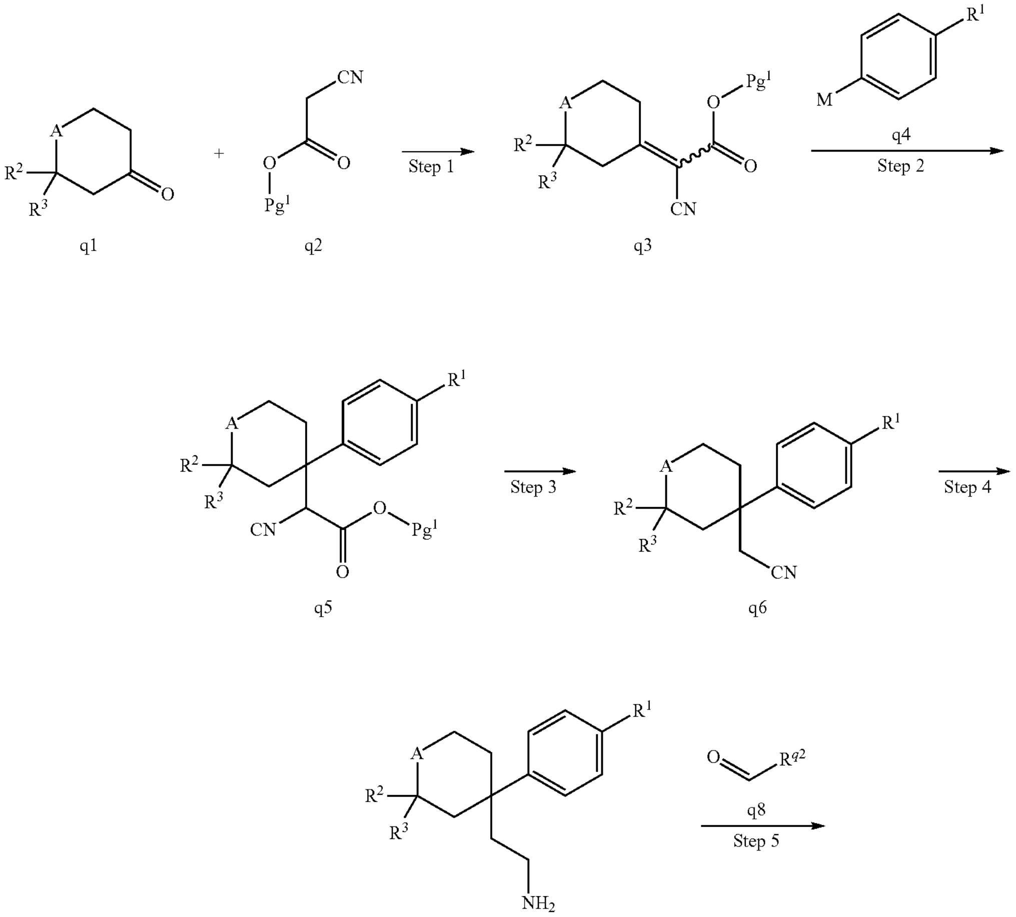

-continued

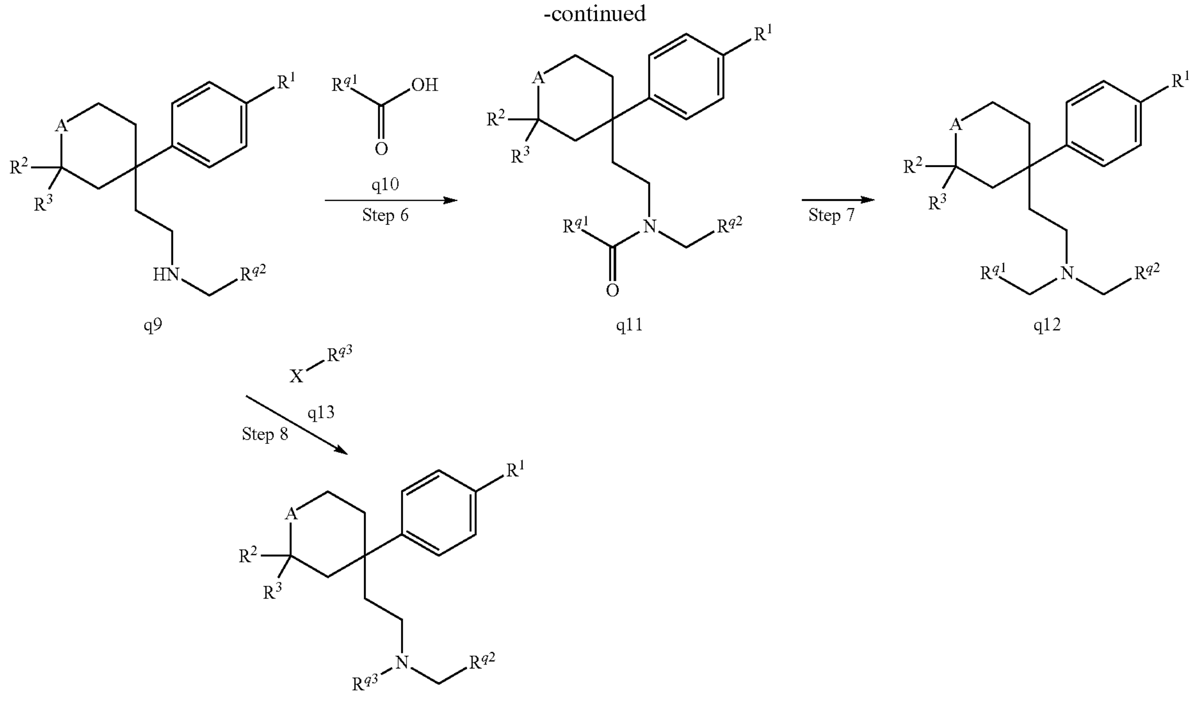

q9 q11 q12 q14 wherein $Pg^1$ is a carboxy-protecting group,

M is a metal or a metal halide (e.g., magnesium halide, lithium, zinc halide, etc.), $R^{q1}$ is a hydrogen atom, a $C_{1-5}$ alkyl group optionally substituted by 1 to 3 halogen atoms, or a $C_{3-6}$ cycloalkyl group optionally substituted by one trifluoromethyl group, $R^{q2}$ is a group represented by the following formula:

[Chem. 68]

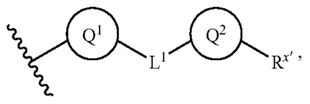

and $R^{q3}$ is a 6-membered heteroaryl group having 1 or 2 nitrogen atoms as ring member atoms (the heteroaryl group is optionally substituted by one halogen atom.

In the first step, compound q3 is obtained by aldol condensation reaction of compound q1 and compound q2. The aldol condensation reaction in this step can be performed by reacting compound q1 with compound q2 using, for example, acetic acid and piperidine as catalysts.

In the second step, compound q5 is obtained by 1,4-nucleophilic addition of compound q4 to the α,β-unsaturated ester of compound q3. The 1,4-nucleophilic addition reaction in this step can be performed, for example, by reacting compound q3 with compound q4 in a solvent such as THE and the like in the presence of a copper reagent such as copper(II) bromide and the like. The reaction temperature is preferably from −78° C. to room temperature.

In the third step, compound q6 is obtained by hydrolysis of the ester group of compound q5 and decarboxylation of the resulting carboxy group. The hydrolysis and decarboxylation reaction in this step can be performed, for example, by reacting compound q5 with a base such as sodium hydroxide and the like under heating in a solvent such as ethylene glycol and the like.

In the fourth step, compound q7 is obtained by reducing the cyano group of compound q6. The reduction reaction in this step can be performed, for example, by reacting compound q7 with a reducing agent such as lithium aluminum hydride and the like under heating in a solvent such as THF and the like.

In the fifth step, compound q9 is obtained from compound q7 and compound q8 by reductive amination reaction. The reductive amination reaction in this step can be performed under the same conditions as in the second step of Method I.

In the sixth step, compound q11 is obtained by condensing compound q9 and compound q10. The condensation reaction in this step can be performed under the same conditions as in the first step of Method J.

In the seventh step, compound q12 is obtained by reducing carbonyl group of compound q11. The reduction reaction in this step can be performed, for example, by reacting compound q11 with a reducing agent such as borane-THF complex and the like under heating in a solvent such as THF and the like.

In the eighth step, compound q14 is obtained from compound q9 and compound q13 by Buchwald amination reaction or aromatic nucleophilic substitution reaction. The Buchwald amination reaction in this step can be performed, for example, by reacting compound q9 with compound q13 under heating in a solvent such as 1,4-dioxane and the like, in the presence of a base such as cesium carbonate and the like and a metal catalyst such as RuPhos Pd G3, BrettPhos Pd G3 and the like. The aromatic nucleophilic substitution reaction in this step can be performed, for example, by reacting compound q9 with compound q13 under heating in a solvent such as 2-butanol, N,N-dimethylacetamide and the like, in the presence of a base such as 1,8-diazabicyclo [5.4.0]-7-undecene, potassium carbonate and the like.

(Method R)

Compound r4, which is a compound represented by the formula (7) wherein $L^1$ is —C(═O)—, can be produced according to the following method.

[Chem. 69]

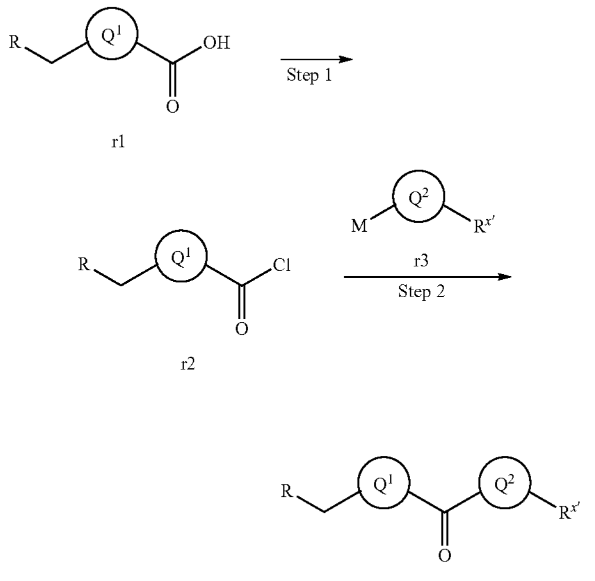

r1 r2 r3 r4 wherein R is a group represented by the following formula:

[Chem. 70]

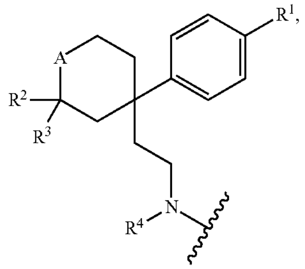

and

M is a dihydroxyboryl group, a pinacolatoboryl group, or the like.

In the first step, carboxylic acid r1 is converted to acid chloride r2. The chlorination reaction in this step can be performed, for example, by reacting compound r1 with a chlorinating agent such as oxalyl chloride, thionyl chloride and the like in a solvent such as dichloromethane and the like, in the presence of DMF.

In the second step, compound r4 is obtained by coupling reaction of compound r2 and compound r3. the coupling reaction in this step can be performed, for example, by reacting compound r2 with compound r3 under heating in a solvent such as toluene and the like, in the presence of a base such as cesium carbonate and the like and a metal catalyst such as tetrakis(triphenylphosphine)palladium(0) and the like. Examples of literature on this step include Catalysts 2019, 9(1), 53.

(Method S)

The $R^1$ moiety in a compound represented by the formula (7) can be produced according to the following production method.

[Chem. 71]

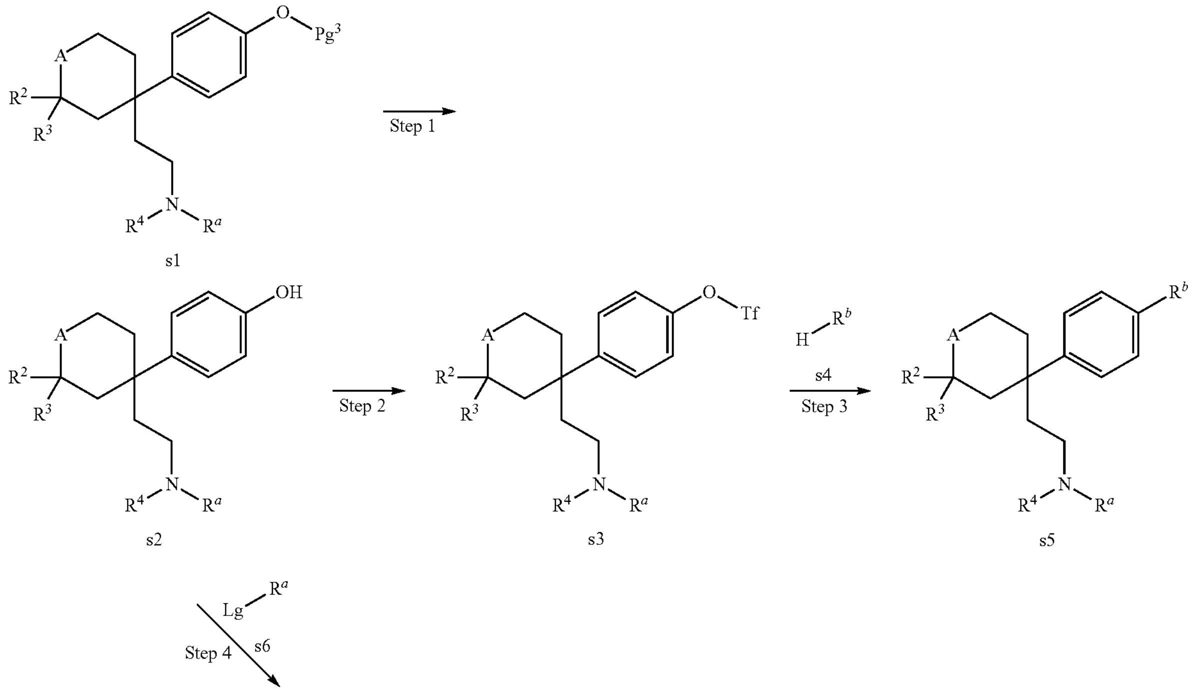

s1 s2 s3 s5

-continued

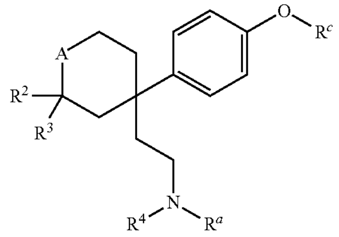

s7 wherein $Pg^3$ is a hydroxy-protecting group (e.g., methyl group, benzyl group, methoxymethyl group, etc.), Lg is a leaving group, $R^a$ is a group represented by the following formula:

[Chem. 72]

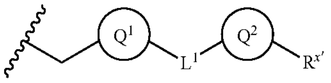

or a group that can be converted to a group represented by the formula, $R^b$ is a $C_{1-3}$ alkylamino group, a di-$C_{1-3}$ alkylamino group, or a 4- to 6-membered saturated heterocyclic group having one nitrogen atom as a ring member atom, and $R^c$ is a $C_{1-6}$ alkyl group optionally substituted by 1 to 3 halogen atoms.

In the first step, compound s2 is obtained from compound s1 by a deprotection reaction of a hydroxy-protecting group $Pg^3$. The deprotection reaction in this step can be performed by a method generally used for deprotection of a hydroxy-protecting group. For example, when $Pg^3$ is a methyl group, the deprotection can be performed by reacting compound s1 with sodium thiomethoxide under heating in a solvent such as DMF and the like. This reaction can also be performed under microwave irradiation. The reaction temperature is preferably 80° C. to 160° C.

In the second step, compound s3 is obtained by triflation of a hydroxy group of compound s2. The triflation reaction in this step can be performed, for example, by reacting compound s2 with a triflation agent such as trifluoromethanesulfonic anhydride and the like in a solvent such as dichloromethane and the like, in the presence of a base such as pyridine and the like.

In the third step, compound s5 is obtained from compound s3 and amine s4 by Buchwald amination reaction. The Buchwald amination reaction in this step can be performed by reacting compound s3 and amine s4 under heating in a solvent such as 1,4-dioxane and the like, in the presence of a ligand such as 2-(di-tert-butylphosphino)biphenyl and the like and a metal catalyst such as tris(dibenzylideneacetone) dipalladium(0) and the like.

In the fourth step, compound s7 is obtained from compound. s2 by alkylation reaction using an alkylating agent s6. The alkylation reaction in this step can be performed, for example, by reacting compound s2 with an alkylating agent s6 such as alkyl halide and the like under heating in a solvent such as DMF and the like, in the presence of a base such as potassium carbonate and the like. The reaction temperature is preferably from room temperature to 150° C.

A production method of a starting compound represented by the formula (8)

[Chem. 73]

(8)

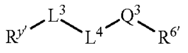

wherein $R^{y\prime}$ is a group that can be converted to a group represented by the following formula:

[Chem. 74]

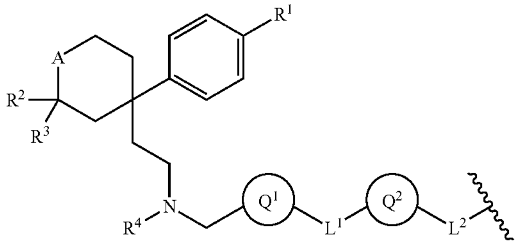

is shown below.

Among the starting compounds (8), a compound wherein $L^4$ is —C(═O)— as shown in the following formula:

[Chem. 75]

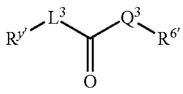

can be produced according to a method similar to that of Method H.

Among the starting compounds (8), a compound wherein $L^4$ is $CH_2$ as shown in the following formula:

[Chem. 76]

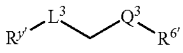

can be produced according to a method similar to that of Method I.

(Method T)

Among the starting compounds (8), compound t6 wherein $L^4$ is NH, and compound t8 wherein $L^4$ is N—$R^9$ ($R^9$ indicates a $C_{1-6}$ alkyl group) can be produced according to the following method.

[Chem. 77]

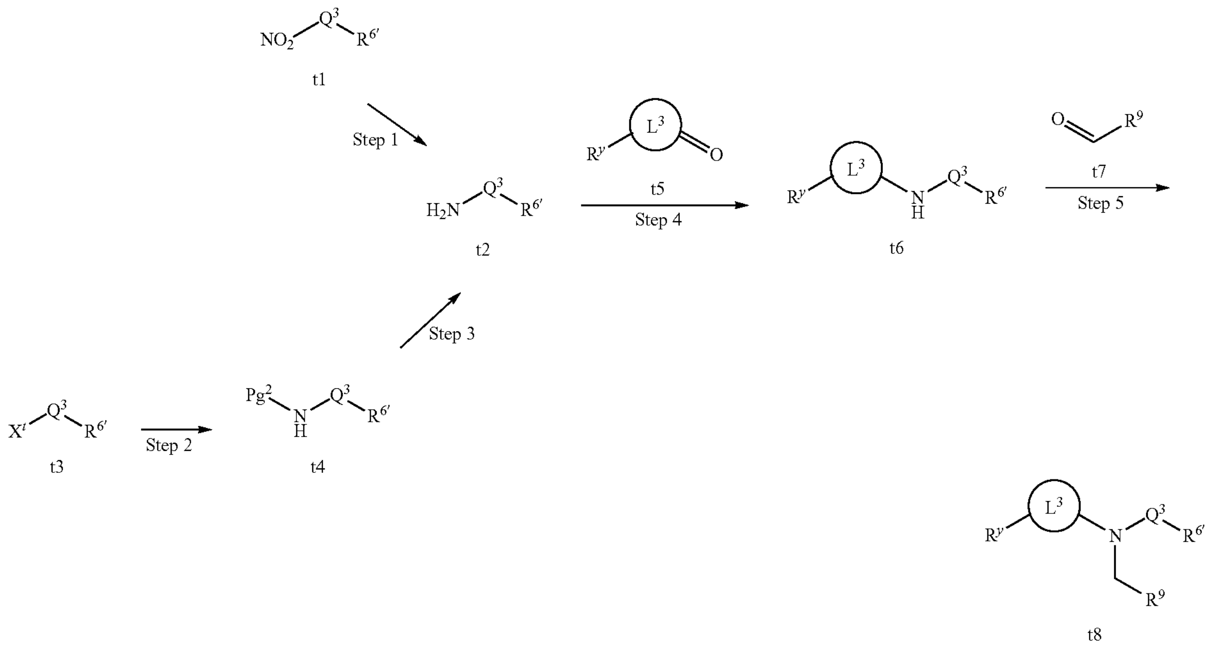

wherein $X^t$ is a halogen atom and $Pg^2$ is an amino-protecting group.

In the first step, compound t2 is obtained from compound t1 by reduction reaction of nitro group. the reduction reaction in this step can be performed by reacting compound t1 with a metal catalyst such as palladium carbon and the like in a solvent such as ethanol, THF and the like under a hydrogen atmosphere.

In the second step, compound t4 is obtained from compound t3 by Buchwald amination reaction. The amination reaction in this step can be performed under the same conditions as in the first step of Method L.

In the third step, compound t2 is obtained by deprotection reaction of the amino-protecting group $Pg^2$ of compound t4. The deprotection reaction in this step can be performed by a method generally used for deprotecting an amino-protecting group. For example, when $Pg^2$ is a tert-butoxycarbonyl group, the deprotection reaction can be performed by reacting compound t4 with an acid such as hydrochloric acid and the like in a solvent such as dichloromethane and the like.

In the fourth step in this step, compound t6 is obtained from compound t2 and compound t5 by reductive amination reaction. The reductive amination reaction in this step can be performed under the same conditions as in the second step of Method I. The reductive amination reaction in this step can also be performed by reacting compound t2 and compound t5 with a reducing agent such as borane-THF complex and the like in a solvent such as THF and the like.

In the fifth step, compound t8 is obtained from compound t6 and compound t7 by reductive amination reaction. The reductive amination reaction in this step can be performed under the same conditions as in the fourth step of this method.

A production method of a starting compound represented by the formula (9):

[Chem. 78]

(9)

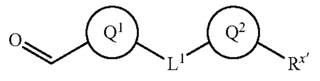

is shown below.

(Method U)

Among the starting compounds (9), compound u3 wherein $L^1$ is oxygen atom, compound u6 wherein $L^1$ is a single bond, and compounds u12 and u13 wherein $Q^1$ is a 7-azaspiro[3.5]nonane ring, can be respectively produced according to the following methods.

[Chem. 79]

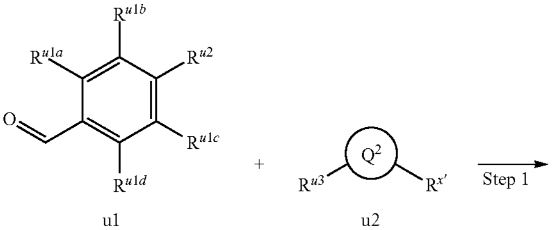

u1 u2

-continued

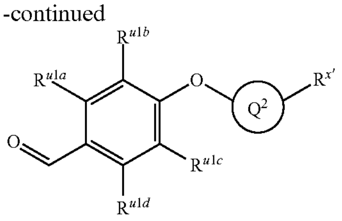

u3

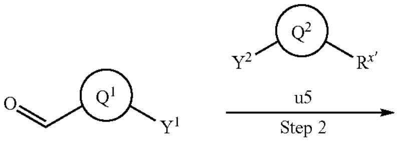

u4

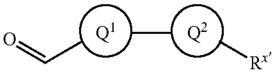

u6

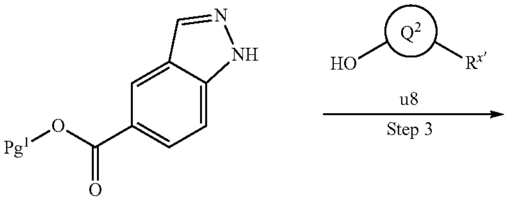

u7

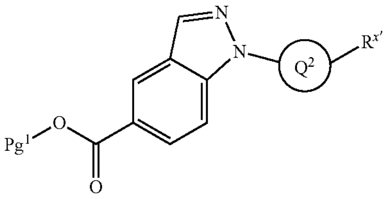

\+ u9

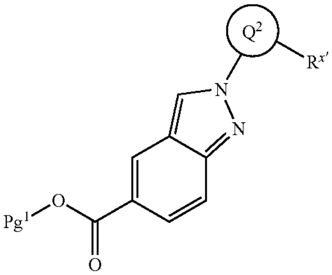

u10

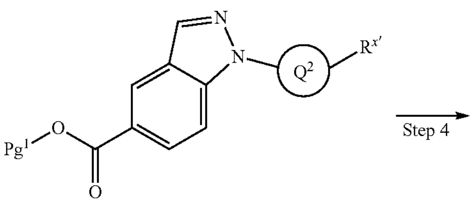

u9

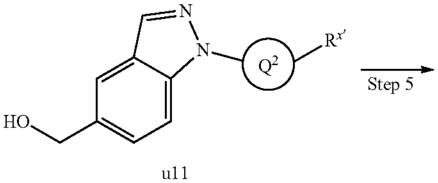

u11

-continued

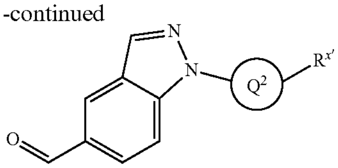

u12

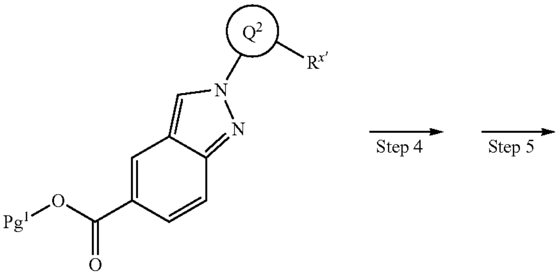

u10

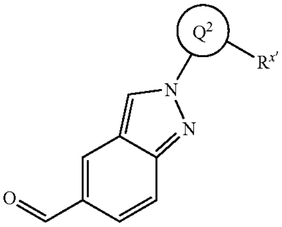

u13 wherein $R^{u1a}$, $R^{u1b}$, $R^{u1c}$, and $R^{u1d}$ are each independently a hydrogen atom, a halogen atom, or a $C_{1-6}$ alkyl group, $R^{u2}$ is a hydroxy group or a leaving group (when $R^{u2}$ is a hydroxy group, $R^{u3}$ is a hydroxy group or a leaving group, or when $R^{u2}$ is a leaving group, $R^{u3}$ is a hydroxy group), $Y^1$ is a halogen atom, a trifluoromethanesulfonyloxy group, a pinacolatoboryl group, or a dihydroxyboryl group (when $Y^1$ is a halogen atom or a trifluoromethanesulfonyloxy group, $Y^2$ is a pinacolatoboryl group or a dihydroxyboryl group, or when $Y^1$ is a pinacolatoboryl group or a dihydroxyboryl group, $Y^2$ is a halogen atom or a trifluoromethanesulfonyloxy group), $R^{x'}$ is a group that can be converted to a group represented by the following formula:

[Chem. 80]

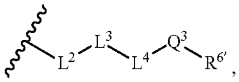

and $Pg^1$ is a carboxy-protecting group.

In the first step, compound u3 is obtained from compound u1 and compound u2. When $R^{u2}$ is a hydroxy group and $R^{u3}$ is a hydroxy group, this reaction can be performed by Mitsunobu reaction. The Mitsunobu reaction in this step can be performed, for example, by reacting compound u1 and compound u2 with phosphine such as triphenylphosphine and the like and azodicarboxylic acid ester such as diisopropyl azodicarboxylate and the like in a solvent such as tetrahydrofuran and the like. When either $R^{u2}$ or $R^{u3}$ is a leaving group, this reaction can be performed by a nucleophilic substitution reaction. The nucleophilic substitution reaction in this step can be performed, for example, by reacting compound u1 and compound u2 with a base such as potassium carbonate, cesium carbonate and the like under heating in a solvent such as DMF, DMA and the like.

In the second step, compound u6 is obtained by coupling reaction of compound u4 and compound u5. The coupling reaction in this step can be performed, for example, by heating compound u4 and compound u5 in a solvent such as aqueous 1,4-dioxane and the like, in the presence of a base such as potassium carbonate and the like and a metal catalyst such as [1,1'-bis(diphenylphosphino)ferrocene]palladium (II) dichloride dichloromethane adduct and the like.

In the third step, compound u9 and compound u10 are obtained from compound u7 and compound u8 by Mitsunobu reaction. The Mitsunobu reaction in this step can be performed, for example, by reacting compound u7 and compound u8 with a phosphorane reagent such as cyanomethylenetributylphosphorane and the like under heating in a solvent such as toluene and the like.

In the fourth step, compound u11 is obtained by reduction reaction of compound u9. The reduction reaction in this step can be performed under the same conditions as in the first step of Method M.

In the fifth step, compound u12 is obtained by oxidation reaction of compound u11. The oxidation reaction in this step can be performed, for example, by reacting compound u11 with an oxidizing agent such as 1,1,1-triacetoxy-1,1-dihydro-1,2-benzoiodoxol-3-(1H)-one, manganese(IV) oxide and the like in a solvent such as dichloromethane and the like.

Compound u13 can be obtained by subjecting compound u10 to the same steps as the fourth step and the fifth step of this method.

12. Activity

In one embodiment of the present invention, the compound or polyfunctional molecule of the present invention specifically binds to SF-1. The binding activity to SF-1 can be measured using any known method, for example, by reacting a test substance, a molecule (e.g., DAX1 peptide) known to specifically bind to SF-1 (particularly, SF-1 ligand binding domain (LBD)), and SF-1 (particularly SF-1-LBD), and quantifying a decrease in the binding rate to SF-1 by the molecule known to specifically bind to SF-1 (e.g., by calculating the $IC_{50}$ value). In general, in such a test system, a test substance with an $IC_{50}$ value of 100 μM or less is considered to specifically bind to SF-1. Thus, in one embodiment of the present invention, the compound or polyfunctional molecule of the present invention has an $IC_{50}$ value of 100 μM or less, preferably an $IC_{50}$ value of 10 μM or less, particularly preferably an $IC_{50}$ value of 1 μM or less, in relation to the decrease in the binding rate to SF-1 by a molecule known to specifically bind to SF-1 (e.g., DAX1 peptide). In another embodiment of the present invention, the compound or polyfunctional molecule of the present invention has an $IC_{50}$ value of 100 μM or less, preferably an $IC_{50}$ value of 10 μM or less, particularly preferably an $IC_{50}$ value of 1 μM or less, in relation to the decrease in the binding rate to SF-1-LBD by a DAX1 peptide, in the test system and test conditions disclosed in Experimental Example 1 of the present specification.

In one embodiment of the present invention, the compound or polyfunctional molecule of the present invention has SF-1 antagonist activity. The SF-1 antagonist activity can be measured using any known method. For example, the activity can be measured by adding a test substance to cells expressing SF-1, culturing the cells for a certain period of time, and quantifying a decrease in the expression level of a target gene of SF-1 (e.g., CYP11A1, CYP17A1, CYP21A2, STAR, etc.) (e.g., by calculating $IC_{50}$ values). In general, in such test system, a test substance having an $IC_{50}$ value of 100 μM or less for a target gene of SF-1 is considered to have antagonist activity against SF-1. Therefore, in one embodiment of the present invention, the compound or polyfunctional molecule of the present invention has an $IC_{50}$ value of 100 μM or less, preferably an $IC_{50}$ value of 10 μM or less, particularly preferably an $IC_{50}$ value of 1 μM or less for a target gene of SF-1 (e.g., CYP11A1, CYP17A1, CYP21A2, and/or STAR). In another embodiment of the present invention, the compound or polyfunctional molecule of the present invention has an $IC_{50}$ value of 100 μM or less, preferably an $IC_{50}$ value of 10 μM or less, particularly preferably an $IC_{50}$ value of 1 μM or less, against CYP11A1, CYP17A1, CYP21A2 and/or STAR in the test system and test conditions disclosed in Experimental Example 2 of the present specification.

In one embodiment of the present invention, the compound or polyfunctional molecule of the present invention has SF-1 degradation inducing activity. The SF-1 degradation inducing activity can be measured using any known method, for example, by adding a test substance to cells expressing SF-1, culturing them for a certain period of time, and then quantifying the expression level of SF-1. The SF-1 degradation inducing activity can also be measured, for example, by knocking in an easily detectable peptide tag (e.g., HiBiT tag) at the endogenous SF-1 gene locus in cells expressing SF-1, adding a test substance to the cells, culturing them for a certain period of time, and then observing the expression level of the peptide tag. In general, in such test system, a test substance with a concentration ($DC_{50}$ value) of SF-1 of 100 μM or less that induces 50% degradation is considered to have SF-1 degradation inducing activity. Accordingly, in one embodiment of the present invention, the compound or polyfunctional molecule of the present invention has a $DC_{50}$ value of 100 μM or less, preferably a $DC_{50}$ value of 10 μM or less, particularly preferably a $DC_{50}$ value of 1 μM or less, against SF-1. In another embodiment of the present invention, the compound or polyfunctional molecule of the present invention has a $DC_{50}$ value of 100 μM or less, preferably a $DC_{50}$ value of 10 μM or less, particularly preferably a $DC_{50}$ value of 1 μM or less, against SF-1 in the test system and test conditions disclosed in Experimental Example 3 of the present specification.

In one embodiment of the present invention, the compound or polyfunctional molecule of the present invention has growth inhibitory activity against tumors in which SF-1 is involved in the development or progression of the tumor. In another embodiment of the present invention, the compound or polyfunctional molecule of the present invention has growth inhibitory activity against adrenocortical carcinoma. In yet another embodiment of the present invention, the compound or polyfunctional molecule of the present invention has growth inhibitory activity against NCI-H295R cells, an adrenocortical carcinoma cell line. The growth inhibitory activity against tumor cells can be measured using any known method, and typically can be measured by adding a test substance to a model cell of the target tumor, culturing the cell for a certain period of time, and then quantifying the growth rate of the tumor cells. In general, in such test system, a test substance with a concentration ($GI_{50}$ value) of 100 μM or less that inhibits 50% of tumor cell growth is considered to have growth inhibitory activity. Therefore, in one embodiment of the present invention, the compound or polyfunctional molecule of the present invention has a $GI_{50}$ value of 100 μM or less, preferably a $GI_{50}$ value of 10 μM or less, particularly preferably a $GI_{50}$ value of 1 μM or less, against tumor cells (e.g., NCI-H295R cells). In another embodiment of the present invention, the compound or polyfunctional molecule of the present invention has a $GI_{50}$ value of 100 μM or less, preferably a $GI_{50}$ value of 10 μM or less, particularly preferably a $GI_{50}$ value of 1 μM or less, against tumor cells (e.g., NCI-H295R cells) in the test system and test conditions disclosed in Experimental Example 4 of the present specification.

In one embodiment of the present invention, the compound or polyfunctional molecule of the present invention has antitumor activity against an animal model (e.g., mice) in which a tumor cell in which SF-1 is involved in the development or progression, such as NCI-H295R cell (adrenocortical carcinoma cell line), VCap cell (prostate cancer cell line), or a tumor derived from a prostate cancer patient, has been subcutaneously transplanted. The antitumor activity in the transplant model can be measured using any known method, for example, using the protocols described in Experimental Example and Experimental Example 6 of the present specification. In addition, the therapeutic effect of the compound or polyfunctional molecule of the present invention against breast cancer can be measured using the protocol described in Experimental Example 7 of the present specification.

EXAMPLE

The present invention is described in detail by the following examples, which are merely an implementation and do not limit the present invention, and may be varied to the extent not departing from the scope of the present invention. In the following examples, "%" indicates mol/mol % for yield, volume % for solvents used in chromatography, and weight % for others.

Nuclear magnetic resonance spectra (1H-NMR, resonance frequency 400 MHz or 500 MHz) are listed as 6 values (ppm) with tetramethylsilane as the standard or with the chemical shift value of the deuterated solvent used as the reference value. Other abbreviations used in the text have the following meanings.

s: singlet
d: doublet
dd: doublet of doublets
t: triplet
dt: doublet of triplets
q: quartet
m: multiplet
br: broad
J: coupling constant
Hz: hertz
$CDCl_3$: deuterochloroform
DMSO-$d_6$: deuterodimethyl sulfoxide
$CD_3OD$: deuterated methanol
1H-NMR: proton nuclear magnetic resonance
HPLC: high performance liquid chromatography
SFC: supercritical fluid chromatography
$sCO_2$: supercritical carbon dioxide
APCI: atmospheric pressure chemical ionization
ESI: electrospray ionization
THF: tetrahydrofuran
DMF: N,N-dimethylformamide
HATU: 1-[bis(dimethylamino)methylene]-1H-1,2,3-triazolo[4,5-b]pyridinium 3-oxide hexafluorophosphate
DIPEA: N,N-diisopropylethylamine
RuPhos Pd G3: (2-dicyclohexylphosphino-2',6'-diisopropyloxy-1,1'-biphenyl) [2-(2'-amino-1,1'-biphenyl)]palladium(II) methanesulfonate
BrettPhos Pd G3: [(2-dicyclohexylphosphino-3,6-dimethoxy-2',4',6'-triisopropyl-1,1'-biphenyl)-2-(2'-amino-1,1'-biphenyl)]palladium(II) methanesulfonate
(S)-(−)-Tol-BINAP: (S)-(−)-2,2'-bis(di-p-tolylphosphino)-1,1'-binaphthyl
XantPhos: 4,5-bis(diphenylphosphino)-9,9-dimethylxanthene (CAS Registry Number: 161265-03-8)
IPA: isopropyl alcohol
DCM: dichloromethane
DMSO: dimethyl sulfoxide
TLC: thin layer chromatography In the following Examples, the structure represented by the formula:

[Chem. 81]

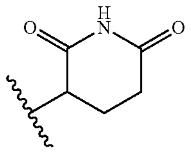

indicates that the asymmetric carbon in the structure has a mixture of α-configuration and β-configuration.

The reagents, solvents, devices, and the like used in the following Examples are commercially available unless otherwise specified. Furthermore, the raw material compounds used are known compounds and commercially available, or compounds synthesized and identified according to a method known per se or a method analogous thereto, unless otherwise specified.

<Example A1> Ethyl cyano (2,2-dimethyltetrahydro-4H-pyran-4-ylidene)acetate

Under ice-cooling, to 2,2-dimethyltetrahydro-4H-pyran-4-one (CAS Registry Number: 1194-16-7) (200 g, 1.56 mol) was added dropwise ethyl cyanoacetate (175 mL, 1.65 mol) over 10 min, acetic acid (18 mL, 0.32 mol) was added dropwise over 5 min, and then piperidine (31 mL, 0.31 mol) was added dropwise over 10 min. The reaction mixture was warmed to room temperature and stirred for 41 hr. The reaction mixture was diluted with ethyl acetate (2 L), and washed successively with 1 mol/L aqueous sodium hydroxide solution (1.5 L), water (1.5 L), and saturated brine. The organic layer was dried over anhydrous sodium sulfate, filtered, and the filtrate was concentrated under reduced pressure and further dried under reduced pressure to give the title compound (324 g, 1.45 mol, yield 93%).

<Example A2> Ethyl [4-(4-chlorophenyl)-2,2-dimethyltetrahydro-2H-pyran-4-yl](cyano)acetate Using the compound obtained in <Example A1> and 4-chlorophenylmagnesium bromide (CAS Registry Number: 873-77-8), the title compound was obtained by the same method as in <Example C3>.

<Example A3> 2-[4-(4-Chlorophenyl)-2,2-dimethyltetrahydro-2H-pyran-4-yl]ethanamine Using the compound obtained in <Example A2>, the title compound was obtained by sequentially performing the same operations as in <Example C4> and <Example C5>.

<Example A4> Ethyl trans-4-(4-formylphenoxy)cyclohexanecarboxylate

To a solution of 4-hydroxybenzaldehyde (CAS Registry Number: 123-08-0) (10.0 g, 81.9 mmol), ethyl cis-4-hydroxycyclohexanecarboxylate (WO 2011143645 A1) (14.8 g, 86.0 mmol), and tri-n-butylphosphine (24.5 mL, 98.3 mmol) in toluene (400 mL) was added at room temperature 1,1'-(azodicarbonyl) dipiperidine (24.8 g, 98.3 mmol) by small portions, and the mixture was stirred at room temperature for 1 hr, and at 95° C. for 3 hr. The reaction mixture was cooled to room temperature, diluted with ethyl acetate (600 mL), and washed successively with water and saturated brine. The organic layer was dried over anhydrous sodium sulfate, filtered, and the filtrate was concentrated under reduced pressure. The precipitated solid was collected by filtration and washed with a mixed solvent of hexane/ethyl acetate (1/1). The filtrate was concentrated under reduced pressure and the residue was purified by silica gel column chromatography (hexane/ethyl acetate) to give the title compound (5.94 g, 21.5 mmol, yield 26%).

<Example A5> Ethyl trans-4-{4-[({2-[4-(4-chlorophenyl)-2,2-dimethyltetrahydro-2H-pyran-4-yl]ethyl)amino)methyl]phenoxy}cyclohexanecarboxylate Using the compounds obtained in <Example A4> and <Example A3>, the title compound was obtained by the same method as in <Example D1>.

<Example A6> Trans-4-(4-{[{2-[4-(4-chlorophenyl)-2,2-dimethyltetrahydro-2H-pyran-4-yl]ethyl)(2,2-dimethylpropanoyl)amino]methyl}phenoxy)cyclohexanecarboxylic acid Using the compound obtained in <Example A5>, the title compound was obtained by sequentially performing the same operations as in <Example D2> and <Example S4>.

<Example B1> Ethyl cyano{2,2-dimethyl-4-[4-(trifluoromethoxy)phenyl]tetrahydro-2H-pyran-4-yl}acetate Using the compound obtained in <Example A1> and 4-(trifluoromethoxy)phenylmagnesium bromide (CAS Registry Number: 169222-42-8, 0.50 mol/L THF solution), the title compound was obtained by the same method as in <Example C3>.

<Example B2> 2-{2,2-Dimethyl-4-[4-(trifluoromethoxy)phenyl]tetrahydro-2H-pyran-4-yl}ethanamine Using the compound obtained in <Example B1>, the title compound was obtained by sequentially performing the same operations as in <Example C4> and <Example C5>.

<Example B3> Ethyl trans-4-(4-{[(2-{2,2-dimethyl-4-[4-(trifluoromethoxy)phenyl]tetrahydro-2H-pyran-4-yl}ethyl)amino]methyl}phenoxy)cyclohexanecarboxylate Using the compounds obtained in <Example A4> and <Example B2>, the title compound was obtained by the same method as in <Example D1>.

<Example B4> Ethyl trans-4-(4-{[(2,2-dimethylpropanoyl) (2-{2,2-dimethyl-4-[4-(trifluoromethoxy)phenyl]tetrahydro-2H-pyran-4-yl}ethyl)amino]methyl}phenoxy)cyclohexanecarboxylate Using the compound obtained in <Example B3>, the title compound was obtained by the same method as in <Example D2>.

<Example B5> Trans-4-(4-{[(2,2-dimethylpropanoyl) (2-{2,2-dimethyl-4-[4-(trifluoromethoxy)phenyl]tetrahydro-2H-pyran-4-yl}ethyl)amino]methyl}phenoxy)cyclohexanecarboxylic acid Using the compound obtained in <Example B4>, the title compound was obtained by the same method as in <Example S4>.

<Example C1> Ethyl (cis-4-hydroxycyclohexyl)acetate

To a solution of cis-2-(4-hydroxycyclohexyl)acetic acid (CAS Registry Number: 68592-22-3) (2.53 g, 16.0 mmol) in ethanol (46 mL) was added sulfuric acid (0.086 mL, 1.60 mmol), and the mixture was heated under reflux for 7 hr. The reaction mixture was cooled to room temperature, and concentrated under reduced pressure. The residue was diluted with ethyl acetate, and washed successively with saturated aqueous sodium hydrogen carbonate solution and saturated brine. The organic layer was dried over anhydrous sodium sulfate, filtered, and the filtrate was concentrated under reduced pressure to give the title compound (2.66 g, 14.3 mmol, yield 89%).

<Example C2> Ethyl [trans-4-(2-chloro-4-formylphenoxy)cyclohexyl]acetate

Using the compound obtained in <Example C1> and 3-chloro-4-hydroxybenzaldehyde (CAS Registry Number: 2420-16-8), the title compound was obtained by the same method as in <Example A4>.

<Example C3> Ethyl cyano[4-(4-methoxyphenyl)-2,2-dimethyltetrahydro-2H-pyran-4-yl]acetate To a solution of ethyl cyano(2,2-dimethyltetrahydro-4H-pyran-4-ylidene)acetate (8.92 g, 40.0 mmol) in THF (131 mL) was added at −78° C. copper(I) bromide-dimethyl sulfide complex (0.805 g, 3.92 mmol) and, after stirring at said temperature for 2 hr, 4-methoxyphenylmagnesium bromide (CAS Registry Number: 13139-86-1) (0.50 mol/L THF solution, 100 mL, 50 mmol) was added dropwise over 20 min at said temperature. The reaction mixture was stirred for 1.5 hr while raising the temperature to room temperature and left standing at room temperature overnight. To the reaction mixture was added at −78° C. copper(I) bromide-dimethyl sulfide complex (0.805 g, 3.92 mmol), and the mixture was stirred at said temperature for 5 min. Then, 4-methoxyphenylmagnesium bromide (0.50 mol/L THF solution, 47 mL, 23.5 mmol) was added dropwise thereto over 5 min at said temperature, and the mixture was stirred for 6 hr while raising the temperature to room temperature. To the reaction mixture was added 1 mol/L hydrochloric acid (80 mL) under ice-cooling, and the mixture was extracted with ethyl acetate. The obtained organic layer was washed with water, dried over anhydrous sodium sulfate, filtered, and the filtrate was concentrated under reduced pressure. The obtained residue was purified by silica gel column chromatography (hexane/ethyl acetate) to give the title compound (6.72 g, 20.3 mmol, yield 51%).

<Example C4> [4-(4-Methoxyphenyl)-2,2-dimethyl-tetrahydro-2H-pyran-4-yl]acetonitrile To a solution of ethyl cyano[4-(4-methoxyphenyl)-2,2-dimethyltetrahydro-2H-pyran-4-yl]acetate (10.8 g, 32.6 mmol) in ethylene glycol (109 mL) was added sodium hydroxide (3.26 g, 81.5 mmol) at room temperature, and the mixture was stirred at 150° C. for 7 hr and left standing at room temperature overnight. To the reaction mixture was added, under ice-cooling, ice, water and 1 mol/L hydrochloric acid and, after adjusting the pH to 1-2, the mixture was extracted with DCM. The obtained organic layer was washed successively with water and saturated brine, dried over anhydrous sodium sulfate, and filtered, and the filtrate was concentrated under reduced pressure. The obtained residue was purified by silica gel column chromatography (hexane/ethyl acetate) to give the title compound (5.91 g, 22.8 mmol, yield 70%).

<Example C5> 2-[4-(4-Methoxyphenyl)-2,2-dimethyltetrahydro-2H-pyran-4-yl]ethanamine To a solution of [4-(4-methoxyphenyl)-2,2-dimethyltetrahydro-2H-pyran-4-yl]acetonitrile (8.72 g, 33.6 mmol) in THF (224 mL) was added lithium aluminum hydride (3.19 g, 84.1 mmol) under ice-cooling over 10 min, and the mixture was stirred for 1.5 hr while raising the temperature to room temperature, at 35° C. for 4 hr, and at 50° C. for 2 hr. After cooling, water (3.2 mL) was added to the reaction mixture under ice-cooling, 1 mol/L aqueous sodium hydroxide solution (3.2 mL) and water (9.0 mL) were added, the resulting precipitate was collected by filtration through celite and washed with THF. The filtrate was concentrated under reduced pressure, the obtained residue was purified by amine-modified silica gel column chromatography (hexane/ethyl acetate and ethyl acetate/methanol) to give the title compound (1.74 g, 6.61 mmol, yield 20%).

<Example C6> Ethyl (trans-4-{2-chloro-4-[({2-[4-(4-methoxyphenyl)-2,2-dimethyltetrahydro-2H-pyran-4-yl]ethyl}amino)methyl]phenoxy}cyclohexyl)acetate Using the compounds obtained in <Example C2> and <Example C5>, the title compound was obtained by the same method as in <Example D1>.

<Example C7> Ethyl [trans-4-(2-chloro-4-{[(2,2-dimethylpropanoyl){2-[4-(4-methoxyphenyl)-2,2-dimethyltetrahydro-2H-pyran-4-yl]ethyl}amino]methyl}phenoxy)cyclohexyl]acetate Using the compound obtained in <Example C6>, the title compound was obtained by the same method as in <Example D2>.

<Example C8> [Trans-4-(2-chloro-4-{[(2,2-dimethylpropanoyl) {2-[4-(4-methoxyphenyl)-2,2-dimethyltetrahydro-2H-pyran-4-yl]ethyl}amino]methyl}phenoxy)cyclohexyl]acetic acid Using the compound obtained in <Example C7>, the title compound was obtained by the same method as in <Example S4>.

<Example D1> Ethyl trans-4-{4-[({2-[4-(4-methoxyphenyl)-2,2-dimethyltetrahydro-2H-pyran-4-yl]ethyl}amino)methyl]phenoxy}cyclohexanecarboxylate To a solution of 2-[4-(4-methoxyphenyl)-2,2-dimethyltetrahydro-2H-pyran-4-yl]ethanamine (3.89 g, 14.8 mmol) in toluene (72.4 mL) was added ethyl trans-4-(4-formylphenoxy)cyclohexanecarboxylate (4.00 g, 14.5 mmol) at room temperature, and the mixture was heated under reflux under a Dean-Stark apparatus. The mixture was stirred for 7 hr while gradually removing the solvent and left standing at room temperature overnight. The reaction mixture was heated under reflux under a Dean-Stark apparatus. The mixture was stirred for 1 hr while gradually removing the solvent and, after cooling, the organic solvent was evaporated under reduced pressure. The obtained residue was dissolved in methanol (145 mL), sodium borohydride (0.714 g, 17.4 mmol) was added thereto, under ice-cooling, and the mixture was stirred at said temperature for 5 min, and stirred for 1.5 hr while raising the temperature to room temperature. To the reaction mixture were added saturated aqueous ammonium chloride solution and water under ice-cooling, and the mixture was left standing overnight. The reaction mixture was extracted with DCM, and the obtained organic layer was dried over anhydrous sodium sulfate and filtered, and the filtrate was concentrated under reduced pressure. The obtained residue was purified by silica gel column chromatography (DCM/methanol) to give the title compound (5.13 g, 9.79 mmol, yield 68%).

<Example D2> Ethyl trans-4-(4-{[(2,2-dimethylpropanoyl) {2-[4-(4-methoxyphenyl)-2,2-dimethyltetrahydro-2H-pyran-4-yl]ethyl}amino]methyl}phenoxy)cyclohexanecarboxylate To a solution of ethyl trans-4-{4-[({2-[4-(4-methoxyphenyl)-2,2-dimethyltetrahydro-2H-pyran-4-yl]ethyl}amino)methyl]phenoxy}cyclohexanecarboxylate (1.11 g, 2.12 mmol) in DCM (21 mL) were added, under ice-cooling, triethylamine (0.588 mL, 4.24 mmol) and pivaloyl chloride (421 mg, 3.49 mmol), and the mixture was stirred at room temperature for 2.5 hr. To the reaction mixture was added, under ice-cooling, water, and the mixture was extracted with DCM. The obtained organic layer was dried over anhydrous sodium sulfate and filtered, and the filtrate was concentrated under reduced pressure. The obtained residue was purified by silica gel column chromatography (hexane/ethyl acetate) to give the title compound (1.19 g, 1.96 mmol, yield 92%).

<Example D3> Trans-4-(4-{[(2,2-dimethylpropanoyl){2-[4-(4-methoxyphenyl)-2,2-dimethyltetrahydro-2H-pyran-4-yl]ethyl}amino]methyl}phenoxy)cyclohexanecarboxylic acid To a solution of ethyl trans-4-(4-{[(2,2-dimethylpropanoyl){2-[4-(4-methoxyphenyl)-2,2-dimethyltetrahydro-2H-pyran-4-yl]ethyl}amino]methyl}phenoxy)cyclohexanecarboxylate (1.18 g, 1.94 mmol) in methanol (19.4 mL) was added at room temperature 1 mol/L aqueous sodium hydroxide solution (9.71 mL, 9.71 mmol), and the mixture was stirred at said temperature for 30 min and left standing overnight. To the reaction mixture was neutralized, under ice-cooling, with 1 mol/L hydrochloric acid (9.71 mL, 9.71 mmol), and the organic solvent was evaporated under reduced pressure. The mixture was extracted with DCM, and the obtained organic layer was dried over anhydrous sodium sulfate and filtered, and the filtrate was concentrated under reduced pressure. The obtained residue was purified by silica gel column chromatography (DCM/methanol) to give the title compound (943 mg, 1.63 mmol, yield 84%).

<Example E1> Ethyl trans-4-(4-{[(2,2-dimethylpropanoyl){2-[(4R)-4-(4-methoxyphenyl)-2,2-dimethyltetrahydro-2H-pyran-4-yl]ethyl}amino]methyl}phenoxy)cyclohexanecarboxylate The racemic ethyl trans-4-(4-{[(2,2-dimethylpropanoyl){2-[4-(4-methoxyphenyl)-2,2-dimethyltetrahydro-2H-pyran-4-yl]ethyl}amino]methyl}phenoxy)cyclohexanecarboxylate was optically resolved by chiral HPLC [column: CHIRALPAK IC (registered trademark, Daicel Corporation), mobile phase: hexane/ethanol=50/50 (V/V)] to obtain the title compound as the component eluted first.

<Example E2> Trans-4-(4-{[(2,2-dimethylpropanoyl) {2-[(4R)-4-(4-methoxyphenyl)-2,2-dimethyltetrahydro-2H-pyran-4-yl]ethyl)amino]methyl}phenoxy)cyclohexanecarboxylic acid Using the compound obtained in <Example E1>, the title compound was obtained by the same method as in <Example S4>.

<Example F1> Trans-4-(4-{[(2,2-dimethylpropanoyl){2-[4-(4-hydroxyphenyl)-2,2-dimethyltetrahydro-2H-pyran-4-yl]ethyl}amino]methyl}phenoxy)cyclohexanecarboxylic acid To a solution of trans-4-(4-{[(2,2-dimethylpropanoyl){2-[4-(4-methoxyphenyl)-2,2-dimethyltetrahydro-2H-pyran-4-yl]ethyl}amino]methyl}phenoxy)cyclohexanecarboxylic acid (200 mg, 0.345 mmol) in DMF (3.45 mL) was added sodium thiomethoxide (0.484 g, 6.90 mmol) at room temperature, and the mixture was stirred at 100° C. for 8 hr and left standing at room temperature overnight. To the reaction mixture were added saturated aqueous ammonium chloride solution and water at room temperature, and the mixture was extracted with ethyl acetate and DCM. The obtained organic layer was dried over anhydrous sodium sulfate and filtered, and the filtrate was concentrated under reduced pressure. The obtained residue was purified by silica gel column chromatography (DCM/methanol) to give the title compound (117 mg, 0.207 mmol, yield 60%).

<Example F2> Ethyl trans-4-(4-{[(2,2-dimethylpropanoyl){2-[4-(4-hydroxyphenyl)-2,2-dimethyltetrahydro-2H-pyran-4-yl]ethyl}amino]methyl}phenoxy)cyclohexanecarboxylate To a solution of trans-4-(4-{[(2,2-dimethylpropanoyl){2-[4-(4-hydroxyphenyl)-2,2-dimethyltetrahydro-2H-pyran-4-yl]ethyl)amino]methyl}phenoxy)cyclohexanecarboxylic acid (1.33 g, 2.35 mmol) in DMF (23.5 mL) were added DIPEA (2.05 mL, 11.8 mmol) and iodoethane (0.940 mL, 11.8 mmol) at room temperature, and the mixture was stirred at room temperature for 1 hr and left standing at room temperature overnight. To the reaction mixture were added DIPEA (0.819 mL, 4.70 mmol) and iodoethane (0.376 mL, 4.70 mmol) at room temperature, and the mixture was stirred at said temperature for 10 hr and left standing at room temperature for 2 days. To the reaction mixture was added water at room temperature, and the mixture was extracted with ethyl acetate. The obtained organic layer was washed successively with water and saturated brine, dried over anhydrous sodium sulfate and filtered, and the filtrate was concentrated under reduced pressure. The obtained residue was purified by silica gel column chromatography (hexane/ethyl acetate) to give the title compound (1.43 g, 2.41 mmol, yield: quantitative).

<Example F3> Ethyl trans-4-(4-{[(2,2-dimethylpropanoyl) (2-{2,2-dimethyl-4-[4-(propan-2-yloxy)phenyl]tetrahydro-2H-pyran-4-yl}ethyl)amino]methyl}phenoxy)cyclohexanecarboxylate To a solution of ethyl trans-4-(4-{[(2,2-dimethylpropanoyl){2-[4-(4-hydroxyphenyl)-2,2-dimethyltetrahydro-2H-pyran-4-yl]ethyl}amino]methyl}phenoxy)cyclohexanecarboxylate (80.0 mg, 0.135 mmol) in DMF (1.32 mL) were added potassium carbonate (146 mg, 1.06 mmol) and 2-bromopropane (0.0991 mL, 1.06 mmol) at room temperature, and the mixture was stirred at 130° C. for 4.5 hr and left standing at room temperature for 4 days. To the reaction mixture was added water at room temperature, and the mixture was extracted with ethyl acetate. The obtained organic layer was washed with water, dried over anhydrous sodium sulfate and filtered, and the filtrate was concentrated under reduced pressure. The obtained residue was purified by silica gel column chromatography (hexane/ethyl acetate) to give the title compound (78.7 mg, 0.124 mmol, yield 92%).

<Example F4> Trans-4-(4-{[(2,2-dimethylpropanoyl) (2-{2,2-dimethyl-4-[4-(propan-2-yloxy)phenyl]tetrahydro-2H-pyran-4-yl}ethyl)amino]methyl}phenoxy)cyclohexanecarboxylic acid Using the compound obtained in <Example F3>, the title compound was obtained by the same method as in <Example S4>.

<Example G1> Ethyl trans-4-(4-{[(2,2-dimethylpropanoyl){2-[2,2-dimethyl-4-(4-{[(trifluoromethyl)sulfonyl]oxy}phenyl)tetrahydro-2H-pyran-4-yl]ethyl)amino]methyl}phenoxy)cyclohexanecarboxylate To a solution of ethyl trans-4-(4-{[(2,2-dimethylpropanoyl) {2-[4-(4-hydroxyphenyl)-2,2-dimethyltetrahydro-2H-pyran-4-yl]ethyl}amino]methyl}phenoxy)cyclohexanecarboxylate (800 mg, 1.32 mmol) in DCM (6.59 mL) was added, under ice-cooling, pyridine (1.32 mL, 16.3 mmol), then, trifluoromethanesulfonic anhydride (0.333 mL, 1.98 mmol) was added thereto by small portions, and the mixture was stirred at said temperature for 30 min and at room temperature for 1 hr. To the reaction mixture was added, under ice-cooling, water, and the mixture was extracted with mixed solvent of hexane/ethyl acetate (ratio 2/1). The obtained organic layer was washed successively with water and saturated brine, dried over anhydrous sodium sulfate and filtered, and the filtrate was concentrated under reduced pressure. The obtained residue was purified by silica gel column chromatography (hexane/ethyl acetate) to give the title compound (915 mg, 1.26 mmol, yield 96%).

<Example G2> Ethyl trans-4-(0.4-{[(2,2-dimethylpropanoyl) (2-{2,2-dimethyl-4-[4-(pyrrolidin-1-yl) phenyl]tetrahydro-2H-pyran-4-yl}ethyl)amino] methyl}phenoxy)cyclohexanecarboxylate To a solution of ethyl trans-4-(4-{[(2,2-dimethylpropanoyl) {2-[2,2-dimethyl-4-(4-{[(trifluoromethyl)sulfonyl] oxy}phenyl)tetrahydro-2H-pyran-4-yl]ethyl}amino] methyl}phenoxy)cyclohexanecarboxylate (50.0 mg, 0.0689 mmol) in 1,4-dioxane (1.38 mL) were added tris(dibenzylideneacetone)dipalladium(0) (6.3 mg, 0.0069 mmol), 2-(di-tert-butylphosphino)biphenyl (4.1 mg, 0.0138 mmol), pyrrolidine (CAS Registry Number: 123-75-1) (0.0085 mL, 0.103 mmol) and tripotassium phosphate (20.5 mg, 0.0964 mmol) at room temperature, and the mixture was stirred at 95° C. for 9 hr and left standing at room temperature for 3 days. To the reaction mixture was added water at room temperature, and the mixture was extracted with ethyl acetate. The obtained organic layer was washed with water, dried over anhydrous sodium sulfate and filtered, and the filtrate was concentrated under reduced pressure. The obtained residue was purified by silica gel column chromatography (hexane/ethyl acetate) to give the title compound (36.2 mg, 0.0560 mmol, yield 81%).

<Example G3> Trans-4-(4-{[(2,2-dimethylpropanoyl) (2-{2,2-dimethyl-4-[4-(pyrrolidin-1-yl) phenyl]tetrahydro-2H-pyran-4-yl}ethyl)amino] methyl}phenoxy)cyclohexanecarboxylic acid Using the compound obtained in <Example G2>, the title compound was obtained by the same method as in <Example S4>.

<Example H1> Trans-4-(4-{[(2,2-dimethylpropanoyl) {2-[4-(4-methoxyphenyl)-2,2-dimethyltetrahydro-2H-pyran-4-yl]ethyl}amino] methyl}phenoxy)-N-(dimethylsulfamoyl) cyclohexanecarboxamide To a solution of trans-4-(4-{[(2,2-dimethylpropanoyl) {2-[4-(4-methoxyphenyl)-2,2-dimethyltetrahydro-2H-pyran-4-yl]ethyl}amino]methyl}phenoxy)cyclohexanecarboxylic acid (85 mg, 0.15 mmol), 1-(3-dimethylaminopropyl)-3-ethylcarbodiimide hydrochloride (CAS Registry Number: 25952-53-8) (56 mg, 0.29 mmol), and 4-dimethylaminopyridine (54 mg, 0.44 mmol) in DCM (2 mL) was added N,N-dimethylsulfamide (CAS Registry Number: 3984-14-3) (36 mg, 0.29 mmol) at room temperature, and the mixture was stirred at room temperature for one day. The reaction mixture was concentrated under reduced pressure. The residue was diluted with ethyl acetate, and washed successively with 1 mol/L hydrochloric acid, water and saturated brine. The organic layer was dried over anhydrous sodium sulfate and filtered, and the filtrate was concentrated under reduced pressure. The residue was purified by silica gel column chromatography (DCM/methanol) to give the title compound (64 mg, 0.093 mmol, yield 62%).

<Example I1> Ethyl trans-4-(4-{[{2-[4-(4-methoxyphenyl)-2,2-dimethyltetrahydro-2H-pyran-4-yl] ethyl)(pyridin-2-yl)amino]methyl}phenoxy)cyclohexanecarboxylate To a mixture of ethyl trans-4-{4-[({2-[4-(4-methoxyphenyl)-2,2-dimethyltetrahydro-2H-pyran-4-yl]ethyl}amino) methyl]phenoxy}cyclohexanecarboxylate (60 mg, 0.11 mmol) and 1,4-dioxane (1 mL) were successively added 2-bromopyridine (CAS Registry Number: 109-04-6) (0.030 mL, 0.31 mmol), cesium carbonate (120 mg, 0.368 mmol), and RuPhos Pd G3 (4 mg, 0.005 mmol), and the mixture was stirred at 100° C. for 2 hr. To the reaction mixture were added tripotassium phosphate (100 mg, 0.471 mmol), 2-bromopyridine (0.030 mL, 0.31 mmol), and RuPhos Pd G3 (4 mg, 0.005 mmol), and the mixture was stirred at 100° C. for 8 hr. To the reaction mixture was added RuPhos Pd G3 (4 mg, 0.005 mmol), and the mixture was stirred at 100° C. for 3 hr. To the reaction mixture were added BrettPhos Pd G3 (4 mg, 0.004 mmol) and cesium carbonate (120 mg, 0.368 mmol), and the mixture was stirred at 100° C. for 4 hr. To the reaction mixture was added water, and the mixture was extracted with ethyl acetate. The obtained organic layers were all combined, dried over anhydrous sodium sulfate and filtered, and the filtrate was concentrated under reduced pressure. The obtained residue was purified by silica gel column chromatography (hexane/ethyl acetate) to give the title compound (29.6 mg, 0.0493 mmol, yield 43%).

<Example I2> trans-4-(4-{[{2-[4-(4-Methoxyphenyl)-2,2-dimethyltetrahydro-2H-pyran-4-yl]ethyl} (pyridin-2-yl)amino]methyl}phenoxy)cyclohexanecarboxylic acid Using the compound obtained in <Example I1>, the title compound was obtained by the same method as in <Example S4>.

<Example J1> Methyl 3-[4-(4-formylphenoxy)phenyl]-2,2-dimethylpropanoate

Using methyl 3-(4-hydroxyphenyl)-2,2-dimethylpropanoate (WO2008130514 A1) and 4-fluorobenzaldehyde (CAS Registry Number: 459-57-4), the title compound was obtained by the same method as in <Example P1>.

<Example J2> Methyl 3-(4-{4-[({2-[4-(4-methoxyphenyl)-2,2-dimethyltetrahydro-2H-pyran-4-yl] ethyl}amino)methyl]phenoxy}phenyl)-2,2-dimethylpropanoate 2-[4-(4-Methoxyphenyl)-2,2-dimethyltetrahydro-2H-pyran-4-yl]ethanamine (309 mg, 1.17 mmol) and methyl 3-[4-(4-formylphenoxy)phenyl]-2,2-dimethylpropanoate (367 mg, 1.17 mmol) were dissolved in 1,2-dichloroethane (6.0 mL), acetic acid (0.60 mL) was added, and the mixture was stirred at room temperature for 1 hr. Thereto was added sodium triacetoxyborohydride (324 mg, 1.53 mmol), and the mixture was stirred at room temperature for 20 hr. To the reaction mixture were added water and saturated aqueous sodium hydrogen carbonate solution, and the mixture was extracted with DCM. The organic layer was dried over anhydrous magnesium sulfate and filtered, and the filtrate was concentrated under reduced pressure. The obtained residue was purified by silica gel column chromatography (ethyl acetate/methanol) to give the title compound (462 mg, 0.825 mmol, yield 70%).

<Example J3> Methyl 3-[4-(4-{[(2,2-dimethylpropanoyl){2-[4-(4-methoxyphenyl)-2,2-dimethyltetrahydro-2H-pyran-4-yl]ethyl}amino]methyl}phenoxy) phenyl]-2,2-dimethylpropanoate Methyl 3-(4-{4-[({2-[4-(4-methoxyphenyl)-2,2-dimethyltetrahydro-2H-pyran-4-yl]ethyl)amino)methyl]

phenoxy}phenyl)-2,2-dimethylpropanoate (241 mg, 0.431 mmol) and pivalic acid (52.8 mg, 0.517 mmol) were dissolved in DMF (6.0 mL), HATU (205 mg, 0.538 mmol) and DIPEA (0.187 mL, 1.08 mmol) were added, and the mixture was stirred under a nitrogen atmosphere at room temperature for 3 days. Water was added to the reaction mixture, and the mixture was extracted with ethyl acetate. The organic layer was washed with saturated brine, dried over anhydrous magnesium sulfate and filtered, and the filtrate was concentrated under reduced pressure. The obtained residue was purified by silica gel column chromatography (hexane/ethyl acetate) to give the title compound (247 mg, 0.384 mmol, yield 89%).

<Example J4> 3-[4-(4-{[(2,2-Dimethylpropanoyl){2-[4-(4-methoxyphenyl)-2,2-dimethyltetrahydro-2H-pyran-4-yl]ethyl}amino]methyl}phenoxy)phenyl]-2,2-dimethylpropanoic acid Using the compound obtained in <Example J3>, the title compound was obtained by the same method as in <Examples 4>.

<Example K1> Benzyl (cis-4-hydroxycyclohexyl)acetate

To a solution of 4-hydroxyphenylacetic acid (CAS Registry Number: 156-38-7) (10.0 g, 65.7 mmol) in ethanol (200 mL) was added rhodium-alumina (10.0 g), and the mixture was stirred under a hydrogen atmosphere at 50° C. for 8 hr. Insoluble materials were filtered off through celite and washed with ethanol. The obtained solution was concentrated to about 200 mL, rhodium-alumina (10.0 g) was added thereto, and the mixture was stirred under a hydrogen atmosphere at 50° C. for 4 hr. Insoluble materials were filtered off through celite and washed with ethanol. The filtrate was concentrated under reduced pressure. The residue was dissolved in DMF (130 mL) and potassium carbonate (18.2 g, 131 mmol) was added at room temperature. Under water cooling, benzyl bromide (11.7 mL, 98.6 mmol) was added dropwise thereto, and the mixture was stirred at room temperature overnight. The reaction mixture was diluted with diethyl ether, washed successively with water, 1 mol/L hydrochloric acid, and saturated brine, dried over anhydrous sodium sulfate and filtered, and the filtrate was concentrated under reduced pressure. The residue was purified by silica gel column chromatography (hexane/ethyl acetate) to give the title compound (7.65 g, 30.8 mmol, yield 47%).

<Example K2> Benzyl [trans-4-(4-formylphenoxy)cyclohexyl]acetate

Using the compound obtained in <Example K1> and 4-hydroxybenzaldehyde (CAS Registry Number: 123-08-0), the title compound was obtained by the same method as in <Example A4>.

<Example K3> Benzyl (trans-4-{4-[({2-[4-(4-methoxyphenyl)-2,2-dimethyltetrahydro-2H-pyran-4-yl]ethyl}amino)methyl]phenoxy}cyclohexyl)acetate Using the compounds obtained in <Example K2> and <Example C5>, the title compound was obtained by the same method as in <Example D1>.

<Example K4> Benzyl [trans-4-(4-{[{2-[4-(4-methoxyphenyl)-2,2-dimethyltetrahydro-2H-pyran-4-yl]ethyl}(3,3,3-trifluoropropyl)amino]methyl}phenoxy)cyclohexyl]acetate Using the compound obtained in <Example K3> and 3,3,3-trifluoropropionaldehyde (CAS Registry Number: 460-40-2), the title compound was obtained by the same method as in <Example T1>.

<Example K5> [Trans-4-(4-{[{2-[4-(4-methoxyphenyl)-2,2-dimethyltetrahydro-2H-pyran-4-yl]ethyl}(3,3,3-trifluoropropyl)amino]methyl}phenoxy)cyclohexyl]acetic acid Using the compound obtained in <Example K4>, the title compound was obtained by the same method as in <Example S4>.

<Example L1> Ethyl trans-4-(4-{[(2-{2,2-dimethyl-4-[4-(methylamino)phenyl]tetrahydro-2H-pyran-4-yl}ethyl) (2,2-dimethylpropanoyl)amino]methyl}phenoxy)cyclohexanecarboxylate Using the compound obtained in <Example G1> and methylamine (2.0 mol/L THF solution), the title compound was obtained by the same method as in <Example G2>.

<Example L2> Trans-4-(4-{[(2-{2,2-dimethyl-4-[4-(methylamino)phenyl]tetrahydro-2H-pyran-4-yl}ethyl) (2,2-dimethylpropanoyl)amino]methyl}phenoxy)cyclohexanecarboxylic acid Using the compound obtained in <Example L1>, the title compound was obtained by the same method as in <Example S4>.

<Example M1> 2-[(4R)-4-(4-Methoxyphenyl)-2,2-dimethyltetrahydro-2H-pyran-4-yl]ethanamine The racemic 2-[4-(4-methoxyphenyl)-2,2-dimethyltetrahydro-2H-pyran-4-yl]ethanamine was optically resolved by chiral HPLC [column: CHIRALCEL OZ-H (registered trademark, Daicel Corporation), mobile phase: hexane/IPA=60/40 (V/V)] to obtain the title compound as the component eluted later.

Analysis conditions column: CHIRALCEL OJ-H (registered trademark, Daicel Corporation), size: 0.46 cm×25 cm, flow rate: 1.0 mL/min, temperature: 30° C., mobile phase: hexane/isopropyl alcohol/diethylamine=70/30/0.2 (V/V/V), retention time: R form <Example M1> 5.1 min, S form 6.7 min <Example M2> 3,3,3-Trifluoro-N-{2-[(4R)-4-(4-methoxyphenyl)-2,2-dimethyltetrahydro-2H-pyran-4-yl]ethyl}-2,2-dimethylpropanamide To a solution of 3,3,3-trifluoro-2,2-dimethylpropanoic acid (CAS Registry Number: 889940-13-0) (18.0 g, 115 mmol) in DMF (150 mL) was added HATU (43.8 g, 115 mmol), and the mixture was stirred at room temperature for 20 min. The reaction mixture was cooled to 0° C., and stirred for 5 min. To the reaction mixture were successively added dropwise a solution of 2-[(4R)-4-(4-methoxyphenyl)-2,2-dimethyltetrahydro-2H-pyran-4-yl]ethanamine (25.2 g, 95.7 mmol) in DMF (150 mL) and DIPEA (50 mL, 287 mmol), and the mixture was stirred at room temperature for 24 hr.

The reaction mixture was diluted with ethyl acetate, washed successively with aqueous sodium hydrogen carbonate solution, water, and saturated brine, dried over anhydrous sodium sulfate and filtered, and the filtrate was concentrated under reduced pressure. The residue was purified by silica gel column chromatography (hexane/ethyl acetate) and dried under reduced pressure to give the title compound (36.2 g, 90.2 mmol, yield 94%).

<Example M3> 3,3,3-Trifluoro-N-{2-[(4R)-4-(4-methoxyphenyl)-2,2-dimethyltetrahydro-2H-pyran-4-yl]ethyl}-2,2-dimethylpropan-1-amine To a solution of 3,3,3-trifluoro-N-{2-[(4R)-4-(4-methoxyphenyl)-2,2-dimethyltetrahydro-2H-pyran-4-yl]ethyl}-2,2-dimethylpropanamide (24.7 g, 61.5 mmol) in THF (60 mL) was added borane-THF complex (0.89 mol/L THF solution, 240 mL, 210 mmol), and the mixture was stirred with heating under reflux for 9 hr. The reaction mixture was cooled to room temperature, methanol (60 mL) was added, and the mixture was stirred with heating under reflux for 3 hr. The reaction mixture was cooled to room temperature and concentrated under reduced pressure. To the residue was added ethyl acetate, and the mixture was washed successively with water and saturated brine, dried over anhydrous sodium sulfate and filtered, and the filtrate was concentrated under reduced pressure. The residue was purified by silica gel column chromatography (DCM/methanol) and dried under reduced pressure to give the title compound (22.1 g, 57.0 mmol, yield 93%).

<Example M4> Ethyl trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexanecarboxylate Using the compounds obtained in <Example M3> and <Example A4>, the title compound was obtained by the same method as in <Example T1>.

<Example M5> Trans-4-(4-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}phenoxy)cyclohexanecarboxylic acid Using the compound obtained in <Example M4>, the title compound was obtained by the same method as in <Example S4>.

<Example N1> N-[4-(4-Bromophenoxy)benzyl]-N-{2-[4-(4-methoxyphenyl)-2,2-dimethyltetrahydro-2H-pyran-4-yl]ethyl}-2,2-dimethylpropanamide Using the compound obtained in <Example C5> and 4-(4-bromophenoxy)benzaldehyde (Bioorg. Med. Chem. Lett., 2004, 14, 4179-4183.), the title compound was obtained by sequentially performing the same operations as in <Example D1> and <Example D2>.

<Example N2> N-{4-[(4-{[Dimethyl(oxide)-$\Delta^6$-sulfanilidene]amino}cyclohexyl)oxy]benzyl}-N-{2-[4-(4-methoxyphenyl)-2,2-dimethyltetrahydro-2H-pyran-4-yl]ethyl}-2,2-dimethylpropanamide To a solution of N-[4-(4-bromophenoxy)benzyl]-N-{2-[4-(4-methoxyphenyl)-2,2-dimethyltetrahydro-2H-pyran-4-yl]ethyl}-2,2-dimethylpropanamide (150 mg, 0.246 mmol) in toluene (5 mL) were added dimethylsulfoximine (CAS Registry Number: 1520-31-6) (35 mg, 0.38 mmol), (S)-(−)-Tol-BINAP (26 mg, 0.038 mmol), cesium carbonate (161 mg, 0.494 mmol), and palladium(II) acetate (6 mg, 0.03 mmol), and the mixture was stirred with heating under reflux for 9 hr under a nitrogen atmosphere. To the reaction mixture were added dimethylsulfoximine (40 mg, 0.429 mmol), cesium carbonate (170 mg, 0.522 mmol), (S)-(−)-Tol-BINAP (28 mg, 0.041 mmol), and palladium(II) acetate (7 mg, 0.03 mmol), and the mixture was stirred with heating under reflux for 8 hr under a nitrogen atmosphere. To the reaction mixture were further added (S)-(−)-Tol-BINAP (27 mg, 0.040 mmol) and palladium(II) acetate (8 mg, 0.04 mmol), and the mixture was stirred with heating under reflux for 4 hr under a nitrogen atmosphere. The reaction mixture was filtered, and the filtrate was concentrated under reduced pressure. The residue was purified by silica gel chromatography (DCM/methanol) to give the title compound (7 mg, 0.01 mmol, yield 4%).

<Example O1> Ethyl trans-4-(4-{[(5-fluoropyrimidin-2-yl) {2-[4-(4-methoxyphenyl)-2,2-dimethyltetrahydro-2H-pyran-4-yl]ethyl}amino]methyl}phenoxy)cyclohexanecarboxylate To a mixture of ethyl trans-4-{4-[({2-[4-(4-methoxyphenyl)-2,2-dimethyltetrahydro-2H-pyran-4-yl]ethyl}amino)methyl]phenoxy}cyclohexanecarboxylate (65.5 mg, 0.125 mmol) and 2-butanol (1.5 mL, 16 mmol) were successively added 2-chloro-5-fluoropyrimidine (CAS Registry Number: 62802-42-0) (0.030 mL, 0.24 mmol), 1,8-diazabicyclo[5.4.0]-7-undecene (0.040 mL, 0.27 mmol), and cesium fluoride (1 mg, 0.007 mmol), and the mixture was stirred at 150° C. for 1.5 hr under microwave irradiation. To the reaction mixture were added water and saturated brine, and the mixture was extracted with ethyl acetate. The obtained organic layers were combined, dried over anhydrous sodium sulfate and filtered, and the filtrate was concentrated under reduced pressure. The residue was purified by silica gel column chromatography (hexane/ethyl acetate) to give the title compound (47.4 mg, 0.0765 mmol, yield 61%).

<Example O2> Trans-4-(4-{[(5-fluoropyrimidin-2-yl) {2-[4-(4-methoxyphenyl)-2,2-dimethyltetrahydro-2H-pyran-4-yl]ethyl}amino]methyl}phenoxy)cyclohexanecarboxylic acid Using the compound obtained in <Example O1>, the title compound was obtained by the same method as in <Example S4>.

<Example P1> Methyl 2-[4-(4-formylphenoxy)phenyl]propanoate

4-Fluorobenzaldehyde (CAS Registry Number: 459-57-4) (0.637 mL, 5.94 mmol) and methyl 2-(4-hydroxyphenyl)propanoate (J. Med. Chem., 2007, 50, 3984-4002.) (1.07 g, 5.94 mmol) were dissolved in N,N-dimethylacetamide (10 mL), potassium carbonate (2.46 g, 17.8 mmol) was added, and the mixture was stirred at 130° C. for 8 hr, cooled to room temperature, and left standing overnight. Water was added to the reaction mixture, and the mixture was extracted with ethyl acetate. The organic layer was washed with saturated brine, dried over anhydrous magnesium sulfate and filtered, and the filtrate was concentrated under reduced pressure. The residue was purified by silica gel column chromatography (hexane/ethyl acetate) to give the title compound (878 mg, 3.09 mmol, yield 52%).

<Example P2> Methyl 2-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl) amino]methyl}phenoxy)phenyl]propanoate Using the compounds obtained in <Example M3> and <Example P1>, the title compound was obtained by the same method as in <Example T1>.

<Example P3> 2-[4-(4-{[{2-[(4R)-4-(4-Methoxyphenyl)-2,2-dimethyltetrahydro-2H-pyran-4-yl] ethyl}(3,3,3-trifluoro-2,2-dimethylpropyl)amino] methyl}phenoxy)phenyl]propanoic acid Using the compound obtained in <Example P2>, the title compound was obtained by the same method as in <Example S4>.

<Example Q1> Methyl 4-[({2-[4-(4-methoxyphenyl)-2,2-dimethyltetrahydro-2H-pyran-4-yl] ethyl}amino)methyl]-2-methylbenzoate Using the compound obtained in <Example C5> and methyl 4-formyl-2-methylbenzoate (CAS Registry Number: 74733-23-6), the title compound was obtained by the same method as in <Example J2>.

<Example Q2> Methyl 4-{[{2-[4-(4-methoxyphenyl)-2,2-dimethyltetrahydro-2H-pyran-4-yl]ethyl}(3,3,3-trifluoro-2,2-dimethylpropanoyl)amino]methyl}-2-methylbenzoate 3,3,3-Trifluoro-2,2-dimethylpropanoic acid (CAS Registry Number: 889940-13-0) (1.25 g, 8.04 mmol) was dissolved in DCM (10 mL), DMF (0.05 mL) was added, and the mixture was stirred at room temperature. Oxalyl chloride (0.748 mL, 8.84 mmol) was added thereto, and the mixture was stirred at room temperature for 1 hr. The solution was added to a solution of methyl 4-[({2-[4-(4-methoxyphenyl)-2,2-dimethyltetrahydro-2H-pyran-4-yl]ethyl}amino) methyl]-2-methylbenzoate (1.14 g, 2.68 mmol) and triethylamine (2.23 mL, 16.1 mmol) in DCM (15 mL), and the mixture was stirred at room temperature for 24 hr. To the reaction mixture were added water and saturated aqueous sodium hydrogen carbonate solution, and the mixture was extracted with DCM. The organic layer was dried over anhydrous magnesium sulfate and filtered, and the filtrate was concentrated under reduced pressure. The residue was purified by silica gel column chromatography (hexane/ethyl acetate) to give the title compound (1.12 g, 1.99 mmol, yield 74%).

<Example Q3> 4-{[{2-[4-(4-Methoxyphenyl)-2,2-dimethyltetrahydro-2H-pyran-4-yl]ethyl}(3,3,3-trifluoro-2,2-dimethylpropanoyl)amino]methyl}-2-methylbenzoic acid Using the compound obtained in <Example Q2>, the title compound was obtained by the same method as in <Example S4>.

<Example Q4> 3-[4-(4-{[{2-[4-(4-Methoxyphenyl)-2,2-dimethyltetrahydro-2H-pyran-4-yl]ethyl}(3,3,3-trifluoro-2,2-dimethylpropanoyl)amino]methyl}-2-methylbenzoyl)phenyl]propanoic acid 4-{[{2-[4-(4-Methoxyphenyl)-2,2-dimethyltetrahydro-2H-pyran-4-yl]ethyl}(3,3,3-trifluoro-2,2-dimethylpropanoyl)amino]methyl}-2-methylbenzoic acid (1.06 g, 1.93 mmol) was dissolved in DCM (10 mL), DMF (0.05 mL) was added, and the mixture was stirred at room temperature. Oxalyl chloride (0.539 mL, 6.36 mmol) was added thereto, and the mixture was stirred at room temperature for 1.5 hr. The solvent was evaporated to give the corresponding acid chloride (1.06 g, 1.87 mmol, yield 97%). To the obtained acid chloride (191 mg, 0.336 mmol) were added [4-(2-ethoxycarbonylethyl)phenyl]boronic acid (CAS Registry Number: 660440-57-3) (60.0 mg, 0.270 mmol), toluene (8.0 mL), cesium carbonate (225 mg, 0.692 mmol) and tetrakis (triphenylphosphine)palladium(0) (40.6 mg, 0.0351 mmol), and the mixture was stirred at 80° C. for 6 hr. The reaction mixture was cooled to room temperature, water was added, and the mixture was extracted with ethyl acetate. The organic layer was washed with saturated brine, dried over anhydrous magnesium sulfate and filtered, and the filtrate was concentrated under reduced pressure. The residue was purified by silica gel column chromatography (hexane/ethyl acetate). The obtained crudely purified product was dissolved in ethanol (4.0 mL), 1 mol/L aqueous sodium hydroxide solution (0.754 mL, 0.754 mmol) was added, and the mixture was stirred at room temperature for 16 hr. The reaction mixture was concentrated under reduced pressure, and the residue was neutralized by adding water and 2 mol/L hydrochloric acid, and extracted with ethyl acetate. The organic layer was washed with saturated brine, dried over anhydrous magnesium sulfate and filtered, and the filtrate was concentrated under reduced pressure. The residue was purified by silica gel column chromatography (hexane/ethyl acetate) to give the title compound (15.0 mg, 0.0220 mmol, yield 15%).

<Example R1> Ethyl (2S)-2-ethoxy-3-[4-(4-formylphenoxy)phenyl]propanoate

Using 4-fluorobenzaldehyde (CAS Registry Number: 459-57-4) and ethyl (2S)-2-ethoxy-3-(4-hydroxyphenyl) propanoate (CAS Registry Number: 222555-06-8), the title compound was obtained by the same method as in <Example P1>.

<Example R2> Ethyl (2S)-2-ethoxy-3-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)phenyl]propanoate Using the compounds obtained in <Example M3> and <Example R1>, the title compound was obtained by the same method as in <Example T1>.

<Example R3> (2S)-2-Ethoxy-3-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)phenyl]propanoic acid Using the compound obtained in <Example R2>, the title compound was obtained by the same method as in <Example S4>.

<Example S1> Ethyl (cis-4-hydroxycyclohexyl)acetate

Under a nitrogen atmosphere, to a solution of ethyl 2-(4-oxocyclohexyl)acetate (CAS Registry Number: 58012-34-3) (7.75 g, 42.1 mmol) in THF (170 mL) was added dropwise at −78° C. lithium tri(sec-butyl)borohydride (1.07 mol/L THF solution, 39.3 mL, 42.1 mmol) over 30 min. After dropwise addition, the mixture was stirred at −78° C. for 2 hr. To the reaction mixture were added saturated aqueous ammonium chloride solution and water, the mixture was returned to room temperature, THF was evaporated under reduced pressure, and the mixture was extracted with ethyl acetate. The organic layer was washed with saturated brine, dried over anhydrous sodium sulfate and filtered, and the filtrate was concentrated under reduced pressure. The residue was purified by silica gel column chromatography (hexane/ethyl acetate) to give the title compound (6.13 g, 32.9 mmol, yield 78%).

<Example S2> Ethyl {trans-4-[(5-formylpyridin-2-yl)oxy]cyclohexyl)acetate

Using the compound obtained in <Example S1> and 6-hydroxynicotinaldehyde (CAS Registry Number: 106984-91-2), the title compound was obtained by the same method as in <Example A4>.

<Example S3> Ethyl {trans-4-[(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}pyridin-2-yl)oxy]cyclohexyl}acetate Using the compounds obtained in <Example S2> and <Example M3>, the title compound was obtained by the same method as in <Example T1>.

<Example S4> {Trans-4-[(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}pyridin-2-yl)oxy]cyclohexyl)acetic acid To a solution of ethyl {trans-4-[(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}pyridin-2-yl)oxy]cyclohexyl}acetate (390 mg, 0.588 mmol) in methanol (11.8 mL) was added 1 mol/L aqueous sodium hydroxide solution (2.94 mL, 2.94 mmol) at room temperature, and the mixture was stirred at 50° C. for 30 min and left standing at room temperature overnight. To the reaction mixture was added 1 mol/L hydrochloric acid (2.94 mL, 2.94 mmol) at room temperature, and the mixture was extracted with DCM. The organic layer was dried over anhydrous sodium sulfate and filtered, and the filtrate was concentrated under reduced pressure. The residue was purified by silica gel column chromatography (hexane/ethyl acetate) to give the title compound (265 mg, 0.418 mmol, yield 71%).

<Example T1> Benzyl [trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexyl]acetate To a solution of 3,3,3-trifluoro-N-{2-[(4R)-4-(4-methoxyphenyl)-2,2-dimethyltetrahydro-2H-pyran-4-yl]ethyl}-2,2-dimethylpropan-1-amine (450 mg, 1.16 mmol) in methanol (11.6 mL) were added benzyl [trans-4-(4-formylphenoxy)cyclohexyl]acetate (450 mg, 1.28 mmol) and acetic acid (0.199 mL, 3.48 mmol) at room temperature, and the mixture was stirred at 50° C. for 1 hr. After cooling, to the reaction mixture was added sodium cyanoborohydride (137 mg, 2.18 mmol) under ice-cooling, and the mixture was stirred at room temperature 3 hr and left standing for 2 days. The reaction mixture was stirred at 50° C. for 1.5 hr. After cooling the reaction mixture, ice, water and sodium hydrogen carbonate were added under ice-cooling, and the mixture was extracted with DCM. The obtained organic layer was washed with saturated brine, dried over anhydrous sodium sulfate and filtered, and the filtrate was concentrated under reduced pressure. The residue was purified by silica gel column chromatography (hexane/ethyl acetate) to give the title compound (569 mg, 0.785 mmol, yield 68%).

<Example T2> [Trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)cyclohexyl]acetic acid Using the compound obtained in <Example T1>, the title compound was obtained by the same method as in <Examples 4>.

<Example U1> N-[4-(Benzyloxy)benzyl]-2-[(4R)-4-(4-methoxyphenyl)-2,2-dimethyltetrahydro-2H-pyran-4-yl]ethanamine Using the compound obtained in <Example M1> and 4-benzyloxybenzaldehyde (CAS Registry Number: 4397-53-9), the title compound was obtained by the same method as in <Example D1>.

<Example U2> N-[4-(Benzyloxy)benzyl]-3,3-difluoro-N-{2-[(4R)-4-(4-methoxyphenyl)-2,2-dimethyltetrahydro-2H-pyran-4-yl]ethyl}-2,2-dimethylpropanamide Using the compound obtained in <Example U1> and 3,3-difluoro-2,2-dimethylpropanoic acid (CAS Registry Number: 1022154-50-2), the title compound was obtained by the same method as in <Example Q2>.

<Example U3> 3,3-Difluoro-N-(4-hydroxybenzyl)-N-{2-[(4R)-4-(4-methoxyphenyl)-2,2-dimethyltetrahydro-2H-pyran-4-yl]ethyl}-2,2-dimethylpropanamide To a solution of N-[4-(benzyloxy)benzyl]-3,3-difluoro-N-{2-[(4R)-4-(4-methoxyphenyl)-2,2-dimethyltetrahydro-2H-pyran-4-yl]ethyl}-2,2-dimethylpropanamide (920 mg, 1.59 mmol) in ethanol (30 mL) was added 10% palladium carbon (400 mg), and the mixture was stirred under a hydrogen atmosphere at room temperature for 4 hr. The reaction mixture was diluted with ethyl acetate, insoluble materials were filtered off through celite. The filtrate was concentrated under reduced pressure, and the residue was purified by silica gel column chromatography (DCM/methanol) to give the title compound (714 mg, 1.46 mmol, yield 92%).

<Example U4> (cis-4-{[tert-Butyl(diphenyl)silyl]oxy}cyclohexyl)methyl 4-methylbenzenesulfonate To a solution of (cis-4-{[tert-butyl(diphenyl)silyl]oxy)cyclohexyl)methanol (WO2007126041 A1) (8.20 g, 22.2 mmol) in DCM (200 mL) were added triethylamine (4.63 mL, 33.4 mmol) and para-toluenesulfonyl chloride (4.67 g, 24.5 mmol), and the mixture was stirred with heating under reflux for 7 hr. The reaction mixture was cooled to room temperature, ethanol (2 mL) was added, and the mixture was stirred at room temperature for 10 hr. Water and saturated brine were added thereto, and the mixture was extracted with ethyl acetate. The organic layers were combined, washed with saturated brine, dried over anhydrous sodium sulfate and filtered, and the filtrate was concentrated under reduced pressure. The residue was purified by silica gel column chromatography (hexane/ethyl acetate) to give the title compound (8.89 g, 17.0 mmol, yield 76%).

<Example U5> tert-Butyl({cis-4-[(methylsulfanyl)methyl]cyclohexyl}oxy)diphenylsilane To a solution of (cis-4-{[tert-butyl(diphenyl)silyl]oxy}cyclohexyl)methyl 4-methylbenzenesulfonate (8.89 g, 17.0 mmol) in THF (400 mL) was added sodium thiomethoxide (9.54 g, 136 mmol), and the mixture was stirred with heating under reflux for 10 hr. The reaction mixture was cooled to room temperature, water and saturated brine were added, and the mixture was extracted with ethyl acetate. The organic layer was washed with saturated brine, dried over anhydrous sodium sulfate and filtered, and the filtrate was concentrated under reduced pressure. The residue was purified by silica gel column chromatography (hexane/ethyl acetate) to give the title compound (6.28 g, 15.8 mmol, yield 93%).

<Example U6> tert-Butyl({cis-4-[(methylsulfinyl)methyl]cyclohexyl}oxy)diphenylsilane To a solution of tert-butyl({cis-4-[(methylsulfanyl)methyl]cyclohexyl}oxy)diphenylsilane (6.28 g, 15.8 mmol) in methanol (100 mL) and water (25 mL) was added sodium periodate (4.04 g, 18.9 mmol), and the mixture was stirred at room temperature for 15 hr. To the reaction mixture were added saturated brine and water, and the mixture was extracted with ethyl acetate. The organic layers were combined, washed with saturated brine, dried over anhydrous sodium sulfate, filtered, and concentrated under reduced pressure. The residue was purified by silica gel column chromatography (DCM/methanol) to give the title compound (6.41 g, 15.5 mmol, yield 98%).

<Example U7> Benzyl {[(cis-4-{[tert-butyl(diphenyl)silyl]oxy}cyclohexyl)methyl](methyl)oxide-$\lambda^6$-sulfanilidene}carbamate To a solution of tert-butyl({cis-4-[(methylsulfinyl)methyl]cyclohexyl}oxy)diphenylsilane (6.41 g, 15.5 mmol) and benzyl carbamate (CAS Registry Number: 621-84-1) (7.01 g, 46.4 mmol) in DCM (250 mL) were added, under a nitrogen atmosphere, magnesium oxide (4.98 g, 124 mmol), iodobenzene diacetate (14.9 g, 46.4 mmol), and rhodium(II) acetate dimer (1.37 g, 3.09 mmol), and the mixture was stirred with heating under reflux for 7 hr. Insoluble materials were filtered off, and concentrated under reduced pressure. The residue was purified by silica gel column chromatography (hexane/ethyl acetate) to give the title compound (3.97 g, 7.04 mmol, yield 46%).

<Example U8> Benzyl {[(cis-4-hydroxycyclohexyl)methyl](methyl)oxide-$\lambda^6$-sulfanilidene}carbamate To a solution of benzyl {[(cis-4-{[tert-butyl(diphenyl)silyl]oxy}cyclohexyl)methyl](methyl)oxide-$\lambda^6$-sulfanilidene}carbamate (3.97 g, 7.04 mmol) in THF (30 mL) was added tetrabutylammonium fluoride (1.0 mol/L THF solution, 30 mL, 30 mmol), and the mixture was stirred at 65° C. for 2 hr. The reaction mixture was cooled to room temperature, water and saturated brine were added, and the mixture was extracted with ethyl acetate. The organic layers were combined, washed with saturated brine, dried over anhydrous sodium sulfate and filtered, and the filtrate was concentrated under reduced pressure. The residue was purified by silica gel column chromatography (DCM/methanol) to give the title compound (1.70 g, 5.22 mmol, yield 74%).

<Example U9> Benzyl {(RIr (S)-[(cis-4-hydroxycyclohexyl)methyl](methyl)oxide-$\lambda^6$-sulfanilidene}carbamate The racemic benzyl{[(cis-4-hydroxycyclohexyl)methyl](methyl)oxide-$\lambda^6$-sulfanylidene}carbamate was optically resolved by chiral HPLC [column: CHIRALPAK IC (registered trademark, Daicel Corporation), mobile phase: hexane/ethanol=40/60 (V/V)] to obtain the title compound as the component eluted first.

<Example U10> Benzyl [(RIr (S)-{[trans-4-(4-{[(3,3-difluoro-2,2-dimethylpropanoyl){2-[(4R)-4-(4-methoxyphenyl)-2,2-dimethyltetrahydro-2H-pyran-4-yl]ethyl}amino]methyl}phenoxy)cyclohexyl]methyl)(methyl)oxide-$\lambda^6$-sulfanilidene]carbamate Using the compounds obtained in <Example U9> and <Example U3>, the title compound was obtained by the same method as in <Example A4>.

<Example U11> 3,3-Difluoro-N-{2-[(4R)-4-(4-methoxyphenyl)-2,2-dimethyltetrahydro-2H-pyran-4-yl]ethyl}-2,2-dimethyl-N-{4-[(trans-4-{[(R) or (S)—S-methylsulfonimidoyl]methyl}cyclohexyl)oxy]benzyl}propanamide Using the compound obtained in <Example U10>, the title compound was obtained by the same method as in <Example U3>.

<Example V1> tert-Butyl 2'-fluoro-4'-formyl-2,3,4,5-tetrahydro[biphenyl]-4-carboxylate 4-Bromo-3-fluorobenzaldehyde (CAS Registry Number: 133059-43-5) (4.00 g, 19.7 mmol), tert-butyl 4-(4,4,5,5-tetramethyl-1,3,2-dioxaborolan-2-yl)-3-cyclohexene-1-carboxylate (CAS Registry Number: 1562375-30-7) (6.38 g, 20.7 mmol), [1,1'-bis(diphenylphosphino)ferrocene]palladium(II) dichloride DCM adduct (0.804 g, 0.985 mmol), and sodium carbonate (6.27 g, 59.2 mmol) were dissolved in a mixed solvent of 1,4-dioxane (45 mL) and water (5 mL), and the mixture was stirred with heating under a nitrogen atmosphere at 85° C. for 4 hr. The reaction mixture was cooled to room temperature, saturated aqueous sodium hydrogen carbonate solution was added, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (6.03 g, 19.8 mmol, yield: quantitative).

<Example V2> tert-Butyl (4R)-2'-fluoro-4'-formyl-2,3,4,5-tetrahydro[biphenyl]-4-carboxylate <Example V3> tert-butyl (4S)-2'-fluoro-4'-formyl-2,3,4,5-tetrahydro[biphenyl]-4-carboxylate The racemic tert-butyl 2'-fluoro-4'-formyl-2,3,4,5-tetrahydro[biphenyl]-4-carboxylate was purified by chiral HPLC [column: CHIRALPAK IG (registered trademark, Daicel Corporation), mobile phase: acetonitrile] to obtain R form <Example V2> as the component eluted first and S form <Example V3> as the component eluted later.

Analysis conditions column: CHIRALPAK IG (registered trademark, Daicel Corporation), size: 0.46 cm×25 cm, flow rate: 1.0 mL/min, temperature: 40° C., mobile phase: acetonitrile, retention time: R form <Example V2> 4.8 min, S form <Example V3> 5.6 min <Example V4> tert-Butyl (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate tert-Butyl (4R)-2'-fluoro-4'-formyl-2,3,4,5-tetrahydro[biphenyl]-4-carboxylate (0.115 g, 0.378 mmol) and 3,3,3-trifluoro-N-{2-[(4R)-4-(4-methoxyphenyl)-2,2-dimethyltetrahydro-2H-pyran-4-yl]ethyl}-2,2-dimethylpropan-1-amine (0.147 g, 0.379 mmol) were dissolved in DCM (4 mL), sodium triacetoxyborohydride (0.157 g, 0.741 mmol) was added, and the mixture was stirred at room temperature for 20 hr. To the reaction mixture was added saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (hexane/ethyl acetate) to give the title compound (0.196 g, 0.290 mmol, yield 77%).

<Example V5> (4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-carboxylic acid monohydrochloride tert-Butyl (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-carboxylate (0.196 g, 0.290 mmol) was dissolved in DCM (2 mL), 4 mol/L hydrogen chloride/1,4-dioxane solution (1.2 mL, 4.8 mmol) was added, and the mixture was stirred at room temperature for 24 hr. The reaction mixture was concentrated under reduced pressure to give the title compound (0.237 g, 0.361 mmol, yield: quantitative).

<Example W1> tert-Butyl 4'-formyl-2,3,4,5-tetrahydro[biphenyl]-4-carboxylate

A suspension of tert-butyl 4-(4,4,5,5-tetramethyl-1,3,2-dioxaborolan-2-yl)-3-cyclohexene-1-carboxylate (CAS Registry Number: 1562375-30-7) (WO2017051355) (1.14 g, 3.70 mmol), 4-bromobenzaldehyde (CAS Registry Number: 1122-91-4) (694 mg, 3.75 mmol), [1,1'-bis(diphenylphosphino)ferrocene]dichloropalladium(II) DCM adduct (306 mg, 0.375 mmol), and potassium carbonate (2.0 mol/L aqueous solution, 3.5 mL, 7.0 mmol) in 1,4-dioxane (7.5 mL) was stirred under a nitrogen atmosphere at 90° C. for 2 hr. The reaction mixture was cooled to room temperature, ethyl acetate and water were added, insoluble materials were filtered off through celite, and two layers were separated. The organic layer was dried over sodium sulfate and filtered, and the filtrate was concentrated under reduced pressure. The residue was purified by silica gel column chromatography (hexane/ethyl acetate) to give the title compound (836 mg, 2.92 mmol, yield 79%).

<Example W2> tert-Butyl (4R)-4'-formyl-2,3,4,5-tetrahydro[biphenyl]-4-carboxylate <Example W3> tert-Butyl (4S)-4'-formyl-2,3,4,5-tetrahydro[biphenyl]-4-carboxylate The racemic tert-butyl 4'-formyl-2,3,4,5-tetrahydro[biphenyl]-4-carboxylate was purified by chiral SFC [column: CHIRALPAK IG (registered trademark, Daicel Corporation), mobile phase: sCO2/acetonitrile=60/40 (V/V)] to obtain R form <Example W2> as the component eluted first and S form <Example W3> as the component eluted later. Analysis conditions column: CHIRALPAK IG-3 (registered trademark, Daicel Corporation), size: 0.46 cm×5 cm, flow rate: 3.0 mL/min, temperature: 35° C., mobile phase: sCO2/acetonitrile (0.05% diethylamine)=60/40 (V/V), retention time: R form <Example W2> 0.9 min, S form <Example W3> 1.4 min <Example W4> tert-Butyl (4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate A solution of 3,3,3-trifluoro-N-{2-[(4R)-4-(4-methoxyphenyl)-2,2-dimethyltetrahydro-2H-pyran-4-yl]ethyl}-2,2-dimethylpropan-1-amine (16.7 g, 43.1 mmol) and tert-butyl (4R)-4'-formyl-2,3,4,5-tetrahydro[biphenyl]-4-carboxylate (12.8 g, 44.7 mmol) in DCM (200 mL) was stirred at room temperature for 15 min. To the reaction mixture was added sodium triacetoxyborohydride (18.6 g, 87.8 mmol), and the mixture was stirred for 5 hr. To the reaction mixture were added saturated aqueous sodium hydrogen carbonate solution and water, and the mixture was extracted with DCM. The organic layer was dried over sodium sulfate and filtered, and the filtrate was concentrated under reduced pressure. The residue was purified by silica gel column chromatography (hexane/ethyl acetate) to give the title compound (26.2 g, 39.8 mmol, yield 92%).

<Example W5> [(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methanol Under ice-cooling, to a suspension of lithium aluminum hydride (3.01 g, 79.3 mmol) in THF (170 mL) was added dropwise a solution of tert-butyl (4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl)-2,3,4,5-tetrahydro[biphenyl]-4-carboxylate (26.2 g, 39.8 mmol) in THF (200 mL), and the mixture was stirred at the said temperature for 2.5 hr. To the reaction mixture were added sodium sulfate decahydrate and ethyl acetate, and the mixture was stirred at room temperature. Insoluble materials were filtered off, and the filtrate was concentrated under reduced pressure to give the title compound (23.8 g, 40.5 mmol, yield: quantitative).

<Example X1> [(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl methanesulfonate

[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methanol (0.783 g, 1.33 mmol) and triethylamine (0.56 mL, 4.0 mmol) were dissolved in THF (13 mL), methanesulfonic anhydride (0.473 g, 2.71 mmol) was added at 0° C., and the mixture was stirred at room temperature for 16 hr. To the reaction mixture was added saturated aqueous sodium hydrogen carbonate solution, and the mixture was extracted with ethyl acetate. The organic layer was washed with saturated brine, dried over anhydrous sodium sulfate and filtered, and the filtrate was concentrated under reduced pressure to give the title compound (0.878 g, 1.32 mmol, yield 99%).

<Example X2> tert-Butyl 4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazine-1-carboxylate

[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl methanesulfonate (0.878 g, 1.32 mmol) and 1-(tert-butoxycarbonyl)piperazine (CAS Registry Number: 57260-71-6) (1.37 g, 7.37 mmol) were dissolved in DMF (6 mL), sodium iodide (0.0425 g, 0.284 mmol) was added, and the mixture was stirred with heating at 110° C. for 4 hr. To the reaction mixture was added saturated aqueous sodium hydrogen carbonate solution, and the mixture was extracted with ethyl acetate. The organic layer was washed successively with water and saturated brine, dried over anhydrous sodium sulfate and filtered, and the filtrate was concentrated under reduced pressure. The residue was purified by silica gel column chromatography (hexane/ethyl acetate) to give the title compound (0.877 g, 1.16 mmol, yield 88%).

<Example Y1> tert-Butyl (2-{[1-(2,6-dioxopiperidin-3-yl)-3-methyl-2-oxo-2,3-dihydro-1H-benzimidazol-5-yl]amino}ethyl)carbamate To a suspension of 3-(5-amino-3-methyl-2-oxo-2,3-dihydro-1H-benzimidazol-1-yl)piperidine-2,6-dione (WO2021170109 A1) (391 mg, 1.43 mmol) and N-Boc-2-aminoacetaldehyde (CAS Registry Number: 89711-08-0) (364 mg, 2.29 mmol) in methanol (7 mL) and N,N-dimethylacetamide (7 mL) was added acetic acid (0.245 mL, 4.28 mmol), and the mixture was stirred at room temperature for 30 min. To the reaction mixture was added sodium cyanoborohydride (365 mg, 5.81 mmol), and the mixture was stirred at room temperature for 15 hr. To the reaction mixture were added saturated aqueous sodium hydrogen carbonate solution and water, and the mixture was extracted with ethyl acetate. The organic layers were combined, washed successively with water and saturated brine, dried over sodium sulfate and filtered, and the filtrate was concentrated under reduced pressure. The residue was purified by silica gel column chromatography (DCM/methanol) to give the title compound (375 mg, 0.898 mmol, yield 63%).

<Example Y2> 3-{5-[(2-Aminoethyl)amino]-3-methyl-2-oxo-2,3-dihydro-1H-benzimidazol-1-yl}piperidine-2,6-dione dihydrochloride Using the compound obtained in <Example Y1>, the title compound was obtained by the same method as in <Example AO5>.

<Example Y3> Methyl (4'-formyl-2,3,4,5-tetrahydro[biphenyl]-4-yl)acetate

Using 4-bromobenzaldehyde (CAS Registry Number: 1122-91-4) and methyl [4-(4,4,5,5-tetramethyl-1,3,2-dioxaborolan-2-yl)-3-cyclohexen-1-yl]acetate (CAS Registry Number: 1109277-66-8), the title compound was obtained by the same method as in <Example W1>.

<Example Y4> Methyl (4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)acetate To a solution of methyl (4'-formyl-2,3,4,5-tetrahydro[biphenyl]-4-yl)acetate (283 mg, 1.0956 mmol) and 3,3,3-trifluoro-N-{2-[(4R)-4-(4-methoxyphenyl)-2,2-dimethyltetrahydro-2H-pyran-4-yl]ethyl}-2,2-dimethylpropan-1-amine (300 mg, 0.774 mmol) in methanol (4 mL) was added acetic acid (0.133 mL, 2.32 mmol), and the mixture was stirred at room temperature for 25 min. To the reaction mixture was added sodium cyanoborohydride (158 mg, 2.51 mmol), and the mixture was stirred for 19 hr at room temperature. To the reaction mixture was added sodium cyanoborohydride (210 mg, 3.34 mmol), and the mixture was stirred for 5 hr at room temperature. To the reaction mixture was added saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (hexane/ethyl acetate) to give the title compound (233 mg, 0.370 mmol, yield 48%).

<Example Y5> (4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)acetic acid To a solution of methyl (4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)acetate (233 mg, 0.370 mmol) in THF (2 mL) and methanol (3 mL) was added 1 mol/L aqueous sodium hydroxide solution (1 mL, 1 mmol), and the mixture was stirred at room temperature for 20 hr. To the reaction mixture were added 1 mol/L hydrochloric acid (1 mL, 1 mmol), and the mixture was extracted with DCM. The organic layer dried over sodium sulfate and filtered, and the filtrate was concentrated under reduced pressure. The residue was dried under reduced pressure to give the title compound (219 mg, 0.357 mmol, yield 96%).

<Example Y6> N-(2-{[1-(2,6-Dioxopiperidin-3-yl)-3-methyl-2-oxo-2,3-dihydro-1H-benzimidazol-5-yl]amino}ethyl)-2-(4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)acetamide Using the compounds obtained in <Example Y5> and <Example Y$^2$>, the title compound was obtained by the same method as in <Example BM9>.

<Example Z1> tert-Butyl [4-(4-formylphenoxy)piperidin-1-yl]acetate

Using tert-butyl 4-(4-formylphenoxy)piperidine-1-carboxylate (WO2015069110 A1), the title compound was obtained by the same method as in <Example AK7>.

<Example Z2> tert-Butyl [4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)piperidin-1-yl]acetate Using the compounds obtained in <Example M3> and <Example Z1>, the title compound was obtained by the same method as in <Example Y4>.

<Example Z3> [4-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)piperidin-1-yl]acetic acid dihydrochloride Using the compound obtained in <Example Z2>, the title compound was obtained by the same method as in <Example V5>.

<Example Z4> 3-Bromo-1-{[2-(trimethylsilyl)ethoxy]methyl}piperidine-2,6-dione

To a suspension of 3-bromopiperidine-2,6-dione (CAS Registry Number: 62595-74-8) (25.5 g, 133 mmol) in DCM (250 mL) were successively added, under ice-cooling, DIPEA (45 mL, 258 mmol) and [2-(chloromethoxy)ethyl]trimethylsilane (29 mL, 170 mmol), and the mixture was stirred at said temperature for 40 min. The reaction mixture was warmed to room temperature and stirred for 16 hr. The reaction mixture was washed with water, and the organic layer was dried over sodium sulfate and filtered, and the filtrate was concentrated under reduced pressure. The residue was purified by silica gel column chromatography (hexane/ethyl acetate) to give the title compound (36.5 g, 113 mmol, yield 85%).

<Example Z5> 3-(3-Methyl-4-nitro-2-oxo-2,3-dihydro-1H-benzimidazol-1-yl)-1-{[2-(trimethylsilyl)ethoxy]methyl}piperidine-2,6-dione A suspension of 1-methyl-7-nitro-1,3-dihydro-2H-benzimidazol-2-one (WO2020200291 A1) (3.29 g, 17.0 mmol), 3-bromo-1-{[2-(trimethylsilyl)ethoxy]methyl}piperidine-2,6-dione (11.38 g, 35.31 mmol), and cesium carbonate (16.7 g, 51.3 mmol) in DMF (80 mL) was stirred under a nitrogen atmosphere at room temperature for 26 hr. The reaction mixture was diluted with ethyl acetate and washed successively with water and saturated brine. The organic layer was dried over sodium sulfate and filtered, and the filtrate was concentrated under reduced pressure. The residue was purified by silica gel column chromatography (hexane/ethyl acetate) to give the title compound (6.76 g, 15.6 mmol, yield 91%).

<Example Z6> 3-(4-Amino-3-methyl-2-oxo-2,3-dihydro-1H-benzimidazol-1-yl)-1-{[2-(trimethylsilyl)ethoxy]methyl}piperidine-2,6-dione Using the compound obtained in <Example Z5>, the title compound was obtained by the same method as in <Example BK5>.

<Example Z7> N-[1-(2,6-Dioxo-1-{[2-(trimethylsilyl)ethoxy]methyl}piperidin-3-yl)-3-methyl-2-oxo-2,3-dihydro-1H-benzimidazol-4-yl]-2-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)piperidin-1-yl]acetamide Using the compounds obtained in <Example Z6> and <Example Z3>, the title compound was obtained by the same method as in <Example BM9>.

<Example Z8> N-[1-(2,6-Dioxopiperidin-3-yl)-3-methyl-2-oxo-2,3-dihydro-1H-benzimidazol-4-yl]-2-[4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)piperidin-1-yl]acetamide Using the compound obtained in <Example Z7>, the title compound was obtained by the same method as in <Example BK9>.

<Example AA1> Ethyl (4'-formyl[biphenyl]-3-yl)acetate

Using 4-bromobenzaldehyde (CAS Registry Number: 1122-91-4) and [3-(2-ethoxy-2-oxoethyl)phenyl]boronic acid (CAS Registry Number: 1256345-69-3), the title compound was obtained by the same method as in <Example W1>.

<Example AA2> Ethyl (4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)[biphenyl]-3-yl)acetate Using the compounds obtained in <Example AA1> and <Example M3>, the title compound was obtained by the same method as in <Example Y4>.

<Example AA3> (4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}[biphenyl]-3-yl)acetic acid Using the compound obtained in <Example AA2>, the title compound was obtained by the same method as in <Example Y5>.

<Example AA4> N-(2-{[1-(2,6-Dioxopiperidin-3-yl)-3-methyl-2-oxo-2,3-dihydro-1H-benzimidazol-5-yl]amino}ethyl)-2-(4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}[biphenyl]-3-yl)acetamide Using the compounds obtained in <Example AA3> and <Example Y2>, the title compound was obtained by the same method as in <Example BM9>.

<Example AB1> Ethyl cyano(4,4-difluorocyclohexylidene)acetate

Using 4,4-difluorocyclohexanone (CAS Registry Number: 22515-18-0), the title compound was obtained by the same method as in <Example A1>.

<Example AB2> N-{2-[4,4-Difluoro-1-(4-methoxyphenyl)cyclohexyl]ethyl}-3,3,3-trifluoro-2,2-dimethylpropan-1-amine Using the compound obtained in <Example AB1>, the title compound was obtained by sequentially performing the same operations as in <Example C3>, <Example C4>, <Example C5>, <Example M2> and <Example M3>.

<Example AB3> Methyl [4-(4-formylphenoxy)piperidin-1-yl]acetate

Using tert-butyl 4-(4-formylphenoxy)piperidine-1-carboxylate (WO2015069110 A1) and methyl bromoacetate (CAS Registry Number: 96-32-2), the title compound was obtained by the same method as in <Example AK7>.

<Example AB4> Methyl [4-(4-{[{2-[4,4-difluoro-1-(4-methoxyphenyl)cyclohexyl]ethyl}(3,3,3-trifluoro-2,2-dimethylpropyl)amino]methyl}phenoxy)piperidin-1-yl]acetate Using the compounds obtained in <Example AB3> and <Example AB2>, the title compound was obtained by the same method as in <Example Y4>.

<Example AB5> [4-(4-{[{2-[4,4-Difluoro-1-(4-methoxyphenyl)cyclohexyl]ethyl}(3,3,3-trifluoro-2,2-dimethylpropyl)amino]methyl}phenoxy)piperidin-1-yl]acetic acid Using the compound obtained in <Example AB4>, the title compound was obtained by the same method as in <Example Y5>.

<Example AB6> 2-[4-(4-{[{2-[4,4-Difluoro-1-(4-methoxyphenyl)cyclohexyl]ethyl}(3,3,3-trifluoro-2,2-dimethylpropyl)amino]methyl}phenoxy)piperidin-1-yl]-N-[1-(2,6-dioxopiperidin-3-yl)-3-methyl-2-oxo-2,3-dihydro-1H-benzimidazol-4-yl]acetamide Using the compound obtained in <Example AB5> and 3-(4-amino-3-methyl-2-oxo-2,3-dihydro-1H-benzimidazol-1-yl)piperidine-2,6-dione (WO2021170109 A1), the title compound was obtained by the same method as in <Example BM9>.

<Example AC1> Ethyl cyano(tetrahydro-4H-pyran-4-ylidene)acetate

Using tetrahydro-4H-pyran-4-one (CAS Registry Number: 29943-42-8), the title compound was obtained by the same method as in <Example A1>.

<Example AC2> 3,3,3-Trifluoro-N-{2-[4-(4-methoxyphenyl)tetrahydro-2H-pyran-4-yl]ethyl}-2,2-dimethylpropan-1-amine Using the compound obtained in <Example AC1>, the title compound was obtained by sequentially performing the same operations as in <Example C3>, <Example C4>, <Example C5>, <Example M2> and <Example M3>.

<Example AC3> Methyl [4-(4-{[{2-[4-(4-methoxyphenyl)tetrahydro-2H-pyran-4-yl]ethyl}(3,3,3-trifluoro-2,2-dimethylpropyl)amino]methyl}phenoxy)piperidin-1-yl]acetate Using the compounds obtained in <Example AB3> and <Example AC2>, the title compound was obtained by the same method as in <Example Y4>.

<Example AC4> [4-(4-{[{2-[4-(4-Methoxyphenyl)tetrahydro-2H-pyran-4-yl]ethyl}(3,3,3-trifluoro-2,2-dimethylpropyl)amino]methyl}phenoxy)piperidin-1-yl]acetic acid Using the compound obtained in <Example AC3>, the title compound was obtained by the same method as in <Example Y5>.

<Example AC5> N-[1-(2,6-Dioxo-1-{[2-(trimethylsilyl)ethoxy]methyl}piperidin-3-yl)-3-methyl-2-oxo-2,3-dihydro-1H-benzimidazol-4-yl]-2-[4-(4-{[{2-[4-(4-methoxyphenyl)tetrahydro-2H-pyran-4-yl]ethyl}(3,3,3-trifluoro-2,2-dimethylpropyl)amino]methyl}phenoxy)piperidin-1-yl]acetamide Using the compounds obtained in <Example AC4> and <Example Z6>, the title compound was obtained by the same method as in <Example BM9>.

<Example AC6> N-[1-(2,6-Dioxopiperidin-3-yl)-3-methyl-2-oxo-2,3-dihydro-1H-benzimidazol-4-yl]-2-[4-(4-{[{2-[4-(4-methoxyphenyl)tetrahydro-2H-pyran-4-yl]ethyl}(3,3,3-trifluoro-2,2-dimethylpropyl)amino]methyl}phenoxy)piperidin-1-yl]acetamide Using the compound obtained in <Example AC5>, the title compound was obtained by the same method as in <Example BK9>.

<Example AD1> N-[1-(2,6-Dioxopiperidin-3-yl)-3-methyl-2-oxo-2,3-dihydro-1H-benzimidazol-4-yl]-2-[2-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetamide Using the compound obtained in <Example AK9> and 3-(4-amino-3-methyl-2-oxo-2,3-dihydro-1H-benzimidazol- 1-yl)piperidine-2,6-dione (WO2021170109 A1), the title compound was obtained by the same method as in <Example BM9>.

<Example AE1> N-[1-(2,6-Dioxopiperidin-3-yl)-3-methyl-2-oxo-2,3-dihydro-1H-benzimidazol-5-yl]-2-[2-(4-{[{2-[(4R)-4-(4-methoxyphenyl)-2,2-dimethyl-tetrahydro-2H-pyran-4-yl]ethyl}(3,3,3-trifluoro-2,2-dimethylpropyl)amino]methyl}phenoxy)-7-azaspiro[3.5]nonan-7-yl]acetamide Using the compound obtained in <Example AK9> and 3-(5-amino-3-methyl-2-oxo-2,3-dihydro-1H-benzimidazol-1-yl)piperidine-2,6-dione (WO2021170109 A1), the title compound was obtained by the same method as in <Example BM9>.

<Example AF1> N-[2-(2,6-Dioxopiperidin-3-yl)-1-oxo-2,3-dihydro-1H-isoindol-5-yl]-2-[2-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetamide Using the compound obtained in <Example AK9> and 3-(5-amino-1-oxo-1,3-dihydro-2H-isoindol-2-yl)piperidine-2,6-dione (ACS Med. Chem. Lett., 2021, 12, 1733.), the title compound was obtained by the same method as in <Example BM9>.

<Example AG1> Ethyl 4'-formyl-2,3,4,5-tetrahydro[biphenyl]-4-carboxylate

Using 4-bromobenzaldehyde (CAS Registry Number: 1122-91-4) and ethyl 4-(4,4,5,5-tetramethyl-1,3,2-dioxaborolan-2-yl)-3-cyclohexene-1-carboxylate (CAS Registry Number: 1049004-32-1), the title compound was obtained by the same method as in <Example W1>.

<Example AG2> Ethyl 4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate Using the compounds obtained in <Example M3> and <Example AG1>, the title compound was obtained by the same method as in <Example W4>.

<Example AG3> (4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methanol To a solution of ethyl 4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate (439 mg, 0.697 mmol) in toluene (3.5 mL) was added, under ice-cooling, diisobutylaluminum hydride (1 mol/L toluene solution, 1.7 mL, 1.7 mmol), and the mixture was stirred at said temperature for 20 min. To the reaction mixture were added saturated Rochelle salt solution, and the mixture was stirred at room temperature for 1 hr. The reaction mixture was extracted with ethyl acetate, the organic layer was dried over sodium sulfate and filtered, and the filtrate was concentrated under reduced pressure. The residue was purified by silica gel column chromatography (hexane/ethyl acetate) to give the title compound (388 mg, 0.660 mmol, yield 94%).

<Example AG4> (4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl methanesulfonate Using the compound obtained in <Example AG3>, the title compound was obtained by the same method as in <Example X1>.

<Example AG5> 3,3,3-Trifluoro-N-{2-[(4R)-4-(4-methoxyphenyl)-2,2-dimethyltetrahydro-2H-pyran-4-yl]ethyl}-2,2-dimethyl-N-{[4'-(piperazin-1-ylmethyl)-2',3',4',5'-tetrahydro[biphenyl]-4-yl]methyl}propan-1-amine dihydrochloride Using the compound obtained in <Example AG4>, the title compound was obtained by sequentially performing the same operations as in <Example X2> and <Example AO5>.

<Example AG6> 2,4,6-Trichlorophenyl 2-(2,6-dioxopiperidin-3-yl)-1-oxo-2,3-dihydro-1H-isoindole-5-carboxylate Using 3-(5-bromo-1-oxo-1,3-dihydro-2H-isoindol-2-yl)-2,6-piperidinedione (WO2019038717 A1), the title compound was obtained by the same method as in <Example BY5>.

<Example AG7> 3-[5-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]piperazin-1-yl}carbonyl)-1-oxo-1,3-dihydro-2H-isoindol-2-yl]piperidine-2,6-dione Using the compounds obtained in <Example AG6> and <Example AG5>, the title compound was obtained by the same method as in <Example BI1>.

<Example AH1> 3-(4-Bromo-3-methyl-2-oxo-2,3-dihydro-1H-benzimidazol-1-yl)-1-{[2-(trimethylsilyl)ethoxy]methyl}piperidine-2,6-dione Using 7-bromo-1-methyl-1,3-dihydro-2H-benzimidazol-2-one (CAS Registry Number: 913297-44-6), the title compound was obtained by the same method as in <Example Z5>.

<Example AH2> 2,4,6-Trichlorophenyl 1-(2,6-dioxo-1-{[2-(trimethylsilyl)ethoxy]methyl}piperidin-3-yl)-3-methyl-2-oxo-2,3-dihydro-1H-benzimidazole-4-carboxylate Using the compound obtained in <Example AH1>, the title compound was obtained by the same method as in <Example BY5>.

<Example AH3> 3-[4-({4-[(4'-{[{2-[(4R)-4-(4-Methoxyphenyl)-2,2-dimethyltetrahydro-2H-pyran-4-yl]ethyl)(3,3,3-trifluoro-2,2-dimethylpropyl) amino]methyl}-2,3,4,5-tetrahydro[biphenyl]-4-yl) methyl]piperazin-1-yl}carbonyl)-3-methyl-2-oxo-2,3-dihydro-1H-benzimidazol-1-yl]-1-{[2-(trimethylsilyl)ethoxy]methyl}piperidine-2,6-dione Using the compounds obtained in <Example AH2> and <Example AG5>, the title compound was obtained by the same method as in <Example BI1>.

<Example AH4> 3-[4-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl) amino]methyl}-2,3,4,5-tetrahydro[biphenyl]-4-yl) methyl]piperazin-1-yl}carbonyl)-3-methyl-2-oxo-2,3-dihydro-1H-benzimidazol-1-yl]piperidine-2,6-dione Using the compound obtained in <Example AH3>, the title compound was obtained by the same method as in <Example BK9>.

<Example AI1> Ethyl cis-4-(4-formylphenyl)cyclohexanecarboxylate

<Example AI2> Ethyl trans-4-(4-formylphenyl)cyclohexanecarboxylate

Under a hydrogen atmosphere, a suspension of ethyl 4'-formyl-2,3,4,5-tetrahydro[biphenyl]-4-carboxylate (1.1 g, 4.30 mmol) and 7.5% palladium carbon (350 mg) in ethanol (30 mL) was stirred for 1.5 hr. The catalyst was filtered off through celite, and the filtrate was concentrated under reduced pressure. The residue was dissolved in chloroform (30 mL), manganese(IV) oxide (1.9 g) was added and the mixture was heated under reflux for 1 hr. Insoluble materials were filtered off from the reaction mixture through celite, and the filtrate was concentrated under reduced pressure. The residue was separated and purified by silica gel column chromatography (hexane/ethyl acetate) to give the title cis isomer (730 mg, 2.80 mmol, yield 66%) and trans isomer (320 mg, 1.22 mmol, yield 29%).

<Example AI3> Ethyl cis-4-(4-{[{2-[(4R)-4-(4-methoxyphenyl)-2,2-dimethyltetrahydro-2H-pyran-4-yl]ethyl}(3,3,3-trifluoro-2,2-dimethylpropyl) amino]methyl}phenyl)cyclohexanecarboxylate Using the compounds obtained in <Example M3> and <Example AI1>, the title compound was obtained by the same method as in <Example W4>.

<Example AI4> [Cis-4-(4-{[{2-[(4R)-4-(4-methoxyphenyl)-2,2-dimethyltetrahydro-2H-pyran-4-yl] ethyl}(3,3,3-trifluoro-2,2-dimethylpropyl)amino] methyl}phenyl)cyclohexyl]methanol Using the compound obtained in <Example AI3>, the title compound was obtained by the same method as in <Example W5>.

<Example AI5> Cis-4-(4-{[{2-[(4R)-4-(4-methoxyphenyl)-2,2-dimethyltetrahydro-2H-pyran-4-yl] ethyl)}(3,3,3-trifluoro-2,2-dimethylpropyl)amino] methyl}phenyl)cyclohexanecarbaldehyde Under ice-cooling, to a solution of [cis-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino] methyl}phenyl)cyclohexyl]methanol (520 mg, 0.88 mmol) in DCM (10 mL) was added 1,1,1-triacetoxy-1,1-dihydro-1,2-benzoiodoxol-3-(1H)-one (CAS Registry Number: 87413-09-0) (490 mg, 1.15 mmol), and the mixture was stirred for 1 hr. To the reaction mixture was added aqueous sodium hydrogen carbonate solution, and the mixture was stirred and then extracted with chloroform. The organic layer was washed with saturated brine, dried over magnesium sulfate, filtered, and the filtrate was concentrated under reduced pressure. The residue was purified by silica gel column chromatography (hexane/ethyl acetate) to give the title compound (346 mg, 0.58 mmol, yield 66%).

<Example AI6> tert-Butyl 4-{[cis-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl] methyl}piperazine-1-carboxylate Using the compound obtained in <Example AI5> and 1-(tert-butoxycarbonyl)piperazine (CAS Registry Number: 57260-71-6), the title compound was obtained by the same method as in <Example W4>.

<Example AI7> 3,3,3-Trifluoro-N-{2-[(4R)-4-(4-methoxyphenyl)-2,2-dimethyltetrahydro-2H-pyran-4-yl]ethyl}-2,2-dimethyl-N-{4-[cis-4-(piperazin-1-ylmethyl)cyclohexyl]benzyl}propan-1-amine At room temperature, to a solution of tert-butyl 4-{[cis-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl] methyl}piperazine-1-carboxylate (390 mg, 0.51 mmol) in DCM (5 mL) was added 4 mol/L hydrogen chloride/1,4-dioxane solution (3 mL, 12 mmol). After completion of the reaction, the reaction mixture was concentrated under reduced pressure. The residue was basified by adding aqueous sodium hydrogen carbonate solution and extracted with chloroform. The organic layer was washed with saturated brine, dried over magnesium sulfate and filtered, and the filtrate was concentrated under reduced pressure to give the title compound (320 mg, 0.49 mmol, yield 94%).

<Example AI8> tert-Butyl 3-methyl-2-oxo-2,3-dihydro-1H-benzimidazole-5-carboxylate Using tert-butyl 4-amino-3-(methylamino)benzoate (Bioorg. Med. Chem. Lett., 2002, 12, 3129.), the title compound was obtained by the same method as in <Example AN2>.

<Example AI9> tert-Butyl 1-(2,6-dioxopiperidin-3-yl)-3-methyl-2-oxo-2,3-dihydro-1H-benzimidazole-5-carboxylate Under ice-cooling, to a solution of tert-butyl 3-methyl-2-oxo-2,3-dihydro-1H-benzimidazole-5-carboxylate (260 mg, 0.46 mmol) in THF (5 mL) was added sodium hydride (55% oil, 50 mg, 1.15 mmol), and the mixture was stirred for 30 min. Then, 3-bromopiperidine-2,6-dione (CAS Registry Number: 62595-74-8) (200 mg, 1.04 mmol) was added thereto, and the mixture was stirred at 60° C. for 1.5 hr. After cooling, to the reaction mixture was added water and the mixture was extracted with ethyl acetate. The organic layer was washed with saturated brine, dried over magnesium sulfate and filtered, and the filtrate was concentrated under reduced pressure. The residue was purified by silica gel column chromatography (hexane/ethyl acetate) to give the title compound (165 mg, 0.46 mmol, yield 44%).

<Example AI10> 1-(2,6-Dioxopiperidin-3-yl)-3-methyl-2-oxo-2,3-dihydro-1H-benzimidazole-5-carboxylic acid At room temperature, to a solution of tert-butyl 1-(2,6-dioxopiperidin-3-yl)-3-methyl-2-oxo-2,3-dihydro-1H-benzimidazole-5-carboxylate (165 mg, 0.46 mmol) in DCM (3 mL) was added trifluoroacetic acid (3 mL), and the mixture was stirred for 2 hr. The reaction mixture was concentrated under reduced pressure to give a crude crystal, and the crystal was washed with a small amount of chloroform/ethyl acetate to give the title compound (74 mg, 0.24 mmol, yield 53%).

<Example AI11> 3-{5-[(4-{[Cis-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl]methyl}piperazin-1-yl)carbonyl]-3-methyl-2-oxo-2,3-dihydro-1H-benzimidazol-1-yl}piperidine-2,6-dione At room temperature, to a solution of 3,3,3-trifluoro-N-{2-[(4R)-4-(4-methoxyphenyl)-2,2-dimethyltetrahydro-2H-pyran-4-yl]ethyl}-2,2-dimethyl-N-{4-[cis-4-(piperazin-1-ylmethyl) cyclohexyl]benzyl}propan-1-amine (45 mg, 0.066 mmol) and 1-(2,6-dioxopiperidin-3-yl)-3-methyl-2-oxo-2,3-dihydro-1H-benzimidazole-5-carboxylic acid (20 mg, 0.066 mmol) in DMF (2 mL) was added 3H-1,2,3-triazolo[4,5-b]pyridin-3-ol (CAS Registry Number: 39968-33-7) (10 mg, 0.066 mmol), and dissolved. Then, 1-(3-dimethylaminopropyl)-3-ethylcarbodiimide hydrochloride (CAS Registry Number: 25952-53-8) (25 mg, 0.099 mmol) was added thereto, and the mixture was stirred for 15 hr. The reaction mixture was diluted with chloroform, and washed successively with water and saturated brine. The organic layer was dried over magnesium sulfate and filtered, and the filtrate was concentrated under reduced pressure. The residue was purified by silica gel column chromatography (chloroform/methanol) to give the title compound (55 mg, 0.058 mmol, yield 88%).

<Example AJ1> Ethyl trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexanecarboxylate Using the compounds obtained in <Example M3> and <Example AI2>, the title compound was obtained by the same method as in <Example W4>.

<Example AJ2> [Trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl]methanol Using the compound obtained in <Example AJ1>, the title compound was obtained by the same method as in <Example W5>.

<Example AJ3> Trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexanecarbaldehyde Using the compound obtained in <Example AJ2>, the title compound was obtained by the same method as in <Example AI5>.

<Example AJ4> tert-Butyl 4-{[trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl]methyl}piperazine-1-carboxylate Using the compound obtained in <Example AJ3> and 1-(tert-butoxycarbonyl)piperazine (CAS Registry Number: 57260-71-6), the title compound was obtained by the same method as in <Example W4>.

<Example AJ5> 3,3,3-Trifluoro-N-{2-[(4R)-4-(4-methoxyphenyl)-2,2-dimethyltetrahydro-2H-pyran-4-yl]ethyl}-2,2-dimethyl-N-{4-[trans-4-(piperazin-1-ylmethyl)cyclohexyl]benzyl}propan-1-amine Using the compound obtained in <Example AJ4>, the title compound was obtained by the same method as in <Example AI7>.

<Example AJ6> 3-{5-[(4-{[Trans-4-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenyl)cyclohexyl]methyl}piperazin-1-yl)carbonyl]-3-methyl-2-oxo-2,3-dihydro-1H-benzimidazol-1-yl}piperidine-2,6-dione Using the compounds obtained in <Example AJ5> and <Example AI10>, the title compound was obtained by the same method as in <Example AI11>.

<Example AK1> tert-Butyl 7-amino-8-bromo-3,4-dihydroisoquinoline-2(1H)-carboxylate A solution of tert-butyl 7-amino-3,4-dihydroisoquinoline-2(1H)-carboxylate (CAS Registry Number: 171049-41-5) (1.13 g, 4.55 mmol) in acetonitrile (50 mL) was cooled to 0° C., N-bromosuccinimide (0.83 g, 4.66 mmol) was added, and the mixture was stirred at room temperature for 15 hr. The reaction mixture was concentrated under reduced pressure, and the residue was purified by silica gel column chromatography (hexane/ethyl acetate) to give the title compound (1.43 g, 4.37 mmol, yield 96%).

<Example AK2> tert-Butyl 8-bromo-7-[(methylcarbamoyl)amino]-3,4-dihydroisoquinoline-2(1H)-carboxylate To a solution of tert-butyl 7-amino-8-bromo-3,4-dihydroisoquinoline-2(1H)-carboxylate (1.8 g, 5.5 mmol) in DCM (28 mL) was added DIPEA (3.8 mL, 22 mmol), N-methylcarbamoyl chloride (CAS Registry Number: 6452-47-7) (1.5 g, 17 mmol) was added at 0° C., and the mixture was stirred at room temperature for 17 hr. To the reaction mixture were added N-methylcarbamoyl chloride (1.0 g, 11 mmol) and DIPEA (1.9 mL, 11 mmol), and the mixture was stirred at room temperature for 3 days. The reaction mixture was concentrated under reduced pressure, and the residue was purified by silica gel column chromatography (ethyl acetate/methanol) to give the title compound (1.86 g, 4.84 mmol, yield 88%).

<Example AK3> tert-Butyl 1-methyl-2-oxo-1,2,3,6,7,9-hexahydro-8H-imidazo[4,5-h]isoquinoline-8-carboxylate To a solution of tert-butyl 8-bromo-7-[(methylcarbamoyl)amino]-3,4-dihydroisoquinoline-2(1H)-carboxylate (1.57 g, 4.09 mmol) in DMSO (41 mL) were added copper(I) iodide (160 mg, 0.817 mmol), trans-4-hydroxy-L-proline (230 mg, 1.75 mmol), and tripotassium phosphate (1.73 g, 8.17 mmol) at room temperature, and the mixture was stirred at 160° C. for 5 hr. The reaction mixture was cooled to room temperature, saturated aqueous ammonium chloride solution was added, and the mixture was extracted with ethyl acetate. The organic layer was dried over sodium sulfate and filtered, and the filtrate was concentrated under reduced pressure. The residue was purified by silica gel column chromatography (hexane/ethyl acetate) to give the title compound (540 mg, 1.78 mmol, yield 44%).

<Example AK4> tert-Butyl 3-[2,6-bis(benzyloxy)pyridin-3-yl]-1-methyl-2-oxo-1,2,3,6,7,9-hexahydro-8H-imidazo[4,5-h]isoquinoline-8-carboxylate To a suspension of tert-butyl 1-methyl-2-oxo-1,2,3,6,7,9-hexahydro-8H-imidazo[4,5-h]isoquinoline-8-carboxylate (540 mg, 1.78 mmol), 2,6-bis(benzyloxy)-3-(4,4,5,5-tetramethyl-1,3,2-dioxaborolan-2-yl)pyridine (WO2021262812 A1) (1.11 g, 2.66 mmol), and copper(II) acetate (644 mg, 3.56 mmol) in acetonitrile (3.6 mL) was added triethylamine (0.74 mL, 5.34 mmol), and the mixture was stirred at 80° C. for 10 hr. The reaction mixture was purified by silica gel column chromatography (hexane/ethyl acetate) to give the title compound (1.0 g, 1.7 mmol, yield 95%).

<Example AK5> tert-Butyl 3-(2,6-dioxopiperidin-3-yl)-1-methyl-2-oxo-1,2,3,6,7,9-hexahydro-8H-imidazo[4,5-h]isoquinoline-8-carboxylate To a solution of tert-butyl 3-[2,6-bis(benzyloxy)pyridin-3-yl]-1-methyl-2-oxo-1,2,3,6,7,9-hexahydro-8H-imidazo[4,5-h]isoquinoline-8-carboxylate (1.0 g, 1.7 mmol) in ethyl acetate (16 mL)-ethanol (16 mL) was added ASCA-2 (manufactured by N.E. Chemcat Corporation) (670 mg), and the mixture was stirred under a hydrogen atmosphere at room temperature for 6 hr. The reaction mixture was filtered through celite, and the filtrate was concentrated under reduced pressure. The residue was purified by silica gel column chromatography (hexane/ethyl acetate, ethyl acetate/methanol) to give the title compound (380 mg, 0.92 mmol, yield 54%).

<Example AK6> tert-Butyl 2-(4-formylphenoxy)-7-azaspiro[3.5]nonane-7-carboxylate A suspension of tert-butyl 2-[(methylsulfonyl)oxy]-7-azaspiro[3.5]nonane-7-carboxylate (J. Med. Chem., 2014, 57, 3, 733.) (7.02 g, 22.0 mmol), 4-hydroxybenzaldehyde (CAS: 123-08-0) (2.66 g, 21.8 mmol), and cesium carbonate (13.8 g, 42.4 mmol) in DMF (45 mL) was stirred at 100° C. for 4 hr. The l0 reaction mixture was cooled to room temperature and diluted with ethyl acetate (150 mL). The mixture was washed successively with water (150 mL) and saturated brine (100 mL), dried over sodium sulfate and filtered, and the filtrate was concentrated under reduced pressure. The residue was purified by silica gel column chromatography (hexane/ethyl acetate) to give the title compound (6.63 g, 19.2 mmol, yield 87%).

<Example AK7> tert-Butyl [2-(4-formylphenoxy)-7-azaspiro[3.5]nonan-7-yl]acetate

To a solution of tert-butyl 2-(4-formylphenoxy)-7-azaspiro[3.5]nonane-7-carboxylate (6.63 g, 19.2 mmol) in DCM (50 mL) was added 4 mol/L hydrogen chloride/1,4-dioxane solution (50 mL, 200 mmol), and the mixture was stirred at room temperature for 1 hr. The reaction mixture was concentrated under reduced pressure. After drying, to a suspension of the residue and potassium carbonate (12.4 g, 89.7 mmol) in DMF (40 mL) was added tert-butyl bromoacetate (3.22 mL, 22.0 mmol), and the mixture was stirred at room temperature for 4 hr. The reaction mixture was diluted with ethyl acetate (100 mL), and washed successively with water (100 mL) and saturated brine (100 mL). The organic layer was dried over sodium sulfate and filtered, and the filtrate was concentrated under reduced pressure. The residue was purified by silica gel column chromatography (hexane/ethyl acetate) to give the title compound (6.57 g, 18.3 mmol, yield 92%).

<Example AK8> tert-Butyl [2-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetate Using the compounds obtained in <Example M3> and <Example AK7>, the title compound was obtained by the same method as in <Example W4>.

<Example AK9> [2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetic acid dihydrochloride Using the compound obtained in <Example AK8>, the title compound was obtained by the same method as in <Example V5>.

<Example AK10> 3-(8-{[2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetyl}-1-methyl-2-oxo-1,2,6,7,8,9-hexahydro-3H-imidazo[4,5-h]isoquinolin-3-yl)piperidine-2,6-dione To a solution of tert-butyl 3-(2,6-dioxopiperidin-3-yl)-1-methyl-2-oxo-1,2,3,6,7,9-hexahydro-8H-imidazo[4,5-h]isoquinoline-8-carboxylate (21.4 mg, 0.0516 mmol) in DCM (1 mL) was added trifluoroacetic acid (0.5 mL) at room temperature, and the mixture was stirred at room temperature for 2 hr. The reaction mixture was concentrated under reduced pressure, and the obtained residue was diluted with ethanol (2 mL) and THE (2 mL). Then, [2-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetic acid dihydrochloride (36.0 mg, 0.0483 mmol), DIPEA (0.100 mL, 0.584 mmol), and 4-(4,6-dimethoxy-1,3,5-triazin-2-yl)-

4-methylmorpholinium chloride (CAS Registry Number: 3945-69-5) (30.0 mg, 0.0794 mmol) were added thereto, and the mixture was stirred at room temperature for 19 hr. To the reaction mixture was added saturated aqueous sodium hydrogen carbonate solution, and the mixture was extracted with ethyl acetate. The organic layer was dried over sodium sulfate and filtered, and the filtrate was concentrated under reduced pressure. The residue was purified by amine-modified silica gel column chromatography (ethyl acetate/methanol) to give the title compound (27.9 mg, 0.0287 mmol, yield 60%).

<Example AL1> tert-Butyl 5-amino-4,6-dibromo-1,3-dihydro-2H-isoindole-2-carboxylate tert-Butyl 5-amino-1,3-dihydro-2H-isoindole-2-carboxylate (CAS Registry Number: 264916-06-5) (200 mg, 0.85 mmol) was dissolved in a mixed solvent of DCM (12 mL)-methanol (6 mL), calcium carbonate (230 mg, 2.30 mmol) and benzyltrimethylammonium tribromide (700 mg, 1.80 mmol) were added at room temperature, and the mixture was stirred for 30 min. The reaction mixture was filtered, and the filtrate was concentrated under reduced pressure. The residue was purified by silica gel column chromatography (hexane/ethyl acetate) to give the title compound (340 mg, 0.87 mmol, yield: quantitative).

<Example AL2> tert-Butyl 5-amino-4-bromo-1,3-dihydro-2H-isoindole-2-carboxylate

To a mixture of tert-butyl 5-amino-4,6-dibromo-1,3-dihydro-2H-isoindole-2-carboxylate (33 mg, 0.084 mmol), palladium(II) acetate (2.1 mg, 0.0094 mmol), and (+/−)-2,2'-bis(diphenylphosphino)-1,1'-binaphthalene (5.1 mg, 0.084 mmol) was added THE (1 mL), and the mixture was stirred at room temperature for 10 min. To the reaction mixture was added N,N'-dimethylethylenediamine (0.020 mL, 0.019 mmol), and the mixture was stirred for 10 min. Then, sodium borohydride (4.0 mg, 0.11 mmol) was added thereto, and the mixture was stirred at room temperature for 17 hr. To the reaction mixture was added a small amount of methanol, and the mixture was purified by silica gel column chromatography (hexane/ethyl acetate) to give the title compound (0.022 g, 0.070 mmol, yield 83%).

<Example AL3> tert-Butyl 3-(2,6-dioxopiperidin-3-yl)-1-methyl-2-oxo-2,3,6,8-tetrahydroimidazo[4,5-e]isoindole-7(1H)-carboxylate Using the compound obtained in <Example AL2>, the title compound was obtained by sequentially performing the same operations as in <Example AK2>, <Example AK3>, <Example AK4> and <Example AK5>.

<Example AL4> 3-[7-{[2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetyl}-1-methyl-2-oxo-1,6,7,8-tetrahydroimidazo[4,5-e]isoindole-3(2H)-yl]piperidine-2,6-dione Using the compound obtained in <Example AL3>, the title compound was obtained by the same method as in <Example AK10>.

<Example AM1> 4-[(4R)-2,2-Dimethyl-4-{2-[(3,3,3-trifluoro-2,2-dimethylpropyl)amino]ethyl)tetrahydro-2H-pyran-4-yl]phenol A suspension of 3,3,3-trifluoro-N-{2-[(4R)-4-(4-methoxyphenyl)-2,2-dimethyltetrahydro-2H-pyran-4-yl]ethyl}-2,2-dimethylpropan-1-amine (2.00 g, 5.16 mmol) and sodium thiomethoxide (1.16 g, 16.6 mmol) in DMF (10 mL) was stirred under microwave irradiation at 150° C. for 1 hr. The reaction mixture was diluted with ethyl acetate, and washed successively with water and saturated brine. The organic layer was dried over sodium sulfate and filtered, and the filtrate was concentrated under reduced pressure. The residue was purified by silica gel column chromatography (DCM/methanol) to give the title compound (1.97 g, 5.27 mmol, yield: quantitative).

<Example AM2> tert-Butyl {2-[(4R)-4-(4-hydroxyphenyl)-2,2-dimethyltetrahydro-2H-pyran-4-yl]ethyl}(3,3,3-trifluoro-2,2-dimethylpropyl)carbamate To a solution of 4-((4R)-2,2-dimethyl-4-{2-[(3,3,3-trifluoro-2,2-dimethylpropyl)amino]ethyl}tetrahydro-2H-pyran-4-yl]phenol (1.97 g, 5.27 mmol) and triethylamine (2 mL, 14 mmol) in THF (25 mL) was added di-tert-butyl dicarbonate (1.79 g, 8.20 mmol), and the mixture was stirred at room temperature for 4.5 hr. The reaction mixture was concentrated under reduced pressure, and the residue was purified by silica gel column chromatography (hexane/ethyl acetate) to give the title compound (1.92 g, 4.05 mmol, yield 77%).

<Example AM3> tert-Butyl (2-{(4R)-4-[4-(difluoromethoxy)phenyl]-2,2-dimethyltetrahydro-2H-pyran-4-yl}ethyl) (3,3,3-trifluoro-2,2-dimethylpropyl)carbamate To a solution of tert-butyl {2-[(4R)-4-(4-hydroxyphenyl)-2,2-dimethyltetrahydro-2H-pyran-4-yl]ethyl}(3,3,3-trifluoro-2,2-dimethylpropyl)carbamate (443 mg, 0.935 mmol) in acetonitrile (5 mL)-water (1 mL) were successively added, under ice-cooling, 50% aqueous potassium hydroxide solution (0.348 mL, 4.68 mmol) and diethyl (bromodifluoromethyl)phosphonate (CAS Registry Number: 65094-22-6) (0.250 mL, 1.40 mmol), and the mixture was stirred at said temperature for 40 min. The reaction mixture was diluted with ethyl acetate and washed with saturated aqueous ammonium chloride solution. The organic layer was dried over sodium sulfate and filtered, and the filtrate was concentrated under reduced pressure. The residue was purified by silica gel column chromatography (hexane/ethyl acetate) to give the title compound (356 mg, 0.680 mmol, yield 73%).

<Example AM4> N-(2-{(4R)-4-[4-(Difluoromethoxy)phenyl]-2,2-dimethyltetrahydro-2H-pyran-4-yl}ethyl)-3,3,3-trifluoro-2,2-dimethylpropan-1-amine To a solution of tert-butyl (2-{(4R)-4-[4-(difluoromethoxy)phenyl]-2,2-dimethyltetrahydro-2H-pyran-4-yl}ethyl) (3,3,3-trifluoro-2,2-dimethylpropyl)carbamate (426 mg, 0.812 mmol) in DCM (0.5 mL) was added trifluoroacetic acid (0.5 mL), and the mixture was stirred at room temperature for 1 hr. The reaction mixture was diluted with ethyl acetate and washed with saturated aqueous sodium hydrogen carbonate solution. The organic layer was dried over sodium sulfate and filtered, and the filtrate was concentrated under reduced pressure. The residue was purified by silica gel column chromatography (DCM/methanol) to give the title compound (297 mg, 0.701 mmol, yield 86%).

<Example AM5> Ethyl 4'-{[(2-{(4R)-4-[4-(difluoromethoxy)phenyl]-2,2-dimethyltetrahydro-2H-pyran-4-yl}ethyl) (3,3,3-trifluoro-2,2-dimethylpropyl)amino]methyl}-2,3,4,5-tetrahydro[biphenyl]-4-carboxylate Using the compounds obtained in <Example AG1> and <Example AM4>, the title compound was obtained by the same method as in <Example W4>.

<Example AM6> tert-Butyl 4-[(4'-{[(2-{(4R)-4-[4-(difluoromethoxy)phenyl]-2,2-dimethyltetrahydro-2H-pyran-4-yl}ethyl) (3,3,3-trifluoro-2,2-dimethylpropyl)amino]methyl}-2,3,4,5-tetrahydro[biphenyl]-4-yl)methyl]piperazine-1-carboxylate Using the compound obtained in <Example AM5>, the title compound was obtained by sequentially performing the same operations as in <Example AG3>, <Example X1> and <Example X2>.

<Example AM7> 3-(5-Bromo-3-methyl-2-oxo-2,3-dihydro-1H-benzimidazol-1-yl)-1-{[2-(trimethylsilyl)ethoxy]methyl}piperidine-2,6-dione A solution of 6-bromo-1-methyl-1,3-dihydro-2H-benzimidazol-2-one (CAS Registry Number: 305790-48-1) (23.8 g, 105 mmol), 3-bromo-1-{[2-(trimethylsilyl)ethoxy]methyl}piperidine-2,6-dione (68.3 g, 212 mmol), and cesium carbonate (102 g, 313 mmol) in DMF (300 mL) was stirred at room temperature for 45 hr. The reaction mixture was diluted with ethyl acetate (600 mL), and washed with water (600 mL). The aqueous layer was extracted with ethyl acetate, and the organic layers were combined and washed successively with water and saturated brine. The organic layer was dried over sodium sulfate and filtered, and the filtrate was concentrated under reduced pressure. The residue was purified by silica gel column chromatography (hexane/ethyl acetate), and the obtained solid was washed with hexane to give the title compound (32.7 g, 69.8 mmol, yield 67%).

<Example AM8> 2,4,6-Trichlorophenyl 1-(2,6-dioxo-1-{[2-(trimethylsilyl)ethoxy]methyl}piperidin-3-yl)-3-methyl-2-oxo-2,3-dihydro-1H-benzimidazole-5-carboxylate To a mixture of 3-(5-bromo-3-methyl-2-oxo-2,3-dihydro-1H-benzimidazol-1-yl)-1-{[2-(trimethylsilyl)ethoxy]methyl}piperidine-2,6-dione (1.13 g, 2.41 mmol), 2,4,6-trichlorophenyl formate (CAS Registry Number: 4525-65-9) (816 mg, 3.62 mmol), palladium(II) acetate (27.1 mg, 0.121 mmol), and XantPhos (140 mg, 0.241 mmol) were added toluene (24.0 mL) and triethylamine (0.592 mL, 4.27 mmol) at room temperature, and the mixture was stirred under a carbon monoxide atmosphere at 100° C. for 3 hr. The reaction mixture was concentrated under reduced pressure, and the residue was purified by silica gel column chromatography (hexane/ethyl acetate) to give the title compound (1.48 g, 2.27 mmol, yield 94%).

<Example AM9> 3-[5-({4-[(4'-{[(2-{(4R)-4-[4-(Difluoromethoxy)phenyl]-2,2-dimethyltetrahydro-2H-pyran-4-yl}ethyl) (3,3,3-trifluoro-2,2-dimethylpropyl)amino]methyl}-2,3,4,5-tetrahydro[biphenyl]-4-yl)methyl]piperazin-1-yl}carbonyl)-3-methyl-2-oxo-2,3-dihydro-1H-benzimidazol-1-yl]-1-{[2-(trimethylsilyl)ethoxy]methyl}piperidine-2,6-dione To a solution of tert-butyl 4-[(4'-{[(2-{(4R)-4-[4-(difluoromethoxy)phenyl]-2,2-dimethyltetrahydro-2H-pyran-4-yl}ethyl) (3,3,3-trifluoro-2,2-dimethylpropyl)amino]methyl}-2,3,4,5-tetrahydro[biphenyl]-4-yl)methyl]piperazine-1-carboxylate (51.3 mg, 0.0648 mmol) in DCM (0.5 mL) was added 4 mol/L hydrogen chloride/1,4-dioxane solution (0.5 mL, 2 mmol), and the mixture was stirred at room temperature for 2 hr and concentrated under reduced pressure. To the residue were added 2,4,6-trichlorophenyl 1-(2,6-dioxo-1-{[2-(trimethylsilyl)ethoxy]methyl}piperidin-3-yl)-3-methyl-2-oxo-2,3-dihydro-1H-benzimidazole-5-carboxylate (45.8 mg, 0.0747 mmol), 4-dimethylaminopyridine (2.1 mg, 0.017 mmol), acetonitrile (1 mL), and DIPEA (0.0564 mL, 0.324 mmol), and the mixture was stirred at room temperature for 22 hr. The reaction mixture was diluted with ethyl acetate and washed with saturated aqueous sodium hydrogen carbonate solution. The organic layer was dried over sodium sulfate and filtered, and the filtrate was concentrated under reduced pressure. The residue was purified by silica gel column chromatography (ethyl acetate/methanol) to give the title compound (68.0 mg, 0.0614 mmol, yield 95%).

<Example AM10> 3-[5-({4-[(4'-{[(2-{(4R)-4-[4-(Difluoromethoxy)phenyl]-2,2-dimethyltetrahydro-2H-pyran-4-yl}ethyl) (3,3,3-trifluoro-2,2-dimethylpropyl)amino]methyl}-2,3,4,5-tetrahydro[biphenyl]-4-yl)methyl]piperazin-1-yl}carbonyl)-3-methyl-2-oxo-2,3-dihydro-1H-benzimidazol-1-yl]piperidine-2,6-dione Using the compound obtained in <Example AM9>, the title compound was obtained by the same method as in <Example BK9>.

<Example AN1> 1,2,3,4-Tetrahydroquinoxalin-5-amine

To a solution of 5-aminoquinoxaline (CAS Registry Number: 16566-20-4) (450 mg, 3.10 mmol) in THF (15 mL) was added borane-THF complex (1 mol/L THF solution, 7.5 mL, 7.5 mmol) at room temperature, and the mixture was stirred for 15 min. To the reaction mixture was added methanol (15 mL), and the mixture was stirred at room temperature for 2 hr and concentrated under reduced pressure. The residue was purified by silica gel column chromatography (ethyl acetate/methanol) to give the title compound (414 mg, 2.77 mmol, yield 90%).

<Example AN2> 5,6-Dihydro-4H-imidazo[1,5,4-de]quinoxalin-2(1H)-one

A solution of 1,2,3,4-tetrahydroquinoxalin-5-amine (414 mg, 2.77 mmol) in THF (10 mL) was cooled to 0° C., 1,1'-carbonyldiimidazole (550 mg, 3.39 mmol) was added and the mixture was stirred at room temperature for 17 hr. The reaction mixture was concentrated under reduced pressure, and the residue was purified by silica gel column chromatography (ethyl acetate/methanol) to give the title compound (403 mg, 2.30 mmol, yield 83%).

<Example AN3> 6-{[2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetyl)-5,6-dihydro-4H-imidazo[1,5,4-de]quinoxaline-2(1H)-one Using the compounds obtained in <Example AK9> and <Example AN2>, the title compound was obtained by the same method as in <Example BM9>.

<Example AN4> 3-[6-{[2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetyl}-2-oxo-5,6-dihydro-4H-imidazo[1,5,4-de]quinoxalin-1(2H)-yl]-1-{[2-(trimethylsilyl)ethoxy]methyl}piperidine-2,6-dione Using the compound obtained in <Example AN3>, the title compound was obtained by the same method as in <Example Z5>.

<Example AN5> 3-[6-{[2-(4-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetyl}-2-oxo-5,6-dihydro-4H-imidazo[1,5,4-de]quinoxalin-1(2H)-yl]piperidine-2,6-dione Using the compound obtained in <Example AN4>, the title compound was obtained by the same method as in <Example BK9>.

<Example AO1> Benzyl 4-{[(2R)-1-amino-5-tert-butoxy-1,5-dioxopentan-2-yl]amino}-3-nitrobenzoate A suspension of tert-butyl D-α-glutaminate monohydrochloride (CAS Registry Number: 66575-26-6) (460 mg, 1.93 mmol), benzyl 4-fluoro-3-nitrobenzoate (Org. Lett., 2016, 18, 3706.) (633 mg, 2.30 mmol), and potassium carbonate (814 mg, 5.89 mmol) in DMF (4 mL) was stirred at room temperature for 5 hr. The reaction mixture was diluted with ethyl acetate and washed successively with water and saturated brine. The organic layer was dried over sodium sulfate and filtered, and the filtrate was concentrated under reduced pressure. The residue was purified by silica gel column chromatography (hexane/ethyl acetate) to give the title compound (368 mg, 0.804 mmol, yield 42%).

<Example AO2> Benzyl 1-[(2R)-1-amino-5-tert-butoxy-1,5-dioxopentan-2-yl]-2-oxo-2,3-dihydro-1H-benzimidazole-5-carboxylate To a solution of benzyl 4-{[(2R)-1-amino-5-tert-butoxy-1,5-dioxopentan-2-yl]amino}-3-nitrobenzoate (317 mg, 0.693 mmol) in acetone (5 mL)-water (1 mL) were added ammonium chloride (369 mg, 6.90 mmol) and zinc powder (426 mg, 6.52 mmol), and the mixture was stirred at room temperature for 10 min. The reaction mixture was diluted with ethyl acetate, insoluble materials were filtered off through celite, washed with saturated brine, dried over sodium sulfate and filtered, and the filtrate was concentrated under reduced pressure. The residue was dissolved in THF (7 mL), 1,1'-carbonyldiimidazole (186 mg, 1.15 mmol) was added, and the mixture was stirred at room temperature for 5 hr. To the reaction mixture was added 1,1'-carbonyldiimidazole (117 mg, 0.722 mmol), and the mixture was stirred at room temperature for 2 hr. To the reaction mixture was added 1,1'-carbonyldiimidazole (66.5 mg, 0.410 mmol), and the mixture was stirred at room temperature for 1.5 hr. The reaction mixture was diluted with methanol and concentrated under reduced pressure. The residue was purified by silica gel column chromatography (DCM/methanol) to give the title compound (226 mg, 0.498 mmol, yield 72%).

<Example AO3> Benzyl 1-[(2R)-1-amino-5-tert-butoxy-1,5-dioxopentan-2-yl]-3-methyl-2-oxo-2,3-dihydro-1H-benzimidazole-5-carboxylate To a suspension of benzyl 1-[(2R)-1-amino-5-tert-butoxy-1,5-dioxopentan-2-yl]-2-oxo-2,3-dihydro-1H-benzimidazole-5-carboxylate (226 mg, 0.498 mmol) and potassium carbonate (205 mg, 1.48 mmol) in DMF (1 mL) was added iodomethane (0.062 mL, 1.0 mmol), and the mixture was stirred at room temperature for 4 hr. The reaction mixture was diluted with ethyl acetate, and washed successively with water and saturated brine. The organic layer was dried over sodium sulfate and filtered, and the filtrate was concentrated under reduced pressure and further dried under reduced pressure to give the title compound (207 mg, 0.443 mmol, yield 89%).

<Example AO4> 1-[(2R)-1-Amino-5-tert-butoxy-1,5-dioxopentan-2-yl]-3-methyl-2-oxo-2,3-dihydro-1H-benzimidazole-5-carboxylic acid A suspension of benzyl 1-[(2R)-1-amino-5-tert-butoxy-1,5-dioxopentan-2-yl]-3-methyl-2-oxo-2,3-dihydro-1H-benzimidazole-5-carboxylate (195 mg, 0.417 mmol), and 10% palladium carbon (223 mg) in ethyl acetate (2 mL)-ethanol (2 mL) was stirred under a hydrogen atmosphere at room temperature for 2 hr. The reaction mixture was diluted with chloroform, insoluble materials were filtered off through celite, and the filtrate was concentrated under reduced pressure to give the title compound (150 mg, 0.397 mmol, yield 95%).

<Example AO5> 3,3,3-Trifluoro-N-{2-[(4R)-4-(4-methoxyphenyl)-2,2-dimethyltetrahydro-2H-pyran-4-yl]ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride To a solution of tert-butyl 4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazine-1-carboxylate (13.8 g, 18.3 mmol) in DCM (50 mL) was added 4 mol/L hydrogen chloride/1,4-dioxane solution (50 mL, 200 mmol), and the mixture was stirred at room temperature for 3 hr. The reaction mixture was concentrated under reduced pressure, the precipitated solid was washed with diethyl ether, and dried under reduced pressure at 60° C. to give the title compound (13.8 g, 18.9 mmol, yield: quantitative).

<Example AO6> tert-Butyl (4R)-5-amino-4-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]methyl}piperazin-1-yl)carbonyl]-3-methyl-2-oxo-2,3-dihydro-1H-benzimidazol-1-yl}-5-oxopentanoate 3,3,3-Trifluoro-N-{2-[(4R)-4-(4-methoxyphenyl)-2,2-dimethyltetrahydro-2H-pyran-4-yl]ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (0.15 g, 0.21 mmol), 1-[(2R)-1-amino-5-tert-butoxy-1,5-dioxopentan-2-yl]-3-methyl-2-oxo-2,3-dihydro-1H-benzimidazole-5-carboxylic acid (0.075 g, 0.20 mmol), and DIPEA (0.17 mL, 1.0 mmol) were dissolved in DMF (1.0 mL), HATU (0.11 g, 0.29 mmol) was added, and the mixture was stirred at room temperature for 20 hr. To the reaction mixture was added saturated aqueous sodium hydrogen carbonate solution, and the mixture was extracted with ethyl acetate. The organic layer was washed successively with water and saturated brine, dried over sodium sulfate and filtered, and the filtrate was concentrated under reduced pressure. The residue was purified by silica gel column chromatography (DCM/methanol) to give the title compound (0.17 g, 0.16 mmol, yield 83%).

<Example AO7> (3R)-3-{5-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione tert-Butyl (4R)-5-amino-4-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}-5-oxopentanoic acid (0.167 g, 0.164 mmol) were dissolved in acetonitrile (2.0 mL), benzenesulfonic acid (0.0552 g, 0.349 mmol) was added, and the mixture was stirred with heating at 90° C. for 7 hr. The reaction mixture was cooled to room temperature, saturated aqueous sodium hydrogen carbonate solution was added, and the mixture was extracted with ethyl acetate. The organic layer was washed with saturated brine, dried over sodium sulfate and filtered, and the filtrate was concentrated under reduced pressure. The residue was purified by silica gel column chromatography (DCM/methanol) to give the title compound (0.104 g, 0.110 mmol, yield 67%).

<Example AP1> Benzyl 4-{[(2S)-1-amino-5-tert-butoxy-1,5-dioxopentan-2-yl]amino}-3-nitrobenzoate A suspension of tert-butyl L-α-glutaminate monohydrochloride (CAS Registry Number: 108607-02-9) (280 mg, 1.17 mmol), benzyl 4-fluoro-3-nitrobenzoate (Org. Lett., 2016, 18, 3706.) (433 mg, 1.57 mmol), and potassium carbonate (482 mg, 3.49 mmol) in DMF (2 mL) was stirred at room temperature for 4.5 hr. The reaction mixture was diluted with ethyl acetate, and washed successively with water and saturated brine. The organic layer was dried over sodium sulfate and filtered, and the filtrate was concentrated under reduced pressure. The residue was purified by silica gel column chromatography (hexane/ethyl acetate) to give the title compound (299 mg, 0.654 mmol, yield 56%).

<Example AP2> Benzyl 1-[(2S)-1-amino-5-tert-butoxy-1,5-dioxopentan-2-yl]-2-oxo-2,3-dihydro-1H-benzimidazole-5-carboxylate To a solution of benzyl 4-{[(2S)-1-amino-5-tert-butoxy-1,5-dioxopentan-2-yl]amino}-3-nitrobenzoate (1.09 g, 2.38 mmol) in acetone (15 mL)-water (3 mL) were added ammonium chloride (1.10 g, 20.6 mmol) and zinc powder (1.36 g, 20.8 mmol), and the mixture was stirred at room temperature for 5 min. The reaction mixture was diluted with ethyl acetate, insoluble materials were filtered off through celite, and the filtrate was washed with saturated brine. The organic layer was dried over sodium sulfate and filtered, and the filtrate was concentrated under reduced pressure. The residue was dissolved in THF (24 mL), 1,1'-carbonyldiimidazole (580 mg, 3.58 mmol) was added, and the mixture was stirred at room temperature for hr. To the reaction mixture was added 1,1'-carbonyldiimidazole (366 mg, 2.26 mmol), and the mixture was stirred for 1.5 hr. To the reaction mixture was added 1,1'-carbonyldiimidazole (222 mg, 1.37 mmol), and the mixture was stirred for 1.5 hr. The reaction mixture was diluted with methanol, and concentrated under reduced pressure. The residue was purified by silica gel column chromatography (DCM/methanol) to give the title compound (839 mg, 1.85 mmol, yield 78%).

<Example AP3> Benzyl 1-[(2S)-1-amino-5-tert-butoxy-1,5-dioxopentan-2-yl]-3-methyl-2-oxo-2,3-dihydro-1H-benzimidazole-5-carboxylate To a suspension of benzyl 1-[(2S)-1-amino-5-tert-butoxy-1,5-dioxopentan-2-yl]-2-oxo-2,3-dihydro-1H-benzimidazole-5-carboxylate (839 mg, 1.85 mmol) and potassium carbonate (757 mg, 5.48 mmol) in DMF (4 mL) was added iodomethane (0.230 mL, 3.69 mmol), and the mixture was stirred at room temperature for 4 hr. The reaction mixture was diluted with ethyl acetate, and washed successively with water and saturated brine. The organic layer was dried over sodium sulfate and filtered, and the filtrate was concentrated under reduced pressure and successively dried under reduced pressure to give the title compound (783 mg, 1.67 mmol, yield 91%).

<Example AP4> 1-[(2S)-1-Amino-5-tert-butoxy-1,5-dioxopentan-2-yl]-3-methyl-2-oxo-2,3-dihydro-1H-benz-imidazole-5-carboxylic acid To a suspension of benzyl 1-[(2S)-1-amino-5-tert-butoxy-1,5-dioxopentan-2-yl]-3-methyl-2-oxo-2,3-dihydro-1H-benzimidazole-5-carboxylate (780 mg, 1.67 mmol) in ethyl acetate (8 mL)-ethanol (8 mL) was added 10% palladium carbon (859 mg), and the mixture was stirred under a hydrogen atmosphere at room temperature for 2 hr. The reaction mixture was diluted with chloroform, and insoluble materials were filtered off through celite. The filtrate was concentrated under reduced pressure, and successively dried under reduced pressure to give the title compound (647 mg, 1.71 mmol, yield: quantitative).

<Example AP5> tert-Butyl (4S)-5-amino-4-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}-5-oxopentanoate 3,3,3-Trifluoro-N-{2-[(4R)-4-(4-methoxyphenyl)-2,2-dimethyltetrahydro-2H-pyran-4-yl]ethyl}-2,2-dimethyl-N-

{[(4'R)-4'-(piperazin-1-ylmethyl)-2',3',4',5'-tetrahydro[biphenyl]-4-yl]methyl}propan-1-amine dihydrochloride (0.155 g, 0.213 mmol), 1-[(2S)-1-amino-5-tert-butoxy-1,5-dioxopentan-2-yl]-3-methyl-2-oxo-2,3-dihydro-1H-benzimidazole-5-carboxylic acid (0.0761 g, 0.202 mmol), and DIPEA (0.173 mL, 1.01 mmol) were dissolved in DMF (1.0 mL), HATU (0.116 g, 0.304 mmol) was added, and the mixture was stirred at room temperature for 19 hr. To the reaction mixture was added saturated aqueous sodium hydrogen carbonate solution, and the mixture was extracted with hexane/ethyl acetate. The organic layer was washed successively with water and saturated brine, dried over sodium sulfate and filtered, and the filtrate was concentrated under reduced pressure. The residue was purified by silica gel column chromatography (DCM/methanol) to give the title compound (0.164 g, 0.161 mmol, yield 80%).

<Example AP6> (3S)-3-{5-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione tert-Butyl (4S)-5-amino-4-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}-5-oxopentanoate (0.164 g, 0.161 mmol) was dissolved in acetonitrile (2.0 mL), benzenesulfonic acid (0.0536 g, 0.339 mmol) was added, and the mixture was stirred with heating at 90° C. for 24 hr. To the reaction mixture was added saturated aqueous sodium hydrogen carbonate solution, and the mixture was extracted with ethyl acetate. The organic layer was washed with saturated brine, dried over sodium sulfate and filtered, and the filtrate was concentrated under reduced pressure. The residue was purified by silica gel column chromatography (DCM/methanol) to give the title compound (0.105 g, 0.112 mmol, yield 69%).

<Example AQ1> N-[2-(2,6-Dioxopiperidin-3-yl)-1,3-dioxo-2,3-dihydro-1H-isoindol-5-yl]-2-[2-(4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}phenoxy)-7-azaspiro[3.5]nonan-7-yl]acetamide Using the compound obtained in <Example AK9> and 5-amino-2-(2,6-dioxo-3-piperidinyl)-1H-isoindole-1,3(2H)-dione (CAS Registry Number: 191732-76-0), the title compound was obtained by the same method as in <Example BM9>.

<Example AR1> N-{2-[(4R)-4-(4-Methoxyphenyl)-2,2-dimethyltetrahydro-2H-pyran-4-yl]ethyl}-1-(trifluoromethyl)cyclobutanecarboxamide Using the compound obtained in <Example M1> and 1-(trifluoromethyl)cyclobutanecarboxylic acid (CAS Registry Number: 277756-45-3), the title compound was obtained by the same method as in <Example M2>.

<Example AR2> 2-[(4R)-4-(4-Methoxyphenyl)-2,2-dimethyltetrahydro-2H-pyran-4-yl]-N-{[1-(trifluoromethyl)cyclobutyl]methyl}ethanamine Using the compound obtained in <Example AR1>, the title compound was obtained by the same method as in <Example M3>.

<Example AR3> Ethyl 4'-[({2-[(4R)-4-(4-methoxyphenyl)-2,2-dimethyltetrahydro-2H-pyran-4-yl]ethyl}{[1-(trifluoromethyl)cyclobutyl]methyl}amino)methyl]-2,3,4,5-tetrahydro[biphenyl]-4-carboxylate Using the compounds obtained in <Example AR2> and <Example AG1>, the title compound was obtained by the same method as in <Example W4>.

<Example AR4> tert-Butyl 4-({4'-[({2-[(4R)-4-(4-methoxyphenyl)-2,2-dimethyltetrahydro-2H-pyran-4-yl]ethyl}{[1-(trifluoromethyl)cyclobutyl]methyl}amino)methyl]-2,3,4,5-tetrahydro[biphenyl]-4-yl}methyl)piperazine-1-carboxylate Using the compound obtained in <Example AR3>, the title compound was obtained by sequentially performing the same operations as in <Example AG3>, <Example X1> and <Example X2>.

<Example AR5> 2-[(4R)-4-(4-Methoxyphenyl)-2,2-dimethyltetrahydro-2H-pyran-4-yl]-N-{[4'-(piperazin-1-ylmethyl)-2',3',4',5'-tetrahydro[biphenyl]-4-yl]methyl}-N-{[1-(trifluoromethyl)cyclobutyl]methyl}ethanamine dihydrochloride Using the compound obtained in <Example AR4>, the title compound was obtained by the same method as in <Example AO5>.

<Example AR6> 3-(5-{[4-({4'-[({2-[(4R)-4-(4-Methoxyphenyl)-2,2-dimethyltetrahydro-2H-pyran-4-yl]ethyl}{[1-(trifluoromethyl)cyclobutyl]methyl}amino)methyl]-2,3,4,5-tetrahydro[biphenyl]-4-yl}methyl)piperazin-1-yl]carbonyl}-3-methyl-2-oxo-2,3-dihydro-1H-benzimidazol-1-yl)-1-{[2-(trimethylsilyl)ethoxy]methyl}piperidine-2,6-dione Using the compounds obtained in <Example AR5> and <Example AM8>, the title compound was obtained by the same method as in <Example BI1>.

<Example AR7> 3-(5-{[4-({4'-[({2-[(4R)-4-(4-Methoxyphenyl)-2,2-dimethyltetrahydro-2H-pyran-4-yl]ethyl}{[1-(trifluoromethyl)cyclobutyl]methyl}amino)methyl]-2,3,4,5-tetrahydro[biphenyl]-4-yl}methyl)piperazin-1-yl]carbonyl}-3-methyl-2-oxo-2,3-dihydro-1H-benzimidazol-1-yl)piperidine-2,6-dione Using the compound obtained in <Example AR6>, the title compound was obtained by the same method as in <Example BK9>.

<Example AS1> 1-(2,6-Dioxo-1-{[2-(trimethylsilyl)ethoxy]methyl}piperidin-3-yl)-3-methyl-2-oxo-2,3-dihydro-1H-benzimidazole-5-carbaldehyde A suspension of 3-(5-bromo-3-methyl-2-oxo-2,3-dihydro-1H-benzimidazol-1-yl)-1-{[2-(trimethylsilyl)ethoxy]

methyl}piperidine-2,6-dione (5.71 g, 12.2 mmol), triethylsilane (4.0 mL, 25 mmol), triethylamine (5.0 mL, 36 mmol), and [1,1'-bis(diphenylphosphino)ferrocene]dichloropalladium(II) (1.37 g, 1.87 mmol) in DMF (60 mL) was stirred under a carbon monoxide atmosphere at 95° C. for 7 hr. The reaction mixture was diluted with ethyl acetate, and washed successively with water and saturated brine. The organic layer was dried over sodium sulfate and filtered, and the filtrate was concentrated under reduced pressure. The residue was purified by silica gel column chromatography (hexane/ethyl acetate) to give the title compound (2.12 g, 5.08 mmol, yield 42%).

<Example AS2> Benzyl 4-{[1-(2,6-dioxo-1-{[2-(trimethylsilyl)ethoxy]methyl}piperidin-3-yl)-3-methyl-2-oxo-2,3-dihydro-1H-benzimidazol-5-yl]methyl}piperazine-1-carboxylate To a solution of 1-(2,6-dioxo-1-{[2-(trimethylsilyl)ethoxy]methyl}piperidin-3-yl)-3-methyl-2-oxo-2,3-dihydro-1H-benzimidazole-5-carbaldehyde (1.36 g, 3.26 mmol), 1-carbobenzoxypiperazine (CAS Registry Number: 31166-44-6) (0.811 mL, 4.23 mmol), and acetic acid (0.559 mL, 9.76 mmol) in DCM (15 mL) was added sodium triacetoxyborohydride (1.48 g, 6.98 mmol), and the mixture was stirred at room temperature for 4 hr. To the reaction mixture was added saturated aqueous sodium hydrogen carbonate solution and the mixture was extracted with DCM. The organic layer was dried over sodium sulfate and filtered, and the filtrate was concentrated under reduced pressure. The residue was purified by silica gel column chromatography (ethyl acetate/methanol) to give the title compound (1.64 g, 2.64 mmol, yield 81%).

<Example AS3> Benzyl 4-{[1-(2,6-dioxopiperidin-3-yl)-3-methyl-2-oxo-2,3-dihydro-1H-benzimidazol-5-yl]methyl}piperazine-1-carboxylate Using the compound obtained in <Example AS2>, the title compound was obtained by the same method as in <Example BK9>.

<Example AS4> 3-[3-Methyl-2-oxo-5-(piperazin-1-ylmethyl)-2,3-dihydro-1H-benzimidazol-1-yl]piperidine-2,6-dione To a solution of benzyl 4-{[1-(2,6-dioxopiperidin-3-yl)-3-methyl-2-oxo-2,3-dihydro-1H-benzimidazol-5-yl]methyl}piperazine-1-carboxylate (917 mg, 1.87 mmol) in ethyl acetate (20 mL) was added 10% palladium carbon (2.33 g), and the mixture was stirred under a hydrogen atmosphere at room temperature for 1.5 hr. The reaction mixture was purged with nitrogen, diluted with 10% IPA/chloroform (30 mL) and IPA (4 mL), and insoluble materials were filtered off through celite, and washed with 33% IPA/chloroform. The filtrate and washing were combined, and concentrated under reduced pressure. The precipitated solid was washed with ethyl acetate to give the title compound (317 mg, 0.887 mmol, yield 48%).

<Example AS5> Ethyl 4'-formyl-2'-methyl-2,3,4,5-tetrahydro[biphenyl]-4-carboxylate Using ethyl 4-(4,4,5,5-tetramethyl-1,3,2-dioxaborolan-2-yl)-3-cyclohexene-1-carboxylate (CAS Registry Number: 1049004-32-1) and 4-bromo-3-methylbenzaldehyde (CAS Registry Number: 78775-11-8), the title compound was obtained by the same method as in <Example W1>.

<Example AS6> Ethyl 4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2'-methyl-2,3,4,5-tetrahydro[biphenyl]-4-carboxylate Using the compounds obtained in <Example M3> and <Example AS5>, the title compound was obtained by the same method as in <Example W4>.

<Example AS7> 3-[5-({4-[(4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2'-methyl-2,3,4,5-tetrahydro[biphenyl]-4-yl)carbonyl]piperazin-1-yl}methyl)-3-methyl-2-oxo-2,3-dihydro-1H-benzimidazol-1-yl]piperidine-2,6-dione Using the compounds obtained in <Example AS6> and <Example AS4>, the title compound was obtained by the same method as in <Example AU2>.

<Example AT1> Ethyl 3'-fluoro-4'-formyl-2,3,4,5-tetrahydro[biphenyl]-4-carboxylate Using ethyl 4-(4,4,5,5-tetramethyl-1,3,2-dioxaborolan-2-yl)-3-cyclohexene-1-carboxylate (CAS Registry Number: 1049004-32-1) and 4-bromo-2-fluorobenzaldehyde (CAS Registry Number: 57848-46-1), the title compound was obtained by the same method as in <Example W1>.

<Example AT2> Ethyl 3'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate Using the compounds obtained in <Example M3> and <Example AT1>, the title compound was obtained by the same method as in <Example W4>.

<Example AT3> 3-[5-({4-[(3'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperazin-1-yl}methyl)-3-methyl-2-oxo-2,3-dihydro-1H-benzimidazol-1-yl]piperidine-2,6-dione Using the compounds obtained in <Example AT2> and <Example AS4>, the title compound was obtained by the same method as in <Example AU2>.

<Example AU1> Ethyl 2',6'-difluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-carboxylate Using 4-bromo-3,5-difluorobenzaldehyde (CAS Registry Number: 135564-22-6) and ethyl 4-(4,4,5,5-tetramethyl-1,3,2-dioxaborolan-2-yl)-3-cyclohexene-1-carboxylate (CAS Registry Number: 1049004-32-1), the title compound was obtained by sequentially performing the same operations as in <Example W1> and <Example W4>.

<Example AU2> tert-Butyl 4-[(2',6'-difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperazine-1-carboxylate Ethyl 2',6'-difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate (0.124 g, 0.186 mmol) was dissolved in a mixed solvent of THF (0.60 mL)-ethanol (0.60 mL), 1 mol/L aqueous sodium hydroxide solution (0.60 mL, 0.60 mmol) was added, and the mixture was stirred at room temperature for 22.5 hr. To the reaction mixture were added 1 mol/L hydrochloric acid (0.60 mL, 0.60 mmol) and water, and the mixture was extracted with ethyl acetate. The organic layer was dried over sodium sulfate and filtered, and the filtrate was concentrated under reduced pressure. The residue was dissolved in DMF (2 mL), DIPEA (0.109 mL, 0.637 mmol), HATU (0.113 g, 0.298 mmol), and 1-(tert-butoxycarbonyl)piperazine (CAS Registry Number: 57260-71-6) (0.060 g, 0.322 mmol) were added, and the mixture was stirred at room temperature for 22 hr. To the reaction mixture was added saturated aqueous sodium hydrogen carbonate solution, and the mixture was extracted with ethyl acetate. The organic layer was dried over sodium sulfate and filtered, and the filtrate was concentrated under reduced pressure. The residue was purified by silica gel column chromatography (hexane/ethyl acetate) to give the title compound (0.149 g, 0.185 mmol, yield 99%).

<Example AU3> 3-[5-({4-[(2',6'-Difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperazin-1-yl}methyl)-3-methyl-2-oxo-2,3-dihydro-1H-benzimidazol-1-yl]-1-([2-(trimethylsilyl)ethoxy]methyl}piperidine-2,6-dione tert-Butyl 4-[(2',6'-difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperazine-1-carboxylate (0.149 g, 0.185 mmol) was dissolved in DCM (1 mL), trifluoroacetic acid (0.5 mL) was added, and the mixture was stirred at room temperature for 2 hr. To the reaction mixture was added saturated aqueous sodium hydrogen carbonate solution and the mixture was extracted with DCM. The organic layer was dried over sodium sulfate and filtered, and the filtrate was concentrated under reduced pressure. To the residue were added 1-(2,6-dioxo-1-{[2-(trimethylsilyl)ethoxy]methyl}piperidin-3-yl)-3-methyl-2-oxo-2,3-dihydro-1H-benzimidazole-5-carbaldehyde (0.091 g, 0.218 mmol), DCM (1 mL), acetic acid (0.032 mL, 0.56 mmol), and sodium triacetoxyborohydride (0.092 g, 0.43 mmol), and the mixture was stirred at room temperature for 1.5 hr. To the reaction mixture was added 1-(2,6-dioxo-1-{[2-(trimethylsilyl)ethoxy]methyl}piperidin-3-yl)-3-methyl-2-oxo-2,3-dihydro-1H-benzimidazole-5-carbaldehyde (0.020 g, 0.048 mmol), and the mixture was stirred at room temperature for 6 hr. The reaction mixture was purified by silica gel column chromatography (ethyl acetate/methanol) to give the title compound (0.146 g, 0.132 mmol, yield 71%).

<Example AU4> 3-[5-({4-[(2',6'-Difluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl)carbonyl]piperazin-1-yl}methyl)-3-methyl-2-oxo-2,3-dihydro-1H-benzimidazol-1-yl]piperidine-2,6-dione Using the compound obtained in <Example AU3>, the title compound was obtained by the same method as in <Example BK9>.

<Example AV1> Ethyl 2',3'-difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate Using ethyl 4-(4,4,5,5-tetramethyl-1,3,2-dioxaborolan-2-yl)-3-cyclohexene-1-carboxylate (CAS Registry Number: 1049004-32-1) and 4-bromo-2,3-difluorobenzaldehyde (CAS Registry Number: 644985-24-0), the title compound was obtained by sequentially performing the same operations as in <Example W1> and <Example W4>.

<Example AV2> 3-[5-({4-[(2',3'-Difluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperazin-1-yl}methyl)-3-methyl-2-oxo-2,3-dihydro-1H-benzimidazol-1-yl]piperidine-2,6-dione Using the compound obtained in <Example AV1>, the title compound was obtained by sequentially performing the same operations as in <Example AU2>, <Example AU3> and <Example BK9>.

<Example AW1> 7-Iodo-5,6-dihydro-4H-imidazo[4,5,1-ij]quinoline-2(1H)-one

Under ice-cooling, to a solution of 5,6-dihydro-4H-imidazo[4,5,1-ij]quinoline-2(1H)-one (CAS Registry Number: 4024-28-6) (3.80 g, 22.1 mmol) in DMF (150 mL) was added N-iodosuccinimide (5.5 g, 24 mmol), and the mixture was stirred at 40° C. for 10 hr. N-Iodosuccinimide (2.5 g, 11 mmol) was added, and the mixture was further stirred for 5 hr. The reaction mixture was added to water, and the precipitated solid was collected by filtration, washed with water, and dried to give the title compound (5.49 g, 18.3 mmol, yield 82%).

<Example AW2> 3-(7-Iodo-2-oxo-5,6-dihydro-4H-imidazo[4,5,1-ij]quinolin-1(2H)-yl)-1-{[2-(trimethylsilyl)ethoxy]methyl}piperidine-2,6-dione At room temperature, to a solution of 7-iodo-5,6-dihydro-4H-imidazo[4,5,1-ij]quinoline-2(1H)-one (5.0 g, 17 mmol) and 3-bromo-1-{[2-(trimethylsilyl)ethoxy]methyl}piperidine-2,6-dione (11 g, 34 mmol) in DMF (80 mL) was added cesium carbonate (11 g, 34 mmol), and the mixture was stirred with heating at 50° C. for 6 hr. After cooling, the reaction mixture was diluted with ethyl acetate, washed successively with an aqueous citric acid solution and saturated brine. The organic layer was dried over magnesium sulfate and filtered, and the filtrate was concentrated under reduced pressure. The residue was purified by amine-modified silica gel column chromatography (hexane/ethyl acetate) to give the title compound (5.1 g, 9.4 mmol, yield 57%).

<Example AW3> 2,4,6-Trichlorophenyl 1-(2,6-dioxo-1-{[2-(trimethylsilyl)ethoxy]methyl}piperidin-3-yl)-2-oxo-1,2,5,6-tetrahydro-4H-imidazo[4,5,1-ij]quinoline-7-carboxylate At room temperature, to a solution of 3-(7-iodo-2-oxo-5,6-dihydro-4H-imidazo[4,5,1-ij]quinolin-1(2H)-yl)-1-{[2-(trimethylsilyl)ethoxy]methyl}piperidine-2,6-dione (2.2 g, 4.1 mmol) in toluene (30 mL) were added 2,4,6-trichlorophenyl formate (CAS Registry Number: 4525-65-9) (1.4 g, 6.1 mmol) and XantPhos (250 mg, 0.41 mmol), and then palladium(II) acetate (50 mg, 0.20 mmol) and triethylamine (1.0 mL, 7.2 mmol) were added, and the mixture was stirred under heating under a carbon monoxide atmosphere at 100° C. for 3 hr. After cooling, the reaction mixture was diluted with ethyl acetate, insoluble materials were filtered off through celite, and the filtrate was concentrated under reduced pressure. The residue was purified by silica gel column chromatography (hexane/ethyl acetate) to give the title compound (1.9 g, 3.1 mmol, yield 75%).

<Example AW4> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}-1-{[2-(trimethylsilyl)ethoxy]methyl}piperidine-2,6-dione At room temperature, to a suspension of 2,4,6-trichlorophenyl 1-(2,6-dioxo-1-{[2-(trimethylsilyl)ethoxy]methyl}piperidin-3-yl)-2-oxo-1,2,5,6-tetrahydro-4H-imidazo[4,5,1-ij]quinoline-7-carboxylate (407 mg, 0.637 mmol) and 3,3,3-trifluoro-N-{2-[(4R)-4-(4-methoxyphenyl)-2,2-dimethyltetrahydro-2H-pyran-4-yl]ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (527 mg, 0.724 mmol) in acetonitrile (5 mL) were added 4-dimethylaminopyridine (25 mg, 0.19 mmol) and DIPEA (0.8 mL, 3.8 mmol), and the mixture was stirred for 18 hr. Water was added to the reaction mixture, and the mixture was extracted with chloroform. The organic layer was washed with saturated brine, dried over magnesium sulfate and filtered, and the filtrate was concentrated under reduced pressure. The residue was purified by silica gel column chromatography (chloroform/methanol) to give the title compound (654 mg, 0.596 mmol, yield 94%).

<Example AW5> 3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione At room temperature, to a solution of 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}-1-{[2-(trimethylsilyl)ethoxy]methyl}piperidine-2,6-dione (651 mg, 0.594 mmol) in DCM (2 mL) was added trifluoroacetic acid (0.5 mL), and the mixture was stirred for 1 hr. The reaction mixture was concentrated under reduced pressure, and the residue was neutralized by adding aqueous sodium hydrogen carbonate solution, and extracted with chloroform. The organic layer was washed with saturated brine, dried over magnesium sulfate and filtered, and the filtrate was concentrated under reduced pressure. The residue was dissolved in ethyl acetate (2 mL), N,N'-dimethylethylenediamine (0.13 mL, 1.2 mmol) was added, and the mixture was stirred for 1 hr. The reaction mixture was diluted with ethyl acetate, was washed successively with water and saturated brine, the organic layer was dried over magnesium sulfate and filtered, and the filtrate was concentrated under reduced pressure. The residue was purified by silica gel column chromatography (chloroform/methanol) to give the title compound (547 mg, 0.566 mmol, yield 95%).

<Example AX1> N-{[4'-(Bromomethyl)-2',3',4',5'-tetrahydro[biphenyl]-4-yl]methyl}-3,3,3-trifluoro-N-{2-[(4R)-4-(4-methoxyphenyl)-2,2-dimethyltetrahydro-2H-pyran-4-yl]ethyl}-2,2-dimethylpropan-1-amine To a solution of (4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl methanesulfonate (53.0 mg, 0.0796 mmol) in acetone (1 mL) was added lithium bromide (20.0 mg, 0.230 mmol), and the mixture was stirred at 70° C. for 4 hr. To the reaction mixture was added acetone (1 mL), and the mixture was stirred again at 70° C. for 4 hr, and cooled to room temperature. The reaction mixture was diluted with ethyl acetate and washed with saturated aqueous sodium hydrogen carbonate solution. The organic layer was dried over sodium sulfate and filtered, and the filtrate was concentrated under reduced pressure, and successively dried under reduced pressure to give the title compound (42.1 mg, 0.0647 mmol, yield 81%).

<Example AX2> tert-Butyl 4-[(4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]-3-oxopiperazine-1-carboxylate To a solution of N-{[4'-(bromomethyl)-2',3',4',5'-tetrahydro[biphenyl]-4-yl]methyl}-3,3,3-trifluoro-N-{2-[(4R)-4-(4-methoxyphenyl)-2,2-dimethyltetrahydro-2H-pyran-4-yl]ethyl}-2,2-dimethylpropan-1-amine (42.1 mg, 0.0647 mmol) and 1-Boc-3-oxopiperazine (CAS Registry Number: 76003-29-7) (26.5 mg, 0.132 mmol) in DMF (1 mL) was added sodium hydride (55% oil, 9.0 mg, 0.21 mmol), and the mixture was stirred at room temperature for hr. To the reaction mixture was added saturated aqueous sodium hydrogen carbonate solution, and the mixture was extracted with ethyl acetate. The obtained organic layers were combined, washed successively with water and saturated brine, dried over sodium sulfate and filtered, and the filtrate was concentrated under reduced pressure. The residue was purified by silica gel column chromatography (hexane/ethyl acetate) to give the title compound (34.8 mg, 0.0452 mmol, yield 70%).

<Example AX3> 3-[5-({4-[(4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl)methyl]-3-oxopiperazin-1-yl}methyl)-3-methyl-2-oxo-2,3-dihydro-1H-benzimidazol-1-yl]piperidine-2,6-dione Using the compound obtained in <Example AX2>, the title compound was obtained by sequentially performing the same operations as in <Example AU3> and <Example BK9>.

<Example AY1> 3-(3-Methyl-5-nitro-2-oxo-2,3-dihydro-1H-benzimidazol-1-yl)-1-{[2-(trimethylsilyl)ethoxy]methyl}piperidine-2,6-dione Using 1-methyl-6-nitro-1,3-dihydro-2H-benzimidazol-2-one (WO2019060693 A1), the title compound was obtained by the same method as in <Example Z5>.

<Example AY2> 3-(5-Amino-3-methyl-2-oxo-2,3-dihydro-1H-benzimidazol-1-yl)-1-{[2-(trimethylsilyl)ethoxy]methyl}piperidine-2,6-dione Using the compound obtained in <Example AY1>, the title compound was obtained by the same method as in <Example BK5>.

<Example AY3> N-[1-(2,6-Dioxo-1-{[2-(trimethylsilyl)ethoxy]methyl}piperidin-3-yl)-3-methyl-2-oxo-2,3-dihydro-1H-benzimidazol-5-yl]-2-nitrobenzenesulfonamide Using the compound obtained in <Example AY2>, the title compound was obtained by the same method as in <Example CC1>.

<Example AY4> tert-Butyl (trans-3-{[1-(2,6-dioxo-1-{[2-(trimethylsilyl)ethoxy]methyl}piperidin-3-yl)-3-methyl-2-oxo-2,3-dihydro-1H-benzimidazol-5-yl][(2-nitrophenyl)sulfonyl]amino}cyclobutyl)carbamate N-[1-(2,6-dioxo-1-{[2-(trimethylsilyl)ethoxy]methyl}piperidin-3-yl)-3-methyl-2-oxo-2,3-dihydro-1H-benzimidazol-5-yl]-2-nitrobenzenesulfonamide (0.367 g, 0.622 mmol), cis-tert-butyl 3-hydroxycyclobutylcarbamate (CAS Registry Number: 389890-43-1) (0.175 g, 0.934 mmol), and triphenylphosphine (0.245 g, 0.934 mmol) were dissolved in THF (2 mL), diisopropyl azodicarboxylate (0.20 mL, 0.93 mmol) was added at 0° C., and the mixture was stirred at room temperature for 51 hr. To the reaction mixture were added cis-tert-butyl 3-hydroxycyclobutylcarbamate (0.175 g, 0.934 mmol), triphenylphosphine (0.245 g, 0.934 mmol), and diisopropyl azodicarboxylate (0.20 mL, 0.93 mmol) at 0° C., and the mixture was stirred at room temperature for 43 hr. The reaction mixture was concentrated under reduced pressure, and the residue was purified by silica gel column chromatography (hexane/ethyl acetate) to give the title compound (0.366 g, 0.482 mmol, yield 78%).

<Example AY5> tert-Butyl (trans-3-{[1-(2,6-dioxo-1-{[2-(trimethylsilyl)ethoxy]methyl}piperidin-3-yl)-3-methyl-2-oxo-2,3-dihydro-1H-benzimidazol-5-yl]amino}cyclobutyl)carbamate tert-Butyl (trans-3-{[1-(2,6-dioxo-1-{[2-(trimethylsilyl)ethoxy]methyl}piperidin-3-yl)-3-methyl-2-oxo-2,3-dihydro-1H-benzimidazol-5-yl][(2-nitrophenyl)sulfonyl]amino}cyclobutyl)carbamate (0.366 g, 0.482 mmol) was dissolved in DMF (2 mL), 4-bromobenzenethiol (0.182 g, 9.65 mmol) and potassium carbonate (0.200 g, 1.45 mmol) were added, and the mixture was stirred at room temperature for 4 hr. To the reaction mixture was added saturated aqueous sodium hydrogen carbonate solution, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (0.164 g, 0.286 mmol, yield 59%).

<Example AY6> 3-{5-[(Trans-3-aminocyclobutyl)amino]-3-methyl-2-oxo-2,3-dihydro-1H-benzimidazol-1-yl}-1-(hydroxymethyl)piperidine-2,6-dione dihydrochloride Using the compound obtained in <Example AY5>, the title compound was obtained by the same method as in <Example AO5>.

<Example AY7> 4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid Using the compound obtained in <Example AG2>, the title compound was obtained by the same method as in <Example Y5>.

<Example AY8> N-(Trans-3-{[1-(2,6-dioxopiperidin-3-yl)-3-methyl-2-oxo-2,3-dihydro-1H-benzimidazol-5-yl]amino}cyclobutyl)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxamide Using the compounds obtained in <Example AY6> and <Example AY7>, the title compound was obtained by the same method as in <Example BM9>.

<Example AZ1> Methyl 1-[7-(tert-butoxycarbonyl)-7-azaspiro[3.5]nonan-2-yl]-1H-indazole-5-carboxylate <Example AZ2> Methyl 2-[7-(tert-butoxycarbonyl)-7-azaspiro[3.5]nonan-2-yl]-2H-indazole-5-carboxylate To a suspension of methyl indazole-5-carboxylate (CAS Registry Number: 473416-12-5) (327 mg, 1.86 mmol), and tert-butyl 2-hydroxy-7-azaspiro[3.5]nonane-7-carboxylate (CAS Registry Number: 240401-28-9) (470 mg, 1.95 mmol) in toluene (9 mL) was added cyanomethylenetributylphosphorane (CAS Registry Number: 157141-27-0) (1.0 mL, 3.8 mmol), and the mixture was stirred at 90° C. for 1.5 hr. The reaction mixture was cooled to room temperature, and concentrated under reduced pressure. The residue was purified by silica gel column chromatography (hexane/ethyl acetate) to give <Example AZ1> (500 mg, 1.25 mmol, yield 67%), and <Example AZ2> (235 mg, 0.588 mmol, yield 32%).

<Example AZ3> tert-Butyl 2-[5-(hydroxymethyl)-2H-indazol-2-yl]-7-azaspiro[3.5]nonane-7-carboxylate Using the compound obtained in <Example AZ2>, the title compound was obtained by the same method as in <Example W5>.

<Example AZ4> tert-Butyl 2-(5-formyl-2H-indazol-2-yl)-7-azaspiro[3.5]nonane-7-carboxylate To a solution of tert-butyl 2-[5-(hydroxymethyl)-2H-indazol-2-yl]-7-azaspiro[3.5]nonane-7-carboxylate (233 mg, 0.627 mmol) in chloroform (6 mL) was added manganese (IV) oxide (291 mg), and the mixture was stirred at room temperature for 22 hr. To the reaction mixture was added manganese(IV) oxide (345 mg), and the mixture was stirred for 5.5 hr. The reaction mixture was diluted with ethyl acetate, insoluble materials were filtered off through celite, and the filtrate was concentrated under reduced pressure. The residue was purified by silica gel column chromatography (hexane/ethyl acetate) to give the title compound (120 mg, 0.325 mmol, yield 52%).

<Example AZ5> tert-Butyl 2-(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2H-indazol-2-yl)-7-azaspiro[3.5]nonane-7-carboxylate Using the compounds obtained in <Example M3> and <Example AZ4>, the title compound was obtained by the same method as in <Example W4>.

<Example AZ6> tert-Butyl [2-(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2H-indazol-2-yl)-7-azaspiro[3.5]nonan-7-yl]acetate To a solution of tert-butyl 2-(5-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2H-indazol-2-yl)-7-azaspiro[3.5]nonane-7-carboxylate (115 mg, 0.155 mmol) in DCM (1 mL) was added 4 mol/L hydrogen chloride/1,4-dioxane solution (1 mL, 4 mmol), and the mixture was stirred at room temperature for 1.5 hr. The reaction mixture was concentrated under reduced pressure. The residue was dissolved in acetonitrile (1 mL), potassium carbonate (103 mg, 0.745 mmol) and tert-butyl bromoacetate (CAS Registry Number: 5292-43-3) (0.0341 mL, 0.233 mmol) were added, and the mixture was stirred at room temperature for 20 hr. To the reaction mixture was added DMF (1 mL), and the mixture was stirred at room temperature for 5 hr. The reaction mixture was diluted with ethyl acetate and washed successively with water and saturated brine. The organic layer was dried over sodium sulfate and filtered, and the filtrate was concentrated under reduced pressure. The residue was purified by silica gel column chromatography (ethyl acetate/methanol) to give the title compound (110 mg, 0.146 mmol, yield 94%).

<Example AZ7> [2-(5-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2H-indazol-2-yl)-7-azaspiro[3.5]nonan-7-yl]acetic acid dihydrochloride Using the compound obtained in <Example AZ6>, the title compound was obtained by the same method as in <Example V5>.

<Example AZ8> N-[1-(2,6-Dioxopiperidin-3-yl)-3-methyl-2-oxo-2,3-dihydro-1H-benzimidazol-5-yl]-2-[2-(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2H-indazol-2-yl)-7-azaspiro[3.5]nonan-7-yl]acetamide Using the compound obtained in <Example AZ7> and 3-(5-amino-3-methyl-2-oxo-2,3-dihydro-1H-benzimidazol-1-yl)piperidine-2,6-dione (WO2021170109 A1), the title compound was obtained by the same method as in <Example BM9>.

<Example BA1> tert-Butyl 2-[5-(hydroxymethyl)-1H-indazol-1-yl]-7-azaspiro[3.5]nonane-7-carboxylate Using the compound obtained in <Example AZ1>, the title compound was obtained by the same method as in <Example W5>.

<Example BA2> tert-Butyl 2-(5-formyl-1H-indazol-1-yl)-7-azaspiro[3.5]nonane-7-carboxylate Using the compound obtained in <Example BA1>, the title compound was obtained by the same method as in <Example AZ4>.

<Example BA3> tert-Butyl 2-(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-1H-indazol-1-yl)-7-azaspiro[3.5]nonane-7-carboxylate Using the compounds obtained in <Example M3> and <Example BA2>, the title compound was obtained by the same method as in <Example W4>.

<Example BA4> tert-Butyl [2-(5-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-1H-indazol-1-yl)-7-azaspiro[3.5]nonan-7-yl]acetate Using the compound obtained in <Example BA3>, the title compound was obtained by the same method as in <Example AZ6>.

<Example BA5> [2-(5-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-1H-indazol-1-yl)-7-azaspiro[3.5]nonan-7-yl]acetic acid dihydrochloride Using the compound obtained in <Example BA4>, the title compound was obtained by the same method as in <Example V5>.

<Example BA6> N-[1-(2,6-Dioxopiperidin-3-yl)-3-methyl-2-oxo-2,3-dihydro-1H-benzimidazol-5-yl]-2-[2-(5-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-1H-indazol-1-yl)-7-azaspiro[3.5]nonan-7-yl]acetamide Using the compound obtained in <Example BA5> and 3-(5-amino-3-methyl-2-oxo-2,3-dihydro-1H-benzimidazol-1-yl)piperidine-2,6-dione (WO2021170109 A1), the title compound was obtained by the same method as in <Example BM9>.

<Example BB1> tert-Butyl 3-fluoro-4-oxocyclohexanecarboxylate tert-Butyl 4-Oxocyclohexanecarboxylate (CAS Registry Number: 38446-95-6) (1.01 g, 5.09 mmol) and triethylamine (1.4 mL, 10 mmol) were dissolved in DCM (17 mL), trimethylsilyl trifluoromethanesulfonate (1.1 mL, 6.1 mmol) was added at 0° C., and the mixture was stirred for 20 min. To the reaction mixture was added saturated aqueous sodium hydrogen carbonate solution, and the mixture was extracted with DCM. The organic layer was washed with saturated aqueous sodium hydrogen carbonate solution, dried over magnesium sulfate and filtered, and the filtrate was concentrated under reduced pressure. The residue was dissolved in acetonitrile (17 mL), 1-chloromethyl-4-fluoro-1,4-diazoniabicyclo[2.2.2]octane bis(tetrafluoroborate) (CAS Registry Number: 140681-55-6) (2.17 g, 6.11 mmol) was added at 0° C., and the mixture was stirred at room temperature for 2.5 hr. To the reaction mixture was added saturated aqueous sodium hydrogen carbonate solution, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (0.849 g, 3.93 mmol, yield 77%).

<Example BB2> tert-Butyl 6-fluoro-4'-formyl-2,3,4,5-tetrahydro[biphenyl]-4-carboxylate tert-Butyl 3-fluoro-4-oxocyclohexanecarboxylate (0.436 g, 2.02 mmol) was dissolved in THE (4 mL), lithium bis(trimethylsilyl)amide (1.12 mol/L THF solution, 2.0 mL, 2.2 mmol) was added under a nitrogen atmosphere at −78° C., and the mixture was stirred for 30 min. To the reaction mixture was added a solution of N-phenylbis(trifluoromethanesulfonimide) (0.792 g, 2.22 mmol) in THE (4 mL) at −78° C., and the mixture was stirred at room temperature for 1 hr. The reaction mixture was diluted with ethyl acetate and washed successively with 1 mol/L aqueous sodium hydroxide solution, saturated aqueous ammonium chloride solution, and saturated brine. The organic layer was dried over sodium sulfate and filtered, and the filtrate was concentrated under reduced pressure. The residue and (4-formylphenyl) boronic acid (CAS Registry Number: 87199-17-5) (0.363 g, 2.42 mmol) were dissolved in a mixed solvent of 1,4-dioxane (10 mL)-water (1 mL), sodium carbonate (0.641 g, 6.05 mmol) and [1,1'-bis(diphenylphosphino)ferrocene]palladium(II) dichloride DCM adduct (0.165 g, 0.202 mmol) were added, and the mixture was stirred with heating under a nitrogen atmosphere at 85° C. for 1 hr. The reaction mixture was cooled to room temperature, saturated aqueous sodium hydrogen carbonate solution was added, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (0.212 g, 0.697 mmol, yield 35%).

<Example BB3> tert-Butyl 6-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl) amino]methyl}-2,3,4,5-tetrahydro[biphenyl]-4-carboxylate Using the compounds obtained in <Example M3> and <Example BB2>, the title compound was obtained by the same method as in <Example W4>.

<Example BB4> 6-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl) amino]methyl}-2,3,4,5-tetrahydro[biphenyl]-4-carboxylic acid monohydrochloride Using the compound obtained in <Example BB3>, the title compound was obtained by the same method as in <Example V5>.

<Example BB5> tert-Butyl 4-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]methyl}piperazine-1-carboxylate Using the compound obtained in <Example AW2>, the title compound was obtained by the same method as in <Example BQ1>.

<Example BB6> 1-(Hydroxymethyl)-3-[2-oxo-7-(piperazin-1-ylmethyl)-5,6-dihydro-4H-imidazo[4,5,1-ij]quinolin-1(2H)-yl]piperidine-2,6-dione dihydrochloride Using the compound obtained in <Example BB5>, the title compound was obtained by the same method as in <Example AO5>.

<Example BB7> 3-[7-({4-[(6-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl) amino]methyl}-2,3,4,5-tetrahydro[biphenyl]-4-yl) carbonyl]piperazin-1-yl}methyl)-2-oxo-5,6-dihydro-4H-imidazo[4,5,1-ij]quinolin-1(2H)-yl]piperidine-2,6-dione Using the compounds obtained in <Example BB4> and <Example BB6>, the title compound was obtained by the same method as in <Example BW3>.

<Example BC1> 6-Bromo-$N^2$-methylpyridine-2,3-diamine

To a solution of 6-bromo-N-methyl-3-nitropyridin-2-amine (CAS Registry Number: 924293-34-5) (300 mg, 1.29 mmol) in THF (9 mL) was added a solution of ammonium chloride (280 mg, 5.17 mmol) in water (4.5 mL). After ice-cooling, zinc powder (850 mg, 12.9 mmol) was gradually added and, after stirring for 30 min, insoluble materials were filtered off through celite. The filtrate was extracted with ethyl acetate. The organic layer was washed with saturated brine, dried over magnesium sulfate and filtered, and the filtrate was concentrated under reduced pressure to give the title compound (225 mg, 1.11 mmol, yield 86%).

<Example BC2> 5-Bromo-3-methyl-1,3-dihydro-2H-imidazo[4,5-b]pyridin-2-one

Using the compound obtained in <Example BC1>, the title compound was obtained by the same method as in <Example AN2>.

<Example BC3> 3-(5-Bromo-3-methyl-2-oxo-2,3-dihydro-1H-imidazo[4,5-b]pyridin-1-yl)-1-{[2-(trimethylsilyl)ethoxy]methyl}piperidine-2,6-dione Using the compound obtained in <Example BC2>, the title compound was obtained by the same method as in <Example Z5>.

<Example BC4> 2,4,6-Trichlorophenyl 1-(2,6-dioxo-1-{[2-(trimethylsilyl)ethoxy]methyl}piperidin-3-yl)-3-methyl-2-oxo-2,3-dihydro-1H-imidazo[4,5-b]pyridine-5-carboxylate Using the compound obtained in <Example BC3>, the title compound was obtained by the same method as in <Example BY5>.

<Example BC5> 3-[5-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]piperazin-1-yl}carbonyl)-3-methyl-2-oxo-2,3-dihydro-1H-imidazo[4,5-b]pyridin-1-yl]-1-{[2-(trimethylsilyl)ethoxy]methyl}piperidine-2,6-dione Using the compounds obtained in <Example AG5> and <Example BC4>, the title compound was obtained by the same method as in <Example BI1>.

<Example BC6> 3-[5-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]piperazin-1-yl}carbonyl)-3-methyl-2-oxo-2,3-dihydro-1H-imidazo[4,5-b]pyridin-1-yl]piperidine-2,6-dione Using the compound obtained in <Example BC5>, the title compound was obtained by the same method as in <Example BK9>.

<Example BD1> N-{[Trans-4-(4-chlorophenyl)cyclohexyl]methyl}-3,3,3-trifluoro-N-{2-[(4R)-4-(4-methoxyphenyl)-2,2-dimethyltetrahydro-2H-pyran-4-yl]ethyl)-2,2-dimethylpropan-1-amine Using the compound obtained in <Example M3> and trans-4-(4-chlorophenyl)cyclohexanecarbaldehyde (Org. Process Res. Dev., 2012, 16, 10, 1607-1617.), the title compound was obtained by the same method as in <Example W4>.

<Example BD2> tert-Butyl [4-(trans-4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}cyclohexyl)phenyl]carbamate To N-{[trans-4-(4-chlorophenyl)cyclohexyl]methyl}-3,3,3-trifluoro-N-{2-[(4R)-4-(4-methoxyphenyl)-2,2-dimethyltetrahydro-2H-pyran-4-yl]ethyl)-2,2-dimethylpropane-1-amine (300 mg, 0.505 mmol), tert-butyl carbamate (CAS Registry Number: 4248-19-5) (95 mg, 0.81 mmol), 1,2,3,4,5-pentaphenyl-1'-(di-tert-butylphosphino)ferrocene (80 mg, 0.112 mmol), tris(dibenzylideneacetone)dipalladium(0) (60 mg, 0.066 mmol), and cesium carbonate (310 mg, 0.95 mmol) was added tert-butyl alcohol (4 mL), and the mixture was stirred with heating under a nitrogen atmosphere at 100° C. for 5 hr. The reaction mixture was filtered through celite, and the filtrate was concentrated under reduced pressure. The residue was purified by silica gel column chromatography (hexane/ethyl acetate) to give the title compound (200 mg, 0.30 mmol, yield 59%).

<Example BD3> 4-(Trans-4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}cyclohexyl)aniline dihydrochloride Using the compound obtained in <Example BD2>, the title compound was obtained by the same method as in <Example AO5>.

<Example BD4> tert-Butyl 3-{[1-(2,6-dioxopiperidin-3-yl)-3-methyl-2-oxo-2,3-dihydro-1H-benzimidazol-5-yl]amino}cyclobutanecarboxylate Using 3-(5-amino-3-methyl-2-oxo-2,3-dihydro-1H-benzimidazol-1-yl)piperidine-2,6-dione (WO2021170109 A1) and tert-butyl 3-oxocyclobutanecarboxylate (CAS Registry Number: 145549-76-4), the title compound was obtained by the same method as in <Example BM7>.

<Example BD5> 3-{[1-(2,6-Dioxopiperidin-3-yl)-3-methyl-2-oxo-2,3-dihydro-1H-benzimidazol-5-yl]amino)cyclobutanecarboxylic acid At room temperature, to a solution of tert-butyl 3-{[1-(2,6-dioxopiperidin-3-yl)-3-methyl-2-oxo-2,3-dihydro-1H-benzimidazol-5-yl]amino}cyclobutanecarboxylate (245 mg, 0.57 mmol) in DCM (2 mL) was added trifluoroacetic acid (2 mL). After completion of the reaction, the reaction mixture was concentrated under reduced pressure. The residue was azeotropically distilled with chloroform, and the obtained solid was dried under reduced pressure to give the title compound (210 mg, 0.56 mmol, yield 98%).

<Example BD6> 3-{[1-(2,6-Dioxopiperidin-3-yl)-3-methyl-2-oxo-2,3-dihydro-1H-benzimidazol-5-yl]amino)-N-[4-(trans-4-{[{2-[(4R)-4-(4-methoxyphenyl)-2,2-dimethyltetrahydro-2H-pyran-4-yl]ethyl}(3,3-trifluoro-2,2-dimethylpropyl)amino]methyl}cyclohexyl)phenyl]cyclobutanecarbox amide Using the compounds obtained in <Example BD5> and <Example BD3>, the title compound was obtained by the same method as in <Example BM9>.

<Example BE1> Ethyl 4'-[(tert-butoxycarbonyl)amino]-3'-fluoro-2,3,4,5-tetrahydro[biphenyl]-4-carboxylate Using tert-butyl (4-bromo-2-fluorophenyl)carbamate (CAS Registry Number: 209958-42-9) and ethyl 4-(4,4,5,5-tetramethyl-1,3,2-dioxaborolan-2-yl)-3-cyclohexene-1- carboxylate (CAS Registry Number: 1049004-32-1), the title compound was obtained by the same method as in <Example W1>.

<Example BE2> tert-Butyl [3-fluoro-4'-(hydroxymethyl)-2',3',4',5'-tetrahydro[biphenyl]-4-yl]carbamate Using the compound obtained in <Example BE1>, the title compound was obtained by the same method as in <Example AG3>.

<Example BE3> tert-Butyl (3-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2',3',4',5'-tetrahydro[biphenyl]-4-yl)carbamate Using the compound obtained in <Example BE2>, the title compound was obtained by sequentially performing the same operations as in <Example AI5> and <Example W4>.

<Example BE4> 3-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2',3',4',5'-tetrahydro[biphenyl]-4-amine dihydrochloride Using the compound obtained in <Example BE3>, the title compound was obtained by the same method as in <Example AO5>.

<Example BE5> 3-{[1-(2,6-Dioxopiperidin-3-yl)-3-methyl-2-oxo-2,3-dihydro-1H-benzimidazol-5-yl]amino}-N-(3-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2',3',4',5'-tetrahydro[biphenyl]-4-yl)cyclobutanecarboxamide Using the compounds obtained in <Example BE4> and <Example BD5>, the title compound was obtained by the same method as in <Example BM9>.

<Example BF1> 5,8-Dibromo-1,2,3,4-tetrahydroquinoline

A suspension of 5,8-dibromoquinoline (CAS Registry Number: 81045-39-8) (3.49 g, 12.2 mmol), diethyl 1,4-dihydro-2,6-dimethyl-3,5-pyridinedicarboxylate (CAS Registry Number: 1149-23-1) (7.69 g, 30.4 mmol), and boric acid (121 mg, 1.96 mmol) in 1,2-dichloroethane (50 mL) was stirred at 60° C. for 5 hr. The reaction mixture was cooled to room temperature, ethanol (40 mL) and 10 mol/L aqueous sodium hydroxide solution (10 mL, 100 mmol) were added, and the mixture was stirred at room temperature for 2 hr. Water was added to the reaction mixture, and the mixture was extracted with DCM. The obtained organic layer was washed with saturated aqueous sodium hydrogen carbonate solution, dried over sodium sulfate and filtered, and the filtrate was concentrated under reduced pressure. To the residue was added diethyl ether, insoluble materials were filtered off, and the filtrate was concentrated under reduced pressure. The residue was purified by silica gel column chromatography (hexane/DCM) to give the title compound (2.28 g, 7.84 mmol, yield 64%).

<Example BF2> tert-Butyl $N^2$-[(5,8-dibromo-3,4-dihydroquinolin-1(2H)-yl)carbonyl]-L-α-glutaminate Under ice-cooling, to a solution of triphosgene (1.39 g, 4.68 mmol) in DCM (15 mL) was added dropwise a solution of 5,8-dibromo-1,2,3,4-tetrahydroquinoline (2.28 g, 7.84 mmol) in DCM (6 mL) over 5 min. To the reaction mixture was added pyridine (1 mL, 12 mmol), and the mixture was stirred at said temperature for 40 min. To the reaction mixture was added 1 mol/L hydrochloric acid, and the mixture was extracted with DCM. The obtained organic layers were combined and washed with 1 mol/L hydrochloric acid, dried over sodium sulfate and filtered, and the filtrate was concentrated under reduced pressure. The residue was dissolved in acetonitrile (20 mL), tert-butyl L-α-glutaminate hydrochloride (CAS Registry Number: 108607-02-9) (1.93 g, 8.09 mmol) and triethylamine (3 mL, 21.5 mmol) were added, and the mixture was stirred at 50° C. for 2 hr. The reaction mixture was cooled to room temperature, saturated aqueous sodium hydrogen carbonate solution and water were added, and the mixture was extracted with ethyl acetate. The organic layer was dried over sodium sulfate and filtered, and the filtrate was concentrated under reduced pressure. The residue was purified by silica gel column chromatography (hexane/ethyl acetate) to give the title compound (2.25 g, 4.33 mmol, yield 55%).

<Example BF3> tert-Butyl (4S)-5-amino-4-(7-bromo-2-oxo-5,6-dihydro-4H-imidazo[4,5,1-ij]quinolin-1(2H)-yl)-5-oxopentanoate A suspension of tert-butyl $N^2$-[(5,8-dibromo-3,4-dihydroquinolin-1(2H)-yl)carbonyl]-L-α-glutaminate (2.25 g, 4.33 mmol), trans-4-hydroxy-L-proline (229 mg, 1.75 mmol), tripotassium phosphate (2.66 g, 12.5 mmol), and copper(I) iodide (155 mg, 0.814 mmol) in DMSO (15 mL) was stirred under a nitrogen atmosphere at 50° C. for 80 min. The reaction mixture was cooled to room temperature, diluted with ethyl acetate, and washed with water. The organic layer was dried over sodium sulfate and filtered, and the filtrate was concentrated under reduced pressure. The residue was purified by silica gel column chromatography (hexane/ethyl acetate) to give the title compound (1.81 g, 4.13 mmol, yield 95%).

<Example BF4> 2,4,6-Trichlorophenyl 1-[(2S)-1-amino-5-tert-butoxy-1,5-dioxopentan-2-yl]-2-oxo-1,2,5,6-tetrahydro-4H-imidazo[4,5,1-ij]quinoline-7-carboxylate To a suspension of tert-butyl (4S)-5-amino-4-(7-bromo-2-oxo-5,6-dihydro-4H-imidazo[4,5,1-ij]quinolin-1(2H)-yl)-5-oxopentanoate (387 mg, 0.883 mmol), 2,4,6-trichlorophenyl formate (CAS Registry Number: 4525-65-9) (304 mg, 1.35 mmol), palladium(II) acetate (23.8 mg, 0.106 mmol), and XantPhos (101 mg, 0.175 mmol) in toluene (4 mL) was added triethylamine (0.246 mL, 1.76 mmol), and the mixture was stirred under a carbon monoxide atmosphere at 80° C. for 2 hr, and at 90° C. for 2.5 hr. The reaction mixture was cooled to room temperature, and purified by silica gel column chromatography (hexane/ethyl acetate) to give the title compound (480 mg, 0.824 mmol, yield 93%).

<Example BF5> tert-Butyl (4S)-5-amino-4-{7-[(4-{[(4R)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl)-2,3,4,5-tetrahydro[biphenyl]-4-yl]methyl}piperazin-1-yl) carbonyl]-2-oxo-5,6-dihydro-4H-imidazo[4,5,1-ij] quinolin-1(2H)-yl}-5-oxopentanoate To a solution of 2,4,6-trichlorophenyl 1-[(2S)-1-amino-5-tert-butoxy-1,5-dioxopentan-2-yl]-2-oxo-1,2,5,6-tetrahydro-4H-imidazo[4,5,1-ij]quinoline-7-carboxylate (70.5 mg, 0.0967 mmol), 3,3,3-trifluoro-N-{2-[(4R)-4-(4-methoxyphenyl)-2,2-dimethyltetrahydro-2H-pyran-4-yl] ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (75.4 mg, 0.104 mmol), and DIPEA (0.0842 mL, 0.483 mmol) in acetonitrile (1 mL) was added 4-dimethylaminopyridine (catalytic amount), and the mixture was stirred at room temperature for 25 hr. The reaction mixture was heated to 60° C., and stirred for 4.5 hr. The reaction mixture was diluted with ethyl acetate, and washed with saturated aqueous sodium hydrogen carbonate solution. The organic layer was dried over sodium sulfate and filtered, and the filtrate was concentrated under reduced pressure. The residue was purified by silica gel column chromatography (ethyl acetate/methanol) to give the title compound (58.4 mg, 0.0561 mmol, yield 58%).

<Example BF6> (3S)-3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij}quinolin-1(2H)-yl}piperidine-2,6-dione To a solution of tert-butyl (4S)-5-amino-4-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl] methyl}piperazin-1-yl)carbonyl]-2-oxo-5,6-dihydro-4H-imidazo[4,5,1-ij]quinolin-1(2H)-yl}-5-oxopentanoate (58.4 mg, 0.0561 mmol) in acetonitrile (1 mL) was added benzenesulfonic acid (23.1 mg, 0.146 mmol), and the mixture was stirred at 80° C. for 4 hr. To the reaction mixture was added benzenesulfonic acid (23.1 mg, 0.146 mmol), and the mixture was stirred at 80° C. for 3.5 hr. The reaction mixture was cooled to room temperature, saturated aqueous sodium hydrogen carbonate solution was added, and the mixture was extracted with ethyl acetate. The organic layer was dried over sodium sulfate and filtered, and the filtrate was concentrated under reduced pressure. The residue was purified by silica gel column chromatography (DCM/methanol), and the obtained solid was washed with hexane/ethyl acetate and dried under reduced pressure at 50° C. to give the title compound (36.7 mg, 0.0379 mmol, yield 68%).

<Example BG1> tert-Butyl $N^2$-[(5,8-dibromo-3,4-dihydroquinolin-1(2H)-yl)carbonyl]-D-α-glutaminate To a solution of triphosgene (984 mg, 3.32 mmol) in DCM (15 mL) was added dropwise, under ice-cooling, a solution of 5,8-dibromo-1,2,3,4-tetrahydroquinoline (1.66 g, 5.70 mmol) in DCM (4 mL) over 5 min. To the reaction mixture was added dropwise pyridine (0.65 mL, 8.1 mmol) over 10 min, and the mixture was stirred at said temperature for 40 min. To the reaction mixture was added 1 mol/L hydrochloric acid, and the mixture was extracted with DCM. The organic layers were combined, washed with 1 mol/L hydrochloric acid, dried over sodium sulfate and filtered, and the filtrate was concentrated under reduced pressure. The residue was dissolved in acetonitrile (14 mL), tert-butyl D-α-glutaminate monohydrochloride (CAS Registry Number: 66575-26-6) (1.37 g, 5.74 mmol) and triethylamine (2.5 mL, 18 mmol) were added, and the mixture was stirred at room temperature for 2.5 hr. To the reaction mixture was added saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (hexane/ethyl acetate) to give the title compound (2.45 g, 4.72 mmol, yield 83%).

<Example BG2> tert-Butyl (4R)-5-amino-4-(7-bromo-2-oxo-5,6-dihydro-4H-imidazo[4,5,1-ij]quinolin-1(2H)-yl)-5-oxopentanoate A suspension of tert-butyl $N^2$-[(5,8-dibromo-3,4-dihydroquinolin-1(2H)-yl)carbonyl]-D-α-glutaminate (2.45 g, 4.72 mmol), trans-4-hydroxy-L-proline (244 mg, 1.86 mmol), tripotassium phosphate (3.12 g, 14.7 mmol), and copper(I) iodide (171 mg, 0.898 mmol) in DMSO (15 mL) was stirred at 60° C. for 1.5 hr. The reaction mixture was cooled to room temperature, and diluted with ethyl acetate. The mixture was washed successively with water and saturated brine, dried over sodium sulfate and filtered, and the filtrate was concentrated under reduced pressure. The residue was purified by silica gel column chromatography (hexane/ethyl acetate, DCM/methanol) to give the title compound (1.02 g, 2.33 mmol, yield 49%).

<Example BG3> 2,4,6-Trichlorophenyl 1-[(2R)-1-amino-5-tert-butoxy-1,5-dioxopentan-2-yl]-2-oxo-1,2,5,6-tetrahydro-4H-imidazo[4,5,1-ij]quinoline-7-carboxylate To a solution of tert-butyl (4R)-5-amino-4-(7-bromo-2-oxo-5,6-dihydro-4H-imidazo[4,5,1-ij]quinolin-1(2H)-yl)-5-oxopentanoate (312 mg, 0.712 mmol), 2,4,6-trichlorophenyl formate (CAS Registry Number: 4525-65-9) (199 mg, 0.883 mmol), palladium(II) acetate (16.2 mg, 0.0722 mmol), and XantPhos (73.3 mg, 0.127 mmol) in toluene (3 mL) was added triethylamine (0.198 mL, 1.42 mmol), and the mixture was stirred under a carbon monoxide atmosphere at 90° C. for 4 hr. The reaction mixture was cooled to room temperature, and purified by silica gel column chromatography (DCM/ethyl acetate) to give the title compound (363 mg, 0.623 mmol, yield 87%).

<Example BG4> tert-Butyl (4R)-5-amino-4-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl) carbonyl]-2-oxo-5,6-dihydro-4H-imidazo[4,5,1-ij] quinolin-1(2H)-yl}-5-oxopentanoate To a solution of 3,3,3-trifluoro-N-{2-[(4R)-4-(4-methoxyphenyl)-2,2-dimethyltetrahydro-2H-pyran-4-yl] ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (89.8 mg, 0.123 mmol), 2,4,6-trichlorophenyl 1-[(2R)-1-amino-5-tert-butoxy-1,5-dioxopentan-2-yl]-2-oxo-1,2,5,6-tetrahydro-4H-imidazo[4,5,1-ij]quinoline-7-carboxylate (92.5 mg, 0.159 mmol), and DIPEA (0.107 mL, 0.614 mmol) in acetonitrile (1 mL) was added 4-dimethylaminopyridine (catalytic amount), and the mixture was stirred at room temperature for 27 hr. The reaction mixture was heated to 60° C., and stirred for 4.5 hr. The reaction mixture was cooled to room temperature, diluted with ethyl acetate, and washed with saturated aqueous sodium hydrogen carbonate solution. The organic layer was dried over sodium sulfate and filtered, and the filtrate was concentrated under reduced pressure. The residue was purified by silica gel column chromatography (ethyl acetate/methanol) to give the title compound (84.7 mg, 0.0813 mmol, yield 66%).

<Example BG5> (3R)-3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione To a solution of tert-butyl (4R)-5-amino-4-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}-5-oxopentanoate (84.7 mg, 0.0813 mmol) in acetonitrile (1 mL) was added benzenesulfonic acid (36.8 mg, 0.233 mmol), and the mixture was stirred at 80° C. for 3 hr. To the reaction mixture was added benzenesulfonic acid (20.5 mg, 0.130 mmol), and the mixture was stirred for 3.5 hr. The reaction mixture was cooled to room temperature, saturated aqueous sodium hydrogen carbonate solution was added, and the mixture was successively extracted with DCM and ethyl acetate. The organic layers were combined, dried over sodium sulfate, and filtered, and the filtrate was concentrated under reduced pressure. The residue was purified by silica gel column chromatography (DCM/methanol), and the obtained solid was washed with hexane/ethyl acetate, and dried under reduced pressure at 50° C. to give the title compound (57.2 mg, 0.0591 mmol, yield 73%).

<Example BH1> tert-Butyl 2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate Using the compounds obtained in <Example M3> and <Example V1>, the title compound was obtained by the same method as in <Example W4>.

<Example BH2> 2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride Using the compound obtained in <Example BH1>, the title compound was obtained by the same method as in <Example V5>.

<Example BH3> 3-{7-[Methyl(piperidin-4-yl)amino]-2-oxo-5,6-dihydro-4H-imidazo[4,5,1-ij]quinolin-1(2H)-yl}-1-{[2-(trimethylsilyl)ethoxy]methyl}piperidine-2,6-dione tert-Butyl 4-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino}piperidine-1-carboxylate (0.160 g, 0.261 mmol) was dissolved in DCM (4 mL), paraformaldehyde (0.078 g), acetic acid (0.045 mL, 0.79 mmol), and sodium triacetoxyborohydride (0.276 g, 1.30 mmol) were added, and the mixture was stirred at room temperature for 1 hr. To the reaction mixture was added 37% aqueous formaldehyde solution (0.097 mL, 1.3 mmol), and the mixture was stirred at room temperature for 30 min. To the reaction mixture was added saturated aqueous sodium hydrogen carbonate solution, and the mixture was extracted with DCM. The organic layer was washed with saturated brine, dried over sodium sulfate and filtered, and the filtrate was concentrated under reduced pressure. The residue was dissolved in acetonitrile (2 mL), para-toluenesulfonic acid monohydrate (0.198 g, 1.04 mmol) was added, and the mixture was stirred at room temperature for 2 hr. To the reaction mixture was added saturated aqueous sodium hydrogen carbonate solution, and the mixture was extracted with DCM. The organic layer was dried over sodium sulfate and filtered, and the filtrate was concentrated under reduced pressure to give the title compound (0.120 g, 0.227 mmol, yield 87%).

<Example BH4> 3-{7-[{1-[(2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperidin-4-yl}(methyl)amino]-2-oxo-5,6-dihydro-4H-imidazo[4,5,1-ij]quinolin-1(1H)-yl}-1-{[2-(trimethylsilyl)ethoxy]methyl}piperidine-2,6-dione Using the compounds obtained in <Example BH3> and <Example BH2>, the title compound was obtained by the same method as in <Example BM9>.

<Example BH5> 3-{7-[{1-[(2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)carbonyl]piperidin-4-yl}(methyl)amino]-2-oxo-5,6-dihydro-4H-imidazo[4,5,1-ij]quinolin-1(2H)-yl}piperidine-2,6-dione Using the compound obtained in <Example BH4>, the title compound was obtained by the same method as in <Example BK9>.

<Example BI1> 3-{5-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}-1-{[2-(trimethylsilyl)ethoxy]methyl}piperidine-2,6-dione To a solution of 3,3,3-trifluoro-N-{2-[(4R)-4-(4-methoxyphenyl)-2,2-dimethyltetrahydro-2H-pyran-4-yl]ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (210 mg, 0.289 mmol), 2,4,6-trichlorophenyl 1-(2,6-dioxo-1-{[2-(trimethylsilyl)ethoxy]methyl}piperidin-3-yl)-3-methyl-2-oxo-2,3-dihydro-1H-benzimidazole-5-carboxylate (194 mg, 0.317 mmol), and DIPEA (0.250 mL, 1.44 mmol) in acetonitrile (1.5 mL) was added 4-dimethylaminopyridine (catalytic amount), and the mixture was stirred at room temperature for 18.5 hr. The reaction mixture was diluted with ethyl acetate, and washed with saturated aqueous sodium hydrogen carbonate solution. The organic layer was dried over sodium sulfate and filtered, and the filtrate was concentrated under reduced pressure. The residue was purified by silica gel column chromatography (ethyl acetate/methanol) to give the title compound (197 mg, 0.184 mmol, yield 64%).

<Example BI2> 3-{5-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}piperidine-2,6-dione To a solution of 3-{5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-3-methyl-2-oxo-2,3-dihydro-1H-benzimidazol-1-yl}-1-{[2-(trimethylsilyl)ethoxy]methyl}piperidine-2,6-dione (197 mg, 0.184 mmol) in DCM (0.5 mL) was added trifluoroacetic acid (0.5 mL), and the mixture was stirred at room temperature for 50 min. The reaction mixture was diluted with ethyl acetate and washed with saturated aqueous sodium hydrogen carbonate solution. The organic layer was dried over sodium sulfate and filtered, and the filtrate was concentrated under reduced pressure. The residue was dissolved in ethyl acetate (2 mL), N,N'-dimethylethylenediamine (0.0217 mL, 0.202 mmol) was added, and the mixture was stirred at room temperature for 40 min. The reaction mixture was diluted with ethyl acetate, and washed with saturated aqueous sodium hydrogen carbonate solution. The organic layer was dried over sodium sulfate and filtered, and the filtrate was concentrated under reduced pressure. The residue was purified by silica gel column chromatography (DCM/methanol), and the obtained solid was washed with hexane/ethyl acetate, and dried under reduced pressure at 50° C. to give the title compound (93.8 mg, 0.0997 mmol, yield 54%).

<Example BJ1> 6-Bromo-N-methylpyridine-3,4-diamine

At room temperature, to a solution of 2-bromo-N-methyl-5-nitropyridin-4-amine (CAS Registry Number: 1234014-33-5) (300 mg, 1.29 mmol) in acetic acid (10 mL) was added iron powder (290 mg, 5.17 mmol). After completion of the reaction, the reaction mixture was diluted with ethyl acetate, insoluble materials were filtered off through celite, and the filtrate was concentrated under reduced pressure. The residue was neutralized with aqueous sodium hydrogen carbonate solution. Insoluble materials were collected again by filtration through celite, and the filtrate was diluted with ethyl acetate, and washed with saturated brine. The organic layer was dried over magnesium sulfate and filtered, and the filtrate was concentrated under reduced pressure to give the title compound (240 mg, 1.18 mmol, yield 91%).

<Example BJ2> 6-Bromo-1-methyl-1,3-dihydro-2H-imidazo[4,5-c]pyridin-2-one

Using the compound obtained in <Example BJ1>, the title compound was obtained by the same method as in <Example AN2>.

<Example BJ3> 3-(6-Bromo-1-methyl-2-oxo-1,2-dihydro-3H-imidazo[4,5-c]pyridin-3-yl)-1-{[2-(trimethylsilyl)ethoxy]methyl}piperidine-2,6-dione Using the compound obtained in <Example BJ2>, the title compound was obtained by the same method as in <Example Z5>.

<Example BJ4> 2,4,6-Trichlorophenyl 3-(2,6-dioxo-1-{[2-(trimethylsilyl)ethoxy]methyl}piperidin-3-yl)-1-methyl-2-oxo-2,3-dihydro-1H-imidazo[4,5-c]pyridine-6-carboxylate Using the compound obtained in <Example BJ3>, the title compound was obtained by the same method as in <Example BY5>.

<Example BJ5> 3-[6-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]piperazin-1-yl}carbonyl)-1-methyl-2-oxo-1,2-dihydro-3H-imidazo[4,5-c]pyridin-3-yl]-1-{[2-(trimethylsilyl)ethoxy]methyl}piperidine-2,6-dione Using the compounds obtained in <Example AG5> and <Example BJ4>, the title compound was obtained by the same method as in <Example BI1>.

<Example BJ6> 3-[6-({4-[(4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl)methyl]piperazin-1-yl}carbonyl)-1-methyl-2-oxo-1,2-dihydro-3H-imidazo[4,5-c]pyridin-3-yl]piperidine-2,6-dione Using the compound obtained in <Example BJ5>, the title compound was obtained by the same method as in <Example BK9>.

<Example BK1> 8-Bromo-5-nitro-1,2,3,4-tetrahydroquinoline

A suspension of 8-bromo-5-nitroquinoline (CAS Registry Number: 139366-35-1) (5.02 g, 19.8 mmol), diethyl 1,4-dihydro-2,6-dimethyl-3,5-pyridinedicarboxylate (CAS Registry Number: 1149-23-1) (11.1 g, 43.8 mmol), and para-toluenesulfonic acid monohydrate (701 mg, 3.69 mmol) in 1,2-dichloroethane (80 mL) was stirred at 60° C. for 80 min. The reaction mixture was cooled to room temperature, ethanol (40 mL), and 5 mol/L aqueous sodium hydroxide solution (20 mL, 100 mmol) were added, and the mixture was stirred at room temperature for 3 hr. Ethanol (40 mL) was further added thereto, and the mixture was stirred for 3 hr. To the reaction mixture were added water and saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (hexane/DCM) to give the title compound (2.83 g, 11.0 mmol, yield 56%).

<Example BK2> 8-Bromo-N-(2,6-dioxopiperidin-3-yl)-5-nitro-3,4-dihydroquinoline-1(2H)-carboxamide Under ice-cooling, to a solution of triphosgene (1.90 g, 6.40 mmol) in DCM (20 mL) were successively added dropwise a solution of 8-bromo-5-nitro-1,2,3,4-tetrahydroquinoline (2.64 g, 10.3 mmol) in DCM (20 mL), and pyridine (2.0 mL, 25 mmol), and the mixture was stirred at 0° C. for 10 min, and warmed to room temperature, and stirred for 2 hr. To the reaction mixture was added 1 mol/L hydrochloric acid, and the mixture was extracted with DCM. The organic layers were combined, dried over sodium sulfate and filtered, and the filtrate was concentrated under reduced pressure. To the residue were added 3-aminopiperidine-2,6-dione monohydrochloride (CAS Registry Number: 24666-56-6) (1.74 g, 10.6 mmol), acetonitrile (35 mL), and triethylamine (7 mL, 50 mmol), and the mixture was stirred at 60° C. for 1 hr and left standing at room temperature overnight. To the reaction mixture were added water and ethyl acetate, insoluble materials were filtered off through celite, two layers were separated and the aqueous layer was extracted with ethyl acetate. The organic layer was dried over sodium sulfate and filtered, and the filtrate was concentrated under reduced pressure. The residue was purified by silica gel column chromatography (hexane/ethyl acetate) to give the title compound (3.75 g, 9.12 mmol, yield 89%).

<Example BK3> 8-Bromo-N-(2,6-dioxo-1-{[2-(trimethylsilyl)ethoxy]methyl}piperidin-3-yl)-5-nitro-3,4-dihydroquinoline-1(2H)-carboxamide To a solution of 8-bromo-N-(2,6-dioxopiperidin-3-yl)-5-nitro-3,4-dihydroquinoline-1(2H)-carboxamide (311 mg, 0.756 mmol) and DIPEA (0.254 mL, 1.46 mmol) in DCM (2.5 mL) was added 2-(trimethylsilyl)ethoxymethyl chloride (0.142 mL, 0.802 mmol) under ice-cooling, and the mixture was stirred at said temperature for 15 min, and then warmed to room temperature and stirred for 1.5 hr. To the reaction mixture was added 2-(trimethylsilyl)ethoxymethyl chloride (0.0402 mL, 0.227 mmol), and the mixture was stirred at room temperature for 1 hr. DIPEA (0.134 mL, 0.769 mmol) was added, and the mixture was stirred at room temperature for 15 hr. The reaction mixture was purified by silica gel column chromatography (hexane/ethyl acetate) to give the title compound (327 mg, 0.604 mmol, yield 80%).

<Example BK4> 3-(7-Nitro-2-oxo-5,6-dihydro-4H-imidazo[4,5,1-ij]quinolin-1(2H)-yl)-1-{[2-(trimethylsilyl)ethoxy]methyl}piperidine-2,6-dione A suspension of 8-bromo-N-(2,6-dioxo-1-{[2-(trimethylsilyl)ethoxy]methyl}piperidin-3-yl)-5-nitro-3,4-dihydroquinoline-1(2H)-carboxamide (4.22 g, 7.79 mmol), trans-4-hydroxy-L-proline (370 mg, 2.82 mmol), copper(I) iodide (269 mg, 1.41 mmol), and potassium triphosphate (5.00 g, 23.6 mmol) in DMSO (25 mL) was stirred at 60° C. for 1 hr. The mixture was cooled to room temperature and left standing for 13 hr. The reaction mixture was diluted with ethyl acetate, and washed with water. The organic layer was dried over sodium sulfate and filtered, and the filtrate was concentrated under reduced pressure. The residue was purified by silica gel column chromatography (hexane/ethyl acetate) to give the title compound (2.67 g, 5.80 mmol, yield 74%).

<Example BK5> 3-(7-Amino-2-oxo-5,6-dihydro-4H-imidazo[4,5,1-ij]quinolin-1(2H)-yl)-1-{[2-(trimethylsilyl)ethoxy]methyl}piperidine-2,6-dione To a solution of 3-(7-nitro-2-oxo-5,6-dihydro-4H-imidazo[4,5,1-ij]quinolin-1(2H)-yl)-1-{[2-(trimethylsilyl)ethoxy]methyl}piperidine-2,6-dione (2.67 g, 5.80 mmol) in ethyl acetate (60 mL) was added 10% palladium carbon (2.43 g), and the mixture was stirred under a hydrogen atmosphere at room temperature for 1 hr. The reaction mixture was diluted with ethyl acetate, insoluble materials were filtered off through celite, and the filtrate was concentrated under reduced pressure to give the title compound (2.26 g, 5.25 mmol, yield 91%).

<Example BK6> tert-Butyl 4-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino}piperidine-1-carboxylate Under ice-cooling, to a solution of 3-(7-amino-2-oxo-5,6-dihydro-4H-imidazo[4,5,1-ij]quinolin-1(2H)-yl)-1-{[2-(trimethylsilyl)ethoxy]methyl}piperidine-2,6-dione (1.65 g, 3.83 mmol) and tert-butyl 4-oxo-1-piperidinecarboxylate (CAS Registry Number: 79099-07-3) (840 mg, 4.22 mmol) in DCM (20 mL) was gradually added sodium triacetoxyborohydride (1.62 g, 7.66 mmol), and the mixture was stirred for 1 hr. The reaction mixture was warmed to room temperature, further stirred for 2 hr, and the reaction was discontinued by adding water. The mixture was neutralized by adding aqueous sodium hydrogen carbonate solution and extracted with chloroform. The organic layer was washed with saturated brine, dried over magnesium sulfate and filtered, and the filtrate was concentrated under reduced pressure. The residue was purified by silica gel column chromatography (chloroform/methanol) to give the title compound (2.28 g, 3.71 mmol, yield 96%).

<Example BK7> 3-[2-Oxo-7-(piperidin-4-ylamino)-5,6-dihydro-4H-imidazo[4,5,1-ij]quinolin-1(2H)-yl]-1-{[2-(trimethylsilyl)ethoxy]methyl}piperidine-2,6-dione tert-Butyl 4-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino}piperidine-1-carboxylate (0.505 g, 0.823 mmol) was dissolved in acetonitrile (6 mL), para-toluenesulfonic acid monohydrate (0.621 g, 3.26 mmol) was added, and the mixture was stirred at room temperature for 4 hr. To the reaction mixture was added saturated aqueous sodium hydrogen carbonate solution, and the mixture was extracted with ethyl acetate. The organic layer was washed with saturated brine, dried over sodium sulfate and filtered, and the filtrate was concentrated under reduced pressure to give the title compound (0.427 g, 0.831 mmol, yield: quantitative).

<Example BK8> 3-{7-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}-1-{[2-(trimethylsilyl)ethoxy]methyl}piperidine-2,6-dione To a solution of (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride (17.9 g, 27.3 mmol), 3-[2-oxo-7-(piperidin-4-ylamino)-5,6-dihydro-4H-imidazo[4,5,1-ij]quinolin-1(2H)-yl]-1-{[2-(trimethylsilyl)ethoxy]methyl}piperidine-2,6-dione (14.2 g, 27.6 mmol), and DIPEA (24 mL, 138 mmol) in DMF (135 mL) was added HATU (12.4 g, 32.6 mmol), and the mixture was stirred at room temperature for 22 hr. The reaction mixture was diluted with ethyl acetate and washed successively with water, saturated aqueous sodium hydrogen carbonate solution and saturated brine. The organic layer was dried over sodium sulfate and filtered, and the filtrate was concentrated under reduced pressure. The residue was purified by silica gel column chromatography (ethyl acetate/methanol) to give the title compound (27.0 g, 24.2 mmol, yield 89%).

<Example BK9> 3-{7-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione To a solution of 3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}-1-{[2-(trimethylsilyl)ethoxy]methyl)piperidine-2,6-dione (27.0 g, 24.2 mmol) in DCM (30 mL) was added trifluoroacetic acid (30 mL), and the mixture was stirred at room temperature for 1.5 hr. The reaction mixture was concentrated under reduced pressure, and the residue was neutralized by adding DCM, water, and sodium hydrogen carbonate. Two layers were separated and successively extracted with DCM and ethyl acetate. The organic layer was dried over sodium sulfate and filtered, and the filtrate was concentrated under reduced pressure. The residue was suspended in ethyl acetate (240 mL), N,N'-dimethylethylenediamine (3 mL, 28 mmol) was added, and the mixture was stirred at room temperature for 1 hr. To the reaction mixture were added saturated aqueous sodium hydrogen carbonate solution and water, and the mixture was extracted with ethyl acetate. The organic layer was dried over sodium sulfate and filtered, and the filtrate was concentrated under reduced pressure. The residue was purified by silica gel column chromatography (DCM/methanol) and the obtained solid was washed with diethyl ether, and dried under reduced pressure at 50° C. to give the title compound (18.0 g, 18.3 mmol, yield 76%).

<Example BL1> tert-Butyl (4S)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl)-2,3,4,5-tetrahydro[biphenyl]-4-carboxylate Using the compounds obtained in <Example M3> and <Example V3>, the title compound was obtained by the same method as in <Example W4>.

<Example BL2> (4S)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride Using the compound obtained in <Example BL1>, the title compound was obtained by the same method as in <Example V5>.

<Example BL3> 3-{7-[(1-{[(4S)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethyl-propyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}-1-{[2-(trimethylsilyl)ethoxy]methyl}piperidine-2,6-dione Using the compounds obtained in <Example BK7> and <Example BL2>, the title compound was obtained by the same method as in <Example BM9>.

<Example BL4> 3-{7-[(1-{[(4S)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethyl-propyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione Using the compound obtained in <Example BL3>, the title compound was obtained by the same method as in <Example BK9>.

<Example BM1>
6-Chloro-8-nitro-3,4-dihydro-2H-1,4-benzoxazine

At room temperature, to a suspension of 6-chloro-8-nitro-2H-1,4-benzoxazin-3(4H)-one (CAS Registry Number: 870064-73-6) (5.6 g, 24 mmol) in THE (20 mL) was added dropwise borane-THF complex (0.89 mol/L THE solution, 55 mL, 49 mmol). The reaction mixture was heated under reflux for 3 hr. After confirming the reaction by TLC, the reaction mixture was ice-cooled, 80% aqueous ethanol solution (30 mL) was gradually added. After the completion of foaming, triethylamine (3 mL) was added, and the mixture was heated under reflux for 1 hr. After cooling, the reaction mixture was concentrated under reduced pressure to about ⅓. To the residue was added water, and the precipitated solid was collected by filtration, washed with water, and dried under reduced pressure to give the title compound (4.8 g, 22 mmol, yield 91%).

<Example BM2> 5,7-Dibromo-6-chloro-8-nitro-3,4-dihydro-2H-1,4-benzoxazine

6-Chloro-8-nitro-3,4-dihydro-2H-1,4-benzoxazine (4.8 g, 22 mmol) was dissolved in DMF (75 mL), and N-bromo-succinimide (8.2 g, 45 mmol) and acetic acid (4 mL, 67 mmol) were added. After confirming the completion of the reaction by TLC, water was added to the reaction mixture, and the mixture was stirred. The precipitated solid was collected by filtration, washed with water, and dried under reduced pressure to give the title compound (7.1 g, 19 mmol, yield 85%).

<Example BM3> 5,7-Dibromo-6-chloro-N-(2,6-dioxopiperidin-3-yl)-8-nitro-2,3-dihydro-4H-1,4-benzoxazine-4-carboxamide Under ice-cooling, to a solution of triphosgene (4.50 g, 15.0 mmol) in DCM (150 mL) was added dropwise a solution of 5,7-dibromo-6-chloro-8-nitro-3,4-dihydro-2H-1,4-benzoxazine (11.2 g, 30.1 mmol) in DCM (150 mL), and then pyridine (7.5 mL, 90 mmol) was added. After confirming the reaction by TLC, the reaction mixture was added to ice-cooled 1 mol/L hydrochloric acid (95 mL), and the mixture was extracted with chloroform. The organic layer was washed with saturated brine, dried over magnesium sulfate and filtered, and the filtrate was concentrated under reduced pressure. The residue was dissolved in acetonitrile (150 mL), 3-aminopiperidine-2,6-dione monohydrochloride (CAS Registry Number: 24666-56-6) (5.5 g, 33 mmol) and triethylamine (21 mL, 150 mmol) were added, and the mixture was stirred for 1 hr. Water was added to the reaction mixture, and the mixture was concentrated under reduced pressure to half. The precipitated solid was collected by filtration, washed with water, and dried under reduced pressure to give the title compound (11.7 g, 22.2 mmol, yield 73%).

<Example BM4> 5,7-Dibromo-6-chloro-N-(2,6-dioxo-1-{[2-(trimethylsilyl)ethoxy]methyl}piperidin-3-yl)-8-nitro-2,3-dihydro-4H-1,4-benzoxazine-4-carboxamide Using the compound obtained in <Example BM3>, the title compound was obtained by the same method as in <Example BY3>.

<Example BM5> 3-(8-Bromo-9-chloro-7-nitro-2-oxo-4,5-dihydroimidazo[1,5,4-de][1,4]benzoxazin-1(2H)-yl)-1-{[2-(trimethylsilyl)ethoxy]methyl}piperidine-2,6-dione To a solution of 5,7-dibromo-6-chloro-N-(2,6-dioxo-1-{[2-(trimethylsilyl)ethoxy]methyl}piperidin-3-yl)-8-nitro-2,3-dihydro-4H-1,4-benzoxazine-4-carboxamide (10.5 g, 16.0 mmol) in DMSO (80 mL) were added trans-4-hydroxy-L-proline (760 mg, 5.76 mmol) and tripotassium phosphate (10.5 g, 48.0 mmol), copper(I) iodide (610 mg, 3.20 mmol) was added, and the mixture was heated under a nitrogen atmosphere at 60° C. for 5 hr. The reaction mixture was cooled, diluted with ethyl acetate, and insoluble materials were filtered off through celite. The filtrate was acidified by adding 10% aqueous citric acid solution and extracted with ethyl acetate. The organic layer was washed successively with water and saturated brine, dried over magnesium sulfate and filtered, and the filtrate was concentrated under reduced pressure. The residue was purified by silica gel column chromatography (hexane/ethyl acetate) to give the title compound (0.83 g, 11.4 mmol, yield 71%).

<Example BM6> 3-(7-Amino-2-oxo-4,5-dihydroimidazo[1,5,4-de][1,4]benzoxazin-1(2H)-yl)-1-{[2-(trimethylsilyl)ethoxy]methyl}piperidine-2,6-dione To a solution of 3-(8-bromo-9-chloro-7-nitro-2-oxo-4,5-dihydroimidazo[1,5,4-de][1,4]benzoxazin-1(2H)-yl)-1-{[2-(trimethylsilyl)ethoxy]methyl}piperidine-2,6-dione (22.3 g, 38.7 mmol) in ethyl acetate (300 mL) were added triethylamine (20 mL, 155 mmol) and 10% palladium carbon (8.0 g) and, after being purged with hydrogen, the mixture was stirred for 2 hr. Insoluble materials were filtered off through celite, washed with ethyl acetate, and the filtrate was concentrated under reduced pressure to half. To the residue were added again 10% palladium carbon (8.0 g) and triethylamine (20 mL, 155 mmol) and, after being purged with hydrogen, the mixture was stirred for 2 hr. The catalyst was filtered off, and the filtrate was concentrated under reduced pressure. To the residue was added aqueous sodium hydrogen carbonate solution, and the mixture was extracted with chloroform. The organic layer was washed with saturated brine, dried over magnesium sulfate and filtered, and the filtrate was concentrated under reduced pressure. To the residue was added IPA, and the precipitated solid was collected by filtration to give the title compound (12.7 g, 29.4 mmol, yield 75%).

<Example BM7> tert-Butyl 4-{[1-(2,6-dioxo-1-{[2-(trimethylsilyl)ethoxy]methyl}piperidin-3-yl)-2-oxo-1,2,4,5-tetrahydroimidazo[1,5,4-de][1,4]benzoxazin-7-yl]amino}piperidine-1-carboxylate To a solution of 3-(7-amino-2-oxo-4,5-dihydroimidazo[1,5,4-de][1,4]benzoxazin-1(2H)-yl)-1-{[2-(trimethylsilyl)ethoxy]methyl}piperidine-2,6-dione (12.7 g, 29.4 mmol) in DCM (75 mL) was added tert-butyl 4-oxo-1-piperidinecarboxylate (CAS Registry Number: 79099-07-3) (5.90 g, 29.4 mmol). After stirring for about 5 min, the reaction mixture was concentrated under reduced pressure. To the residue was added chloroform, and the mixture was azeotropically distilled, dissolved again in DCM (150 mL), and ice-cooled. Sodium triacetoxyborohydride (12.5 g, 58.7 mmol) was gradually added thereto, and the mixture was stirred at said temperature for 1 hr, the ice bath was removed and the temperature was raised to room temperature. After confirming the completion of the reaction by TLC, water was added to the reaction mixture and the mixture was stirred, basified by adding aqueous sodium hydrogen carbonate solution, and extracted with chloroform. The organic layer was dried over magnesium sulfate and filtered, and the filtrate was concentrated under reduced pressure. The residue was purified by silica gel column chromatography (hexane/ethyl acetate) to give the title compound (17.5 g, 28.4 mmol, yield 96%).

<Example BM8> 3-[2-Oxo-7-(piperidin-4-ylamino)-4,5-dihydroimidazo[1,5,4-de][1,4]benzoxazin-1(2H)-yl]-1-{[2-(trimethylsilyl)ethoxy]methyl}piperidine-2,6-dione At room temperature, to a solution of tert-butyl 4-{[1-(2,6-dioxo-1-{[2-(trimethylsilyl)ethoxy]methyl}piperidin-3-yl)-2-oxo-1,2,4,5-tetrahydroimidazo[1,5,4-de][1,4]benzoxazin-7-yl]amino}piperidine-1-carboxylate (17.5 g, 28.4 mmol) in acetonitrile (300 mL) was added para-toluenesulfonic acid monohydrate (11.0 g, 56.8 mmol), and the mixture was heated at 50° C. for 2 hr. After cooling, the reaction mixture was concentrated under reduced pressure to half. The residue was basified by adding aqueous sodium hydrogen carbonate solution and extracted with chloroform. The organic layer was washed with saturated brine, dried over magnesium sulfate and filtered, and the filtrate was concentrated under reduced pressure. The residue was purified by amine-modified silica gel column chromatography (chloroform/methanol) to give the title compound (13.1 g, 25.4 mmol, yield 89%).

<Example BM9> 3-{7-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-4,5-dihydroimidazo[1,5,4-de][1,4]benzoxazin-1(2H)-yl}-1-{[2-(trimethylsilyl)ethoxy]methyl}piperidine-2,6-dione At room temperature, to a solution of (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)

amino]methyl}-2,3,4,5-tetrahydro[biphenyl]-4-carboxylic acid monohydrochloride (18.0 g, 27.4 mmol) and 3-[2-oxo-7-(piperidin-4-ylamino)-4,5-dihydroimidazo[1,5,4-de][1,4]benzoxazin-1(2H)-yl]-1-{[2-(trimethylsilyl)ethoxy]methyl}piperidine-2,6-dione (14.2 g, 27.4 mmol) in DMF (150 mL) was added HATU (12.6 g, 32.9 mmol), and DIPEA (24 mL, 137 mmol) was added. After completion of the reaction, the reaction mixture was diluted with ethyl acetate and washed with water and saturated brine. The organic layer was dried over magnesium sulfate and filtered, and the filtrate was concentrated under reduced pressure. The residue was purified by silica gel column chromatography (chloroform/methanol) to give the title compound (30.0 g, 26.8 mmol, yield 97%).

<Example BM10> 3-{7-[(1-{[(4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-2-oxo-4,5-dihydroimidazo[1,5,4-de][1,4]benzoxazin-1(2H)-yl}piperidine-2,6-dione Using the compound obtained in <Example BM9>, the title compound was obtained by the same method as in <Example BK9>.

<Example BN1> 3-{7-[(1-{[(4S)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-4,5-dihydroimidazo[1,5,4-de][1,4]benzoxazin-1(2H)-yl}-1-{[2-(trimethylsilyl)ethoxy]methyl}piperidine-2,6-dione Using the compounds obtained in <Example BM8> and <Example BL2>, the title compound was obtained by the same method as in <Example BM9>.

<Example BN2> 3-{7-[(1-{[(4S)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-4,5-dihydroimidazo[1,5,4-de][1,4]benzoxazin-1(2H)-yl}piperidine-2,6-dione Using the compound obtained in <Example BN1>, the title compound was obtained by the same method as in <Example BK9>.

<Example BO1> (4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-carboxylic acid Using the compound obtained in <Example W4>, the title compound was obtained by the same method as in <Example V5>.

<Example BO2> tert-Butyl 4-{[2-(2,6-dioxopiperidin-3-yl)-1-oxo-2,3-dihydro-1H-isoindol-5-yl]amino}piperidine-1-carboxylate Using 3-(5-amino-1-oxo-1,3-dihydro-2H-isoindol-2-yl)piperidine-2,6-dione (ACS Med. Chem. Lett., 2021, 12, 1733.), the title compound was obtained by the same method as in <Example BR1>.

<Example BO3> 3-[1-Oxo-5-(piperidin-4-ylamino)-1,3-dihydro-2H-isoindol-2-yl]piperidine-2,6-dione dihydrochloride Using the compound obtained in <Example BO2>, the title compound was obtained by the same method as in <Example AO5>.

<Example BO4> 3-{5-[(1-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}piperidin-4-yl)amino]-1-oxo-1,3-dihydro-2H-isoindol-2-yl}piperidine-2,6-dione Using the compounds obtained in <Example BO3> and <Example BO1>, the title compound was obtained by the same method as in <Example BM9>.

<Example BP1> 6-Bromo-4-fluoro-1-methyl-1,3-dihydro-2H-benzimidazol-2-one

Using 5-bromo-3-fluoro-N-methyl-2-nitroaniline (WO2018039384 A1), the title compound was obtained by sequentially performing the same operations as in <Example BJ1> and <Example AN2>.

<Example BP2> 3-(5-Bromo-7-fluoro-3-methyl-2-oxo-2,3-dihydro-1H-benzimidazol-1-yl)-1-{[2-(trimethylsilyl)ethoxy]methyl}piperidine-2,6-dione Using the compound obtained in <Example BP1>, the title compound was obtained by the same method as in <Example Z5>.

<Example BP3> tert-Butyl 4-{[1-(2,6-dioxo-1-{[2-(trimethylsilyl)ethoxy]methyl}piperidin-3-yl)-7-fluoro-3-methyl-2-oxo-2,3-dihydro-1H-benzimidazol-5-yl]methyl}piperazine-1-carboxylate Using the compound obtained in <Example BP2>, the title compound was obtained by the same method as in <Example BQ1>.

<Example BP4> 3-[7-Fluoro-3-methyl-2-oxo-5-(piperazin-1-ylmethyl)-2,3-dihydro-1H-benzimidazol-1-yl]-1-{[2-(trimethylsilyl)ethoxy]methyl}piperidine-2,6-dione Using the compound obtained in <Example BP3>, the title compound was obtained by the same method as in <Example BM8>.

<Example BP5> 3-{7-Fluoro-5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl}-2,3,4,5-tetrahydro[biphenyl]-4-yl]carbonyl}piperazin-1-yl)methyl]-3-methyl-2-oxo-2,3-dihydro-1H-benzimidazol-1-yl}-1-{[2-(trimethylsilyl)ethoxy]methyl}piperidine-2,6-dione Using the compounds obtained in <Example BO1> and <Example BP4>, the title compound was obtained by the same method as in <Example BM9>.

<Example BP6> 3-{7-Fluoro-5-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl}-2,3,4,5-tetrahydro[biphenyl]-4-yl]carbonyl}piperazin-1-yl)methyl]-3-methyl-2-oxo-2,3-dihydro-1H-benzimidazol-1-yl}piperidine-2,6-dione Using the compound obtained in <Example BP5>, the title compound was obtained by the same method as in <Example BK9>.

<Example BQ1> tert-Butyl 4-{[1-(2,6-dioxo-1-{[2-(trimethylsilyl)ethoxy]methyl}piperidin-3-yl)-3-methyl-2-oxo-2,3-dihydro-1H-benzimidazol-5-yl]methyl}piperazine-1-carboxylate 3-(5-Bromo-3-methyl-2-oxo-2,3-dihydro-1H-benzimidazol-1-yl)-1-{[2-(trimethylsilyl)ethoxy]methyl}piperidine-2,6-dione (0.201 g, 0.429 mmol), potassium (4-tert-butoxy-carbonylpiperazin-1-yl)methyltrifluoroborate (CAS Registry Number: 936329-97-4) (0.261 g, 0.852 mmol), cesium carbonate (0.433 g, 1.33 mmol), and (SP-4-3)-[dicyclohexyl[2',4',6'-tris(1-methylethyl) [1,1'-biphenyl]-2-yl]phosphine](methanesulfonate-κO) [2'-(methylamino-κN) [1,1'-biphenyl]-2-yl-κC]palladium(II) (CAS Registry Number: 1599466-81-5) (0.018 g, 0.021 mmol) were dissolved in a mixed solvent of 1,4-dioxane (4 mL) and water (0.4 mL), and the mixture was stirred with heating under a nitrogen atmosphere at 85° C. for 3 hr. The reaction mixture was cooled to room temperature, water was added, and the mixture was extracted with ethyl acetate. The organic layer was dried over sodium sulfate and filtered, and the filtrate was concentrated under reduced pressure. The residue was purified by silica gel column chromatography (ethyl acetate/methanol) to give the title compound (0.219 g, 3.73 mmol, yield 87%).

<Example BQ2> 3-[3-Methyl-2-oxo-5-(piperazin-1-ylmethyl)-2,3-dihydro-1H-benzimidazol-1-yl]-1-{[2-(trimethylsilyl)ethoxy]methyl}piperidine-2,6-dione Using the compound obtained in <Example BQ1>, the title compound was obtained by the same method as in <Example BM8>.

<Example BQ3> 3-{5-[(4-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl}-2,3,4,5-tetrahydro[biphenyl]-4-yl]carbonyl}piperazin-1-yl)methyl]-3-methyl-2-oxo-2,3-dihydro-1H-benzimidazol-1-yl}-1-{[2-(trimethylsilyl)ethoxy]methyl}piperidine-2,6-dione Using the compounds obtained in <Example V5> and <Example BQ2>, the title compound was obtained by the same method as in <Example BM9>.

<Example BQ4> 3-{5-[(4-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethyl-propyl)amino]methyl}-2,3,4,5-tetrahydro[biphenyl]-4-yl]carbonyl}piperazin-1-yl)methyl]-3-methyl-2-oxo-2,3-dihydro-1H-benzimidazol-1-yl}piperidine-2,6-dione Using the compound obtained in <Example BQ3>, the title compound was obtained by the same method as in <Example BK9>.

<Example BR1> tert-Butyl 4-{[1-(2,6-dioxopiperidin-3-yl)-3-methyl-2-oxo-2,3-dihydro-1H-benzimidazol-5-yl]amino}piperidine-1-carboxylate To a suspension of 3-(5-amino-3-methyl-2-oxo-2,3-dihydro-1H-benzimidazol-1-yl)piperidine-2,6-dione (WO2021170109 A1) (0.606 g, 2.21 mmol), tert-butyl 4-oxo-1-piperidinecarboxylate (CAS Registry Number: 79099-07-3) (0.880 g, 4.42 mmol) in DCM (18 mL)-acetic acid (6 mL) was added dropwise borane-THF complex (0.89 mol/L THF solution, 5.0 mL, 4.5 mmol) at 0° C., and the mixture was stirred at said temperature for 3 hr. To the reaction mixture were added ice and saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (ethyl acetate/methanol) to give the title compound (0.951 g, 2.08 mmol, yield 94%).

<Example BR2> 3-[3-Methyl-2-oxo-5-(piperidin-4-ylamino)-2,3-dihydro-1H-benzimidazol-1-yl]piperidine-2,6-dione dihydrochloride Using the compound obtained in <Example BR1>, the title compound was obtained by the same method as in <Example AO5>.

<Example BR3> 3-{5-[(1-{[(4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethyl-propyl)amino]methyl}-2,3,4,5-tetrahydro[biphenyl]-4-yl]carbonyl}piperidin-4-yl)amino]-3-methyl-2-oxo-2,3-dihydro-1H-benzimidazol-1-yl}piperidine-2,6-dione Using the compounds obtained in <Example V5> and <Example BR2>, the title compound was obtained by the same method as in <Example BM9>.

<Example BS1> tert-Butyl 4-{[2-(2,6-dioxopiperidin-3-yl)-3-oxo-2,3-dihydro-1H-isoindol-5-yl]amino}piperidine-1-carboxylate To a solution of 3-(6-nitro-1-oxoisoindolin-2-yl)piperidine-2,6-dione (WO2017197056 A1) (0.103 g, 0.356 mmol) and tert-butyl 4-oxo-1-piperidinecarboxylate (CAS Registry Number: 79099-07-3) (0.108 g, 0.542 mmol) in DMF (3 mL)-acetic acid (1 mL) was added 10% palladium carbon (0.100 g), and the mixture was stirred under a hydrogen atmosphere at room temperature for 2.5 hr, and stirred with heating at 50° C. for 3 hr. The reaction mixture was filtered through celite, the filtrate was neutralized with saturated aqueous sodium hydrogen carbonate solution and extracted with DCM. The organic layer was dried over sodium sulfate and filtered, and the filtrate was concentrated under reduced pressure. The residue was washed with diethyl ether to give the title compound (0.096 g, 0.22 mmol, yield 61%).

<Example BS2> 3-[1-Oxo-6-(piperidin-4-ylamino)-1,3-dihydro-2H-isoindol-2-yl]piperidine-2,6-dione dihydrochloride Using the compound obtained in <Example BS1>, the title compound was obtained by the same method as in <Example AO5>.

<Example BS3> 3-{6-[(1-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl) amino]methyl}-2,3,4,5-tetrahydro[biphenyl]-4-yl] carbonyl}piperidin-4-yl)amino]-1-oxo-1,3-dihydro-2H-isoindol-2-yl}piperidine-2,6-dione Using the compounds obtained in <Example BO1> and <Example BS2>, the title compound was obtained by the same method as in <Example BM9>.

<Example BT1> 5-Fluoro-6-iodo-1-methyl-1,3-dihydro-2H-benzimidazol-2-one

5-Fluoro-1-methyl-1,3-dihydro-2H-benzimidazol-2-one (ACS Med. Chem. Lett., 2014, 5, 11, 1190.) (1.2 g, 7.2 mmol) was dissolved in acetic acid (15 mL), N-iodosuccinimide (1.8 g, 7.9 mmol) was added at room temperature, and the mixture was stirred for 18 hr. Water was added to the reaction mixture, and the precipitated solid was collected by filtration and dried under reduced pressure to give the title compound (1.5 g, 5.1 mmol, yield 71%).

<Example BT2> 3-(6-Fluoro-5-iodo-3-methyl-2-oxo-2,3-dihydro-1H-benzimidazol-1-yl)-1-{[2-(trimethylsilyl)ethoxy]methyl}piperidine-2,6-dione Using the compound obtained in <Example BT1>, the title compound was obtained by the same method as in <Example Z5>.

<Example BT3> tert-Butyl [1-(2,6-dioxo-1-{[2-(trimethylsilyl)ethoxy]methyl}piperidin-3-yl)-6-fluoro-3-methyl-2-oxo-2,3-dihydro-1H-benzimidazol-5-yl]carbamate To 3-(6-fluoro-5-iodo-3-methyl-2-oxo-2,3-dihydro-1H-benzimidazol-1-yl)-1-{[2-(trimethylsilyl)ethoxy] methyl}piperidine-2,6-dione (50 mg, 0.094 mmol) were added tert-butyl carbamate (CAS Registry Number: 4248-19-5) (22 mg, 0.187 mmol), 7-methyl-1,5,7-triazabicyclo [4.4.0]dec-5-ene (CAS Registry Number: 84030-20-6) (43 mg, 0.28 mmol), [(2-di-tert-butylphosphino-2',4',6'-triisopropyl-1,1'-biphenyl)-2-(2'-amino-1,1'-biphenyl)]palladium (II) methanesulfonate (CAS Registry Number: 1447963-75-8) (7.5 mg, 0.0094 mmol), and DMSO (0.7 mL) at room temperature, and the mixture was stirred for 6 hr. Water was added to the reaction mixture, and the mixture was extracted with ethyl acetate. The organic layers were combined, washed with saturated brine, dried over sodium sulfate and filtered, and the filtrate was concentrated under reduced pressure. The residue was purified by silica gel column chromatography (hexane/ethyl acetate) to give the title compound (20 mg, 0.038 mmol, yield 41%).

<Example BT4> 3-(5-Amino-6-fluoro-3-methyl-2-oxo-2,3-dihydro-1H-benzimidazol-1-yl)-1-(hydroxymethyl)piperidine-2,6-dione To a solution of tert-butyl [1-(2,6-dioxo-1-{[2-(trimethylsilyl)ethoxy]methyl}piperidin-3-yl)-6-fluoro-3-methyl-2-oxo-2,3-dihydro-1H-benzimidazol-5-yl]carbamate (20 mg, 0.038 mmol) in DCM (1 mL) was added trifluoroacetic acid (0.5 mL) at room temperature, and the mixture was stirred for 1 hr. The reaction mixture was concentrated under reduced pressure, and the residue was purified by silica gel column chromatography (ethyl acetate/methanol) to give the title compound (5.5 mg, 0.038 mmol, yield 50%).

<Example BT5> tert-Butyl 4-{[1-(2,6-dioxopiperidin-3-yl)-6-fluoro-3-methyl-2-oxo-2,3-dihydro-1H-benzimidazol-5-yl]amino)piperidine-1-carboxylate Using the compound obtained in <Example BT4>, the title compound was obtained by the same method as in <Example BR1>.

<Example BT6> 3-{6-Fluoro-5-[(1-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-3-methyl-2-oxo-2,3-dihydro-1H-benzimidazol-1-yl}piperidine-2,6-dione Using the compounds obtained in <Example BT5> and <Example BO1>, the title compound was obtained by the same method as in <Example CD2>.

<Example BU1> 4,5-Dihydroimidazo[1,5,4-de][1,4]benzoxazin-2(1H)-one

Under ice-cooling, to a solution of 3,4-dihydro-2H-1,4-benzoxazin-5-amine (CAS Registry Number: 137469-91-1) (2.3 g, mmol) in DCM (50 mL) was added dropwise a solution of triphosgene (2.3 g, 7.7 mmol) in DCM (5 mL), and pyridine (3.7 mL, 46 mmol) was gradually added. After completion of the reaction, the reaction mixture was concentrated under reduced pressure. To the residue was added water, and the mixture was extracted with chloroform. The organic layer was washed successively with 1 mol/L hydrochloric acid and saturated brine, dried over magnesium sulfate and filtered, and the filtrate was concentrated under reduced pressure, and dried under reduced pressure to give the title compound (2.1 g, 12 mmol, yield 78%).

<Example BU2> 7-Iodo-4,5-dihydroimidazo[1,5,4-de][1,4]benzoxazin-2(1H)-one

Using the compound obtained in <Example BU1>, the title compound was obtained by the same method as in <Example AW1>.

<Example BU3> 3-(7-Iodo-2-oxo-4,5-dihydroimidazo[1,5,4-de][1,4]benzoxazin-1(2H)-yl)-1-{[2-(trimethylsilyl)ethoxy]methyl}piperidine-2,6-dione Using the compound obtained in <Example BU2>, the title compound was obtained by the same method as in <Example Z5>.

<Example BU4> 2,4,6-Trichlorophenyl 1-(2,6-dioxo-1-{[2-(trimethylsilyl)ethoxy]methyl}piperidin-3-yl)-2-oxo-1,2,4,5-tetrahydroimidazo[1,5,4-de][1,4]benzoxazine-7-carboxylate Using the compound obtained in <Example BU3>, the title compound was obtained by the same method as in <Example BY5>.

<Example BU5> 3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl)-2,3,4,5-tetrahydro[biphenyl]-4-yl]methyl}piperazin-1-yl)carbonyl]-2-oxo-4,5-dihydroimidazo[1,5,4-de][1,4]benzoxazin-1(2H)-yl)-1-{[2-(trimethylsilyl)ethoxy]methyl}piperidine-2,6-dione Using the compounds obtained in <Example BU4> and <Example AO5>, the title compound was obtained by the same method as in <Example BI1>.

<Example BU6> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-4,5-dihydroimidazo[1,5,4-de][1,4]benzoxazin-1(2H)-yl}piperidine-2,6-dione Using the compound obtained in <Example BU5>, the title compound was obtained by the same method as in <Example BK9>.

<Example BV1> tert-Butyl [(3S*,4S*)-4-(2-fluoro-3-nitrophenoxy)THF-3-yl]carbamate Using tert-butyl [(3R*,4S*)-4-hydroxytetrahydrofuran-3-yl]carbamate (WO2020012334 A1) and 2-fluoro-3-nitrophenol (CAS Registry Number: 179816-26-3), the title compound was obtained by the same method as in <Example AY4>.

<Example BV2> (3S*, 4S*)-4-(2-Fluoro-3-nitrophenoxy)tetrahydrofuran-3-amine monohydrochloride Using the compound obtained in <Example BV1>, the title compound was obtained by the same method as in <Example AO5>.

<Example BV3> (3aS*,9aS*)-8-Nitro-3,3a,9,9a-tetrahydro-1H-furo[3,4-b][1,4]benzoxazine At room temperature, to a solution of (3S*,4S*)-4-(2-fluoro-3-nitrophenoxy)tetrahydrofuran-3-amine monohydrochloride (554 mg, 1.99 mmol) in DMF (15 mL) was added potassium carbonate (550 mg, 3.98 mmol), and the mixture was stirred at 60° C. for 2 hr. The reaction mixture was cooled to room temperature, water was added, and the mixture was extracted with ethyl acetate. The organic layer was washed with saturated brine, dried over magnesium sulfate and filtered, and the filtrate was concentrated under reduced pressure to give the title compound (460 mg, 2.07 mmol, yield: quantitative).

<Example BV4> (3aS*,9aS*)-3,3a,9,9a-Tetrahydro-1H-furo[3,4-b][1,4]benzoxazin-8-amine Using the compound obtained in <Example BV3>, the title compound was obtained by the same method as in <Example BK5>.

<Example BV5> (6aS*,9aS*)-6a,7,9,9a-Tetrahydrofuro[3,4-b]imidazo[1,5,4-de][1,4]benzoxazin-1(2H)-one Using the compound obtained in <Example BV4>, the title compound was obtained by the same method as in <Example BU1>.

<Example BV6> (6aS*,9aS*)-5-Iodo-6a,7,9,9a-tetrahydrofuro[3,4-b]imidazo[1,5,4-de][1,4]benzoxazin-1(2H)-one Using the compound obtained in <Example BV5>, the title compound was obtained by the same method as in <Example AW1>.

<Example BV7> 3-[(6aS*,9aS*)-5-Iodo-1-oxo-6a,7,9,9a-tetrahydrofuro[3,4-b]imidazo[1,5,4-de][1,4]benzoxazin-2(1H)-yl]-1-{[2-(trimethylsilyl)ethoxy]methyl}piperidine-2,6-dione Using the compound obtained in <Example BV6>, the title compound was obtained by the same method as in <Example Z5>.

<Example BV8> 2,4,6-Trichlorophenyl (6aS*,9aS*)-2-(2,6-dioxo-1-{[2-(trimethylsilyl)ethoxy]methyl}piperidin-3-yl)-1-oxo-1,2,6a,7,9,9a-hexahydrofuro[3,4-b]imidazo[1,5,4-de][1,4]benzoxazine-5-carboxylate Using the compound obtained in <Example BV7>, the title compound was obtained by the same method as in <Example BY5>.

<Example BV9> 3-[(6aS*,9aS*)-5-((4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-1-oxo-6a,7,9,9a-tetrahydrofuro[3,4-b]imidazo[1,5,4-de][1,4]benzoxazin-2(1H)-yl]-1-{[2-(trimethylsilyl)ethoxy]methyl}piperidine-2,6-dione Using the compounds obtained in <Example BV8> and <Example AO5>, the title compound was obtained by the same method as in <Example BI1>.

<Example BV10> 3-[(6aS*,9aS*)-5-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl) carbonyl]-1-oxo-6a, 7,9,9a-tetrahydrofuro[3,4-b]imidazo[1,5,4-de][1,4]benzoxazin-2(1H)-yl]piperidine-2,6-dione Using the compound obtained in <Example BV9>, the title compound was obtained by the same method as in <Example BK9>.

<Example BW1> tert-Butyl 3-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino}azetidine-1-carboxylate Using the compound obtained in <Example BK5> and tert-butyl 3-oxoazetidine-1-carboxylate (CAS Registry Number: 398489-26-4), the title compound was obtained by the same method as in <Example AS2>.

<Example BW2> 3-[7-(Azetidin-3-ylamino)-2-oxo-5,6-dihydro-4H-imidazo[4,5,1-ij]quinolin-1(2H)-yl]-1-(hydroxymethyl)piperidine-2,6-dione dihydrochloride Using the compound obtained in <Example BW1>, the title compound was obtained by the same method as in <Example AO5>.

<Example BW3> 3-{7-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}azetidin-3-yl)amino]-2-oxo-5,6-dihydro-4H-imidazo[4,5,1-ij]quinolin-1(2H)-yl}piperidine-2,6-dione 3-[7-(Azetidin-3-ylamino)-2-oxo-5,6-dihydro-4H-imidazo[4,5,1-ij]quinolin-1(2H)-yl]-1-(hydroxymethyl)piperidine-2,6-dione dihydrochloride (0.138 g, 0.301 mmol), (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride (0.110 g, 0.168 mmol), and HATU (0.083 g, 0.22 mmol) were dissolved in DMF (2 mL), DIPEA (0.142 mL, 0.830 mmol) was added, and the mixture was stirred at room temperature for 19 hr. To the reaction mixture was added saturated aqueous sodium hydrogen carbonate solution, and the mixture was extracted with ethyl acetate. The organic layer was dried over sodium sulfate and filtered, and the filtrate was concentrated under reduced pressure. The residue was dissolved in ethyl acetate (1 mL), and N,N'-dimethylethylenediamine (0.020 mL, 0.19 mmol) was added. The reaction mixture was purified by silica gel column chromatography (ethyl acetate/methanol) to give the title compound (0.061 g, 0.064 mmol, yield 38%).

<Example BX1> 7-Fluoro-6-iodo-1-methyl-1,3-dihydro-2H-benzimidazol-2-one

7-Fluoro-1-methyl-1,3-dihydro-2H-benzimidazol-2-one (WO2016097749 A1) (0.40 g, 2.4 mmol) was dissolved in acetic acid (10 mL), N-iodosuccinimide (0.61 g, 2.7 mmol) was added at room temperature, and the mixture was stirred for 18 hr. Water was added to the reaction mixture, and the precipitated solid was collected by filtration, and dried under reduced pressure to give the title compound (0.66 g, 2.3 mmol, yield 96%).

<Example BX2> 3-(4-Fluoro-5-iodo-3-methyl-2-oxo-2,3-dihydro-1H-benzimidazol-1-yl)-1-{[2-(trimethylsilyl)ethoxy]methyl}piperidine-2,6-dione Using the compound obtained in <Example BX1>, the title compound was obtained by the same method as in <Example Z5>.

<Example BX3> tert-Butyl [1-(2,6-dioxo-1-{[2-(trimethylsilyl)ethoxy]methyl}piperidin-3-yl)-4-fluoro-3-methyl-2-oxo-2,3-dihydro-1H-benzimidazol-5-yl]carbamate Using the compound obtained in <Example BX2>, the title compound was obtained by the same method as in <Example BT3>.

<Example BX4> tert-Butyl 4-{[1-(2,6-dioxopiperidin-3-yl)-4-fluoro-3-methyl-2-oxo-2,3-dihydro-1H-benzimidazol-5-yl]amino}piperidine-1-carboxylate To a solution of tert-butyl [1-(2,6-dioxo-1-{[2-(trimethylsilyl)ethoxy]methyl}piperidin-3-yl)-4-fluoro-3-methyl-2-oxo-2,3-dihydro-1H-benzimidazol-5-yl]carbamate (62 mg, 0.12 mmol) in DCM (1 mL) was added trifluoroacetic acid (1 mL) at room temperature, and the mixture was stirred for 1 hr and concentrated under reduced pressure. A solution of the residue and tert-butyl 4-oxo-1-piperidinecarboxylate (CAS Registry Number: 79099-07-3) in DCM (0.8 mL)-acetic acid (0.3 mL) was cooled to 0° C., borane-THF complex (0.89 mol/mL THF solution, 0.27 mL, 0.24 mmol) was added dropwise, and the mixture was stirred at said temperature for 5 min. To the reaction mixture were added ice and saturated aqueous sodium hydrogen carbonate solution, and the mixture was extracted with ethyl acetate. The organic layers were combined, washed with saturated brine, dried over sodium sulfate and filtered, and the filtrate was concentrated under reduced pressure. The residue was diluted with ethyl acetate (2 mL), N,N'-dimethylethylenediamine (0.014 mL, 0.13 mmol) was added and the mixture was stirred at room temperature for 30 min, and concentrated under reduced pressure. The residue was purified by silica gel column chromatography (ethyl acetate/methanol) to give the title compound (51 mg, 0.11 mmol, yield 89%).

<Example BX5> 3-[4-Fluoro-3-methyl-2-oxo-5-(piperidin-4-ylamino)-2,3-dihydro-1H-benzimidazol-1-yl]piperidine-2,6-dione dihydrochloride Using the compound obtained in <Example BX4>, the title compound was obtained by the same method as in <Example AO5>.

<Example BX6> 3-{4-Fluoro-5-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-3-methyl-2-oxo-2,3-dihydro-1H-benzimidazol-1-yl}piperidine-2,6-dione Using the compounds obtained in <Example BX5> and <Example V5>, the title compound was obtained by the same method as in <Example BM9>.

<Example BY1> 5,8-dibromo-1,2,3,4-tetrahydroquinoxaline

To a suspension of 5,8-dibromoquinoxaline (CAS Registry Number: 148231-12-3) (4.47 g, 15.5 mmol) in ethanol (75 mL) was added sodium borohydride (4.67 g, 123 mmol), and the mixture was stirred at 50° C. for 1 hr. The reaction mixture was cooled to room temperature, water was added, and the mixture was concentrated under reduced pressure, and extracted with DCM. The organic layer was dried over sodium sulfate and filtered, and the filtrate was concentrated under reduced pressure. To the residue was added IPA, and the mixture was dissolved at 60° C. and stirred at room temperature. The precipitated solid was collected by filtration, washed with hexane, and dried under reduced pressure at 60° C. to give the title compound (2.64 g, 9.04 mmol, yield 58%).

<Example BY2> 5,8-Dibromo-N-(2,6-dioxopiperidin-3-yl)-3,4-dihydroquinoxaline-1(2H)-carboxamide A solution of 5,8-dibromo-1,2,3,4-tetrahydroquinoxaline (6.31 g, 21.6 mmol) in DCM (40 mL) was ice-cooled, and a solution of triphosgene (2.69 g, 9.08 mmol) in DCM (40 mL) was added dropwise. After stirring at said temperature for 5 min, triethylamine (6.00 mL, 43.3 mmol) was added dropwise, and the mixture was stirred at said temperature for 45 min. Water was added to the reaction mixture, and the mixture was extracted with DCM. The organic layer was dried over magnesium sulfate and filtered, and the filtrate was concentrated under reduced pressure. To a solution of the residue in acetonitrile (110 mL) were added 3-aminopiperidine-2,6-dione monohydrochloride (CAS Registry Number: 24666-56-6) (3.91 g, 23.8 mmol) and triethylamine (15 mL, 108 mmol), and the mixture was stirred at 50° C. for 3 hr. Water was added to the reaction mixture, and the mixture was extracted with DCM. The organic layer was dried over magnesium sulfate and filtered, and the filtrate was concentrated under reduced pressure. The residue was slurry washed with IPA/diethyl ether to give the title compound (6.77 g, 15.2 mmol, yield 70%).

<Example BY3> 5,8-Dibromo-N-(2,6-dioxo-1-{[2-(trimethylsilyl)ethoxy]methyl}piperidin-3-yl)-3,4-dihydroquinoxaline-1(2H)-carboxamide To a solution of 5,8-dibromo-N-(2,6-dioxopiperidin-3-yl)-3,4-dihydroquinoxaline-1(2H)-carboxamide (6.77 g, 15.2 mmol) in DMF (60 mL) were added, under ice-cooling, 1,8-diazabicyclo[5.4.0]-7-undecene (4.53 mL, 30.4 mmol) and 2-(trimethylsilyl)ethoxymethyl chloride (4.0 mL, 23 mmol), and the mixture was stirred at room temperature for 2 hr, and then heated to 40° C. and stirred for 30 min. The reaction mixture cooled to room temperature, 2-(trimethylsilyl)ethoxymethyl chloride (0.53 mL, 3.0 mmol) was added. The mixture was stirred at room temperature for 2 hr and left standing overnight at room temperature. Water was added to the reaction mixture, and the mixture was extracted with ethyl acetate. The organic layer was washed with saturated brine, dried over magnesium sulfate and filtered, and the filtrate was concentrated under reduced pressure to give the title compound (7.54 g, 13.1 mmol, yield 86%).

<Example BY4> 3-(7-Bromo-2-oxo-5,6-dihydro-4H-imidazo[1,5,4-de]quinoxalin-1(2H)-yl)-1-{[2-(trimethylsilyl)ethoxy]methyl}piperidine-2,6-dione A suspension of 5,8-dibromo-N-(2,6-dioxo-1-{[2-(trimethylsilyl)ethoxy]methyl}piperidin-3-yl)-3,4-dihydroquinoxaline-1(2H)-carboxamide (7.54 g, 13.1 mmol), copper(I) iodide (250 mg, 1.31 mmol), trans-4-hydroxy-L-proline (345 mg, 2.63 mmol), and tripotassium phosphate (5.55 g, 26.2 mmol) in DMSO (52 mL) was stirred at 80° C. for 2 hr. The reaction mixture was cooled to room temperature, filtered through celite, and insoluble material was filtered off. The filtrate was diluted with ethyl acetate and washed successively with water and saturated brine. The organic layer was dried over magnesium sulfate and filtered, and the filtrate was concentrated under reduced pressure. The residue was purified by silica gel column chromatography (hexane/ethyl acetate) to give the title compound (4.51 g, 9.10 mmol, yield 70%).

<Example BY5> 2,4,6-Trichlorophenyl 1-(2,6-dioxo-1-{[2-(trimethylsilyl)ethoxy]methyl}piperidin-3-yl)-2-oxo-1,2,5,6-tetrahydro-4H-imidazo[1,5,4-de]quinoxaline-7-carboxylate A solution of 3-(7-bromo-2-oxo-5,6-dihydro-4H-imidazo[1,5,4-de]quinoxalin-1(2H)-yl)-1-{[2-(trimethylsilyl)ethoxy]methyl}piperidine-2,6-dione (1.00 g, 2.02 mmol), palladium(II) acetate (22 mg, 0.098 mmol), XantPhos (117 mg, 0.202 mmol), and 2,4,6-trichlorophenyl formate (CAS Registry Number: 4525-65-9) (680 mg, 3.02 mmol) in toluene (10 mL) was deaerated, and purged with nitrogen. Then, triethylamine (0.560 mL, 4.04 mmol) was added, and the mixture was stirred under a carbon monoxide atmosphere at 110° C. for 4 hr. To the reaction mixture were added palladium(II) acetate (22 mg, 0.098 mmol) and XantPhos (117 mg, 0.202 mmol), and the mixture was stirred again at 110° C. for 4 hr. The reaction mixture was cooled to room temperature, filtered through celite, washed with ethyl acetate, and insoluble material was filtered off. The filtrate was concentrated under reduced pressure. The residue was purified by silica gel column chromatography (hexane/ethyl acetate) to give the title compound (814 mg, 1.27 mmol, yield 63%).

<Example BY6> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}-1-{[2-(trimethylsilyl)ethoxy]methyl}piperidine-2,6-dione To a suspension of 2,4,6-trichlorophenyl 1-(2,6-dioxo-1-{[2-(trimethylsilyl)ethoxy]methyl}piperidin-3-yl)-2-oxo-1,2,5,6-tetrahydro-4H-imidazo[1,5,4-de]quinoxaline-7-carboxylate (14.0 g, 21.9 mmol) and 3,3,3-trifluoro-N-{2-[(4R)-4-(4-methoxyphenyl)-2,2-dimethyltetrahydro-2H-pyran-4-yl]ethyl}-2,2-dimethyl-N-{[(4'R)-4'-(piperazin-1-ylmethyl)-2',3',4',5'-tetrahydro[biphenyl]-4-yl]methyl}propan-1-amine dihydrochloride (15.5 g, 21.3 mmol) in acetonitrile (150 mL) were added DIPEA (19 mL, 109 mmol) and 4-dimethylaminopyridine (800 mg, 6.55 mmol), and the mixture was stirred at room temperature for 4 days. The reaction mixture was diluted with ethyl acetate, washed successively with saturated aqueous sodium hydrogen carbonate solution and saturated brine, dried over magnesium sulfate and filtered, and the filtrate was concentrated under reduced pressure. The residue was purified by silica gel column chromatography (ethyl acetate/methanol) to give the title compound (19.1 g, 17.4 mmol, yield 80%).

<Example BY7> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione To a solution of 3-{7-[(4-{[(4R)-4'-{[{2-[(4R)-4-(4-methoxyphenyl)-2,2-dimethyltetrahydro-2H-pyran-4-yl]

ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}-1-{[2-(trimethylsilyl)ethoxy]methyl}piperidine-2,6-dione (23.1 g, 21.0 mmol) in DCM (42 mL) was added trifluoroacetic acid (42 mL), and the mixture was stirred at room temperature for 1.5 hr. The reaction mixture was concentrated under reduced pressure, diluted with ethyl acetate, saturated aqueous sodium hydrogen carbonate solution was added and the mixture was stirred. Two layers were separated, and the aqueous layer was extracted with ethyl acetate. The organic layers were combined, dried over magnesium sulfate and filtered, and the filtrate was concentrated under reduced pressure. To a solution of the residue in ethyl acetate (105 mL) was added N,N'-dimethylethylenediamine (2.49 mL, 23.2 mmol), and the mixture was stirred at room temperature for 1.5 hr. The reaction mixture was diluted with ethyl acetate, and washed successively with saturated aqueous sodium hydrogen carbonate solution and saturated brine. The organic layer was dried over magnesium sulfate and filtered, and the filtrate was concentrated under reduced pressure, and the residue was purified by silica gel column chromatography (ethyl acetate/methanol). The obtained solid was slurry washed with hexane/ethyl acetate, and dried under reduced pressure at 60° C. to give the title compound (14.0 g, 14.5 mmol, yield 69%).

<Example BZ1> tert-Butyl (4S)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylate Using the compounds obtained in <Example M3> and <Example W3>, the title compound was obtained by the same method as in <Example W4>.

<Example BZ2> [(4S)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methanol Using the compound obtained in <Example BZ1>, the title compound was obtained by the same method as in <Example W5>.

<Example BZ3> [(4S)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl methanesulfonate Using the compound obtained in <Example BZ2>, the title compound was obtained by the same method as in <Example X1>.

<Example BZ4> tert-Butyl 4-{[(4S)-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazine-1-carboxylate Using the compound obtained in <Example BZ3>, the title compound was obtained by the same method as in <Example X2>.

<Example BZ5> 3,3,3-Trifluoro-N-{2-[(4R)-4-(4-methoxyphenyl)-2,2-dimethyltetrahydro-2H-pyran-4-yl]ethyl}-2,2-dimethyl-N-{[(4'S)-4'-(piperazin-1-ylmethyl)-2',3',4',5'-tetrahydro[biphenyl]-4-yl]methyl}propan-1-amine dihydrochloride Using the compound obtained in <Example BZ4>, the title compound was obtained by the same method as in <Example AO5>.

<Example BZ6> 3-{7-[(4-{[(4S)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}-1-{[2-(trimethylsilyl)ethoxy]methyl}piperidine-2,6-dione Using the compounds obtained in <Example BZ5> and <Example BY5>, the title compound was obtained by the same method as in <Example BI1>.

<Example BZ7> 3-{7-[(4-{[(4S)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione Using the compound obtained in <Example BZ6>, the title compound was obtained by the same method as in <Example BK9>.

<Example CA1> 4-{[1-(2,6-Dioxopiperidin-3-yl)-3-methyl-2-oxo-2,3-dihydro-1H-benzimidazol-5-yl]amino}-N-[4-(trans-4-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}cyclohexyl)phenyl]piperidine-1-carboxamide To a solution of triphosgene (14.2 mg, 0.0479 mmol) in DCM (1 mL) were successively added, under ice-cooling, 4-(trans-4-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}cyclohexyl)aniline dihydrochloride (50.5 mg, 0.0826 mmol) and triethylamine (0.0576 mL, 0.413 mmol), and the mixture was stirred at said temperature for 1 hr. The reaction mixture was warmed to room temperature, and stirred for 1 hr. To the reaction mixture were added 3-[3-methyl-2-oxo-5-(piperidin-4-ylamino)-2,3-dihydro-1H-benzimidazol-1-yl]piperidine-2,6-dione dihydrochloride (35.9 mg, 0.0834 mmol) and triethylamine (0.0576 mL, 0.413 mmol), and the mixture was stirred for 15 min. To the reaction mixture was added 3-[3-methyl-2-oxo-5-(piperidin-4-ylamino)-2,3-dihydro-1H-benzimidazol-1-yl]piperidine-2,6-dione dihydrochloride (33.4 mg, 0.0776 mmol), and the mixture was further stirred for 45 min. To the reaction mixture was added saturated aqueous sodium hydrogen carbonate solution, and the mixture was extracted with DCM. The organic layer was dried over sodium sulfate and filtered, and the filtrate was concentrated under reduced pressure. The residue was purified by silica gel column chromatography (DCM/methanol). The obtained solid was washed with hexane/ethyl acetate and dried under reduced pressure to give the title compound (26.1 mg, 0.0272 mmol, yield 33%).

<Example CB1> 9-Nitro-1,2,3,4-tetrahydro-5H-1,4-benzodiazepine-5-one

Methyl 2-fluoro-3-nitrobenzoate (CAS Registry Number: 946126-94-9) (5.00 g, 25.1 mmol) was dissolved in DMF (50 mL), potassium carbonate (4.86 g, 35.2 mmol) and N-(tert-butoxycarbonyl)-1,2-diaminoethane (CAS Registry Number: 57260-73-8) (4.0 mL, 25 mmol) were added, and the mixture was stirred at room temperature for 3 hr. To the reaction mixture was added N-(tert-butoxycarbonyl)-1,2-diaminoethane (1.0 mL, 6.3 mmol), and the mixture was stirred at room temperature for 15 hr. Water was added to the reaction mixture, and the mixture was extracted with ethyl acetate. The organic layer was washed with saturated aqueous ammonium chloride solution, dried over sodium sulfate and filtered, and the filtrate was concentrated under reduced pressure. The residue was dissolved in DCM (40 mL), 4 mol/L hydrogen chloride/1,4-dioxane solution (65 mL, 260 mmol) was added, and the mixture was stirred at room temperature for 2 hr and concentrated under reduced pressure. The residue was suspended in ethanol (100 mL), sodium carbonate (27.1 g, 256 mmol) was added, and the mixture was stirred with heating at 90° C. for 5 hr. The reaction mixture was concentrated under reduced pressure, water was added and the mixture was stirred. The resulting solid was collected by filtration while washing with water and dried under reduced pressure to give the title compound (5.42 g, 26.2 mmol, yield: quantitative).

<Example CB2> tert-Butyl 9-nitro-1,2,3,5-tetrahydro-4H-1,4-benzodiazepine-4-carboxylate 9-Nitro-1,2,3,4-tetrahydro-5H-1,4-benzodiazepin-5-one (5.20 g, 25.1 mmol) was suspended in DCM (50 mL), DIPEA (9.0 mL, 53 mmol) and di-tert-butyl dicarbonate (7.57 g, 34.7 mmol) were added, and the mixture was stirred at room temperature for 30 min. To the reaction mixture were added DCM (200 mL) and 4-dimethylaminopyridine (0.68 g, 5.6 mmol), and the mixture was stirred with heating at 40° C. for 2.5 hr. The reaction mixture was concentrated under reduced pressure. The residue was dissolved in ethyl acetate and washed successively with saturated aqueous ammonium chloride solution and saturated brine. The organic layer was dried over sodium sulfate and filtered, and the filtrate was concentrated under reduced pressure. The residue was dissolved in THF (100 mL), borane-THF complex (0.89 mol/L THE solution, 56 mL, 50 mmol) was added dropwise thereto, and the mixture was stirred with heating at 60° C. for 30 min. The reaction mixture was cooled to room temperature, water was added, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (5.58 g, 19.0 mmol, yield 76%).

<Example CB3> tert-Butyl 2-oxo-1,2,4,5-tetrahydroimidazo[4,5,1-jk][1,4]benzodiazepine-6(7H)-carboxylate tert-Butyl 9-nitro-1,2,3,5-tetrahydro-4H-1,4-benzodiazepine-4-carboxylate (5.58 g, 19.0 mmol) was dissolved in THE (100 mL), 10% palladium carbon (5.28 g) was added, and the mixture was stirred under a hydrogen atmosphere at room temperature for 1 hr, and then stirred with heating at 40° C. for 1.5 hr. To the reaction mixture was added ethanol (50 mL), and the mixture was stirred with heating at 80° C. for 2 hr. The reaction mixture was filtered through celite and the filtrate was concentrated under reduced pressure. The residue was dissolved in THE (100 mL), 1,1'-carbonyldiimidazole (4.63 g, 28.6 mmol) was added, and the mixture was stirred with heating at 60° C. for 1 hr. To the reaction mixture was added 1 mol/L aqueous sodium hydroxide solution, and the mixture was extracted with ethyl acetate. The organic layer was washed with saturated brine, dried over sodium sulfate and filtered, and the filtrate was concentrated under reduced pressure. The residue was purified by silica gel column chromatography (ethyl acetate/methanol) to give the title compound (4.57 g, 15.8 mmol, yield 83%).

<Example CB4> tert-Butyl 8-iodo-2-oxo-1,2,4,5-tetrahydroimidazo[4,5,1-jk][1,4]benzodiazepine-6(7H)-carboxylate Using the compound obtained in <Example CB3>, the title compound was obtained by the same method as in <Example AW1>.

<Example CB5> tert-Butyl 1-(2,6-dioxo-1-{[2-(trimethylsilyl)ethoxy]methyl}piperidin-3-yl)-8-iodo-2-oxo-1,2,4,5-tetrahydroimidazo[4,5,1-jk][1,4]benzodiazepine-6(7H)-carboxylate Using the compound obtained in <Example CB4>, the title compound was obtained by the same method as in <Example Z5>.

<Example CB6> tert-Butyl 1-(2,6-dioxo-1-{[2-(trimethylsilyl)ethoxy]methyl}piperidin-3-yl)-8-formyl-2-oxo-1,2,4,5-tetrahydroimidazo[4,5,1-jk][1,4]benzodiazepine-6(7H)-carboxylate tert-Butyl 1-(2,6-dioxo-1-{[2-(trimethylsilyl)ethoxy]methyl}piperidin-3-yl)-8-iodo-2-oxo-1,2,4,5-tetrahydroimidazo[4,5,1-jk][1,4]benzodiazepine-6(7H)-carboxylate (0.502 g, 0.765 mmol), saccharin (CAS Registry Number: 81-07-2) (0.209 g, 1.14 mmol), [1,1'-bis(diphenylphosphino)ferrocene]palladium(II) dichloride DCM adduct (0.062 g, 0.076 mmol), sodium carbonate (0.121 g, 1.14 mmol), and triethylsilane (0.182 mL, 1.14 mmol) were dissolved in DMF (6 mL), and the mixture was stirred with heating at 85° C. for 3 hr under a carbon monoxide atmosphere. The reaction mixture was cooled to room temperature, water was added, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (0.432 g, 0.773 mmol, yield: quantitative).

<Example CB7> tert-Butyl 8-({4-[(benzyloxy)carbonyl]piperazin-1-yl}methyl)-1-(2,6-dioxo-1-{[2-(trimethylsilyl)ethoxy]methyl}piperidin-3-yl)-2-oxo-1,2,4,5-tetrahydroimidazo[4,5,1-jk][1,4]benzodiazepine-6(7H)-carboxylate Using the compound obtained in <Example CB6>, the title compound was obtained by the same method as in <Example AS2>.

<Example CB8> tert-Butyl 1-(2,6-dioxo-1-{[2-(trimethylsilyl)ethoxy]methyl}piperidin-3-yl)-2-oxo-8-(piperazin-1-ylmethyl)-1,2,4,5-tetrahydroimidazo[4,5,1-jk][1,4]benzodiazepine-6(7H)-carboxylate Using the compound obtained in <Example CB7>, the title compound was obtained by the same method as in <Example AS4>.

<Example CB9> tert-Butyl 1-(2,6-dioxo-1-{[2-(trimethylsilyl)ethoxy]methyl}piperidin-3-yl)-8-[(4-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperazin-1-yl)methyl]-2-oxo-1,2,4,5-tetrahydroimidazo[4,5,1-jk][1,4]benzodiazepine-6(7H)-carboxylate Using the compounds obtained in <Example CB8> and <Example V5>, the title compound was obtained by the same method as in <Example BM9>.

<Example CB10> 3-{8-[(4-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperazin-1-yl)methyl]-6-methyl-2-oxo-4,5,6,7-tetrahydroimidazo[4,5,1-jk][1,4]benzodiazepin-1(2H)-yl}piperidine-2,6-dione tert-Butyl 1-(2,6-dioxo-1-{[2-(trimethylsilyl)ethoxy]methyl}piperidin-3-yl)-8-[(4-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperazin-1-yl)methyl]-2-oxo-1,2,4,5-tetrahydroimidazo[4,5,1-jk][1,4]benzodiazepine-6(7H)-carboxylate (0.256 g, 0.208 mmol) was dissolved in acetonitrile (2 mL), para-toluenesulfonic acid monohydrate (0.258 g, 1.36 mmol) was added, and the mixture was stirred at room temperature for 5 hr. To the reaction mixture was added para-toluenesulfonic acid monohydrate (0.045 g, 0.24 mmol), and the mixture was stirred at room temperature for 18 hr. To the reaction mixture was added para-toluenesulfonic acid monohydrate (0.083 g, 0.44 mmol), and the mixture was stirred at room temperature for 23 hr. To the reaction mixture was added saturated aqueous sodium hydrogen carbonate solution, and the mixture was extracted with ethyl acetate. The organic layer was dried over sodium sulfate and filtered, and the filtrate was concentrated under reduced pressure. The residue was dissolved in DCM (2 mL), acetic acid (0.120 mL, 2.10 mmol), sodium triacetoxyborohydride (0.240 g, 1.13 mmol), and 37% aqueous formaldehyde solution (0.100 mL, 1.34 mmol) were added, and the mixture was stirred at room temperature for 3.5 hr. To the reaction mixture was added saturated aqueous sodium hydrogen carbonate solution, and the mixture was extracted with DCM. The organic layer was dried over sodium sulfate and filtered, and the filtrate was concentrated under reduced pressure. The residue was dissolved in DCM (1 mL), trifluoroacetic acid (1.0 mL) was added, and the mixture was stirred at room temperature for 1.5 hr. To the reaction mixture was added saturated aqueous sodium hydrogen carbonate solution, and the mixture was extracted with ethyl acetate. The organic layer was dried over sodium sulfate and filtered, and the filtrate was concentrated under reduced pressure. The residue was dissolved in ethyl acetate (1 mL), N,N'-dimethylethylenediamine (0.023 mL, 0.21 mmol) was added, and the mixture was left standing at room temperature for 30 min. The reaction mixture was purified by silica gel column chromatography (DCM/methanol) to give the title compound (0.106 g, 0.105 mmol, yield 50%).

<Example CC1> N-[1-(2,6-Dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]-2-nitrobenzenesulfonamide 3-(7-Amino-2-oxo-5,6-dihydro-4H-imidazo[4,5,1-ij]quinolin-1(2H)-yl)-1-{[2-(trimethylsilyl)ethoxy]methyl}piperidine-2,6-dione (0.200 g, 0.464 mmol) was dissolved in pyridine (2 mL), 2-nitrobenzenesulfonyl chloride (CAS Registry Number: 1694-92-4) (0.134 g, 0.605 mmol) was added, and the mixture was stirred at room temperature for 4 hr. To the reaction mixture was added 20% aqueous citric acid solution, and the mixture was extracted with ethyl acetate. The organic layer was washed with saturated brine, dried over sodium sulfate and filtered, and the filtrate was concentrated under reduced pressure. The residue was purified by silica gel column chromatography (hexane/ethyl acetate) to give the title compound (0.301 g, 0.489 mmol, yield: quantitative).

<Example CC2> tert-Butyl (7-exo)-7-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino}-3-oxa-9-azabicyclo[3.3.1]nonane-9-carboxylate Using the compound obtained in <Example CC1> and tert-butyl (7-endo)-7-hydroxy-3-oxa-9-azabicyclo[3.3.1]nonane-9-carboxylate (CAS Registry Number: 1148006-31-8), the title compound was obtained by sequentially performing the same operations as in <Example AY4> and <Example AY5>.

<Example CC3> 3-[7-{[(7-Exo)-9-{[(4R)-2'-fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl}-3-oxa-9-azabicyclo[3.3.1]nonan-7-yl]amino}-2-oxo-5,6-dihydro-4H-imidazo[4,5,1-ij]quinolin-1(2H)-yl]piperidine-2,6-dione tert-Butyl (7-exo)-7-{[1-(2,6-dioxo-1-{[2-(trimethylsilyl)ethoxy]methyl}piperidin-3-yl)-2-oxo-1,2,5,6-tetrahydro-4H-imidazo[4,5,1-ij]quinolin-7-yl]amino)-3-oxa-9-azabicyclo[3.3.1]nonane-9-carboxylate (0.103 g, 0.157 mmol) was dissolved in DCM (1 mL), trifluoroacetic acid (1 mL) was added, and the mixture was stirred at room temperature for 1 hr. The reaction mixture was concentrated under reduced pressure, (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride (0.085 g, 0.13 mmol), HATU (0.073 g, 0.19 mmol), DMF (2 mL), and DIPEA (0.22 mL, 1.3 mmol) were added to the residue, and the mixture was stirred at room temperature for 16 hr. To the reaction mixture was added DIPEA (0.22 mL, 1.3 mmol), and the mixture was left standing at room temperature for 10 min. To the reaction mixture was added saturated aqueous sodium hydrogen carbonate solution, and the mixture was extracted with ethyl acetate. The organic layer was washed successively with water and saturated brine, dried over sodium sulfate and filtered, and the filtrate was concentrated under reduced pressure. The residue was dissolved in ethyl acetate (1 mL), N,N'-dimethylethylenediamine (0.015 mL, 0.14 mmol) was added, and the mixture was left standing at room temperature for 1 hr. The reaction mixture was purified by silica gel column chromatography (ethyl acetate/methanol) to give the title compound (0.081 g, 0.079 mmol, yield 61%).

<Example CD1> tert-Butyl 4-{[1-(2,6-dioxopiperidin-3-yl)-3-methyl-2-oxo-2,3-dihydro-1H-benzimidazol-4-yl]amino}piperidine-1-carboxylate Using 3-(4-amino-3-methyl-2-oxo-2,3-dihydro-1H-benzimidazol-1-yl)piperidine-2,6-dione (WO2021170109 A1), the title compound was obtained by the same method as in <Example BR1>.

<Example CD2> 3-{4-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-3-methyl-2-oxo-2,3-dihydro-1H-benzimidazol-1-yl}piperidine-2,6-dione To a solution of tert-butyl 4-{[1-(2,6-dioxopiperidin-3-yl)-3-methyl-2-oxo-2,3-dihydro-1H-benzimidazol-4-yl]amino}piperidine-1-carboxylate (143 mg, 0.312 mmol) in DCM (1 mL) was added trifluoroacetic acid (1 mL) at room temperature, and the mixture was stirred for 30 min. The reaction mixture was concentrated under reduced pressure, and the residue was diluted with DMF (3 mL). DIPEA (0.55 mL, 3.21 mmol), (4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-carboxylic acid monohydrochloride (200 mg, 0.312 mmol), and HATU (145 mg, 0.381 mmol) were added thereto, and the mixture was stirred at room temperature for 3 hr. To the reaction mixture was added saturated aqueous sodium hydrogen carbonate solution, and the mixture was extracted with ethyl acetate. The obtained organic layers were combined, washed with saturated brine, dried over sodium sulfate and filtered, and the filtrate was concentrated under reduced pressure. The residue was purified by silica gel column chromatography (ethyl acetate/methanol) to give the title compound (242 mg, 0.252 mmol, yield 81%).

<Example CE1> (3S)-3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione <Example CF1> (3R)-3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione The diastereomeric mixture of 3-{7-[(4-{[(4R)-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione (1.04 g, 1.07 mmol) was optically resolved by chiral HPLC [column: CHIRALPAK IF (registered trademark, Daicel Corporation), mobile phase: ethyl acetate/THF=90/10 (V/V)] to obtain S form as the component eluted first and R form as the component eluted later. The obtained solids were respectively washed with hexane/ethyl acetate and dried under reduced pressure at 60° C. to obtain S form <Example CE1> (306 mg, 0.316 mmol, yield 29%) and R form <Example CF1> (304 mg, 0.314 mmol, yield 29%).

Analysis conditions column: CHIRALPAK IF (registered trademark, Daicel Corporation), size: 0.46 cm×15 cm, flow rate: 1.0 mL/min, temperature: 40° C., mobile phase: ethyl acetate/THF=90/10 (V/V), retention time: S form <Example CE1> 6.2 min, R form <Example CF1> 8.5 min <Example CG1> <Example CH1> (3S) or (3R)-{7-[(1-{[(4R)-2'-Fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione The diastereomeric mixture of 3-{7-[(1-{[(4R)-2'-fluoro-4'-{[{2-[(4R)-4-(4-methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]carbonyl}piperidin-4-yl)amino]-2-oxo-5,6-dihydro-4H-imidazo[4,5,1-ij]quinolin-1(2H)-yl}piperidine-2,6-dione (0.103 g, 0.105 mmol) was optically resolved by chiral HPLC [column: CHIRALPAK IF (registered trademark, Daicel Corporation), mobile phase: ethyl acetate/THF=90/10 (V/V)] to obtain <Example CG1> (0.0400 g, 0.0406 mmol, yield: 39%) as the component eluted first and <Example CH1> (0.0407 g, 0.0413 mmol, yield: 40%) as the component eluted later.

Analysis conditions column: CHIRALPAK IF (registered trademark, Daicel Corporation), size: 0.46 cm×15 cm, flow rate: 1.0 mL/min, temperature: 40° C., mobile phase: ethyl acetate/THF=90/10 (V/V), retention time: <Example CG1> 6.7 min, <Example CH1> 10 min <Example CI1> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione monobenzenesulfonate The compound (300 mg) obtained in Example AW5 was dissolved in acetonitrile (3.0 mL), benzenesulfonic acid monohydrate (54.7 mg) was added at room temperature, and the mixture was stirred for 27 hr. The precipitated solid was collected by filtration, and dried at room temperature for 15 hr to give the title compound (278 mg) as crystals (elemental analysis Found; C: 63.54%, H: 6.90%, N: 7.25%, F: 4.83%, S: 2.68%).

$^1$H-NMR (DMSO-$D_6$) δ: 11.12 (1H, s), 9.32 (1H, br s), 7.61-7.57 (2H, m), 7.34-7.26 (5H, m), 7.19 (2H, d, J=9.2 Hz), 7.07 (2H, d, J=8.1 Hz), 7.02 (1H, d, J=8.1 Hz), 6.97 (1H, d, J=8.0 Hz), 6.81 (2H, d, J=8.8 Hz), 6.12 (1H, s), 5.40-5.35 (1H, m), 4.89-4.82 (0.4H, m), 4.57 (1H, br s), 3.84-3.75 (2H, m), 3.73-3.60 (5H, m), 3.59-3.52 (2.5H, m), 3.48-3.41 (3.5H, m), 3.21-2.97 (5H, m), 2.96-2.87 (1.5H, m), 2.81-2.60 (5.5H, m), 2.47-2.30 (7H, m), 2.27-2.19 (2H, m), 2.14-2.00 (7H, m), 2.00-1.92 (4H, m), 1.86-1.78 (2H, m), 1.77-1.70 (1.7H, m), 1.59-1.49 (3H, m), 1.47-1.34 (3.5H, m), 1.17 (3H, d, J=6.3 Hz), 1.15 (0.4H, s), 1.06 (3.7H, s), 0.86 (7H, s), 0.56 (4.3H, s);

MS (m/z): 968 $(M+H)^+$.

The obtained crystals were measured using a powder X-ray diffractometer (MiniFlex600-C, manufactured by Rigaku Corporation), and the results are shown in FIG. 1. In FIG. 1 showing the diffraction pattern of powder X-ray diffraction (CuKα, λ=1.54 angstroms, scanning speed=10°/min), the peaks characteristic of the present crystals are shown in Table 1.

TABLE 1

| Peak No. | 2θ | d value | relative intensity |
|---|---|---|---|
| 1 | 2.15 | 41.00 | 100 |
| 2 | 8.30 | 10.64 | 15 |
| 3 | 10.29 | 8.59 | 17 |
| 4 | 14.75 | 6.00 | 35 |
| 5 | 17.19 | 5.15 | 36 |
| 6 | 20.00 | 4.44 | 27 |
| 7 | 21.34 | 4.16 | 32 |
| 8 | 22.68 | 3.92 | 26 |
| 9 | 23.77 | 3.74 | 25 |
| 10 | 25.23 | 3.53 | 16 |

<Example CJ1> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[4,5,1-ij]quinolin-1(2H)-yl}piperidine-2,6-dione monoethanesulfonate The compound (300 mg) obtained in Example AWS was dissolved in acetonitrile (1.5 mL), ethanesulfonic acid (25.5 μL) was added at room temperature, and the mixture was stirred for 30 min. Successively, isopropyl acetate (0.60 mL) was added 5 times every 10 min at room temperature, and the mixture was stirred for 24 hr. The precipitated solid was collected by filtration and dried at room temperature for 15 hr to give the title compound (264 mg) as crystals (elemental analysis Found; C: 61.93%, H: 7.29%, N: 7.43%, F: 4.98%, S: 2.75%).

$^1$H-NMR (DMSO-$D_6$) δ: 11.12 (1H, s), 9.35 (1H, br s), 7.28 (2H, d, J=8.1 Hz), 7.19 (2H, d, J=8.8 Hz), 7.07 (2H, d, J=8.1 Hz), 7.02 (1H, d, J=8.1 Hz), 6.97 (1H, d, J=8.0 Hz), 6.81 (2H, d, J=8.9 Hz), 6.12 (1H, s), 5.41-5.35 (1H, m), 4.90-4.82 (0.4H, m), 4.57 (1H, br s), 3.84-3.75 (2.2H, m), 3.73-3.60 (5H, m), 3.59-3.52 (2.2H, m), 3.48-3.40 (3H, m), 3.20-3.11 (3H, m), 2.97-2.88 (1.5H, m), 2.78 (2H, s), 2.75-2.66 (1.5H, m), 2.66-2.63 (0.6H, m), 2.63-2.60 (1H, m), 2.47-2.44 (1.6H, m), 2.44-2.30 (9H, m), 2.26-2.20 (2H, m), 2.14-2.00 (8H, m), 2.00-1.93 (4H, m), 1.86-1.78 (2H, m), 1.77-1.70 (2H, m), 1.58-1.50 (3H, m), 1.47-1.33 (4H, m), 1.17 (3H, d, J=6.3 Hz), 1.15-1.13 (0.6H, m), 1.08-1.03 (7H, m), 0.86 (7H, s), 0.56 (4H, s);

MS (m/z): 968 $(M+H)^+$.

The obtained crystals were measured using a powder X-ray diffractometer (MiniFlex600-C, manufactured by Rigaku Corporation), and the results are shown in FIG. 2. In FIG. 2 showing the diffraction pattern of powder X-ray diffraction (CuKα, λ=1.54 angstroms, scanning speed=10°/min), the peaks characteristic of the present crystals are shown in Table 2.

TABLE 2

| Peak No. | 2θ | d value | relative intensity |
|---|---|---|---|
| 1 | 2.21 | 39.88 | 100 |
| 2 | 12.04 | 7.35 | 26 |
| 3 | 14.87 | 5.95 | 40 |
| 4 | 17.69 | 5.01 | 35 |
| 5 | 18.93 | 4.68 | 32 |
| 6 | 20.41 | 4.35 | 31 |
| 7 | 22.42 | 3.96 | 28 |
| 8 | 23.19 | 3.83 | 30 |
| 9 | 24.13 | 3.69 | 21 |
| 10 | 27.98 | 3.19 | 13 |

<Example CK1> 3-{7-[(1-{[(4R)-2'-Fluoro-4'-{[{2-[(4R)-4-(4-methoxyphenyl)-2,2-dimethyltetrahydro-2H-pyran-4-yl]ethyl)(3,3,3-trifluoro-2,2-dimethylpropyl)amino]methyl}-2,3,4,5-tetrahydro[biphenyl]-4-yl]carbonyl]piperidin-4-yl)amino]-2-oxo-5,6-dihydro-4H-imidazo[4,5,1-ij]quinolin-1(2H)-yl}piperidine-2,6-dione mono-10-camphorsulfonate The compound (300 mg) obtained in Example BK9 was dissolved in acetonitrile (6.0 mL), 10-camphorsulfonic acid solution (72.1 mg) was added at room temperature, and the mixture was stirred for 27 hr. The precipitated solid was collected by filtration, and dried at room temperature for 15 hr to give the title compound (352 mg) as crystals (elemental analysis Found; C: 62.46%, H: 7.15%, N: 7.15%, F: 6.19%, S: 2.68%).

$^1$H-NMR (DMSO-$D_6$) δ: 11.09 (1H, s), 10.51 (1H, br s), 7.35-7.26 (0.3H, m), 7.21-7.13 (3H, m), 6.93-6.87 (2.2H, m), 6.80 (2H, d, J=8.8 Hz), 5.94 (1H, s), 5.33 (1H, br s), 4.46 (1H, br s), 4.07 (1H, br s), 3.80-3.72 (1.5H, m), 3.70 (3H, s), 3.59-3.52 (2.5H, m), 3.46 (2H, s), 3.11 (1H, s), 2.97-2.87 (2.5H, m), 2.86 (0.6H, s), 2.84 (0.7H, s), 2.75-2.58 (4.7H, m), 2.41-2.28 (6H, m), 2.27-2.18 (3.2H, m), 2.13-2.03 (4.4H, m), 2.03-1.96 (2.3H, m), 1.95-1.90 (1.8H, m), 1.89-1.82 (2.3H, m), 1.82-1.80 (1H, m), 1.80-1.77 (1H, m), 1.77-1.70 (1H, m), 1.70-1.59 (1.2H, m), 1.57-1.49 (2.3H, m), 1.42-1.35 (1.5H, m), 1.30-1.22 (2.3H, m), 1.16-1.14 (0.4H, m), 1.05 (5.8H, d, J=6.5 Hz), 0.92-0.87 (5.4H, m), 0.74 (3H, s), 0.56 (3H, s);

MS (m/z): 986 $(M+H)^+$.

The obtained crystals were measured using a powder X-ray diffractometer (MiniFlex600-C, manufactured by Rigaku Corporation), and the results are shown in FIG. 3. In FIG. 3 showing the diffraction pattern of powder X-ray diffraction (CuKα, λ=1.54 angstroms, scanning speed=10°/min), the peaks characteristic of the present crystals are shown in Table 3.

TABLE 3

| Peak No. | 2θ | d value | relative intensity |
|---|---|---|---|
| 1 | 3.89 | 22.69 | 100 |
| 2 | 6.81 | 12.96 | 16 |
| 3 | 7.68 | 11.51 | 47 |
| 4 | 8.20 | 10.78 | 25 |
| 5 | 10.28 | 8.60 | 18 |

TABLE 3-continued

| Peak No. | 2θ | d value | relative intensity |
|---|---|---|---|
| 6 | 13.15 | 6.73 | 24 |
| 7 | 15.97 | 5.55 | 46 |
| 8 | 16.81 | 5.27 | 45 |
| 9 | 18.58 | 4.77 | 46 |
| 10 | 23.56 | 3.77 | 24 |

<Example CL1> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monoethanesulfonate The compound (3.0 g) obtained in Example BY7 was dissolved in acetonitrile (45.0 mL), a solution of ethanesulfonic acid in acetonitrile (0.21 mol/L; 15.0 mL) was added at 40° C. over 3 hr, and the mixture was stirred at 40° C. for 1 hr. Successively, and the mixture was stirred at room temperature for 20 hr. The precipitated solid was collected by filtration and dried at 40° C. for 18 hr to give the title compound (3.0 g) as crystals (elemental analysis Found; C: 61.97%, H: 7.00%, N: 9.02%, F: 5.34%, S: 2.89%).

$^1$H-NMR (DMSO-$D_6$) δ: 11.10 (1H, br s), 9.33 (1H, br s), 7.28 (2.5H, d, J=8.2 Hz), 7.19 (2.5H, d, J=8.8 Hz), 7.07 (2.5H, d, J=8.2 Hz), 6.89 (1H, d, J=8.2 Hz), 6.82 (2.5H, d, J=8.9 Hz), 6.52 (1H, d, J=8.3 Hz), 6.12 (1.1H, s), 6.05 (1H, s), 5.33-5.30 (1.1H, m), 4.15 (1.6H, br s), 3.90-3.79 (1.7H, m), 3.71 (3.1H, s), 3.62-3.49 (4H, m), 3.45 (4.1H, s), 3.41-3.36 (1.5H, m), 3.17-3.10 (4.1H, m), 2.94-2.88 (1.1H, m), 2.71-2.59 (2.3H, m), 2.48-2.44 (0.7H, m), 2.44-2.40 (1H, m), 2.40-2.30 (5H, m), 2.26-2.19 (0.5H, m), 2.15-2.07 (2.1H, m), 2.05-1.93 (2H, m), 1.86-1.78 (0.5H, m), 1.77-1.70 (0.5H, m), 1.57-1.50 (2H, m), 1.47-1.33 (2H, m), 1.15-1.14 (0.5H, m), 1.08-1.03 (6.5H, m), 0.86 (6.5H, s), 0.56 (6.5H, s);

MS (m/z): 969 $(M+H)^+$.

The obtained crystals were measured using a powder X-ray diffractometer (MiniFlex600-C, manufactured by Rigaku Corporation), and the results are shown in FIG. 4. In FIG. 4 showing the diffraction pattern of powder X-ray diffraction (CuKα, λ=1.54 angstroms, scanning speed=10°/min), the peaks characteristic of the present crystals are shown in Table 4.

TABLE 4

| Peak No. | 2θ | d value | relative intensity |
|---|---|---|---|
| 1 | 2.27 | 38.85 | 44 |
| 2 | 8.18 | 10.80 | 70 |
| 3 | 9.88 | 8.94 | 74 |
| 4 | 13.09 | 6.76 | 59 |
| 5 | 14.57 | 6.08 | 100 |
| 6 | 15.80 | 5.60 | 74 |
| 7 | 16.91 | 5.24 | 94 |
| 8 | 17.77 | 4.99 | 72 |
| 9 | 18.87 | 4.70 | 73 |
| 10 | 20.14 | 4.41 | 80 |

<Example CM1> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monosalicylate The compound (50 mg) obtained in Example BY7 was dissolved in acetonitrile (1.5 mL), and a solution of salicylic acid in acetonitrile (0.10 mol/L; 0.050 mL) was added, and the mixture was stirred at room temperature for 19 hr. Successively, a solution of salicylic acid in acetonitrile (0.10 mol/L; 0.45 mL) was added over 8 hr, and the mixture was stirred at room temperature for 14 hr. The precipitated solid was collected by filtration and dried at 40° C. to give the title compound (55 mg) as crystals (elemental analysis Found; C: 65.12%, H: 6.92%, N: 8.80%, F: 5.18%, S: 0.00%).

$^1$H-NMR (DMSO-$D_6$) δ: 11.09 (1H, s), 7.76-7.44 (1H, m), 7.44-7.37 (1H, m), 7.26 (2H, d, J=8.2 Hz), 7.19 (2H, d, J=8.9 Hz), 7.05 (2H, d, J=8.2 Hz), 6.89-6.79 (5H, m), 6.48 (1H, d, J=8.2 Hz), 6.11 (1H, br s), 5.94 (1H, br s), 5.33-5.28 (1H, m), 3.86-3.79 (2.4H, m), 3.70 (3.3H, s), 3.62-3.50 (5H, m), 3.46-3.40 (5H, m), 2.95-2.86 (1.3H, m), 2.71-2.59 (4.2H, m), 2.45-2.29 (7.4H, m), 2.26-2.19 (1.4H, m), 2.13-2.07 (2.2H, m), 2.06-1.99 (1.3H, m), 1.96-1.78 (4.5H, m), 1.77-1.70 (1.2H, m), 1.58-1.50 (2.2H, m), 1.41-1.30 (2.2H, m), 1.15 (0.4H, s), 1.06 (3H, s), 0.86 (6H, s), 0.56 (3H, s);

MS (m/z): 969 $(M+H)^+$.

The obtained crystals were measured using a powder X-ray diffractometer (MiniFlex600-C, manufactured by Rigaku Corporation), and the results are shown in FIG. 5. In FIG. 5 showing the diffraction pattern of powder X-ray diffraction (CuKα, λ=1.54 angstroms, scanning speed=10°/min), the peaks characteristic of the present crystals are shown in Table 5.

TABLE 5

| Peak No. | 2θ | d value | relative intensity |
|---|---|---|---|
| 1 | 2.20 | 40.15 | 100 |
| 2 | 4.34 | 20.37 | 53 |
| 3 | 9.45 | 9.35 | 45 |
| 4 | 10.97 | 8.06 | 45 |
| 5 | 13.23 | 6.69 | 39 |
| 6 | 16.98 | 5.22 | 79 |
| 7 | 18.09 | 4.90 | 75 |
| 8 | 20.20 | 4.39 | 70 |
| 9 | 21.32 | 4.16 | 67 |
| 10 | 25.19 | 3.53 | 44 |

<Example CN1> 3-{7-[(4-{[(4R)-4'-{[{2-[(4R)-4-(4-Methoxyphenyl)-2,2-dimethyltetrahydro-2H-pyran-4-yl]ethyl)(3,3,3-trifluoro-2,2-dimethylpropyl)amino]methyl)-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione monobenzenesulfonate The compound (50 mg) obtained in Example BY7 was dissolved in acetonitrile (1.5 mL), and a solution of benzenesulfonic acid monohydrate in acetonitrile (0.10 mol/L; 0.10 mL) was added, and the mixture was stirred at room temperature for 15 hr. Successively, a solution of benzenesulfonic acid monohydrate in acetonitrile (0.10 mol/L; 0.15 mL) was added over 4 hr, and the mixture was stirred at room temperature for 3 hr. Furthermore, a solution of benzenesulfonic acid monohydrate in acetonitrile (0.10 mol/L; 0.25 mL) was added at 40° C. over 2 hr, and the mixture was stirred at room temperature for 15 hr. The precipitated solid was collected by filtration and dried at 40° C. to give the title compound (51 mg) as crystals (elemental analysis Found; C: 62.46%, H: 6.75%, N: 8.53%, F: 4.99%, S: 2.74%).

$^1$H-NMR (DMSO-$D_6$) δ: 11.10 (1H, s), 9.31 (1H, br s), 7.62-7.57 (2H, m), 7.34-7.25 (5H, m), 7.19 (2H, d, J=8.8 Hz), 7.07 (2H, d, J=8.2 Hz), 6.89 (1H, d, J=8.2 Hz), 6.82 (2H, d, J=8.9 Hz), 6.52 (1H, d, J=8.3 Hz), 6.12 (1H, s), 6.05 (1H, s), 5.35-5.28 (1H, m), 4.15 (2H, br s), 3.89-3.80 (2H, m), 3.71 (3H, s), 3.60-3.50 (4H, m), 3.49-3.41 (4H, m), 3.19-3.06 (4H, m), 2.96-2.86 (1H, m), 2.71-2.58 (3H, m), 2.46 (1H, s), 2.44-2.29 (6H, m), 2.27-2.19 (1H, m), 2.15-2.07 (3H, m), 2.06-1.93 (3H, m), 1.86-1.78 (1H, m), 1.77-1.70 (1H, m), 1.58-1.50 (2H, m), 1.47-1.34 (2H, m), 1.06 (3H, s), 0.86 (6H, s), 0.56 (3H, s);

MS (m/z): 969 $(M+H)^+$.

The obtained crystals were measured using a powder X-ray diffractometer (MiniFlex600-C, manufactured by Rigaku Corporation), and the results are shown in FIG. 6. In FIG. 6 showing the diffraction pattern of powder X-ray diffraction (CuKα, λ=1.54 angstroms, scanning speed=10°/min), the peaks characteristic of the present crystals are shown in Table 6.

TABLE 6

| Peak No. | 2θ | d value | relative intensity |
|---|---|---|---|
| 1 | 2.19 | 40.35 | 100 |
| 2 | 8.87 | 9.97 | 10 |
| 3 | 10.86 | 8.14 | 17 |
| 4 | 12.55 | 7.05 | 13 |
| 5 | 13.05 | 6.78 | 13 |
| 6 | 14.99 | 5.91 | 13 |
| 7 | 17.84 | 4.97 | 21 |
| 8 | 20.62 | 4.30 | 12 |
| 9 | 21.43 | 4.14 | 13 |
| 10 | 25.27 | 3.52 | 10 |

<Example CO1> 3-{7-[(4-{[(4R)-4'-{[{2-[(4R)-4-(4-Methoxyphenyl)-2,2-dimethyltetrahydro-2H-pyran-4-yl]ethyl}(3,3,3-trifluoro-2,2-dimethylpropyl)amino]methyl}-2,3,4,5-tetrahydro[biphenyl]-4-yl]methyl}piperazin-1-yl)carbonyl]-2-oxo-5,6-dihydro-4H-imidazo[1,5,4-de]quinoxalin-1(2H)-yl}piperidine-2,6-dione mono-10-camphorsulfonate The compound (50 mg) obtained in Example BY7 was dissolved in acetonitrile (1.5 mL), and a solution of 10-camphorsulfonic acid in acetonitrile (0.10 mol/L; 0.10 mL) was added, and the mixture was stirred at room temperature for 18 hr. Successively, a solution of 10-camphorsulfonic acid in acetonitrile (0.10 mol/L; 0.40 mL) was added at 40° C. over 8 hr, and the mixture was stirred at room temperature for 17 hr. The precipitated solid was collected by filtration, and dried at 40° C. to give the title compound (59 mg) as crystals (elemental analysis Found; C: 63.38%, H: 7.06%, N: 8.09%, F: 4.78%, S: 2.62%).

$^1$H-NMR (DMSO-$D_6$) δ: 11.10 (1H, s), 9.31 (1H, br s), 7.28 (2H, d, J=8.2 Hz), 7.14 (2H, d, J=8.8 Hz), 7.07 (2H, d, J=8.2 Hz), 6.89 (1H, d, J=8.2 Hz), 6.82 (2H, d, J=8.9 Hz), 6.52 (1H, d, J=8.2 Hz), 6.12 (1H, s), 6.05 (0.5H, s), 5.35-5.30 (1H, m), 4.15 (2H, br s), 3.88-3.80 (2H, m), 3.71 (3H, s), 3.61-3.51 (4H, m), 3.48-3.41 (4H, m), 3.18-3.07 (4.7H, m), 2.95-2.87 (1.5H, m), 2.86 (0.5H, s), 2.83 (0.5H, s), 2.74-2.59 (4.5H, m), 2.44-2.30 (9H, m), 2.26-2.20 (3H, m), 2.14-2.08 (4H, m), 2.05-2.00 (2H, m), 2.00-1.94 (3H, m), 1.93 (1.5H, d, J=4.6 Hz), 1.88-1.78 (4.5H, m), 1.77 (0.8H, s), 1.77-1.70 (2.3H, m), 1.58-1.50 (3.7H, m), 1.47-1.34 (5H, m), 1.29-1.23 (3.6H, m), 1.16-1.13 (1H, m), 1.06 (7H, d, J=7.4 Hz), 0.86 (7H, s), 0.74 (4H, s), 0.56 (3H, s);

MS (m/z): 969 $(M+H)^+$.

The obtained crystals were measured using a powder X-ray diffractometer (MiniFlex600-C, manufactured by Rigaku Corporation), and the results are shown in FIG. 7. In FIG. 7 showing the diffraction pattern of powder X-ray diffraction (CuKα, λ=1.54 angstroms, scanning speed=10°/min), the peaks characteristic of the present crystals are shown in Table 7.

TABLE 7

| Peak No. | 2θ | d value | relative intensity |
|---|---|---|---|
| 1 | 2.20 | 40.08 | 71 |
| 2 | 7.82 | 11.29 | 43 |
| 3 | 11.05 | 8.00 | 45 |
| 4 | 12.42 | 7.12 | 89 |
| 5 | 13.34 | 6.63 | 61 |
| 6 | 15.23 | 5.81 | 77 |
| 7 | 16.49 | 5.37 | 100 |
| 8 | 17.86 | 4.96 | 55 |
| 9 | 20.15 | 4.40 | 57 |
| 10 | 24.36 | 3.65 | 44 |

The physicochemical data of the compounds described in the Examples are shown below in Table 8 to Table 57.

In the Tables, Ex indicates the Example number, and Data indicates the physicochemical data.

Other abbreviations used in the text have the following meanings:

Boc: tert-butoxycarbonyl group tBu: tert-butyl group

TABLE 8

| Ex | Data |
|---|---|
| A1 | $^1$H-NMR ($CDCl_3$) δ: 1.24 (3H, s), 1.27 (3H, s), 1.32-1.38 (3H, m), 2.66 (1H, s), 2.72 (1H, t, J = 5.8 Hz), 3.05 (1H, s), 3.12 (1H, t, J = 5.8 Hz), 3.83 (1H, t, J = 5.8 Hz), 3.91 (1H, t, J = 5.8 Hz), 4.24-4.32 (2H, m). MS m/z: 224 $(M + H)^+$. |
| A2 | $^1$H-NMR ($CDCl_3$) δ: 0.66 (1.5H, s), 0.71 (1.5H, s), 1.00-1.05 (3H, m), 1.25 (1.5H, s), 1.27 (1.5H, s), 1.87 (0.5H, d, J = 14.0 Hz), 1.92-2.00 (0.5H, m), 2.03-2.12 (1H, m), 2.38-2.43 (0.5H, m), 2.54-2.60 (0.5H, m), 2.61-2.73 (1H, m), 3.51 (0.5H, s), 3.52 (0.5H, s), 3.64-3.74 (1H, m), 3.76-3.86 (1H, m), 3.89-4.00 (2H, m), 7.26-7.32 (1H, m), 7.34-7.41 (3H, m). MS m/z: 336 $(M + H)^+$. |
| A3 | $^1$H-NMR ($CDCl_3$) δ: 0.67 (3H, s), 1.19 (3H, s), 1.53-1.76 (4H, m), 2.10-2.18 (2H, m), 2.25-2.32 (1H, m), 2.45-2.54 (1H, m), 3.74-3.79 (2H, m), 7.21-7.25 (2H, m), 7.28-7.32 (2H, m). MS m/z: 268 $(M + H)^+$. |

TABLE 8-continued

| Ex | Data |
|---|---|
| A4 | $^1$H-NMR ($CDCl_3$) δ: 1.27 (3H, t, J = 7.0 Hz), 1.47-1.70 (4H, m), 2.06-2.15 (2H, m), 2.16-2.24 (2H, m), 2.33-2.42 (1H, m), 4.12-4.19 (2H, m), 4.30-4.38 (1H, m), 6.95-7.01 (2H, m), 7.80-7.85 (2H, m), 9.87 (1H, s). |
| A5 | $^1$H-NMR ($CDCl_3$) δ: 0.66 (3H, s), 1.19 (3H, s), 1.26 (3H, t, J = 7.3 Hz), 1.39-1.71 (7H, m), 1.74-1.84 (1H, m), 2.02-2.21 (6H, m), 2.24-2.47 (3H, m), 3.50 (2H, s), 3.73-3.77 (2H, m), 4.10-4.21 (3H, m), 6.79 (2H, d, J = 8.5 Hz), 7.05 (2H, d, J = 8.5 Hz), 7.22 (2H, d, J = 8.5 Hz), 7.29 (2H, d, J = 8.5 Hz). MS m/z: 528 $(M + H)^+$. |
| A6 | $^1$H-NMR ($CDCl_3$) δ: 0.64 (3H, s), 1.17-1.21 (9H, m), 1.17 (3H, s), 1.43-1.78 (8H, m), 2.04-2.24 (6H, m), 2.38-2.47 (1H, m), 2.47-2.60 (1H, m), 3.02-3.17 (1H, m), 3.64-3.73 (2H, m), 4.15-4.26 (2H, m), 4.45 (1H, d, J = 14.6 Hz), 6.77 (2H, d, J = 8.5 Hz), 6.82 (2H, d, J = 8.5 Hz), 7.14 (2H, d, J = 8.5 Hz), 7.25 (2H, d, J = 8.5 Hz). MS m/z: 584 $(M + H)^+$. |
| B1 | $^1$H-NMR ($CDCl_3$) δ: 0.65-0.73 (3H, m), 0.93-1.00 (3H, m), 1.26-1.29 (3H, m), 1.93-2.18 (2H, m), 2.39-2.75 (2H, m), 3.61-3.55 (1H, m), 3.65-3.96 (4H, m), 7.21-7.27 (2H, m), 7.39 (1H, d, J = 8.5 Hz), 7.49 (1H, d, J = 8.5 Hz). |
| B2 | $^1$H-NMR ($CDCl_3$) δ: 0.67 (3H, s), 1.20 (3H, s), 1.47-1.79 (4H, m), 2.08-2.18 (2H, m), 2.27-2.34 (1H, m), 2.46-2.55 (1H, m), 3.75-3.80 (2H, m), 7.15-7.20 (2H, m), 7.31 (2H, d, J = 8.5 Hz). MS m/z: 318 $(M + H)^+$. |
| B3 | $^1$H-NMR ($CDCl_3$) δ: 0.66 (3H, s), 1.19 (3H, s), 1.26 (3H, t, J = 7.3 Hz), 1.40-1.73 (7H, m), 1.75-1.84 (1H, m), 2.03-2.21 (6H, m), 2.26-2.47 (3H, m), 3.51 (2H, s), 3.74-3.78 (2H, m), 4.10-4.20 (3H, m), 6.79 (2H, d, J = 8.5 Hz), 7.05 (2H, d, J = 8.5 Hz), 7.16 (2H, d, J = 8.5 Hz), 7.30 (2H, d, J = 8.5 Hz). MS m/z: 578 $(M +H)^+$. |

TABLE 9

| Ex | Data |
|---|---|
| B4 | $^1$H-NMR ($CDCl_3$) δ: 0.63 (3H, s), 1.12-1.19 (9H, m), 1.17 (3H, s), 1.27 (3H, t, J = 7.3 Hz), 1.40-1.81 (8H, m), 2.02-2.22 (6H, m), 2.30-2.40 (1H, m), 2.47-2.65 (1H, m), 3.02-3.13 (1H, m), 3.67-3.73 (2H, m), 4.09-4.21 (3H, m), 4.29 (1H, d, J = 15.3 Hz), 4.40 (1H, d, J = 15.3 Hz), 6.76 (2H, d, J = 8.5 Hz), 6.85 (2H, d, J = 8.5 Hz), 7.11-7.15 (2H, m), 7.21-7.25 (2H, m). MS m/z: 662 $(M + H)^+$. |
| B5 | $^1$H-NMR ($CDCl_3$) δ: 0.64 (3H, s), 1.12-1.20 (9H, m), 1.17 (3H, s), 1.43-1.83 (8H, m), 2.03-2.23 (6H, m), 2.38-2.47 (1H, m), 2.48-2.64 (1H, m), 3.02-3.15 (1H, m), 3.66-3.75 (2H, m), 4.13-4.22 (1H, m), 4.29 (1H, d, J = 15.3 Hz), 4.40 (1H, d, J = 15.3 Hz), 6.76 (2H, d, J = 8.5 Hz), 6.86 (2H, d, J = 8.5 Hz), 7.11-7.16 (2H, m), 7.21-7.26 (2H, m). MS m/z: 634 $(M + H)^+$. |
| C1 | $^1$H-NMR ($CDCl_3$) δ: 1.23-1.30 (4H, m), 1.37-1.65 (5H, m), 1.67-1.77 (2H, m), 1.82-1.94 (1H, m), 2.24 (2H, d, J = 6.7 Hz), 3.95-4.02 (1H, m), 4.13 (2H, q, J = 7.1 Hz). |
| C2 | $^1$H-NMR ($CDCl_3$) δ: 1.10-1.23 (2H, m), 1.27 (3H, t, J = 7.0 Hz), 1.53-1.69 (2H, m), 1.85-1.98 (3H, m), 2.14-2.22 (2H, m), 2.25 (2H, d, J = 6.7 Hz), 4.15 (2H, q, J = 7.3 Hz), 4.28-4.38 (1H, m), 7.03 (1H, d, J = 8.5 Hz), 7.73 (1H, dd, J = 8.5, 1.8 Hz), 7.90 (1H, d, J = 1.8 Hz), 9.84 (1H, s). MS m/z: 325 $(M + H)^+$. |
| C3 | $^1$H-NMR ($CDCl_3$) δ: 0.65-0.72 (3H, m), 1.02 (3H, t, J = 7.3 Hz), 1.24-1.27 (3H, m), 1.80-2.10 (2H, m), 2.37-2.74 (2H, m), 3.48-3.52 (1H, m), 3.67-3.85 (2H, m), 3.81 (3H, s), 3.89-3.98 (2H, m), 6.87-6.92 (2H, m), 7.24 (1H, d, J = 8.5 Hz), 7.34 (1H, d, J = 8.5 Hz). MS m/z: 332 $(M + H)^+$. |
| C4 | $^1$H-NMR ($CDCl_3$) δ: 0.72 (3H, s), 1.23 (3H, s), 1.73-1.84 (2H, m), 2.27-2.32 (1H, m), 2.38-2.53 (3H, m), 3.76-3.84 (5H, m), 6.89-6.94 (2H, m), 7.27-7.31 (2H, m). MS m/z: 260 $(M + H)^+$. |
| C5 | $^1$H-NMR ($CDCl_3$) δ: 0.67 (3H, s), 1.19 (3H, s), 1.49-1.76 (4H, m), 2.10-2.22 (2H, m), 2.27-2.34 (1H, m), 2.46-2.55 (1H, m), 3.72-3.84 (2H, m), 3.81 (3H, s), 6.86 (2H, d, J = 8.5 Hz), 7.20 (2H, d, J = 8.5 Hz). MS m/z: 264 $(M + H)^+$. |
| C6 | $^1$H-NMR ($CDCl_3$) δ: 0.67 (3H, s), 1.01-1.22 (5H, m), 1.26 (3H, t, J = 7.0 Hz), 1.40-2.50 (17H, m), 3.46 (2H, s), 3.74-3.80 (2H, m), 3.81 (3H, s), 4.03-4.18 (3H, m), 6.82-6.88 (3H, m), 6.92-6.98 (1H, m), 7.15-7.21 (3H, m). MS m/z: 572 $(M + H)^+$. |
| C7 | $^1$H-NMR ($CDCl_3$) δ: 0.65 (3H, s), 1.05-1.21 (14H, m), 1.27 (3H, t, J = 7.3 Hz), 1.48-2.25 (14H, m), 2.54-2.70 (1H, m), 3.11-3.22 (1H, m), 3.67-3.77 (2H, m), 3.81 (3H, s), 4.05-4.21 (4H, m), 4.36-4.43 (1H, m), 4.58-4.62 (1H, m), 6.74-6.86 (4H, m), 6.91-6.96 (1H, m), 7.09-7.20 (2H, m). MS m/z: 656 $(M + H)^+$. |

TABLE 10

| Ex | Data |
|---|---|
| C8 | $^1$H-NMR ($CDCl_3$) δ: 0.65 (3H, s), 1.07-1.22 (14H, m), 1.42-2.23 (13H, m), 2.29 (2H, d, J = 6.7 Hz), 2.56-2.69 (1H, m), 3.11-3.21 (1H, m), 3.70-3.77 (2H, m), 3.81 (3H, s), 4.06-4.13 (1H, m), 4.17 (1H, d, J = 15.2 Hz), 4.39 (1H, d, J = 15.8 Hz), 6.76-6.86 (4H, m), 6.92-6.94 (1H, m), 7.10-7.16 (2H, m). MS m/z: 628 $(M + H)^+$. |
| D1 | $^1$H-NMR ($CDCl_3$) δ: 0.67 (3H, s), 1.18 (3H, s), 1.26 (3H, t, J = 7.3 Hz), 1.40-1.68 (7H, m), 1.74-1.83 (1H, m), 2.02-2.20 (6H, m), 2.27-2.37 (2H, m), 2.41-2.49 (1H, m), 3.49 (2H, s), 3.71-3.80 (2H, m), 3.81 (3H, s), 4.09-4.19 (3H, m), 6.79 (2H, |

TABLE 10-continued

| Ex | Data |
|---|---|
| | d, J = 8.5 Hz), 6.85 (2H, d, J = 8.5 Hz), 7.06 (2H, d, J = 8.5 Hz), 7.19 (2H, d, J = 8.5 Hz). MS m/z: 524 $(M + H)^+$. |
| D2 | $^1$H-NMR ($CDCl_3$) δ: 0.65 (3H, s), 1.12-1.18 (12H, m), 1.23-1.30 (3H, m), 1.41-1.80 (12H, m), 2.02-2.23 (5H, m), 2.29-2.39 (1H, m), 2.53-2.71 (1H, m), 3.03-3.17 (1H, m), 3.67-3.78 (2H, m), 3.81 (3H, s), 4.27 (1H, d, J = 15.9 Hz), 4.40 (1H, d, J = 15.9 Hz), 6.75 (2H, d, J = 8.5 Hz), 6.80-6.88 (4H, m), 7.12 (2H, d, J = 8.5 Hz). MS m/z: 608 $(M + H)^+$. |
| D3 | $^1$H-NMR ($CDCl_3$) δ: 0.65 (3H, s), 1.10-1.19 (12H, m), 1.42-1.80 (8H, m), 2.04-2.23 (6H, m), 2.37-2.47 (1H, m), 2.52-2.74 (1H, m), 3.03-3.16 (1H, m), 3.67-3.78 (2H, m), 3.81 (3H, s), 4.13-4.22 (1H, m), 4.27 (1H, d, J = 15.3 Hz), 4.40 (1H, d, J = 15.3 Hz), 6.75 (2H, d, J = 8.5 Hz), 6.80-6.88 (4H, m), 7.12 (2H, d, J = 8.5 Hz). MS m/z: 580 $(M + H)^+$. |
| E1 | $^1$H-NMR ($CDCl_3$) δ: 0.65 (3H, s), 1.15 (9H, br s), 1.16 (3H, s), 1.27 (3H, t, J = 7.3 Hz), 1.41-1.80 (8H, m), 2.02-2.23 (6H, m), 2.34 (1H, tt, J = 11.3, 3.8 Hz), 2.53-2.74 (1H, m), 3.03-3.16 (1H, m), 3.65-3.78 (2H, m), 3.81 (3H, s), 4.11-4.20 (1H, m), 4.14 (2H, q, J = 7.3 Hz), 4.27 (1H, d, J = 15.3 Hz), 4.40 (1H, d, J = 15.3 Hz), 6.75 (2H, d, J = 8.5 Hz), 6.82 (2H, d, J = 8.5 Hz), 6.85 (2H, d, J = 8.5 Hz), 7.12 (2H, d, J = 8.5 Hz). MS m/z: 608 $(M + H)^+$. |
| E2 | $^1$H-NMR ($CDCl_3$) δ: 0.65 (3H, s), 1.08-1.20 (12H, m), 1.40-1.79 (8H, m), 2.03-2.24 (6H, m), 2.38-2.47 (1H, m), 2.56-2.69 (1H, m), 3.05-3.15 (1H, m), 3.68-3.77 (2H, m), 3.81 (3H, s), 4.11-4.21 (1H, m), 4.27 (1H, d, J = 15.3 Hz), 4.40 (1H, d, J = 15.3 Hz), 6.75 (2H, d, J = 8.5 Hz), 6.80-6.88 (4H, m), 7.12 (2H, d, J = 8.5 Hz). MS m/z: 580 $(M + H)^+$. |
| F1 | $^1$H-NMR ($CDCl_3$) δ: 0.66 (3H, s), 1.06-1.27 (12H, m), 1.42-2.23 (14H, m), 2.37-2.48 (1H, m), 2.58-2.73 (1H, m), 3.02-3.15 (1H, m), 3.66-3.77 (2H, m), 4.13-4.22 (1H, m), 4.30 (1H, d, J = 15.3 Hz), 4.42 (1H, d, J = 15.3 Hz), 6.73-6.80 (4H, m), 6.87 (2H, d, J = 8.5 Hz), 7.07 (2H, d, J = 8.5 Hz). MS m/z: 566 $(M + H)^+$. |

TABLE 11

| Ex | Data |
|---|---|
| F2 | $^1$H-NMR ($CDCl_3$) δ: 0.65 (3H, s), 1.13-1.18 (12H, m), 1.27 (3H, t, J = 7.3 Hz), 1.40-1.68 (7H, m), 1.69-1.80 (1H, m), 2.02-2.21 (6H, m), 2.30-2.39 (1H, m), 2.58-2.73 (1H, m), 3.01-3.14 (1H, m), 3.67-3.77 (2H, m), 4.09-4.21 (3H, m), 4.30 (1H, d, J = 15.3 Hz), 4.41 (1H, d, J = 15.3 Hz), 5.08 (1H, s), 6.73-6.79 (4H, m), 6.87 (2H, d, J = 8.5 Hz), 7.07 (2H, d, J = 8.5 Hz). MS m/z: 594 $(M + H)^+$. |
| F3 | $^1$H-NMR ($CDCl_3$) δ: 0.66 (3H, s), 1.07-1.18 (9H, m), 1.16 (3H, s), 1.26 (3H, t, J = 7.3 Hz), 1.32-1.36 (6H, m), 1.40-1.79 (8H, m), 2.04-2.22 (6H, m), 2.29-2.40 (1H, m), 2.57-2.75 (1H, m), 3.03-3.16 (1H, m), 3.66-3.79 (2H, m), 4.10-4.20 (3H, m), 4.28 (1H, d, J = 15.3 Hz), 4.38 (1H, d, J = 15.3 Hz), 4.48-4.58 (1H, m), 6.75 (2H, d, J = 8.5 Hz), 6.81 (2H, d, J = 8.5 Hz), 6.86 (2H, d, J = 8.5 Hz), 7.10 (2H, d, J = 8.5 Hz). MS m/z: 636 $(M + H)^+$. |
| F4 | $^1$H-NMR ($CDCl_3$) δ: 0.66 (3H, s), 1.07-1.18 (9H, m), 1.16 (3H, s), 1.34 (6H, d, J = 6.1 Hz), 1.42-1.82 (8H, m), 2.04-2.23 (6H, m), 2.37-2.46 (1H, m), 2.58-2.76 (1H, m), 3.05-3.16 (1H, m), 3.67-3.78 (2H, m), 4.12-4.21 (1H, m), 4.28 (1H, d, J = 15.3 Hz), 4.39 (1H, d, J = 15.3 Hz), 4.47-4.58 (1H, m), 6.76 (2H, d, J = 8.5 Hz), 6.81 (2H, d, J = 8.5 Hz), 6.88 (2H, d, J = 8.5 Hz), 7.10 (2H, d, J = 8.5 Hz). MS m/z: 608 $(M + H)^+$. |
| G1 | $^1$H-NMR ($CDCl_3$) δ: 0.62 (3H, s), 1.13-1.20 (12H, m), 1.27 (3H, t, J = 7.3 Hz), 1.41-1.80 (8H, m), 2.00-2.21 (6H, m), 2.30-2.40 (1H, m), 2.49-2.61 (1H, m), 3.00-3.12 (1H, m), 3.63-3.77 (2H, m), 4.09-4.22 (3H, m), 4.36 (2H, s), 6.78 (2H, d, J = 8.5 Hz), 6.88 (2H, d, J = 8.5 Hz), 7.20 (2H, d, J = 8.5 Hz), 7.29 (2H, d, J = 8.5 Hz). MS m/z: 726 $(M + H)^+$. |
| G2 | $^1$H-NMR ($CDCl_3$) δ: 0.70 (3H, s), 1.13-1.20 (12H, m), 1.27 (3H, t, J = 7.3 Hz), 1.40-1.80 (8H, m), 1.99-2.21 (10H, m), 2.30-2.39 (1H, m), 2.64-2.78 (1H, m), 3.07-3.19 (1H, m), 3.24-3.31 (4H, m), 3.65-3.81 (2H, m), 4.09-4.18 (3H, m), 4.21 (1H, d, J = 15.3 Hz), 4.41 (1H, d, J = 15.3 Hz), 6.49 (2H, d, J = 8.5 Hz), 6.72 (2H, d, J = 8.5 Hz), 6.85 (2H, d, J = 8.5 Hz), 7.04 (2H, d, J = 8.5 Hz), MS m/z: 647 $(M + H)^+$. |
| G3 | $^1$H-NMR ($CDCl_3$) δ: 0.70 (3H, s), 1.10-1.20 (12H, m), 1.42-1.81 (8H, m), 1.99-2.22 (10H, m), 2.36-2.45 (1H, m), 2.62-2.80 (1H, m), 3.06-3.20 (1H, m), 3.25-3.32 (4H, m), 3.66-3.81 (2H, m), 4.11-4.26 (2H, m), 4.41 (1H, d, J = 15.3 Hz), 6.49 (2H, d, J = 8.5 Hz), 6.72 (2H, d, J = 8.5 Hz), 6.85 (2H, d, J = 8.5 Hz), 7.04 (2H, d, J = 8.5 Hz). MS m/z: 619 $(M + H)^+$. |

TABLE 12

| Ex | Data |
|---|---|
| H1 | $^1$H-NMR ($CDCl_3$) δ: 0.65 (3H, s), 1.08-1.26 (12H, m), 1.42-1.80 (8H, m), 2.00-2.28 (7H, m), 2.57-2.69 (1H, m), 2.96 (6H, s), 3.05-3.16 (1H, m), 3.68-3.75 (2H, m), 3.81 (3H, s), 4.13-4.20 (1H, m), 4.23-4.30 (1H, m), 4.37-4.44 (1H, m), 6.72-6.76 (2H, m), 6.80-6.89 (4H, m), 7.10-7.15 (2H, m), 7.98-8.03 (1H, m). MS m/z: 686 $(M + H)^+$. |
| I1 | $^1$H-NMR ($CDCl_3$) δ: 0.69 (3H, s), 1.16 (3H, s), 1.26 (3H, t, J = 7.0 Hz), 1.39-1.81 (8H, m), 2.00-2.11 (3H, m), 2.12-2.20 (2H, m), 2.24-2.37 (2H, m), 2.71-2.81 (1H, m), 3.20-3.31 (1H, m), 3.70-3.85 (2H, m), 3.84 (3H, s), 4.09-4.18 (1H, m), 4.13 (2H, q, J = 7.0 Hz), 4.48 (2H, s), 5.98 (1H, d, J = 8.5 Hz), 6.46 (1H, dd, J = 6.7, 4.9 Hz), 6.75 (2H, d, J = 8.5 Hz), 6.89 (2H, d, J = 8.5 Hz), 6.97 (2H, d, J = 8.5 Hz), 7.20 (2H, d, J = 8.5 Hz), 7.24-7.29 (1H, m), 8.08 (1H, dd, J = 4.9, 1.8 Hz). MS m/z: 601 $(M + H)^+$. |
| I2 | $^1$H-NMR ($CDCl_3$) δ: 0.69 (3H, s), 1.16 (3H, s), 1.39-1.81 (8H, m), 2.02-2.22 (5H, m), 2.22-2.33 (1H, m), 2.34-2.44 (1H, m), 2.70-2.82 (1H, m), 3.19-3.30 (1H, m), 3.72-3.87 (5H, m), 4.10-4.20 (1H, m), 4.49 (2H, s), 5.98 (1H, d, J = 8.5 Hz), 6.42-6.50 (1H, m), 6.75 (2H, d, J = 7.9 Hz), 6.89 (2H, d, J = 7.9 Hz), 6.97 (2H, d, J = 7.9 Hz), 7.18-7.31 (3H, m), 8.07-8.11 (1H, m). MS m/z: 573 $(M + H)^+$. |
| J1 | $^1$H-NMR ($CDCl_3$) δ: 1.21 (6H, s), 2.87 (2H, s), 3.68 (3H, s), 6.98 (2H, d, J = 8.6 Hz), 7.04 (2H, d, J = 8.6 Hz), 7.14 (2H, d, J = 8.6 Hz), 7.84 (2H, d, J = 8.6 Hz), 9.92 (1H, s). |
| J2 | $^1$H-NMR ($CDCl_3$) δ: 0.68 (3H, s), 1.18 (9H, s), 1.58-1.67 (3H, m), 1.78-1.81 (1H, m), 2.13-2.16 (2H, m), 2.29-2.32 (1H, m), 2.45-2.47 (1H, m), 2.82 (2H, s), 3.54 (2H, s), 3.66 (3H, s), 3.73-3.83 (5H, m), 6.84-6.91 (6H, m), 7.04 (2H, d, J = 8.6 Hz), 7.11 (2H, d, J = 8.6 Hz), 7.20 (2H, d, J = 8.6 Hz). |
| J3 | $^1$H-NMR ($CDCl_3$) δ: 0.66 (3H, s), 1.11-1.21 (18H, m), 1.53-1.79 (4H, m), 2.07-2.23 (2H, m), 2.57-2.70 (1H, m), 2.84 (2H, s), 3.09-3.22 (1H, m), 3.67 (3H, s), 3.69-3.76 (2H, m), 3.77 (3H, s), 4.28 (1H, d, J = 15.3 Hz), 4.46 (1H, d, J = 15.3 Hz), 6.80-6.92 (8H, m), 7.06 (2H, d, J = 8.6 Hz), 7.13 (2H, d, J = 8.6 Hz). |
| J4 | $^1$H-NMR ($CDCl_3$) δ: 0.65 (3H, s), 1.10-1.33 (18H, m), 1.51-1.67 (3H, m), 1.71-1.80 (1H, m), 2.06-2.21 (2H, m), 2.58-2.72 (1H, m), 2.87 (2H, s), 3.06-3.15 (1H, m), 3.70-3.75 (2H, m), 3.77 (3H, s), 4.27 (1H, d, J = 15.3 Hz), 4.48 (1H, d, J = 15.3 Hz), 6.79-6.94 (8H, m), 7.11-7.15 (4H, m). MS m/z: 630 $(M + H)^+$. |
| K1 | $^1$H-NMR ($CDCl_3$) δ: 1.20-1.25 (1H, m), 1.37-1.63 (5H, m), 1.66-1.75 (2H, m), 1.83-1.97 (1H, m), 2.31 (2H, d, J = 7.3 Hz), 3.94-4.02 (1H, m), 5.12 (2H, s), 7.29-7.41 (5H, m). |

TABLE 13

| Ex | Data |
|---|---|
| K2 | $^1$H-NMR ($CDCl_3$) δ: 1.09-1.23 (2H, m), 1.44-1.57 (2H, m), 1.82-1.97 (3H, m), 2.10-2.20 (2H, m), 2.31 (2H, d, J = 6.7 Hz), 4.22-4.32 (1H, m), 5.13 (2H, s), 6.93-6.99 (2H, m), 7.31-7.41 (5H, m), 7.78-7.84 (2H, m), 9.87 (1H, s). MS m/z: 353 $(M + H)^+$. |
| K3 | $^1$H-NMR ($CDCl_3$) δ: 0.67 (3H, s), 1.04-1.20 (5H, m), 1.36-1.91 (9H, m), 2.07-2.17 (4H, m), 2.25-2.33 (3H, m), 2.39-2.49 (1H, m), 3.48 (2H, s), 3.70-3.83 (5H, m), 4.03-4.14 (1H, m), 5.12 (2H, s), 6.75-6.80 (2H, m), 6.82-6.87 (2H, m), 7.02-7.07 (2H, m), 7.16-7.21 (2H, m), 7.31-7.40 (5H, m). MS m/z: 600 $(M + H)^+$. |
| K4 | $^1$H-NMR ($CDCl_3$) δ: 0.66 (3H, s), 1.06-1.18 (5H, m), 1.39-1.66 (5H, m), 1.68-1.77 (1H, m), 1.82-2.02 (6H, m), 2.06-2.31 (7H, m), 2.45-2.54 (2H, m), 3.29 (1H, d, J = 14.0 Hz), 3.36 (1H, d, J = 14.0 Hz), 3.68-3.78 (2H, m), 3.80 (3H, s), 4.05-4.14 (1H, m), 5.12 (2H, s), 6.76 (2H, d, J = 8.5 Hz), 6.83 (2H, d, J = 8.5 Hz), 7.02 (2H, d, J = 8.5 Hz), 7.13 (2H, d, J = 8.5 Hz), 7.29-7.40 (5H, m). MS m/z: 696 $(M + H)^+$. |
| K5 | $^1$H-NMR ($CDCl_3$) δ: 0.67 (3H, s), 1.07-1.26 (5H, m), 1.42-2.31 (19H, m), 2.47-2.56 (2H, m), 3.28-3.41 (2H, m), 3.69-3.79 (2H, m), 3.81 (3H, s), 4.07-4.17 (1H, m), 6.74-6.80 (2H, m), 6.81-6.87 (2H, m), 6.99-7.05 (2H, m), 7.11-7.16 (2H, m). MS m/z: 606 $(M + H)^+$. |
| L1 | $^1$H-NMR ($CDCl_3$) δ: 0.69 (3H, s), 1.10-1.18 (12H, m), 1.26 (3H, t, J = 7.3 Hz), 1.40-1.79 (8H, m), 2.02-2.22 (6H, m), 2.30-2.39 (1H, m), 2.64-2.77 (1H, m), 2.84 (3H, s), 3.04-3.18 (1H, m), 3.62-3.79 (3H, m), 4.09-4.20 (3H, m), 4.25 (1H, d, J = 15.3 Hz), 4.40 (1H, d, J = 15.3 Hz), 6.55 (2H, d, J = 8.5 Hz), 6.75 (2H, d, J = 8.5 Hz), 6.87 (2H, d, J = 8.5 Hz), 7.02 (2H, d, J = 8.5 Hz). MS m/z: 607 $(M + H)^+$. |
| L2 | $^1$H-NMR ($CDCl_3$) δ: 0.69 (3H, s), 1.09-1.20 (12H, m), 1.43-1.79 (8H, m), 2.05-2.23 (6H, m), 2.37-2.46 (1H, m), 2.64-2.79 (1H, m), 2.84 (3H, s), 3.04-3.18 (1H, m), 3.65-3.80 (2H, m), 4.12-4.22 (1H, m), 4.26 (1H, d, J = 15.3 Hz), 4.40 (1H, d, J = 15.3 Hz), 6.56 (2H, d, J = 8.5 Hz), 6.75 (2H, d, J = 8.5 Hz), 6.87 (2H, d, J = 8.5 Hz), 7.02 (2H, d, J = 8.5 Hz), MS m/z: 579 $(M + H)^+$. |
| M1 | $^1$H-NMR ($CDCl_3$) δ: 0.67 (3H, s), 1.19 (3H, s), 1.49-1.76 (4H, m), 2.10-2.22 (2H, m), 2.27-2.34 (1H, m), 2.46-2.55 (1H, m), 3.72-3.84 (2H, m), 3.81 (3H, s), 6.86 (2H, d, J = 8.5 Hz), 7.20 (2H, d, J = 8.5 Hz). |
| M2 | $^1$H-NMR ($CDCl_3$) δ: 0.67 (3H, s), 1.18 (3H, s), 1.25 (3H, s), 1.25 (3H, s), 1.57-1.70 (3H, m), 1.72-1.81 (1H, m), 2.16 (1H, dd, J = 14.0, 2.4 Hz), 2.35 (1H, dd, J = 14.0, 2.4 Hz), 2.71-2.82 (1H, m), 3.17-3.27 (1H, m), 3.76-3.83 (5H, m), 5.39 (1H, br s), 6.89 (2H, d, J = 8.5 Hz), 7.22 (2H, d, J = 8.5 Hz). MS m/z: 402 $(M + H)^+$. |

TABLE 14

| Ex | Data |
|---|---|
| M3 | $^1$H-NMR ($CDCl_3$) δ: 0.67 (3H, s), 1.01 (3H, s), 1.02 (3H, s), 1.19 (3H, s), 1.51-1.79 (4H, m), 2.04-2.18 (2H, m), 2.29-2.43 (4H, m), 3.72-3.84 (5H, m), 6.86 (2H, d, J = 9.2 Hz), 7.20 (2H, d, J = 9.2 Hz). MS m/z: 388 $(M + H)^+$. |
| M4 | $^1$H-NMR ($CDCl_3$) δ: 0.66 (3H, s), 0.89 (6H, s), 1.16 (3H, s), 1.26 (3H, t, J = 7.1 Hz), 1.40-1.65 (7H, m), 1.67-1.77 (1H, m), 1.81-1.91 (1H, m), 2.02-2.39 (10H, m), 3.39 (1H, d, J = 13.4 Hz), 3.43 (1H, d, J = 13.4 Hz), 3.65-3.80 (2H, m), 3.79 (3H, s), 4.09-4.21 (1H, m), 4.14 (2H, q, J = 7.1 Hz), 6.76 (2H, d, J = 8.5 Hz), 6.81 (2H, d, J = 9.2 Hz), 7.04 (2H, d, J = 8.5 Hz), 7.10 (2H, d, J = 9.2 Hz). MS m/z: 648 $(M + H)^+$ |
| M5 | $^1$H-NMR ($CDCl_3$) δ: 0.66 (3H, s), 0.89 (6H, s), 1.16 (3H, s), 1.41-1.78 (8H, m), 1.82-1.93 (1H, m), 2.04-2.37 (9H, m), 2.43 (1H, tt, J = 11.3, 3.6 Hz), 3.39 (1H, d, J = 13.5 Hz), 3.43 (1H, d, J = 13.5 Hz), 3.65-3.82 (2H, m), 3.80 (3H, s), 4.13-4.22 (1H, m), 6.77 (2H, d, J = 8.6 Hz), 6.81 (2H, d, J = 8.6 Hz), 7.04 (2H, d, J = 8.6 Hz), 7.10 (2H, d, J = 8.6 Hz). MS m/z: 620 $(M + H)^+$ |
| N1 | $^1$H-NMR ($CDCl_3$) δ: 0.66 (3H, s), 1.07-1.34 (12H, m), 1.53-1.80 (4H, m), 2.07-2.23 (2H, m), 2.58-2.70 (1H, m), 3.11-3.22 (1H, m), 3.69-3.80 (5H, m), 4.26 (1H, d, J = 15.8 Hz), 4.48 (1H, d, J = 15.8 Hz), 6.78-6.95 (8H, m), 7.14 (2H, d, J = 8.5 Hz), 7.44 (2H, d, J = 8.5 Hz). MS m/z: 608 $[M(^{79}Br) + H]^+$, 610 $[M(^{81}Br) + H]^+$. |
| N2 | $^1$H-NMR ($CDCl_3$) δ: 0.65 (3H, s), 1.06-1.34 (13H, m), 1.51-1.80 (3H, m), 1.98-2.24 (2H, m), 2.53-2.75 (1H, m), 3.08-3.20 (7H, m), 3.68-3.82 (5H, m), 4.27 (1H, d, J = 15.2 Hz), 4.44 (1H, d, J = 15.2 Hz), 6.79-6.93 (8H, m), 7.04-7.08 (2H, m), 7.10-7.16 (2H, m). MS m/z: 621 $(M + H)^+$ |
| O1 | $^1$H-NMR ($CDCl_3$) δ: 0.69 (3H, s), 1.17 (3H, s), 1.26 (3H, t, J = 7.1 Hz), 1.37-1.81 (8H, m), 2.02-2.11 (3H, m), 2.12-2.21 (2H, m), 2.23-2.38 (2H, m), 2.73-2.85 (1H, m), 3.37-3.49 (1H, m), 3.71-3.86 (2H, m), 3.84 (3H, s), 4.09-4.19 (1H, m), 4.14 (2H, q, J = 7.1 Hz), 4.32 (1H, d, J = 15.3 Hz), 4.58 (1H, d, J = 15.3 Hz), 6.72 (2H, d, J = 8.5 Hz), 6.87 (2H, d, J = 8.5 Hz), 6.88 (2H, d, J = 8.5 Hz), 7.18 (2H, d, J = 8.5 Hz), 8.12 (2H, s). MS m/z: 620 $(M + H)^+$ |
| O2 | $^1$H-NMR ($CDCl_3$) δ: 0.69 (3H, s), 1.17 (3H, s), 1.38-1.82 (8H, m), 2.01-2.21 (5H, m), 2.23-2.31 (1H, m), 2.41 (1H, tt, J = 11.0, 3.7 Hz), 2.73-2.85 (1H, m), 3.37-3.48 (1H, m), 3.71-3.86 (2H, m), 3.83 (3H, s), 4.10-4.20 (1H, m), 4.32 (1H, d, J = 15.0 Hz), 4.58 (1H, d, J = 15.0 Hz), 6.72 (2H, d, J = 8.5 Hz), 6.83-6.91 (4H, m), 7.18 (2H, d, J = 8.5 Hz), 8.12 (2H, s). MS m/z: 592 $(M + H)^+$ |
| P1 | $^1$H-NMR ($CDCl_3$) δ: 1.53 (3H, d, J = 7.4 Hz), 3.70 (3H, s), 3.76 (1H, q, J = 7.4 Hz), 7.05-7.07 (4H, m), 7.35 (2H, d, J = 8.6 Hz), 7.85 (2H, d, J = 8.6 Hz), 9.93 (1H, s). |

TABLE 15

| Ex | Data |
|---|---|
| P2 | $^1$H-NMR ($CDCl_3$) δ: 0.66 (3H, s), 0.91 (6H, s), 1.16 (3H, s), 1.47-1.65 (6H, m), 1.69-1.77 (1H, m), 1.81-1.93 (1H, m), 2.05-2.16 (2H, m), 2.25-2.34 (1H, m), 2.36-2.41 (2H, m), 3.46 (2H, s), 3.67-3.79 (9H, m), 6.81 (2H, d, J = 8.6 Hz), 6.88 (2H, d, J = 8.6 Hz), 6.92 (2H, d, J = 8.6 Hz), 7.08-7.13 (4H, m), 7.26 (2H, d, J = 8.6 Hz). |
| P3 | $^1$H-NMR ($CDCl_3$) δ: 0.66 (3H, s), 0.91 (6H, s), 1.16 (3H, s), 1.47-1.64 (6H, m), 1.71-1.74 (1H, m), 1.87-1.90 (1H, m), 2.08-2.13 (2H, m), 2.28-2.31 (1H, m), 2.37 (2H, s), 3.44-3.48 (2H, m), 3.68-3.79 (6H, m), 6.80 (2H, d, J = 8.6 Hz), 6.88 (2H, d, J = 8.6 Hz), 6.93 (2H, d, J = 8.6 Hz), 7.10-7.12 (4H, m), 7.28 (2H, d, J = 8.6 Hz). MS m/z: 612 $(M + H)^+$. |
| Q1 | $^1$H-NMR ($CDCl_3$) δ: 0.67 (3H, s), 1.18 (3H, s), 1.57-1.68 (3H, m), 1.75-1.84 (1H, m), 2.10-2.19 (2H, m), 2.25-2.32 (1H, m), 2.40-2.48 (1H, m), 2.55 (3H, s), 3.57 (2H, s), 3.72-3.83 (5H, m), 3.87 (3H, s), 6.85 (2H, d, J = 9.2 Hz), 7.00-7.05 (2H, m), 7.19 (2H, d, J = 8.6 Hz), 7.82 (1H, d, J = 8.0 Hz). |
| Q2 | $^1$H-NMR ($CDCl_3$) δ: 0.64 (3H, s), 1.16 (3H, s), 1.33-1.36 (6H, m), 1.54-1.80 (4H, m), 2.10-2.21 (2H, m), 2.54 (3H, s), 2.70 (1H, br s), 3.18-3.23 (1H, m), 3.74-3.79 (5H, m), 3.89 (3H, s), 4.30 (1H, d, J = 15.9 Hz), 4.48 (1H, d, J = 15.9 Hz), 6.81-6.83 (4H, m), 7.11-7.13 (2H, m), 7.80 (1H, d, J = 8.0 Hz). |
| Q3 | $^1$H-NMR ($CDCl_3$) δ: 0.65 (3H, s), 1.17 (3H, s), 1.34 (6H, br s), 1.54-1.80 (4H, m), 2.13-2.19 (2H, m), 2.59 (3H, s), 2.70 (1H, br s), 3.22-3.26 (1H, m), 3.70-3.77 (2H, m), 3.80 (3H, s), 4.31 (1H, d, J = 15.9 Hz), 4.51 (1H, d, J = 15.9 Hz), 6.83-6.86 (4H, m), 7.12-7.14 (2H, m), 7.94 (1H, d, J = 8.0 Hz). |
| Q4 | $^1$H-NMR ($CDCl_3$) δ: 0.65 (3H, s), 1.18 (3H, s), 1.35 (6H, br s), 1.56-1.82 (4H, m), 2.14-2.21 (2H, m), 2.27 (3H, s), 2.72-2.74 (3H, m), 3.04 (2H, t, J = 7.4 Hz), 3.20-3.25 (1H, m), 3.73-3.79 (5H, m), 4.34 (1H, d, J = 15.9 Hz), 4.53 (1H, d, J = 15.9 Hz), 6.83-6.85 (4H, m), 7.15-7.19 (3H, m), 7.31 (2H, d, J = 8.0 Hz), 7.71 (2H, d, J = 8.0 Hz). MS m/z: 682 $(M + H)^+$. |
| R1 | $^1$H-NMR ($CDCl_3$) δ: 1.19 (3H, t, J = 7.1 Hz), 1.26 (3H, t, J = 7.4 Hz), 2.99-3.07 (2H, m), 3.36-3.40 (1H, m), 3.63-3.67 (1H, m), 4.02-4.04 (1H, m), 4.18-4.21 (2H, m), 7.01-7.04 (4H, m), 7.29 (2H, d, J = 8.6 Hz), 7.84 (2H, d, J = 8.6 Hz), 9.92 (1H, s). |

TABLE 16

| Ex | Data |
|---|---|
| R2 | $^1$H-NMR ($CDCl_3$) δ: 0.66 (3H, s), 0.91 (6H, s), 1.17-1.19 (6H, m), 1.25 (3H, q, J = 7.2 Hz), 1.47-1.64 (3H, m), 1.71-1.75 (1H, m), 1.87-1.90 (1H, m), 2.07-2.13 (2H, m), 2.28-2.31 (1H, m), 2.37 (2H, s), 2.99-3.00 (2H, m), 3.35-3.39 (1H, m), 3.43-3.47 (2H, m), 3.61-3.64 (1H, m), 3.71-3.74 (2H, m), 3.78 (3H, s), 3.99-4.01 (1H, m), 4.19 (2H, q, J = 7.2 Hz), 6.81 (2H, d, J = 9.2 Hz), 6.87 (2H, d, J = 8.6 Hz), 6.90 (2H, d, J = 8.6 Hz), 7.09-7.11 (4H, m), 7.21 (2H, d, J = 8.6 Hz). |
| R3 | $^1$H-NMR ($CDCl_3$) δ: 0.66 (3H, s), 0.92 (6H, s), 1.16 (3H, s), 1.21 (3H, t, J = 7.1 Hz), 1.44-1.57 (2H, m), 1.60-1.63 (1H, m), 1.70-1.73 (1H, m), 1.85-1.88 (1H, m), 2.07-2.10 (2H, m), 2.27-2.30 (1H, m), 2.37 (2H, s), 2.99-3.02 (1H, m), 3.11-3.15 (1H, m), 3.47-3.51 (3H, m), 3.60-3.63 (1H, m), 3.69-3.75 (2H, m), 3.78 (3H, s), 4.08-4.10 (1H, m), 6.81 (2H, d, J = 8.6 Hz), 6.87 (2H, d, J = 8.6 Hz), 6.90 (2H, d, J = 8.6 Hz), 7.09-7.12 (4H, m), 7.20 (2H, d, J = 8.6 Hz). MS m/z: 686 $(M + H)^+$. |
| S1 | $^1$H-NMR ($CDCl_3$) δ: 1.22-1.31 (4H, m), 1.37-1.65 (5H, m), 1.66-1.76 (2H, m), 1.81-1.94 (1H, m), 2.24 (2H, d, J = 6.7 Hz), 3.95-4.02 (1H, m), 4.13 (2H, q, J = 7.1 Hz). |
| S2 | $^1$H-NMR ($CDCl_3$) δ: 1.13-1.31 (5H, m), 1.45-1.58 (2H, m), 1.78-1.92 (3H, m), 2.13-2.21 (2H, m), 2.24 (2H, d, J = 6.7 Hz), 4.14 (2H, q, J = 7.1 Hz), 5.04-5.15 (1H, m), 6.77 (1H, d, J = 8.5 Hz), 8.04 (1H, dd, J = 8.5, 2.4 Hz), 8.59 (1H, d, J = 2.4 Hz), 9.93 (1H, s). MS m/z: 292 $(M + H)^+$ |
| S3 | $^1$H-NMR ($CDCl_3$) δ: 0.66 (3H, s), 0.89 (6H, s), 1.15-1.28 (2H, m), 1.16 (3H, s), 1.27 (3H, t, J = 7.3 Hz), 1.39-2.39 (19H, m), 3.34-3.44 (2H, m), 3.66-3.78 (2H, m), 3.79 (3H, s), 4.14 (2H, q, J = 7.3 Hz), 4.87-4.97 (1H, m), 6.56 (1H, d, J = 8.5 Hz), 6.80 (2H, d, J = 8.5 Hz), 7.10 (2H, d, J = 8.5 Hz), 7.33 (1H, dd, J = 8.5, 2.4 Hz), 7.89 (1H, d, J = 2.4 Hz). MS m/z: 663 $(M + H)^+$. |
| S4 | $^1$H-NMR ($CDCl_3$) δ: 0.65 (3H, s), 0.89 (6H, s), 1.16 (3H, s), 1.17-2.39 (21H, m), 3.34-3.44 (2H, m), 3.67-3.77 (2H, m), 3.79 (3H, s), 4.87-4.97 (1H, m), 6.56 (1H, d, J = 8.5 Hz), 6.78-6.82 (2H, m), 7.10 (2H, d, J = 8.5 Hz), 7.33 (1H, dd, J = 8.5, 2.4 Hz), 7.90 (1H, d, J = 2.4 Hz). MS m/z: 635 $(M + H)^+$. |
| T1 | $^1$H-NMR ($CDCl_3$) δ: 0.66 (3H, s), 0.88 (6H, s), 1.06-1.19 (2H, m), 1.16 (3H, s), 1.38-2.36 (19H, m), 3.35-3.46 (2H, m), 3.66-3.78 (2H, m), 3.79 (3H, s), 4.04-4.14 (1H, m), 5.13 (2H, s), 6.75 (2H, d, J = 8.5 Hz), 6.80 (2H, d, J = 8.5 Hz), 7.03 (2H, d, J = 8.5 Hz), 7.10 (2H, d, J = 8.5 Hz), 7.31-7.40 (5H, m). MS m/z: 724 $(M + H)^+$ |
| T2 | $^1$H-NMR ($CDCl_3$) δ: 0.66 (3H, s), 0.89 (6H, s), 1.08-1.22 (2H, m), 1.16 (3H, s), 1.40-2.39 (19H, m), 3.35-3.46 (2H, m), 3.66-3.77 (2H, m), 3.79 (3H, s), 4.07-4.16 (1H, m), 6.76 (2H, d, J = 8.5 Hz), 6.81 (2H, d, J = 8.5 Hz), 7.04 (2H, d, J = 8.5 Hz), 7.10 (2H, d, J = 8.5 Hz). MS m/z: 634 $(M + H)^+$ |

TABLE 17

| Ex | Data |
|---|---|
| U1 | $^1$H-NMR ($CDCl_3$) δ: 0.67 (3H, s), 1.18 (3H, s), 1.55-1.68 (3H, m), 1.73-1.83 (1H, m), 2.08-2.16 (2H, m), 2.26-2.32 (1H, m), 2.40-2.48 (1H, m), 3.50 (2H, s), 3.71-3.84 (5H, m), 5.03 (2H, s), 6.83-6.89 (4H, m), 7.07 (2H, d, J = 8.8 Hz), 7.18 (2H, d, J = 8.8 Hz), 7.25-7.45 (5H, m). MS m/z: 460 $(M + H)^+$. |
| U2 | $^1$H-NMR ($CDCl_3$) δ: 0.65 (3H, s), 0.96-1.37 (6H, m), 1.50-1.81 (7H, m), 2.01-2.24 (2H, m), 2.49-2.81 (1H, m), 3.00-3.15 (1H, m), 3.64-3.77 (2H, m), 3.80 (3H, s), 4.21-4.44 (2H, m), 5.04 (2H, s), 6.11 (1H, t, J = 56.7 Hz), 6.77-6.94 (6H, m), 7.01-7.18 (2H, m), 7.30-7.47 (5H, m). MS m/z: 580 $(M + H)^+$. |
| U3 | MS m/z: 490 $(M + H)^+$. |
| U4 | $^1$H-NMR ($CDCl_3$) δ: 1.05 (9H, s), 1.18-1.33 (2H, m), 1.40-1.76 (7H, m), 2.46 (3H, s), 3.90 (2H, d, J = 6.7 Hz), 3.98 (1H, brs), 7.99-7.47 (8H, m), 7.63 (4H, d, J = 6.7 Hz), 7.82 (2H, d, J = 7.9 Hz). |
| U5 | NMR (CDCl3) δ: 1.05 (9H, s), 1.21-1.41 (2H, m), 1.48-1.74 (7H, m), 2.12 (3H, s), 2.49 (2H, d, J = 6.7 Hz), 4.01 (1H, brs), 7.34-7.47 (6H, m), 7.68 (4H, d, J = 6.3 Hz). |
| U6 | NMR (CDCl3) δ: 1.09 (9H, s), 1.34-1.47 (2H, m), 1.52-1.85 (6H, m), 1.96 (1H, m), 2.55 (1H, dd, J = 12.7, 9.6 Hz), 2.61 (3H, s), 2.79 (1H, dd, J = 12.7, 4.7 Hz), 4.04 (1H, brs), 7.34-7.49 (6H, m), 7.67 (4H, d, J = 6.3 Hz). |
| U7 | $^1$H-NMR ($CDCl_3$) δ: 1.09 (9H, s), 1.34-1.46 (2H, m), 1.62-1.81 (6H, m), 2.12 (1H, m), 3.22 (1H, dd, J = 14.1, 6.3 Hz), 3.28 (3H, s), 3.45 (1H, dd, J = 14.1, 6.3 Hz), 4.00 (1H, brs), 5.15 (2H, s), 7.30-7.53 (11H, m), 7.62-7.69 (4H, m). |
| U8 | $^1$H-NMR ($CDCl_3$) δ: 1.57-1.82 (8H, m), 2.21 (1H, m), 3.20 (1H, dd, J = 14.3, 6.5 Hz), 3.28 (3H, s), 3.43 (1H, dd, J = 14.1, 5.9 Hz), 4.02 (1H, brs), 5.15 (2H, s), 7.30-7.41 (5H, m). |
| U9 | $^1$H-NMR ($CDCl_3$) δ: 1.33-1.36 (1H, m), 1.55-1.78 (8H, m), 2.14-2.24 (1H, m), 3.18 (1H, dd, J = 14.3, 6.5 Hz), 3.25 (3H, s), 3.41 (1H, dd, J = 14.3, 6.5 Hz), 3.97-4.02 (1H, m), 5.13 (2H, s), 7.27-7.42 (5H, m). |
| U10 | $^1$H-NMR ($CDCl_3$) δ: 0.65 (3H, s), 0.93-1.36 (11H, m), 1.39-1.82 (6H, m), 2.02-2.25 (7H, m), 2.65 (1H, brs), 3.07 (1H, m), 3.16 (1H, dd, J = 14.1, 6.3 Hz), 3.26 (3H, s), 3.43 (1H, dd, J = 14.1, 5.9 Hz), 3.63-3.78 (2H, m), 3.80 (3H, s), 4.10 (1H, m), 4.21-4.40 (2H, m), 5.13 (2H, s), 6.10 (1H, t, J = 56.6 Hz), 6.74 (2H, d, J = 8.2 Hz), 6.79-6.90 (4H, m), 7.13 (2H, d, J = 7.8 Hz), 7.27-7.43 (5H, m). MS m/z: 819 $(M + Na)^+$. |

TABLE 18

| Ex | Data |
|---|---|
| U11 | $^1$H-NMR ($CDCl_3$) δ: 0.65 (3H, s), 0.93-1.37 (11H, m), 1.44-1.81 (6H, m), 1.99-2.25 (7H, m), 2.49-2.78 (2H, m), 2.93-3.14 (6H, m), 3.61-3.78 (2H, m), 3.81 (3H, s), 4.12 (1H, m), 4.22-4.42 (2H, m), 6.10 (1H, t, J = 56.5 Hz), 6.76 (2H, d, J = 8.6 Hz), 6.79-6.91 (4H, m), 7.06-7.19 (2H, m). MS m/z: 663 $(M + H)^+$. |
| V1 | $^1$H-NMR ($CDCl_3$) δ: 1.47 (9H, s), 1.73-1.90 (1H, m), 2.06-2.17 (1H, m), 2.46-2.61 (5H, m), 6.02-6.11 (1H, m), 7.40 (1H, dd, J = 7.7 Hz, 7.9 Hz), 7.53 (1H, d, J = 10.4 Hz, 1.5 Hz), 7.61 (1H, dd, J = 7.9, 1.5 Hz), 9.95 (1H, d, J = 1.8 Hz). |
| V2 | $^1$H-NMR ($CDCl_3$) δ: 1.47 (9H, s), 1.73-1.90 (1H, m), 2.06-2.17 (1H, m) 2.46-2.61 (5H, m), 6.02-6.11 (1H, m), 7.40 (1H, dd, J = 7.7 Hz, 7.9 Hz), 7.53 (1H, dd, J = 10.4 Hz, 1.5 Hz), 7.61 (1H, dd, J = 7.9, 1.5 Hz), 9.95 (1H, d, J = 1.8 Hz). |
| V3 | $^1$H-NMR ($CDCl_3$) δ: 1.47 (9H, s), 1.73-1.90 (1H, m), 2.06-2.17 (1H, m), 2.46-2.61 (5H, m), 6.02-6.11 (1H, m), 7.40 (1H, dd, J = 7.7 Hz, 7.9 Hz), 7.53 (1H, dd, J = 10.4 Hz, 1.5 Hz), 7.61 (1H, dd, J = 7.9, 1.5 Hz), 9.95 (1H, d, J = 1.8 Hz). |
| V4 | $^1$H-NMR ($CDCl_3$) δ: 0.66 (3H, s), 0.94 (3H, s), 0.94 (3H, s), 1.16 (3H, s), 1.44-1.66 (3H, m), 1.48 (9H, s), 1.66-1.93 (3H, m), 2.02-2.16 (3H, m), 2.23-2.34 (1H, m), 2.34-2.50 (6H, m), 2.50-2.60 (1H, m), 3.46 (2H, dd, J = 16.4, 14.6 Hz), 3.64-3.80 (2H, m), 3.78 (3H, s), 5.88-5.94 (1H, m), 6.75-6.87 (4H, m), 7.03-7.13 (3H, m). |
| V5 | MS m/z: 620 $(M + H)^+$. |
| W1 | $^1$H-NMR ($CDCl_3$) δ: 1.47 (9H, s), 1.77-1.88 (1H, m), 2.13-2.21 (1H, m), 2.43-2.59 (5H, m), 6.27-6.31 (1H, m), 7.53 (2H, d, J = 8.5 Hz), 7.83 (2H, d, J = 8.5 Hz), 9.98 (1H, s). MS m/z: 287 $(M + H)^{+.}$ |
| W2 | $^1$H-NMR ($CDCl_3$) δ: 1.47 (9H, s), 1.77-1.88 (1H, m), 2.13-2.21 (1H, m), 2.43-2.59 (5H, m), 6.27-6.31 (1H, m), 7.53 (2H, d, J = 8.5 Hz), 7.83 (2H, d, J = 8.5 Hz), 9.98 (1H, s). |
| W3 | $^1$H-NMR ($CDCl_3$) δ: 1.47 (9H, s), 1.77-1.88 (1H, m), 2.13-2.21 (1H, m), 2.48-2.59 (5H, m), 6.27-6.31 (1H, m), 7.53 (2H, d, J = 8.5 Hz), 7.83 (2H, d, J = 8.5 Hz), 9.98 (1H, s). |
| W4 | $^1$H-NMR ($CDCl_3$) δ: 0.66 (3H, s), 0.91 (3H, s), 0.92 (3H, s), 1.16 (3H, s), 1.44-1.64 (11H, m), 1.69-1.92 (3H, m), 2.04-2.18 (3H, m), 2.24-2.56 (9H, m), 3.43-3.51 (2H, m), 3.65-3.75 (2H, m), 3.78 (3H, s), 6.08-6.11 (1H, m), 6.80 (2H, d, J = 8.5 Hz), 7.06-7.11 (4H, m), 7.24 (2H, d, J = 8.5 Hz). MS m/z: 658 $(M + H)^+$. |
| W5 | $^1$H-NMR ($CDCl_3$) δ: 0.66 (3H, s), 0.91 (3H, s), 0.91 (3H, s), 1.16 (3H, s), 1.35 (1H, t, J = 5.5 Hz), 1.40-1.64 (3H, m), 1.69-1.77 (1H, m), 1.83-1.93 (3H, m), 1.94-2.14 (4H, m), 2.25-2.40 (4H, m), 2.45-2.51 (2H, m), 3.42-3.52 (2H, m), 3.57-3.79 (7H, m), 6.09-6.13 (1H, m), 6.80 (2H, d, J = 8.0 Hz), 7.07-7.12 (4H, m), 7.26 (2H, d, J = 8.0 Hz). MS m/z: 588 $(M + H)^+$. |

TABLE 19

| Ex | Data |
|---|---|
| X1 | $^1$H-NMR ($CDCl_3$) δ: 0.66 (3H, s), 0.91 (3H, s), 0.91 (3H, s), 1.16 (3H, s), 1.44-1.66 (4H, m), 1.67-1.79 (1H, m), 1.81-1.93 (1H, m), 1.91-2.22 (5H, m), 2.22-2.57 (6H, m), 3.04 (3H, s), 3.45 (1H, d, J = 14.0 Hz), 3.50 (1H, d, J = 14.0 Hz), 3.64-3.80 (2H, m), 3.78 (3H, s), 4.19 (2H, d, J = 6.1 Hz), 6.04-6.11 (1H, m), 6.80 (2H, d, J = 8.5 Hz), 7.06-7.13 (4H, m), 7.25 (2H, d, J = 8.5 Hz). MS m/z: 666 $(M + H)^+$. |
| X2 | $^1$H-NMR ($CDCl_3$) δ: 0.66 (3H, s), 0.90 (3H, s), 0.91 (3H, s), 1.16 (3H, s), 1.32-1.66 (4H, m), 1.56 (9H, s), 1.66-1.79 (1H, m), 1.79-1.93 (3H, m), 1.93-2.03 (1H, m), 2.03-2.14 (2H, m), 2.21-2.51 (12H, m), 3.38-3.54 (6H, m), 3.64-3.80 (2H, m), 3.78 (3H, s), 6.07-6.12 (1H, m), 6.80 (2H, d, J = 8.8 Hz), 7.08 (2H, d, J = 7.9 Hz), 7.10 (2H, d, J = 8.8 Hz), 7.26 (2H, d, J = 7.9 Hz). MS m/z: 756 $(M + H)^+$. |
| Y1 | $^1$H-NMR ($CDCl_3$) δ: 1.46 (9H, s), 2.19-2.26 (1H, m), 2.62-2.74 (1H, m), 2.76-2.86 (1H, m), 2.89-2.97 (1H, m), 3.25 (2H, t, J = 5.8 Hz), 3.35-3.43 (5H, m), 3.98 (1H, br s), 4.81 (1H, br s), 5.17 (1H, dd, J = 12.8, 5.5 Hz), 6.32-6.36 (2H, m), 6.60 (1H, d, J = 9.1 Hz), 8.04 (1H, s). MS m/z: 362 $(M\text{-}tBu + H)^+$. |
| Y2 | $^1$H-NMR (DMSO-$D_6$) δ: 1.92-2.02 (1H, m), 2.54-2.73 (2H, m), 2.83-3.05 (3H, m), 3.26-3.37 (5H, m), 5.28 (1H, dd, J = 12.8, 5.5 Hz), 6.40-6.46 (1H, m), 6.55-6.59 (1H, m), 6.91 (1H, d, J = 8.5 Hz), 7.87-8.03 (3H, m), 11.08 (1H, s). MS m/z: 318 $(M + H)^+$. |
| Y3 | $^1$H-NMR ($CDCl_3$) δ: 1.44-1.54 (1H, m), 1.91-2.02 (2H, m), 2.13-2.24 (1H, m), 2.36 (2H, d, J = 7.3 Hz), 2.39-2.48 (1H, m), 2.48-2.56 (2H, m), 3.71 (3H, s), 6.24-6.27 (1H, m), 7.53 (2H, d, J = 8.5 Hz), 7.82 (2H, d, J = 8.5 Hz), 9.98 (1H, s). MS m/z: 259 $(M + H)^+$. |
| Y4 | $^1$H-NMR ($CDCl_3$) δ: 0.66 (3H, s), 0.91 (3H, s), 0.92 (3H, s), 1.16 (3H, s), 1.42-1.65 (5H, m), 1.68-1.78 (1H, m), 1.82-1.09 (3H, m), 2.04-2.23 (3H, m), 2.25-2.42 (6H, m), 2.45-2.50 (2H, m), 3.43-3.52 (2H, m), 3.67-3.76 (4H, m), 3.78 (3H, s), 6.04-6.08 (1H, m), 6.80 (2H, d, J = 9.7 Hz), 7.08 (2H, d, J = 6.7 Hz), 7.10 (2H, d, J = 6.7 Hz), 7.25 (2H, d, J = 9.7 Hz). MS m/z: 630 $(M + H)^+$. |
| Y5 | $^1$H-NMR ($CDCl_3$) δ: 0.66 (3H, s), 0.91 (3H, s), 0.92 (3H, s), 1.16 (3H, s), 1.43-1.77 (3H, m), 1.82-2.24 (4H, m), 2.25-2.51 (7H, m), 3.43-3.51 (2H, m), 3.64-3.76 (2H, m), 3.78 (3H, s), 6.05-6.09 (1H, m), 6.80 (2H, d, J = 9.1 Hz), 7.08 (2H, d, J = 5.2 Hz), 7.10 (2H, d, J = 5.2 Hz), 7.25 (7H, d, J = 9.1 Hz). MS m/z: 616 $(M + H)^+$. |

TABLE 20

| Ex | Data |
|---|---|
| Y6 | $^1$H-NMR ($CDCl_3$) δ: 0.66 (3H, s), 0.91 (6H, s), 1.16 (3H, s), 1.39-1.80 (4H, m), 1.80-1.99 (4H, m), 2.04-2.14 (3H, m), 2.14-2.49 (10H, m), 2.63-2.74 (1H, m), 2.75-2.86 (1H, m), 2.88-2.98 (1H, m), 3.26-3.32 (2H, m), 3.37 (3H, s), 3.40-3.62 (4H, m), 3.64-3.76 (2H, m), 0.78 (3H, s), 5.16 (1H, dd, J = 12.5, 5.2 Hz), 5.82-5.87 (1H, m), 6.03-6.07 (1H, m), 6.32-6.38 (2H, m), 6.61 (1H, d, J = 8.5 Hz), 6.80 (2H, d, J = 8.5 Hz), 7.07-7.14 (4H, m), 7.24 (2H, d, J = 8.5 Hz), 8.14 (1H, s). MS m/z: 915 $(M + H)^+$. |
| Z1 | $^1$H-NMR ($CDCl_3$) δ: 1.48 (9H, s), 1.87-1.96 (2H, m), 2.03-2.10 (2H, m), 2.52-2.59 (2H, m), 2.78-2.85 (2H, m), 3.16 (2H, s), 4.44-4.52 (1H, m), 6.99 (2H, d, J = 8.5 Hz), 7.82 (2H, d, J = 8.5 Hz), 9.87 (1H, s). MS m/z: 320 $(M + H)^+$. |
| Z2 | $^1$H-NMR ($CDCl_3$) δ: 0.66 (3H, s), 0.89 (6H, s), 1.16 (3H, s), 1.45-1.65 (12H, m), 1.67-1.77 (1H, m), 1.81-1.90 (3H, m), 1.97-2.15 (4H, m), 2.23-2.37 (3H, m), 2.46-2.55 (2H, m), 2.78-2.85 (2H, m), 3.15 (2H, s), 3.36-3.45 (2H, m), 3.66-3.82 (5H, m), 4.26-4.33 (1H, m), 6.77 (2H, d, J = 8.5 Hz), 6.80 (2H, d, J = 8.5 Hz), 7.04 (2H, d, J = 8.5 Hz), 7.10 (2H, d, J = 8.5 Hz). MS m/z: 691 $(M + H)^+$. |
| Z3 | MS m/z: 635 $(M + H)^+$. |
| Z4 | $^1$H-NMR ($CDCl_3$) δ: 0.00 (9H, s), 0.91-0.97 (2H, m), 2.23-2.31 (1H, m), 2.37-2.48 (1H, m), 2.72-2.82 (1H, m), 3.03-3.13 (1H, m), 3.59-3.64 (2H, m), 4.63-4.75 (1H, m), 5.20-5.29 (2H, m). |
| Z5 | $^1$H-NMR ($CDCl_3$) δ: 0.00 (9H, s), 0.92-0.98 (2H, m), 2.20-2.29 (1H, m), 2.67-2.80 (1H, m), 2.85-2.94 (1H, m), 3.05-3.12 (1H, m), 3.55 (3H, s), 3.60-3.69 (2H, m), 5.21-5.32 (3H, m), 6.99 (1H, d, J = 7.9 Hz), 7.12 (1H, t, J = 8.2 Hz), 7.66 (1H, d, J = 8.5 Hz). MS m/z: 407 $(M-C_2H_4 + H)^+$. |
| Z6 | $^1$H-NMR ($CDCl_3$) δ: 0.00 (9H, s), 0.93-0.99 (2H, m), 2.15-2.22 (1H, m), 2.67-2.79 (1H, m), 2.80-2.91 (1H, m), 3.00-3.07 (1H, m), 3.61-3.68 (2H, m), 3.71-3.76 (5H, m), 5.18 (1H, dd, J = 12.8, 5.5 Hz), 5.27 (1H, d, J = 9.2 Hz), 5.31 (1H, d, J = 9.2 Hz), 6.29 (1H, d, J = 8.2 Hz), 6.46 (1H, d, J = 8.2 Hz), 6.85 (1H, t, J = 8.2 Hz). MS m/z: 427 $(M + Na)^+$. |
| Z7 | $^1$H-NMR ($CDCl_3$) δ: 0.00 (9H, s), 0.66 (3H, s), 0.89 (6H, s), 0.96 (2H, t, J = 8.5 Hz), 1.16 (3H, s), 1.47-1.64 (3H, m), 1.68-1.78 (1H, m), 1.82-1.95 (3H, m), 2.00-2.15 (4H, m), 2.18-2.36 (4H, m), 2.58-2.80 (3H, m), 2.82-2.99 (3H, m), 3.02-3.10 (1H, m), 3.26 (2H, s), 3.37-3.47 (2H, m), 3.62-3.77 (7H, m), 3.80 (3H, s), 4.35-4.41 (1H, m), 5.21 (1H, dd, J = 13.1, 5.2 Hz), 5.27 (1H, d, J = 9.1 Hz), 5.31 (1H, d, J = 9.1 Hz), 6.67 (1H, d, J = 7.9 Hz), 6.79 (2H, d, J = 6.1 Hz), 6.81 (2H, d, J = 6.1 Hz), 7.01-7.13 (5H, m), 7.30 (1H, d, J = 7.9 Hz), 9.29 (1H, s). |

TABLE 21

| Ex | Data |
|---|---|
| Z8 | $^1$H-NMR ($CDCl_3$) δ: 0.66 (3H, s), 0.89 (6H, s), 1.16 (3H, s), 1.43-1.66 (3H, m), 1.68-1.78 (1H, m), 1.82-1.96 (3H, m), 1.99-2.16 (4H, m), 2.19-2.38 (4H, m), 2.56-3.00 (7H, m), 3.26 (2H, s), 3.37-3.47 (2H, m), 3.62-3.84 (8H, m), 4.34-4.43 (1H, m), 5.20 (1H, dd, J = 12.5, 5.2 Hz), 6.70 (1H, d, J = 7.9 Hz), 6.79 (2H, d, J = 6.7 Hz), 6.81 (2H, d, J = 6.7 Hz), 7.03-7.14 (5H, m), 7.31 (1H, d, J = 7.9 Hz), 8.12 (1H, s), 9.29 (1H, s). MS m/z: 891 $(M + H)^+$. |
| AA1 | $^1$H-NMR ($CDCl_3$) δ: 1.28 (3H, t, J = 7.3 Hz), 3.70 (2H, s), 4.18 (2H, q, J = 7.1 Hz), 7.33-7.37 (1H, m), 7.42-7.47 (1H, m), 7.52-7.58 (2H, m), 7.73-7.78 (2H, m), 7.94-7.98 (2H, m), 10.06 (1H, s). MS m/z: 269 $(M + H)^+$. |
| AA2 | $^1$H-NMR ($CDCl_3$) δ: 0.66 (3H, s), 0.93-0.96 (6H, m), 1.16 (3H, s), 1.27 (3H, t, J = 7.1 Hz), 1.48-1.66 (3H, m), 1.71-1.79 (1H, m), 1.86-1.95 (1H, m), 2.06-2.15 (2H, m), 2.28-2.44 (3H, m), 3.54 (2H, dd, J = 17.3, 13.7 Hz), 3.67-3.77 (7H, m), 4.18 (2H, q, J = 7.1 Hz), 6.77-6.81 (2H, m), 7.09-7.12 (2H, m), 7.19-7.23 (2H, m), 7.27 (1H, d, J = 8.5 Hz), 7.38-7.42 (1H, m), 7.45-7.52 (4H, m). MS m/z: 640 $(M + H)^+$. |
| AA3 | $^1$H-NMR ($CDCl_3$) δ; 0.66 (3H, s), 0.93-0.96 (6H, m), 1.17 (3H, s), 1.48-1.66 (3H, m), 1.71-1.79 (1H, m), 1.86-1.94 (1H, m), 2.06-2.14 (2H, m), 2.28-2.43 (3H, m), 3.53 (2H, dd, J = 17.0, 14.6 Hz), 3.68-3.77 (7H, m), 6.79 (2H, d, J = 8.5 Hz), 7.10 (2H, d, J = 9.1 Hz), 7.20 (2H, d, J = 8.5 Hz), 7.27 (1H, d, J = 6.1 Hz), 7.38-7.47 (3H, m), 7.49-7.52 (2H, m). MS m/z: 612 $(M + H)^+$. |
| AA4 | $^1$H-NMR ($CDCl_3$) δ: 0.66 (3H, s), 0.95 (6H, s), 1.16 (3H, s), 1.46-1.93 (6H, m), 2.07-2.44 (6H, m), 2.60-2.93 (3H, m), 3.20-3.35 (5H, m), 3.47-3.59 (4H, m), 3.65-3.77 (7H, m), 5.12-5.18 (1H, m), 5.87-5.93 (1H, m), 6.25-6.30 (2H, m), 6.57 (1H, d, J = 8.5 Hz), 6.78 (2H, d, J = 6.7 Hz), 7.08-7.23 (5H, m), 7.39-7.54 (5H, m), 8.31 (1H, s). MS m/z: 911 $(M + H)^+$. |
| AB1 | $^1$H-NMR ($CDCl_3$) δ: 1.36 (3H, t, J = 7.5 Hz), 2.05-2.24 (4H, m), 2.89 (2H, t, J = 7.0 Hz), 3.22 (2H, t, J = 7.0 Hz), 4.30 (2H, q, J = 7.5 Hz). MS m/z: 228 $(M - H)^+$. |
| AB2 | $^1$H-NMR ($CDCl_3$) δ: 1.02 (6H, s), 1.65-1.82 (6H, m), 1.89-2.00 (2H, m), 2.25-2.33 (4H, m), 2.43 (2H, s), 3.81 (3H, s), 6.89 (2H, d, J = 9.1 Hz), 7.22 (2H, d, J = 9.1 Hz). MS m/z: 394 $(M + H)^+$. |
| AB3 | $^1$H-NMR ($CDCl_3$) δ: 1.95 (2H, tt, J = 12.5, 4.2 Hz), 2.10 (2H, tt, J = 10.0, 3.0 Hz), 2.56-2.61 (2H, m), 2.81-2.86 (2H, m), 3.30 (2H, s), 3.77 (3H, s), 4.49-4.54 (1H, m), 7.02 (2H, d, J = 8.5 Hz), 7.85 (2H, d, J = 8.5 Hz), 9.90 (1H, s). MS m/z: 278 $(M + H)^+$. |

TABLE 22

| Ex | Data |
|---|---|
| AB4 | $^1$H-NMR ($CDCl_3$) δ: 0.90 (6H, s), 1.62-1.72 (6H, m), 1.82-1.92 (4H, m), 1.99-2.07 (2H, m), 2.10-2.17 (4H, m), 2.36 (2H, s), 2.48-2.55 (2H, m), 2.78-2.84 (2H, m), 3.27 (2H, s), 3.42 (2H, s), 3.74 (3H, s), 3.80 (3H, s), 4.28-4.34 (1H, m), 6.78 (2H, d, J = 8.5 Hz), 6.83 (2H, d, J = 8.5 Hz), 7.03 (2H, d, J = 8.5 Hz), 7.13 (2H, d, J = 8.5 Hz). MS m/z: 655 $(M + H)^+$. |
| AB5 | MS m/z: 641 $(M + H)^+$. |
| AB6 | $^1$H-NMR ($CDCl_3$) δ: 0.90 (6H, s), 1.60-1.82 (6H, m), 1.82-1.98 (4H, m), 1.98-2.39 (9H, m), 2.55-3.04 (7H, m), 3.26 (2H, s), 3.43 (2H, s), 3.66 (3H, s), 3.80 (3H, s), 4.34-4.44 (1H, m), 5.19 (1H, dd, J = 12.5, 5.2 Hz), 6.70 (1H, d, J = 7.9 Hz), 6.80 (2H, d, J = 8.5 Hz), 6.84 (2H, d, J = 8.5 Hz), 7.03-7.09 (3H, m), 7.13 (2H, d, J = 8.5 Hz), 7.31 (1H, d, J = 7.9 Hz), 8.02 (1H, s), 9.29 (1H, s). MS m/z: 897 $(M + H)^+$. |
| AC1 | $^1$H-NMR ($CDCl_3$) δ: 1.36 (3H, t, J = 7.0 Hz), 2.80 (2H, t, J = 5.5 Hz), 3.19 (2H, t, J = 5.5 Hz), 3.80 (2H, t, J = 5.5 Hz), 3.88 (2H, t, J = 5.5 Hz), 4.29 (2H, q, J = 7.1 Hz). |
| AC2 | $^1$H-NMR ($CDCl_3$) δ: 1.03 (6H, s), 1.73-1.87 (4H, m), 2.09-2.16 (2H, m), 2.25-2.31 (2H, m), 2.43 (2H, s), 3.51-3.59 (2H, m), 3.74-3.83 (5H, m), 6.89 (2H, d, J = 8.5 Hz), 7.18 (2H, d, J = 8.5 Hz). MS m/z: 360 $(M + H)^+$. |
| AC3 | $^1$H-NMR ($CDCl_3$) δ: 0.90 (6H, s), 1.68-1.79 (4H, m), 1.82-1.94 (2H, m), 1.96-2.14 (6H, m), 2.37 (2H, s), 2.48-2.54 (2H, m), 2.77-2.84 (2H, m), 3.27 (2H, s), 3.43 (2H, s), 3.48-3.56 (2H, m), 3.67-3.76 (5H, m), 3.80 (3H, s), 4.28-4.34 (1H, m), 6.78 (2H, d, J = 8.5 Hz), 6.83 (2H, d, J = 8.5 Hz), 7.05 (2H, d, J = 8.5 Hz), 7.09 (2H, d, J = 8.5 Hz). MS m/z: 621 $(M + H)^+$ |
| AC4 | MS m/z: 607 $(M + H)^+$ |
| AC5 | MS m/z: 993 $(M + H)^+$ |
| AC6 | $^1$H-NMR ($CDCl_3$) δ: 0.91 (6H, s), 1.68-1.80 (4H, m), 1.84-1.95 (2H, m), 1.96-2.15 (6H, m), 2.20-2.28 (1H, m), 2.38 (2H, s), 2.56-2.66 (2H, m), 2.69-2.89 (2H, m), 2.89-3.01 (3H, m), 3.26 (2H, s), 3.45 (2H, s), 3.47-3.57 (2H, m), 3.64-3.74 (5H, m), 3.80 (3H, s), 4.35-4.43 (1H, m), 5.19 (1H, dd, J = 12.8, 5.5 Hz), 6.70 (1H, d, J = 7.9 Hz), 6.80 (2H, d, J = 8.5 Hz), 6.83 (2H, d, J = 8.5 Hz), 7.04-7.12 (5H, m), 7.31 (1H, d, J = 7.9 Hz), 8.04 (1H, s), 9.29 (1H, s). MS m/z: 863 $(M + H)^+$ |

TABLE 23

| Ex | Data |
|---|---|
| AD1 | $^1$H-NMR ($CDCl_3$) δ: 0.66 (3H, s), 0.89 (6H, s), 1.16 (3H, s), 1.46-1.65 (2H, m), 1.67-1.78 (5H, m), 1.81-1.91 (1H, m), 1.93-2.01 (2H, m), 2.05-2.14 (2H, m), 2.20-2.35 (4H, m), 2.37-2.46 (2H, m), 2.52-2.69 (4H, m), 2.72-2.88 (2H, m), 2.93-3.00 (1H, m), 3.18 (2H, s), 3.36-3.46 (2H, m), 3.64-3.83 (9H, m), 4.63-4.68 (1H, m), 5.19 (1H, dd, J = 12.1, 5.5 Hz), 6.64-6.71 (3H, m), 6.81 (2H, d, J = 8.5 Hz), 7.02-7.13 (5H, m), 7.33 (1H, d, J = 7.9 Hz), 8.01 (1H, s), 9.32 (1H, s). MS m/z: 931 $(M + H)^+$. |
| AE1 | $^1$H-NMR ($CDCl_3$) δ: 0.66 (3H, s), 0.89 (6H, s), 1.16 (3H, s), 1.45-1.66 (3H, m), 1.67-2.01 (7H, m), 2.03-2.15 (2H, m), 2.20-2.64 (10H, m), 2.66-2.90 (2H, m), 2.91-3.01 (1H, m), 3.08-3.15 (2H, m), 3.37-3.48 (5H, m), 3.65-3.82 (6H, m), 4.61-4.70 (1H, m), 5.20 (1H, dd, J = 13.1, 5.2 Hz), 6.67 (2H, d, J = 8.5 Hz), 6.72 (1H, d, J = 8.5 Hz), 6.81 (2H, d, J = 8.5 Hz), 6.90-6.98 (1H, m), 7.04 (2H, d, J = 8.5 Hz), 7.11 (2H, d, J = 8.5 Hz), 7.71 (1H, s), 8.02 (1H, s), 9.22 (1H, s). MS m/z: 931 $(M + H)^+$. |
| AF1 | $^1$H-NMR ($CDCl_3$) δ: 0.66 (3H, s), 0.89 (6H, s), 1.16 (3H, s), 1.43-1.65 (2H, m), 1.66-1.92 (5H, m), 1.92-2.03 (2H, m), 2.03-2.17 (2H, m), 2.18-2.67 (11H, m), 2.76-2.99 (2H, m), 3.07-3.17 (2H, m), 3.35-3.46 (3H, m), 3.63-3.81 (6H, m), 4.34 (1H, d, J = 15.9 Hz), 4.48 (1H, d, J = 15.9 Hz), 4.60-4.70 (1H, m), 5.21 (1H, dd, J = 13.1, 5.2 Hz), 6.67 (2H, d, J = 8.5 H), 6.81 (2H, d, J = 8.5 Hz), 7.05 (2H, d, J = 8.5 Hz), 7.11 (2H, d, J = 8.5 Hz), 7.24-7.35 (1H, m), 7.84 (1H, d, J = 8.5 Hz), 7.90 (1H, s), 8.18 (1H, s), 9.52 (1H, s). MS m/z: 916 $(M + H)^+$. |
| AG1 | $^1$H-NMR ($CDCl_3$) δ: 1.29 (3H, t, J = 7.3 Hz), 1.83-1.93 (1H, m), 2.18-2.25 (1H, m), 2.46-2.68 (5H, m), 4.18 (2H, q, J = 7.3 Hz), 6.28-6.32 (1H, m), 7.53 (2H, d, J = 7.9 Hz), 7.83 (2H, d, J = 7.9 Hz), 9.99 (1H, s). MS m/z: 259 $(M + H)^+$. |
| AG2 | $^1$H-NMR ($CDCl_3$) δ: 0.66 (3H, s), 0.91 (3H, s), 0.91 (3H, s), 1.16 (3H, s), 1.28 (3H, t, J = 7.0 Hz), 1.46-1.65 (3H, m), 1.68-1.78 (1H, m), 1.80-1.91 (2H, m), 2.05-2.14 (2H, m), 2.16-2.23 (1H, m), 2.25-2.35 (1H, m), 2.36 (2H, s), 2.43-2.54 (4H, m), 2.56-2.65 (1H, m), 3.45 (1H, d, J = 14.0 Hz), 3.50 (1H, d, J = 14.0 Hz), 3.66-3.75 (2H, m), 3.78 (3H, s), 4.18 (2H, q, J = 7.0 Hz), 6.08-6.12 (1H, m), 6.80 (2H, d, J = 9.1 Hz), 7.09 (2H, d, J = 9.1 Hz), 7.10 (2H, d, J = 9.1 Hz), 7.25 (2H, d, J = 9.1 Hz). MS m/z: 630 $(M + H)^+$. |
| AG3 | $^1$H-NMR ($CDCl_3$) δ: 0.66 (3H, s), 0.91 (6H, s), 1.16 (3H, s), 1.35 (1H, t, J = 5.5 Hz), 1.39-1.65 (3H, m), 1.68-1.78 (1H, m), 1.82-2.14 (6H, m), 2.25-2.41 (4H, m), 2.43-2.53 (2H, m), 3.45 (1H, d, J = 14.0 Hz), 3.50 (1H, d, J = 14.0 Hz), 3.57-3.81 (8H, m), 6.09-6.13 (1H, m), 6.80 (2H, d, J = 8.5 Hz), 7.09 (2H, d, J = 8.5 Hz), 7.10 (2H, d, J = 8.5 Hz), 7.26 (2H, d, J = 8.5 Hz). MS m/z: 588 $(M + H)^+$. |

TABLE 24

| Ex | Data |
|---|---|
| AG4 | $^1$H-NMR ($CDCl_3$) δ: 0.66 (3H, s), 0.91 (3H, s), 0.91 (3H, s), 1.16 (3H, s), 1.46-1.64 (3H, m), 1.69-1.78 (1H, m), 1.83-1.93 (1H, m), 1.97-2.19 (6H, m), 2.24-2.45 (4H, m), 2.46-2.54 (2H, m), 3.04 (3H, s), 3.45 (1H, d, J = 14.0 Hz), 3.50 (1H, d, J = 14.0 Hz), 3.65-3.75 (2H, m), 3.78 (3H, s), 4.19 (2H, d, J = 6.7 Hz), 6.05-6.09 (1H, m), 6.80 (2H, d, J = 8.5 Hz), 7.09 (2H, d, J = 8.5 Hz), 7.10 (2H, d, J = 8.5 Hz), 7.25 (2H, d, J = 8.5 Hz). MS m/z: 666 $(M + H)^+$. |
| AG5 | MS m/z: 656 $(M + H)^+$. |
| AG6 | $^1$H-NMR (DMSO-$D_6$) δ: 1.97-2.10 (1H, m), 2.36-2.50 (1H, m), 2.57-2.69 (1H, m), 2.86-2.99 (1H, m), 4.50 (1H, d, J = 18.0 Hz), 4.62 (1H, d, J = 18.0 Hz), 5.18 (1H, dd, J = 13.4, 5.5 Hz), 7.97 (2H, s), 7.99 (1H, d, J = 7.9 Hz), 8.32 (1H, dd, J = 7.9, 1.2 Hz), 8.48 (1H, d, J = 1.2 Hz), 11.06 (1H, s). MS m/z: 467 $(M + H)^+$. |
| AG7 | $^1$H-NMR ($CDCl_3$) δ: 0.66 (3H, s), 0.88-0.93 (6H, m), 1.16 (3H, s), 1.36-1.67 (3H, m), 1.68-2.15 (7H, m), 2.20-2.61 (14H, m), 2.81-3.00 (2H, m), 3.36-3.52 (4H, m), 3.64-3.93 (8H, m), 4.39 (1H, d, J = 16.4 Hz), 4.54 (1H, d, J = 16.4 Hz), 5.24 (1H, dd, J = 13.4, 4.9 Hz), 6.08-6.12 (1H, m), 6.80 (2H, d, J = 8.5 Hz), 7.07-7.12 (4H, m), 7.24-7.29 (2H, m), 7.51 (1H, d, J = 8.5 Hz), 7.54 (1H, s), 7.91-7.96 (2H, m). MS m/z: 926 $(M + H)^+$. |
| AH1 | $^1$H-NMR ($CDCl_3$) δ: −0.03 (9H, s), 0.93 (2H, t, J = 8.3 Hz), 2.13-2.21 (1H, m), 2.63-2.75 (1H, m), 2.81-2.88 (1H, m), 2.99-3.06 (1H, m), 3.58-3.66 (2H, m), 3.76 (3H, s), 5.18 (1H, dd, J = 12.7, 5.4 Hz), 5.25 (2H, q, J = 9.8 Hz), 6.68 (1H, d, J = 7.8 Hz), 6.87 (1H, t, J = 8.1 Hz), 7.20 (1H, d, J = 8.3 Hz). MS m/z: 440 $[M(^{79}Br) - C_2H_4 + H]^+$, 442 $[M(^{81}Br) - C_2H_4 + H]^+$. |
| AH2 | MS m/z: 634 $(M + Na)^+$. |
| AH3 | MS m/z: 1071 $(M + H)^+$. |
| AH4 | $^1$H-NMR (DMSO-$D_6$) δ: 0.55 (3H, s), 0.86 (6H, s), 1.06 (3H, s), 1.24-1.44 (2H, m), 1.46-1.61 (2H, m), 1.67-1.97 (5H, m), 2.00-2.16 (3H, m), 2.17-2.57 (12H, m), 2.58-2.80 (2H, m), 2.82-3.00 (1H, m), 3.27 (3H, s), 3.30-3.37 (2H, m), 3.44 (2H, s), 3.50-3.61 (2H, m), 3.65-3.84 (2H, m), 3.70 (3H, s), 5.43 (1H, dd, J = 12.2, 4.9 Hz), 6.08-6.14 (1H, m), 6.81 (2H, d, J = 8.5 Hz), 6.95 (1H, d, J = 7.3 Hz), 7.04 (2H, d, J = 8.5 Hz), 7.07-7.13 (1H, m), 7.16-7.22 (1H, m), 7.19 (2H, d, J = 8.5 Hz), 7.26 (2H, d, J = 8.5 Hz), 11.15 (1H, s). MS m/z: 941 $(M + H)^+$. |
| AI1 | $^1$H-NMR ($CDCl_3$) δ: 1.29 (3H, t, J = 7.0 Hz), 1.58-1.84 (6H, m), 2.23-2.33 (2H, m), 2.58-2.67 (1H, m), 2.69-2.75 (1H, m), 4.20 (2H, q, J = 7.0 Hz), 7.36 (2H, d, J = 7.9 Hz), 7.81 (2H, d, J = 7.9 Hz), 9.97 (1H, s). MS m/z: 261 $(M + H)^+$. |

TABLE 25

| Ex | Data |
|---|---|
| AI2 | $^1$H-NMR ($CDCl_3$) δ: 1.28 (3H, t, J = 7.0 Hz), 1.43-1.69 (4H, m), 1.95-2.03 (2H, m), 2.09-2.18 (2H, m), 2.31-2.42 (1H, m), 2.57-2.68 (1H, m), 4.15 (2H, q, J = 7.0 Hz), 7.37 (2H, d, J = 7.9 Hz), 7.82 (2H, t, J = 3.9 Hz), 9.98 (1H, s). MS m/z: 261 $(M + H)^+$. |
| AI3 | $^1$H-NMR ($CDCl_3$) δ: 0.66 (3H, s), 0.89 (6H, s), 1.15 (3H, s), 1.29 (3H, t, J = 7.0 Hz), 1.44-1.80 (10H, m), 1.87 (1H, td, J = 12.5, 3.6 Hz), 2.03-2.14 (2H, m), 2.20-2.39 (5H, m), 2.47-2.55 (1H, m), 2.67-2.72 (1H, m), 3.43 (1H, d, J = 14.0 Hz), 3.48 (1H, d, J = 14.0 Hz), 3.65-3.81 (5H, m), 4.19 (2H, q, J = 7.0 Hz), 6.80 (2H, d, J = 8.5 Hz), 7.05-7.14 (6H, m). MS m/z: 632 $(M + H)^+$. |
| AI4 | $^1$H-NMR ($CDCl_3$) δ: 0.66 (3H, s), 0.90 (6H, s), 1.15 (3H, s), 1.24-1.33 (1H, m), 1.42-1.93 (13H, m), 2.03-2.15 (2H, m), 2.23-2.39 (3H, m), 2.54-2.66 (1H, m), 3.43 (1H, d, J = 14.0 Hz), 3.49 (1H, d, J = 14.0 Hz), 3.65-3.81 (8H, m), 6.80 (2H, d, J = 9.1 Hz), 7.05-7.13 (6H, m), MS m/z: 590 $(M + H)^+$. |
| AI5 | $^1$H-NMR ($CDCl_3$) δ: 0.66 (3H, s), 0.89 (6H, s), 1.15 (3H, s), 1.36-1.91 (11H, m), 2.02-2.14 (2H, m), 2.23-2.59 (7H, m), 3.42 (1H, d, J = 14.0 Hz), 3.47 (1H, d, J = 14.0 Hz), 3.65-3.83 (5H, m), 6.80 (2H, d, J = 8.5 Hz), 6.99-7.12 (6H, m), 9.79 (1H, s). MS m/z 588 $(M + H)^+$. |
| AI6 | $^1$H-NMR ($CDCl_3$) δ: 0.66 (3H, s), 0.90 (6H, s), 1.15 (3H, s), 1.48-1.78 (21H, m), 1.83-1.98 (2H, m), 2.02-2.13 (2H, m), 2.23-2.45 (9H, m), 2.50-2.60 (1H, m), 3.38-3.51 (6H, m), 3.65-3.82 (5H, m), 6.80 (2H, d, J = 9.1 Hz), 7.05-7.13 (6H, m). MS m/z: 758 $(M + H)^+$. |
| AI7 | $^1$H-NMR ($CDCl_3$) δ: 0.66 (3H, s), 0.90 (6H, s), 1.15 (3H, s), 1.42-1.79 (14H, m), 1.82-1.99 (2H, m), 2.03-2.14 (2H, m), 2.24-2.60 (10H, m), 2.84-2.94 (4H, m), 3.43 (1H, d, J = 14.0 Hz), 3.48 (1H, d, J = 14.0 Hz), 3.66-3.80 (4H, m), 6.80 (2H, d, J = 8.5 Hz), 7.04-7.14 (6H, m). MS m/z: 658 $(M + H)^+$. |
| AI8 | $^1$H-NMR ($CDCl_3$) δ: 1.65 (9H, s), 3.51 (3H, s), 7.14 (1H, d, J = 7.9 Hz), 7.67 (1H, s), 7.83 (1H, dd, J = 8.2, 1.5 Hz), 10.00 (1H, br s). MS m/z: 249 $(M + H)^+$. |
| AI9 | $^1$H-NMR ($CDCl_3$) δ: 1.65 (9H, s), 3.51 (3H, s), 7.14 (1H, d, J = 7.9 Hz), 7.67 (1H, s), 7.83 (1H, dd, J = 8.2, 1.5 Hz), 10.00 (1H, br s). MS m/z: 360 $(M + H)^+$. |

TABLE 26

| Ex | Data |
|---|---|
| AI10 | $^1$H-NMR (DMSO-D$_6$) δ: 2.00-2.04 (1H, m), 2.59-2.75 (2H, m), 2.85-2.90 (1H, m), 3.37 (3H, s), 5.42 (1H, dd, J = 12.5, 5.2 Hz), 7.21 (1H, d, J = 8.5 Hz), 7.67-7.72 (2H, m), 11.14 (1H, s), 12.77 (1H, br s). MS m/z: 304 (M + H)$^+$. |
| AI11 | $^1$H-NMR (CDCl$_3$) δ: 0.66 (3H, s), 0.89 (6H, s), 1.15 (3H, s), 1.41-1.78 (13H, m), 1.82-1.98 (2H, m), 2.03-2.14 (2H, m), 2.19-2.60 (11H, m), 2.66-2.90 (2H, m), 2.93-3.02 (1H, m), 3.40-3.55 (6H, m), 3.64-3.84 (7H, m), 5.24 (1H, dd, J = 12.8, 5.5 Hz), 6.76-6.85 (3H, m), 7.05-7.18 (8H, m), 8.11 (1H, s). MS m/z: 943 (M + H)$^+$. |
| AJ1 | $^1$H-NMR (CDCl$_3$) δ: 0.66 (3H, s), 0.90 (6H, s), 1.15 (3H, s), 1.27 (3H, t, J = 7.0 Hz), 1.40-1.66 (7H, m), 1.67-1.78 (1H, m), 1.82-1.191 (1H, m), 1.92-2.00 (2H, m), 2.03-2.15 (4H, m), 2.24-2.40 (4H, m), 2.44-2.53 (1H, m), 3.44 (1H, d, J = 14.0 Hz), 3.49 (1H, d, J = 14.0 Hz), 3.64-3.82 (5H, m), 4.15 (2H, q, J = 7.0 Hz), 6.80 (2H, d, J = 9.1 Hz), 7.04-7.12 (6H, m), MS m/z: 632 (M + H)$^+$. |
| AJ2 | $^1$H-NMR (CDCl$_3$) δ: 0.66 (3H, s), 0.91 (6H, s), 1.16 (3H, s), 1.32 (1H, t, J = 5.5 Hz), 1.41-1.78 (8H, m), 1.82-1.98 (6H, m, 2.03-2.14 (2H, m), 2.24-2.51 (4H, m), 3.42-3.55 (4H, m), 3.66-3.81 (5H, m), 6.81 (2H, d, J = 9.1 Hz), 7.08 (4H, s), 7.10 (2H, d, J = 9.1 Hz). MS m/z: 590 (M + H)$^+$. |
| AJ3 | $^1$H-NMR (CDCl$_3$) δ: 0.66 (3H, s), 0.90 (6H, s), 1.15 (3H, s), 1.37-1.93 (10H, m), 1.99-2.20 (6H, m), 2.24-2.38 (4H, m), 3.44 (1H, d, J = 14.0 Hz), 3.49 (1H, d, J = 14.0 Hz), 3.64-3.84 (5H, m), 6.80 (2H, d, J = 9.1 Hz), 7.00-7.14 (6H, m), 9.69 (1H, s). MS m/z: 588 (M + H)$^+$. |
| AJ4 | $^1$H-NMR (CDCl$_3$) δ: 0.66 (3H, s), 0.90 (6H, s), 0.97-1.11 (2H, m), 1.15 (3H, s), 1.37-1.78 (17H, m), 1.82-1.98 (5H, m), 2.03-2.13 (2H, m), 2.15-2.21 (2H, m), 2.25-2.53 (7H, m), 3.38-3.52 (6H, m), 3.65-3.83 (5H, m), 6.80 (2H, d, J = 9.1 Hz), 7.04-7.15 (6H, m). MS m/z; 758 (M + H)$^+$. |
| AJ5 | $^1$H-NMR (CDCl$_3$) δ: 0.66 (3H, s), 0.90 (6H, s), 0.98-1.11 (2H, m), 1.15 (3H, s), 1.36-1.78 (10H, m), 1.83-1.98 (4H, m), 2.03-2.13 (2H, m), 2.14-2.20 (2H, m), 2.24-2.54 (7H, m), 2.83-2.99 (4H, m), 3.43 (1H, d, J = 14.0 Hz), 3.48 (1H, d, J = 14.0 Hz), 3.65-3.82 (5H, m), 6.80 (2H, d, J = 9.1 Hz), 7.03-7.13 (6H, m). MS m/z: 658 (M + H)$^+$. |
| AJ6 | $^1$H-NMR (CDCl$_3$) δ: 0.66 (3H, s), 0.90 (6H, s), 0.99-1.12 (2H, m), 1.15 (3H, s), 1.37-1.77 (10H, m), 1.82-1.98 (4H, m), 2.03-2.13 (2H, m), 2.17-2.61 (11H, m), 2.66-2.90 (2H, m), 2.93-3.02 (1H, m), 3.38-3.59 (6H, m), 3.64-3.88 (6H, m), 5.24 (1H, dd, J = 12.8, 5.5 Hz), 6.77-6.83 (3H, m), 7.06-7.18 (8H, m), 8.08 (1H, s). MS m/z: 943 (M + H)$^+$. |

TABLE 27

| Ex | Data |
|---|---|
| AK1 | MS m/z: 271 (M − tBu + H)$^+$. |
| AK2 | $^1$H-NMR (CDCl$_3$) δ: 1.53 (9H, s), 2 79-2.87 (2H, m), 2.91 (3H, d, J = 5.1 Hz), 3.59-3.69 (2H, m), 4.50-4.60 (2H, m), 4.70-4.80 (1H, m), 6.61-6.72 (1H, m), 7.06-7.16 (1H, m), 7.80-7.91 (1H, m). MS m/z: 328 (M − tBu + H)$^+$. |
| AK3 | $^1$H-NMR (CDCl$_3$) δ: 1.53 (9H, s), 2.86-2.97 (2H, m), 3.62-3.76 (2H, m), 3.71 (3H, s), 5.02-5.05 (2H, m), 6,83-6.96 (2H, m), 8.22-8.36 (1H, m). MS m/z: 304 (M + H)$^+$ |
| AK4 | $^1$H-NMR (CDCl$_3$) δ: 1.54 (9H, s), 2.88-2.97 (2H, m), 3.63-3.73 (2H, m), 3.73-3.82 (3H, m), 5.08 (2H, s), 5.29-5.52 (4H, m), 6.51-6.57 (2H, m), 6.77-6.85 (1H, m), 7.24-7.31 (6H, m), 7.36-7.46 (4H, m), 7.60 (1H, d, J = 8.2 Hz). MS m/z: 593 (M + H)$^+$. |
| AK5 | $^1$H-NMR (CDCl$_3$) δ: 1.53 (9H, s), 2.21-2.30 (1H, m), 2.69-3.02 (5H, m), 3.60-3.79 (5H, m), 4.99-5.07 (2H, m), 5.18-5.27 (1H, m), 6.67 (1H, d, J = 8.2 Hz), 6.88 (1H, d, J = 8.2 Hz), 8.03 (1H, s). MS m/z: 359 (M − tBu + H)$^+$. |
| AK6 | $^1$H-NMR (CDCl$_3$) δ: 1.46 (9H, s), 1.58-1.64 (4H, m), 1.96-2.01 (2H, m), 2.42-2.49 (2H, m), 3.30-3.35 (2H, m), 3.37-3.41 (2H, m), 4.73-4.81 (1H, m), 6.89 (2H, d, J = 8.5 Hz), 7.82 (2H, d, J = 8.5 Hz), 9.88 (1H, s). MS m/z: (M − tBu + H)$^+$. |
| AK7 | $^1$H-NMR (CDCl$_3$) δ: 1.46 (9H, s), 1.69-1.74 (4H, m), 1.92-1.99 (2H, m), 2.39-2.57 (6H, m), 3.10 (2H, s), 4.70-4.78 (1H, m), 6.89 (2H, d, J = 8.5 Hz), 7.81 (2H, d, J = 8.5 Hz), 9.87 (1H, s). MS m/z: 360 (M + H)$^+$. |
| AK8 | $^1$H-NMR (CDCl$_3$) δ: 0.66 (3H, s), 0.89 (6H, s), 1.16 (3H, s), 1.42-1.64 (12H, m), 1.66-1.76 (5H, m), 1.80-1.95 (3H, m), 2.04-2.14 (2H, m), 2.22-2.57 (9H, m), 3.09 (2H, s), 3.38 (1H, d, J = 14.0 Hz), 3.43 (1H, d, J = 14.0 Hz), 3.66-3.82 (5H, m), 4.58-4.66 (1H, m), 6.66 (2H, d, J = 8.5 Hz), 6.81 (2H, d, J = 8.5 Hz), 7.02 (2H, d, J = 8.5 Hz), 7.10 (2H, d, J = 8.5 Hz). MS m/z: 731 (M + H)$^+$. |
| AK9 | MS m/z: 675 (M + H)$^+$. |
| AK10 | $^1$H-NMR (CDCl$_3$) δ: 0.67 (3H, s), 0.89 (6H, s), 1.16 (3H, s), 1.43-1.77 (12H, m), 1.77-1.97 (3H, m), 2.04-2.16 (2H, m), 2.18-2.51 (7H, m), 2.69-3.00 (5H, m), 3.23-3.29 (2H, m), 3.41 (2H, d, J = 4.3 Hz), 3.68-3.85 (9H, m), 4.58-4.67 (1H, m), 5.07-5.26 (2H, m), 5.37-5.41 (1H, m), 6.63-6.69 (3H, m), 6.81 (2H, d, J = 9.0 Hz), 6.87 (1H, d, J = 7.8 Hz), 7.03 (2H, d, J = 8.2 Hz), 7.11 (2H, d, J = 8.6 Hz), 8.01 (1H, s). MS m/z: 971 (M + H)$^+$ |
| AL1 | $^1$H-NMR (CDCl$_3$) δ: 1.51 (4.5H, s), 1.53 (4.5H, s), 4.52-4.68 (6H, m), 7.26 (1H, d, J = 26.6 Hz). MS m/z: 291 [M($^{79}$Br $^{79}$Br) − Boc + H]$^+$, 293 [M($^{79}$Br $^{79}$Br) − Boc + H]$^+$, 295 [M($^{81}$Br $^{81}$Br) − Boc + H]$^+$. |

TABLE 28

| Ex | Data |
|---|---|
| AL2 | $^1$H-NMR ($CDCl_3$) δ: 1.51 (4.5H, s), 1.53 (4.5H, s), 4.07 (2H, s), 4.54-4.70 (4H, m), 6.69 (1H, dd, J = 8.2, 5.5 Hz), 6.94 (0.5H, d, J = 8.2 Hz), 6.99 (0.5H, d, J = 7.8 Hz). MS m/z: 257 [M($^{79}$Br) − tBu + H]$^+$, 259 [M($^{81}$Br) − tBu + H]$^+$. |
| AL3 | $^1$H-NMR ($CDCl_3$) δ: 1.51-1.58 (9H, m), 2.20-2.30 (1H, m), 2.69-3.02 (3H, m), 3.53-3.59 (3H, m), 4.63-4.72 (2H, m), 4.92-5.05 (2H, m), 5.19-5.24 (1H, m), 6.73 (1H, dd, J = 11.7, 4.7 Hz), 6.90-7.02 (1H, m), 7.98-8.08 (1H, m). MS m/z: 401 (M + H)$^+$. |
| AL4 | $^1$H-NMR ($CDCl_3$) δ: 0.67 (3H, s), 0.89 (3H, s), 1.16 (3H, s), 1.44-1.98 (12H, m), 2.03-2.60 (12H, m), 2.69-3.02 (2H, m), 3.20-3.28 (2H, m), 3.41 (2H, d, J = 3.9 Hz), 3.58 (3H, s), 3.58-3.77 (3H, m), 3.80 (3H, s), 4.59-5.32 (5H, m), 6.67 (2H, d, J = 8.6 Hz), 6.73-6.79 (1H, m), 6.81 (2H, d, J = 9.0 Hz), 6.94-7.01 (1H, m), 7.04 (2H, d, J = 8.2 Hz), 7.11 (2H, d, J = 9.0 Hz), 8.00 (1H, s). MS m/z: 957 (M + H)$^+$. |
| AM1 | $^1$H-NMR ($CDCl_3$) δ: 0.68 (3H, s), 1.04 (3H, s), 1.05 (3H, s), 1.18 (3H, s), 1.53-1.67 (4H, m), 1.72-1.81 (1H, m), 2.10-2.18 (2H, m), 2.26-2.33 (1H, m), 2.36-2.44 (1H, m), 2.46 (2H, s), 3.72-3.82 (2H, m), 6.69 (2H, d, J = 8.5 Hz), 7.11 (2H, d, J = 8.5 Hz). MS m/z: 374 (M + H)$^+$. |
| AM2 | $^1$H-NMR ($CDCl_3$) δ: 0.69 (3H, s), 0.93 (3H, s), 0.98 (3H, s), 1.19 (3H, s), 1.40 (9H, s), 1.54-1.75 (3H, m), 2.06-2.12 (1H, m), 2.22-2.29 (1H, m), 2.41-2.51 (1H, m), 2.80-2.97 (1H, m), 2.98-3.09 (1H, m), 3.16-3.25 (2H, m), 3.74-3.82 (2H, m), 4.71 (1H, s), 6.81 (2H, d, J = 9.1 Hz), 7.11-7.17 (2H, m). MS m/z: 374 (M − Boc + H)$^+$. |
| AM3 | $^1$H-NMR ($CDCl_3$) δ: 0.69 (3H, s), 0.93 (3H, s), 0.98 (3H, s), 1.20 (3H, s), 1.37-1.44 (9H, m), 1.57-1.77 (4H, m), 2.09-2.14 (1H, m), 2.24-2.31 (1H, m), 2.38-2.48 (1H, m), 2.76-3.25 (3H, m), 3.76-3.81 (2H, m), 6.49 (1H, t, J = 73.8 Hz), 7.11 (2H, d, J = 8.5 Hz), 7.26-7.31 (2H, m). MS m/z: 424 (M − Boc + H)$^+$. |
| AM4 | $^1$H-NMR ($CDCl_3$) δ: 0.66 (3H, s), 1.02 (6H, s), 1.20 (3H, s), 1.54-1.79 (4H, m), 2.03-2.11 (1H, m), 2.12-2.18 (1H, m), 2.30-2.44 (4H, m), 3.74-3.79 (2H, m), 6.52 (1H, t, J = 74.1 Hz), 7.08 (2H, d, J = 8.5 Hz), 7.29 (2H, d, J = 8.5 Hz). MS m/z: 424 (M + H)$^+$. |
| AM5 | $^1$H-NMR ($CDCl_3$) δ: 0.64 (3H, s), 0.92 (6H, s), 1.17 (3H, s), 1.29 (3H, t, J = 7.3 Hz), 1.51-1.69 (3H, m), 1.69-1.90 (3H, m), 2.04-2.16 (2H, m), 2.16-2.33 (2H, m), 2.33-2.41 (2H, m), 2.42-2.55 (4H, m), 2.56-2.65 (1H, m), 3.48 (2H, s), 3.70-3.73 (2H, m), 4.18 (2H, q, J = 7.1 Hz), 6.09-6.12 (1H, m), 6.44 (1H, t, J = 74.1 Hz), 7.00 (2H, d, J = 9.1 Hz), 7.08 (2H, d, J = 9.1 Hz), 7.18 (2H, d, J = 9.1 Hz), 7.25 (2H, d, J = 9.1 Hz). |

TABLE 29

| Ex | Data |
|---|---|
| AM6 | $^1$H-NMR ($CDCl_3$) δ: 0.64 (3H, s), 0.93 (6H, s), 1.17 (3H, s), 1.34-1.60 (3H, m), 1.47 (9H, s), 1.60-1.93 (5H, m), 1.95-2.02 (1H, m), 2.04-2.14 (2H, m), 2.22-2.50 (12H, m), 3.41-3.49 (6H, m), 3.69-3.73 (2H, m), 6.09-6.12 (1H, m), 6.44 (1H, t, J = 74.1 Hz), 7.00 (2H, d, J = 8.5 Hz), 7.08 (2H, d, J = 8.5 Hz), 7.17 (2H, d, J = 8.5 Hz), 7.26 (2H, d, J = 8.5 Hz). MS m/z: 792 (M + H)$^+$. |
| AM7 | $^1$H-NMR ($CDCl_3$) δ: 0.00 (9H, s), 0.92-0.98 (2H, m), 2.18-2.26 (1H, m), 2.62-2.75 (1H, m), 2.82-2.92 (1H, m), 3.02-3.09 (1H, m), 3.42 (3H, s), 3.61-3.67 (2H, m), 5.19 (1H, dd, J = 12.8, 5.5 Hz), 5.25 (1H, d, J = 9.7 Hz), 5.30 (1H, d, J = 9.7 Hz), 6.65 (1H, d, J = 9.1 Hz), 7.16-7.20 (2H, m). MS m/z: 490 [M($^{79}$Br) + Na]$^+$, 492 [M($^{81}$Br) + Na]$^+$. |
| AM8 | $^1$H-NMR ($CDCl_3$) δ: 0.00 (9H, s), 0.91-1.00 (2H, m), 2.22-2.32 (1H, m), 2.68-2.83 (1H, m), 2.85-2.97 (1H, m), 3.05-3.14 (1H, m), 3.53 (3H, s), 3.60-3.71 (2H, m), 5.23-5.35 (3H, m), 6.91 (1H, d, J = 8.5 Hz), 7.44 (2H, s), 7.89 (1H, d, J = 1.2 Hz), 8.05 (1H, dd, J = 8.5, 1.2 Hz), MS m/z: 634 (M + Na)$^+$. |
| AM9 | $^1$H-NMR ($CDCl_3$) δ: 0.00 (9H, s), 0.64 (3H, s), 0.86-1.00 (8H, s), 1.17 (3H, s), 1.37-1.68 (6H, m), 1.68-1.95 (2H, m), 1.95-2.15 (4H, m), 2.18-2.59 (14H, m), 2.62-3.11 (3H, m), 3.45-3.49 (6H, m), 3.62-3.74 (5H, m), 5.20-5.34 (3H, m), 6.09-6.13 (1H, m), 6.43 (1H, t, J = 74.4 Hz), 6.78 (1H, d, J = 7.9 Hz), 6.99 (2H, d, J = 8.5 Hz), 7.05-7.19 (5H, m), 7.21-7.31 (3H, m). MS m/z: 1107 (M + H)$^+$. |
| AM10 | $^1$H-NMR ($CDCl_3$) δ: 0.64 (3H, s), 0.92 (6H, s), 1.17 (3H, s), 1.35-1.49 (1H, m), 1.49-1.93 (8H, m), 1.96-2.16 (3H, m), 2.20-2.57 (13H, m), 2.65-3.04 (3H, m), 3.32-3.91 (10H, m), 5.20-5.27 (1H, m), 6.08-6.13 (1H, m), 6.43 (1H, t, J = 74.4 Hz), 6.81 (1H, d, J = 8.5 Hz), 6.99 (2H, d, J = 7.9 Hz), 7.07 (2H, d, J = 7.9 Hz), 7.10-7.19 (4H, m), 7.25 (2H, d, J = 7.9 Hz), 8.05 (1H, s). MS m/z: 977 (M + H)$^+$. |
| AN1 | MS m/z: 150 (M + H)$^+$. |
| AN2 | $^1$H-NMR ($CDCl_3$) δ: 3.52-3.55 (2H, m), 3.96 (1H, s), 4.00 (2H, dd, J = 5.7, 4.5 Hz), 6.41 (1H, t, J = 4.1 Hz), 6.54 (1H, d, J = 7.8 Hz), 6.86 (1H, t, J = 8.0 Hz), 8.24 (1H, s). MS m/z: 176 (M + H)$^+$. |
| AN3 | $^1$H-NMR ($CDCl_3$) δ: 0.67 (3H, s), 0.89 (6H, s), 1.16 (3H, s), 1.46-1.77 (9H, m), 1.83-2.00 (3H, m), 2.03-2.15 (2H, m), 2.23-2.62 (9H, m), 3.35-3.57 (4H, m), 3.65-3.78 (2H, m), 3.80 (3H, s), 3.93-4.05 (2H, m), 4.11-4.19 (2H, m), 4.60-4.68 (1H, m), 6.39-6.54 (1H, m), 6.66 (2H, d, J = 8.6 Hz), 6.81 (2H, d, J = 9.0 Hz), 6.83-6.89 (1H, m), 7.00-7.06 (3H, m), 7.11 (2H, d, J = 9.0 Hz). MS m/z: 832 (M + H)$^+$. |
| AN4 | MS m/z: 1073 (M + H)$^+$. |

TABLE 30

| Ex | Data |
|---|---|
| AN5 | $^1$H-NMR ($CDCl_3$) δ: 0.67 (3H, s), 0.89 (6H, s), 1.16 (3H, s), 1.45-2.15 (19H, m), 2.18-2.59 (5H, m), 2.66-3.03 (2H, m), 3.35-3.46 (4H, m), 3.66-3.78 (2H, m), 3.80 (3H, s), 3.99-4.23 (4H, m), 4.58-4.69 (1H, m), 5.16-5.25 (1H, m), 6.60-6.69 (3H, m), 6.81 (2H, d, J = 9.0 Hz), 7.00-7.07 (3H, m), 7.11 (2H, dd, J = 6.7, 2.0 Hz), 7.23-7.31 (1H, m), 8.00-8.08 (1H, m). MS m/z: 943 $(M + H)^+$. |
| AO1 | $^1$H-NMR ($CDCl_3$) δ: 1.45 (9H, s), 2.15-2.35 (2H, m), 2.49 (2H, t, J = 7.0 Hz), 4.16-4.22 (1H, m), 5.36 (2H, s), 5.46 (1H, br s), 6.19 (1H, br s), 6.80 (1H, d, J = 9.1 Hz), 7.34-7.46 (5H, m), 8.11 (1H, dd, J = 9.1, 2.1 Hz), 8.63 (1H, d, J = 6.1 Hz), 8.93 (1H, d, J = 2.1 Hz). MS m/z: 402 $(M - tBu + H)^+$. |
| AO2 | $^1$H-NMR ($CDCl_3$) δ: 1.38 (9H, s), 2.22 (2H, t, J = 7.3 Hz), 2.34-2.45 (1H, m), 2.54-2.64 (1H, m), 5.10 (1H, dd, J = 9.7, 5.5 Hz), 5.35 (2H, s), 5.65 (1H, br s), 6.46 (1H, br s), 7.19 (1H, d, J = 8.5 Hz), 7.33-7.46 (5H, m), 7.75 (1H, d, J = 1.8 Hz), 7.87 (1H, dd, J = 8.5, 1.8 Hz), 9.24 (1H, s). MS m/z: 476 $(M + Na)^+$. |
| AO3 | $^1$H-NMR ($CDCl_3$) δ: 1.40 (9H, s), 2.14-2.28 (2H, m), 2.35-2.45 (1H, m), 2.53-2.63 (1H, m), 3.47 (3H, s), 5.06 (1H, dd, J = 9.7, 6.1 Hz), 5.38 (2H, s), 5.48 (1H, br s), 6.42 (1H, br s), 7.19 (1H, d, J = 8.5 Hz), 7.32-7.48 (5H, m), 7.72 (1H, s), 7.90 (1H, d, J = 8.5 Hz). MS m/z: 490 $(M + Na)^+$. |
| AO4 | $^1$H-NMR ($CDCl_3$) δ: 1.41 (9H, s), 2.19-2.28 (2H, m), 2.37-2.47 (1H, m), 2.54-2.66 (1H, m), 3.50 (3H, s), 5.07-5.12 (1H, m), 5.61 (1H, br s), 6.45 (1H, br s), 7.24 (1H, d, J = 7.9 Hz), 7.74 (1H, s), 7.92 (1H, d, J = 7.9 Hz). MS m/z: 400 $(M + Na)^+$. |
| AO5 | MS m/z: 656 $(M + H)^+$. |
| AO6 | $^1$H-NMR ($CDCl_3$) δ: 0.66 (3H, s), 0.90 (6H, s), 1.16 (3H, s), 1.21-1.76 (8H, m), 1.41 (9H, s), 1.79-1.95 (3H, m), 1.95-2.67 (20H, m), 3.39-3.55 (2H, m), 3.46 (3H, s), 3.66-3.82 (2H, m), 3.78 (3H, s), 5.07 (1H, dd, J = 9.7, 6.1 Hz), 5.36 (1H, br s), 6.08-6.13 (1H, m), 6.39 (1H, br s), 6.80 (2H, d, J = 9.1 Hz), 7.04-7.20 (7H, m), 7.26 (2H, d, J = 5.5 Hz). MS m/z: 1015 $(M + H)^+$. |
| AO7 | $^1$H-NMR ($CDCl_3$) δ: 0.65 (3H, s), 0.91 (3H, s), 0.91 (3H, s), 1.16 (3H, s), 1.35-1.067 (6H, m), 1.67-1.80 (1H, m), 1.80-1.95 (3H, m), 1.95-2.03 (1H, m), 2.03-2.16 (3H, m), 2.20-2.59 (13H, m), 2.65-2.79 (1H, m), 2.79-2.91 (1H, m), 2.92-3.02 (1H, m), 3.40-3.54 (5H, m), 3.63-3.85 (6H, m), 5.24 (1H, dd, J = 12.5, 5.2 Hz), 6.07-6.12 (1H, m), 6.77-6.83 (3H, m), 7.05-7.18 (6H, m), 7.23-7.29 (2H, m), 8.02-8.10 (1H, m). MS m/z: 941 $(M + H)^+$. |
| AP1 | $^1$H-NMR ($CDCl_3$) δ: 1.45 (9H, s), 2.15-2.35 (2H, m), 2.49 (2H, t, J = 7.0 Hz), 4.16-4.22 (1H, m), 5.36 (2H, s), 5.46 (1H, br s), 6.19 (1H, br s), 6.80 (1H, d, J = 9.1 Hz), 7.34-7.46 (5H, m), 8.11 (1H, dd, J = 9.1, 2.1 Hz), 8.63 (1H, d, J = 6.1 Hz), 8.93 (1H, d, J = 2.1 Hz). MS m/z: 402 $(M - tBu + H)^+$. |

TABLE 31

| Ex | Data |
|---|---|
| AP2 | $^1$H-NMR ($CDCl_3$) δ: 1.38 (9H, s), 2.22 (2H, t, J = 7.3 Hz), 2.34-2.45 (1H, m), 2.54-2.64 (1H, m), 5.10 (1H, dd, J = 9.7, 5.5 Hz), 5.35 (2H, s), 5.69 (1H, br s), 6.49 (1H, br s), 7.19 (1H, d, J = 8.5 Hz), 7.33-7.46 (5H, m), 7.75 (1H, d, J = 1.8 Hz), 7.87 (1H, dd, J = 8.5, 1.8 Hz), 9.37 (1H, s). MS m/z: 476 $(M + Na)^+$. |
| AP3 | $^1$H-NMR ($CDCl_3$) δ: 1.40 (9H, s), 2.14-2.28 (2H, m), 2.35-2.45 (1H, m), 2.53-2.63 (1H, m), 3.47 (3H, s), 5.06 (1H, dd, J = 9.7, 6.1 Hz), 5.38 (2H, s), 6.38 (1H, br s), 7.19 (1H, d, J = 8.5 Hz), 7.32-7.48 (5H, m), 7.72 (1H, s), 7.90 (1H, d, J = 8.5 Hz). MS m/z: 490 $(M + Na)^+$. |
| AP4 | $^1$H-NMR ($CDCl_3$) δ: 1.41 (9H, s), 2.19-2.28 (2H, m), 2.37-2.47 (1H, m), 2.54-2.66 (1H, m), 3.50 (3H, s), 5.07-5.12 (1H, m), 5.91 (1H, br s), 6.56 (1H, br s), 7.24 (1H, d, J = 7.9 Hz), 7.74 (1H, s), 7.92 (1H, d, J = 7.9 Hz). MS m/z: 400 $(M + Na)^+$. |
| AP5 | $^1$H-NMR ($CDCl_3$) δ: 0.65 (3H, s), 0.90 (3H, s), 0.91 (3H, s), 1.15 (3H, s), 1.35-1.80 (8H, m), 1.41 (9H, s), 1.80-1.94 (3H, m), 1.94-2.64 (20H, m), 3.41-3.54 (2H, m), 3.46 (3H, s), 3.63-3.83 (2H, m), 3.78 (3H, s), 5.06 (1H, dd, J = 9.4, 5.8 Hz), 5.37 (1H, br s), 6.07-6.14 (1H, m), 6.39 (1H, br s), 6.80 (2H, d, J = 8.5 Hz), 7.05-7.19 (7H, m), 7.25 (2H, d, J = 5.5 Hz). MS m/z: 1015 $(M + H)^+$. |
| AP6 | $^1$H-NMR ($CDCl_3$) δ: 0.66 (3H, s), 0.90 (3H, s), 0.91 (3H, s), 1.16 (3H, s), 1.33-1.66 (6H, m), 1.66-1.79 (1H, m), 1.78-1.95 (3H, m), 1.95-2.03 (1H, m), 2.05-2.16 (2H, m), 2.20-2.62 (13H, m), 2.66-2.79 (1H, m), 2.85 (1H, dt, J = 22.3, 7.6 Hz), 2.93-3.02 (1H, m), 3.39-3.57 (6H, m), 3.62-3.86 (6H, m), 5.24 (1H, dd, J = 12.5, 5.2 Hz), 6.07-6.13 (1H, m), 6.78-6.83 (3H, m), 7.05-7.18 (6H, m), 7.23-7.29 (2H, m), 8.07 (1H, br s). MS m/z: 941 $(M + H)^+$. |
| AQ1 | $^1$H-NMR ($CDCl_3$) δ: 0.66 (3H, s), 0.89 (6H, s), 1.16 (3H, s), 1.46-1.66 (5H, m), 1.69-1.91 (5H, m), 1.94-2.02 (2H, m), 2.02-2.21 (3H, m), 2.21-2.39 (3H, m), 2.39-2.48 (1H, m), 2.48-2.65 (3H, m), 2.69-2.96 (3H, m), 3.15 (2H, s), 3.36-3.46 (2H, m), 3.65-3.81 (6H, m), 4.61-4.70 (1H, m), 4.94-5.02 (1H, m), 6.67 (2H, d, J = 8.5 Hz), 6.81 (2H, d, J = 9.1 Hz), 7.05 (2H, d, J = 8.5 Hz), 7.10 (2H, d, J = 8.5 Hz), 7.85 (1H, d, J = 8.5 Hz), 7.98 (1H, s), 8.03-8.07 (2H, m), 9.72 (1H, s). MS m/z: 930 $(M + H)^+$. |
| AR1 | $^1$H-NMR ($CDCl_3$) δ: 0.67 (3H, s), 1.19 (3H, s), 1.57-1.71 (3H, m), 1.73-2.04 (3H, m), 2.16 (1H, dd, J = 14.0, 2.4 Hz), 2.25-2.44 (5H, m), 2.74-2.84 (1H, m), 3.22-3.32 (1H, m), 3.74-3.85 (5H, m), 5.11 (1H, br s), 6.89 (2H, d, J = 8.5 Hz), 7.23 (2H, d, J = 8.5 Hz). MS m/z: 414 $(M + H)^+$. |

TABLE 32

| Ex | Data |
|---|---|
| AR2 | $^1$H-NMR ($CDCl_3$) δ: 0.67 (3H, s), 1.19 (3H, s), 1.53-1.69 (3H, m), 1.73-1.96 (5H, m), 2.09-2.22 (4H, m), 2.30-2.37 (1H, m), 2.39-2.47 (1H, m), 2.61 (2H, s), 3.72-3.85 (5H, m), 6.86 (2H, d, J = 8.5 Hz), 7.20 (2H, d, J = 8.5 Hz). MS m/z: 400 $(M + H)^+$. |
| AR3 | $^1$H-NMR ($CDCl_3$) δ: 0.66 (3H, s), 1.16 (3H, s), 1.28 (3H, t, J = 7.3 Hz), 1.47-1.68 (3H, m), 1.68-1.95 (7H, m), 2.00-2.30 (6H, m), 2.40-2.54 (6H, m), 2.55-2.67 (1H, m), 3.38-3.49 (2H, m), 3.66-3.76 (2H, m), 3.78 (3H, s), 4.17 (2H, q, J = 7.1 Hz), 6.08-6.12 (1H, m), 6.80 (2H, d, J = 8.5 Hz), 7.10 (2H, d, J = 8.5 Hz), 7.12 (2H, d, J = 8.5 Hz), 7.25 (2H, d, J = 8.5 Hz). MS m/z: 642 $(M + H)^+$. |
| AR4 | $^1$H-NMR ($CDCl_3$) δ: 0.66 (3H, s), 1.16 (3H, s), 1.44-1.66 (13H, m), 1.68-1.94 (8H, m), 1.95-2.17 (5H, m), 2.22-2.48 (12H, m), 3.39-3.49 (6H, m), 3.66-3.75 (2H, m), 3.79 (3H, s), 6.08-6.12 (1H, m), 6.80 (2H, d, J = 9.1 Hz), 7.10 (2H, d, J = 9.1 Hz), 7.11 (2H, d, J = 7.9 Hz), 7.26 (2H, d, J = 7.9 Hz). MS m/z: 768 (M + H)+. |
| AR5 | MS m/z: 668 $(M + H)^+$. |
| AR6 | $^1$H-NMR ($CDCl_3$) δ: 0.00 (9H, s), 0.65 (3H, s), 0.93-0.99 (2H, m), 1.16 (3H, s), 1.36-1.66 (8H, m), 1.67-1.95 (6H, m), 1.95-2.55 (17H, m), 2.64-2.76 (1H, m), 2.83-2.96 (1H, m), 3.02-3.10 (1H, m), 3.39-3.49 (6H, m), 3.61-3.81 (9H, m), 5.20-5.33 (3H, m), 6.08-6.12 (1H, m), 6.76-6.82 (3H, m), 7.07-7.17 (6H, m), 7.24-7.29 (2H, m). MS m/z: 1083 $(M + H)^+$. |
| AR7 | $^1$H-NMR ($CDCl_3$) δ: 0.65 (3H, s), 1.16 (3H, s), 1.42-1.69 (4H, m), 1.69-2.19 (12H, m), 2.19-2.56 (13H, m), 2.64-3.03 (3H, m), 3.39-3.88 (15H, m), 5.24 (1H, dd, J = 12.5, 5.2 Hz), 6.08-6.14 (1H, m), 6.77-6.85 (3H, m), 7.06-7.19 (6H, m), 7.23-7.30 (2H, m), 8.07 (1H, s). MS m/z: 953 $(M + H)^+$. |
| AS1 | $^1$H-NMR ($CDCl_3$) δ: 0.00 (9H, s), 0.92-0.99 (2H, m), 2.22-2.29 (1H, m), 2.69-2.80 (1H, m), 2.85-2.95 (1H, m), 3.05-3.12 (1H, m), 3.50 (3H, s), 3.61-3.69 (2H, m), 5.22-5.34 (3H, m), 6.91 (1H, d, J = 8.5 Hz), 7.58-7.62 (2H, m), 9.95 (1H, s). MS m/z: 390 $(M - C_2H_4 + H)^+$. |
| AS2 | $^1$H-NMR ($CDCl_3$) δ: 0.00 (9H, s), 0.93-0.98 (2H, m), 2.18-2.25 (1H, m), 2.36-2.45 (4H, m), 2.64-2.77 (1H, m), 2.82-2.92 (1H, m), 3.01-3.10 (1H, m), 3.44 (3H, s), 3.49-3.54 (6H, m), 3.61-3.68 (2H, m), 5.13 (2H, s), 5.20-5.33 (3H, m), 6.70 (1H, d, J = 7.9 Hz), 6.97 (1H, d, J = 7.9 Hz), 7.03 (1H, s), 7.29-7.38 (5H, m). MS m/z: 622 $(M + H)^+$. |
| AS3 | $^1$H-NMR ($CDCl_3$) δ: 2.22-2.27 (1H, m), 2.41 (4H, s), 2.67-2.98 (3H, m), 3.44 (3H, s), 3.48-3.55 (6H, m), 5.13 (2H, s), 5.21 (1H, dd, J = 12.5, 5.2 Hz), 6.73 (1H, d, J = 8.5 Hz, 7.00 (1H, d, J = 8.5 Hz), 7.03 (1H, s), 7.29-7.39 (5H, m), 8.04 (1H, s). MS m/z: 492 $(M + H)^+$. |

TABLE 33

| Ex | Data |
|---|---|
| AS4 | MS m/z: 358 $(M + H)^+$. |
| AS5 | $^1$H-NMR ($CDCl_3$) δ: 1.29 (3H, t, J = 7.3 Hz), 1.82-1.96 (1H, m), 2.09-2.19 (1H, m), 2.22-2.36 (2H, m), 2.34 (3H, s), 2.40-2.49 (2H, m), 2.67 (1H, tt, J = 11.5, 3.8 Hz), 4.19 (2H, q, J = 7.3 Hz), 5.58-5.64 (1H, m), 7.22 (1H, d, J = 7.9 Hz), 7.65 (1H, d, J = 7.9 Hz), 7.68 (1H, s), 9.96 (1H, s). |
| AS6 | $^1$H-NMR ($CDCl_3$) δ: 0.66 (3H, s), 0.91 (6H, s), 1.16 (3H, s), 1.29 (3H, t, J = 7.3 Hz), 1.45-1.66 (3H, m), 1.68-1.79 (1H, m), 1.80-1.93 (2H, m), 2.02-2.18 (3H, m), 2.21 (3H, s), 2.23-2.38 (5H, m), 2.39-2.46 (2H, m), 2.59-2.70 (1H, m), 3.45 (2H, dd, J = 19.4, 14.0 Hz), 3.65-3.81 (2H, m), 3.78 (3H, s), 4.18 (2H, q, J = 7.1 Hz), 5.50-5.56 (1H, m), 6.80 (2H, d, J = 8.5 Hz), 6.92 (1H, s), 6.93 (2H, d, J = 6.7 Hz), 7.10 (2H, d, J = 8.5 Hz). |
| AS7 | $^1$H-NMR ($CDCl_3$) δ: 0.66 (3H, s), 0.91 (3H, s), 0.92 (3H, s), 1.16 (3H, s), 1.43-1.68 (5H, m), 1.68-1.82 (1H, m), 1.82-2.00 (3H, m), 2.00-2.16 (2H, m), 2.17-2.41 (10H, m), 2.41-2.63 (5H, m), 2.63-3.08 (4H, m), 3.34-3.52 (5H, m), 3.52-3.63 (3H, m), 3.63-3.87 (6H, m), 5.16-5.31 (1H, m), 5.50-5.62 (1H, m), 6.69-6.88 (3H, m), 6.88-7.17 (7H, m), 8.02-8.14 (1H, m). MS m/z: 955 $(M + H)^+$. |
| AT1 | $^1$H-NMR ($CDCl_3$) δ: 1.29 (3H, t, J = 7.0 Hz), 1.79-1.93 (1H, m), 2.15-2.26 (1H, m), 2.43-2.57 (4H, m), 2.58-2.69 (1H, m), 4.18 (2H, q, J = 7.1 Hz), 6.30-6.36 (1H, m), 7.15 (1H, d, J = 12.1 Hz), 7.29 (1H, d, J = 9.1 Hz), 7.81 (1H, t, J = 7.6 Hz), 10.31 (1H, s). |
| AT2 | $^1$H-NMR ($CDCl_3$) δ: 0.66 (3H, s), 0.87 (3H, s), 0.88 (3H, s), 1.17 (3H, s), 1.29 (3H, t, J = 7.0 Hz), 1.49-1.69 (4H, m), 1.70-1.95 (3H, m), 2.06-2.25 (3H, m), 2.25-2.36 (1H, m), 2.36-2.40 (2H, m), 2.40-2.55 (4H, m), 2.55-2.66 (1H, m), 3.52 (2H, dd, J = 24.0, 14.3 Hz), 3.66-3.81 (2H, m), 3.78 (3H, s), 4.18 (1H, q, J = 7.1 Hz), 6.10-6.17 (1H, m), 6.80 (2H, d, J = 8.5 Hz), 6.98 (1H, d, J = 12.1 Hz), 7.03 (1H, d, J = 7.9 Hz), 7.08 (1H, d, J = 7.3 Hz), 7.12 (2H, d, J = 9.1 Hz). |
| AT3 | $^1$H-NMR ($CDCl_3$) δ: 0.66 (3H, s), 0.86 (3H, s), 0.87 (3H, s), 1.17 (3H, s), 1.44-2.65 (20H, m), 2.65-3.04 (4H, m), 3.39-3.62 (10H, m), 3.62-3.83 (7H, m), 5.10-5.31 (1H, m), 6.10-6.20 (1H, m), 6.68-6.88 (3H, m), 6.88-7.18 (7H, m), 7.99-8.11 (1H, m). MS m/z: 959 $(M + H)^+$. |
| AU1 | $^1$H-NMR ($CDCl_3$) δ: 0.65 (3H, s), 0.97 (6H, s), 1.16 (3H, s), 1.29 (3H, t, J = 7.0 Hz), 1.40-1.65 (3H, m), 1.71 (1H, td, J = 12.1, 3.6 Hz), 1.79-1.94 (2H, m), 2.03-2.19 |

TABLE 33-continued

| Ex | Data |
| --- | --- |
| | (3H, m), 2.21-2.51 (7H, m), 2.67 (1H, tt, J = 11.8, 3.9 Hz), 3.44 (2H, s), 3.63-3.80 (2H, m), 3.77 (3H, s), 4.18 (2H, q, J = 7.3 Hz), 5.74-5.82 (1H, m), 6.66 (2H, d, J = 8.5 Hz), 6.79 (2H, d, J = 8.5 Hz), 7.09 (2H, d, J = 8.5 Hz). MS m/z: 666 $(M + H)^+$. |

TABLE 34

| Ex | Data |
| --- | --- |
| AU2 | $^1$H-NMR ($CDCl_3$) δ: 0.65 (3H, s), 0.97 (6H, s), 1.16 (3H, s), 1.44-1.66 (3H, m), 1.48 (9H, s), 1.66-1.79 (1H, m), 1.79-2.00 (3H, m), 2.05-2.17 (2H, m), 2.17-2.35 (3H, m), 2.35-2.51 (3H, m), 2.51-2.64 (1H, m), 2.79-2.94 (1H, m), 3.33-3.77 (12H, m), 3.78 (3H, s), 5.78-5.85 (1H, m), 6.67 (2H, d, J = 8.5 Hz), 6.79 (2H, d, J = 8.5 Hz), 7.09 (2H, d, J = 8.5 Hz). MS m/z: 806 $(M + H)^+$. |
| AU3 | $^1$H-NMR ($CDCl_3$) δ: 0.00 (9H, s), 0.65 (3H, s), 0.92-1.00 (2H, m), 0.97 (6H, s), 1.16 (3H, s), 1.36-1.99 (6H, m), 2.02-2.35 (8H, m), 2.34-2.64 (8H, m), 2.64-2.79 (1H, m), 2.79-2.95 (2H, m), 3.00-3.11 (1H, m), 3.40-3.48 (5H, m), 3.52-3.81 (9H, m), 3.77 (3H, s), 5.23 (1H, dd, J = 13.7, 5.8 Hz), 5.29 (2H, q, J = 8.9 Hz), 5.78-5.85 (1H, m), 6.67 (2H, d, J = 7.9 Hz), 6.72 (1H, d, J = 7.9 Hz), 6.79 (2H, d, J = 9.1 Hz), 6.99 (1H, d, J = 7.9 Hz), 7.02-7.12 (3H, m). MS m/z: 1107 $(M + H)^+$. |
| AU4 | $^1$H-NMR ($CDCl_3$) δ: 0.65 (3H, s), 0.97 (6H, s), 1.16 (3H, s), 1.40-1.79 (5H, m), 1.79-2.02 (3H, m), 2.02-2.19 (2H, m), 2.19-2.65 (12H, m), 2.65-2.91 (3H, m), 2.91-3.04 (1H, m), 3.37-3.83 (15H, m), 5.13-5.28 (1H, m), 5.77-5.86 (1H, m), 6.61-6.73 (2H, m), 6.73-6.84 (3H, m), 6.97-7.14 (4H, m), 8.07 (1H, br s). MS m/z: 977 $(M + H)^+$. |
| AV1 | $^1$H-NMR ($CDCl_3$) δ: 0.66 (3H, s), 0.90 (3H, s), 0.91 (3H, s), 1.17 (3H, s), 1.29 (3H, t, J = 7.0 Hz), 1.47-1.67 (3H, m), 1.75 (1H, td, J = 12.1, 3.6 Hz), 1.80-1.92 (2H, m), 2.06-2.20 (3H, m), 2.29 (1H, td, J = 12.5, 4.9 Hz), 2.35-2.57 (6H, m), 2.58-2.70 (1H, m), 3.53 (2H, s), 3.67-3.81 (2H, m), 3.78 (3H, s), 4.18 (2H, q, J = 7.3 Hz), 5.94-5.99 (1H, m), 6.80 (2H, d, J = 9.1 Hz), 6.83 (2H, t, J = 4.3 Hz), 7.11 (2H, d, J = 9.1 Hz). MS m/z: 666 $(M + H)^+$. |
| AV2 | $^1$H-NMR ($CDCl_3$) δ: 0.66 (3H, s), 0.90 (3H, s), 0.90 (3H, s), 1.17 (3H, s), 1.45-2.01 (10H, m), 2.03-2.18 (2H, m), 2.18-2.35 (3H, m), 2.35-2.63 (9H, m), 2.63-2.92 (3H, m), 2.92-3.03 (1H, m), 3.40-3.85 (13H, m), 5.13-5.28 (1H, m), 5.92-6.04 (1H, m), 6.69-6.92 (5H, m), 6.97-7.07 (2H, m), 7.07-7.15 (2H, m), 8.08 (1H, br s). MS m/z: 977 $(M + H)^+$. |
| AW1 | $^1$H-NMR (DMSO-$D_6$) δ: 2.00-2.06 (2H, m), 2.59-2.67 (2H, m), 3.63-3.69 (2H, m), 6.66 (1H, d, J = 7.9 Hz), 7.30 (1H, d, J = 7.9 Hz), 10.79 (1H, s). MS m/z: 301 $(M + H)^+$. |
| AW2 | $^1$H-NMR ($CDCl_3$) δ: 0.00 (9H, s), 0.92-0.98 (2H, m), 2.13-2.26 (2H, m), 2.59-2.71 (1H, m), 2.74-2.81 (1H, m), 2.84-2.93 (1H, m), 3.01-3.09 (1H, m), 3.60-3.67 (2H, m), 3.81-3.88 (1H, m), 5.18-5.31 (3H, m), 6.43 (1H, d, J = 7.39 Hz), 7.39 (1H, d, J = 7.9 Hz). MS m/z: 564 $(M + Na)^+$. |

TABLE 35

| Ex | Data |
| --- | --- |
| AW3 | $^1$H-NMR ($CDCl_3$) δ: 0.00 (9H, s), 0.93-1.00 (2H, m), 2.14-2.33 (3H, m), 2.63-2.78 (1H, m), 2.87-2.96 (1H, m), 3.04-3.13 (1H, m), 3.30-3.39 (2H, m), 3.59-3.70 (2H, m), 3.85-3.97 (2H, m), 5.15-5.37 (3H, m), 6.75 (1H, d, J = 8.5 Hz), 7.43 (2H, s), 8.05 (1H, d, J = 8.5 Hz). |
| AW4 | $^1$H-NMR ($CDCl_3$) δ: 0.00 (9H, s), 0.65 (3H, s), 0.87-1.00 (8H, m), 1.16 (3H, s), 1.36-1.64 (6H, m), 1.67-1.79 (1H, m), 1.82-1.92 (3H, m), 1.95-2.01 (1H, m), 2.04-2.99 (20H, m), 3.02-3.12 (1H, m), 3.30-3.39 (2H, m), 3.41-3.53 (2H, m), 3.60-3.97 (10H, m), 5.12-5.43 (3H, m), 6.09 (1H, br s), 6.63 (1H, d, J = 7.9 Hz), 6.80 (2H, d, J = 9.1 Hz), 6.90 (1H, d, J = 7.9 Hz), 7.08-7.10 (4H, m), 7.25 (2H, d, J = 6.1 Hz). MS m/z: 1097 $(M + H)^+$. |
| AW5 | $^1$H-NMR ($CDCl_3$) δ: 0.65 (3H, s), 0.90 (6H, s), 1.15 (3H, s), 1.35-1.65 (7H, m), 1.68-1.78 (1H, m), 1.80-2.02 (4H, m), 2.04-2.19 (4H, m), 2.22-3.05 (16H, m), 3.30-3.40 (2H, m), 3.41-3.53 (2H, m), 3.63-3.98 (9H, m), 5.19-5.25 (1H, br m), 6.09 (1H, br s), 6.66 (1H, d, J = 7.9 Hz), 6.80 (2H, d, J = 9.1 Hz), 6.92 (1H, d, J = 7.9 Hz), 7.06-7.13 (4H, m), 7.25 (2H, d, J = 7.3 Hz), 8.16 (1H, s). MS m/z: 967 $(M + H)^+$. |
| AX1 | $^1$H-NMR ($CDCl_3$) δ: 0.66 (3H, s), 0.91 (6H, s), 1.16 (3H, s), 1.45-1.64 (3H, m), 1.68-1.77 (1H, m), 1.82-1.91 (1H, m), 1.99-2.14 (6H, m), 2.24-2.38 (3H, m), 2.39-2.54 (3H, m), 3.42-3.49 (4H, m), 3.68-3.75 (2H, m), 3.78 (3H, s), 6.05-6.09 (1H, m), 6.80 (2H, d, J = 8.5 Hz), 7.07-7.11 (4H, m), 7.25 (2H, d, J = 8.5 Hz). MS m/z: 650 $[M(^{79}Br) + H]^+$, 652 $[M(^{81}Br) + H]^+$. |

TABLE 35-continued

| Ex | Data |
|---|---|
| AX2 | MS m/z: 770 $(M + H)^+$. |
| AX3 | $^1$H-NMR ($CDCl_3$) δ: 0.66 (3H, s), 0.91 (6H, s), 1.16 (3H, s), 1.39-1.78 (4H, m), 1.81-2.13 (6H, m), 2.20-2.56 (8H, m), 2.64-3.01 (5H, m), 3.20 (2H, s), 3.32-3.53 (9H, m), 3.60 (2H, s), 3.65-3.81 (5H, m), 5.23 (1H, dd, J = 13.1, 5.2 Hz), 6.05-6.09 (1H, m), 6.75 (1H, d, J = 7.9 Hz), 6.80 (2H, d, J = 8.5 Hz), 6.99-7.13 (6H, m), 7.24 (2H, d, J = 8.5 Hz), 8.20 (1H, s). MS m/z: 941 $(M + H)^+$. |
| AY1 | $^1$H-NMR ($CDCl_3$) δ: 0.00 (9H, s), 0.91-0.98 (2H, m), 2.23-2.30 (1H, m), 2.67-2.79 (1H, m), 2.85-2.95 (1H, m), 3.05-3.13 (1H, m), 3.52 (3H, s), 3.61-3.68 (2H, m), 5.21-5.32 (3H, m), 6.86 (1H, d, J = 8.5 Hz), 7.94 (1H, d, J = 2.4 Hz), 8.07 (1H, dd, J = 8.5, 2.4 Hz). MS m/z: 407 $(M - C_2H_4 + H)^+$. |
| AY2 | $^1$H-NMR ($CDCl_3$) δ: 0.00 (9H, s), 0.92-0.99 (2H, m), 2.16-2.23 (1H, m), 2.61-2.73 (1H, m), 2.81-2.91 (1H, m), 2.99-3.07 (1H, m), 3.37 (3H, s), 3.54-3.68 (4H, m), 5.17 (1H, dd, J = 13.1, 5.2 Hz), 5.25-5.31 (2H, m), 6.37-6.41 (2H, m), 6.55 (1H, d, J = 9.1 Hz). |

TABLE 36

| Ex | Data |
|---|---|
| AY3 | $^1$H-NMR ($CDCl_3$) δ: −0.02 (9H, s), 0.91-0.95 (2H, m), 2.14-2.21 (1H, m), 2.59-2.72 (1H, m), 2.81-2.90 (1H, m), 3.00-3.07 (1H, m), 3.40 (3H, s), 3.58-3.65 (2H, m), 5.14 (1H, dd, J = 13.1, 5.2 Hz), 5.22-5.29 (2H, m), 6.61 (1H, d, J = 7.9 Hz), 6.75 (1H, dd, J = 7.9, 1.8 Hz), 7.01 (1H, d, J = 1.8 Hz), 7.30 (1H, s), 7.60 (1H, t, J = 7.9 Hz), 7.72 (1H, t, J = 7.9 Hz), 7.82 (1H, d, J = 7.9 Hz), 7.88 (1H, d, J = 7.9 Hz). MS m/z: 612 $(M + Na)^+$. |
| AY4 | $^1$H-NMR ($CDCl_3$) δ: 0.00 (9H, s), 0.92-1.00 (2H, m), 1.44 (9H, s), 1.70-1.88 (1H, m), 2.16-2.34 (4H, m), 2.60-2.82 (2H, m), 2.82-2.96 (1H, m), 3.01-3.12 (1H, m), 3.35-3.42 (2H, m), 3.58-3.74 (3H, m), 4.53-4.96 (1H, m), 4.96-5.23 (2H, m), 5.28 (2H, dd, J = 14.3, 9.4 Hz), 6.61-6.77 (2H, m), 6.78-6.86 (1H, m), 7.46-7.56 (1H, m), 7.56-7.61 (1H, m), 7.63-7.73 (2H, m). MS m/z: 781 $(M + Na)^+$. |
| AY5 | $^1$H-NMR ($CDCl_3$) δ: 0.00 (9H, s), 0.92-0.99 (2H, m), 1.45 (9H, s), 2.12-2.40 (5H, m), 2.57-2.74 (1H, m), 2.79-2.92 (1H, m), 2.98-3.09 (1H, m), 3.37 (3H, s), 3.57-3.70 (2H, m), 3.70-3.89 (1H, m), 3.89-4.00 (1H, m), 4.20-4.36 (1H, m), 4.69-4.89 (1H, m), 5.17 (1H, dd, J = 13.1, 5.2 Hz), 5.28 (2H, dd, J = 17.0, 9.7 Hz), 6.16-6.26 (2H, m), 6.57 (1H, d, J = 7.9 Hz). |
| AY6 | MS m/z: 374 $(M + H)^+$. |
| AY7 | MS m/z: 602 $(M + H)^+$. |
| AY8 | $^1$H-NMR ($CDCl_3$) δ: 0.66 (3H, s), 0.91 (3H, s), 0.91 (3H, s), 1.16 (3H, s), 1.39-1.67 (8H, m), 1.67-1.85 (1H, m), 1.82-1.97 (2H, m), 2.02-2.17 (3H, m), 2.17-2.62 (8H, m), 2.62-2.75 (1H, m), 2.75-2.89 (1H, m), 2.89-3.01 (1H, m), 3.31-3.40 (3H, m), 3.40-3.57 (2H, m), 3.61-3.83 (5H, m), 3.81-3.93 (1H, m), 3.93-4.04 (1H, m), 4.49-4.69 (1H, m), 5.11-5.23 (1H, m), 5.73-5.88 (1H, m), 6.09-6.16 (1H, m), 6.16-6.29 (2H, m), 6.55-6.65 (1H, m), 6.72-6.83 (2H, m), 7.05-7.16 (4H, m), 7.19-7.30 (2H, m), 8.09 (1H, s). MS m/z: 927 $(M + H)^+$. |
| AZ1 | $^1$H-NHR ($CDCl_3$) δ: 1.47 (9H, s), 1.69-1.77 (4H, m), 2.47-2.61 (4H, m), 3.33-3.39 (2H, m), 3.43-3.49 (2H, m), 3.95 (3H, s), 5.05-5.15 (1H, m), 7.41 (1H, d, J = 8.8 Hz), 8.04 (1H, dd, J = 8.8, 2.0 Hz), 8.14 (1H, s), 8.51 (1H, d, J = 2.0 Hz). MS m/z: 344 $(M - tBu + H)^+$. |
| AZ2 | $^1$H-NMR ($CDCl_3$) δ: 1.47 (9H, s), 1.68-1.75 (4H, m), 2.51-2.62 (4H, m), 3.34-3.39 (2H, m), 3.42-3.47 (2H, m), 3.94 (3H, s), 5.03-5.13 (1H, m), 7.72 (1H, d, J = 9.1 Hz), 7.90 (1H, dd, J = 9.1, 1.8 Hz), 8.09 (1H, s), 8.49 (1H, s). MS m/z: 314 $(M - tBu + H)^+$. |
| AZ3 | $^1$H-NMR ($CDCl_3$) δ: 1.47 (9H, s), 1.66-1.75 (4H, m), 2.48-2.59 (4H, m), 3.33-3.37 (2H, m), 3.41-3.47 (2H, m), 4.75 (2H, s), 5.01-5.09 (1H, m), 7.30 (1H, d, J = 8.5 Hz), 7.61 (1H, s), 7.72 (1H, d, J = 8.5 Hz), 7.94 (1H, s). MS m/z: 372 $(M + H)^+$. |

TABLE 37

| Ex | Data |
|---|---|
| AZ4 | $^1$H-NMR ($CDCl_3$) δ: 1.47 (9H, s), 1.69-1.75 (4H, m), 2.51-2.63 (4H, m), 3.34-3.39 (2H, m), 3.43-3.47 (2H, m), 5.03-5.16 (1H, m), 7.77 (1H, d, J = 9.1 Hz), 7.82 (1H, dd, J = 9.1, 1.8 Hz), 8.18 (1H, s), 8.21 (1H, d, J = 1.8 Hz), 10.00 (1H, s). MS m/z: 370 $(M + H)^+$. |
| AZ5 | $^1$H-NMR ($CDCl_3$) δ: 0.64 (3H, s), 0.89 (3H, s), 0.89 (3H, s), 1.15 (3H, s), 1.44-1.53 (10H, m), 1.59-1.67 (2H, m), 1.67-1.79 (5H, m), 1.86-1.95 (1H, m), 2.05-2.13 (2H, m), 2.29-2.44 (3H, m), 2.49-2.60 (4H, m), 3.34-3.38 (2H, m), 3.42-3.49 (2H, m), 3.48-3.55 (2H, m), 3.64-3.77 (5H, m), 5.03-5.07 (1H, m), 6.77 (2H, d, J = 9.1 Hz), 7.09 (2H, d, J = 9.1 Hz), 7.18 (1H, d, J = 9.1 Hz), 7.27 (1H, s), 7.61 (1H, d, J = 9.1 Hz), 7.87 (1H, s). MS m/z: 741 $(M + H)^+$. |
| AZ6 | $^1$H-NMR ($CDCl_3$) δ: 0.65 (3H, s), 0.88-0.90 (6H, m), 1.15 (3H, s), 1.45-1.66 (12H, m), 1.73-1.96 (6H, m), 2.04-2.13 (2H, m), 2.28-2.62 (11H, m), 3.12 (2H, s), 3.48-3.56 (2H, m), 3.64-3.77 (5H, m), 4.98-5.06 (1H, m), 6.76 (2H, d, J = 8.5 Hz), |

TABLE 37-continued

| Ex | Data |
|---|---|
| | 7.09 (2H, d, J = 8.5 Hz), 7.17 (1H, d, J = 8.5 Hz), 7.26-7.28 (1H, m), 7.61 (1H, d, J = 8.5 Hz), 7.87 (1H, s). MS m/z: 755 $(M + H)^+$. |
| AZ7 | MS m/z: 699 $(M + H)^+$. |
| AZ8 | $^1$H-NMR ($CDCl_3$) δ: 0.65 (3H, s), 0.89 (3H, s), 0.89 (3H, s), 1.15 (3H, s), 1.44-1.66 (3H, m), 1.72-1.83 (1H, m), 1.83-1.95 (4H, m), 2.04-2.15 (2H, m), 2.20-2.42 (4H, m), 2.51-3.01 (12H, m), 3.11-3.17 (2H, m), 3.45 (3H, s), 3.48-3.57 (2H, m), 3.64-3.79 (5H, m), 5.01-5.08 (1H, m), 5.20 (1H, dd, J = 12.8, 5.5 Hz), 6.72-6.79 (3H, m), 6.93-6.98 (1H, m), 7.10 (2H, d, J = 9.1 Hz), 7.19 (1H, d, J = 9.1 Hz), 7.26-7.29 (1H, m), 7.61 (1H, d, J = 9.1 Hz), 7.72 (1H, s), 7.88 (1H, s), 8.06 (1H, s), 9.23 (1H, s). MS m/z: $(M + H)^+$. |
| BA1 | $^1$H-NMR ($CDCl_3$) δ: 1.47 (9H, s), 1.67-1.77 (4H, m), 2.45-2.59 (4H, m), 3.33-3.38 (2H, m), 3.43-3.47 (2H, m), 4.79 (2H, s), 5.03-5.13 (1H, m), 7.40-7.41 (2H, m), 7.70 (1H, s), 8.02 (1H, s). MS m/z: 316 $(M - tBu + H)^+$. |
| BA2 | $^1$H-NMR ($CDCl_3$) δ: 1.47 (9H, s), 1.67-1.78 (4H, m), 2.47-2.62 (4H, m), 3.33-3.39 (2H, m), 3.43-3.48 (2H, m), 5.05-5.16 (1H, m), 7.49 (1H, d, J = 8.5 Hz), 7.93 (1H, d, J = 8.5 Hz), 8.21 (1H, s), 8.25 (1H, s), 10.04 (1H, s). MS m/z: 314 $(M - tBu + H)^+$. |
| BA3 | $^1$H-NMR ($CDCl_3$) δ: 0.64 (3H, s), 0.91 (3H, s), 0.92 (3H, s), 1.15 (3H, s), 1.44-1.65 (11H, m), 1.68-1.81 (5H, m), 1.85-1.94 (1H, m), 2.03-2.13 (2H, m), 2.26-2.61 (8H, m), 3.33-3.39 (2H, m), 3.42-3.49 (2H, m), 3.53-3.61 (2H, m), 3.63-3.77 (5H, m), 5.02-5.10 (1H, m), 6.75 (2H, d, J = 9.1 Hz), 7.08 (2H, d, J = 9.1 Hz), 7.20-7.30 (2H, m), 7.39 (1H, s), 7.97 (1H, s). MS m/z: 741 $(M + H)^+$. |

TABLE 38

| Ex | Data |
|---|---|
| BA4 | $^1$H-NMR ($CDCl_3$) δ: 0.64 (3H, s), 0.91 (3H, s), 0.92 (3H, s), 1.15 (3H, s), 1.45-1.64 (11H, m), 1.70-1.94 (5H, m), 2.04-2.13 (2H, m), 2.26-2.64 (11H, m), 3.12 (2H, s), 3.53-3.61 (2H, m), 3.64-3.77 (5H, m), 4.09-4.15 (2H, m), 4.98-5.06 (1H, m), 6.75 (2H, d, J = 9.1 Hz), 7.08 (2H, d, J = 9.1 Hz), 7.19-7.80 (2H, m), 7.39 (1H, s), 7.96 (1H, s). |
| BA5 | MS m/z: 699 $(M + H)^+$. |
| BA6 | $^1$H-NMR ($CDCl_3$) δ: 0.64 (3H, s), 0.91 (3H, s), 0.92 (3H, s), 1.15 (3H, s), 1.46-1.66 (2H, m), 1.68-1.97 (6H, m), 2.02-2.13 (2H, m), 2.21-3.02 (16H, m), 3.11-3.17 (2H, m), 3.46 (3H, s), 3.52-3.78 (7H, m), 5.00-5.10 (1H, m), 5.20 (1H, dd, J = 12.8, 5.5 Hz), 6.71-6.78 (3H, m), 6.92-6.99 (1H, m), 7.08 (2H, d, J = 9.1 Hz), 7.21-7.31 (2H, m), 7.40 (1H, s), 7.73 (1H, d, J = 1.8 Hz), 7.98 (1H, s), 8.02 (1H, s), 9.25 (1H, s). MS m/z: 955 $(M + H)^+$. |
| BB1 | $^1$H-NMR ($CDCl_3$) δ: 1.40-1.55 (9H, m), 1.71-3.03 (7H, m), 4.83-5.23 (1H, m). |
| BB2 | $^1$H-NMR ($CDCl_3$) δ: 1.48 (9H, s), 1.73-1.97 (1H, m), 2.05-2.25 (1H, m), 2.40-2.61 (3H, m), 2.61-2.82 (2H, m), 7.25-7.44 (2H, m), 7.85 (2H, d, J = 8.5 Hz), 9.99 (1H, s). |
| BB3 | $^1$H-NMR ($CDCl_3$) δ: 0.66 (3H, s), 0.92 (6H, s), 1.16 (3H, s), 1.39-1.67 (3H, m), 1.48 (9H, s), 1.67-1.95 (3H, m), 2.01-2.22 (4H, m), 2.22-2.77 (7H, m), 3.41-3.58 (2H, m), 3.63-3.83 (2H, m), 3.78 (3H, s), 6.80 (2H, d, J = 7.9 Hz), 7.10 (2H, d, J = 7.3 Hz), 7.12 (2H, d, J = 7.3 Hz), 7.27 (2H, d, J = 7.3 Hz). MS m/z: 676 $(M + H)^+$. |
| BB4 | MS m/z: 620 $(M + H)^+$. |
| BB5 | $^1$H-NMR ($CDCl_3$) δ: 0.00 (9H, s), 0.91-1.00 (2H, m), 1.46 (9H, s), 2.07-2.27 (3H, m), 2.27-2.48 (4H, m), 2.60-2.74 (1H, m), 2.81-2.96 (3H, m), 3.00-3.11 (1H, m), 3.29-3.54 (6H, m), 3.57-3.71 (2H, m), 3.87 (2H, t, J = 5.8 Hz), 5.23 (1H, dd, J = 13.1, 5.2 Hz), 5.29 (2H, q, J = 9.7 Hz), 6.55 (1H, d, J = 8.5 Hz), 6.88 (1H, d, J = 7.9 Hz). MS m/z: 636 $(M + Na)^+$. |
| BB6 | MS m/z: 414 $(M + H)^+$. |
| BB7 | $^1$H-NMR ($CDCl_3$) δ: 0.66 (3H, s), 0.92 (6H, s), 1.15 (3H, s), 1.41-1.68 (3H, m), 1.68-1.80 (1H, m), 1.80-1.99 (2H, m), 2.00-2.21 (4H, m), 2.21-2.60 (11H, m), 2.60-2.78 (1H, m), 2.78-3.05 (6H, m), 3.37-3.76 (11H, m), 3.78 (3H, s), 3.83-3.93 (2H, m), 5.15-5.29 (1H, m), 6.55-6.65 (1H, m), 6.73-6.87 (2H, m), 6.87-6.95 (1H, m), 7.03-7.19 (4H, m), 7.19-7.32 (2H, m), 8.07 (1H, s). MS m/z: 985 $(M + H)^+$. |

TABLE 39

| Ex | Data |
|---|---|
| BC1 | MS m/z: 202 $[M(^{79}Br) + H]^+$, 204 $[M(^{81}Br) + H]^+$. |
| BC2 | $^1$H-NMR ($CDCl_3$) δ: 3.49 (3H, s), 7.16 (1H, d, J = 7.9 Hz), 7.18 (1H, t, J = 5.2 Hz), 8.96 (1H, s). MS m/z: 228 $[M(^{79}Br) + H]^+$, 230 $[M(^{81}Br) + H]^+$. |
| BC3 | $^1$H-NMR ($CDCl_3$) δ: 0.01 (9H, s), 0.87-0.99 (2H, m), 2.21-2.31 (1H, m), 2.55-2.67 (1H, m), 2.84-2.93 (1H, m), 3.00-3.12 (1H, m), 3.51 (3H, s), 3.57-3.67 (2H, m), 5.16-5.32 (3H, m), 6.87 (1H, d, J = 7.9 Hz), 7.15 (1H, d, J = 7.9 Hz). MS m/z: 469 $[M(^{79}Br) + H]^+$, 471 $[M(^{81}Br) + H]^+$. |
| BC4 | $^1$H-NMR ($CDCl_3$) δ: 0.01 (9H, s), 0.95-0.99 (2H, m), 2.28-2.35 (1H, m), 2.63-2.75 (1H, m), 2.86-2.98 (1H, m), 3.06-3.15 (1H, m), 3.60-3.69 (5H, m), 5.24-5.34 (3H, m), 7.13 (1H, d, J = 7.9 Hz), 7.44 (2H, s), 8.14 (1H, d, J = 8.5 Hz). |

TABLE 39-continued

| Ex | Data |
|---|---|
| BC5 | $^1$H-NMR ($CDCl_3$) δ: 0.01 (9H, s), 0.66 (3H, s), 0.91 (6H, s), 0.93-0.98 (2H, m), 1.16 (3H, s), 1.37-1.79 (5H, m), 1.83-1.94 (3H, m), 1.97-2.14 (3H, m), 2.23-2.73 (13H, m), 2.86-2.95 (1H, m), 3.04-3.13 (1H, m), 3.42-3.54 (5H, m), 3.60-3.93 (11H, m), 5.21-5.35 (3H, m), 6.11 (1H, br s), 6.80 (2H, d, J = 8.5 Hz), 7.04-7.14 (5H, m), 7.27 (2H, d, J = 8.5 Hz), 7.40 (1H, d, J = 7.9 Hz). MS m/z: 1072 $(M + H)^+$. |
| BC6 | $^1$H-NMR ($CDCl_3$) δ: 0.66 (3H, s), 0.91 (6H, d, J = 3.1 Hz), 1.16 (3H, s), 1.37-1.66 (5H, m), 1.67-1.79 (1H, m), 1.83-2.15 (6H, m), 2.24-2.61 (13H, m), 2.62-2.75 (1H, m), 2.82-2.91 (1H, m), 2.95-3.04 (1H, m), 3.43-3.56 (5H, m), 3.63-3.95 (8H, m), 5.26 (1H, dd, J = 13.1, 5.2 Hz), 6.11 (1H, br s), 6.81 (2H, d, J = 8.5 Hz), 7.07-7.13 (5H, m), 7.27 (2H, d, J = 7.9 Hz), 7.43 (1H, d, J = 7.9 Hz), 8.08 (1H, br s). MS m/z: 942 $(M + H)^+$. |
| BD1 | $^1$H-NMR ($CDCl_3$) δ: 0.68 (3H, s), 0.76-0.94 (3H, m), 0.92 (3H, s), 0.93 (3H, s), 1.17-1.29 (2H, m), 1.18 (3H, s), 1.42-1.82 (8H, m), 1.89-2.41 (9H, m), 3.71-3.83 (2H, m), 3.77 (3H, s), 6.86 (2H, d, J = 9.0 Hz), 7.10 (2H, d, J = 8.6 Hz), 7.18 (2H, d, J = 9.0 Hz), 7.23 (2H, d, J = 8.2 Hz). MS m/z: 594 $(M + H)^+$. |
| BD2 | $^1$H-NMR ($CDCl_3$) δ: 0.58 (3H, s), 0.77-0.92 (3H, m), 0.92 (6H, s), 1.17 (3H, s), 1.19-1.28 (2H, m), 1.41-1.82 (8H, m), 1.50 (9H, s), 1.87-1.98 (1H, m), 2.04-2.38 (8H, m), 3.70-3.83 (5H, m), 6.37 (1H, s), 6.85 (2H, d, J = 9.0 Hz), 7.09 (2H, d, J = 8.6 Hz), 7.17 (2H, d, J = 9.0 Hz), 7.25 (2H, d, J = 6.7 Hz). MS m/z: 675 $(M + H)^+$. |
| BD3 | MS m/z: 575 $(M + H)^+$. |
| BD4 | $^1$H-NMR ($CDCl_3$) δ: 1.44-1.50 (9H, m), 2.00-2.15 (2H, m), 2.17-2.27 (1H, m), 2.62-2.75 (3H, m), 2.76-2.87 (2H, m), 2.89-2.98 (1H, m), 3.38 (1H, s), 3.71-4.21 (2H, m), 5.17 (1H, dd, J = 12.5, 5.2 Hz), 6.20-6.32 (2H, m), 6.60 (1H, d, J = 7.9 Hz), 8.05 (1H, s). MS m/z: 429 $(M + H)^+$. |

TABLE 40

| Ex | Data |
|---|---|
| BD5 | MS m/z: 373 $(M + H)^+$. |
| BD6 | $^1$H-NMR ($CDCl_3$) δ: 0.69 (3H, s), 0.81-0.97 (9H, m), 1.20 (3H, s), 1.23-1.31 (2H, m), 1.47-1.82 (11H, m), 1.94 (1H, t, J = 11.0 Hz), 2.11-2.37 (10H, m), 2.64-2.95 (5H, m), 3.38 (3H, d, J = 1.8 Hz), 3.74-3.82 (5H, m), 3.91-4.01 (1H, m), 5.17 (1H, dd, J = 12.6, 5.2 Hz), 6.26-6.33 (2H, m), 6.61 (1H, d, J = 8.0 Hz), 6.85-6.91 (2H, m), 7.22-7.06 (5H, m), 7.42-7.52 (2H, m), 8.04 (1H, s). MS m/z: 929 $(M + H)^+$. |
| BE1 | $^1$H-NMR ($CDCl_3$) δ: 1.26 (3H, t, J = 7.0 Hz), 1.51 (9H, s), 1.73-1.88 (1H, m), 2.11-2.19 (1H, m), 2.32-2.47 (4H, m), 2.52-2.61 (1H, m), 4.15 (2H, q, J = 7.0 Hz), 6.02-6.09 (1H, m), 6.65 (1H, s), 7.01-7.14 (2H, m), 7.97 (1H, s). MS m/z: 264 $(M - BOC + H)^+$. |
| BE2 | $^1$H-NMR ($CDCl_3$) δ: 1.34-1.49 (1H, m), 1.50 (9H, s), 1.82-2.02 (3H, m), 2.26-2.45 (3H, m), 3.51-3.64 (3H, m), 6.07 (1H, s), 6.64 (1H, s), 7.04-7.16 (2H, m), 7.88-8.04 (1H, m). MS m/z: 222 $(M - BOC + H)^+$. |
| BE3 | $^1$H-NMR ($CDCl_3$) δ: 0.66 (3H, s), 0.92 (6H, s), 1.17 (3H, s), 1.22-1.98 (9H, m), 1.51 (9H, s), 2.04-2.40 (10H, m), 3.68-3.83 (5H, m), 6.00 (1H, s), 6.64 (1H, s), 6.81 (2H, d, J = 8.6 Hz), 7.02-7.13 (2H, m), 7.15 (2H, d, J = 8.6 Hz), 7.97 (1H, s). MS m/z: 691 $(M + H)^+$. |
| BE4 | MS m/z: 591 $(M + H)^+$. |
| BE5 | $^1$H-NMR ($CDCl_3$) δ: 0.68 (3H, s), 0.93 (6H, s), 1.20 (3H, s), 1.23-1.80 (9H, m), 1.85-2.00 (2H, m), 2.00-2.42 (13H, m), 2.63-3.03 (6H, m), 3.38 (3H, d, J = 1.2 Hz), 3.70-3.86 (5H, m), 3.93 (1H, brs), 5.17 (1H, dd, J = 12.9, 5.5 Hz), 6.05 (1H, s), 6.23-6.36 (2H, m), 6.61 (1H, d, J = 8.0 Hz), 6.83 (2H, d, J = 8.6 Hz), 7.05-7.20 (4H, m), 7.99 (1H, s), 8.21-8.34 (1H, m). MS m/z: 945 $(M + H)^+$. |
| BF1 | $^1$H-NMR ($CDCl_3$) δ: 1.91-1.99 (2H, m), 2.78 (2H, t, J = 6.7 Hz), 3.32-3.38 (2H, m), 4.55 (1H, br s), 6.73 (1H, d, J = 7.9 Hz), 7.09 (1H, d, J = 7.9 Hz). MS m/z: 290 $[M(^{79}Br^{79}Br) + H]^+$, 292 $[M(^{79}Br^{81}Br) + H]^+$, 294 $[M(^{81}Br^{81}Br) + H]^+$. |
| BF2 | $^1$H-NMR ($CDCl_3$) δ: 1.40 (9H, s), 1.89-2.07 (4H, m), 2.28-2.36 (1H, m), 2.48-2.56 (1H, m), 2.74-2.84 (2H, m), 3.46-3.98 (2H, m), 4.34-4.40 (1H, m), 5.33 (1H, br s), 5.82 (1H, br s), 6.65 (1H, br s), 7.33 (1H, d, J = 8.5 Hz), 7.37 (1H, d, J = 8.5 Hz). MS m/z: 540 $[M(^{79}Br^{79}Br) + Na]^+$, 542 $[M(^{79}Br^{81}Br) + Na]^+$, 544 $[M(^{81}Br^{81}Br) + Na]^+$. |
| BF3 | $^1$H-NMR ($CDCl_3$) δ: 1.41 (9H, s), 2.13-2.29 (4H, m), 2.31-2.42 (1H, m), 2.50-2.60 (1H, m), 2.83-2.88 (2H, m), 3.82-3.87 (2H, m), 4.99 (1H, dd, J = 9.7, 6.1 Hz), 5.47 (1H, br s), 6.40 (1H, br s), 6.90 (1H, d, J = 7.9 Hz), 7.19 (1H, d, J = 7.9 Hz). MS m/z: 460 $[M(^{79}Br) + Na]^+$, 462 $[M(^{81}Br) + Na]^+$. |

TABLE 41

| Ex | Data |
|---|---|
| BF4 | $^1$H-NMR ($CDCl_3$) δ: 1.42 (9H, s), 2.15-2.33 (4H, m), 2.37-2.48 (1H, m), 2.54-2.65 (1H, m), 3.31-3.37 (2H, m), 3.85-3.95 (2H, m), 5.07 (1H, dd, J = 9.4, 5.8 Hz), 5.41 (1H, br s), 6.38 (1H, br s), 7.15 (1H, d, J = 8.5 Hz), 7.43 (2H, s), 8.08 (1H, d, J = 8.5 Hz). MS m/z: 526 $(M - tBu + H)^+$ |

TABLE 41-continued

| Ex | Data |
|---|---|
| BF5 | $^1$H-NMR ($CDCl_3$) δ: 0.65 (3H, s), 0.90 (6H, s), 1.15 (3H, s), 1.36-1.66 (16H, m), 1.67-1.79 (1H, m), 1.82-1.94 (3H, m), 1.94-2.61 (20H, m), 3.34-3.52 (4H, m), 3.65-3.91 (9H, m), 5.02 (1H, dd, J = 9.7, 5.5 Hz), 5.35 (1H, br s), 6.08-6.11 (1H, m), 6.34 (1H, br s), 6.80 (2H, d, J = 8.5 Hz), 6.93 (1H, d, J = 7.9 Hz), 6.98-7.03 (1H, m), 7.06-7.11 (4H, m), 7.25 (2H, d, J = 8.5 Hz). MS m/z: 1041 $(M + H)^+$ |
| BF6 | $^1$H-NMR ($CDCl_3$) δ: 0.66 (3H, s), 0.90 (3H, s), 0.91 (3H, s), 1.16 (3H, s), 1.35-1.66 (4H, m), 1.68-1.80 (1H, m), 1.83-2.20 (7H, m), 2.21-2.57 (13H, m), 2.77-3.02 (4H, m), 3.32-3.53 (4H, m), 3.65-3.94 (11H, m), 5.19-5.29 (1H, m), 6.08-6.11 (1H, m), 6.67 (1H, d, J = 7.9 Hz), 6.80 (2H, d, J = 8.5 Hz), 6.93 (1H, d, J = 7.9 Hz), 7.07-7.12 (4H, m), 7.25 (2H, d, J = 8.5 Hz), 8.03 (1H, s). MS m/z: 967 $(M + H)^+$. |
| BG1 | $^1$H-NMR ($CDCl_3$) δ: 1.40 (9H, s), 1.89-2.07 (4H, m), 2.28-2.36 (1H, m), 2.48-2.56 (1H, m), 2.74-2.84 (2H, m), 3.46-3.98 (2H, m), 4.34-4.40 (1H, m), 5.33 (1H, br s), 5.82 (1H, br s), 6.65 (1H, br s), 7.33 (1H, d, J = 8.5 Hz), 7.37 (1H, d, J = 8.5 Hz). MS m/z: 540 $[M(^{79}Br^{79}Br) + Na]^+$, 542 $[M(^{79}Br^{81}Br) + Na]^+$, 544 $[M(^{81}Br^{81}Br) + Na]^+$. |
| BG2 | $^1$H-NMR ($CDCl_3$) δ: 1.41 (9H, s), 2.13-2.29 (4H, m), 2.31-2.42 (1H, m), 2.50-2.60 (1H, m), 2.83-2.88 (2H, m), 3.82-3.87 (2H, m), 4.99 (1H, dd, J = 9.7, 6.1 Hz), 5.39 (1H, br s), 6.36 (1H, br s), 6.90 (1H, d, J = 7.9 Hz), 7.19 (1H, d, J = 7.9 Hz). MS m/z: 460 $[M(^{79}Br) + Na]^+$, 462 $[M(^{81}Br) + Na]^+$. |
| BG3 | $^1$H-NMR ($CDCl_3$) δ: 1.42 (9H, s), 2.15-2.33 (4H, m), 2.37-2.48 (1H, m), 2.54-2.65 (1H, m), 3.31-3.37 (2H, m), 3.85-3.95 (2H, m), 5.07 (1H, dd, J = 9.4, 5.8 Hz), 5.41 (1H, br s), 6.38 (1H, br s), 7.15 (1H, d, J = 8.5 Hz), 7.43 (2H, s), 8.08 (1H, d, J = 8.5 Hz). MS m/z: 526 $(M - tBu + H)^+$ |
| BG4 | $^1$H-NMR ($CDCl_3$) δ: 0.65 (3H, s), 0.91 (6H, s), 1.15 (3H, s), 1.42 (9H, s), 1.46-1.65 (6H, m), 1.68-1.80 (1H, m), 1.82-1.93 (3H, m), 1.95-2.60 (21H, m), 3.33-3.52 (4H, m), 3.66-3.91 (9H, m), 5.02 (1H, dd, J = 9.4, 5.8 Hz), 5.36 (1H, br s), 6.08-6.11 (1H, m), 6.34 (1H, br s), 6.80 (2H, d, J = 8.5 Hz), 6.93 (1H, d, J = 7.9 Hz), 6.99-7.02 (1H, m), 7.07-7.11 (4H, m), 7.25 (2H, d, J = 8.5 Hz). MS m/z: 1041 $(M + H)^+$ |
| BG5 | $^1$H-NMR ($CDCl_3$) δ: 0.65 (3H, s), 0.90 (6H, s), 1.16 (3H, s), 1.36-1.65 (4H, m), 1.67-1.78 (1H, m), 1.82-1.94 (3H, m), 1.94-2.21 (4H, m), 2.22-2.57 (13H, m), 2.61-3.02 (4H, m), 3.33-3.52 (4H, m), 3.63-3.94 (11H, m), 5.17-5.32 (1H, m), 6.08-6.11 (1H, m), 6.66 (1H, d, J = 8.5 Hz), 6.80 (2H, d, J = 8.5 Hz), 6.93 (1H, d, J = 8.5 Hz), 7.06-7.12 (4H, m), 7.25 (2H, d, J = 8.5 Hz), 8.06 (1H, s). MS m/z: 967 $(M + H)^+$. |

TABLE 42

| Ex | Data |
|---|---|
| BH1 | $^1$H-NMR ($CDCl_3$) δ: 0.65 (3H, s), 0.94 (3H, s), 0.94 (3H, s), 1.16 (3H, s), 1.45-1.93 (6H, m), 1.47 (9H, s), 2.05-2.15 (3H, m), 2.21-2.34 (1H, m), 2.34-2.49 (6H, m), 2.49-2.60 (1H, m), 3.40-3.52 (2H, m), 3.64-3.83 (2H, m), 3.78 (3H, s), 5.87-5.96 (1H, m), 6.65-6.90 (4H, m), 7.04-7.14 (3H, m). |
| BH2 | MS m/z: 620 $(M + H)^+$. |
| BH3 | $^1$H-NMR ($CDCl_3$) δ: 0.00 (9H, s), 0.91-1.01 (2H, m), 1.40-1.98 (5H, m), 2.00-2.17 (2H, m), 2.17-2.28 (1H, m), 2.58-3.11 (9H, m), 2.64 (3H, s), 3.25-3.38 (1H, m), 3.65 (2H, td, J = 8.2, 2.2 Hz), 3.86 (2H, t, J = 5.8 Hz), 5.22 (1H, dd, J = 13.4, 5.5 Hz), 5.29 (2H, q, J = 9.5 Hz), 6.50-6.58 (1H, m), 6.65-6.74 (1H, m). MS m/z: 528 $(M + H)^+$. |
| BH4 | $^1$H-NMR ($CDCl_3$) δ: 0.00 (9H, s), 0.65 (3H, s), 0.91-1.01 (2H, m), 0.93 (3H, s), 0.94 (3H, s), 1.16 (3H, s), 1.39-1.99 (10H, m), 2.00-2.73 (17H, m), 2.73-2.98 (5H, m), 2.98-3.12 (3H, m), 3.46 (2H, dd, J = 17.0, 14.6 Hz), 3.60-3.80 (4H, m), 3.78 (3H, s), 3.83-3.90 (2H, m), 3.93-4.03 (1H, m), 4.52-4.71 (1H, m), 5.23 (1H, dd, J = 14.9, 6.4 Hz), 5.29 (2H, t, J = 14.3 Hz), 5.88-6.00 (1H, m), 6.56 (1H, d, J = 8.5 Hz), 6.73 (1H, d, J = 8.5 Hz), 6.79 (2H, d, J = 9.1 Hz), 6.85 (2H, d, J = 10.3 Hz), 7.04-7.14 (3H, m). MS m/z: 1129 $(M + H)^+$. |
| BH5 | $^1$H-NMR ($CDCl_3$) δ: 0.66 (3H, s), 0.94 (3H, s), 0.94 (3H, s), 1.16 (3H, s), 1.44-1.66 (5H, m), 1.66-1.77 (1H, m), 1.77-2.00 (5H, m), 2.00-2.17 (3H, m), 2.17-2.76 (13H, m), 2.76-3.12 (8H, m), 3.37-3.53 (2H, m), 3.63-3.82 (5H, m), 3.82-3.95 (2H, m), 3.93-4.04 (1H, m), 4.53-4.72 (1H, m), 5.15-5.28 (1H, m), 5.91-6.01 (1H, m), 6.54-6.64 (1H, m), 6.72-6.82 (3H, m), 6.82-6.92 (2H, m), 7.03-7.14 (3H, m), 8.02 (1H, br s). MS m/z: 999 $(M + H)^+$. |
| BI1 | $^1$H-NMR ($CDCl_3$) δ: 0.00 (9H, s), 0.65 (3H, s), 0.89-1.00 (8H, m), 1.15 (3H, s), 1.36-1.66 (2H, m), 1.69-1.79 (1H, m), 1.82-2.13 (8H, m), 2.18-2.58 (12H, m), 2.64-2.76 (1H, m), 2.83-2.96 (1H, m), 3.02-3.12 (1H, m), 3.43-3.53 (7H, m), 3.61-3.82 (10H, m), 5.21-5.33 (3H, m), 6.08-6.12 (1H, m), 6.76-6.82 (3H, m), 7.07-7.16 (6H, m), 7.24-7.29 (2H, m). MS m/z: 1071 $(M + H)^+$. |
| BI2 | $^1$H-NMR ($CDCl_3$) δ: 0.66 (3H, s), 0.90 (3H, s), 0.91 (3H, s), 1.16 (3H, s), 1.37-1.65 (4H, m), 1.68-1.79 (1H, m), 1.82-1.94 (3H, m), 1.95-2.18 (3H, m), 2.22-2.57 (14H, m), 2.65-3.01 (3H, m), 3.41-3.53 (6H, m), 3.65-3.84 (7H, m), 5.24 (1H, dd, J = 12.8, 5.5 Hz), 6.07-6.12 (1H, m), 6.77-6.83 (3H, m), 7.07-7.18 (6H, m), 7.24-7.28 (2H, m), 8.06 (1H, s). MS m/z: 941 $(M + H)^+$. |

TABLE 43

| Ex | Data |
|---|---|
| BJ1 | $^1$H-NMR ($CDCl_3$) δ: 2.88 (3H, d, J = 5.5 Hz), 3.02 (2H, br s), 4.31 (1H, br s), 6.58 (1H, s), 7.62 (1H, s). MS m/z: 202 [M($^{79}$Br) + H]$^+$, 204 [M($^{81}$Br) + H]$^+$. |
| BJ2 | $^1$H-NMR (DMSO-$D_6$) δ: 3.26 (3H, s), 7.45 (1H, s), 7.92 (1H, s), 11.29 (1H, br s). |
| BJ3 | $^1$H-NMR ($CDCl_3$) δ: 0.01 (9H, s), 0.92-0.98 (2H, m), 2.24-2.30 (1H, m), 2.61-2.77 (1H, m), 2.86-2.95 (1H, m), 3.05-3.15 (1H, m), 3.44 (3H, s), 3.57-3.70 (2H, m), 5.17 (1H, dd, J = 13.4, 5.5 Hz), 5.24 (1H, d, J = 9.2 Hz), 5.29 (1H, d, J = 9.2 Hz), 7.17 (1H, s), 7.83 (1H, s). |
| BJ4 | $^1$H-NMR ($CDCl_3$) δ: 0.00 (9H, s), 0.91-1.00 (2H, m), 2.29-2.36 (1H, m), 2.70-2.84 (1H, m), 2.90-2.99 (1H, m), 3.08-3.16 (1H, m), 3.55 (3H, s), 3.60-3.70 (2H, m), 5.22-5.34 (3H, m), 7.45 (2H, s), 8.05 (1H, s), 8.31 (1H, s). |
| BJ5 | $^1$H-NMR ($CDCl_3$) δ: 0.00 (9H, s), 0.65 (3H, s), 0.87-0.99 (8H, m), 1.15 (3H, s), 1.37-1.64 (4H, m), 1.69-1.77 (1H, m), 1.82-2.13 (6H, m), 2.23-2.60 (13H, m), 2.65-2.77 (1H, m), 2.85-2.97 (1H, m), 3.06-3.15 (1H, m), 3.41-3.53 (5H, m), 3.59-3.90 (11H, m), 5.20-5.33 (3H, m), 6.10 (1H, br s), 6.79 (2H, d, J = 8.5 Hz), 7.06-7.12 (4H, m), 7.26 (2H, d, J = 8.5 Hz), 7.47 (1H, s), 8.01 (1H, s). MS m/z: 1072 (M + H)$^+$. |
| BJ6 | $^1$H-NMR ($CDCl_3$) δ: 0.66 (3H, s), 0.91 (6H, s), 1.16 (3H, s), 1.35-1.80 (5H, m), 1.83-1.95 (3H, m), 1.97-2.04 (1H, m), 2.07-2.13 (2H, m), 2.24-2.63 (13H, m), 2.66-2.79 (1H, m), 2.83-2.92 (1H, m), 2.96-3.04 (1H, m), 3.41-3.54 (5H, m), 3.64-3.92 (9H, m), 5.25 (1H, dd, J = 13.4, 5.5 Hz), 6.10 (1H, br s), 6.80 (2H, d, J = 8.5 Hz), 7.06-7.13 (4H, m), 7.23-7.29 (3H, m), 7.48 (1H, s), 8.05 (1H, s). MS m/z: 942 (M + H)$^+$. |
| BK1 | $^1$H-NMR ($CDCl_3$) δ: 1.89-1.95 (2H, m), 2.97 (2H, t, J = 6.4 Hz), 3.41-3.46 (2H, m), 4.83 (1H, br s), 7.01 (1H, d, J = 8.5 Hz), 7.35 (1H, d, J = 8.5 Hz). MS m/z: 257 [M($^{79}$Br) + H]$^+$, 259 [M($^{81}$Br) + H]$^+$. |
| BK2 | $^1$H-NMR ($CDCl_3$) δ: 1.83-1.95 (1H, m), 1.97-2.10 (2H, m), 2.66-2.86 (3H, m), 2.99-3.14 (2H, m), 3.55-3.98 (2H, m), 4.46-4.53 (1H, m), 5.38-5.45 (1H, m), 7.67 (1H, d, J = 8.5 Hz), 7.70 (1H, d, J = 8.5 Hz), 7.87 (1H, s). MS m/z: 411 [M($^{79}$Br) + H]$^+$, 413 [M($^{81}$Br) + H]$^+$. |
| BK3 | $^1$H-NMR ($CDCl_3$) δ: −0.02 (9H, s), 0.90-0.96 (2H, m), 1.78-1.91 (1H, m), 1.95-2.10 (2H, m), 2.65-2.73 (1H, m), 2.75-2.86 (1H, m), 2.90-2.97 (1H, m), 3.02-3.14 (2H, m), 3.56-3.62 (2H, m), 3.64-3.95 (2H, m), 4.47-4.54 (1H, m), 5.14 (1H, d, J = 9.7 Hz), 5.24 (1H, d, J = 9.7 Hz), 5.53-5.59 (1H, m), 7.68 (1H, d, J = 9.1 Hz), 7.72 (1H, d, J = 9.1 Hz). MS m/z: 513 [M($^{79}$Br) − $C_2H_4$ + H]$^+$, 515 [M($^{81}$Br) − $C_2H_4$ + H]$^+$. |

TABLE 44

| Ex | Data |
|---|---|
| BK4 | $^1$H-NMR ($CDCl_3$) δ: 0.01 (9H, s), 0.93-0.97 (2H, m), 2.16-2.31 (3H, m), 2.63-2.74 (1H, m), 2.85-2.95 (1H, m), 3.05-3.12 (1H, m), 3.34 (2H, t, J = 6.1 Hz), 3.62-3.67 (2H, m), 3.91 (2H, t, J = 5.8 Hz), 5.19-5.33 (3H, m), 6.71 (1H, d, J = 9.1 Hz), 7.96 (1H, d, J = 9.1 Hz). MS m/z: 433 (M − $C_2H_4$ + H)$^+$. |
| BK5 | $^1$H-NMR ($CDCl_3$) δ: 0.00 (9H, s), 0.93-0.97 (2H, m), 2.12-2.25 (3H, m), 2.61-2.69 (3H, m), 2.82-2.92 (1H, m), 3.00-3.08 (1H, m), 3.47-3.51 (2H, m), 3.61-3.67 (2H, m), 3.81-3.87 (2H, m), 5.18 (1H, dd, J = 13.1, 5.2 Hz), 5.26 (1H, d, J = 9.7 Hz), 5.31 (1H, d, J = 9.7 Hz), 6.36 (1H, d, J = 7.9 Hz), 6.44 (1H, d, J = 8.5 Hz). MS m/z: 453 (M + Na)$^+$. |
| BK6 | $^1$H-NMR ($CDCl_3$) δ: 0.00 (9H, s), 0.94-0.98 (2H, m), 1.24-1.39 (2H, m), 1.47 (9H, s), 1.99-2.08 (2H, m), 2.10-2.25 (3H, m), 2.55-2.69 (3H, m), 2.80-2.97 (3H, m), 2.99-3.07 (1H, m), 3.13 (1H, br s), 3.59-3.68 (2H, m), 3.79-3.86 (2H, m), 4.04 (1H, br s), 5.18 (1H, dd, J = 13.1, 5.2 Hz), 5.26 (1H, d, J = 9.7 Hz), 5.30 (1H, d, J = 9.7 Hz), 6.32 (1H, d, J = 8.5 Hz), 6.48 (1H, d, J = 8.5 Hz). MS m/z: 614 (M + H)$^+$. |
| BK7 | MS m/z: 514 (M + H)$^+$. |
| BK8 | $^1$H-NMR ($CDCl_3$) δ: 0.00 (9H, s), 0.65 (3H, s), 0.91-0.99 (8H, m), 1.15 (3H, s), 1.30-1.44 (2H, m), 1.45-1.64 (3H, m), 1.65-1.76 (1H, m), 1.82-1.99 (3H, m), 2.03-2.34 (9H, m), 2.35-2.69 (7H, m), 2.79-2.93 (4H, m), 3.00-3.07 (1H, m), 3.14-3.30 (2H, s), 3.43-3.53 (3H, m), 3.60-3.75 (4H, m), 3.78 (3H, s), 3.81-3.87 (2H, m), 3.95-4.04 (1H, m), 4.51-4.61 (1H, m), 5.14-5.33 (3H, m), 5.94-5.98 (1H, m), 6.33 (1H, d, J = 8.5 Hz), 6.50 (1H, d, J = 8.5 Hz), 6.77-6.87 (4H, m), 7.06-7.11 (3H, m). MS m/z: 1115 (M + H)$^+$. |
| BK9 | $^1$H-NMR ($CDCl_3$) δ: 0.65 (3H, s), 0.94 (6H, s), 1.16 (3H, s), 1.31-1.44 (2H, m), 1.45-1.64 (2H, m), 1.68-1.78 (1H, m), 1.82-2.00 (3H, m), 2.05-2.72 (17H, m), 2.78-2.99 (4H, m), 3.13-3.30 (2H, m), 3.42-3.57 (3H, m), 3.64-3.77 (3H, m), 3.78 (3H, s), 3.81-3.87 (2H, m), 3.96-4.03 (1H, m), 4.53-4.64 (1H, m), 5.14-5.23 (1H, m), 5.94-5.98 (1H, m), 6.36 (1H, d, J = 8.6 Hz), 6.53 (1H, d, J = 8.0 Hz), 6.77-6.87 (4H, m), 7.06-7.12 (3H, m), 8.07 (1H, s). MS m/z: 985 (M + H)$^+$. |
| BL1 | $^1$H-NMR ($CDCl_3$) δ: 0.66 (3H, s), 0.94 (3H, s), 0.94 (3H, s), 1.16 (3H, s), 1.42-1.65 (3H, m), 1.48 (9H, s), 1.66-1.92 (3H, m), 2.02-2.16 (3H, m), 2.22-2.34 (1H, m), 2.34-2.50 (6H, m), 2.50-2.60 (1H, m), 3.46 (2H, t, J = 15.2 Hz), 3.05-3.80 (2H, m), 3.78 (3H, s), 5.87-5.95 (1H, m), 6.76-6.87 (4H, m), 7.03-7.12 (3H, m). |
| BL2 | MS m/z: 620 (M + H)$^+$. |

TABLE 45

| Ex | Data |
|---|---|
| BL3 | $^1$H-NMR ($CDCl_3$) δ: 0.00 (9H, s), 0.65 (3H, s), 0.90-1.01 (8H, m), 1.16 (3H, s), 1.31-1.66 (4H, m), 1.68-1.79 (1H, m), 1.81-2.01 (2H, m), 2.01-2.73 (17H, m), 2.78-2.96 (5H, m), 2.99-3.09 (1H, m), 3.13-3.29 (2H, m), 3.41-3.56 (3H, m), 3.59-3.80 (7H, m), 3.80-3.89 (2H, m), 3.90-4.06 (1H, m), 4.53-4.61 (1H, m), 5.15-5.23 (1H, m), 5.25-5.33 (2H, m), 5.94-5.98 (1H, m), 6.34 (1H, d, J = 8.6 Hz), 6.50 (1H, d, J = 8.6 Hz), 6.77-6.87 (4H, m), 7.06-7.11 (3H, m). MS m/z: 1115 $(M + H)^+$. |
| BL4 | $^1$H-NMR ($CDCl_3$) δ: 0.65 (3H, s), 0.93 (6H, s), 1.15 (3H, s), 1.24-1.64 (5H, m), 1.68-1.76 (1H, m), 1.82-1.99 (3H, m), 2.04-2.71 (17H, m), 2.78-2.97 (4H, m), 3.13-3.30 (2H, m), 3.43-3.57 (3H, m), 3.66-3.75 (2H, m), 3.78 (3H, s), 3.81-3.86 (2H, m), 3.95-4.03 (1H, m), 4.53-4.62 (1H, m), 5.14-5.23 (1H, m), 5.94-5.98 (1H, m), 6.36 (1H, d, J = 8.5 Hz), 6.53 (1H, d, J = 7.9 Hz), 6.77-6.87 (4H, m), 7.05-7.12 (3H, m), 8.02 (1H, s). MS m/z: 985 $(M + H)^+$. |
| BM1 | $^1$H-NMR ($CDCl_3$) δ: 3.52 (2H, td, J = 4.3, 2.4 Hz), 4.21 (1H, br s), 4.36 (2H, t, J = 4.3 Hz), 6.73 (1H, d, J = 2.4 Hz), 7.19 (1H, d, J = 2.4 Hz). |
| BM2 | $^1$H-NMR (DMSO-$D_6$) δ: 3.45 (2H, t, J = 4.6 Hz), 4.24 (2H, t, J = 4.6 Hz), 6.78 (1H, s). |
| BM3 | $^1$H-NMR ($CDCl_3$) δ: 2.00 (1H, dq, J = 27.2, 6.8 Hz), 2.62-2.68 (1H, m), 2.72-2.81 (1H, m), 2.88 (1H, dq, J = 18.1, 2.3 Hz), 3.75-4.14 (2H, m), 4.44 (2H, t, J = 4.9 Hz), 4.53 (1H, dt, J = 13.0, 5.3 Hz), 5.69 (1H, d, J = 4.9 Hz), 7.99 (1H, br s). MS m/z: 524 $[M(^{79}Br^{79}Br) + H]^+$, 526 $[M(^{79}Br^{81}Br) + H]^+$, 528 $[M(^{81}Br^{81}Br) + H]^+$. |
| BM4 | $^1$H-NMR ($CDCl_3$) δ: 0.00 (9H, s), 0.93 (2H, td, J = 8.7, 4.0 Hz), 1.89 (1H, ddd, J = 26.6, 13.2, 4.7 Hz), 2.58-2.65 (1H, m), 2.75-2.84 (1H, m), 2.95 (1H, dq, J = 18.2, 2.4 Hz), 3.59 (2H, dt, J = 9.5, 3.8 Hz), 3.73-4.11 (2H, br m), 4.36-4.44 (2H, m), 4.50 (1H, dt, J = 13.2, 5.0 Hz), 5.14 (1H, d, J = 9.1 Hz), 5.24 (1H, d, J = 9.1 Hz), 5.75 (1H, d, J = 4.9 Hz). |
| BM5 | $^1$H-NMR ($CDCl_3$) δ: 0.01 (9H, s), 0.92-1.01 (2H, m), 2.32 (1H, dq, J = 15.0, 3.3 Hz), 2.71-2.86 (1H, m), 2.95 (1H, tt, J = 15.9, 6.0 Hz), 3.04-3.12 (1H, m), 3.59-3.72 (2H, m), 3.99-4.20 (3H, m), 4.49-4.64 (2H, m), 5.25-5.32 (2H, m), 5.47-5.83 (1H, m). MS m/z: 573 $[M(^{79}Br) - H]^+$, 575$[M(^{81}Br) - H]^+$. |
| BM6 | $^1$H-NMR ($CDCl_3$) δ: 0.00 (9H, s), 0.96 (2H, dq, J = 10.8, 3.6 Hz), 2.20-2.26 (1H, m), 2.64 (1H, ddd, J = 26.7, 13.4, 4.3 Hz), 2.82-2.91 (1H, m), 3.04 (1H, dq, J = 17.6, 2.4 Hz), 3.55 (2H, s), 3.64 (2H, dq, J = 14.0, 2.4 Hz), 4.01 (2H, dd, J = 5.8, 3.9 Hz), 4.42 (2H, t, J = 4.6 Hz), 5.16 (1H, dd, J = 13.1, 5.2 Hz), 5.28 (2H, q, J = 9.7 Hz), 6.23 (1H, d, J = 8.5 Hz), 6.39 (1H, d, J = 8.5 Hz). MS m/z: 455 $(M + Na)^+$. |

TABLE 46

| Ex | Data |
|---|---|
| BM7 | $^1$H-NMR ($CDCl_3$) δ: 0.00 (9H, s), 0.92-0.99 (2H, m), 1.28-1.40 (1H, m), 1.47 (s, 9H), 1.97-2.08 (1H, m), 2.20-2.26 (1H, m), 2.64 (1H, ddd, J = 26.7, 13.4, 1.3 Hz), 2.81-2.99 (3H, m), 3.01-3.08 (1H, m), 3.34-3.44 (1H m), 3.51 (1H, br s), 3.64 (2H, td, J = 8.4, 1.8 Hz), 3.93-4.08 (4H, m), 4.40 (2H, t, J = 4.9 Hz), 5.16 (1H, dd, J = 13.1, 5.2 Hz), 5.26 (1H, d, J = 9.1 Hz), 5.31 (1H, d, J = 9.1 Hz), 6.27 (1H, d, J = 8.5 Hz), 6.32 (1H, d, J = 8.5 Hz). MS m/z: 638 $(M + Na)^+$. |
| BM8 | $^1$H-NMR ($CDCl_3$) δ: −0.01 (9H, s), 0.91-0.98 (2H, m), 2.05 (3H, dd, J = 10.9, 2.4 Hz), 2.19-2.26 (1H, m), 2.58-2.73 (3H, m), 2.82-2.91 (1H, m), 3.00-3.14 (3H, m), 3.32 (1H, s), 3.52 (1H, d, J = 1.8 Hz), 3.63 (2H, tdd, J = 11.9, 6.8, 5.2 Hz), 4.00 (2H, dd, J = 5.5, 3.6 Hz), 4.40 (2H, t, J = 4.6 Hz), 5.15 (1H, dd, J = 13.4, 4.9 Hz), 5.27 (2H, q, J = 9.5 Hz), 6.26 (1H, d, J = 7.9 Hz), 6.32 (1H, d, J = 8.5 Hz). MS m/z: 516 $(M + H)^+$. |
| BM9 | $^1$H-NMR ($CDCl_3$) δ: 0.00 (9H, s), 0.65 (3H, s), 0.90-0.98 (8H, m), 1.16 (3H, s), 1.31-1.75 (7H, m), 1.83-1.98 (3H, m), 2.05-2.71 (13H, m), 2.83-2.92 (2H, m), 2.99-3.09 (1H, m), 3.17-3.31 (1H, m), 3.42-3.82 (11H, m), 3.93-4.05 (3H, m), 4.38-4.44 (2H, m), 4.47-4.59 (1H, m), 5.13-5.20 (1H, m), 5.26 (1H, d, J = 9.1 Hz), 5.31 (1H, d, J = 9.1 Hz), 5.96 (1H, br s), 6.28 (1H, d, J = 8.5 Hz), 6.35 (1H, d, J = 8.5 Hz), 6.79 (2H, d, J = 8.5 Hz), 6.85 (2H, d, J = 8.5 Hz), 7.07-7.10 (3H, m). MS m/z: 1117 $(M + H)^+$. |
| BM10 | $^1$H-NMR ($CDCl_3$) δ: 0.66 (3H, s), 0.94 (6H, br s), 1.16 (3H, s), 1.33-1.63 (5H, m), 1.66-1.77 (1H, m), 1.83-1.98 (3H, m), 2.05-2.18 (4H, m), 2.21-2.72 (9H, m), 2.79-2.97 (4H, m), 3.17-3.32 (1H, m), 3.41-3.62 (4H, m), 3.67-3.75 (2H, m), 3.78 (3H, s), 3.93-4.07 (3H, m), 4.37-4.45 (2H, m), 4.51-4.57 (1H, m), 5.12-5.20 (1H, m), 5.93-5.99 (1H, m), 6.32 (1H, d, J = 8.5 Hz), 6.37 (1H, d, J = 8.5 Hz), 6.79 (2H, d, J = 9.1 Hz), 6.85 (2H, d, J = 9.1 Hz), 7.07-7.10 (3H, m), 8.09 (1H, s). MS m/z: 987 $(M + H)^+$. |
| BN1 | $^1$H-NMR ($CDCl_3$) δ: 0.00 (9H, s), 0.65 (3H, s), 0.93-0.98 (8H, m), 1.16 (3H, s), 1.34-1.58 (7H, m), 1.69-1.75 (1H, m), 1.84-1.95 (3H, m), 2.04-2.71 (11H, m), 2.86-2.91 (3H, m), 3.02-3.08 (1H, m), 3.18-3.28 (1H, m), 3.42-3.54 (4H, m), 3.61-3.67 (2H, m), 3.70-3.75 (2H, m), 3.78 (3H, s), 3.95-4.02 (3H, m), 4.40-4.43 (2H, m), 4.50-4.56 (1H, m), 5.14-5.20 (1H, m), 5.24-5.32 (2H, m), 5.95-5.97 (1H, m), 6.28 (1H, d, J = 8.6 Hz), 6.35 (1H, d, J = 8.6 Hz), 6.78-6.81 (2H, m), 6.84-6.87 (2H, m), 7.06-7.11 (3H, m). MS m/z: 1117 $(M + H)^+$. |

TABLE 47

| Ex | Data |
|---|---|
| BN2 | $^1$H-NMR ($CDCl_3$) δ: 0.65 (3H s), 0.94 (3H, s), 0.94 (3H, s), 1.16 (3H, s), 1.35-1.57 (4H, m), 1.68-1.75 (1H, s), 1.83-1.95 (3H, m), 2.05-2.33 (7H, m), 2.36-2.38 (2H, m), 2.40-2.72 (5H, m), 2.78-2.97 (1H, m), 3.21-3.28 (1H, m), 3.43-3.47 (2H, m). 3.49-3.56 (2H, m), 3.66-3.76 (2H, m), 3.78 (3H, s), 3.97-4.03 (3H, m), 4.40-4.42 (2H, m), 4.52-4.57 (1H, m), 5.12-6.20 (1H, m), 5.95-5.97 (1H, m), 6.31 (1H, d, J = 8.0 Hz), 6.37 (1H, d, J = 8.0 Hz), 6.78-6.81 (2H, m), 6.83-6.87 (2H, m), 7.06-7.11 (3H, m), 8.08 (1H, s). MS m/z: 987 $(M + H)^+$ |
| BO1 | MS m/z: 602 $(M + H)^+$. |
| BO2 | $^1$H-NMR ($CDCl_3$) δ: 1.26-1.49 (1H, m), 1.47 (9H, s), 1.98-2.09 (2H, m), 2.13-2.24 (1H, m), 2.31 (1H, ddd, J = 26.0, 12.9, 6.0 Hz), 2.72-3.02 (5H, m), 3.41-3.59 (1H, m), 3.93-4.16 (3H, m), 4.23 (1H, d, J = 15.2 Hz), 4.38 (1H, d, J = 15.2 Hz), 5.19 (1H, dd, J = 13.1, 5.2 Hz), 6.56 (1H, s), 6.64 (1H, dd, J = 8.5, 1.8 Hz), 7.66 (1H, d, J = 8.5 Hz), 7.90 (1H, br s). MS m/z: 387 $(M - tBu + H)^+$. |
| BO3 | MS m/z: 343 $(M + H)^+$. |
| BO4 | $^1$H-NMR ($CDCl_3$) δ: 0.66 (3H, s), 0.90 (3H, s), 0.91 (3H, s), 1.16 (3H, s), 1.33-1.67 (4H, m), 1.67-1.79 (1H, m), 1.79-2.41 (13H, m), 2.41-2.67 (3H, m), 2.73-3.00 (5H, m), 3.20-3.35 (1H, m), 3.47 (2H, dd, J = 20.7, 14.0 Hz), 3.55-3.84 (6H, m), 3.93-4.09 (2H, m), 4.24 (1H, d, J = 15.8 Hz), 4.39 (1H, d, J = 15.8 Hz), 4.50-4.71 (1H, m), 5.14-5.25 (1H, m), 6.09-6.17 (1H, m), 6.59 (1H, s), 6.66 (1H, d, J = 8.5 Hz), 6.80 (2H, d, J = 8.5 Hz), 7.10 (4H, d, J = 8.5 Hz), 7.25 (2H, d, J = 7.3 Hz), 7.67 (1H, d, J = 7.9 Hz), 7.96 (1H, s). MS m/z: 926 $(M + H)^+$. |
| BP1 | MS m/z: 245 $[M(^{79}Br) + H]^+$, 247 $[M(^{81}Br) + H]^+$. |
| BP2 | $^1$H-NMR ($CDCl_3$) δ: 0.04 (9H, s), 0.98 (2H, t, J = 8.4 Hz), 2.24-2.34 (1H, m), 2.46-2.63 (1H, m), 2.85-3.00 (1H, m), 3.04-3.12 (1H, m), 3.46 (3H, s), 3.59-3.72 (2H, m), 5.30 (2H, d, J = 2.0 Hz), 5.36-5.47 (1H, m), 7.03 (1H, s), 7.04 (1H, d, J = 9.0 Hz). MS m/z: 458 $[M(^{79}Br) - C_2H_4 + H]^+$, 460 $[M(^{81}Br) - C_2H_4 + H]^+$. |
| BP3 | $^1$H-NMR ($CDCl_3$) δ: 0.04 (9H, s), 0.99 (2H, t, J = 8.6 Hz), 1.50 (9H, s), 2.36-2.46 (1H, m), 2.64-2.71 (4H, m), 2.85-3.00 (1H, m), 3.00-3.13 (1H, m), 3.36-3.55 (10H, m), 3.60-3.71 (2H, m), 5.32 (2H, d, J = 1.2 Hz), 5.37-5.50 (1H, m), 6.85 (1H, d, J = 13.5 Hz), 6.86 (1H, s). MS m/z: 522 $(M - tBu - C_2H_4 + H)^+$. |
| BP4 | MS m/z: 506 $(M + H)^+$. |
| BP5 | $^1$H-NMR ($CDCl_3$) δ: 0.03 (9H, s), 0.69 (3H, s), 0.94 (6H, s), 0.99 (2H, t, J = 8.2 Hz), 1.19 (3H, s), 1.46-2.18 (10H, m), 2.24-2.42 (5H, m), 2.44-2.65 (8H, m), 2.78-2.90 (1H, m), 3.03-3.13 (1H, m), 3.49-3.78 (15H, m), 3.82 (3H, s), 5.32 (2H, d, J = 1.2 Hz), 5.39-5.50 (1H, m), 6.14-6.19 (1H, m), 6.81-6.89 (4H, m), 7.11-7.16 (4H, m), 7.29 (2H, d, J = 8.5 Hz). MS m/z: 1089 $(M + H)^+$. |

TABLE 48

| Ex | Data |
|---|---|
| BP6 | $^1$H-NMR ($CDCl_3$) δ: 0.69 (3H, s), 0.94 (3H, s), 0.94 (3H, s), 1.19 (3H, s), 1.47-2.21 (12H, m), 2.28-3.02 (13H, m), 3.44-3.79 (13H, m), 3.81 (3H, s), 5.36-5.50 (1H, m), 6.14-6.19 (1H, m), 6.80-6.92 (4H, m), 7.11-7.16 (4H, m), 7.28 (2H, d, J = 9.4 Hz), 8.00 (1H, s). MS m/z: 959 $(M + H)^+$. |
| BQ1 | $^1$H-NMR ($CDCl_3$) δ: 0.00 (9H, s), 0.96 (2H, t, J = 8.5 Hz), 1.46 (9H, s), 2.15-2.27 (1H, m), 2.33-2.45 (4H, m), 2.71 (1H, ddd, J = 26.1, 13.1, 4.3 Hz), 2.81-2.94 (1H, m), 2.99-3.10 (1H, m), 3.36-3.48 (4H, m), 3.44 (3H, s), 3.53 (2H, s), 3.60-3.70 (2H, m), 5.23 (1H, dd, J = 14.3, 6.4 Hz), 5.29 (2H, q, J = 9.1 Hz), 6.71 (1H, d, J = 7.9 Hz), 6.98 (1H, d, J = 8.5 Hz), 7.04 (1H, s). MS m/z: 588 $(M + H)^+$. |
| BQ2 | MS m/z: 488 $(M + H)^+$. |
| BQ3 | $^1$H-NMR ($CDCl_3$) δ: 0.00 (9H, s), 0.65 (3H, s), 0.91-0.99 (8H, m), 1.16 (2H, s), 1.45-1.61 (4H, m), 1.68-1.77 (1H, m), 1.83-1.99 (3H, m), 2.04-2.14 (2H, m), 2.18-2.33 (3H, m), 2.34-2.60 (8H, m), 2.66-2.97 (5H, m), 3.02-3.10 (1H, m), 3.43-3.48 (5H, m), 3.53-3.75 (9H, m), 3.78 (3H, s), 5.20-5.33 (3H, m), 5.94-5.98 (1H, m), 6.72 (1H, d, J = 7.9 Hz), 6.77-6.87 (4H, m), 6.99 (1H, d, J = 7.9 Hz), 7.03-7.11 (4H, m). MS m/z: 1089 $(M + H)^+$. |
| BQ4 | $^1$H-NMR ($CDCl_3$) δ: 0.65 (3H, s), 0.93 (6H, s), 1.16 (3H, s), 1.44-1.64 (4H, m), 1.66-1.76 (1H, m), 1.82-1.98 (3H, m), 2.05-2.14 (2H, m), 2.21-2.60 (12H, m), 2.67-3.00 (4H, m), 3.42-3.51 (4H, m), 3.53-3.60 (4H, m), 3.63-3.79 (7H, m), 5.22 (1H, dd, J = 12.8, 5.5 Hz), 5.94-5.97 (1H, m), 6.73-6.88 (5H, m), 6.99-7.12 (5H, m), 8.08 (1H, s). MS m/z: 959 $(M + H)^+$. |
| BR1 | $^1$H-NMR ($CDCl_3$) δ: 1.18-1.40 (2H, m), 1.47 (9H, s), 1.98-2.10 (2H, m), 2.15-2.28 (1H, m), 2.68 (1H, ddd, J = 26.1, 12.8, 4.9 Hz), 2.75-2.87 (1H, m), 2.87-3.02 (3H, m), 3.35-3.46 (2H, m), 3.38 (3H, s), 3.92-4.17 (2H, m), 5.17 (1H, dd, J = 13.1, 5.2 Hz), 6.31 (1H, d, J = 1.8 Hz), 6.34 (1H, dd, J = 8.2, 2.1 Hz), 6.60 (1H, d, J = 8.5 Hz), 7.94-8.30 (1H, br m). MS m/z: 402 $(M - tBu + H)^+$. |
| BR2 | MS m/z: 358 $(M + H)^+$. |
| BR3 | $^1$H-NMR ($CDCl_3$) δ: 0.65 (3H, s), 0.94 (3H, s), 0.94 (3H, s), 1.16 (3H, s), 1.29-1.44 (2H, m), 1.44-1.66 (3H, m), 1.66-1.79 (1H, m), 1.79-2.02 (3H, m), 2.02-2.61 (12H, m), 2.62-2.76 (1H, m), 2.76-2.99 (4H, m), 3.20-3.32 (1H, m), 3.39 (3H, s), 3.40-3.59 (4H, m), 3.64-3.80 (2H, m), 3.78 (3H, s), 3.94-4.06 (1H, m), 4.48-4.65 (1H, m), |

TABLE 48-continued

| Ex | Data |
|---|---|
| | 5.17 (1H, dd, J = 13.1, 5.2 Hz), 5.93-5.99 (1H, m), 6.32-6.39 (2H, m), 6.62 (1H, d, J = 7.9 Hz), 6.79 (2H, d, J = 9.1 Hz), 6.85 (2H, d, J = 9.7 Hz), 7.04-7.13 (3H, m), 8.02 (1H, br s). MS m/z: 959 $(M + H)^+$. |

TABLE 49

| Ex | Data |
|---|---|
| BS1 | $^1$H-NMR ($CDCl_3$) δ: 1.24-1.40 (2H, m), 1.47 (9H, s), 2.00-2.12 (2H, m), 2.15-2.27 (1H, m), 2.35 (1H, ddd, J = 26.1, 13.1, 5.2 Hz), 2.76-2.99 (4H, m), 3.41-3.58 (1H, m), 3.59-3.86 (1H, m), 3, 91-4.17 (2H, m), 4.24 (1H, d, J = 15.2 Hz), 4.37 (1H, d, J = 16.2 Hz), 5.21 (1H, dd, J = 13.4, 5.5 Hz), 6.80 (1H, dd, J = 8.2, 2.1 Hz), 7.06 (1H, d, J = 2.4 Hz), 7.22 (1H, t, J = 3.9 Hz), 7.91 (1H, br s). MS m/z: 387 $(M - tBu + H)^+$. |
| BS2 | MS m/z: 343 $(M + H)^+$. |
| BS3 | $^1$H-NMR ($CDCl_3$) δ: 0.66 (3H, s), 0.90 (3H, s), 0.91 (3H, s), 1.16 (3H, s), 1.29-1.57 (4H, m), 1.67-1.80 (1H, m), 1.81-2.67 (15H, m), 2.74-3.03 (6H, m), 3.16-3.35 (1H, m), 3.41-3.55 (2H, m), 3.55-3.85 (7H, m), 3.92-4.06 (1H, m), 4.25 (1H, d, J = 15.2 Hz), 4.38 (1H, d, J = 15.2 Hz), 4.54-4.70 (1H, m), 5.13-5.31 (1H, m), 6.08-6.18 (1H, m), 6.68-6.91 (3H, m), 7.00-7.16 (5H, m), 7.16-7.32 (3H, m), 7.83-7.93 (1H, m). MS m/z: 926 $(M + H)^+$. |
| BT1 | $^1$H-NMR ($CDCl_3$) δ: 3.39 (3H, s), 6.88 (1H, d, J = 7.4 Hz), 7.26 (1H, d, J = 5.9 Hz), 8.61 (1H, s). MS m/z: 293 $(M + H)^+$. |
| BT2 | MS m/z: 506 $(M - C_2H_4 + H)^+$. |
| BT3 | $^1$H-NMR ($CDCl_3$) δ: 0.03 (9H, s), 0.95-1.04 (2H, m), 1.57 (9H, s), 2.18-2.31 (1H, m), 2.58-2.80 (1H, m), 2.82-2.98 (1H, m), 3.05-3.16 (1H, m), 3.46 (3H, s), 3.63-3.73 (2H, m), 5.15-5.26 (1H, m), 5.26-5.38 (2H, m), 6.56-6.65 (1H, m), 6.66-6.99 (1H, m), 7.84-7.93 (1H, m). |
| BT4 | MS m/z: 293 $(M - CH_2OH + H)^+$. |
| BT5 | $^1$H-NMR ($CDCl_3$) δ: 1.36-1.67 (4H, m), 1.51 (9H, s), 2.03-2.11 (1H, m), 2.20-2.31 (1H, m), 2.62-3.11 (5H, m), 3.39-3.50 (1H, m), 3.43 (3H, s), 4.04-4.15 (1H, m), 5.13-5.23 (1H, m), 5.35-5.51 (1H, m), 6.43 (1H, d, J = 7.0 Hz), 6.59 (1H, dd, J = 10.6, 2.7 Hz), 8.03-8.12 (1H, m). MS m/z: 420 (M − tBu + H)+. |
| BT6 | $^1$H-NMR ($CDCl_3$) δ: 0.69 (3H, s), 0.94 (6H, s), 1.19 (3H, s), 1.25-2.77 (22H, m), 2.80-3.04 (5H, m), 3.25-3.83 (7H, m), 3.44 (3H, s), 3.82 (3H, s), 3.97-4.09 (1H, m), 5.12-5.25 (1H, m), 6.13-6.19 (1H, m), 6.45 (1H, d, J = 7.0 Hz), 6.57-6.64 (1H, m), 6.83 (2H, d, J = 9.0 Hz), 7.11-7.15 (4H, m), 7.29 (2H, d, J = 5.9 Hz), 8.04 (1H, s). MS m/z: 959 $(M + H)^+$. |
| BU1 | $^1$H-NMR ($CDCl_3$) δ: 4.02 (2H, dd, J = 6.1, 3.6 Hz), 4.41 (2H, dd, J = 6.1, 3.6 Hz), 6.65 (1H, d, J = 7.9 Hz), 6.69 (1H, d, J = 7.9 Hz), 6.93 (1H, t, J = 7.9 Hz), 8.61 (1H, br s). MS m/z: 177 $(M + H)^+$. |
| BU2 | $^1$H-NMR (DMSO-$D_6$) δ: 3.88 (2H, t, J = 4.6 Hz), 4.44 (2H, t, J = 4.6 Hz), 6.50 (1H, d, J = 8.5 Hz), 7.20 (1H, d, J = 8.5 Hz), 10.87 (1H, s). MS m/z: 303 $(M + H)^+$. |

TABLE 50

| Ex | Data |
|---|---|
| BU3 | $^1$H-NMR ($CDCl_3$) δ: 0.00 (9H, s), 0.89-1.01 (2H, m), 2.20-2.30 (1H, m), 2.57-2.72 (1H, m), 2.84-2.93 (1H, m), 3.02-3.12 (1H, m), 3.61-3.66 (2H, m), 4.00-4.09 (2H, m), 4.49-4.57 (2H, m), 5.18 (1H, dd, J = 13.4, 5.5 Hz), 5.23-5.31 (2H, m), 6.28 (1H, d, J = 7.9 Hz), 7.30 (1H, d, J = 7.9 Hz). MS m/z: 566 $(M + Na)^+$. |
| BU4 | $^1$H-NMR ($CDCl_3$) δ: 0.00 (9H, s), 0.92-0.99 (2H, m), 2.26-2.33 (1H, m), 2.62-2.77 (1H, m), 2.86-2.98 (1H, m), 3.05-3.14 (1H, m), 3.61-3.69 (2H, m), 4.05-4.14 (2H, m), 4.55-4.63 (2H, m), 5.21-5.32 (3H, m), 6.55 (1H, d, J = 8.5 Hz), 7.41 (2H, br s), 7.91 (1H, d, J = 8.5 Hz). MS m/z: 662 $(M + Na)^+$. |
| BU5 | $^1$H-NMR ($CDCl_3$) δ: 0.00 (9H, s), 0.65 (3H, s), 0.88-1.00 (8H, m), 1.16 (3H, s), 1.35-1.65 (3H, m), 1.68-1.78 (1H, m), 1.82-2.15 (6H, m), 2.20-2.78 (14H, m), 2.83-2.95 (1H, m), 3.01-3.12 (1H, m), 3.36-3.53 (4H, m), 3.61-3.93 (9H, m), 4.01-4.12 (2H, m), 4.39-4.53 (2H, m), 5.15-5.35 (3H, m), 6.10 (1H, br s), 6.47 (1H, d, J = 7.9 Hz), 6.80 (2H, d, J = 8.5 Hz), 7.02 (1H, d, J = 8.5 Hz), 7.07-7.11 (4H, m), 7.26 (2H, d, J = 8.5 Hz). MS m/z: 1099 $(M + H)^+$. |
| BU6 | $^1$H-NMR ($CDCl_3$) δ: 0.68 (3H, s), 0.93 (6H, s), 1.18 (3H, s), 1.35-1.69 (5H, m), 1.68-1.78 (1H, m), 1.84-1.96 (3H, m), 1.98-2.05 (1H, m), 2.07-2.17 (2H, m), 2.25-2.61 (13H, m), 2.62-2.73 (1H, m), 2.78-2.90 (1H, m), 2.91-3.01 (1H, m), 3.37-3.56 (4H, m), 3.66-3.93 (7H, m), 4.01-4.10 (2H, m), 4.39-4.51 (2H, m), 5.21-5.25 (1H, br m), 6.12 (1H, br s), 6.53 (1H, d, J = 8.5 Hz), 6.82 (2H, d, J = 8.5 Hz), 7.06 (1H, d, J = 8.5 Hz), 7.10-7.13 (4H, m), 7.28 (1H, d, J = 8.5 Hz), 8.29 (1H, br s). MS m/z: 969 $(M + H)^+$. |

TABLE 50-continued

| Ex | Data |
|---|---|
| BV1 | $^1$H-NMR ($CDCl_3$) δ: 1.38 (9H, s), 3.61-3.70 (1H, m), 3.96-4.05 (1H, m), 4.10-4.23 (2H, m), 4.51-4.58 (1H, m), 4.82-4.89 (1H, m), 7.17-7.25 (2H, m), 7.62-7.66 (1H, m). MS m/z: 243 [(M − Boc) + H]$^+$. |
| BV2 | $^1$H-NMR (DMSO-$D_6$) δ: 3.83-3.90 (2H, m), 3.96-4.14 (3H, m), 5.15-5.21 (1H, m), 7.37 (1H, td, J = 8.5, 1.5 Hz), 7.69-7.76 (2H, m), 8.49 (3H, br s). MS m/z: 243 (M + H)$^+$. |
| BV3 | $^1$H-NMR ($CDCl_3$) δ: 3.59-3.65 (1H, m), 4.13-4.24 (3H, m), 4.26-4.34 (2H, m), 6.62 (1H, dd, J = 8.5, 1.5 Hz), 7.10 (1H, d, J = 8.5 Hz), 7.82 (1H, dd, J = 8.5, 1.5 Hz), 8.08 (1H, br s). MS m/z: 223 (M + H)$^+$. |
| BV4 | $^1$H-NMR ($CDCl_3$) δ: 3.40 (3H, brs), 3.54-3.60 (1H, m), 4.01-4.13 (3H, m), 4.17-4.23 (2H, m), 6.39 (1H, dd, J = 7.9, 1.5 Hz), 6.48 (1H, dd, J = 7.9, 1.5 Hz), 6.63 (1H, t, J = 7.9 Hz). MS m/z: 193 (M + H)$^+$. |
| BV5 | $^1$H-NMR ($CDCl_3$) δ: 3.80-3.85 (1H, m), 4.15 (1H, m), 4.32 (2H, m), 4.66-4.77 (2H, m), 6.70 (1H, d, J = 8.5 Hz), 6.73 (1H, d, J = 8.5 Hz), 6.97 (1H, t, J = 8.5 Hz), 8.72 (1H, br s). MS m/z: 219 (M + H)$^+$. |

TABLE 51

| Ex | Data |
|---|---|
| BV6 | $^1$H-NMR (DMSO-$D_6$) δ: 3.56-3.63 (1H, m), 3.89-3.94 (1H, m), 4.06-4.16 (2H, m), 4.66-4.74 (1H, m), 4.84-4.89 (1H, m), 6.51 (1H, d, J = 8.5 Hz), 7.22 (1H, d, J = 8.5 Hz), 11.01 (1H, br s). MS m/z: 345 (M + H)$^+$. |
| BV7 | $^1$H-NMR ($CDCl_3$) δ: −0.01 (9H, s), 0.89-1.01 (2H, m), 2.21-2.31 (1H, m), 2.56-2.72 (1H, m), 2.83-2.92 (1H, m), 3.03-3.09 (1H, m), 3.54-3.68 (2H, m), 3.79-3.84 (1H, m), 4.18-4.27 (1H, m), 4.30-4.40 (2H, m), 4.64-4.82 (2H, m), 5.10-5.30 (3H, m), 6.31 (1H, d, J = 8.5 Hz), 7.33 (1H, d, J = 8.5 Hz). MS m/z: 608 (M + Na)$^+$. |
| BV8 | $^1$H-NMR ($CDCl_3$) δ: 0.01 (9H, s), 0.93-1.00 (2H, m), 2.26-2.42 (1H, m), 2.56-2.80 (1H, m), 2.86-2.99 (1H, m), 3.06-3.16 (1H, m), 3.53-3.70 (2H, m), 3.89-3.97 (1H, m), 4.21-4.27 (1H, m), 4.31-4.38 (2H, m), 4.68-4.79 (1H, m), 4.86-4.97 (1H, m), 5.14-5.36 (3H, m), 6.56-6.60 (1H, m), 7.42 (2H, s), 7.92-7.95 (1H, m). MS m/z: 704 (M + Na)$^+$. |
| BV9 | $^1$H-NMR ($CDCl_3$) δ: 0.03 (9H, s), 0.68 (3H, s), 0.93 (6H, s), 0.93-0.99 (2H, m), 1.19 (3H, s), 1.37-1.68 (6H, m), 1.68-1.79 (1H, m), 1.86-1.93 (3H, m), 1.96-2.04 (1H, m), 2.05-2.15 (2H, m), 2.24-2.76 (13H, m), 2.83-2.97 (1H, m), 3.03-3.13 (1H, m), 3.36-3.56 (4H, m), 3.61-3.98 (11H, m), 4.15-4.23 (1H, m), 4.28-4.39 (2H, m), 4.65-4.82 (2H, m), 5.14-5.38 (3H, m), 6.13 (1H, br s), 6.54 (1H, d, J = 7.9 Hz), 6.83 (2H, d, J = 9.2 Hz), 7.10-7.13 (4H, m), 7.29 (1H, d, J = 7.9 Hz). MS m/z: 1141 (M + H)$^+$. |
| BV10 | $^1$H-NMR ($CDCl_3$) δ: 0.68 (3H, s), 0.93 (6H, s), 1.18 (3H, s), 1.37-1.69 (5H, m), 1.76 (1H, td, J = 12.5, 3.4 Hz), 1.85-1.97 (3H, m), 2.00-2.03 (1H, m), 2.10-2.13 (2H, m), 2.26-2.77 (14H, m), 2.82-2.91 (1H, m), 2.92-3.04 (1H, m), 3.37-3.57 (4H, m), 3.67-3.99 (8H, m), 4.15-4.24 (1H, m), 4.29-4.43 (2H, m), 4.69-4.84 (2H, m), 5.13-5.34 (1H, m), 6.12 (1H, br s), 6.57 (1H, dd, J = 8.2, 2.7 Hz), 6.82 (2H, d, J = 8.5 Hz), 7.08-7.16 (5H, m), 7.28 (1H, d, J = 7.9 Hz), 8.28 (1H, br s). MS m/z: 1011 (M + H)$^+$. |
| BW1 | $^1$H-NMR ($CDCl_3$) δ: 0.00 (9H, s), 0.92-0.99 (2H, m), 1.45 (9H, s), 2.09-2.27 (3H, m), 2.54-2.71 (3H, m), 2.80-2.93 (1H, m), 2.98-3.09 (1H, m), 3.57-3.68 (3H, m), 3.68-3.77 (2H, m), 3.77-3.90 (2H, m), 4.12-4.22 (1H, m), 4.25-4.35 (2H, m), 5.19 (1H, dd, J = 13.1, 5.2 Hz), 5.28 (2H, q, J = 9.5 Hz), 6.00 (1H, d, J = 8.5 Hz), 6.48 (1H, d, J = 7.9 Hz). |
| BW2 | MS m/z: 386 (M + H)$^+$. |

TABLE 52

| Ex | Data |
|---|---|
| BW3 | $^1$H-NMR ($CDCl_3$) δ: 0.65 (3H, s), 0.90-0.97 (6H, m), 1.16 (3H, s), 1.41-1.66 (2H, m), 1.66-1.79 (1H, m), 1.79-2.59 (16H, m), 2.59-2.76 (3H, m), 2.76-3.03 (2H, m), 3.35-3.54 (2H, m), 3.62-3.91 (10H, m), 3.91-4.01 (1H, m), 4.22-4.37 (1H, m), 4.39-4.51 (1H. m), 4.51-4.65 (1H, m), 5.09-5.27 (1H, m), 5.88-6.00 (1H, m), 6.00-6.09 (1H, m), 6.47-6.58 (1H, m), 6.72-6.91 (4H, m), 7.02-7.14 (3H, m), 7.96-8.06 (1H, m). MS m/z: 957 (M + H)$^+$. |
| BX1 | $^1$H-NMR ($CDCl_3$) δ: 3.58-3.62 (3H, m), 6.70 (1H, d, J = 8.0 Hz), 7.33-7.41 (1H, m), 9.32 (1H, s). MS m/z: 293 (M + H)$^+$. |
| BX2 | $^1$H-NMR ($CDCl_3$) δ: 0.02 (9H, s), 0.91-1.00 (2H, m), 2.16-2.26 (1H, m), 2.61-2.74 (1H, m), 2.81-2.92 (1H, m), 3.01-3.10 (1H, m), 3.59-3.67 (2H, m), 3.61 (3H, d, J = 1.8 Hz), 5.18 (1H, dd, J = 13.5, 5.5 Hz), 5.27 (2H, dd, J = 19.0, 9.2 Hz), 6.39 (1H, d, J = 8.6 Hz), 7.36 (1H, dd, J = 8.0, 5.5 Hz). MS m/z: 506 (M − $C_2H_4$ + H)$^+$. |

TABLE 52-continued

| Ex | Data |
|---|---|
| BX3 | $^1$H-NMR ($CDCl_3$) δ: 0.02 (9H, m), 0.95-1.02 (2H, m), 1.56 (9H, s), 2.18-2.28 (1H, m), 2.69-2.80 (1H, m), 2.84-2.95 (1H, m), 3.04-3.13 (1H, m), 3.62-3.70 (5H, m), 5.17 (1H, dd, J = 12.9, 5.5 Hz), 5.30 (2H, dd, J = 16.8, 9.4 Hz), 6.51-6.55 (1H, m), 6.54 (1H, d, J = 8.6 Hz), 7.63 (1H, s). |
| BX4 | $^1$H-NMR ($CDCl_3$) δ: 1.36-1.45 (1H, m), 1.50 (9H, s), 1.85-1.94 (2H, m), 2.03-2.09 (1H, m), 2.21-2.31 (1H, m), 2.69-3.09 (5H, m), 3.62 (3H, d, J = 2.0 Hz), 3.83-3.93 (2H, m), 4.04-4.13 (2H, m), 5.14-5.23 (1H, m), 6.43-6.50 (2H, m), 8.13 (1H, s). MS m/z: 420 (M − tBu + H)$^+$. |
| BX5 | MS m/z: 376 (M + H)$^+$. |
| BX6 | $^1$H-NMR ($CDCl_3$) δ: 0.69 (3H, s), 0.97 (6H, s), 1.19 (3H, s), 1.39-1.68 (5H, m), 1.69-2.01 (4H, m), 2.04-2.64 (12H, m), 2.66-3.05 (5H, m), 3.20-3.35 (1H, m), 3.43-3.66 (7H, m), 3.69-3.79 (2H, m), 3.81 (3H, s), 3.96-4.11 (1H, m), 4.53-4.69 (1H, m), 5.14-5.24 (1H, m), 6.00 (1H, s), 6.44-6.53 (2H, m), 6.83 (2H, d, J = 9.0 Hz), 6.86-6.93 (2H, m), 7.09-7.16 (3H, m), 8.00 (1H, s). MS m/z: 977 (M + H)$^+$. |
| BY1 | $^1$H-NMR ($CDCl_3$) δ: 3.48-3.50 (4H, m), 4.33 (2H, br s), 6.69 (2H, s). |
| BY2 | $^1$H-NMR ($CDCl_3$) δ: 1.87-2.01 (1H, m), 2.59-2.84 (4H, m), 3.46-3.60 (3H, m), 4.49 (1H, br s), 4.78-4.84 (1H, m), 5.57 (1H, br s), 6.82 (1H, d, J = 8.6 Hz), 7.20 (1H, d, J = 8.6 Hz), 7.90 (1H, br s). MS m/z: 444 [M($^{79}Br^{79}Br$) + H]$^+$, 446 [M($^{79}Br^{81}Br$) + H]$^+$, 448 [M($^{81}Br^{81}Br$) + H]$^+$. |

TABLE 53

| Ex | Data |
|---|---|
| BY3 | $^1$H-NMR ($CDCl_3$) δ: −0.02 (9H, s), 0.88-0.97 (2H, m), 1.81-1.97 (1H, m), 2.61-2.98 (4H, m), 3.50-3.62 (5H, m), 4.51 (1H, br s), 4.79-4.85 (1H, m), 5.12 (1H, d, J = 9.8 Hz), 5.23 (1H, d, J = 9.8 Hz), 5.70 (1H, br s), 6.84 (1H, d, J = 8.6 Hz), 7.22 (1H, d, J = 8.6 Hz). MS m/z: 547 [M($^{79}Br^{79}Br$) − $C_2H_4$ + H]$^+$, 549[M ($^{79}Br^{81}Br$) − $C_2H_4$ + H]$^+$, 551 [M($^{81}Br^{81}Br$) − $C_2H_4$ + H]$^+$. |
| BY4 | $^1$H-NMR ($CDCl_3$) δ: 0.00 (9H, s), 0.92-0.97 (2H, m), 2.20-2.27 (1H, m), 2.58-2.71 (1H, m), 2.82-2.93 (1H, m), 3.01-3.08 (1H, m), 3.58-3.66 (4H, m), 3.99-4.03 (2H, m), 4.34 (1H, br s), 5.18 (1H, dd, J = 13.2, 5.2 Hz), 5.25 (1H, d, J = 9.8 Hz), 5.30 (1H, d, J = 9.8 Hz), 6.17 (1H, d, J = 8.6 Hz), 7.03 (1H, d, J = 8.6 Hz). MS m/z: 517 [M($^{79}Br$) + Na]$^+$, 519 [M($^{81}Br$) + Na]$^+$. |
| BY5 | $^1$H-NMR ($CDCl_3$) δ: 0.00 (9H, s), 0.93-0.99 (2H, m), 2.24-2.32 (1H, m), 2.62-2.75 (1H, m), 2.85-2.96 (1H, m), 3.03-3.11 (1H, m), 3.59-3.71 (4H, m), 4.00-4.07 (2H, m), 5.19-5.34 (3H, m), 6.30 (1H, d, J = 8.6 Hz), 6.71 (1H, s), 7.42 (2H, s), 7.83 (1H, d, J = 8.6 Hz). MS m/z: 611 (M-$C_2H_4$ + H)$^+$. |
| BY6 | $^1$H-NMR ($CDCl_3$) δ: 0.00 (9H, s), 0.65 (3H, s), 0.90 (3H, s), 0.91 (3H, s), 0.93-0.98 (2H, m), 1.15 (3H, s), 1.35-1.64 (4H, m), 1.69-1.77 (1H, m), 1.82-1.92 (3H, m), 1.96-2.51 (16H, m), 2.59-2.73 (1H, m), 2.83-2.94 (1H, m), 3.02-3.08 (1H, m), 3.41-3.76 (12H, m), 3.78 (3H, s), 3.98-4.02 (2H, m), 5.20 (1H, dd, J = 13.2, 5.2 Hz), 5.26 (1H, d, J = 9.8 Hz), 5.31 (1H, d, J = 9.8 Hz), 5.44 (1H, s), 6.09-6.13 (1H, m), 6.20 (1H, d, J = 8.0 Hz), 6.80 (2H, d, J = 8.5 Hz), 6.88 (1H, d, J = 8.0 Hz), 7.08-7.13 (4H, m), 7.26 (2H, d, J = 8.5 Hz). MS m/z: 1098 (M + H)$^+$. |
| BY7 | $^1$H-NMR ($CDCl_3$) δ: 0.66 (3H, s), 0.90 (3H, s), 0.91 (3H, s), 1.16 (3H, s), 1.36-1.65 (4H, m), 1.69-1.78 (1H, m), 1.82-2.14 (6H, m), 2.24-2.53 (13H, m), 2.61-2.74 (1H, m), 2.78-2.99 (2H, m), 3.43-3.76 (10H, m), 3.78 (3H, s), 3.98-4.04 (2H, m), 5.20 (1H, dd, J = 12.8, 5.5 Hz), 5.47 (1H, s), 6.09-6.11 (1H, m), 6.22 (1H, d, J = 8.5 Hz), 6.80 (2H, d, J = 8.5 Hz), 6.89 (1H, d, J = 8.5 Hz), 7.08-7.12 (4H, m), 7.25-7.27 (2H, m), 8.19 (1H, s). MS m/z: 968 (M + H)$^+$. |
| BZ1 | $^1$H-NMR ($CDCl_3$) δ: 0.66 (3H, s), 0.91 (3H, s), 0.91 (3H, s), 1.16 (3H, s), 1.44-1.64 (11H, m), 1.69-1.92 (3H, m), 2.04-2.19 (3H, m), 2.23-2.55 (9H, m), 3.42-3.52 (2H, m), 3.65-3.75 (2H, m), 3.78 (3H, s), 6.08-6.11 (1H, m), 6.79 (2H, d, J = 8.0 Hz), 7.06-7.11 (4H, m), 7.24 (2H, d, J = 8.0 Hz). MS m/z: 658 (M + H)$^+$. |
| BZ2 | $^1$H-NMR ($CDCl_3$) δ: 0.66 (3H, s), 0.91 (3H, s), 0.92 (3H, s), 1.16 (3H, s), 1.36-1.66 (4H, m), 1.69-1.78 (1H, m), 1.80-1.93 (3H, m), 1.94-2.15 (4H, m), 2.25-2.40 (4H, m), 2.43-2.54 (2H, m), 3.42-3.53 (2H, m), 3.57-3.76 (4H, m), 3.78 (3H, s), 6.09-6.13 (1H, m), 6.80 (2H, d, J = 9.2 Hz), 7.07-7.12 (4H, m), 7.26 (2H, d, J = 8.6 Hz). MS m/z: 588 (M + H)$^+$. |

TABLE 54

| Ex | Data |
|---|---|
| BZ3 | $^1$H-NMR ($CDCl_3$) δ: 0.66 (3H, s), 0.91 (3H, s), 0.91 (3H, s), 1.16 (3H, s), 1.45-1.64 (4H, m), 1.69-1.77 (1H, m), 1.83-1.91 (1H, m), 1.97-2.18 (5H, m), 2.25-2.52 (6H, m), 3.04 (3H, s), 3.48 (2H, dd, J = 20.0, 14.0 Hz), 3.66-3.75 (2H, m), 3.78 (3H, s), 4.19 (2H, d, J = 6.1 Hz), 6.05-6.09 (1H, m), 6.80 (2H, d, J = 9.1 Hz), 7.08-7.11 (4H, m), 7.25 (2H, d, J = 8.5 Hz). |

TABLE 54-continued

| Ex | Data |
|---|---|
| BZ4 | $^1$H-NMR ($CDCl_3$) δ: 0.66 (3H, s), 0.90 (3H, s), 0.91 (3H, s), 1.16 (3H, s), 1.34-1.65 (4H, m), 1.47 (9H, s), 1.68-1.78 (1H, m), 1.82-1.92 (3H, m), 1.95-2.02 (1H, m), 2.04-2.14 (2H, m), 2.25-2.48 (12H, m), 3.41-3.49 (6H, m), 3.66-3.76 (2H, m), 3.78 (3H, s), 6.08-6.12 (1H, m), 6.80 (2H, d, J = 8.8 Hz), 7.08 (2H, d, J = 7.9 Hz), 7.10 (2H, d, J = 8.8 Hz), 7.26 (2H, d, J = 7.9 Hz). |
| BZ5 | MS m/z: 656 $(M + H)^+$. |
| BZ6 | $^1$H-NMR ($CDCl_3$) δ: 0.00 (9H, s), 0.66 (3H, s), 0.90 (3H, s), 0.91 (3H, s), 0.94-0.99 (2H, m), 1.16 (3H, s), 1.39-1.64 (4H, m), 1.69-1.78 (1H, m), 1.84-1.91 (3H, m), 1.97-2.48 (16H, m), 2.60-2.72 (1H, m), 2.83-2.94 (1H, m), 3.02-3.09 (1H, m), 3.41-3.75 (12H, m), 3.78 (3H, s), 3.98-4.03 (2H, m), 5.20 (1H, dd, J = 13.2, 5.2 Hz), 5.27 (1H, d, J = 9.8 Hz), 5.31 (1H, d, J = 9.8 Hz), 5.45 (1H, s), 6.08-6.12 (1H, m), 6.19 (1H, d, J = 8.0 Hz), 6.79-6.81 (2H, m), 6.87 (1H, d, J = 8.0 Hz), 7.07-7.12 (4H, m), 7.24-7.28 (2H, m). MS m/z: 1098 $(M + H)^+$. |
| BZ7 | $^1$H-NMR ($CDCl_3$) δ: 0.66 (3H, s), 0.90 (3H, s), 0.91 (3H, s), 1.16 (3H, s), 1.41-1.64 (4H, m), 1.70-1.77 (1H, m), 1.84-2.13 (6H, m), 2.25-2.48 (13H, m), 2.62-2.74 (1H, m), 2.79-3.00 (2H, m), 3.42-3.75 (10H, m), 3.78 (3H, s), 3.98-4.03 (2H, m), 5.20 (1H, dd, J = 13.2, 5.2 Hz), 5.46 (1H, s), 6.08-6.11 (1H, m), 6.22 (1H, d, J = 8.0 Hz), 6.78-6.81 (2H, m), 6.89 (1H, d, J = 8.0 Hz), 7.07-7.11 (4H, m), 7.24-7.27 (2H, m), 8.03 (1H, s). MS m/z: 968 $(M + H)^+$. |
| CA1 | $^1$H-NMR ($CDCl_3$) δ: 0.69 (3H, s), 0.91-0.95 (6H, m), 1.19 (3H, s), 1.33-1.86 (13H, m), 1.88-2.00 (1H, m), 2.04-2.42 (12H, m), 2.63-2.99 (3H, m), 3.05-3.17 (2H, m), 3.37-3.55 (5H, m), 3.73-3.84 (5H, m), 3.98-4.09 (2H, m), 5.13-5.21 (1H, m), 6.30-6.38 (3H, m), 6.62 (1H, d, J = 7.9 Hz), 6.87 (2H, d, J = 9.1 Hz), 7.12 (2H, d, J = 8.5 Hz), 7.19 (2H, d, J = 8.5 Hz), 7.24-7.29 (3H, m), 7.99 (1H, s). MS m/z: 958 $(M + H)^+$. |
| CB1 | $^1$H-NMR ($CDCl_3$) δ: 3.54-3.63 (2H, m), 3.75-3.82 (2H, m), 6.77 (1H, t, J = 7.9 Hz), 6.94 (1H, br s), 8.34-8.40 (2H, m), 9.07 (1H, br s). MS m/z: 208 $(M + H)^+$. |
| CB2 | $^1$H-NMR ($CDCl_3$) δ: 1.33-1.49 (9H, m), 3.44-3.66 (2H, m), 3.66-3.84 (2H, m), 4.43-4.73 (2H, m), 6.59-6.80 (1H, m), 7.22-7.46 (2H, m), 7.93-8.27 (2H, m). MS m/z: 238 $(M - tBu + H)^+$. |

TABLE 55

| Ex | Data |
|---|---|
| CB3 | $^1$H-NMR ($CDCl_3$) δ: 1.35-1.55 (9H, m), 3.73-3.96 (2H, m), 3.96-4.18 (2H, m), 4.63-4.99 (2H, m), 6.78-7.10 (3H, m), 8.86-9.33 (1H, m). MS m/z: 234 $(M - tBu + H)^+$. |
| CB4 | $^1$H-NMR ($CDCl_3$) δ: 1.39-1.57 (9H, m), 3.77-3.93 (2H, m), 4.01-4.19 (2H, m), 4.78-4.91 (2H, m), 6.68-6.79 (1H, m), 7.49-7.58 (1H, m), 9.39-9.68 (1H, br m). MS m/z: 360 $(M - tBu + H)^+$. |
| CB5 | $^1$H-NMR ($CDCl_3$) δ: 0.00 (9H, s), 0.91-0.99 (2H, m), 1.44-1.52 (9H, m), 2.15-2.27 (1H, m), 2.59-2.79 (1H, m), 2.80-2.95 (1H, m), 3.00-3.11 (1H, m), 3.58-3.70 (2H, m), 3.79-3.94 (2H, m), 4.07-4.21 (2H, m), 4.70-4.97 (2H, m), 5.13-5.23 (1H, m), 5.27 (2H, q, J = 9.1 Hz), 6.41 (1H, d, J = 8.5 Hz), 7.52 (1H, t, J = 8.8 Hz). MS m/z: 679 $(M + Na)^+$. |
| CB6 | $^1$H-NMR ($CDCl_3$) δ: 0.01 (9H, s), 0.91-0.99 (2H, m), 1.35-1.51 (9H, m), 2.13-2.32 (1H, m), 2.63-2.96 (2H, m), 3.00-3.14 (1H, m), 3.56-3.74 (2H, m), 3.78-3.98 (2H, m), 4.05-4.23 (2H, m), 5.17-5.37 (5H, m), 6.81-6.87 (1H, m), 7.50-7.59 (1H, m), 10.07 (1H, d, J = 11.0 Hz). MS m/z: 581 $(M + Na)^+$. |
| CB7 | $^1$H-NMR ($CDCl_3$) δ: 0.00 (9H, s), 0.92-1.00 (2H, m), 1.40-1.51 (9H, m), 2.15-2.28 (1H, m), 2.30-2.44 (4H, m), 2.64-2.81 (1H, m), 2.81-2.95 (1H, m), 3.00-3.13 (1H, m), 3.37-3.73 (8H, m), 3.77-3.97 (2H, m), 4.05-4.22 (2H, m), 4.75-5.04 (2H, m), 5.13 (2H, s), 5.16-5.25 (1H, m), 5.29 (2H, q, J = 8.7 Hz), 6.54-6.62 (1H, m), 6.82-6.93 (1H, m), 7.29-7.38 (5H, m). MS m/z: 763 $(M + H)^+$. |
| CB8 | MS m/z: 629 $(M + H)^+$. |
| CB9 | $^1$H-NMR ($CDCl_3$) δ: 0.00 (9H, s), 0.65 (3H, s), 0.90-1.02 (2H, m), 0.94 (6H, s), 1.16 (3H, s), 1.38-1.78 (13H, m), 1.80-1.99 (3H, m), 2.02-2.15 (2H, m), 2.16-2.62 (12H, m), 2.64-2.95 (3H, m), 3.00-3.12 (1H, m), 3.38-3.81 (12H, m), 3.78 (3H, s), 3.81-4.01 (2H, m), 4.07-4.23 (2H, m), 4.81-5.06 (2H, m), 5.17-5.25 (1H, m), 5.29 (2H, dd, J = 16.4, 9.7 Hz), 5.92-5.99 (1H, m), 6.56-6.65 (1H, m), 6.79 (2H, d, J = 9.1 Hz), 6.82-6.94 (3H, m), 7.03-7.13 (3H, m). MS m/z: 1230 $(M + H)^+$. |
| CB10 | $^1$H-NMR ($CDCl_3$) δ: 0.65 (3H, s), 0.94 (6H, s), 1.16 (3H, s), 1.40-1.80 (4H, m), 1.80-2.00 (3H, m), 2.02-2.17 (2H, m), 2.17-2.66 (15H, m), 2.66-2.91 (3H, m), 2.91-3.06 (1H, m), 3.06-3.24 (2H, m), 3.35-3.86 (13H, m), 4.01-4.10 (2H, m), 4.17-4.33 (2H, m), 5.20 (1H, dd, J = 12.5, 5.2 Hz), 5.90-5.99 (1H, m), 6.61 (1H, d, J = 7.9 Hz), 6.79 (2H, d, J = 9.1 Hz), 6.82-6.95 (3H, m), 7.04-7.17 (3H, m), 7.93-8.28 (1H, m). MS m/z: 1014 $(M + H)^+$. |

TABLE 56

| Ex | Data |
|---|---|
| CC1 | $^{1}$H-NMR ($CDCl_3$) δ: −0.02 (9H, s), 0.89-0.98 (2H, m), 2.00-2.12 (2H, m), 2.15-2.26 (1H, m), 2.63 (1H, ddd, J = 26.6, 13.2, 4.7 Hz), 2.79-2.93 (3H, m), 3.04 (1H, dt, J = 17.2, 3.6 Hz), 3.62 (2H, t, J = 8.5 Hz), 3.83 (2H, t, J = 5.8 Hz), 5.16 (1H, dd, J = 13.4, 5.5 Hz), 5.26 (2H, q, J = 8.9 Hz), 6.47 (1H, d, J = 7.9 Hz), 6.63 (1H, d, J = 8.5 Hz), 7.07-7.13 (1H, m), 7.58-7.65 (1H, m), 7.70-7.81 (1H, m), 7.91 (1H, d, J = 7.9 Hz). |
| CC2 | $^{1}$H-NMR ($CDCl_3$) δ: 0.00 (9H, s), 0.90-1.00 (2H, m), 1.39-1.54 (2H, m), 1.49 (9H, s), 2.07-2.34 (5H, m), 2.53-2.74 (3H, m), 2.78-2.95 (2H, m), 2.98-3.09 (1H, m), 3.59-3.69 (2H, m), 3.69-3.92 (6H, m), 3.98-4.08 (1H, m), 4.12-4.20 (1H, m), 4.54-4.75 (1H, m), 5.12-5.22 (1H, m), 5.28 (2H, dd, J = 17.0, 9.7 Hz), 6.42 (1H, d, J = 8.5 Hz), 6.48 (1H, d, J = 8.5 Hz). MS m/z: 678 $(M + Na)^+$. |
| CC3 | $^{1}$H-NMR ($CDCl_3$) δ: 0.65 (3H, s), 0.91-0.97 (6H, s), 1.16 (3H, s), 1.39-1.80 (10H, m), 1.80-3.04 (20H, m), 3.40-3.54 (2H, m), 3.62-3.89 (9H, m), 3.92-4.04 (2H, m), 4.04-4.12 (1H, m), 4.65-4.84 (2H, m), 5.13-5.24 (1H, m), 5.88-6.00 (1H, m), 6.46 (1H, d, J = 8.5 Hz), 6.50-6.54 (1H, m), 6.79 (2H, d, J = 9.1 Hz), 6.83-6.91 (2H, m), 7.02-7.15 (3H, m), 8.01 (1H, br s). MS m/z: 1027 $(M + H)^+$. |
| CD1 | $^{1}$H-NMR ($CDCl_3$) δ: 1.34-1.51 (1H, m), 1.48 (9H, s), 1.56-1.66 (1H, m), 2.02-2.11 (2H, m), 2.17-2.25 (1H, m), 2.68-3.02 (5H, m), 3.39-3.48 (1H, m), 3.54-3.66 (1H, m), 3.75 (3H, s), 3.97-4.10 (2H, m), 5.13-5.21 (1H, m), 6.33 (1H, d, J = 7.8 Hz), 6.52 (1H, d, J = 7.8 Hz), 6.94 (1H, t, J = 8.0 Hz), 8.05-8.23 (1H, m). |
| CD2 | $^{1}$H-NMR ($CDCl_3$) δ: 0.66 (3H, s), 0.95 (3H, s), 0.95 (3H, s), 1.17 (3H, s), 1.39-1.78 (6H, m), 1.83-2.64 (15H, m), 2.69-3.02 (5H, m), 3.20-3.34 (1H, m), 3.43-3.65 (4H, m), 3.66-3.80 (8H, m), 3.95-4.07 (1H, m), 4.50-4.63 (1H, m), 5.11-5.25 (1H, m), 5.94-6.00 (1H, m), 6.32-6.40 (1H, m), 6.55 (1H, d, J = 8.6 Hz), 6.80 (2H, d, J = 9.0 Hz), 6.86 (2H, d, J = 9.4 Hz), 6.96 (1H, t, J = 8.0 Hz), 7.04-7.15 (3H, m), 8.03 (1H, s). MS m/z: 959 $(M + H)^+$. |
| CE1 | $^{1}$H-NMR ($CDCl_3$) δ: 0.66 (3H, s), 0.90 (3H, s), 0.91 (3H, s), 1.16 (3H, s), 1.37-1.64 (4H, m), 1.69-1.77 (1H, m), 1.83-2.14 (6H, m), 2.24-2.51 (13H, m), 2.61-2.73 (1H, m), 2.78-2.99 (2H, m), 3.42-3.75 (10H, m), 3.78 (3H, s), 3.96-4.04 (2H, m), 5.20 (1H, dd, J = 12.8, 5.5 Hz), 5.46 (1H, s), 6.08-6.11 (1H, m), 6.22 (1H, d, J = 8.5 Hz), 6.79-6.81 (2H, m), 6.89 (1H, d, J = 8.5 Hz), 7.07-7.11 (4H, m), 7.25-7.27 (2H, m), 8.15 (1H, s). MS m/z: 968 $(M + H)^+$. |

TABLE 57

| Ex | Data |
|---|---|
| CF1 | $^{1}$H-NMR ($CDCl_3$) δ: 0.66 (3H, s), 0.90 (3H, s), 0.91 (3H, s), 1.16 (3H, s), 1.36-1.64 (4H, m), 1.69-1.77 (1H, m), 1.82-2.13 (6H, m), 2.25-2.51 (13H, m), 2.61-2.73 (1H, m), 2.79-2.99 (2H, m), 3.42-3.75 (10H, m), 3.78 (3H, s), 3.96-4.05 (2H, m), 5.20 (1H, dd, J = 12.8, 5.5 Hz), 5.46 (1H, s), 6.08-6.12 (1H, m), 6.22 (1H, d, J = 8.5 Hz), 6.79-6.81 (2H, m), 6.89 (1H, d, J = 8.5 Hz), 7.08-7.11 (4H, m), 7.25-7.27 (2H, m), 8.11 (1H, s). MS m/z: 968 $(M + H)^+$. |
| CG1 | $^{1}$H-NMR ($CDCl_3$) δ: 0.65 (3H, s), 0.93 (3H, s), 0.94 (3H, s), 1.16 (3H, s), 1.30-1.43 (2H, m), 1.45-1.65 (2H, m), 1.67-1.76 (1H, m), 1.82-2.02 (3H, m), 2.03-2.74 (17H, m), 2.77-2.99 (4H, m), 3.12-3.31 (2H, m), 3.41-3.58 (3H, m), 3.65-3.76 (3H, m), 3.78 (3H, s), 3.80-3.89 (2H, m), 3.92-4.05 (1H, m), 4.52-4.63 (1H, m), 5.13-5.24 (1H, m), 5.96 (1H, d, J = 4.4 Hz), 6.36 (1H, d, J = 8.5 Hz), 6.53 (1H, d, J = 8.5 Hz), 6.76-6.89 (4H, m), 7.05-7.13 (3H, m), 8.04 (1H, s). MS m/z: 985 $(M + H)^+$. |
| CH1 | $^{1}$H-NMR ($CDCl_3$) δ: 0.65 (3H, s), 0.94 (6H, s), 1.16 (3H, s), 1.31-1.45 (2H, m), 1.45-1.67 (2H, m), 1.67-1.77 (1H, m), 1.82-2.01 (3H, m), 2.04-2.74 (17H, m), 2.77-2.99 (4H, m), 3.12-3.30 (2H, m), 3.40-3.57 (3H, m), 3.65-3.76 (3H, m), 3.78 (3H, s), 3.81-3.89 (2H, m), 3.92-4.04 (1H, m), 4.52-4.63 (1H, m), 5.14-5.24 (1H, m), 5.96 (1H, d, J = 4.4 Hz), 6.36 (1H, d, J = 8.5 Hz), 6.53 (1H, d, J = 8.5 Hz), 6.76-6.89 (4H, m), 7.05-7.13 (3H, m), 8.04 (1H, s). MS m/z: 985 $(M + H)^+$. |

The structural-formulas of the compounds described in the Examples are shown below in Table 58 to Table 92.

In the Tables, Ex indicates the Example number and Structure indicates the structural formula.

The following symbols may be used in the structural formulas.

Bn: benzyl group

Boc: tert-butoxycarbonyl group

Cbz: benzyloxycarbonyl group

Et: ethyl group tBu: tert-butyl group

Ms: methanesulfonyl group

Ns: 2-nitrobenzenesulfonyl group

SEM: 2-(trimethylsilyl) ethoxymethyl group

TABLE 58
| Ex | Structure |
|---|---|
| A1 | 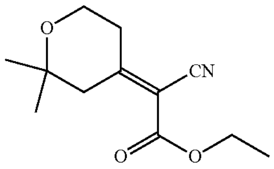 and 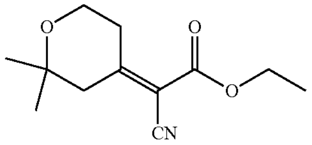 [SMILES: CCOC(=O)/C(C#N)=C1\CCOC(C)(C)C1] in mixture |
| A2 | 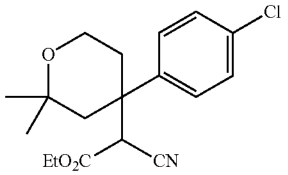 [SMILES: CCOC(=O)C(C#N)C1(c2ccc(Cl)cc2)CCOC(C)(C)C1] |
| A3 | 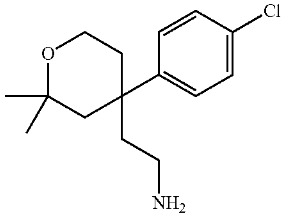 [SMILES: CC1(C)CC(CCN)(c2ccc(Cl)cc2)CCO1] |
| A4 | 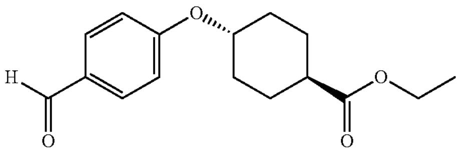 [SMILES: CCOC(=O)[C@H]1CC[C@H](Oc2ccc(C=O)cc2)CC1] |
| A5 | 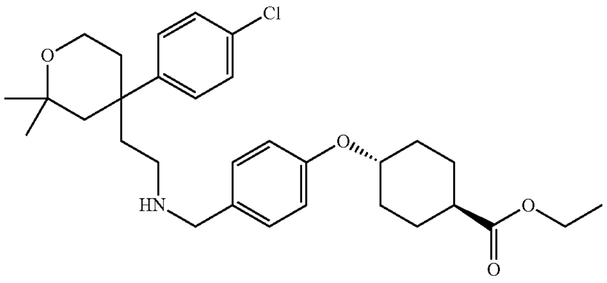 |
| A6 | 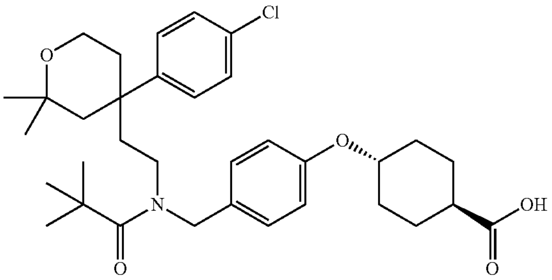 [SMILES: CC1(C)CC(CCN(Cc2ccc(O[C@H]3CC[C@H](C(=O)O)CC3)cc2)C(=O)C(C)(C)C)(c2ccc(Cl)cc2)CCO1] |

TABLE 58-continued
| Ex | Structure |
|---|---|
| B1 | 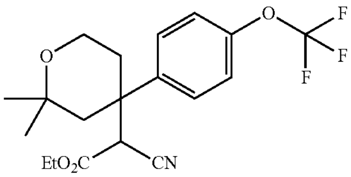 [SMILES: CCOC(=O)C(C#N)C1(c2ccc(OC(F)(F)F)cc2)CCOC(C)(C)C1] |
| B2 | 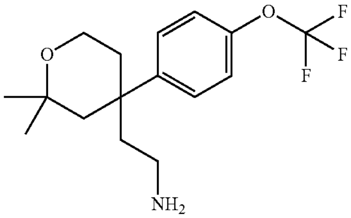 [SMILES: CC1(C)CC(CCN)(c2ccc(OC(F)(F)F)cc2)CCO1] |
| B3 | 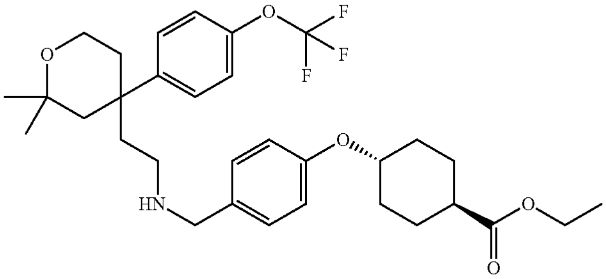 [SMILES: CCOC(=O)[C@H]1CC[C@H](Oc2ccc(CNCCC3(c4ccc(OC(F)(F)F)cc4)CCOC(C)(C)C3)cc2)CC1] |
| B4 | 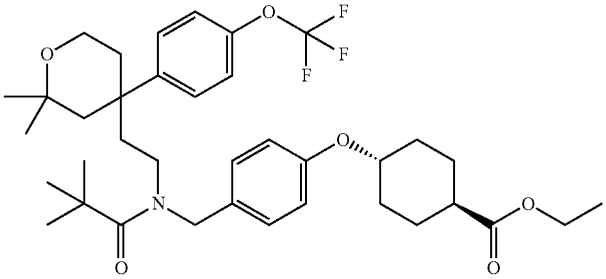 [SMILES: CCOC(=O)[C@H]1CC[C@H](Oc2ccc(CN(CCC3(c4ccc(OC(F)(F)F)cc4)CCOC(C)(C)C3)C(=O)C(C)(C)C)cc2)CC1] |
| B5 | 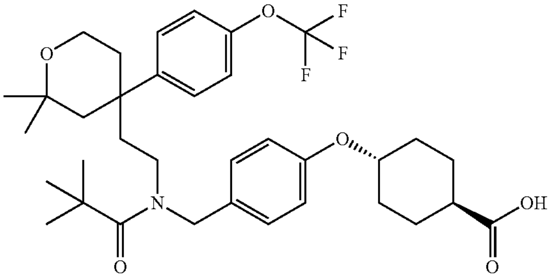 [SMILES: CC1(C)CC(CCN(Cc2ccc(O[C@H]3CC[C@H](C(=O)O)CC3)cc2)C(=O)C(C)(C)C)(c2ccc(OC(F)(F)F)cc2)CCO1] |
| C1 | 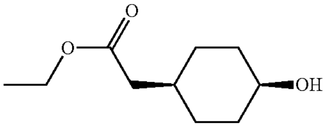 |

TABLE 59
| Ex | Structure |
|---|---|
| C2 | 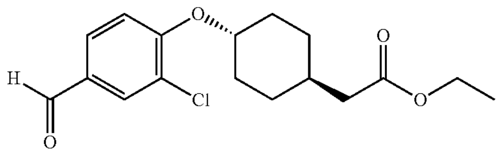 [SMILES: CCOC(=O)C[C@H]1CC[C@H](Oc2ccc(C=O)cc2Cl)CC1] |
| C3 | 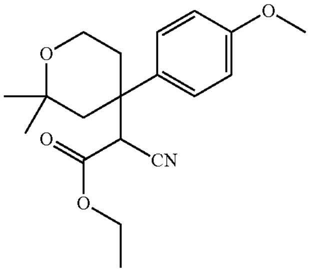 |
| C4 | 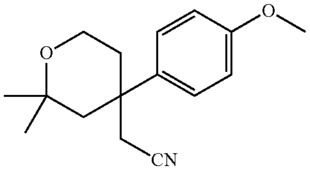 |
| C5 | 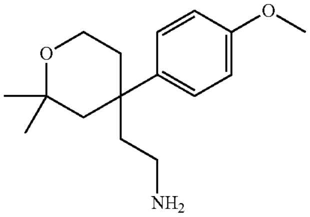 |
| C6 | 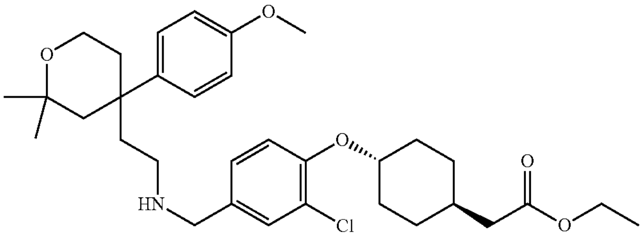 [SMILES: CCOC(=O)C[C@H]1CC[C@H](Oc2ccc(CNCCC3(c4ccc(OC)cc4)CCOC(C)(C)C3)cc2Cl)CC1] |
| C7 | 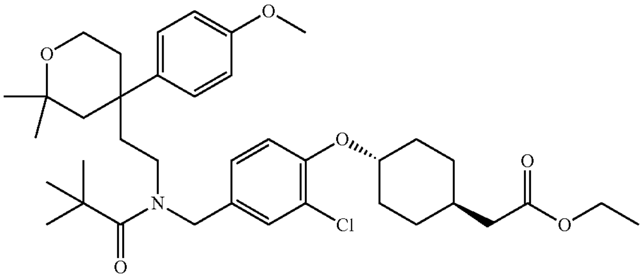 [SMILES: CCOC(=O)C[C@H]1CC[C@H](Oc2ccc(CN(CCC3(c4ccc(OC)cc4)CCOC(C)(C)C3)C(=O)C(C)(C)C)cc2Cl)CC1] |

TABLE 59-continued
| Ex | Structure |
| --- | --- |
| C8 | 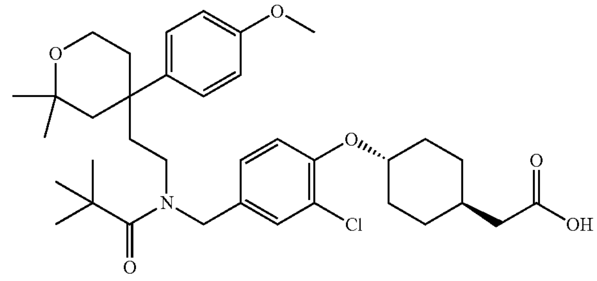 [SMILES: COc1ccc(C2(CCN(Cc3ccc(O[C@H]4CC[C@H](CC(=O)O)CC4)c(Cl)c3)C(=O)C(C)(C)C)CCOC(C)(C)C2)cc1] |
| D1 | 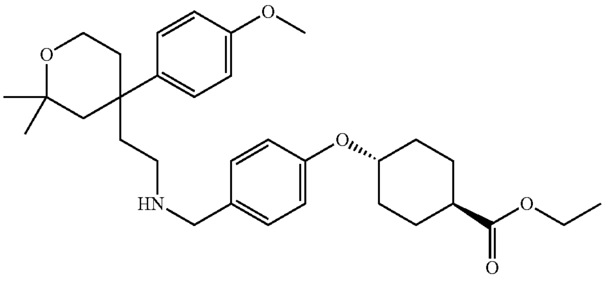 [SMILES: CCOC(=O)[C@H]1CC[C@H](Oc2ccc(CNCCC3(c4ccc(OC)cc4)CCOC(C)(C)C3)cc2)CC1] |
| D2 | 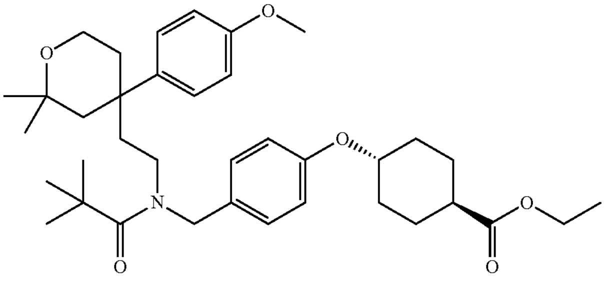 [SMILES: CCOC(=O)[C@H]1CC[C@H](Oc2ccc(CN(CCC3(c4ccc(OC)cc4)CCOC(C)(C)C3)C(=O)C(C)(C)C)cc2)CC1] |
| D3 | 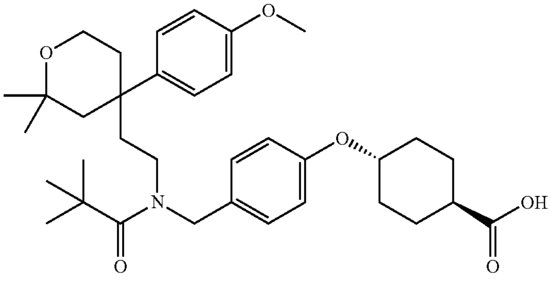 [SMILES: COc1ccc(C2(CCN(Cc3ccc(O[C@H]4CC[C@H](C(=O)O)CC4)cc3)C(=O)C(C)(C)C)CCOC(C)(C)C2)cc1] |
| E1 | 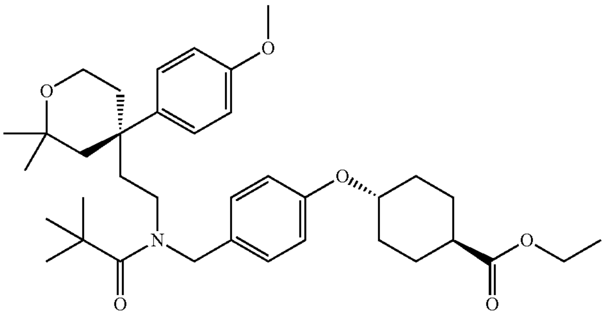 [SMILES: CCOC(=O)[C@H]1CC[C@H](Oc2ccc(CN(CC[C@@]3(c4ccc(OC)cc4)CCOC(C)(C)C3)C(=O)C(C)(C)C)cc2)CC1] |

TABLE 59-continued
| Ex | Structure |
|---|---|
| E2 | 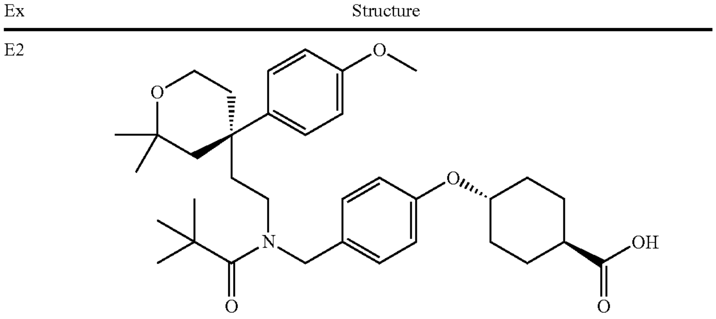 |
TABLE 60
| Ex | Structure |
|---|---|
| F1 | 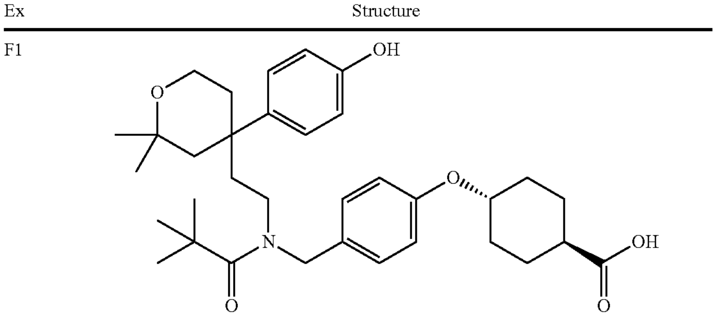 |
| F2 | 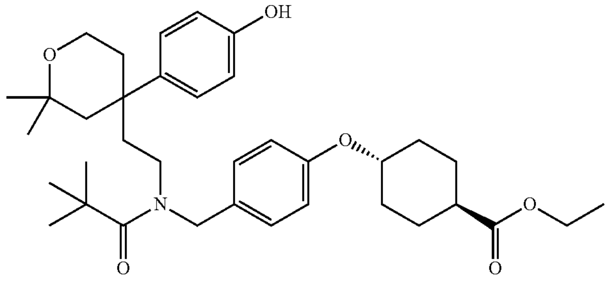 [SMILES: CCOC(=O)[C@H]1CC[C@H](Oc2ccc(CN(CCC3(c4ccc(O)cc4)CCOC(C)(C)C3)C(=O)C(C)(C)C)cc2)CC1] |
| F3 | 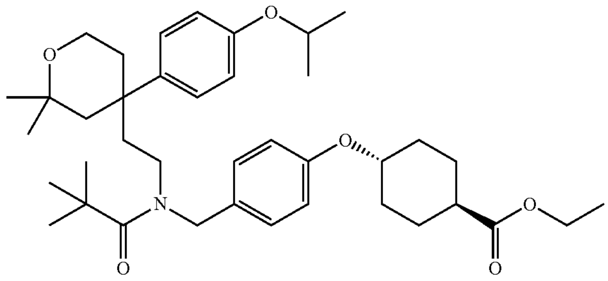 [SMILES: CCOC(=O)[C@H]1CC[C@H](Oc2ccc(CN(CCC3(c4ccc(OC(C)C)cc4)CCOC(C)(C)C3)C(=O)C(C)(C)C)cc2)CC1] |
| F4 | 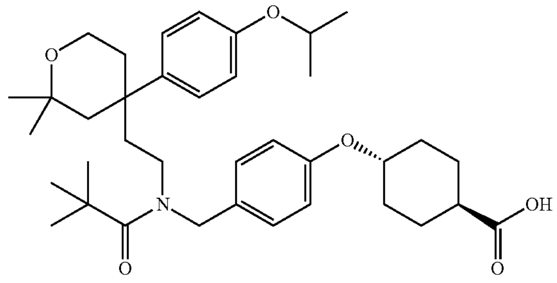 [SMILES: CC(C)Oc1ccc(C2(CCN(Cc3ccc(O[C@H]4CC[C@H](C(=O)O)CC4)cc3)C(=O)C(C)(C)C)CCOC(C)(C)C2)cc1] |

TABLE 60-continued
| Ex | Structure |
| --- | --- |
| G1 | 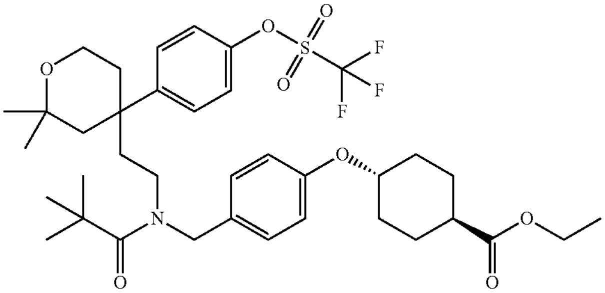 [SMILES: CCOC(=O)[C@H]1CC[C@H](Oc2ccc(CN(CCC3(c4ccc(OS(=O)(=O)C(F)(F)F)cc4)CCOC(C)(C)C3)C(=O)C(C)(C)C)cc2)CC1] |
| G2 | 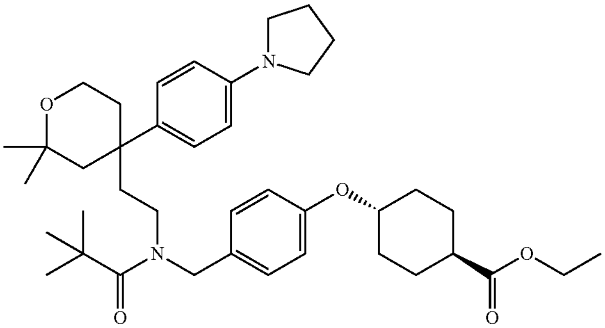 [SMILES: CCOC(=O)[C@H]1CC[C@H](Oc2ccc(CN(CCC3(c4ccc(N5CCCC5)cc4)CCOC(C)(C)C3)C(=O)C(C)(C)C)cc2)CC1] |
| G3 | 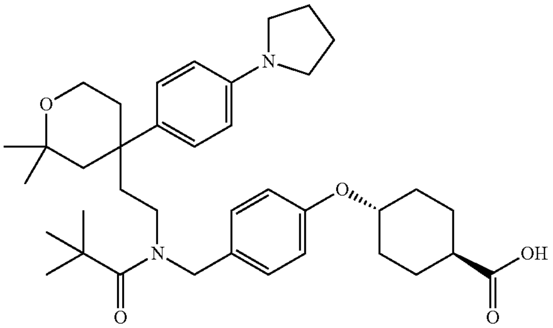 [SMILES: CC1(C)CC(CCN(Cc2ccc(O[C@H]3CC[C@H](C(=O)O)CC3)cc2)C(=O)C(C)(C)C)(c2ccc(N3CCCC3)cc2)CCO1] |
| H1 | 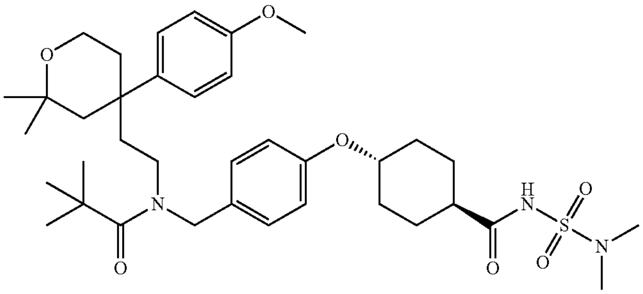 |
| I1 | 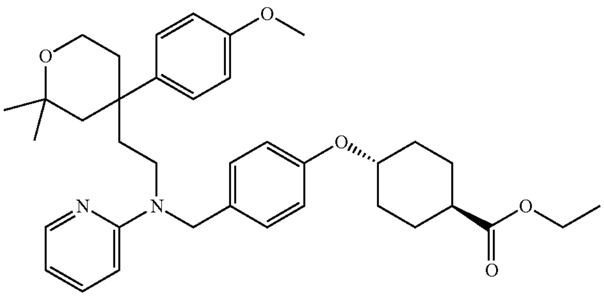 [SMILES: CCOC(=O)[C@H]1CC[C@H](Oc2ccc(CN(CCC3(c4ccc(OC)cc4)CCOC(C)(C)C3)c3ccccn3)cc2)CC1] |

TABLE 60-continued
| Ex | Structure |
| --- | --- |
| I2 | 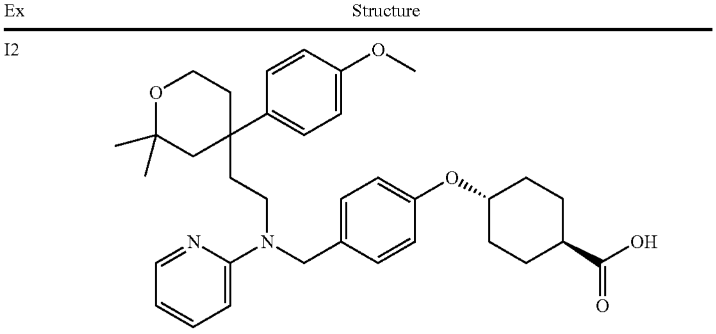 |
TABLE 61
| Ex | Structure |
| --- | --- |
| J1 | 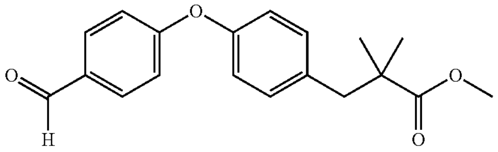 [SMILES: COC(=O)C(C)(C)Cc1ccc(Oc2ccc(C=O)cc2)cc1] |
| J2 | 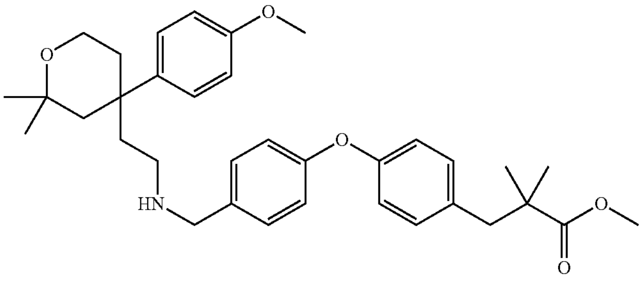 |
| J3 | 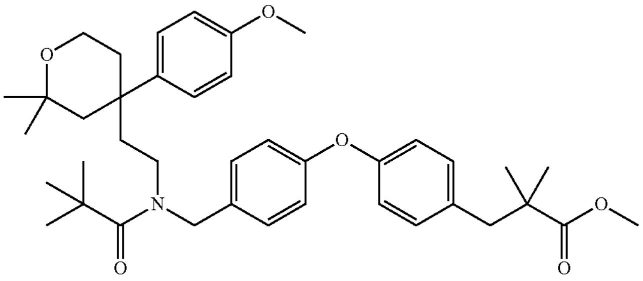 |
| J4 | 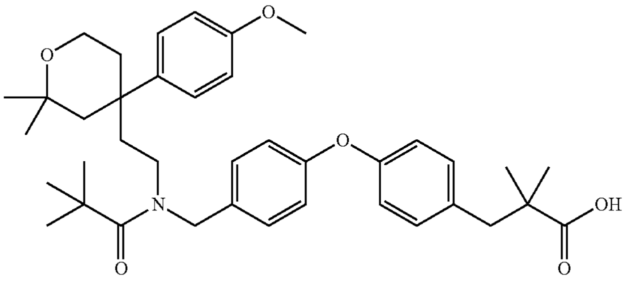 [SMILES: COc1ccc(C2(CCN(Cc3ccc(Oc4ccc(CC(C)(C)C(=O)O)cc4)cc3)C(=O)C(C)(C)C)CCOC(C)(C)C2)cc1] |

TABLE 61-continued
| Ex | Structure |
|---|---|
| K1 | 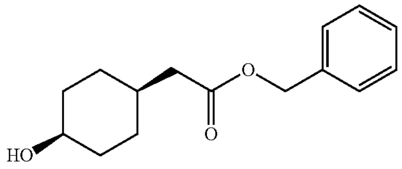 [SMILES: O=C(C[C@H]1CC[C@@H](O)CC1)OCc1ccccc1] |
| K2 | 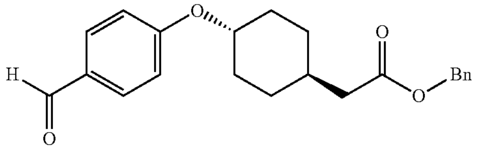 [SMILES: O=Cc1ccc(O[C@H]2CC[C@H](CC(=O)OCc3ccccc3)CC2)cc1] |
| K3 | 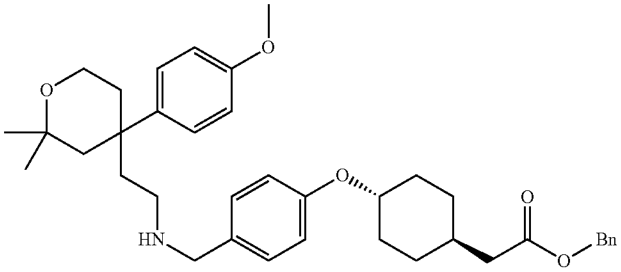 [SMILES: COc1ccc(C2(CCNCc3ccc(O[C@H]4CC[C@H](CC(=O)OCc5ccccc5)CC4)cc3)CCOC(C)(C)C2)cc1] |
| K4 | 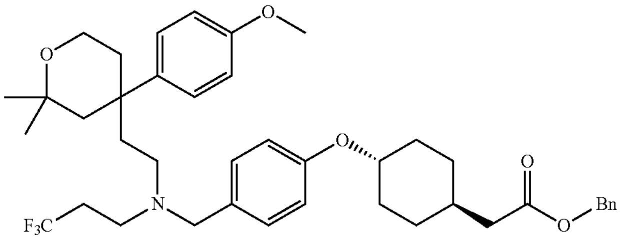 [SMILES: COc1ccc(C2(CCN(CCC(F)(F)F)Cc3ccc(O[C@H]4CC[C@H](CC(=O)OCc5ccccc5)CC4)cc3)CCOC(C)(C)C2)cc1] |
| K5 | 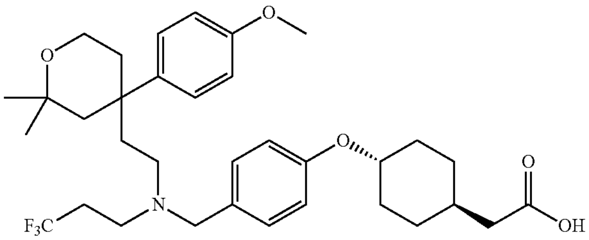 [SMILES: COc1ccc(C2(CCN(CCC(F)(F)F)Cc3ccc(O[C@H]4CC[C@H](CC(=O)O)CC4)cc3)CCOC(C)(C)C2)cc1] |
| L1 | 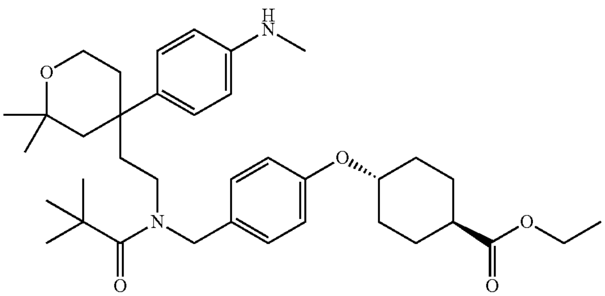 [SMILES: CCOC(=O)[C@H]1CC[C@H](Oc2ccc(CN(CCC3(c4ccc(NC)cc4)CCOC(C)(C)C3)C(=O)C(C)(C)C)cc2)CC1] |

TABLE 61-continued
| Ex | Structure |
|---|---|
| L2 | 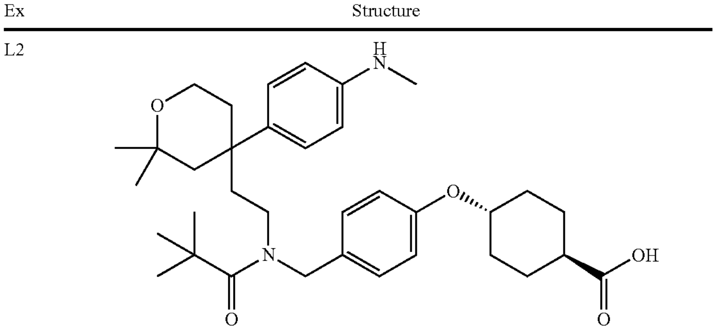 |
| M1 | 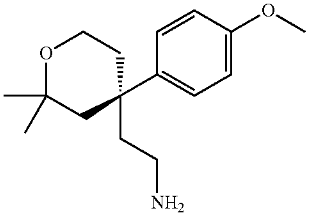 |
TABLE 62
| Ex | Structure |
|---|---|
| M2 | 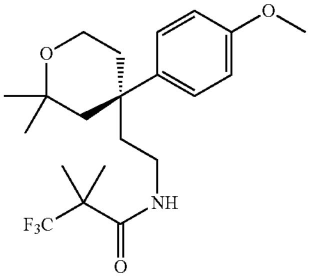 |
| M3 | 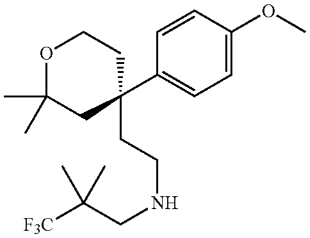 |
| M4 | 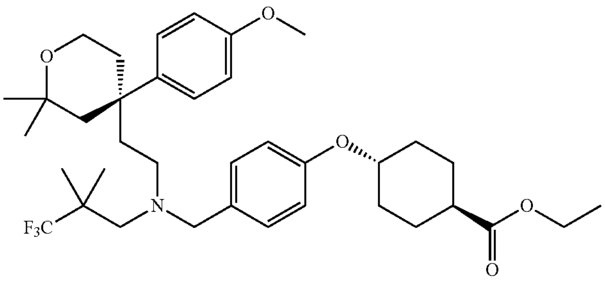 [SMILES: CCOC(=O)[C@H]1CC[C@H](Oc2ccc(CN(CC[C@@]3(c4ccc(OC)cc4)CCOC(C)(C)C3)CC(C)(C)C(F)(F)F)cc2)CC1] |

TABLE 62-continued
| Ex | Structure |
|---|---|
| M5 | 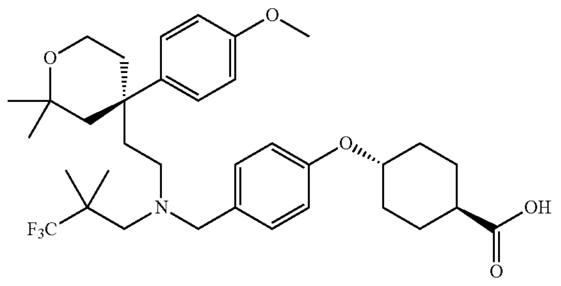 [SMILES: COc1ccc([C@]2(CCN(Cc3ccc(O[C@H]4CC[C@H](C(=O)O)CC4)cc3)CC(C)(C)C(F)(F)F)CCOC(C)(C)C2)cc1] |
| N1 | 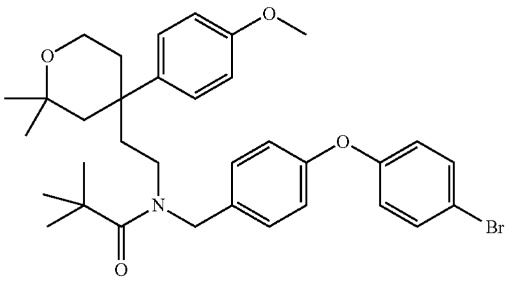 [SMILES: COc1ccc(C2(CCN(Cc3ccc(Oc4ccc(Br)cc4)cc3)C(=O)C(C)(C)C)CCOC(C)(C)C2)cc1] |
| N2 | 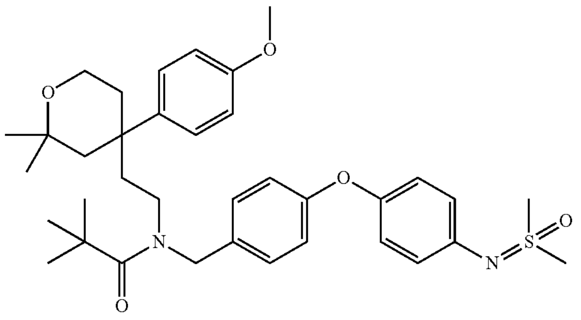 [SMILES: COc1ccc(C2(CCN(Cc3ccc(Oc4ccc(N=S(C)(C)=O)cc4)cc3)C(=O)C(C)(C)C)CCOC(C)(C)C2)cc1] |
| O1 | 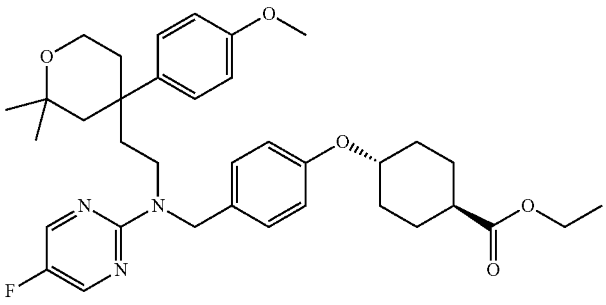 [SMILES: CCOC(=O)[C@H]1CC[C@H](Oc2ccc(CN(CCC3(c4ccc(OC)cc4)CCOC(C)(C)C3)c3ncc(F)cn3)cc2)CC1] |
| O2 | 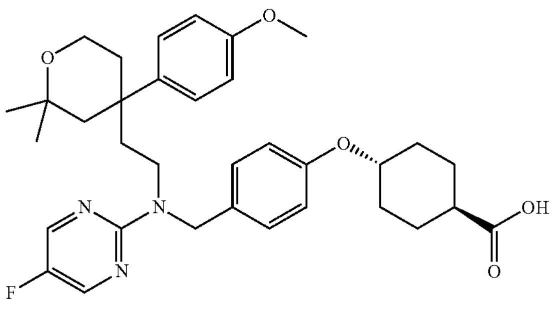 [SMILES: COc1ccc(C2(CCN(Cc3ccc(O[C@H]4CC[C@H](C(=O)O)CC4)cc3)c3ncc(F)cn3)CCOC(C)(C)C2)cc1] |

TABLE 62-continued
| Ex | Structure |
|---|---|
| P1 | 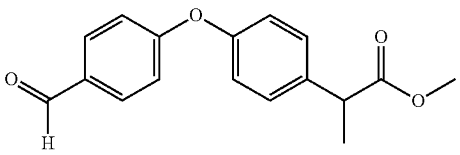 [SMILES: COC(=O)C(C)c1ccc(Oc2ccc(C=O)cc2)cc1] |
| P2 | 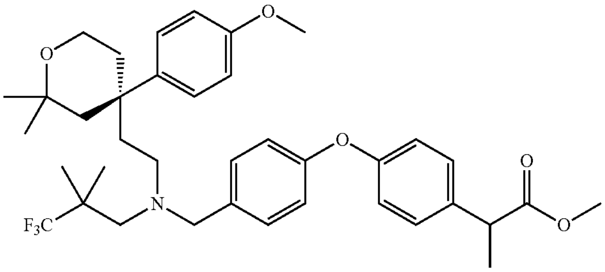 |
TABLE 63
| Ex | Structure |
|---|---|
| P3 | 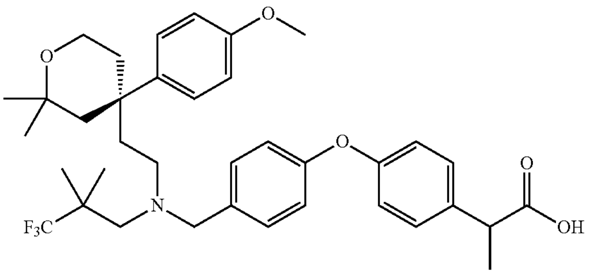 [SMILES: COc1ccc([C@]2(CCN(Cc3ccc(Oc4ccc(C(C)C(=O)O)cc4)cc3)CC(C)(C)C(F)(F)F)CCOC(C)(C)C2)cc1] |
| Q1 | 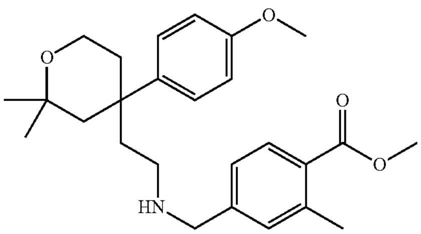 |
| Q2 | 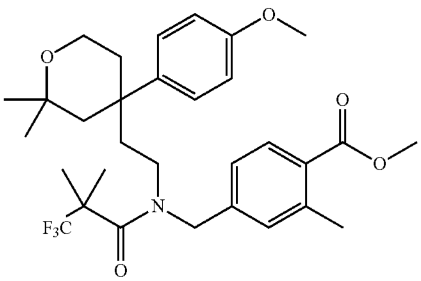 |

TABLE 63-continued
| Ex | Structure |
| --- | --- |
| Q3 | 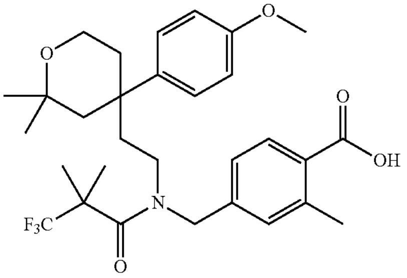 [SMILES: COc1ccc(C2(CCN(Cc3ccc(C(=O)O)c(C)c3)C(=O)C(C)(C)C(F)(F)F)CCOC(C)(C)C2)cc1] |
| Q4 | 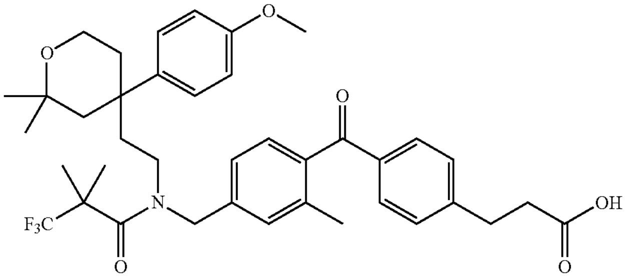 [SMILES: COc1ccc(C2(CCN(Cc3ccc(C(=O)c4ccc(CCC(=O)O)cc4)c(C)c3)C(=O)C(C)(C)C(F)(F)F)CCOC(C)(C)C2)cc1] |
| R1 | 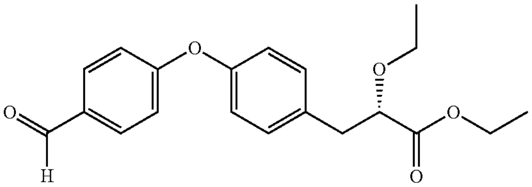 |
| R2 | 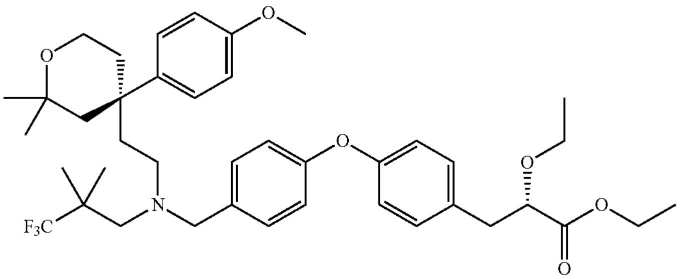 |
| R3 | 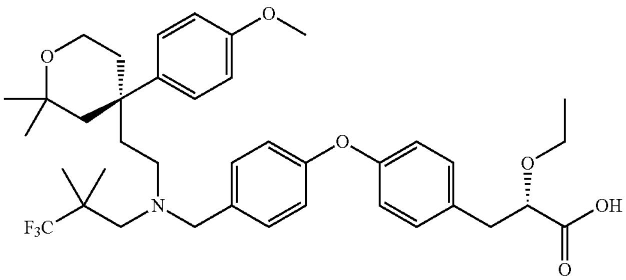 |
| S1 | 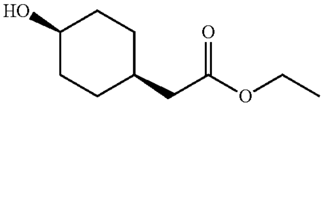 |

TABLE 63-continued
| Ex | Structure |
| --- | --- |
| S2 | 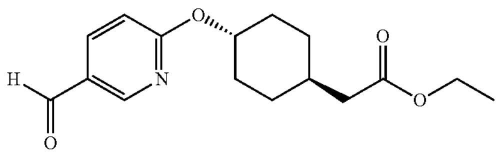 [SMILES: CCOC(=O)C[C@H]1CC[C@H](Oc2ccc(C=O)cn2)CC1] |
| S3 | 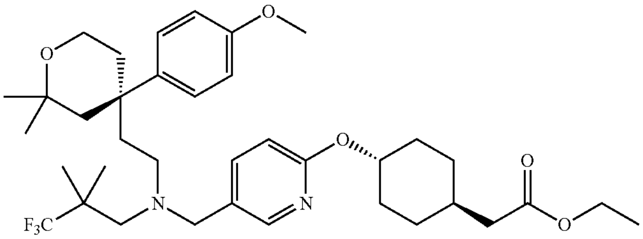 [SMILES: CCOC(=O)C[C@H]1CC[C@H](Oc2ccc(CN(CC[C@@]3(c4ccc(OC)cc4)CCOC(C)(C)C3)CC(C)(C)C(F)(F)F)cn2)CC1] |
| S4 | 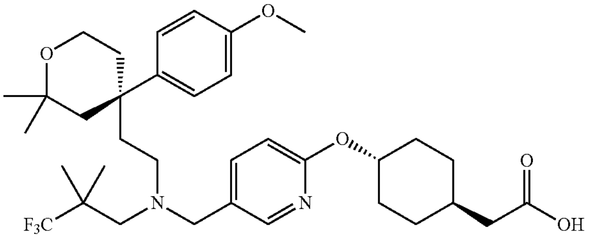 |
TABLE 64
| Ex | Structure |
| --- | --- |
| T1 | 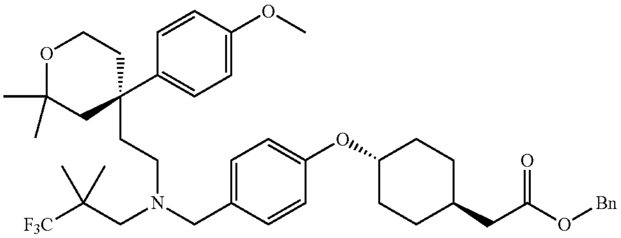 [SMILES: COc1ccc([C@]2(CCN(Cc3ccc(O[C@H]4CC[C@H](CC(=O)OCc5ccccc5)CC4)cc3)CC(C)(C)C(F)(F)F)CCOC(C)(C)C2)cc1] |
| T2 | 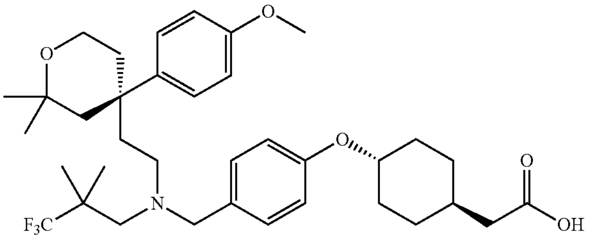 [SMILES: COc1ccc([C@]2(CCN(Cc3ccc(O[C@H]4CC[C@H](CC(=O)O)CC4)cc3)CC(C)(C)C(F)(F)F)CCOC(C)(C)C2)cc1] |
| U1 | 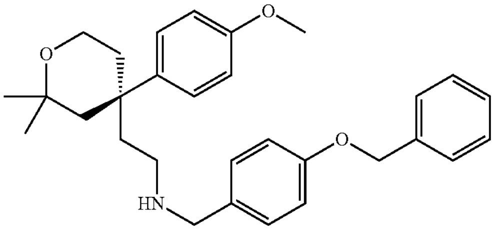 [SMILES: COc1ccc([C@]2(CCNCc3ccc(OCc4ccccc4)cc3)CCOC(C)(C)C2)cc1] |

TABLE 64-continued
| Ex | Structure |
|---|---|
| U2 | 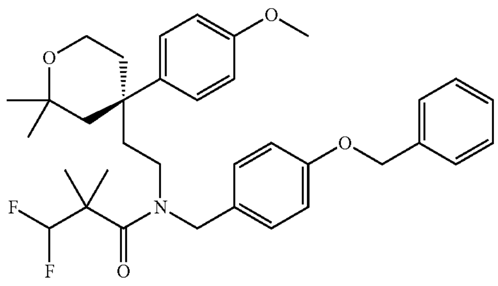 [SMILES: COc1ccc([C@]2(CCN(Cc3ccc(OCc4ccccc4)cc3)C(=O)C(C)(C)C(F)F)CCOC(C)(C)C2)cc1] |
| U3 | 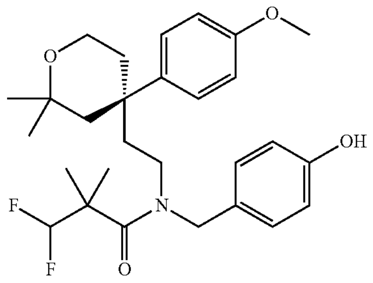 [SMILES: COc1ccc([C@]2(CCN(Cc3ccc(O)cc3)C(=O)C(C)(C)C(F)F)CCOC(C)(C)C2)cc1] |
| U4 | 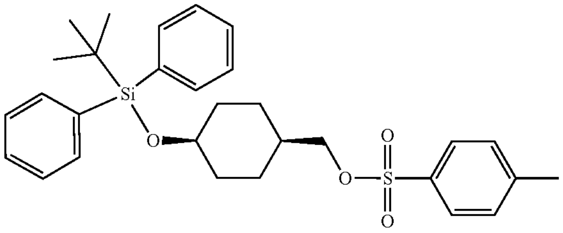 [SMILES: Cc1ccc(S(=O)(=O)OC[C@H]2CC[C@@H](O[Si](c3ccccc3)(c3ccccc3)C(C)(C)C)CC2)cc1] |
| U5 | 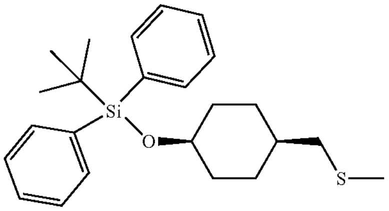 [SMILES: CSC[C@H]1CC[C@@H](O[Si](c2ccccc2)(c2ccccc2)C(C)(C)C)CC1] |
| U6 | 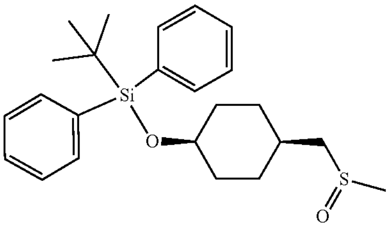 [SMILES: CS(=O)C[C@H]1CC[C@@H](O[Si](c2ccccc2)(c2ccccc2)C(C)(C)C)CC1] |
| U7 | 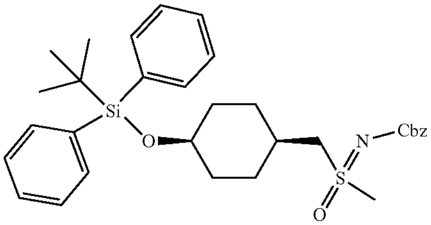 [SMILES: CC(C)(C)[Si](O[C@H]1CC[C@@H](CS(C)(=O)=NC(=O)OCc2ccccc2)CC1)(c1ccccc1)c1ccccc1] |

TABLE 64-continued
| Ex | Structure |
| --- | --- |
| U8 | 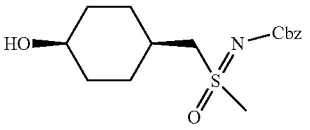 [SMILES: CS(=O)(C[C@H]1CC[C@@H](O)CC1)=NC(=O)OCc1ccccc1] |
| U9 | 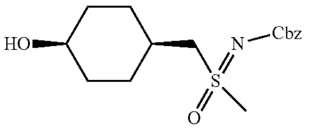 [SMILES: CS(=O)(C[C@H]1CC[C@@H](O)CC1)=NC(=O)OCc1ccccc1] |
| U10 | 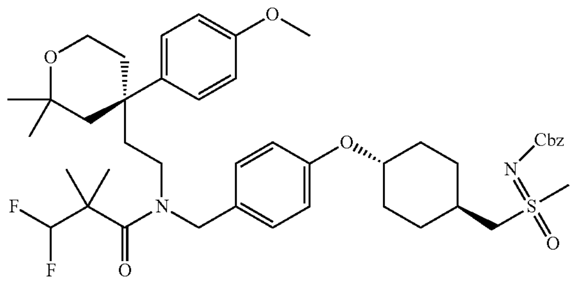 |
TABLE 65
| Ex | Structure |
| --- | --- |
| U11 | 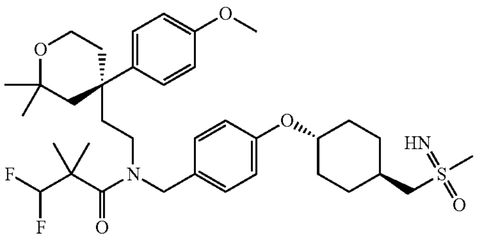 |
| V1 | 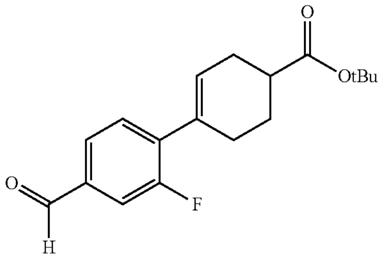 [SMILES: CC(C)(C)OC(=O)C1CC=C(c2ccc(C=O)cc2F)CC1] |
| V2 | 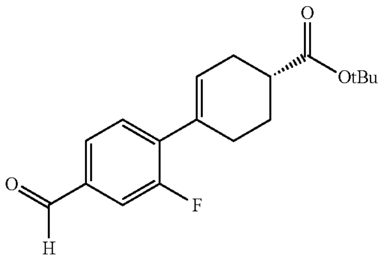 [SMILES: CC(C)(C)OC(=O)[C@H]1CC=C(c2ccc(C=O)cc2F)CC1] |
TABLE 65-continued
| Ex | Structure |
| --- | --- |
| V3 | 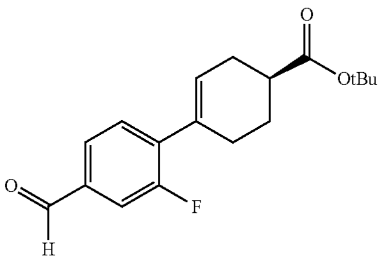 [SMILES: CC(C)(C)OC(=O)[C@@H]1CC=C(c2ccc(C=O)cc2F)CC1] |
| V4 | 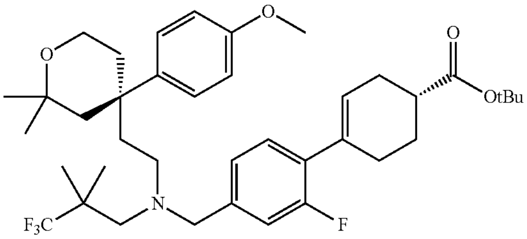 [SMILES: COc1ccc([C@]2(CCN(Cc3ccc(C4=CC[C@H](C(=O)OC(C)(C)C)CC4)c(F)c3)CC(C)(C)C(F)(F)F)CCOC(C)(C)C2)cc1] |
| V5 | 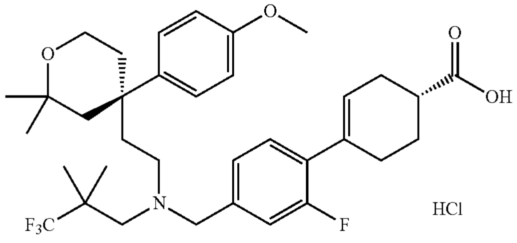 [SMILES: COc1ccc([C@]2(CCN(Cc3ccc(C4=CC[C@H](C(=O)O)CC4)c(F)c3)CC(C)(C)C(F)(F)F)CCOC(C)(C)C2)cc1 ; Cl] |

TABLE 65-continued
| Ex | Structure |
|---|---|
| W1 | 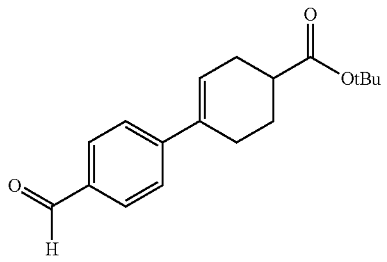 [SMILES: CC(C)(C)OC(=O)C1CC=C(c2ccc(C=O)cc2)CC1] |
| W2 | 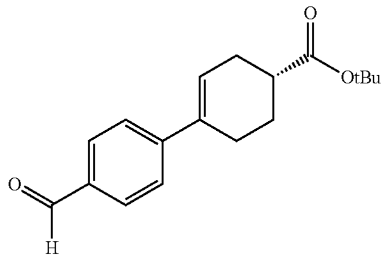 [SMILES: CC(C)(C)OC(=O)[C@H]1CC=C(c2ccc(C=O)cc2)CC1] |
| W3 | 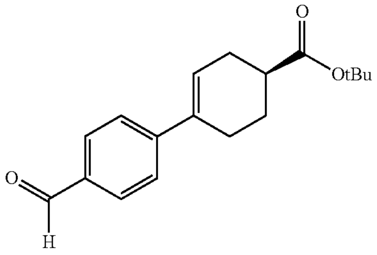 [SMILES: CC(C)(C)OC(=O)[C@@H]1CC=C(c2ccc(C=O)cc2)CC1] |
| W4 | 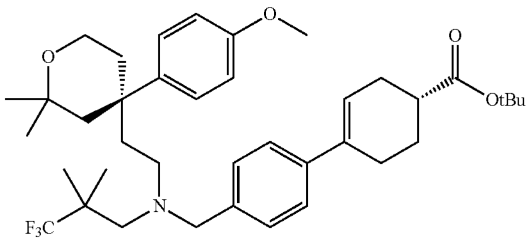 [SMILES: COc1ccc([C@]2(CCN(Cc3ccc(C4=CC[C@H](C(=O)OC(C)(C)C)CC4)cc3)CC(C)(C)C(F)(F)F)CCOC(C)(C)C2)cc1] |
TABLE 66
| Ex | Structure |
|---|---|
| W5 | 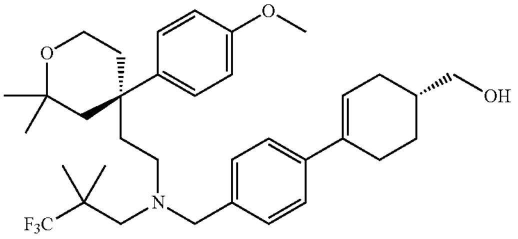 [SMILES: COc1ccc([C@]2(CCN(Cc3ccc(C4=CC[C@H](CO)CC4)cc3)CC(C)(C)C(F)(F)F)CCOC(C)(C)C2)cc1] |
| X1 | 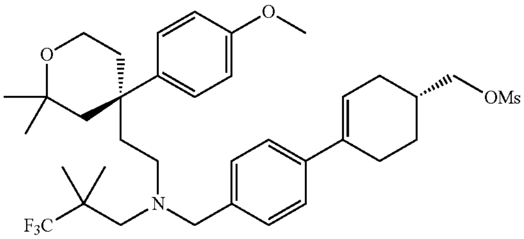 [SMILES: COc1ccc([C@]2(CCN(Cc3ccc(C4=CC[C@H](COS(C)(=O)=O)CC4)cc3)CC(C)(C)C(F)(F)F)CCOC(C)(C)C2)cc1] |
| X2 | 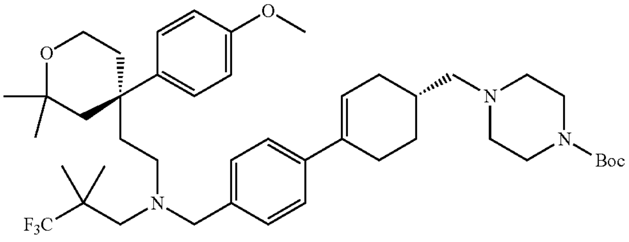 [SMILES: COc1ccc([C@]2(CCN(Cc3ccc(C4=CC[C@H](CN5CCN(C(=O)OC(C)(C)C)CC5)CC4)cc3)CC(C)(C)C(F)(F)F)CCOC(C)(C)C2)cc1] |

TABLE 66-continued
| Ex | Structure |
| --- | --- |
| Y1 | 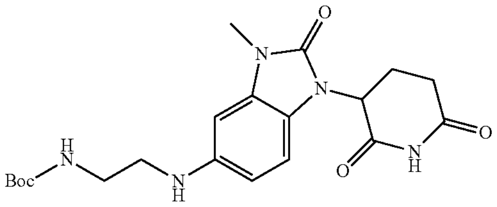 [SMILES: Cn1c(=O)n(C2CCC(=O)NC2=O)c2ccc(NCCNC(=O)OC(C)(C)C)cc21] |
| Y2 | 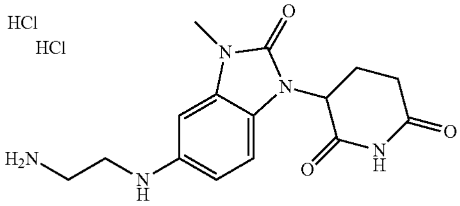 [SMILES: Cl ; Cn1c(=O)n(C2CCC(=O)NC2=O)c2ccc(NCCN)cc21 ; Cl] |
| Y3 | 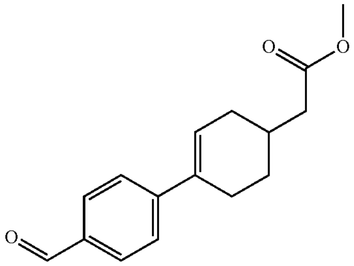 [SMILES: COC(=O)CC1CC=C(c2ccc(C=O)cc2)CC1] |
| Y4 | 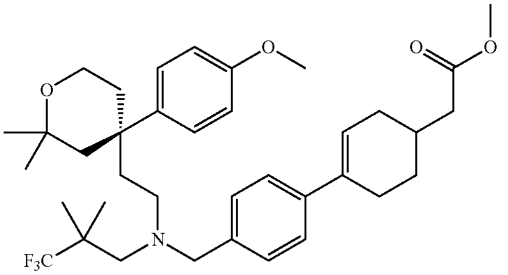 |
| Y5 | 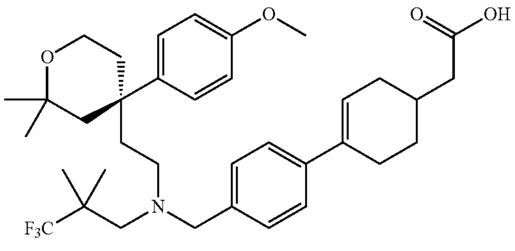 [SMILES: COc1ccc([C@]2(CCN(Cc3ccc(C4=CCC(CC(=O)O)CC4)cc3)CC(C)(C)C(F)(F)F)CCOC(C)(C)C2)cc1] |
| Y6 | 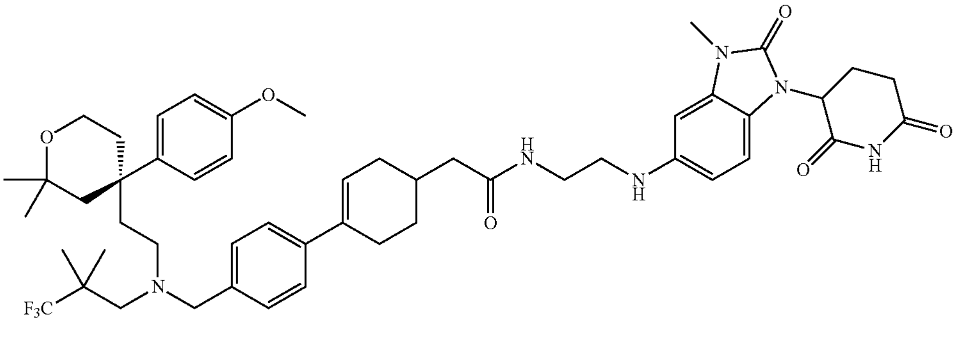 [SMILES: COc1ccc([C@]2(CCN(Cc3ccc(C4=CCC(CC(=O)NCCNc5ccc6c(c5)n(C)c(=O)n6C5CCC(=O)NC5=O)CC4)cc3)CC(C)(C)C(F)(F)F)CCOC(C)(C)C2)cc1] |

TABLE 66-continued
| Ex | Structure |
| --- | --- |
| Z1 | 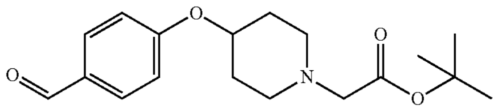 [SMILES: CC(C)(C)OC(=O)CN1CCC(Oc2ccc(C=O)cc2)CC1] |
| Z2 | 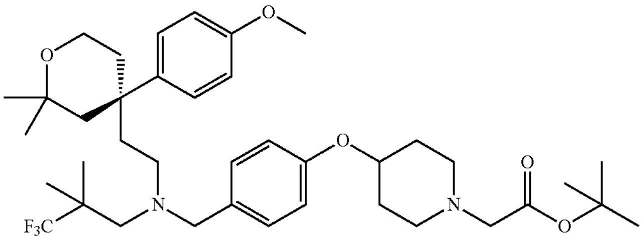 [SMILES: COc1ccc([C@]2(CCN(Cc3ccc(OC4CCN(CC(=O)OC(C)(C)C)CC4)cc3)CC(C)(C)C(F)(F)F)CCOC(C)(C)C2)cc1] |
| Z3 | 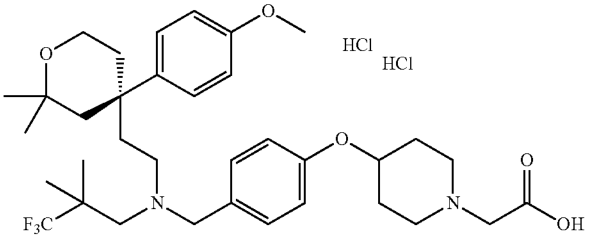 [SMILES: COc1ccc([C@]2(CCN(Cc3ccc(OC4CCN(CC(=O)O)CC4)cc3)CC(C)(C)C(F)(F)F)CCOC(C)(C)C2)cc1 ; Cl ; Cl] |
TABLE 67
| Ex | Structure |
| --- | --- |
| Z4 | 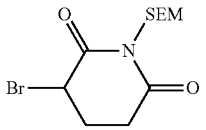 [SMILES: C[Si](C)(C)CCOCN1C(=O)CCC(Br)C1=O] |
| Z5 | 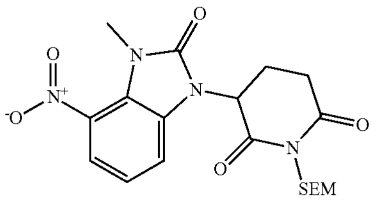 |
| Z6 | 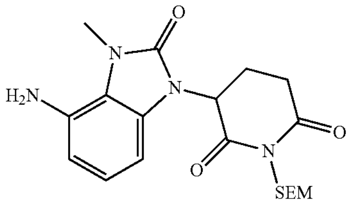 [SMILES: Cn1c(=O)n(C2CCC(=O)N(COCC[Si](C)(C)C)C2=O)c2cccc(N)c21] |

TABLE 67-continued
| Ex | Structure |
|---|---|
| Z7 | 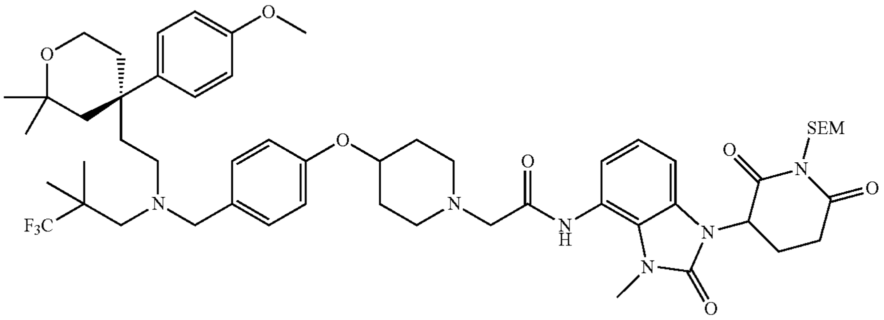 [SMILES: COc1ccc([C@]2(CCN(Cc3ccc(OC4CCN(CC(=O)Nc5cccc6c5n(C)c(=O)n6C5CCC(=O)N(COCC[Si](C)(C)C)C5=O)CC4)cc3)CC(C)(C)C(F)(F)F)CCOC(C)(C)C2)cc1] |
| Z8 | 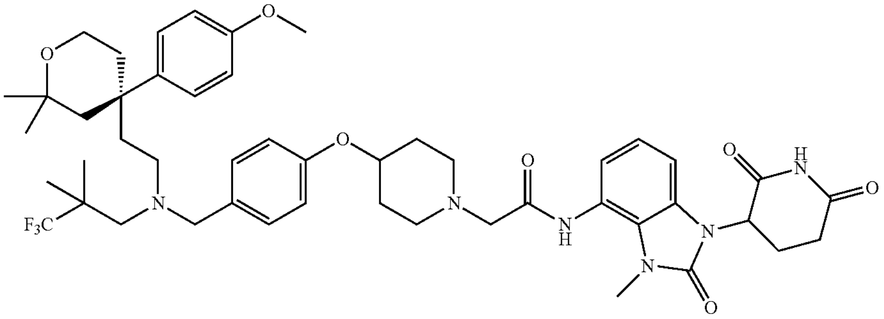 [SMILES: COc1ccc([C@]2(CCN(Cc3ccc(OC4CCN(CC(=O)Nc5cccc6c5n(C)c(=O)n6C5CCC(=O)NC5=O)CC4)cc3)CC(C)(C)C(F)(F)F)CCOC(C)(C)C2)cc1] |
| AA1 | 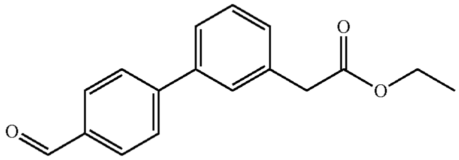 [SMILES: CCOC(=O)Cc1cccc(-c2ccc(C=O)cc2)c1] |
| AA2 | 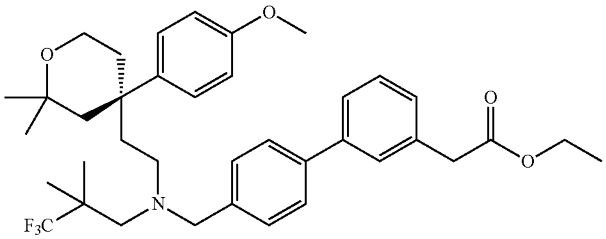 [SMILES: CCOC(=O)Cc1cccc(-c2ccc(CN(CC[C@@]3(c4ccc(OC)cc4)CCOC(C)(C)C3)CC(C)(C)C(F)(F)F)cc2)c1] |
| AA3 | 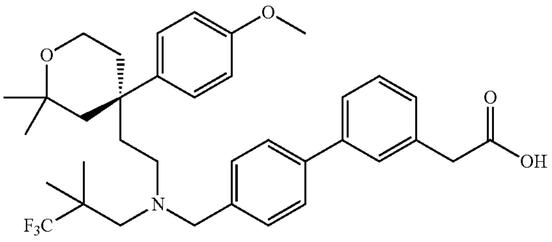 [SMILES: COc1ccc([C@]2(CCN(Cc3ccc(-c4cccc(CC(=O)O)c4)cc3)CC(C)(C)C(F)(F)F)CCOC(C)(C)C2)cc1] |

TABLE 67-continued
| Ex | Structure |
|---|---|
| AA4 | 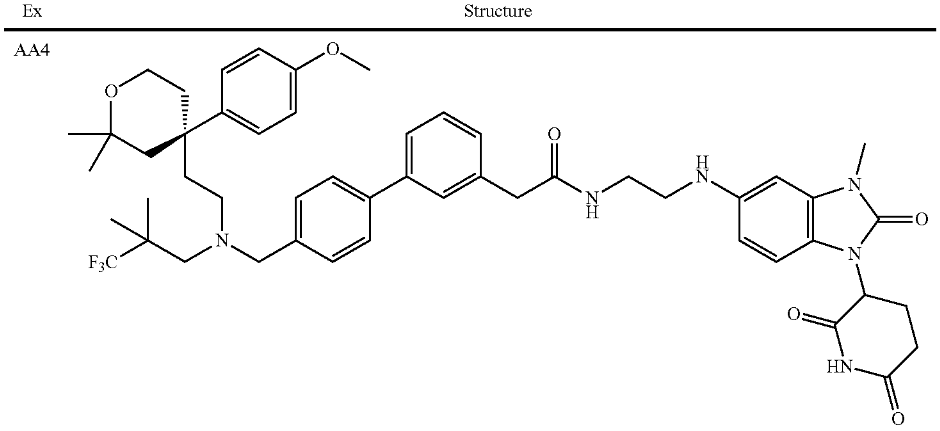 |
| AB1 | 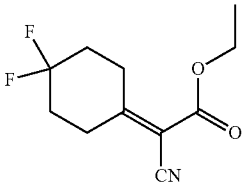 [SMILES: CCOC(=O)C(C#N)=C1CCC(F)(F)CC1] |
| AB2 | 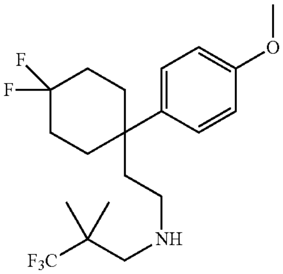 [SMILES: COc1ccc(C2(CCNCC(C)(C)C(F)(F)F)CCC(F)(F)CC2)cc1] |
| AB3 | 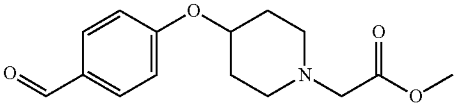 [SMILES: COC(=O)CN1CCC(Oc2ccc(C=O)cc2)CC1] |
TABLE 68
| Ex | Structure |
|---|---|
| AB4 | 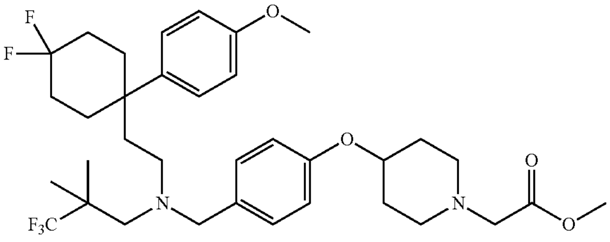 [SMILES: COC(=O)CN1CCC(Oc2ccc(CN(CCC3(c4ccc(OC)cc4)CCC(F)(F)CC3)CC(C)(C)C(F)(F)F)cc2)CC1] |

TABLE 68-continued
| Ex | Structure |
|---|---|
| AB5 | 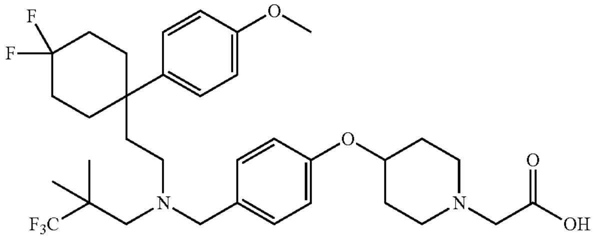 [SMILES: COc1ccc(C2(CCN(Cc3ccc(OC4CCN(CC(=O)O)CC4)cc3)CC(C)(C)C(F)(F)F)CCC(F)(F)CC2)cc1] |
| AB6 | 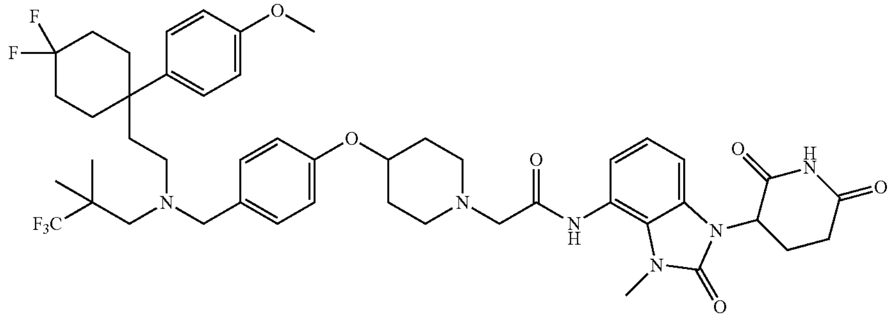 [SMILES: COc1ccc(C2(CCN(Cc3ccc(OC4CCN(CC(=O)Nc5cccc6c5n(C)c(=O)n6C5CCC(=O)NC5=O)CC4)cc3)CC(C)(C)C(F)(F)F)CCC(F)(F)CC2)cc1] |
| AC1 | 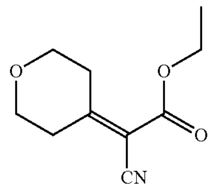 |
| AC2 | 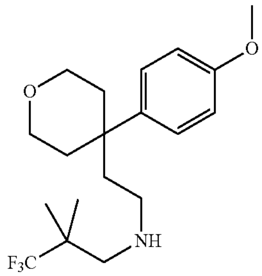 [SMILES: COc1ccc(C2(CCNCC(C)(C)C(F)(F)F)CCOCC2)cc1] |
| AC3 | 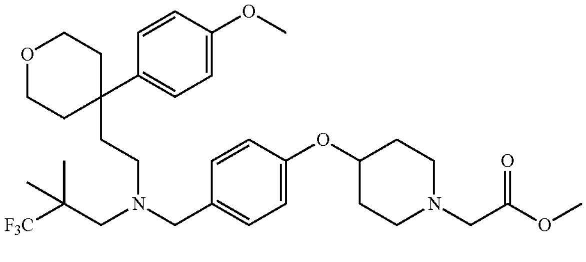 [SMILES: COC(=O)CN1CCC(Oc2ccc(CN(CCC3(c4ccc(OC)cc4)CCOCC3)CC(C)(C)C(F)(F)F)cc2)CC1] |
| AC4 | 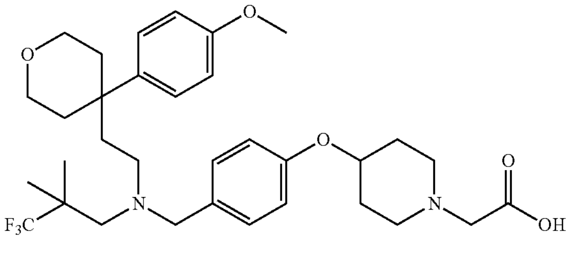 [SMILES: COc1ccc(C2(CCN(Cc3ccc(OC4CCN(CC(=O)O)CC4)cc3)CC(C)(C)C(F)(F)F)CCOCC2)cc1] |

TABLE 68-continued
| Ex | Structure |
|---|---|
| AC5 | 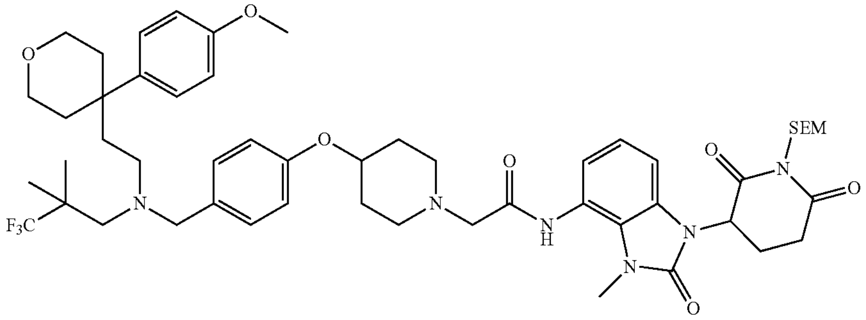 [SMILES: COc1ccc(C2(CCN(Cc3ccc(OC4CCN(CC(=O)Nc5cccc6c5n(C)c(=O)n6C5CCC(=O)N(COCC[Si](C)(C)C)C5=O)CC4)cc3)CC(C)(C)C(F)(F)F)CCOCC2)cc1] |
| AC6 | 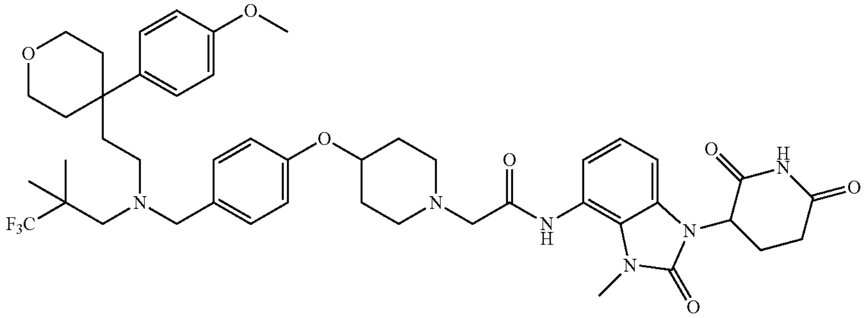 [SMILES: COc1ccc(C2(CCN(Cc3ccc(OC4CCN(CC(=O)Nc5cccc6c5n(C)c(=O)n6C5CCC(=O)NC5=O)CC4)cc3)CC(C)(C)C(F)(F)F)CCOCC2)cc1] |
| AD1 | 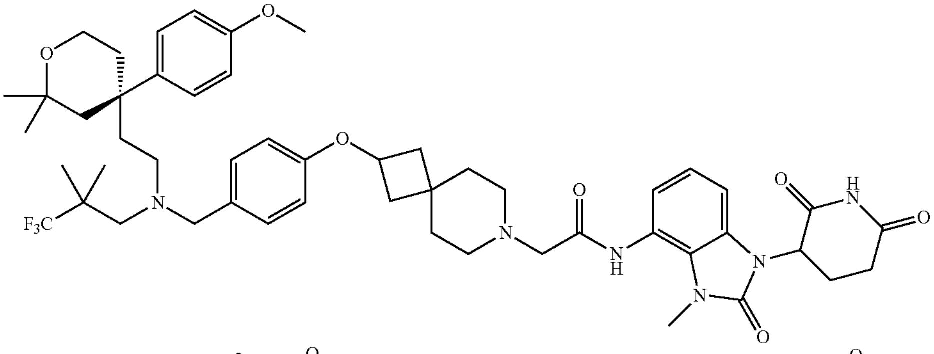 |
| AE1 | 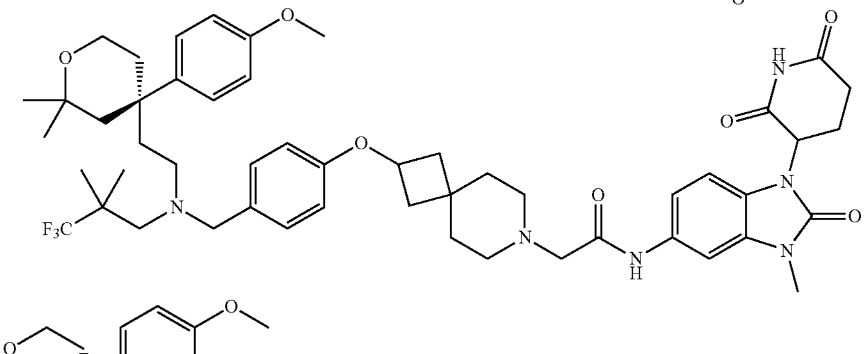 |
| AF1 | 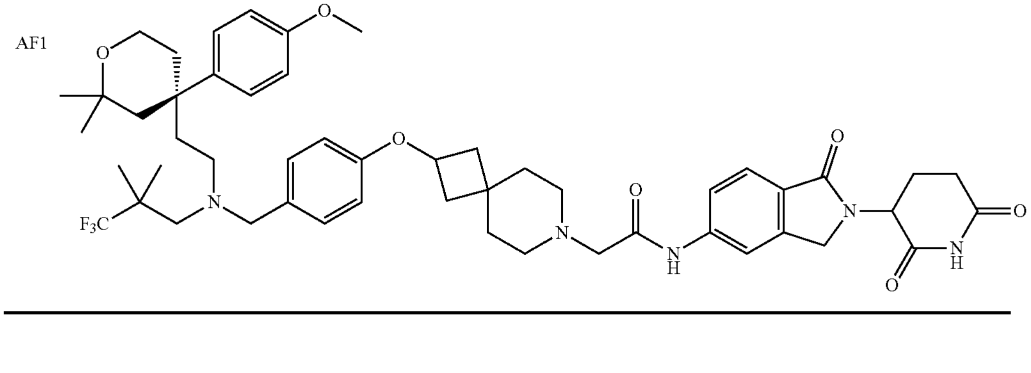 |

TABLE 69
| Ex | Structure |
|---|---|
| AG1 | 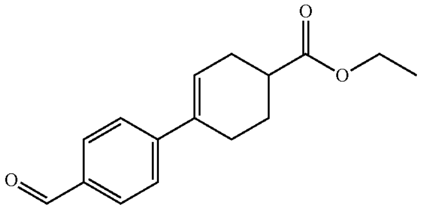 [SMILES: CCOC(=O)C1CC=C(c2ccc(C=O)cc2)CC1] |
| AG2 | 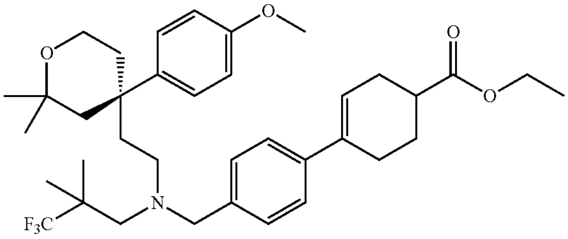 [SMILES: CCOC(=O)C1CC=C(c2ccc(CN(CC[C@@]3(c4ccc(OC)cc4)CCOC(C)(C)C3)CC(C)(C)C(F)(F)F)cc2)CC1] |
| AG3 | 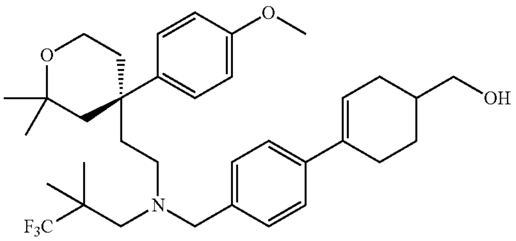 [SMILES: COc1ccc([C@]2(CCN(Cc3ccc(C4=CCC(CO)CC4)cc3)CC(C)(C)C(F)(F)F)CCOC(C)(C)C2)cc1] |
| AG4 | 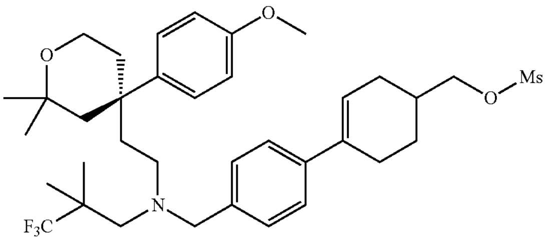 [SMILES: COc1ccc([C@]2(CCN(Cc3ccc(C4=CCC(COS(C)(=O)=O)CC4)cc3)CC(C)(C)C(F)(F)F)CCOC(C)(C)C2)cc1] |
| AG5 | 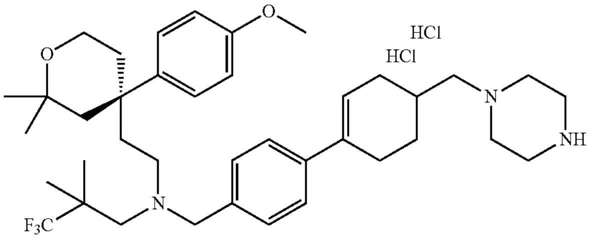 [SMILES: COc1ccc([C@]2(CCN(Cc3ccc(C4=CCC(CN5CCNCC5)CC4)cc3)CC(C)(C)C(F)(F)F)CCOC(C)(C)C2)cc1 ; Cl ; Cl] |
| AG6 | 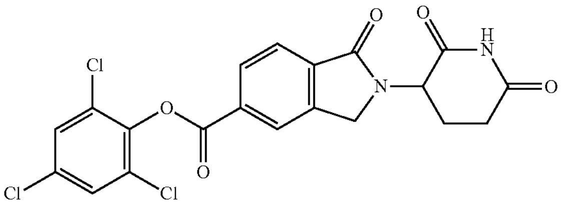 [SMILES: O=C1CCC(N2Cc3cc(C(=O)Oc4c(Cl)cc(Cl)cc4Cl)ccc3C2=O)C(=O)N1] |

TABLE 69-continued
| Ex | Structure |
|---|---|
| AG7 | 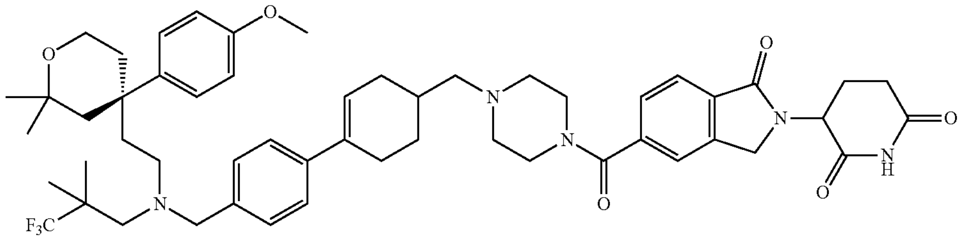 [SMILES: COc1ccc([C@]2(CCN(Cc3ccc(C4=CCC(CN5CCN(C(=O)c6ccc7c(c6)CN(C6CCC(=O)NC6=O)C7=O)CC5)CC4)cc3)CC(C)(C)C(F)(F)F)CCOC(C)(C)C2)cc1] |
| AH1 | 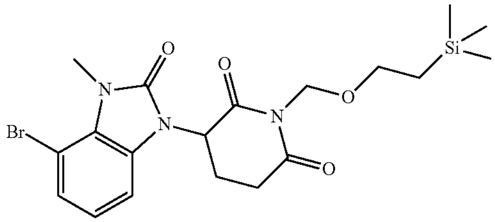 [SMILES: Cn1c(=O)n(C2CCC(=O)N(COCC[Si](C)(C)C)C2=O)c2cccc(Br)c21] |
| AH2 | 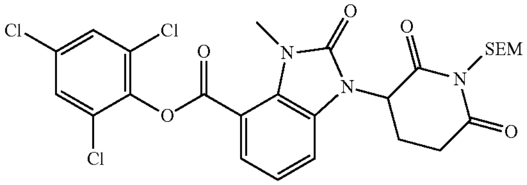 [SMILES: Cn1c(=O)n(C2CCC(=O)N(COCC[Si](C)(C)C)C2=O)c2cccc(C(=O)Oc3c(Cl)cc(Cl)cc3Cl)c21] |
| AH3 | 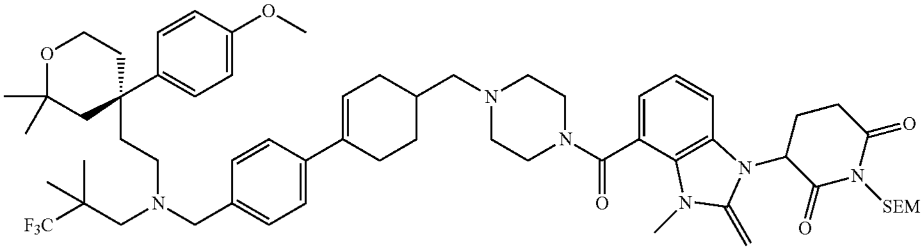 [SMILES: C=C1N(C)c2c(C(=O)N3CCN(CC4CC=C(c5ccc(CN(CC[C@@]6(c7ccc(OC)cc7)CCOC(C)(C)C6)CC(C)(C)C(F)(F)F)cc5)CC4)CC3)cccc2N1C1CCC(=O)N(COCC[Si](C)(C)C)C1=O] |
| AH4 | 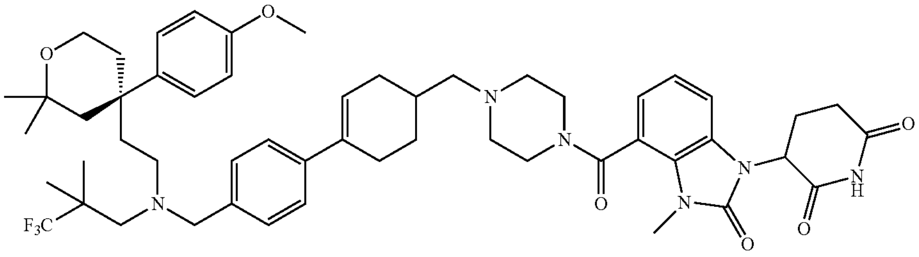 [SMILES: COc1ccc([C@]2(CCN(Cc3ccc(C4=CCC(CN5CCN(C(=O)c6cccc7c6n(C)c(=O)n7C6CCC(=O)NC6=O)CC5)CC4)cc3)CC(C)(C)C(F)(F)F)CCOC(C)(C)C2)cc1] |
| AI1 | 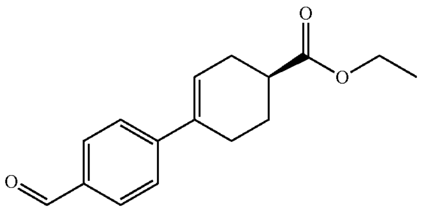 [SMILES: CCOC(=O)[C@@H]1CC=C(c2ccc(C=O)cc2)CC1] |

TABLE 70
| Ex | Structure |
| --- | --- |
| AI2 | 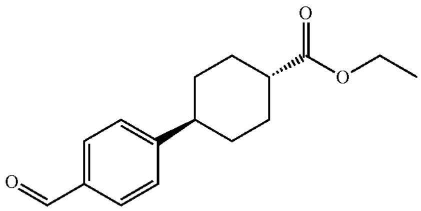 [SMILES: CCOC(=O)[C@H]1CC[C@H](c2ccc(C=O)cc2)CC1] |
| AI3 | 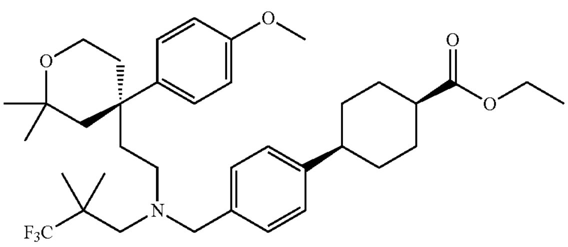 [SMILES: CCOC(=O)[C@H]1CC[C@@H](c2ccc(CN(CC[C@@]3(c4ccc(OC)cc4)CCOC(C)(C)C3)CC(C)(C)C(F)(F)F)cc2)CC1] |
| AI4 | 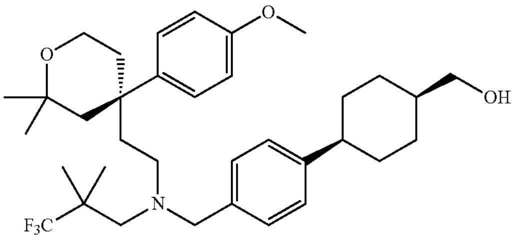 |
| AI5 | 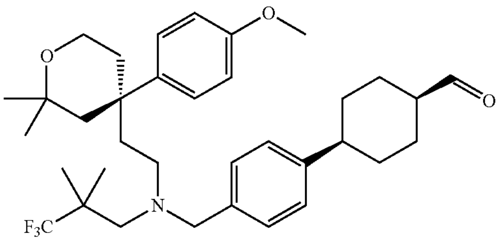 |
| AI6 | 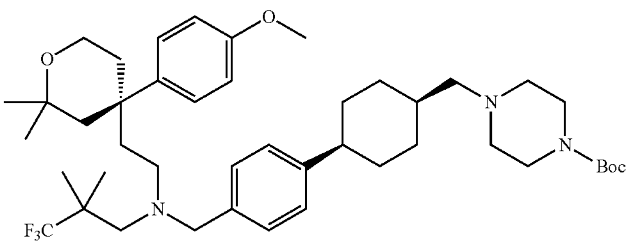 [SMILES: COc1ccc([C@]2(CCN(Cc3ccc([C@H]4CC[C@@H](CN5CCN(C(=O)OC(C)(C)C)CC5)CC4)cc3)CC(C)(C)C(F)(F)F)CCOC(C)(C)C2)cc1] |
| AI7 | 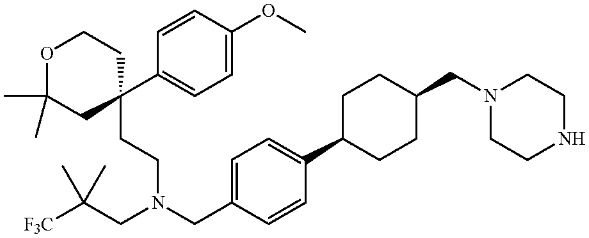 [SMILES: COc1ccc([C@]2(CCN(Cc3ccc([C@H]4CC[C@@H](CN5CCNCC5)CC4)cc3)CC(C)(C)C(F)(F)F)CCOC(C)(C)C2)cc1] |

TABLE 70-continued
| Ex | Structure |
| --- | --- |
| AI8 | 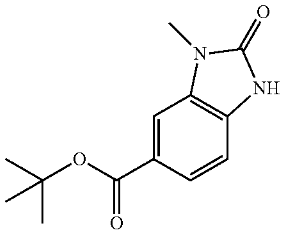 [SMILES: Cn1c(=O)[nH]c2ccc(C(=O)OC(C)(C)C)cc21] |
| AI9 | 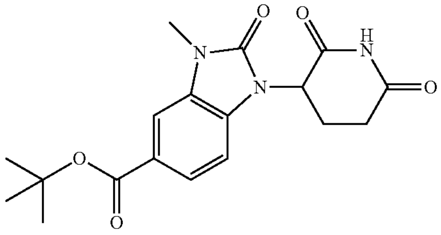 [SMILES: Cn1c(=O)n(C2CCC(=O)NC2=O)c2ccc(C(=O)OC(C)(C)C)cc21] |
| AI10 | 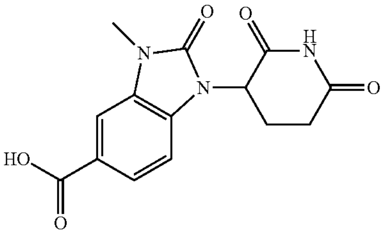 [SMILES: Cn1c(=O)n(C2CCC(=O)NC2=O)c2ccc(C(=O)O)cc21] |
| AI11 | 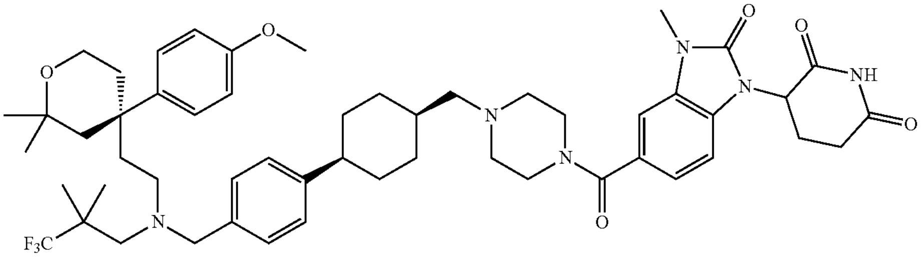 [SMILES: COc1ccc([C@]2(CCN(Cc3ccc([C@H]4CC[C@@H](CN5CCN(C(=O)c6ccc7c(c6)n(C)c(=O)n7C6CCC(=O)NC6=O)CC5)CC4)cc3)CC(C)(C)C(F)(F)F)CCOC(C)(C)C2)cc1] |
| AJ1 | 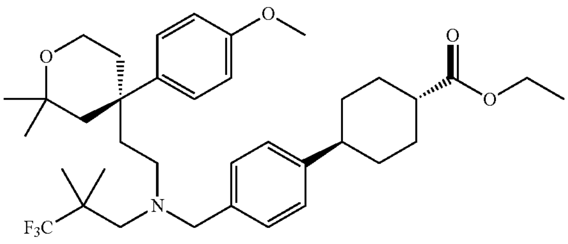 [SMILES: CCOC(=O)[C@H]1CC[C@H](c2ccc(CN(CC[C@@]3(c4ccc(OC)cc4)CCOC(C)(C)C3)CC(C)(C)C(F)(F)F)cc2)CC1] |
| AJ2 | 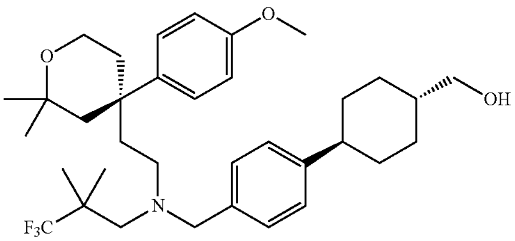 [SMILES: COc1ccc([C@]2(CCN(Cc3ccc([C@H]4CC[C@H](CO)CC4)cc3)CC(C)(C)C(F)(F)F)CCOC(C)(C)C2)cc1] |

TABLE 71
| Ex | Structure |
|---|---|
| AJ3 | 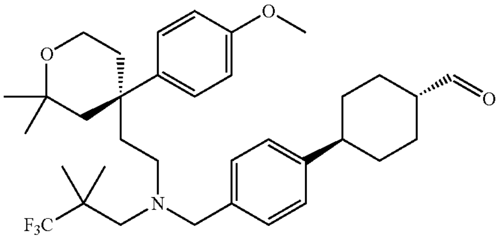 [SMILES: COc1ccc([C@]2(CCN(Cc3ccc([C@H]4CC[C@H](C=O)CC4)cc3)CC(C)(C)C(F)(F)F)CCOC(C)(C)C2)cc1] |
| AJ4 | 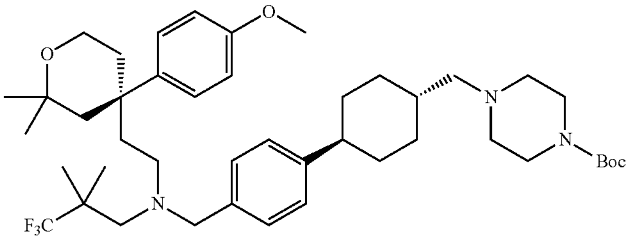 [SMILES: COc1ccc([C@]2(CCN(Cc3ccc([C@H]4CC[C@H](CN5CCN(C(=O)OC(C)(C)C)CC5)CC4)cc3)CC(C)(C)C(F)(F)F)CCOC(C)(C)C2)cc1] |
| AJ5 | 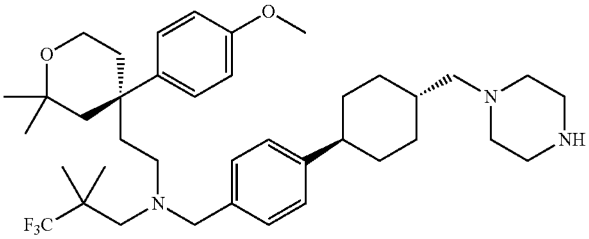 [SMILES: COc1ccc([C@]2(CCN(Cc3ccc([C@H]4CC[C@H](CN5CCNCC5)CC4)cc3)CC(C)(C)C(F)(F)F)CCOC(C)(C)C2)cc1] |
| AJ6 | 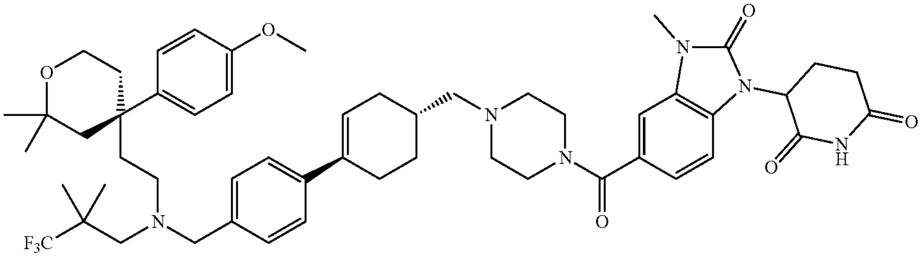 |
| AK1 | 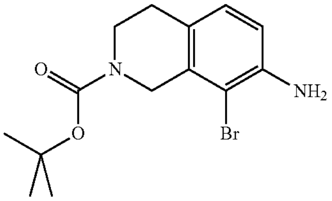 [SMILES: CC(C)(C)OC(=O)N1CCc2ccc(N)c(Br)c2C1] |
| AK2 | 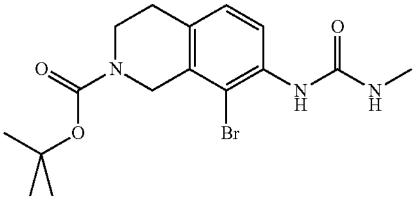 [SMILES: CNC(=O)Nc1ccc2c(c1Br)CN(C(=O)OC(C)(C)C)CC2] |

TABLE 71-continued
| Ex | Structure |
|---|---|
| AK3 | 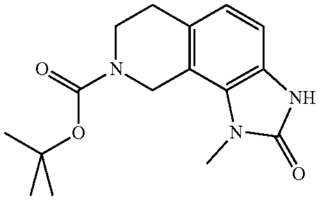 [SMILES: Cn1c(=O)[nH]c2ccc3c(c21)CN(C(=O)OC(C)(C)C)CC3] |
| AK4 | 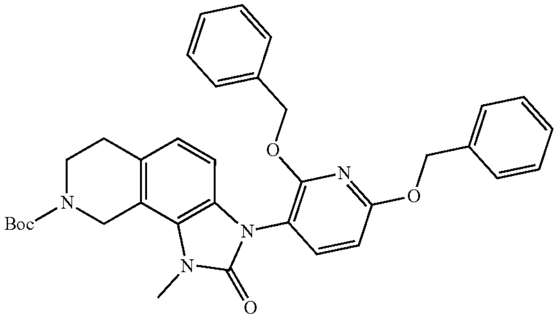 [SMILES: Cn1c(=O)n(-c2ccc(OCc3ccccc3)nc2OCc2ccccc2)c2ccc3c(c21)CN(C(=O)OC(C)(C)C)CC3] |
| AK5 | 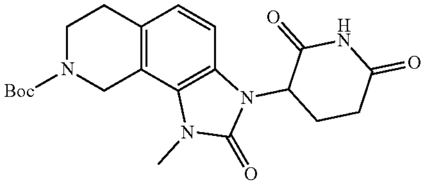 [SMILES: Cn1c(=O)n(C2CCC(=O)NC2=O)c2ccc3c(c21)CN(C(=O)OC(C)(C)C)CC3] |
| AK6 | 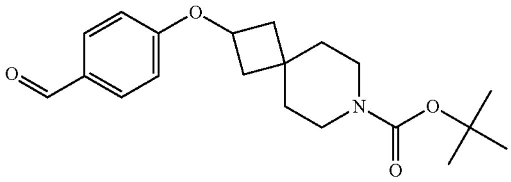 [SMILES: CC(C)(C)OC(=O)N1CCC2(CC1)CC(Oc1ccc(C=O)cc1)C2] |
| AK7 | 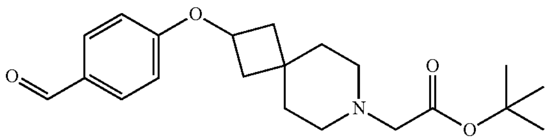 [SMILES: CC(C)(C)OC(=O)CN1CCC2(CC1)CC(Oc1ccc(C=O)cc1)C2] |
| AK8 | 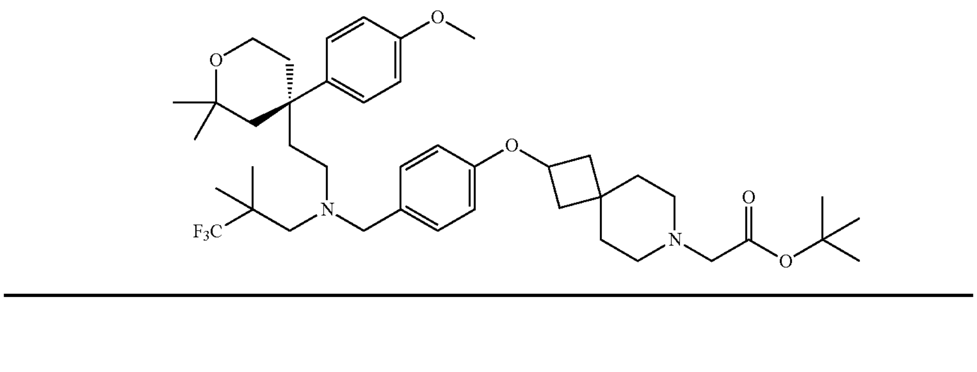 |

TABLE 72
| Ex | Structure |
|---|---|
| AK9 | 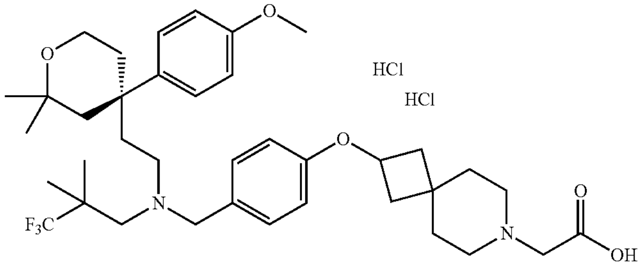 [SMILES: COc1ccc([C@]2(CCN(Cc3ccc(OC4CC5(CCN(CC(=O)O)CC5)C4)cc3)CC(C)(C)C(F)(F)F)CCOC(C)(C)C2)cc1 ; Cl ; Cl] HCl HCl |
| AK10 | 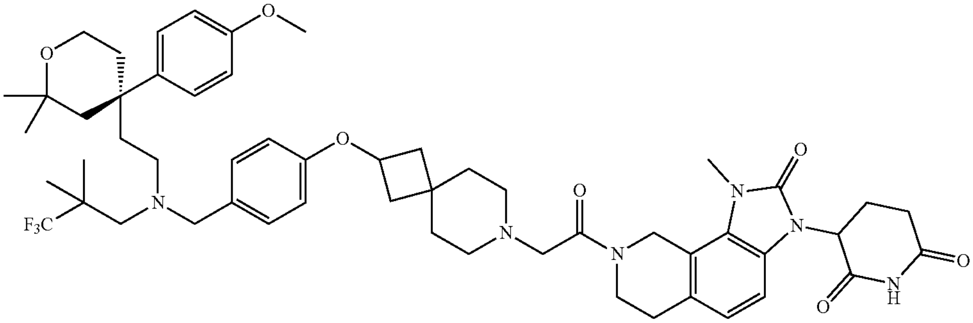 [SMILES: COc1ccc([C@]2(CCN(Cc3ccc(OC4CC5(CCN(CC(=O)N6CCc7ccc8c(c7C6)n(C)c(=O)n8C6CCC(=O)NC6=O)CC5)C4)cc3)CC(C)(C)C(F)(F)F)CCOC(C)(C)C2)cc1] |
| AL1 | 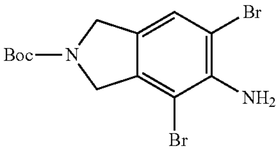 [SMILES: CC(C)(C)OC(=O)N1Cc2cc(Br)c(N)c(Br)c2C1] |
| AL2 | 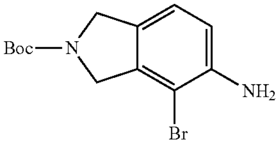 [SMILES: CC(C)(C)OC(=O)N1Cc2ccc(N)c(Br)c2C1] |
| AL3 | 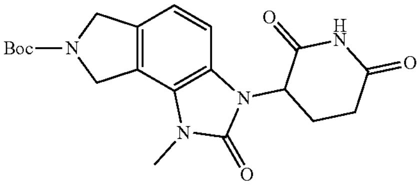 [SMILES: Cn1c(=O)n(C2CCC(=O)NC2=O)c2ccc3c(c21)CN(C(=O)OC(C)(C)C)C3] |
| AL4 | 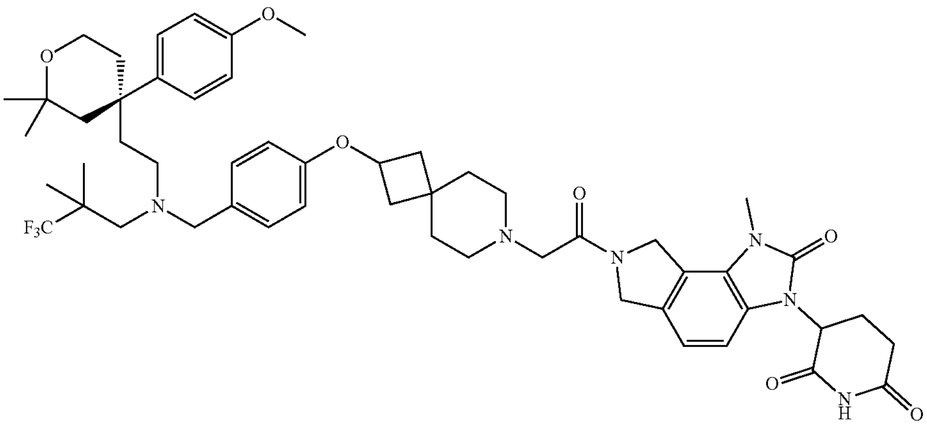 [SMILES: COc1ccc([C@]2(CCN(Cc3ccc(OC4CC5(CCN(CC(=O)N6Cc7ccc8c(c7C6)n(C)c(=O)n8C6CCC(=O)NC6=O)CC5)C4)cc3)CC(C)(C)C(F)(F)F)CCOC(C)(C)C2)cc1] |

TABLE 72-continued
| Ex | Structure |
|---|---|
| AM1 | 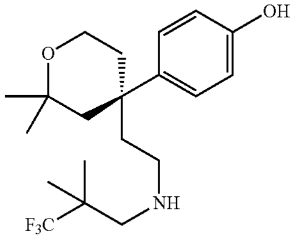 [SMILES: CC1(C)C[C@](CCNCC(C)(C)C(F)(F)F)(c2ccc(O)cc2)CCO1] |
| AM2 | 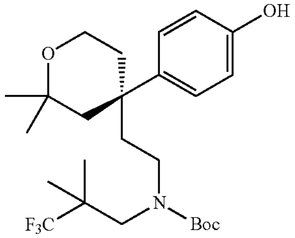 [SMILES: CC(C)(C)OC(=O)N(CC[C@@]1(c2ccc(O)cc2)CCOC(C)(C)C1)CC(C)(C)C(F)(F)F] |
| AM3 | 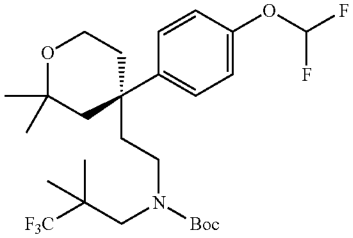 [SMILES: CC(C)(C)OC(=O)N(CC[C@@]1(c2ccc(OC(F)F)cc2)CCOC(C)(C)C1)CC(C)(C)C(F)(F)F] |
| AM4 | 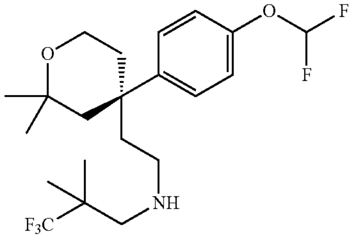 [SMILES: CC1(C)C[C@](CCNCC(C)(C)C(F)(F)F)(c2ccc(OC(F)F)cc2)CCO1] |
TABLE 73
| Ex | Structure |
|---|---|
| AM5 | 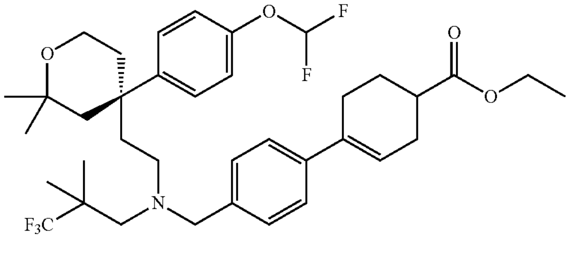 [SMILES: CCOC(=O)C1CC=C(c2ccc(CN(CC[C@@]3(c4ccc(OC(F)F)cc4)CCOC(C)(C)C3)CC(C)(C)C(F)(F)F)cc2)CC1] |

TABLE 73-continued
| Ex | Structure |
| --- | --- |
| AM6 | 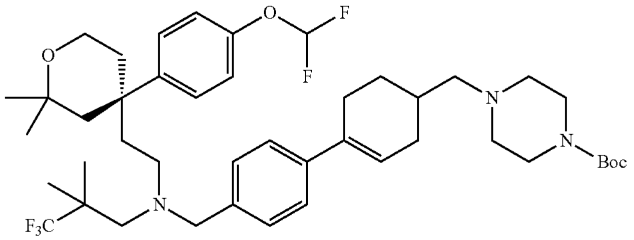 [SMILES: CC(C)(C)OC(=O)N1CCN(CC2CC=C(c3ccc(CN(CC[C@@]4(c5ccc(OC(F)F)cc5)CCOC(C)(C)C4)CC(C)(C)C(F)(F)F)cc3)CC2)CC1] |
| AM7 | 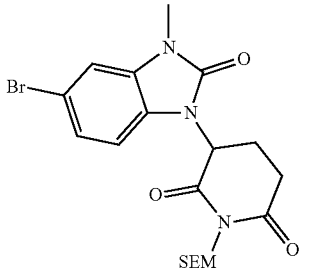 [SMILES: Cn1c(=O)n(C2CCC(=O)N(COCC[Si](C)(C)C)C2=O)c2ccc(Br)cc21] |
| AM8 | 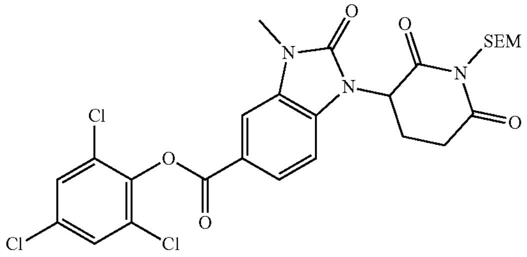 [SMILES: Cn1c(=O)n(C2CCC(=O)N(COCC[Si](C)(C)C)C2=O)c2ccc(C(=O)Oc3c(Cl)cc(Cl)cc3Cl)cc21] |
| AM9 | 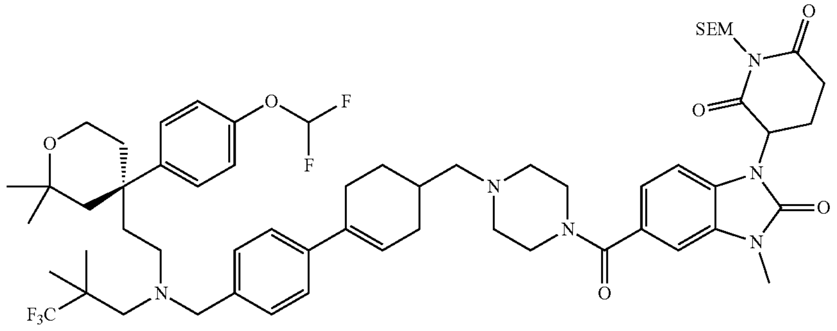 [SMILES: Cn1c(=O)n(C2CCC(=O)N(COCC[Si](C)(C)C)C2=O)c2ccc(C(=O)N3CCN(CC4CC=C(c5ccc(CN(CC[C@@]6(c7ccc(OC(F)F)cc7)CCOC(C)(C)C6)CC(C)(C)C(F)(F)F)cc5)CC4)CC3)cc21] |
| AM10 | 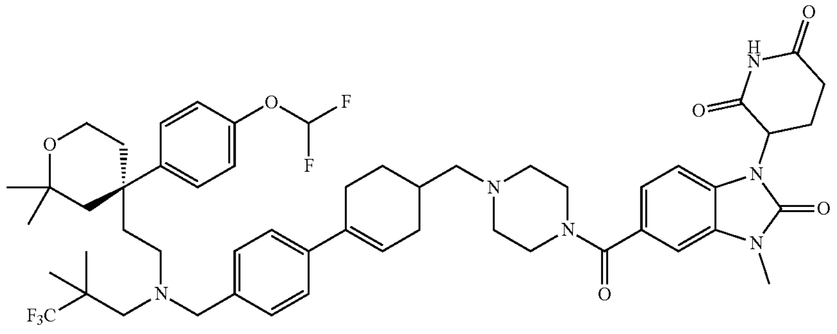 [SMILES: Cn1c(=O)n(C2CCC(=O)NC2=O)c2ccc(C(=O)N3CCN(CC4CC=C(c5ccc(CN(CC[C@@]6(c7ccc(OC(F)F)cc7)CCOC(C)(C)C6)CC(C)(C)C(F)(F)F)cc5)CC4)CC3)cc21] |

TABLE 73-continued
| Ex | Structure |
|---|---|
| AN1 | 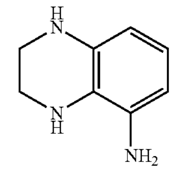 [SMILES: Nc1cccc2c1NCCN2] |
| AN2 | 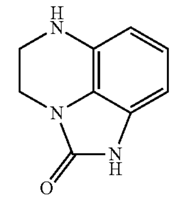 [SMILES: O=c1[nH]c2cccc3c2n1CCN3] |
| AN3 | 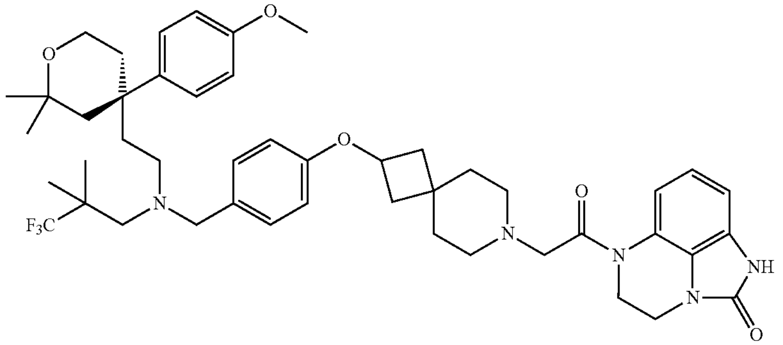 |
| AN4 | 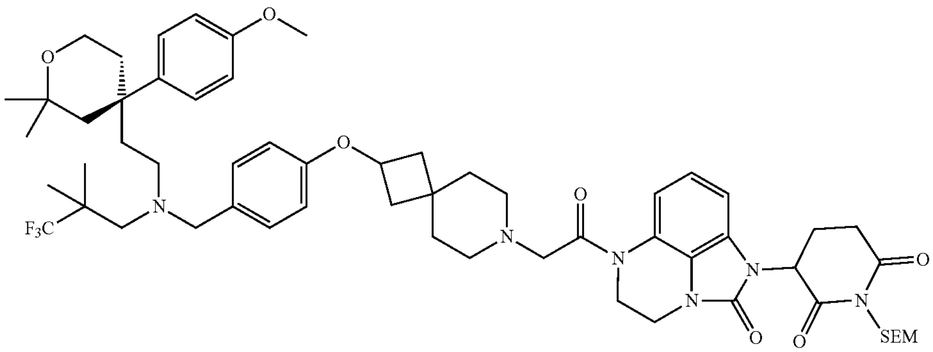 |
TABLE 74
| Ex | Structure |
|---|---|
| AN5 | 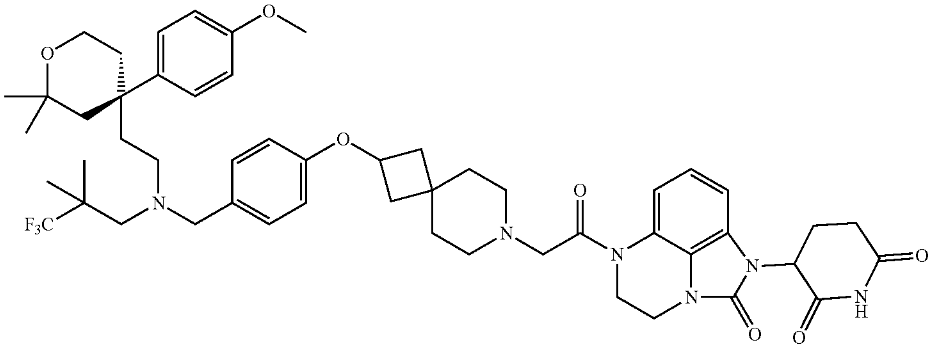 |

TABLE 74-continued
| Ex | Structure |
|---|---|
| AO1 | 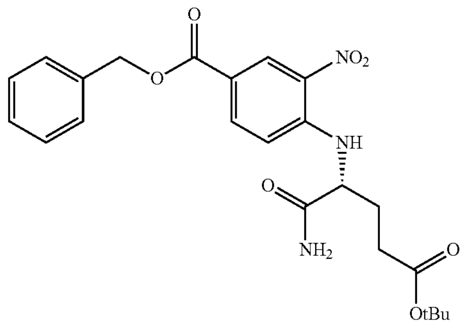 [SMILES: CC(C)(C)OC(=O)CC[C@@H](Nc1ccc(C(=O)OCc2ccccc2)cc1[N+](=O)[O-])C(N)=O] |
| AO2 | 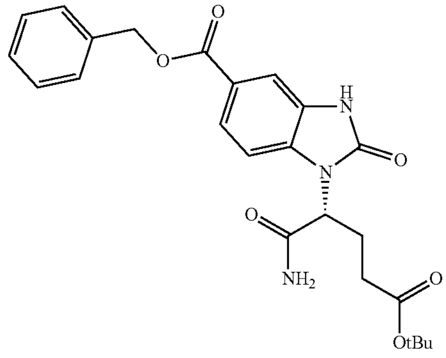 [SMILES: CC(C)(C)OC(=O)CC[C@H](C(N)=O)n1c(=O)[nH]c2cc(C(=O)OCc3ccccc3)ccc21] |
| AO3 | 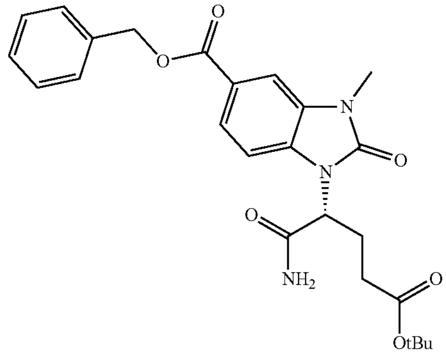 [SMILES: Cn1c(=O)n([C@H](CCC(=O)OC(C)(C)C)C(N)=O)c2ccc(C(=O)OCc3ccccc3)cc21] |
| AO4 | 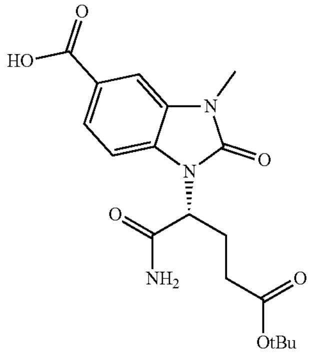 [SMILES: Cn1c(=O)n([C@H](CCC(=O)OC(C)(C)C)C(N)=O)c2ccc(C(=O)O)cc21] |

TABLE 74-continued
| Ex | Structure |
|---|---|
| AO5 | 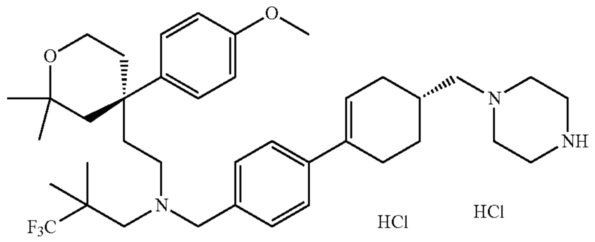 [SMILES: COc1ccc([C@]2(CCN(Cc3ccc(C4=CC[C@H](CN5CCNCC5)CC4)cc3)CC(C)(C)C(F)(F)F)CCOC(C)(C)C2)cc1 ; Cl ; Cl] |
| AO6 | 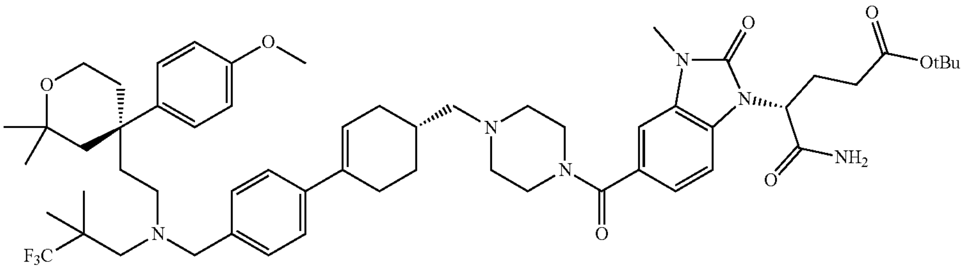 [SMILES: COc1ccc([C@]2(CCN(Cc3ccc(C4=CC[C@H](CN5CCN(C(=O)c6ccc7c(c6)n(C)c(=O)n7[C@H](CCC(=O)OC(C)(C)C)C(N)=O)CC5)CC4)cc3)CC(C)(C)C(F)(F)F)CCOC(C)(C)C2)cc1] |
| AO7 | 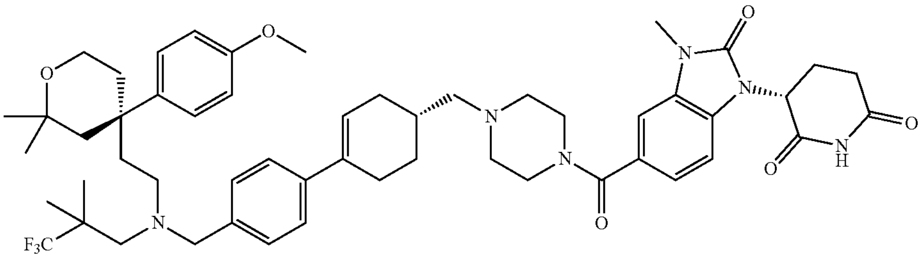 [SMILES: COc1ccc([C@]2(CCN(Cc3ccc(C4=CC[C@H](CN5CCN(C(=O)c6ccc7c(c6)n(C)c(=O)n7[C@@H]6CCC(=O)NC6=O)CC5)CC4)cc3)CC(C)(C)C(F)(F)F)CCOC(C)(C)C2)cc1] |
| AP1 | 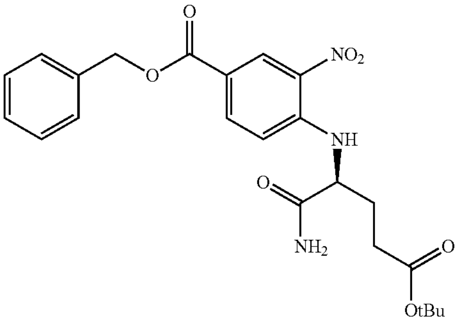 [SMILES: CC(C)(C)OC(=O)CC[C@H](Nc1ccc(C(=O)OCc2ccccc2)cc1[N+](=O)[O-])C(N)=O] |
| AP2 | 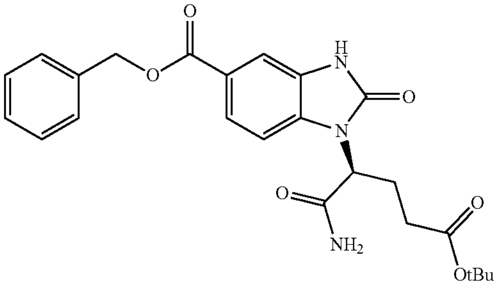 [SMILES: CC(C)(C)OC(=O)CC[C@@H](C(N)=O)n1c(=O)[nH]c2cc(C(=O)OCc3ccccc3)ccc21] |

TABLE 74-continued
| Ex | Structure |
|---|---|
| AP3 | 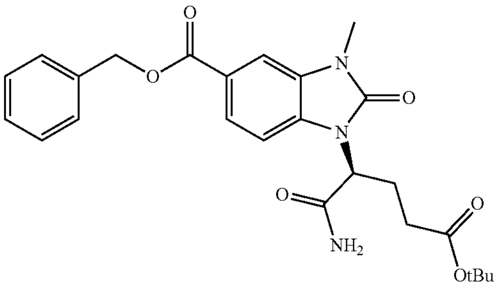 [SMILES: Cn1c(=O)n([C@@H](CCC(=O)OC(C)(C)C)C(N)=O)c2ccc(C(=O)OCc3ccccc3)cc21] |
| AP4 | 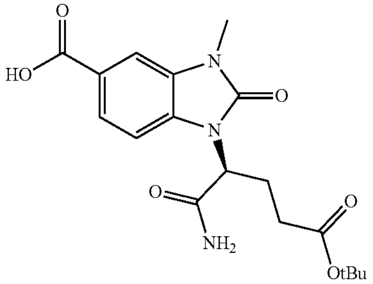 [SMILES: Cn1c(=O)n([C@@H](CCC(=O)OC(C)(C)C)C(N)=O)c2ccc(C(=O)O)cc21] |
TABLE 75
| Ex | Structure |
|---|---|
| AP5 | 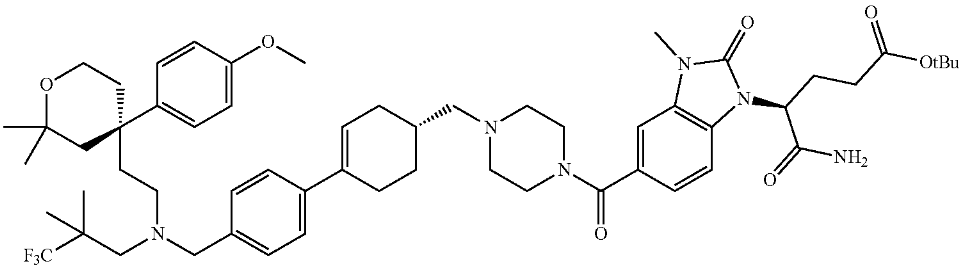 [SMILES: COc1ccc([C@]2(CCN(Cc3ccc(C4=CC[C@H](CN5CCN(C(=O)c6ccc7c(c6)n(C)c(=O)n7[C@@H](CCC(=O)OC(C)(C)C)C(N)=O)CC5)CC4)cc3)CC(C)(C)C(F)(F)F)CCOC(C)(C)C2)cc1] |
| AP6 | 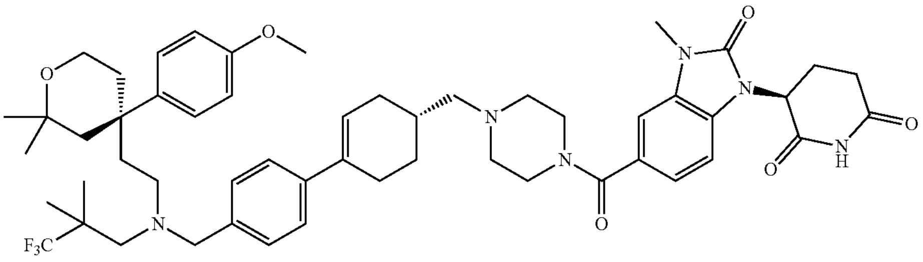 [SMILES: COc1ccc([C@]2(CCN(Cc3ccc(C4=CC[C@H](CN5CCN(C(=O)c6ccc7c(c6)n(C)c(=O)n7[C@H]6CCC(=O)NC6=O)CC5)CC4)cc3)CC(C)(C)C(F)(F)F)CCOC(C)(C)C2)cc1] |
| AQ1 | 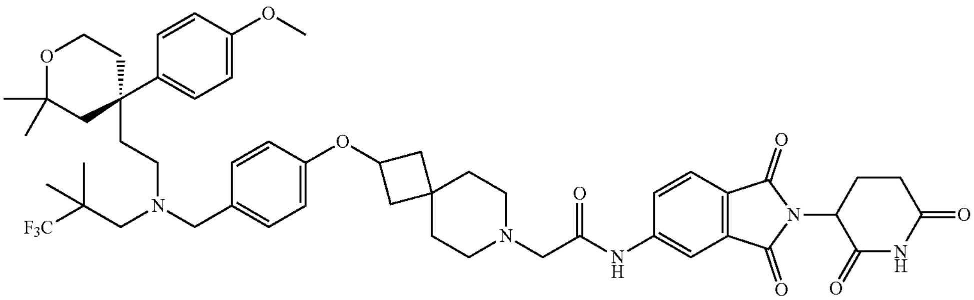 [SMILES: COc1ccc([C@]2(CCN(Cc3ccc(OC4CC5(CCN(CC(=O)Nc6ccc7c(c6)C(=O)N(C6CCC(=O)NC6=O)C7=O)CC5)C4)cc3)CC(C)(C)C(F)(F)F)CCOC(C)(C)C2)cc1] |

TABLE 75-continued
| Ex | Structure |
| --- | --- |
| AR1 | 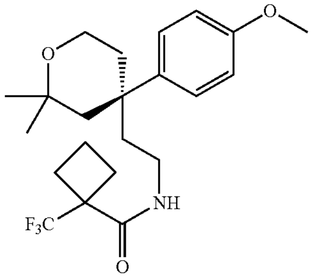 |
| AR2 | 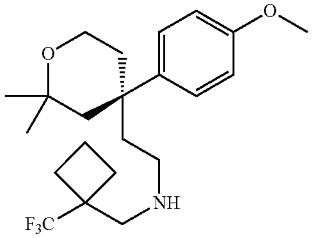 |
| AR3 | 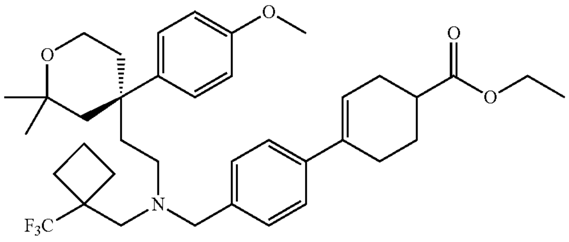 [SMILES: CCOC(=O)C1CC=C(c2ccc(CN(CC[C@@]3(c4ccc(OC)cc4)CCOC(C)(C)C3)CC3(C(F)(F)F)CCC3)cc2)CC1] |
| AR4 | 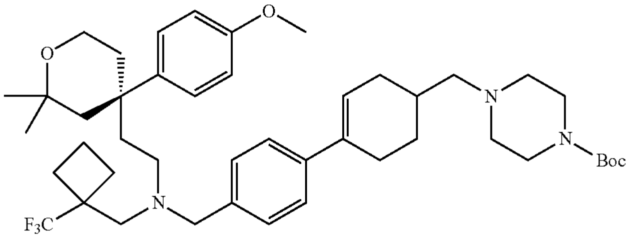 [SMILES: COc1ccc([C@]2(CCN(Cc3ccc(C4=CCC(CN5CCN(C(=O)OC(C)(C)C)CC5)CC4)cc3)CC3(C(F)(F)F)CCC3)CCOC(C)(C)C2)cc1] |
| AR5 | 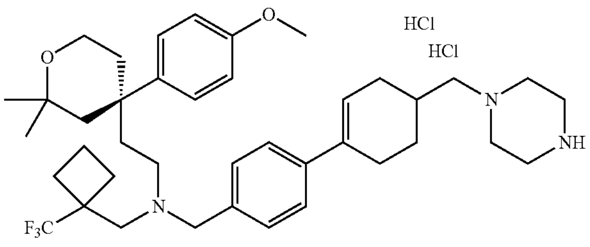 [SMILES: COc1ccc([C@]2(CCN(Cc3ccc(C4=CCC(CN5CCNCC5)CC4)cc3)CC3(C(F)(F)F)CCC3)CCOC(C)(C)C2)cc1 ; Cl ; Cl] |

TABLE 75-continued
| Ex | Structure |
|---|---|
| AR6 | 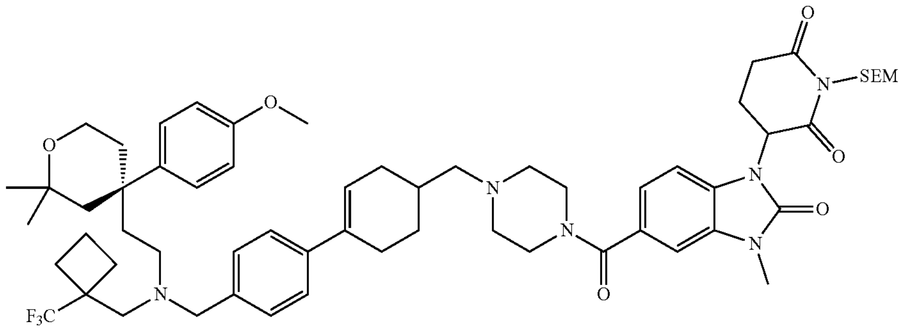 [SMILES: COc1ccc([C@]2(CCN(Cc3ccc(C4=CCC(CN5CCN(C(=O)c6ccc7c(c6)n(C)c(=O)n7C6CCC(=O)N(COCC[Si](C)(C)C)C6=O)CC5)CC4)cc3)CC3(C(F)(F)F)CCC3)CCOC(C)(C)C2)cc1] |
| AR7 | 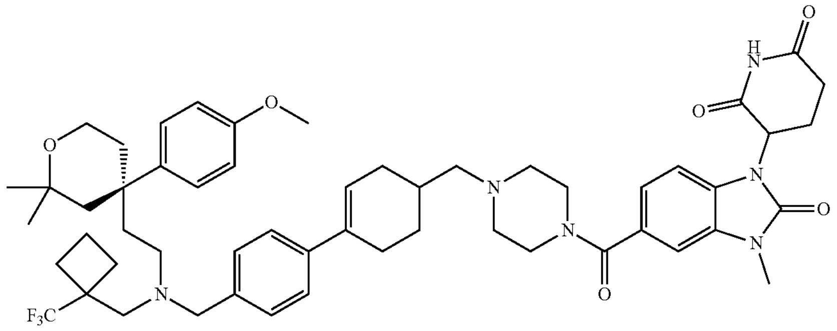 [SMILES: COc1ccc([C@]2(CCN(Cc3ccc(C4=CCC(CN5CCN(C(=O)c6ccc7c(c6)n(C)c(=O)n7C6CCC(=O)NC6=O)CC5)CC4)cc3)CC3(C(F)(F)F)CCC3)CCOC(C)(C)C2)cc1] |
| AS1 | 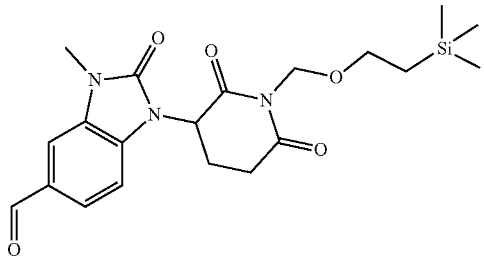 [SMILES: Cn1c(=O)n(C2CCC(=O)N(COCC[Si](C)(C)C)C2=O)c2ccc(C=O)cc21] |
| AS2 | 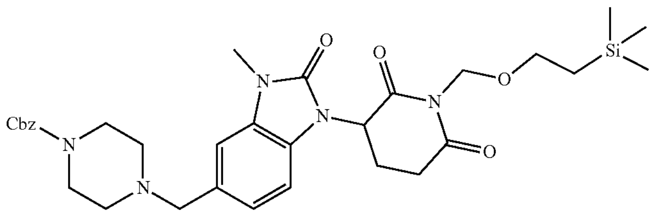 [SMILES: Cn1c(=O)n(C2CCC(=O)N(COCC[Si](C)(C)C)C2=O)c2ccc(CN3CCN(C(=O)OCc4ccccc4)CC3)cc21] |
TABLE 76
| Ex | Structure |
|---|---|
| AS3 | 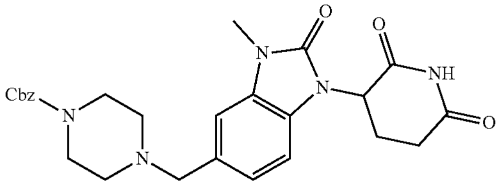 [SMILES: Cn1c(=O)n(C2CCC(=O)NC2=O)c2ccc(CN3CCN(C(=O)OCc4ccccc4)CC3)cc21] |

TABLE 76-continued
| Ex | Structure |
| --- | --- |
| AS4 | 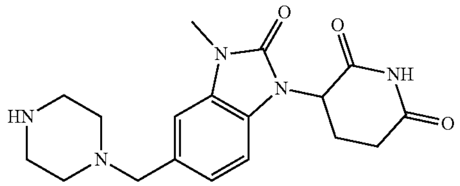 [SMILES: Cn1c(=O)n(C2CCC(=O)NC2=O)c2ccc(CN3CCNCC3)cc21] |
| AS5 | 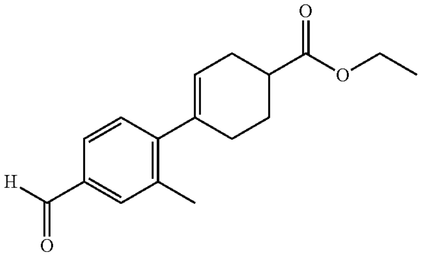 [SMILES: CCOC(=O)C1CC=C(c2ccc(C=O)cc2C)CC1] |
| AS6 | 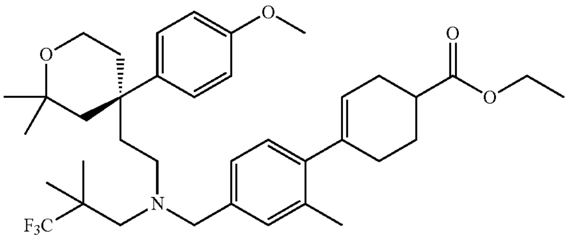 [SMILES: CCOC(=O)C1CC=C(c2ccc(CN(CC[C@@]3(c4ccc(OC)cc4)CCOC(C)(C)C3)CC(C)(C)C(F)(F)F)cc2C)CC1] |
| AS7 | 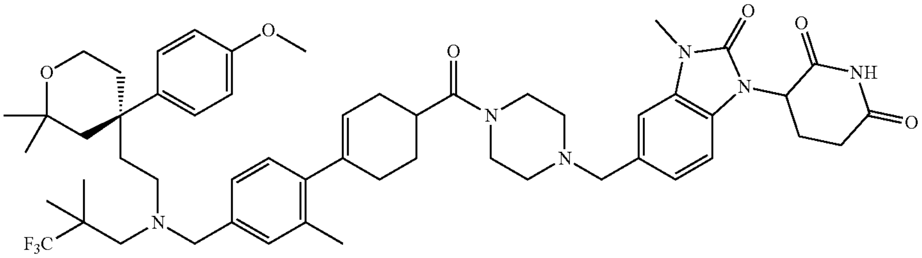 [SMILES: COc1ccc([C@]2(CCN(Cc3ccc(C4=CCC(C(=O)N5CCN(Cc6ccc7c(c6)n(C)c(=O)n7C6CCC(=O)NC6=O)CC5)CC4)c(C)c3)CC(C)(C)C(F)(F)F)CCOC(C)(C)C2)cc1] |
| AT1 | 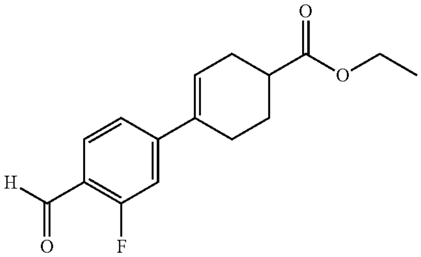 [SMILES: CCOC(=O)C1CC=C(c2ccc(C=O)c(F)c2)CC1] |
| AT2 | 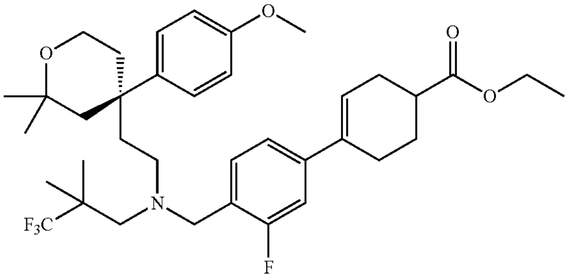 [SMILES: CCOC(=O)C1CC=C(c2ccc(CN(CC[C@@]3(c4ccc(OC)cc4)CCOC(C)(C)C3)CC(C)(C)C(F)(F)F)c(F)c2)CC1] |

TABLE 76-continued
| Ex | Structure |
| --- | --- |
| AT3 | 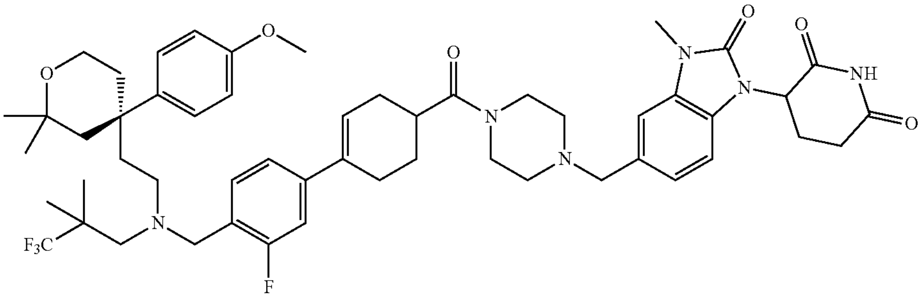 [SMILES: COc1ccc([C@]2(CCN(Cc3ccc(C4=CCC(C(=O)N5CCN(Cc6ccc7c(c6)n(C)c(=O)n7C6CCC(=O)NC6=O)CC5)CC4)cc3F)CC(C)(C)C(F)(F)F)CCOC(C)(C)C2)cc1] |
| AU1 | 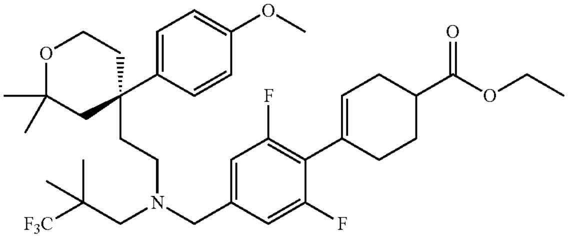 |
| AU2 | 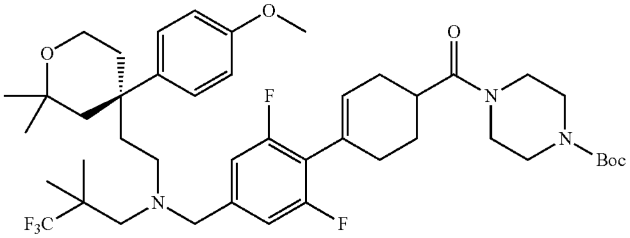 [SMILES: COc1ccc([C@]2(CCN(Cc3cc(F)c(C4=CCC(C(=O)N5CCN(C(=O)OC(C)(C)C)CC5)CC4)c(F)c3)CC(C)(C)C(F)(F)F)CCOC(C)(C)C2)cc1] |
| AU3 | 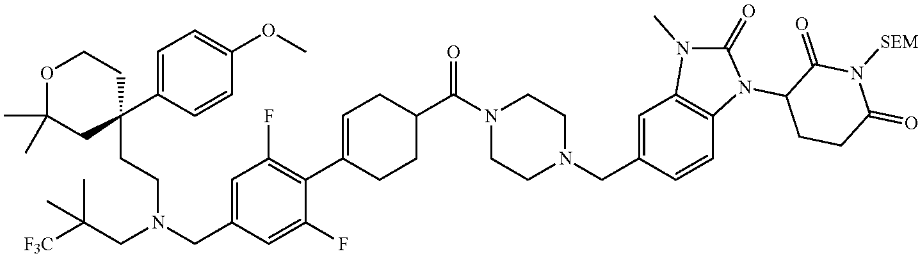 [SMILES: COc1ccc([C@]2(CCN(Cc3cc(F)c(C4=CCC(C(=O)N5CCN(Cc6ccc7c(c6)n(C)c(=O)n7C6CCC(=O)N(COCC[Si](C)(C)C)C6=O)CC5)CC4)c(F)c3)CC(C)(C)C(F)(F)F)CCOC(C)(C)C2)cc1] |
| AU4 | 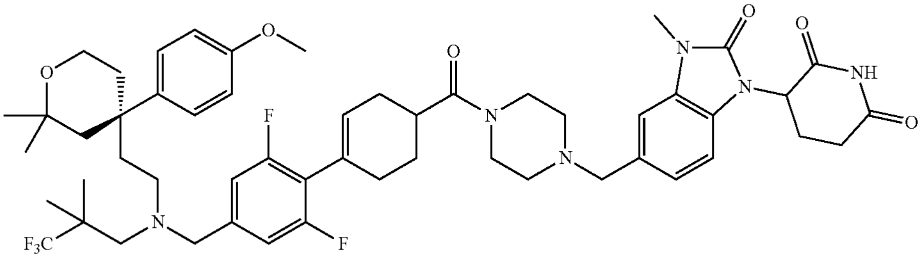 [SMILES: COc1ccc([C@]2(CCN(Cc3cc(F)c(C4=CCC(C(=O)N5CCN(Cc6ccc7c(c6)n(C)c(=O)n7C6CCC(=O)NC6=O)CC5)CC4)c(F)c3)CC(C)(C)C(F)(F)F)CCOC(C)(C)C2)cc1] |

TABLE 77
| Ex | Structure |
| --- | --- |
| AV1 | 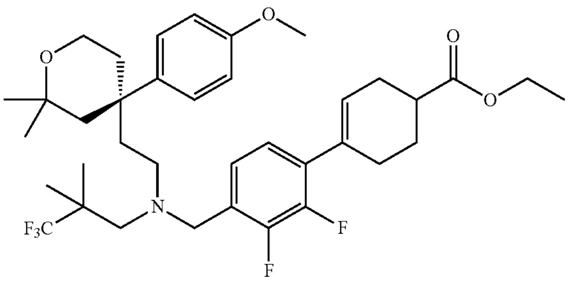 [SMILES: CCOC(=O)C1CC=C(c2ccc(CN(CC[C@@]3(c4ccc(OC)cc4)CCOC(C)(C)C3)CC(C)(C)C(F)(F)F)c(F)c2F)CC1] |
| AV2 | 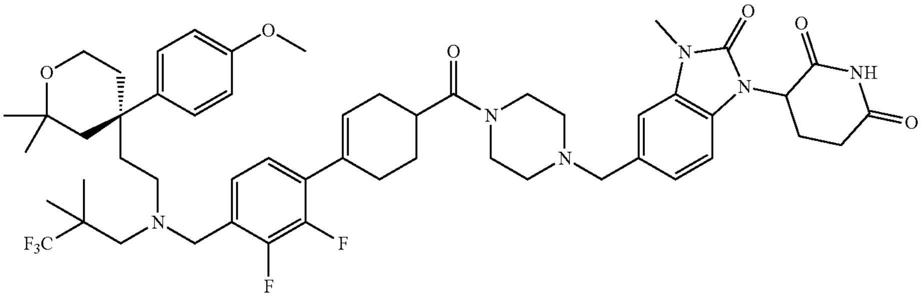 [SMILES: COc1ccc([C@]2(CCN(Cc3ccc(C4=CCC(C(=O)N5CCN(Cc6ccc7c(c6)n(C)c(=O)n7C6CCC(=O)NC6=O)CC5)CC4)c(F)c3F)CC(C)(C)C(F)(F)F)CCOC(C)(C)C2)cc1] |
| AW1 | 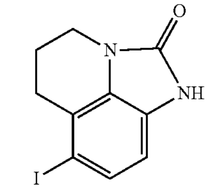 [SMILES: O=c1[nH]c2ccc(I)c3c2n1CCC3] |
| AW2 | 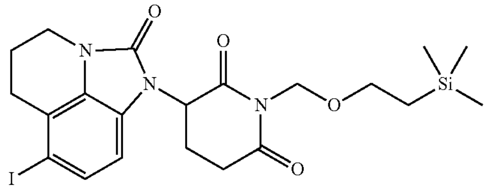 [SMILES: C[Si](C)(C)CCOCN1C(=O)CCC(n2c(=O)n3c4c(c(I)ccc42)CCC3)C1=O] |
| AW3 | 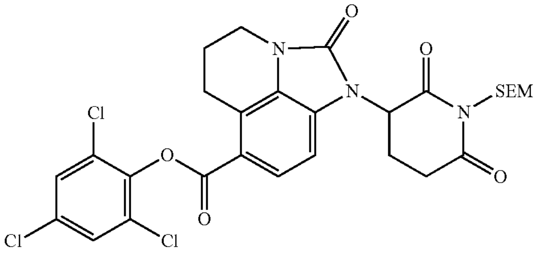 [SMILES: C[Si](C)(C)CCOCN1C(=O)CCC(n2c(=O)n3c4c(c(C(=O)Oc5c(Cl)cc(Cl)cc5Cl)ccc42)CCC3)C1=O] |
| AW4 | 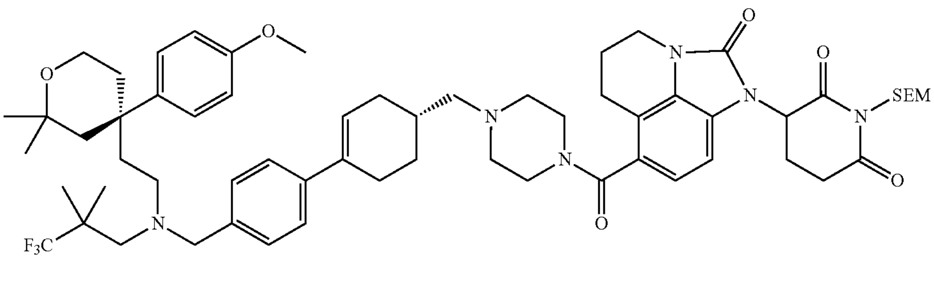 [SMILES: COc1ccc([C@]2(CCN(Cc3ccc(C4=CC[C@H](CN5CCN(C(=O)c6ccc7c8c6CCCn8c(=O)n7C6CCC(=O)N(COCC[Si](C)(C)C)C6=O)CC5)CC4)cc3)CC(C)(C)C(F)(F)F)CCOC(C)(C)C2)cc1] |

TABLE 77-continued
| Ex | Structure |
|---|---|
| AW5 | 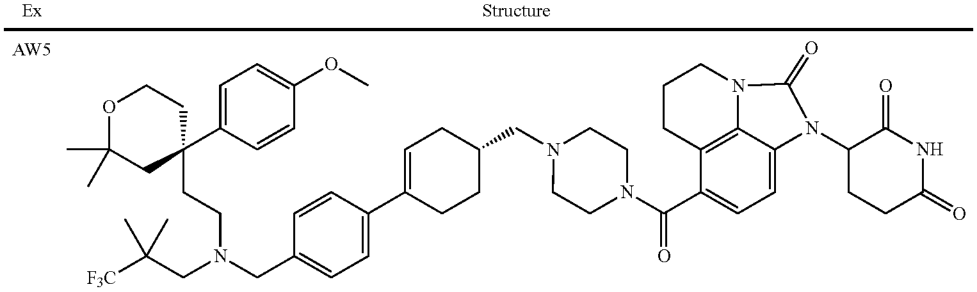 |
| AX1 | 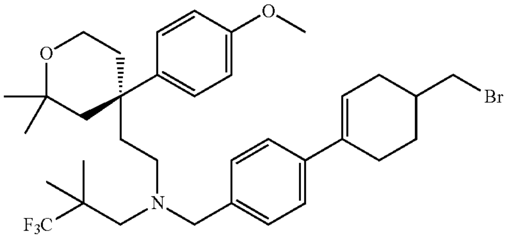 [SMILES: COc1ccc([C@]2(CCN(Cc3ccc(C4=CCC(CBr)CC4)cc3)CC(C)(C)C(F)(F)F)CCOC(C)(C)C2)cc1] |
| AX2 | 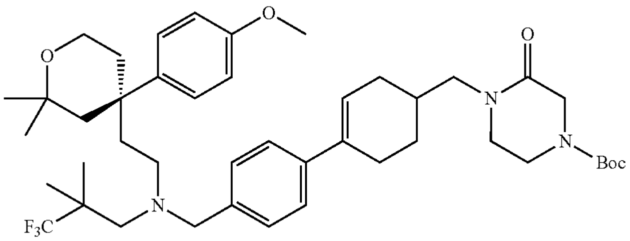 [SMILES: COc1ccc([C@]2(CCN(Cc3ccc(C4=CCC(CN5CCN(C(=O)OC(C)(C)C)CC5=O)CC4)cc3)CC(C)(C)C(F)(F)F)CCOC(C)(C)C2)cc1] |
| AX3 | 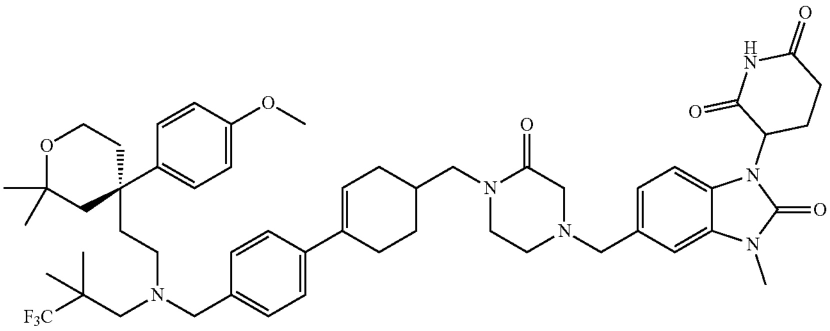 [SMILES: COc1ccc([C@]2(CCN(Cc3ccc(C4=CCC(CN5CCN(Cc6ccc7c(c6)n(C)c(=O)n7C6CCC(=O)NC6=O)CC5=O)CC4)cc3)CC(C)(C)C(F)(F)F)CCOC(C)(C)C2)cc1] |
TABLE 78
| Ex | Structure |
|---|---|
| AY1 | 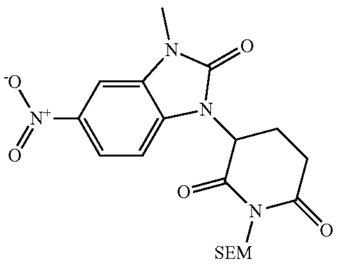 |

TABLE 78-continued
| Ex | Structure |
|---|---|
| AY2 | 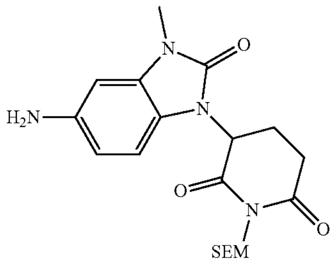 [SMILES: Cn1c(=O)n(C2CCC(=O)N(COCC[Si](C)(C)C)C2=O)c2ccc(N)cc21] |
| AY3 | 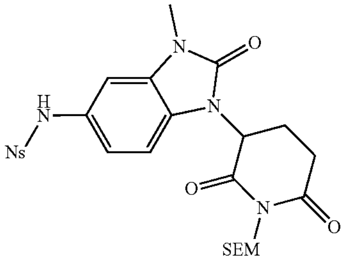 |
| AY4 | 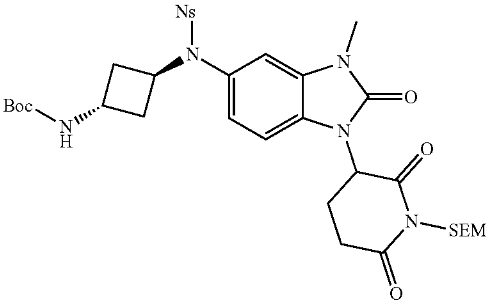 |
| AY5 | 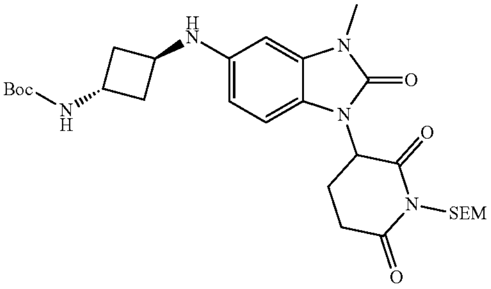 [SMILES: Cn1c(=O)n(C2CCC(=O)N(COCC[Si](C)(C)C)C2=O)c2ccc(N[C@H]3C[C@H](NC(=O)OC(C)(C)C)C3)cc21] |
| AY6 | 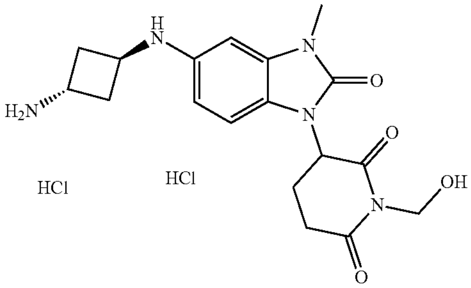 [SMILES: Cn1c(=O)n(C2CCC(=O)N(CO)C2=O)c2ccc(N[C@H]3C[C@H](N)C3)cc21 ; Cl ; Cl] HCl HCl |

TABLE 78-continued
| Ex | Structure |
|---|---|
| AY7 | 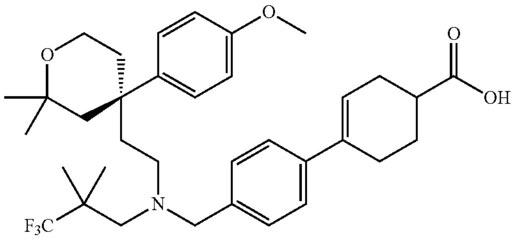 [SMILES: COc1ccc([C@]2(CCN(Cc3ccc(C4=CCC(C(=O)O)CC4)cc3)CC(C)(C)C(F)(F)F)CCOC(C)(C)C2)cc1] |
| AY8 | 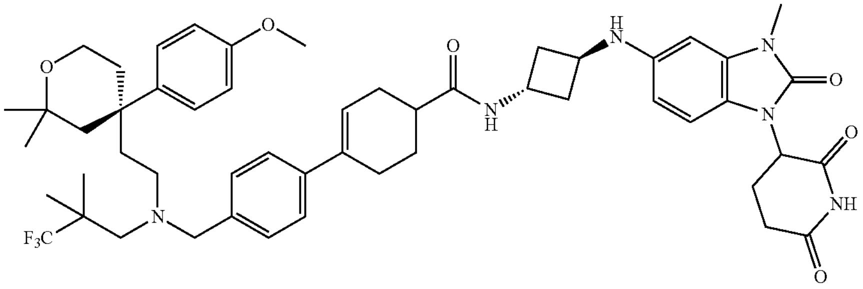 [SMILES: COc1ccc([C@]2(CCN(Cc3ccc(C4=CCC(C(=O)N[C@H]5C[C@H](Nc6ccc7c(c6)n(C)c(=O)n7C6CCC(=O)NC6=O)C5)CC4)cc3)CC(C)(C)C(F)(F)F)CCOC(C)(C)C2)cc1] |
| AZ1 | 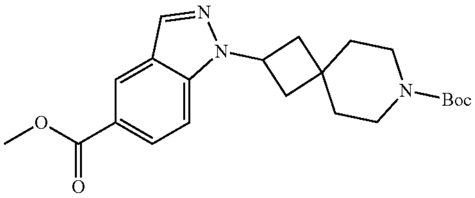 [SMILES: COC(=O)c1ccc2c(cnn2C2CC3(CCN(C(=O)OC(C)(C)C)CC3)C2)c1] |
| AZ2 | 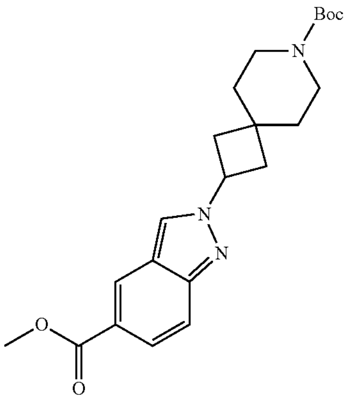 [SMILES: COC(=O)c1ccc2nn(C3CC4(CCN(C(=O)OC(C)(C)C)CC4)C3)cc2c1] |

TABLE 79
| Ex | Structure |
|---|---|
| AZ3 | 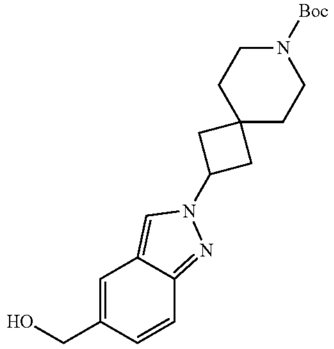 [SMILES: CC(C)(C)OC(=O)N1CCC2(CC1)CC(n1cc3cc(CO)ccc3n1)C2] |
| AZ4 | 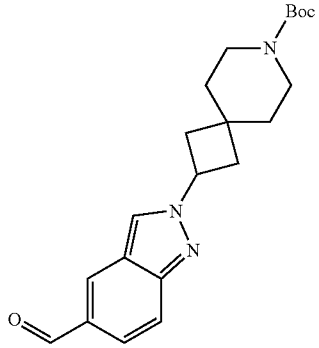 [SMILES: CC(C)(C)OC(=O)N1CCC2(CC1)CC(n1cc3cc(C=O)ccc3n1)C2] |
| AZ5 | 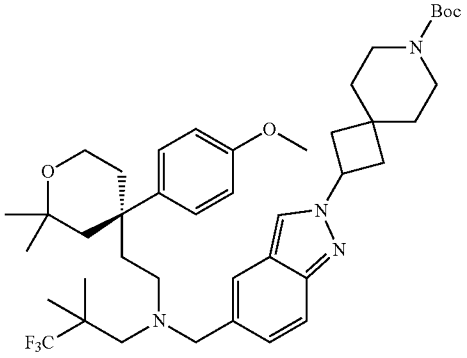 [SMILES: COc1ccc([C@]2(CCN(Cc3ccc4nn(C5CC6(CCN(C(=O)OC(C)(C)C)CC6)C5)cc4c3)CC(C)(C)C(F)(F)F)CCOC(C)(C)C2)cc1] |
| AZ6 | 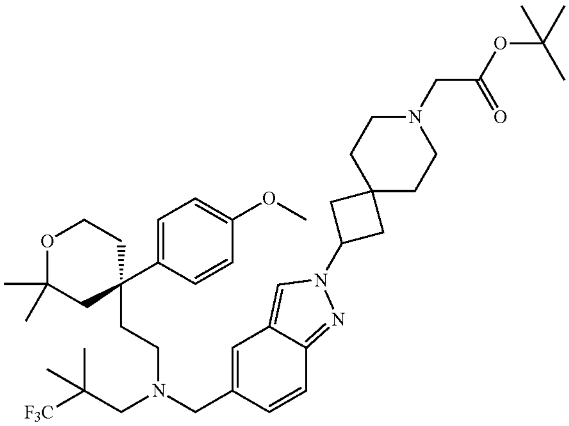 [SMILES: COc1ccc([C@]2(CCN(Cc3ccc4nn(C5CC6(CCN(CC(=O)OC(C)(C)C)CC6)C5)cc4c3)CC(C)(C)C(F)(F)F)CCOC(C)(C)C2)cc1] |

TABLE 79-continued
| Ex | Structure |
|---|---|
| AZ7 | 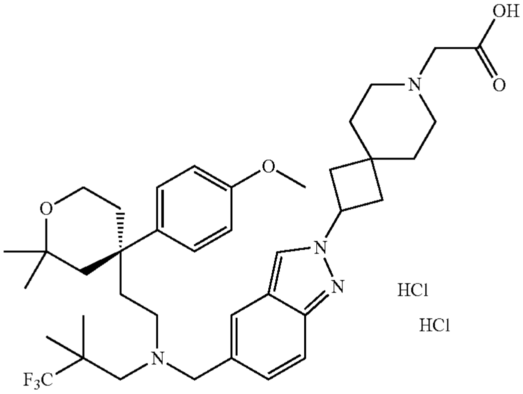 [SMILES: COc1ccc([C@]2(CCN(Cc3ccc4nn(C5CC6(CCN(CC(=O)O)CC6)C5)cc4c3)CC(C)(C)C(F)(F)F)CCOC(C)(C)C2)cc1 ; Cl ; Cl] HCl HCl |
| AZ8 | 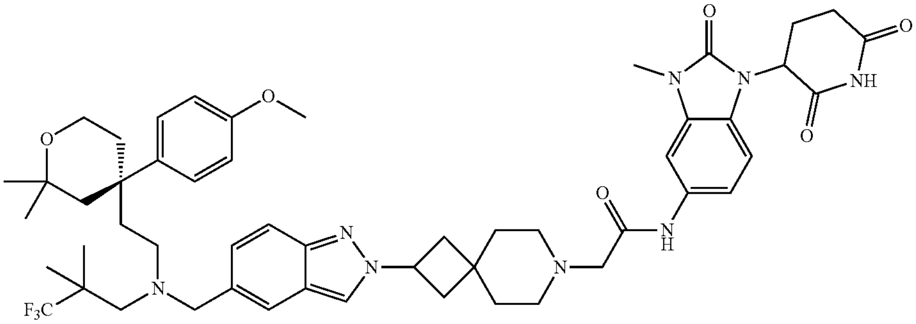 [SMILES: COc1ccc([C@]2(CCN(Cc3ccc4nn(C5CC6(CCN(CC(=O)Nc7ccc8c(c7)n(C)c(=O)n8C7CCC(=O)NC7=O)CC6)C5)cc4c3)CC(C)(C)C(F)(F)F)CCOC(C)(C)C2)cc1] |
| BA1 | 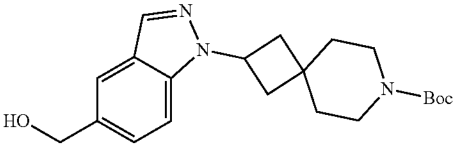 [SMILES: CC(C)(C)OC(=O)N1CCC2(CC1)CC(n1ncc3cc(CO)ccc31)C2] |
| BA2 | 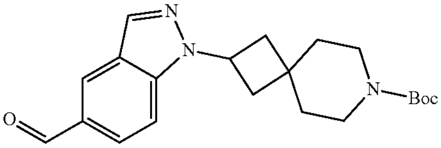 [SMILES: CC(C)(C)OC(=O)N1CCC2(CC1)CC(n1ncc3cc(C=O)ccc31)C2] |
| BA3 | 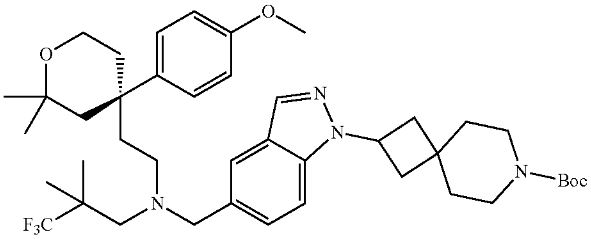 [SMILES: COc1ccc([C@]2(CCN(Cc3ccc4c(cnn4C4CC5(CCN(C(=O)OC(C)(C)C)CC5)C4)c3)CC(C)(C)C(F)(F)F)CCOC(C)(C)C2)cc1] |
| BA4 | 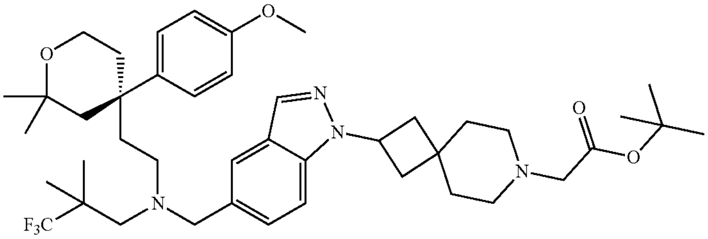 [SMILES: COc1ccc([C@]2(CCN(Cc3ccc4c(cnn4C4CC5(CCN(CC(=O)OC(C)(C)C)CC5)C4)c3)CC(C)(C)C(F)(F)F)CCOC(C)(C)C2)cc1] |

TABLE 80
| Ex | Structure |
| --- | --- |
| BA5 | 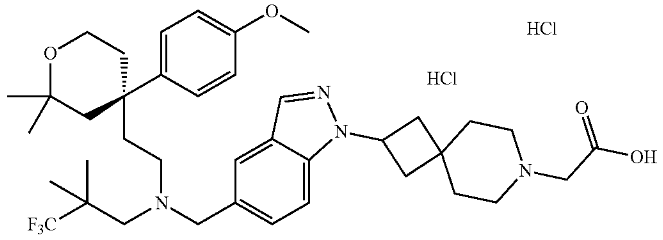 [SMILES: COc1ccc([C@]2(CCN(Cc3ccc4c(cnn4C4CC5(CCN(CC(=O)O)CC5)C4)c3)CC(C)(C)C(F)(F)F)CCOC(C)(C)C2)cc1 ; Cl ; Cl] |
| BA6 | 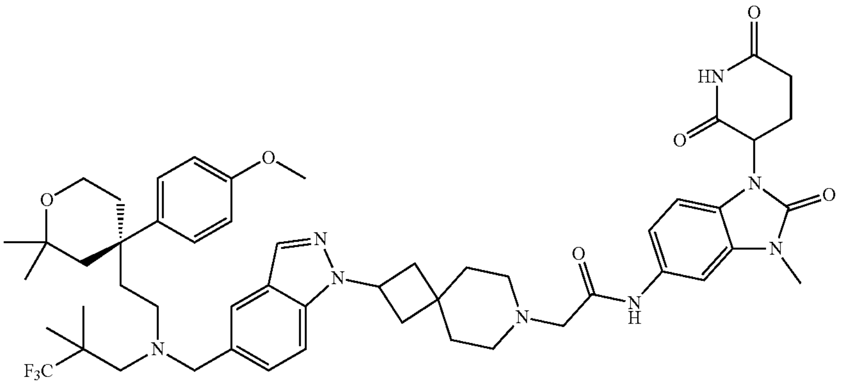 [SMILES: COc1ccc([C@]2(CCN(Cc3ccc4c(cnn4C4CC5(CCN(CC(=O)Nc6ccc7c(c6)n(C)c(=O)n7C6CCC(=O)NC6=O)CC5)C4)c3)CC(C)(C)C(F)(F)F)CCOC(C)(C)C2)cc1] |
| BB1 | 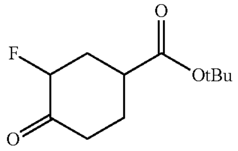 [SMILES: CC(C)(C)OC(=O)C1CCC(=O)C(F)C1] |
| BB2 | 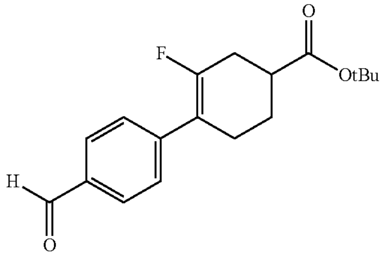 [SMILES: CC(C)(C)OC(=O)C1CCC(c2ccc(C=O)cc2)=C(F)C1] |
| BB3 | 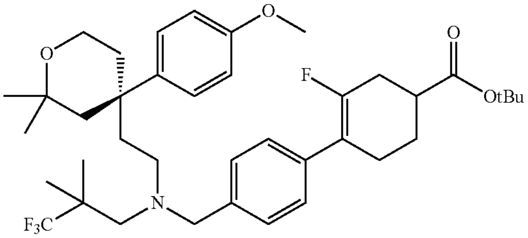 [SMILES: COc1ccc([C@]2(CCN(Cc3ccc(C4=C(F)CC(C(=O)OC(C)(C)C)CC4)cc3)CC(C)(C)C(F)(F)F)CCOC(C)(C)C2)cc1] |
| BB4 | 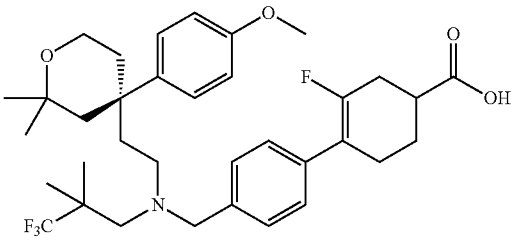 [SMILES: COc1ccc([C@]2(CCN(Cc3ccc(C4=C(F)CC(C(=O)O)CC4)cc3)CC(C)(C)C(F)(F)F)CCOC(C)(C)C2)cc1] |

TABLE 80-continued
| Ex | Structure |
|---|---|
| BB5 | 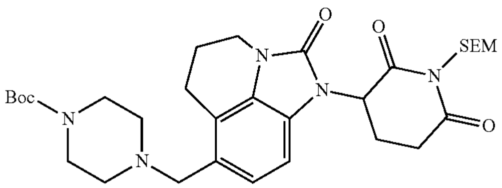 [SMILES: CC(C)(C)OC(=O)N1CCN(Cc2ccc3c4c2CCCn4c(=O)n3C2CCC(=O)N(COCC[Si](C)(C)C)C2=O)CC1] |
| BB6 | 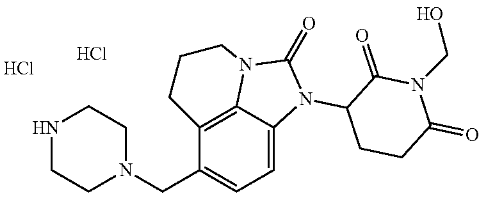 [SMILES: Cl ; O=C1CCC(n2c(=O)n3c4c(c(CN5CCNCC5)ccc42)CCC3)C(=O)N1CO ; Cl] |
| BB7 | 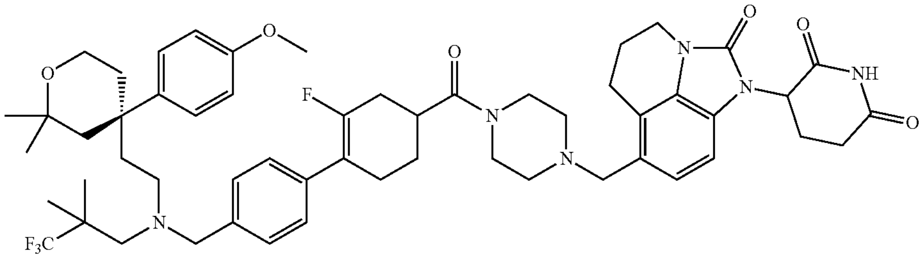 [SMILES: COc1ccc([C@]2(CCN(Cc3ccc(C4=C(F)CC(C(=O)N5CCN(Cc6ccc7c8c6CCCn8c(=O)n7C6CCC(=O)NC6=O)CC5)CC4)cc3)CC(C)(C)C(F)(F)F)CCOC(C)(C)C2)cc1] |
| BC1 | 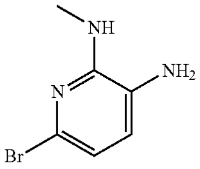 |
| BC2 | 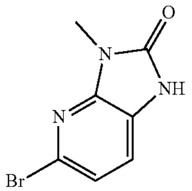 |
| BC3 | 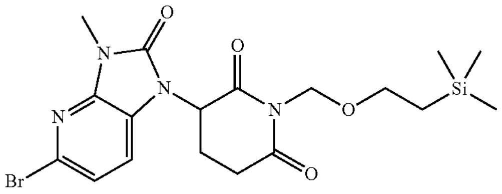 [SMILES: Cn1c(=O)n(C2CCC(=O)N(COCC[Si](C)(C)C)C2=O)c2ccc(Br)nc21] |

TABLE 81
| Ex | Structure |
| --- | --- |
| BC4 | 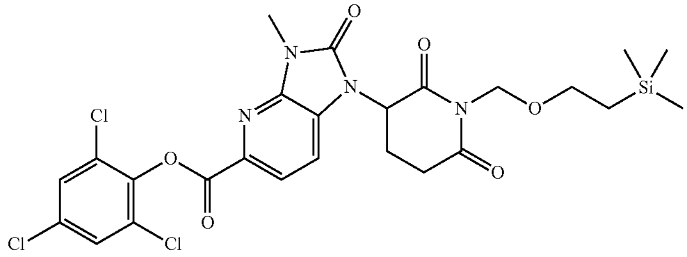 [SMILES: Cn1c(=O)n(C2CCC(=O)N(COCC[Si](C)(C)C)C2=O)c2ccc(C(=O)Oc3c(Cl)cc(Cl)cc3Cl)nc21] |
| BC5 | 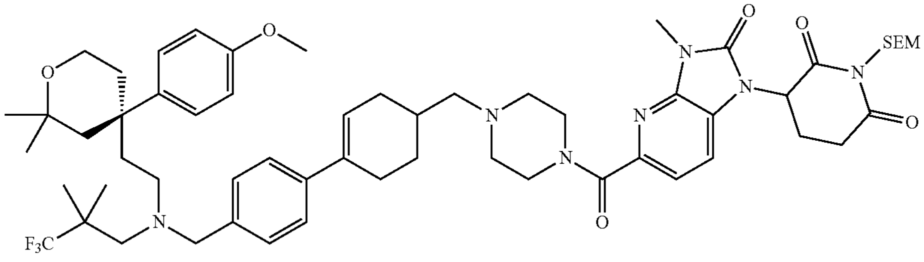 [SMILES: COc1ccc([C@]2(CCN(Cc3ccc(C4=CCC(CN5CCN(C(=O)c6ccc7c(n6)n(C)c(=O)n7C6CCC(=O)N(COCC[Si](C)(C)C)C6=O)CC5)CC4)cc3)CC(C)(C)C(F)(F)F)CCOC(C)(C)C2)cc1] |
| BC6 | 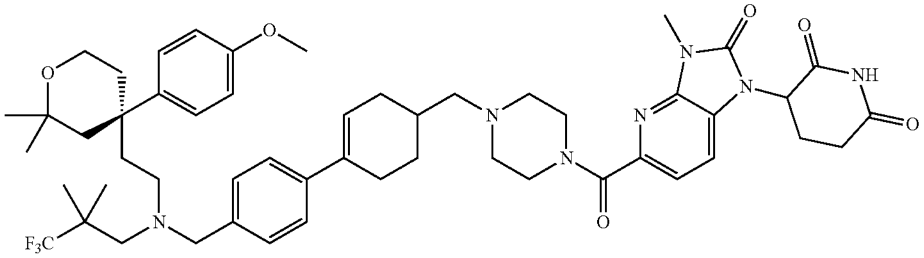 [SMILES: COc1ccc([C@]2(CCN(Cc3ccc(C4=CCC(CN5CCN(C(=O)c6ccc7c(n6)n(C)c(=O)n7C6CCC(=O)NC6=O)CC5)CC4)cc3)CC(C)(C)C(F)(F)F)CCOC(C)(C)C2)cc1] |
| BD1 | 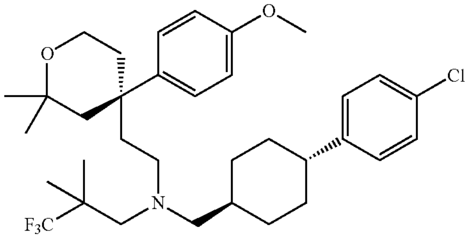 [SMILES: COc1ccc([C@]2(CCN(CC(C)(C)C(F)(F)F)C[C@H]3CC[C@H](c4ccc(Cl)cc4)CC3)CCOC(C)(C)C2)cc1] |
| BD2 | 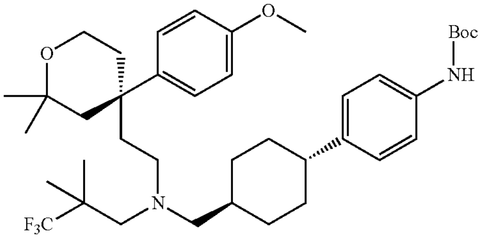 [SMILES: COc1ccc([C@]2(CCN(CC(C)(C)C(F)(F)F)C[C@H]3CC[C@H](c4ccc(NC(=O)OC(C)(C)C)cc4)CC3)CCOC(C)(C)C2)cc1] |
| BD3 | 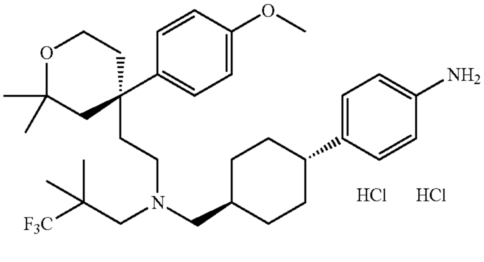 [SMILES: COc1ccc([C@]2(CCN(CC(C)(C)C(F)(F)F)C[C@H]3CC[C@H](c4ccc(N)cc4)CC3)CCOC(C)(C)C2)cc1 ; Cl ; Cl] |

TABLE 81-continued
| Ex | Structure |
|---|---|
| BD4 | 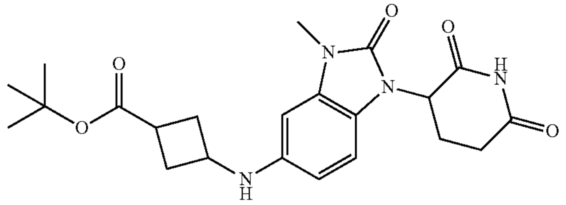 [SMILES: Cn1c(=O)n(C2CCC(=O)NC2=O)c2ccc(NC3CC(C(=O)OC(C)(C)C)C3)cc21] |
| BD5 | 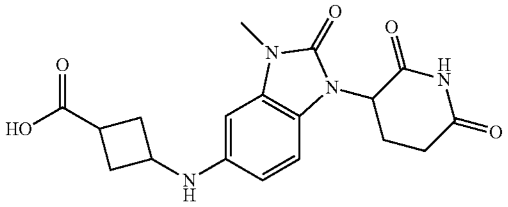 [SMILES: Cn1c(=O)n(C2CCC(=O)NC2=O)c2ccc(NC3CC(C(=O)O)C3)cc21] |
| BD6 | 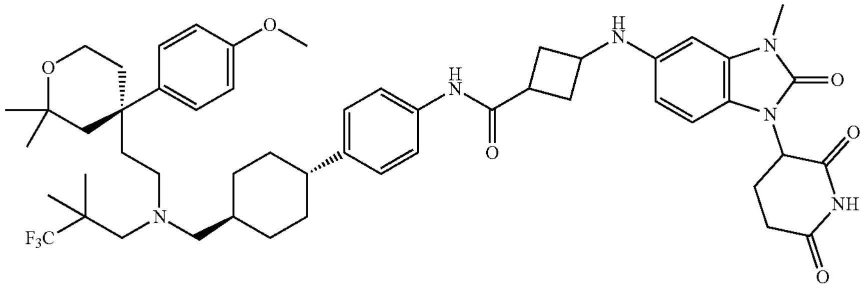 [SMILES: COc1ccc([C@]2(CCN(CC(C)(C)C(F)(F)F)C[C@H]3CC[C@H](c4ccc(NC(=O)C5CC(Nc6ccc7c(c6)n(C)c(=O)n7C6CCC(=O)NC6=O)C5)cc4)CC3)CCOC(C)(C)C2)cc1] |
| BE1 | 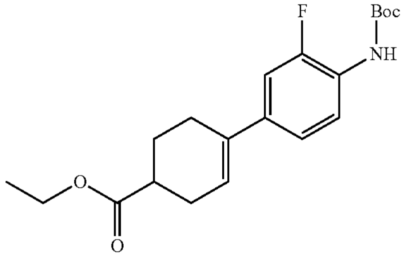 [SMILES: CCOC(=O)C1CC=C(c2ccc(NC(=O)OC(C)(C)C)c(F)c2)CC1] |
| BE2 | 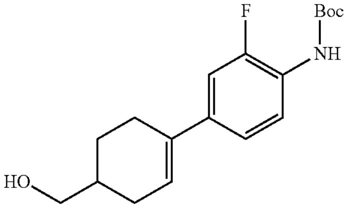 [SMILES: CC(C)(C)OC(=O)Nc1ccc(C2=CCC(CO)CC2)cc1F] |
| BE3 | 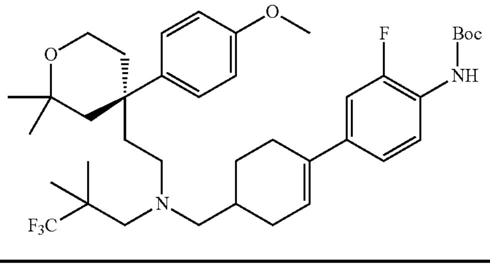 |

TABLE 82
| Ex | Structure |
|---|---|
| BE4 | 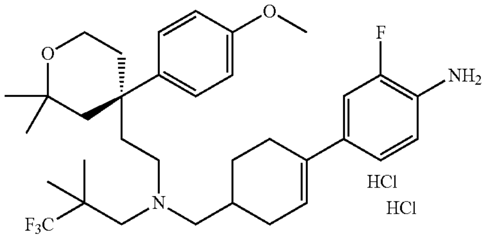 [SMILES: COc1ccc([C@]2(CCN(CC3CC=C(c4ccc(N)c(F)c4)CC3)CC(C)(C)C(F)(F)F)CCOC(C)(C)C2)cc1 ; Cl ; Cl] |
| B35 | 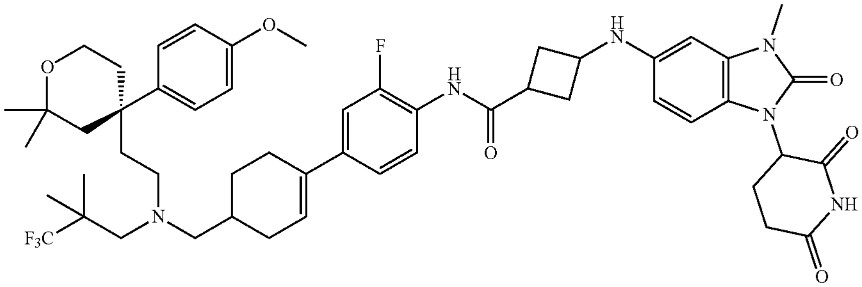 [SMILES: COc1ccc([C@]2(CCN(CC3CC=C(c4ccc(NC(=O)C5CC(Nc6ccc7c(c6)n(C)c(=O)n7C6CCC(=O)NC6=O)C5)c(F)c4)CC3)CC(C)(C)C(F)(F)F)CCOC(C)(C)C2)cc1] |
| BF1 | 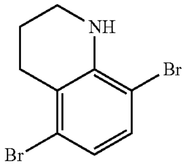 [SMILES: Brc1ccc(Br)c2c1CCCN2] |
| BF2 | 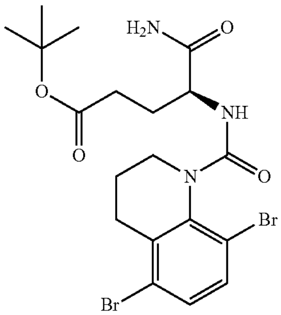 [SMILES: CC(C)(C)OC(=O)CC[C@H](NC(=O)N1CCCc2c(Br)ccc(Br)c21)C(N)=O] |
| BF3 | 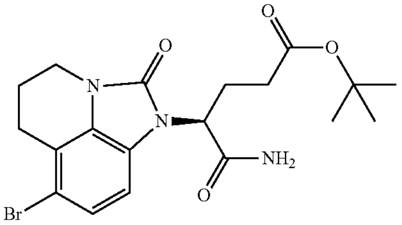 [SMILES: CC(C)(C)OC(=O)CC[C@@H](C(N)=O)n1c(=O)n2c3c(c(Br)ccc31)CCC2] |
| BF4 | 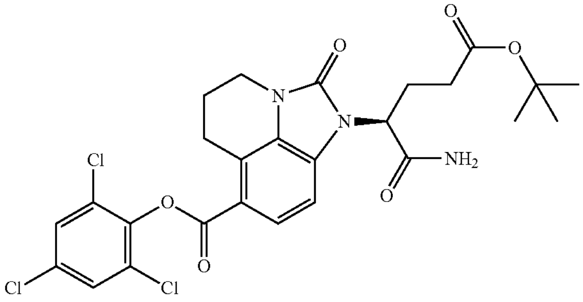 [SMILES: CC(C)(C)OC(=O)CC[C@@H](C(N)=O)n1c(=O)n2c3c(c(C(=O)Oc4c(Cl)cc(Cl)cc4Cl)ccc31)CCC2] |

TABLE 82-continued
| Ex | Structure |
|---|---|
| BF5 | 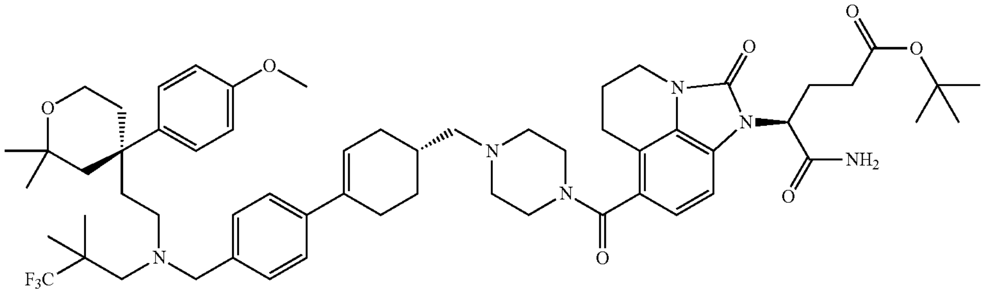 [SMILES: COc1ccc([C@]2(CCN(Cc3ccc(C4=CC[C@H](CN5CCN(C(=O)c6ccc7c8c6CCCn8c(=O)n7[C@@H](CCC(=O)OC(C)(C)C)C(N)=O)CC5)CC4)cc3)CC(C)(C)C(F)(F)F)CCOC(C)(C)C2)cc1] |
| BF6 | 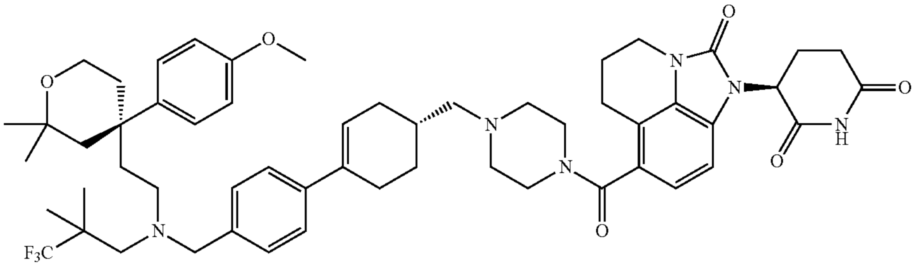 [SMILES: COc1ccc([C@]2(CCN(Cc3ccc(C4=CC[C@H](CN5CCN(C(=O)c6ccc7c8c6CCCn8c(=O)n7[C@H]6CCC(=O)NC6=O)CC5)CC4)cc3)CC(C)(C)C(F)(F)F)CCOC(C)(C)C2)cc1] |
| BG1 | 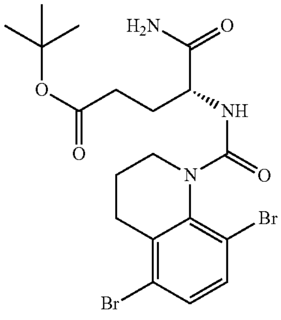 [SMILES: CC(C)(C)OC(=O)CC[C@@H](NC(=O)N1CCCc2c(Br)ccc(Br)c21)C(N)=O] |
| BG2 | 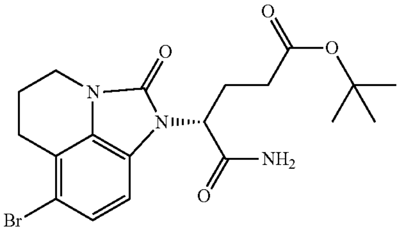 [SMILES: CC(C)(C)OC(=O)CC[C@H](C(N)=O)n1c(=O)n2c3c(c(Br)ccc31)CCC2] |
| BG3 | 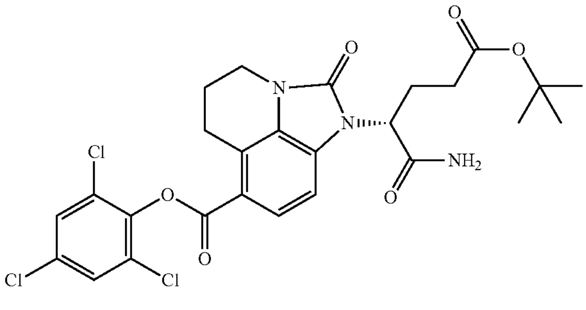 [SMILES: CC(C)(C)OC(=O)CC[C@H](C(N)=O)n1c(=O)n2c3c(c(C(=O)Oc4c(Cl)cc(Cl)cc4Cl)ccc31)CCC2] |

TABLE 82-continued
| Ex | Structure |
|---|---|
| BG4 | 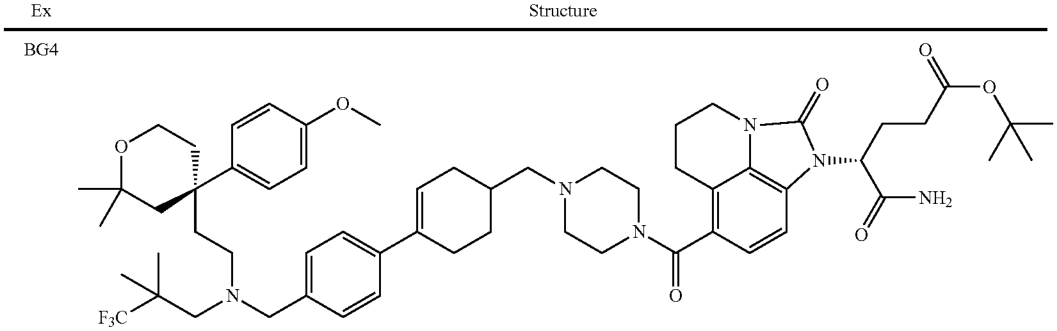 |
TABLE 83
| Ex | Structure |
|---|---|
| BG5 | 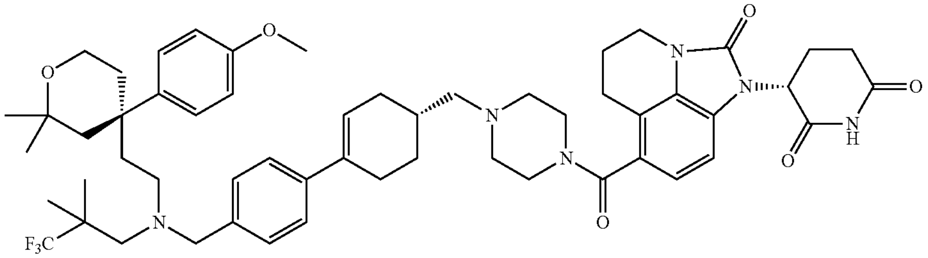 [SMILES: COc1ccc([C@]2(CCN(Cc3ccc(C4=CC[C@H](CN5CCN(C(=O)c6ccc7c8c6CCCn8c(=O)n7[C@@H]6CCC(=O)NC6=O)CC5)CC4)cc3)CC(C)(C)C(F)(F)F)CCOC(C)(C)C2)cc1] |
| BH1 | 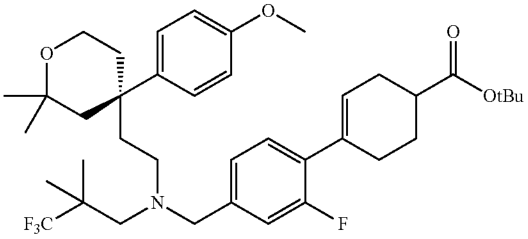 [SMILES: COc1ccc([C@]2(CCN(Cc3ccc(C4=CCC(C(=O)OC(C)(C)C)CC4)c(F)c3)CC(C)(C)C(F)(F)F)CCOC(C)(C)C2)cc1] |
| BH2 | 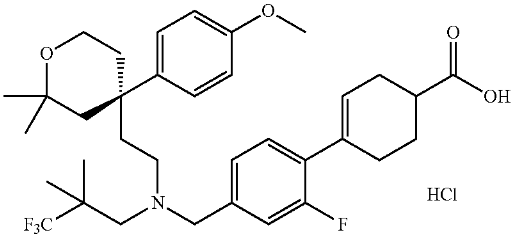 [SMILES: COc1ccc([C@]2(CCN(Cc3ccc(C4=CCC(C(=O)O)CC4)c(F)c3)CC(C)(C)C(F)(F)F)CCOC(C)(C)C2)cc1 ; Cl] |
| BH3 | 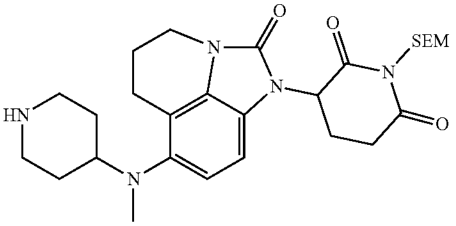 [SMILES: CN(c1ccc2c3c1CCCn3c(=O)n2C1CCC(=O)N(COCC[Si](C)(C)C)C1=O)C1CCNCC1] |

TABLE 83-continued
| Ex | Structure |
|---|---|
| BH4 | 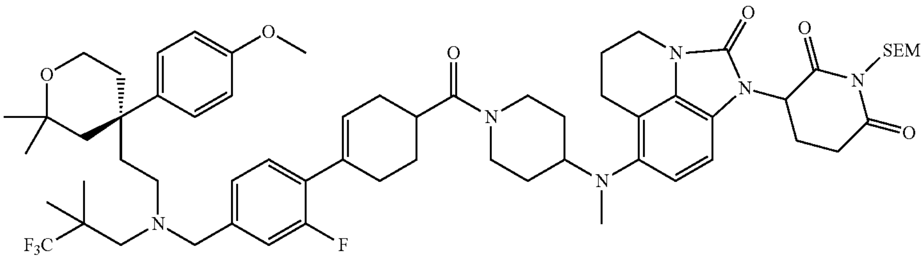 [SMILES: COc1ccc([C@]2(CCN(Cc3ccc(C4=CCC(C(=O)N5CCC(N(C)c6ccc7c8c6CCCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |
| BH5 | 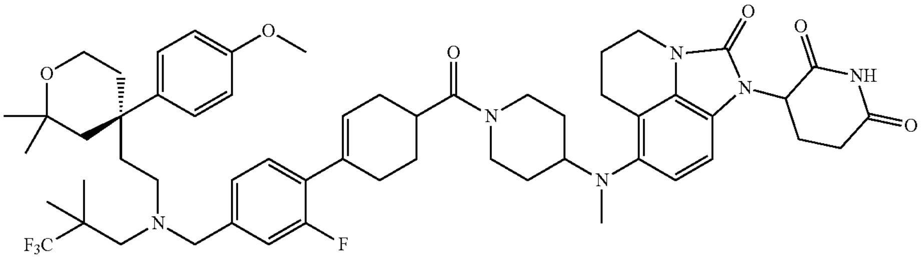 [SMILES: COc1ccc([C@]2(CCN(Cc3ccc(C4=CCC(C(=O)N5CCC(N(C)c6ccc7c8c6CCCn8c(=O)n7C6CCC(=O)NC6=O)CC5)CC4)c(F)c3)CC(C)(C)C(F)(F)F)CCOC(C)(C)C2)cc1] |
| BI1 | 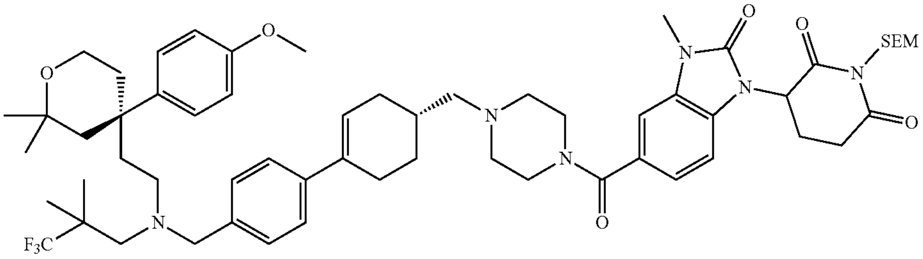 [SMILES: COc1ccc([C@]2(CCN(Cc3ccc(C4=CC[C@H](CN5CCN(C(=O)c6ccc7c(c6)n(C)c(=O)n7C6CCC(=O)N(COCC[Si](C)(C)C)C6=O)CC5)CC4)cc3)CC(C)(C)C(F)(F)F)CCOC(C)(C)C2)cc1] |
| BI2 | 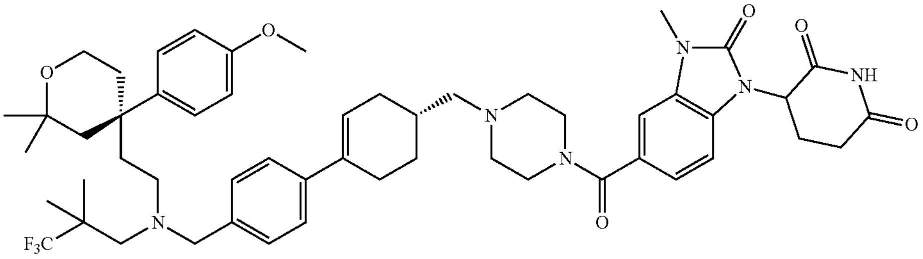 [SMILES: COc1ccc([C@]2(CCN(Cc3ccc(C4=CC[C@H](CN5CCN(C(=O)c6ccc7c(c6)n(C)c(=O)n7C6CCC(=O)NC6=O)CC5)CC4)cc3)CC(C)(C)C(F)(F)F)CCOC(C)(C)C2)cc1] |
| BJ1 | 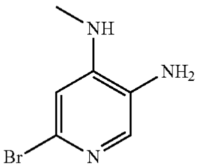 |
| BJ2 | 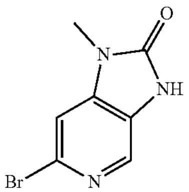 |

TABLE 83-continued
| Ex | Structure |
|---|---|
| BJ3 | 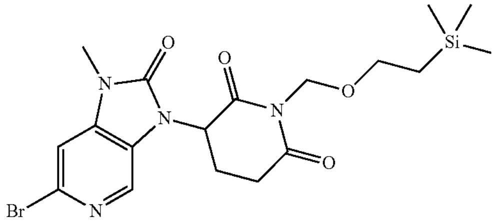 [SMILES: Cn1c(=O)n(C2CCC(=O)N(COCC[Si](C)(C)C)C2=O)c2cnc(Br)cc21] |
| BJ4 | 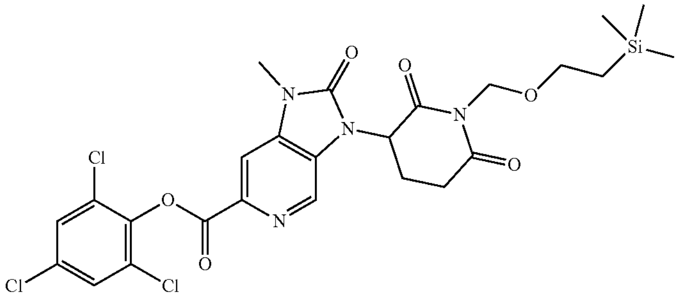 [SMILES: Cn1c(=O)n(C2CCC(=O)N(COCC[Si](C)(C)C)C2=O)c2cnc(C(=O)Oc3c(Cl)cc(Cl)cc3Cl)cc21] |
| BJ5 | 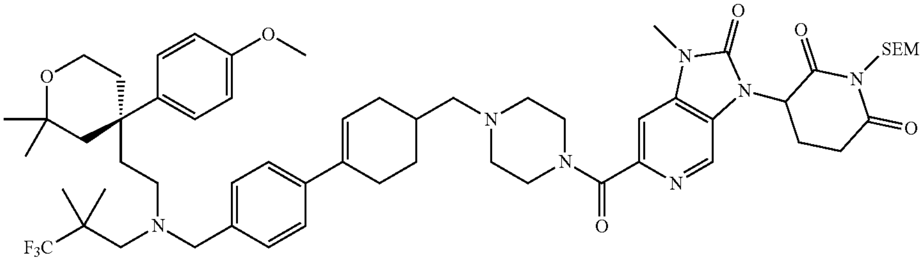 [SMILES: COc1ccc([C@]2(CCN(Cc3ccc(C4=CCC(CN5CCN(C(=O)c6cc7c(cn6)n(C6CCC(=O)N(COCC[Si](C)(C)C)C6=O)c(=O)n7C)CC5)CC4)cc3)CC(C)(C)C(F)(F)F)CCOC(C)(C)C2)cc1] |
| BJ6 | 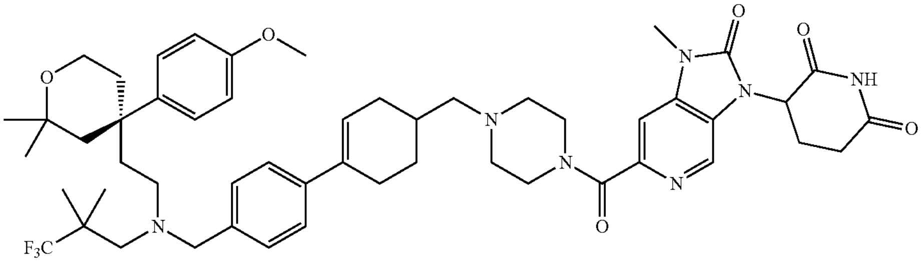 [SMILES: COc1ccc([C@]2(CCN(Cc3ccc(C4=CCC(CN5CCN(C(=O)c6cc7c(cn6)n(C6CCC(=O)NC6=O)c(=O)n7C)CC5)CC4)cc3)CC(C)(C)C(F)(F)F)CCOC(C)(C)C2)cc1] |
TABLE 84
| Ex | Structure |
|---|---|
| BK1 | 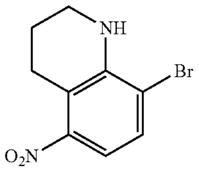 [SMILES: O=[N+]([O-])c1ccc(Br)c2c1CCCN2] |

TABLE 84-continued
| Ex | Structure |
|---|---|
| BK2 | 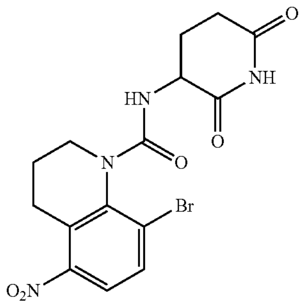 [SMILES: O=C1CCC(NC(=O)N2CCCc3c([N+](=O)[O-])ccc(Br)c32)C(=O)N1] |
| BK3 | 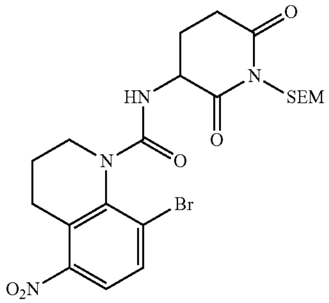 [SMILES: C[Si](C)(C)CCOCN1C(=O)CCC(NC(=O)N2CCCc3c([N+](=O)[O-])ccc(Br)c32)C1=O] |
| BK4 | 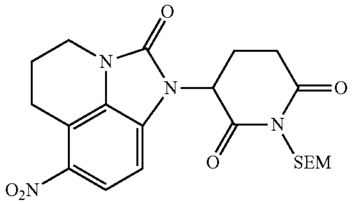 [SMILES: C[Si](C)(C)CCOCN1C(=O)CCC(n2c(=O)n3c4c(c(N)ccc42)CCC3)C1=O] |
| BK5 | 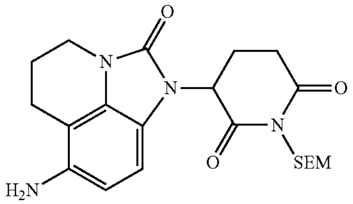 |
| BK6 | 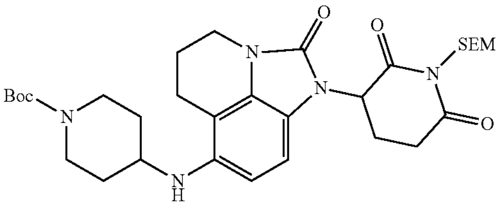 [SMILES: CC(C)(C)OC(=O)N1CCC(Nc2ccc3c4c2CCCn4c(=O)n3C2CCC(=O)N(COCC[Si](C)(C)C)C2=O)CC1] |
| BK7 | 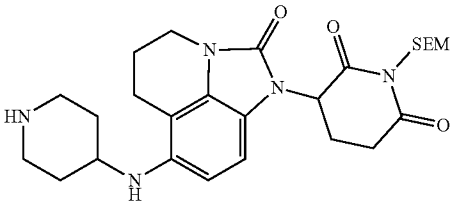 [SMILES: C[Si](C)(C)CCOCN1C(=O)CCC(n2c(=O)n3c4c(c(NC5CCNCC5)ccc42)CCC3)C1=O] |

TABLE 84-continued
| Ex | Structure |
| --- | --- |
| BK8 | 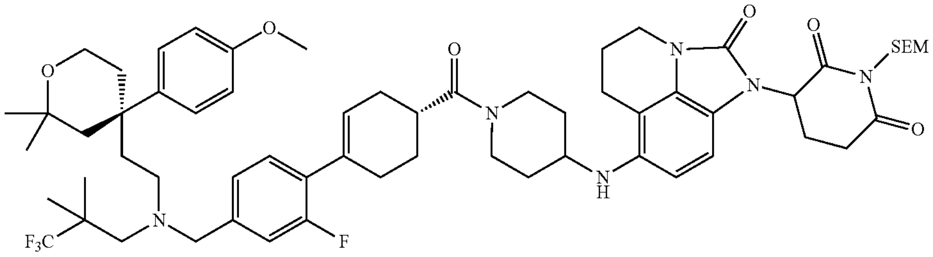 [SMILES: COc1ccc([C@]2(CCN(Cc3ccc(C4=CC[C@H](C(=O)N5CCC(Nc6ccc7c8c6CCCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |
| BK9 | 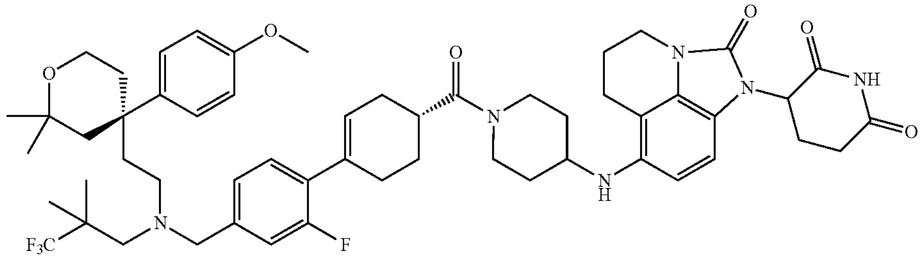 [SMILES: COc1ccc([C@]2(CCN(Cc3ccc(C4=CC[C@H](C(=O)N5CCC(Nc6ccc7c8c6CCCn8c(=O)n7C6CCC(=O)NC6=O)CC5)CC4)c(F)c3)CC(C)(C)C(F)(F)F)CCOC(C)(C)C2)cc1] |
| BL1 | 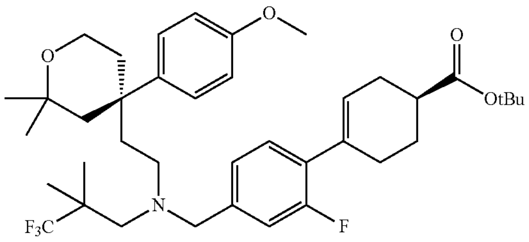 [SMILES: COc1ccc([C@]2(CCN(Cc3ccc(C4=CC[C@@H](C(=O)OC(C)(C)C)CC4)c(F)c3)CC(C)(C)C(F)(F)F)CCOC(C)(C)C2)cc1] |
| BL2 | 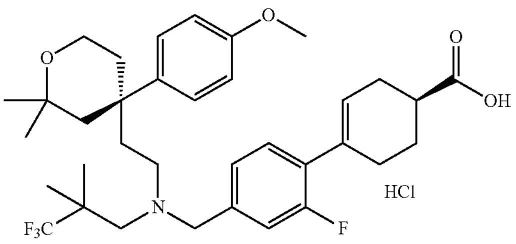 [SMILES: COc1ccc([C@]2(CCN(Cc3ccc(C4=CC[C@@H](C(=O)O)CC4)c(F)c3)CC(C)(C)C(F)(F)F)CCOC(C)(C)C2)cc1 ; Cl] |
| BL3 | 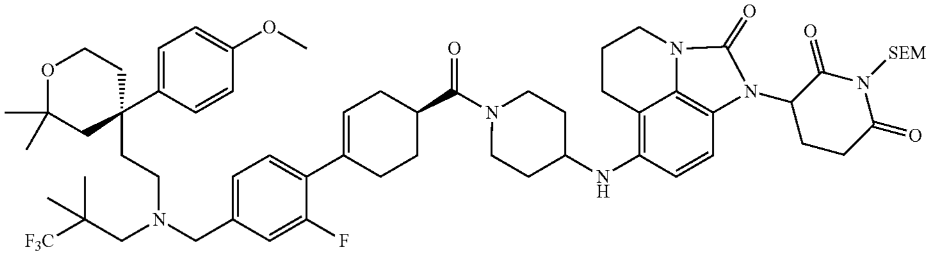 [SMILES: COc1ccc([C@]2(CCN(Cc3ccc(C4=CC[C@@H](C(=O)N5CCC(Nc6ccc7c8c6CCCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |

TABLE 85
| Ex | Structure |
|---|---|
| BL4 | 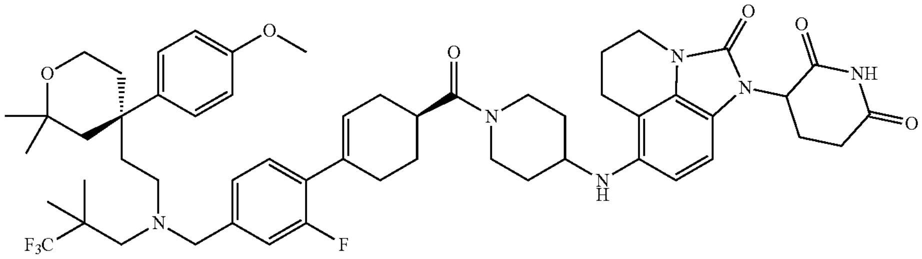 [SMILES: COc1ccc([C@]2(CCN(Cc3ccc(C4=CC[C@@H](C(=O)N5CCC(Nc6ccc7c8c6CCCn8c(=O)n7C6CCC(=O)NC6=O)CC5)CC4)c(F)c3)CC(C)(C)C(F)(F)F)CCOC(C)(C)C2)cc1] |
| BM1 | 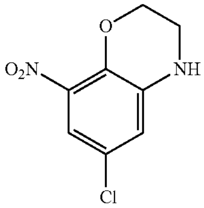 [SMILES: O=[N+]([O-])c1cc(Cl)cc2c1OCCN2] |
| BM2 | 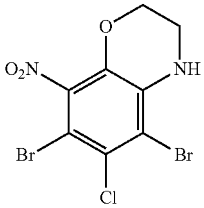 [SMILES: O=[N+]([O-])c1c(Br)c(Cl)c(Br)c2c1OCCN2] |
| BM3 | 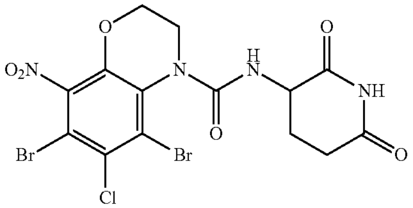 [SMILES: O=C1CCC(NC(=O)N2CCOc3c2c(Br)c(Cl)c(Br)c3[N+](=O)[O-])C(=O)N1] |
| BM4 | 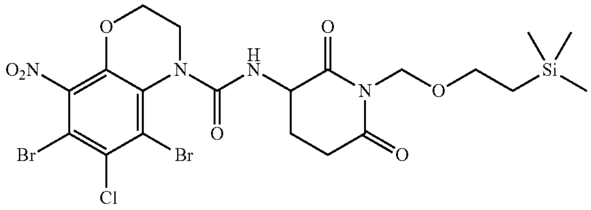 [SMILES: C[Si](C)(C)CCOCN1C(=O)CCC(NC(=O)N2CCOc3c2c(Br)c(Cl)c(Br)c3[N+](=O)[O-])C1=O] |
| BM5 | 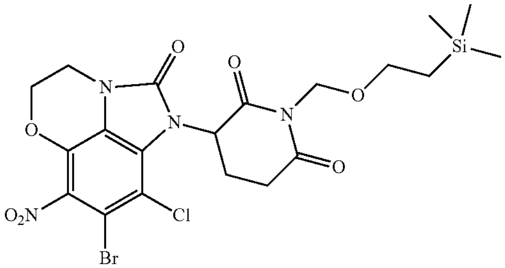 [SMILES: C[Si](C)(C)CCOCN1C(=O)CCC(n2c(=O)n3c4c(c([N+](=O)[O-])c(Br)c(Cl)c42)OCC3)C1=O] |

TABLE 85-continued
| Ex | Structure |
|---|---|
| BM6 | 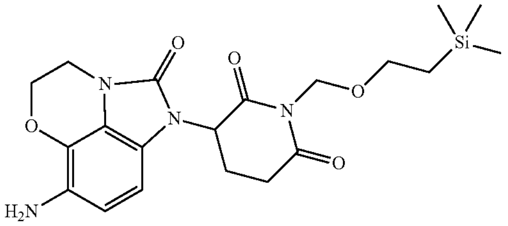 [SMILES: C[Si](C)(C)CCOCN1C(=O)CCC(n2c(=O)n3c4c(c(N)ccc42)OCC3)C1=O] |
| BM7 | 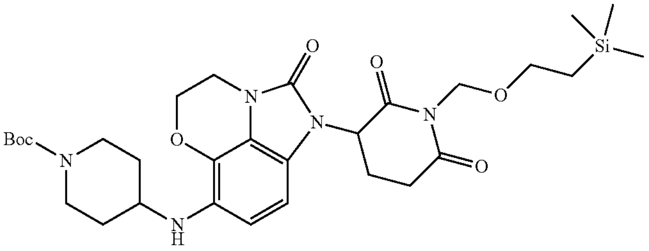 [SMILES: CC(C)(C)OC(=O)N1CCC(Nc2ccc3c4c2OCCn4c(=O)n3C2CCC(=O)N(COCC[Si](C)(C)C)C2=O)CC1] |
| BM8 | 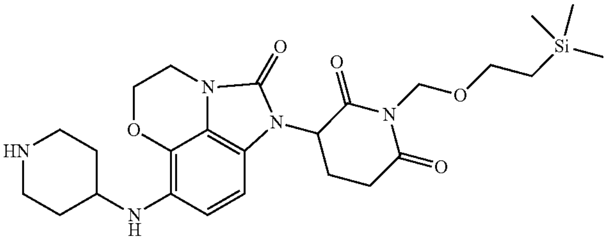 [SMILES: C[Si](C)(C)CCOCN1C(=O)CCC(n2c(=O)n3c4c(c(NC5CCNCC5)ccc42)OCC3)C1=O] |
| BM9 | 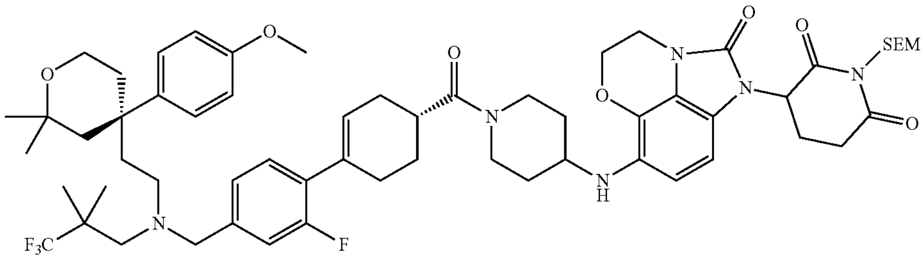 [SMILES: COc1ccc([C@]2(CCN(Cc3ccc(C4=CC[C@H](C(=O)N5CCC(Nc6ccc7c8c6OCCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |
| BM10 | 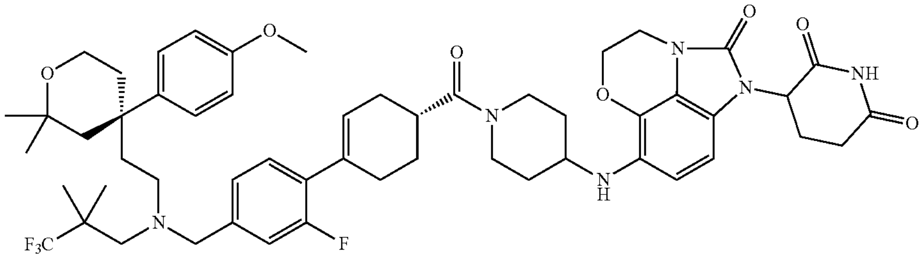 [SMILES: COc1ccc([C@]2(CCN(Cc3ccc(C4=CC[C@H](C(=O)N5CCC(Nc6ccc7c8c6OCCn8c(=O)n7C6CCC(=O)NC6=O)CC5)CC4)c(F)c3)CC(C)(C)C(F)(F)F)CCOC(C)(C)C2)cc1] |
| BN1 | 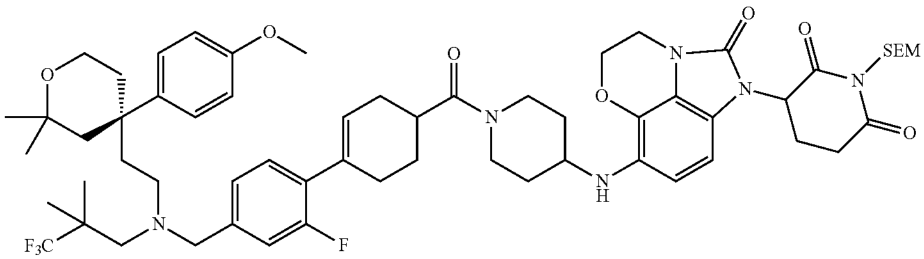 [SMILES: COc1ccc([C@]2(CCN(Cc3ccc(C4=CCC(C(=O)N5CCC(Nc6ccc7c8c6OCCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |

TABLE 85-continued
| Ex | Structure |
|---|---|
| BN2 | 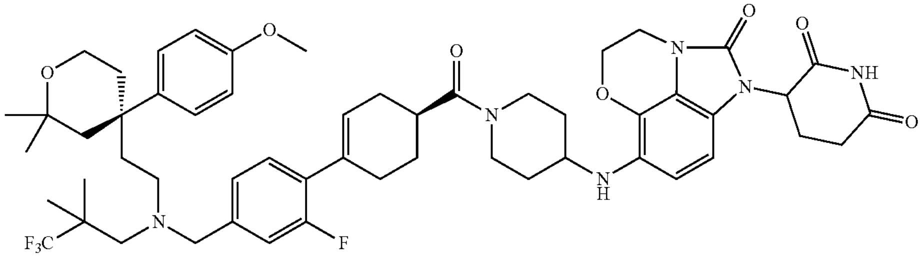 [SMILES: COc1ccc([C@]2(CCN(Cc3ccc(C4=CC[C@@H](C(=O)N5CCC(Nc6ccc7c8c6OCCn8c(=O)n7C6CCC(=O)NC6=O)CC5)CC4)c(F)c3)CC(C)(C)C(F)(F)F)CCOC(C)(C)C2)cc1] |
| BO1 | 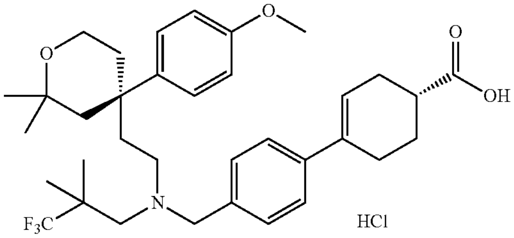 [SMILES: COc1ccc([C@]2(CCN(Cc3ccc(C4=CC[C@H](C(=O)O)CC4)cc3)CC(C)(C)C(F)(F)F)CCOC(C)(C)C2)cc1 ; Cl] HCl |
TABLE 86
| Ex | Structure |
|---|---|
| BO2 | 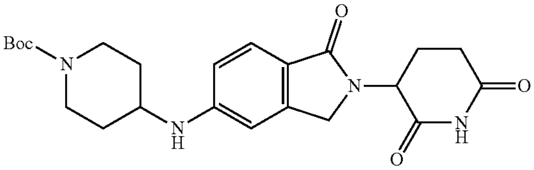 [SMILES: CC(C)(C)OC(=O)N1CCC(Nc2ccc3c(c2)CN(C2CCC(=O)NC2=O)C3=O)CC1] |
| BO3 | 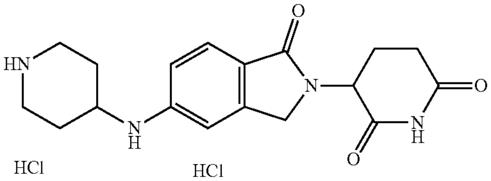 [SMILES: O=C1CCC(N2Cc3cc(NC4CCNCC4)ccc3C2=O)C(=O)N1 ; Cl ; Cl] HCl HCl |
| BO4 | 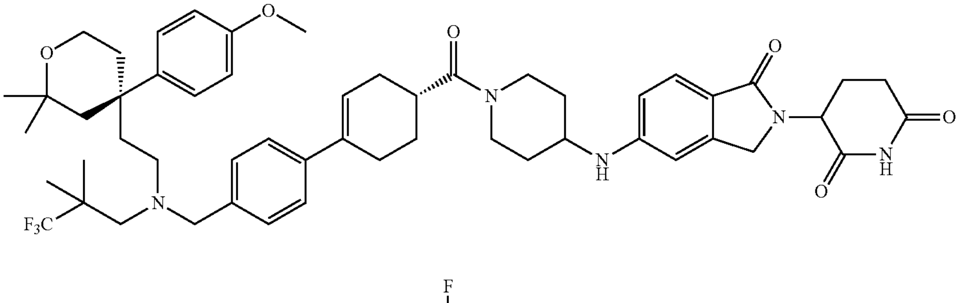 |
| BP1 | 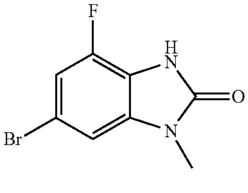 |

TABLE 86-continued
| Ex | Structure |
|---|---|
| BP2 | 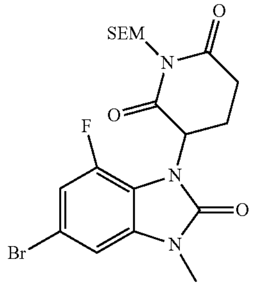 [SMILES: Cn1c(=O)n(C2CCC(=O)N(COCC[Si](C)(C)C)C2=O)c2c(F)cc(Br)cc21] |
| BP3 | 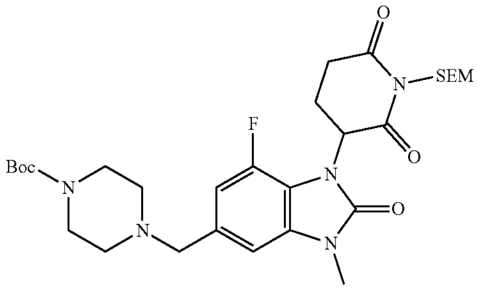 [SMILES: Cn1c(=O)n(C2CCC(=O)N(COCC[Si](C)(C)C)C2=O)c2c(F)cc(CN3CCN(C(=O)OC(C)(C)C)CC3)cc21] |
| BP4 | 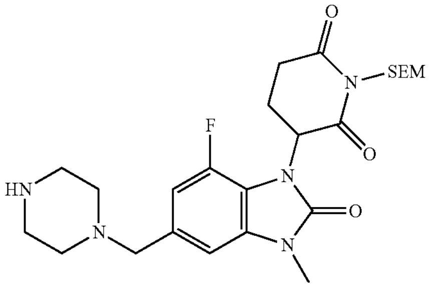 [SMILES: Cn1c(=O)n(C2CCC(=O)N(COCC[Si](C)(C)C)C2=O)c2c(F)cc(CN3CCNCC3)cc21] |
| BP5 | 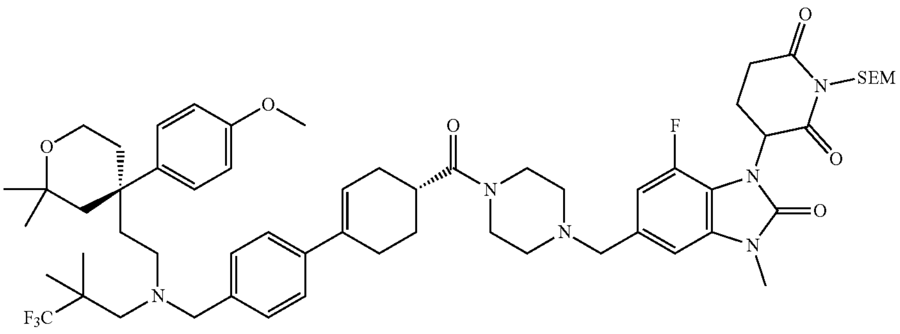 [SMILES: COc1ccc([C@]2(CCN(Cc3ccc(C4=CC[C@H](C(=O)N5CCN(Cc6cc(F)c7c(c6)n(C)c(=O)n7C6CCC(=O)N(COCC[Si](C)(C)C)C6=O)CC5)CC4)cc3)CC(C)(C)C(F)(F)F)CCOC(C)(C)C2)cc1] |
| BP6 | 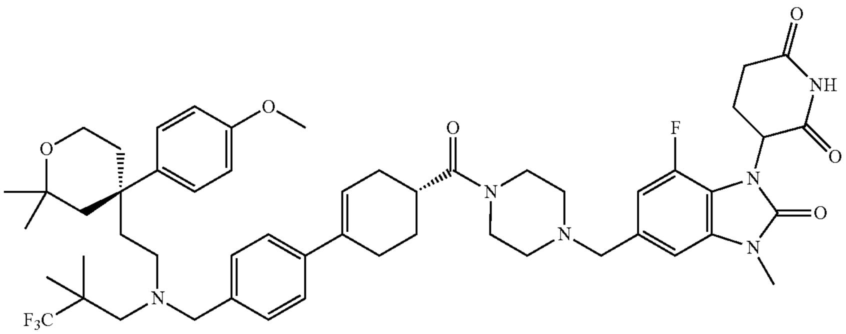 [SMILES: COc1ccc([C@]2(CCN(Cc3ccc(C4=CC[C@H](C(=O)N5CCN(Cc6cc(F)c7c(c6)n(C)c(=O)n7C6CCC(=O)NC6=O)CC5)CC4)cc3)CC(C)(C)C(F)(F)F)CCOC(C)(C)C2)cc1] |

TABLE 86-continued
| Ex | Structure |
|---|---|
| BQ1 | 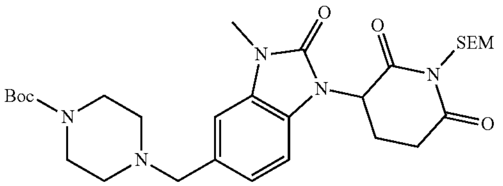 [SMILES: Cn1c(=O)n(C2CCC(=O)N(COCC[Si](C)(C)C)C2=O)c2ccc(CN3CCN(C(=O)OC(C)(C)C)CC3)cc21] |
| BQ2 | 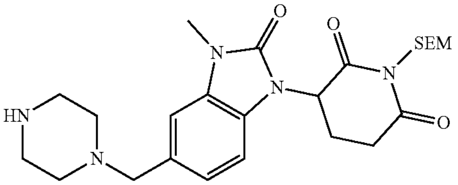 [SMILES: Cn1c(=O)n(C2CCC(=O)N(COCC[Si](C)(C)C)C2=O)c2ccc(CN3CCNCC3)cc21] |
| BQ3 | 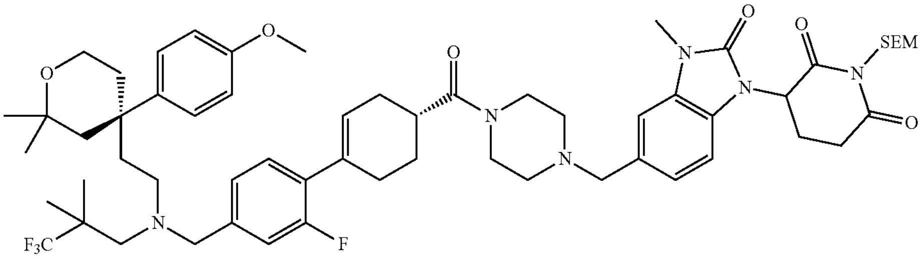 [SMILES: COc1ccc([C@]2(CCN(Cc3ccc(C4=CC[C@H](C(=O)N5CCN(Cc6ccc7c(c6)n(C)c(=O)n7C6CCC(=O)N(COCC[Si](C)(C)C)C6=O)CC5)CC4)c(F)c3)CC(C)(C)C(F)(F)F)CCOC(C)(C)C2)cc1] |
| BQ4 | 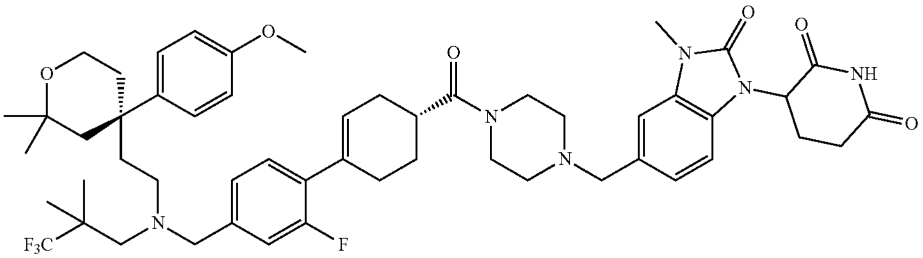 [SMILES: COc1ccc([C@]2(CCN(Cc3ccc(C4=CC[C@H](C(=O)N5CCN(Cc6ccc7c(c6)n(C)c(=O)n7C6CCC(=O)NC6=O)CC5)CC4)c(F)c3)CC(C)(C)C(F)(F)F)CCOC(C)(C)C2)cc1] |
| BR1 | 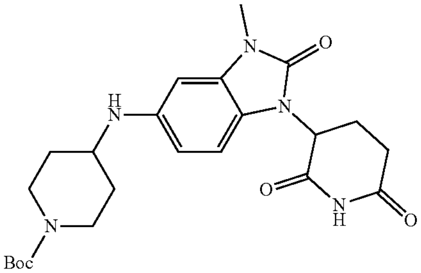 [SMILES: Cn1c(=O)n(C2CCC(=O)NC2=O)c2ccc(NC3CCN(C(=O)OC(C)(C)C)CC3)cc21] |
TABLE 87
| Ex | Structure |
|---|---|
| BR2 | 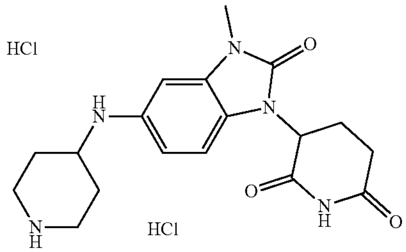 [SMILES: Cl ; Cn1c(=O)n(C2CCC(=O)NC2=O)c2ccc(NC3CCNCC3)cc21 ; Cl] |

TABLE 87-continued
| Ex | Structure |
|---|---|
| BR3 | 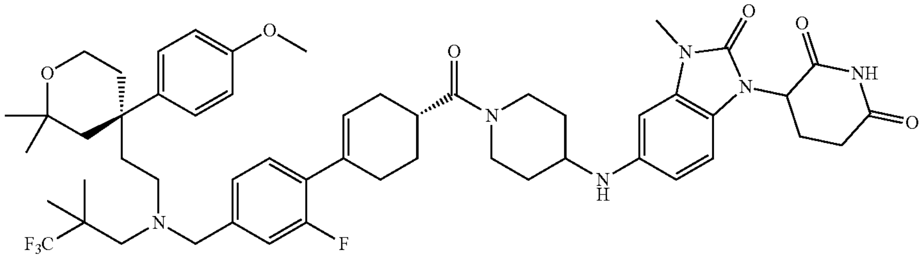 [SMILES: COc1ccc([C@]2(CCN(Cc3ccc(C4=CC[C@H](C(=O)N5CCC(Nc6ccc7c(c6)n(C)c(=O)n7C6CCC(=O)NC6=O)CC5)CC4)c(F)c3)CC(C)(C)C(F)(F)F)CCOC(C)(C)C2)cc1] |
| BS1 | 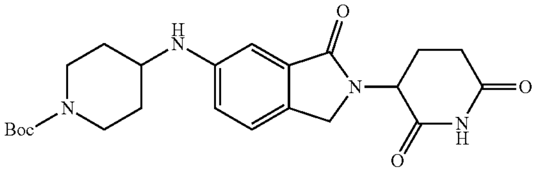 [SMILES: CC(C)(C)OC(=O)N1CCC(Nc2ccc3c(c2)C(=O)N(C2CCC(=O)NC2=O)C3)CC1] |
| BS2 | 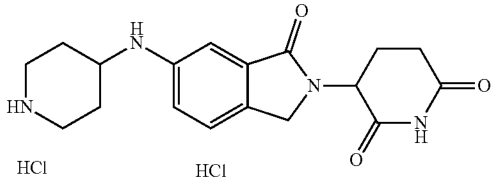 [SMILES: O=C1CCC(N2Cc3ccc(NC4CCNCC4)cc3C2=O)C(=O)N1 ; Cl ; Cl] HCl HCl |
| BS3 | 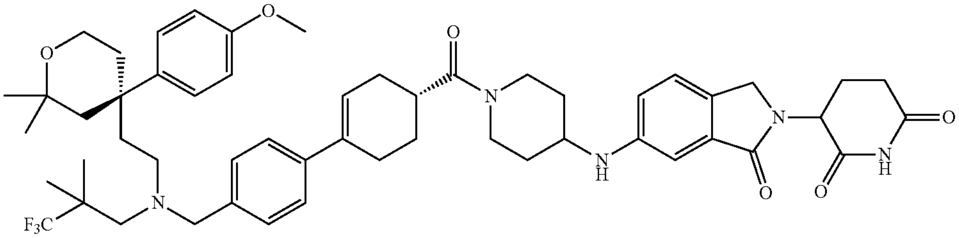 [SMILES: COc1ccc([C@]2(CCN(Cc3ccc(C4=CC[C@H](C(=O)N5CCC(Nc6ccc7c(c6)C(=O)N(C6CCC(=O)NC6=O)C7)CC5)CC4)cc3)CC(C)(C)C(F)(F)F)CCOC(C)(C)C2)cc1] |
| BT1 | 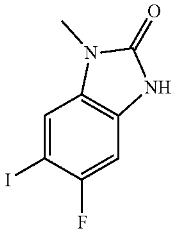 |
| BT2 | 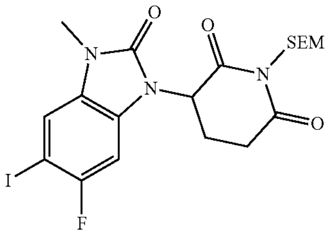 [SMILES: Cn1c(=O)n(C2CCC(=O)N(COCC[Si](C)(C)C)C2=O)c2cc(F)c(I)cc21] |

TABLE 87-continued
| Ex | Structure |
| --- | --- |
| BT3 | 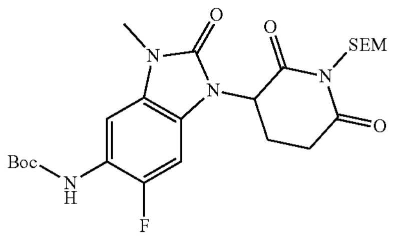 [SMILES: Cn1c(=O)n(C2CCC(=O)N(COCC[Si](C)(C)C)C2=O)c2cc(F)c(NC(=O)OC(C)(C)C)cc21] |
| BT4 | 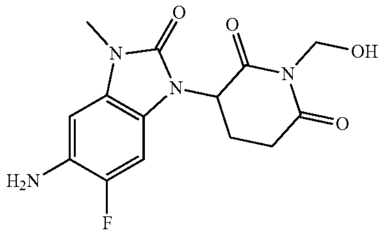 [SMILES: Cn1c(=O)n(C2CCC(=O)N(CO)C2=O)c2cc(F)c(N)cc21] |
| BT5 | 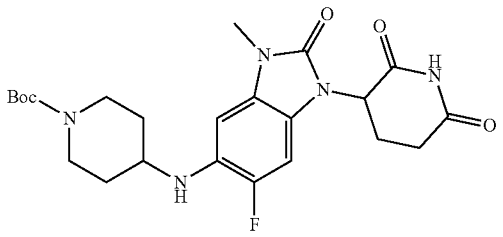 [SMILES: Cn1c(=O)n(C2CCC(=O)NC2=O)c2cc(F)c(NC3CCN(C(=O)OC(C)(C)C)CC3)cc21] |
| BT6 | 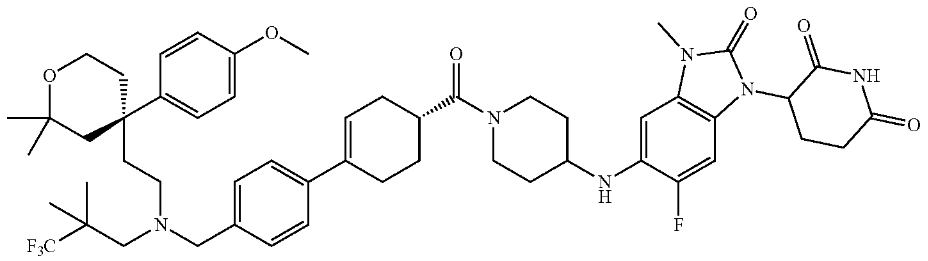 [SMILES: COc1ccc([C@]2(CCN(Cc3ccc(C4=CC[C@H](C(=O)N5CCC(Nc6cc7c(cc6F)n(C6CCC(=O)NC6=O)c(=O)n7C)CC5)CC4)cc3)CC(C)(C)C(F)(F)F)CCOC(C)(C)C2)cc1] |
| BU1 | 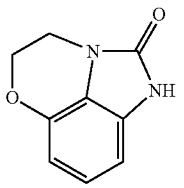 [SMILES: O=c1[nH]c2cccc3c2n1CCO3] |
TABLE 88
| Ex | Structure |
| --- | --- |
| BU2 | 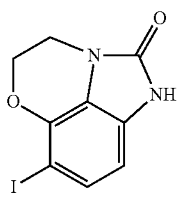 [SMILES: O=c1[nH]c2ccc(I)c3c2n1CCO3] |

TABLE 88-continued
| Ex | Structure |
| --- | --- |
| BU3 | 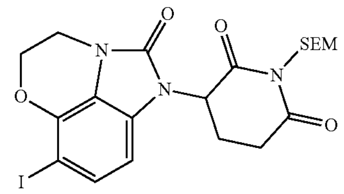 [SMILES: C[Si](C)(C)CCOCN1C(=O)CCC(n2c(=O)n3c4c(c(I)ccc42)OCC3)C1=O] |
| BU4 | 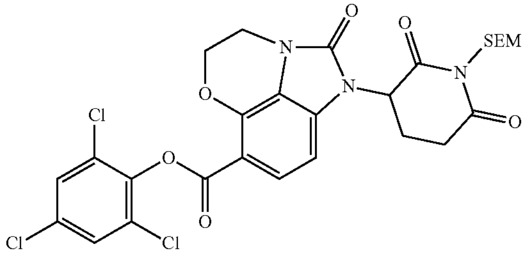 [SMILES: C[Si](C)(C)CCOCN1C(=O)CCC(n2c(=O)n3c4c(c(C(=O)Oc5c(Cl)cc(Cl)cc5Cl)ccc42)OCC3)C1=O] |
| BU5 | 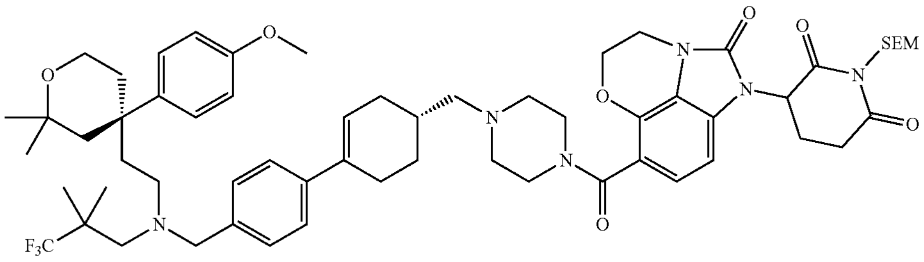 [SMILES: COc1ccc([C@]2(CCN(Cc3ccc(C4=CC[C@H](CN5CCN(C(=O)c6ccc7c8c6OCCn8c(=O)n7C6CCC(=O)N(COCC[Si](C)(C)C)C6=O)CC5)CC4)cc3)CC(C)(C)C(F)(F)F)CCOC(C)(C)C2)cc1] |
| BU6 | 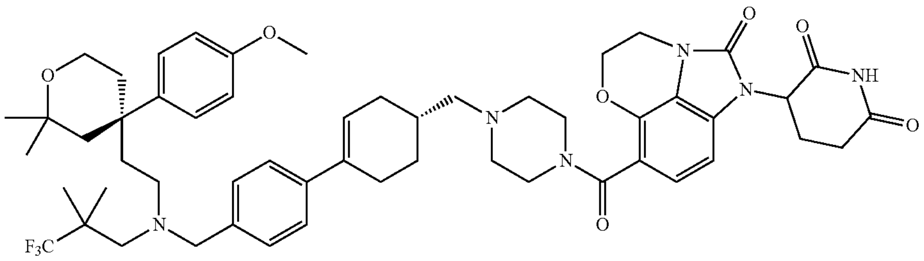 [SMILES: COc1ccc([C@]2(CCN(Cc3ccc(C4=CC[C@H](CN5CCN(C(=O)c6ccc7c8c6OCCn8c(=O)n7C6CCC(=O)NC6=O)CC5)CC4)cc3)CC(C)(C)C(F)(F)F)CCOC(C)(C)C2)cc1] |
| BV1 | 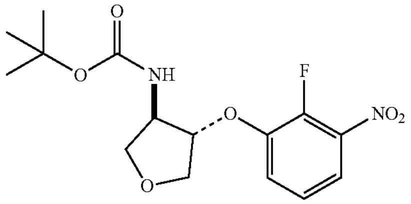 |
| BV2 | 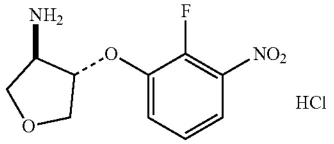 |
| BV3 | 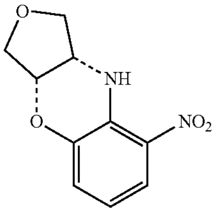 |

TABLE 88-continued
| Ex | Structure |
| --- | --- |
| BV4 | 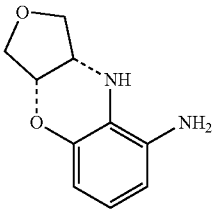 |
| BV5 | 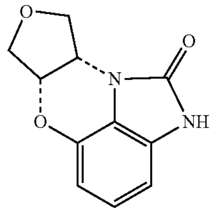 |
| BV6 | 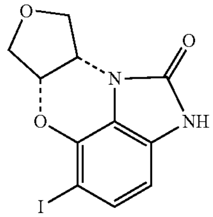 |
| BV7 | 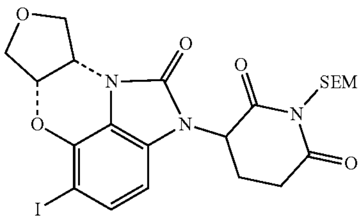 |
| BV8 | 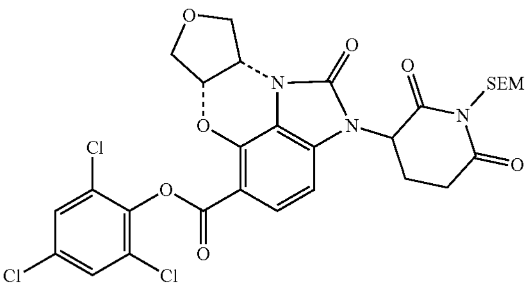 |
| BV9 | 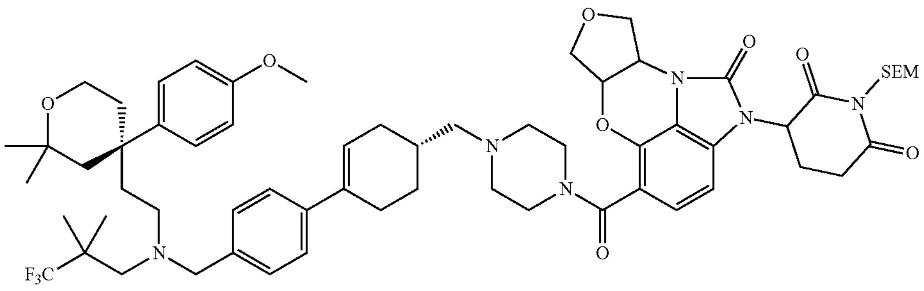 [SMILES: COc1ccc([C@]2(CCN(Cc3ccc(C4=CC[C@H](CN5CCN(C(=O)c6ccc7c8c6OC6COCC6n8c(=O)n7C6CCC(=O)N(COCC[Si](C)(C)C)C6=O)CC5)CC4)cc3)CC(C)(C)C(F)(F)F)CCOC(C)(C)C2)cc1] |

TABLE 89
| Ex | Structure |
|---|---|
| BV10 | 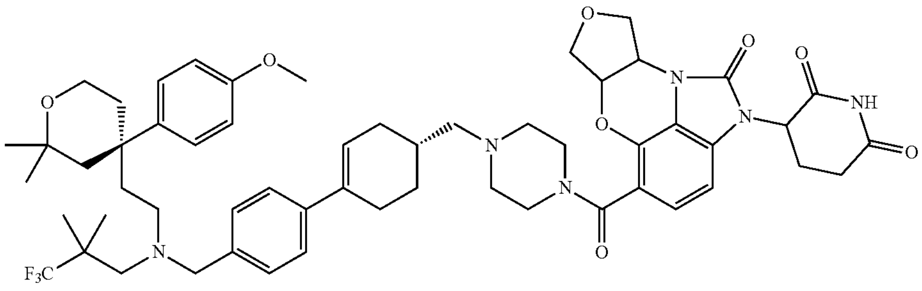 [SMILES: COc1ccc([C@]2(CCN(Cc3ccc(C4=CC[C@H](CN5CCN(C(=O)c6ccc7c8c6OC6COCC6n8c(=O)n7C6CCC(=O)NC6=O)CC5)CC4)cc3)CC(C)(C)C(F)(F)F)CCOC(C)(C)C2)cc1] |
| BW1 | 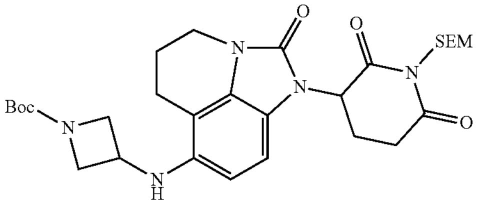 [SMILES: CC(C)(C)OC(=O)N1CC(Nc2ccc3c4c2CCCn4c(=O)n3C2CCC(=O)N(COCC[Si](C)(C)C)C2=O)C1] |
| BW2 | 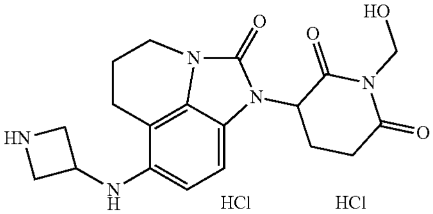 [SMILES: O=C1CCC(n2c(=O)n3c4c(c(NC5CNC5)ccc42)CCC3)C(=O)N1CO ; Cl ; Cl] HCl HCl |
| BW3 | 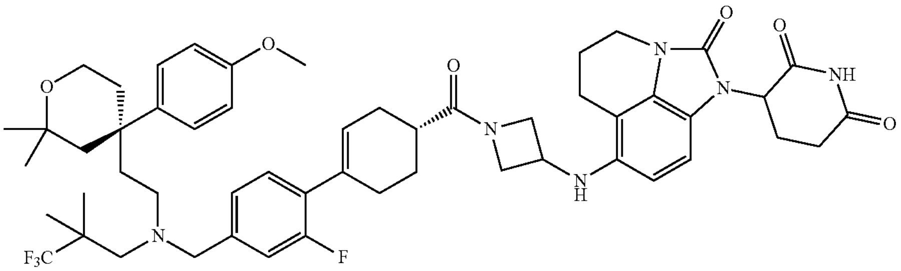 [SMILES: COc1ccc([C@]2(CCN(Cc3ccc(C4=CC[C@H](C(=O)N5CC(Nc6ccc7c8c6CCCn8c(=O)n7C6CCC(=O)NC6=O)C5)CC4)c(F)c3)CC(C)(C)C(F)(F)F)CCOC(C)(C)C2)cc1] |
| BX1 | 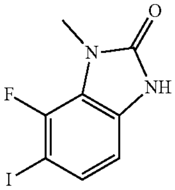 |
| BX2 | 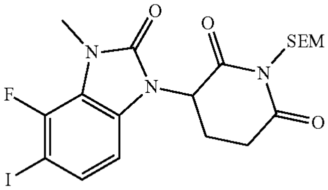 [SMILES: Cn1c(=O)n(C2CCC(=O)N(COCC[Si](C)(C)C)C2=O)c2ccc(I)c(F)c21] |

TABLE 89-continued
| Ex | Structure |
| --- | --- |
| BX3 | 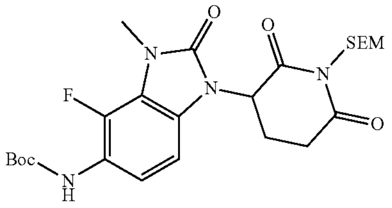 [SMILES: Cn1c(=O)n(C2CCC(=O)N(COCC[Si](C)(C)C)C2=O)c2ccc(NC(=O)OC(C)(C)C)c(F)c21] |
| BX4 | 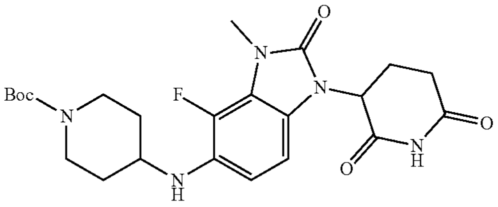 [SMILES: Cn1c(=O)n(C2CCC(=O)NC2=O)c2ccc(NC3CCN(C(=O)OC(C)(C)C)CC3)c(F)c21] |
| BX5 | 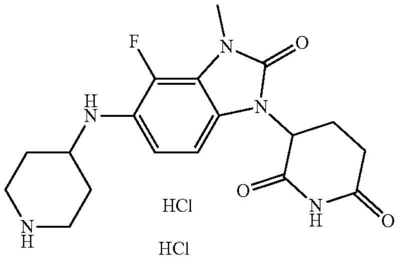 [SMILES: Cn1c(=O)n(C2CCC(=O)NC2=O)c2ccc(NC3CCNCC3)c(F)c21 ; Cl ; Cl] |
| BX6 | 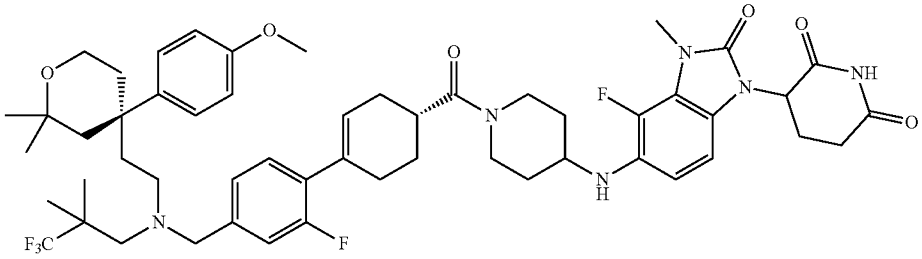 [SMILES: COc1ccc([C@]2(CCN(Cc3ccc(C4=CC[C@H](C(=O)N5CCC(Nc6ccc7c(c6F)n(C)c(=O)n7C6CCC(=O)NC6=O)CC5)CC4)c(F)c3)CC(C)(C)C(F)(F)F)CCOC(C)(C)C2)cc1] |
| BY1 | 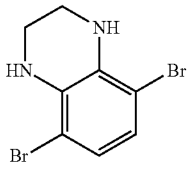 |
| BY2 | 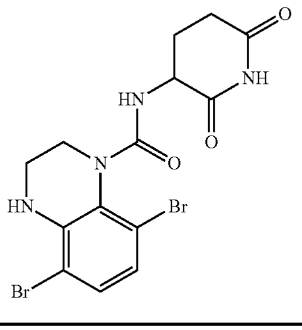 |

TABLE 90
| Ex | Structure |
|---|---|
| BY3 | 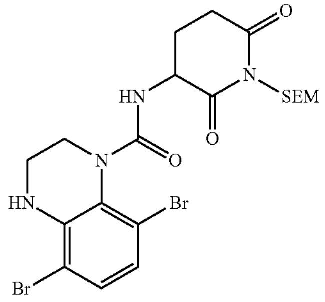 [SMILES: C[Si](C)(C)CCOCN1C(=O)CCC(NC(=O)N2CCNc3c(Br)ccc(Br)c32)C1=O] |
| BY4 | 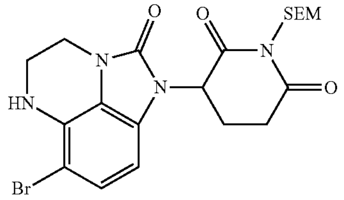 [SMILES: C[Si](C)(C)CCOCN1C(=O)CCC(n2c(=O)n3c4c(c(Br)ccc42)NCC3)C1=O] |
| BY5 | 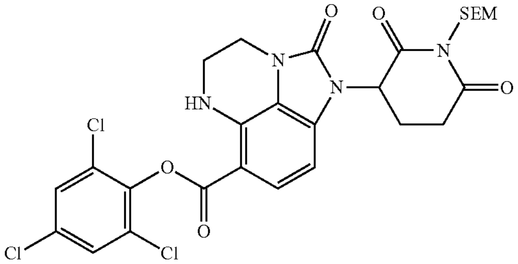 [SMILES: C[Si](C)(C)CCOCN1C(=O)CCC(n2c(=O)n3c4c(c(C(=O)Oc5c(Cl)cc(Cl)cc5Cl)ccc42)NCC3)C1=O] |
| BY6 | 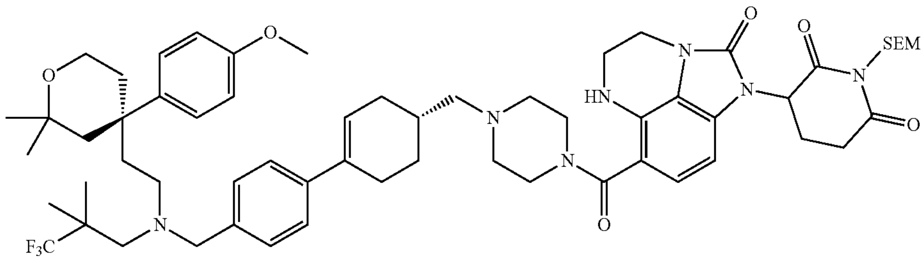 [SMILES: COc1ccc([C@]2(CCN(Cc3ccc(C4=CC[C@H](CN5CCN(C(=O)c6ccc7c8c6NCCn8c(=O)n7C6CCC(=O)N(COCC[Si](C)(C)C)C6=O)CC5)CC4)cc3)CC(C)(C)C(F)(F)F)CCOC(C)(C)C2)cc1] |
| BY7 | 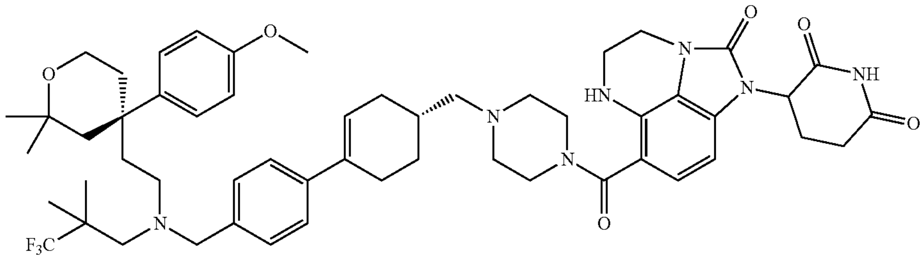 [SMILES: COc1ccc([C@]2(CCN(Cc3ccc(C4=CC[C@H](CN5CCN(C(=O)c6ccc7c8c6NCCn8c(=O)n7C6CCC(=O)NC6=O)CC5)CC4)cc3)CC(C)(C)C(F)(F)F)CCOC(C)(C)C2)cc1] |
| BZ1 | 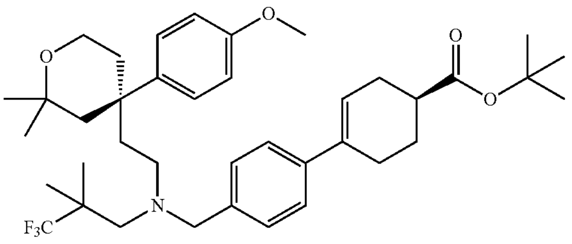 [SMILES: COc1ccc([C@]2(CCN(Cc3ccc(C4=CC[C@@H](C(=O)OC(C)(C)C)CC4)cc3)CC(C)(C)C(F)(F)F)CCOC(C)(C)C2)cc1] |

TABLE 90-continued
| Ex | Structure |
| --- | --- |
| BZ2 | 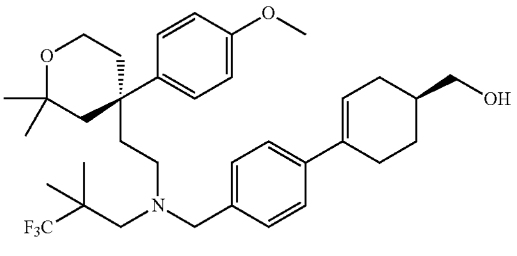 [SMILES: COc1ccc([C@]2(CCN(Cc3ccc(C4=CC[C@@H](CO)CC4)cc3)CC(C)(C)C(F)(F)F)CCOC(C)(C)C2)cc1] |
| BZ3 | 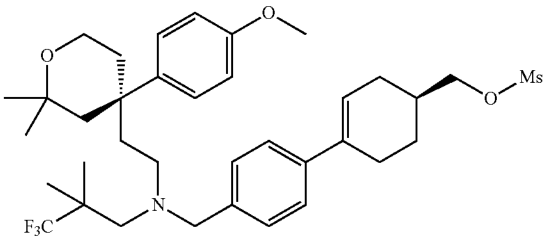 [SMILES: COc1ccc([C@]2(CCN(Cc3ccc(C4=CC[C@@H](COS(C)(=O)=O)CC4)cc3)CC(C)(C)C(F)(F)F)CCOC(C)(C)C2)cc1] |
| BZ4 | 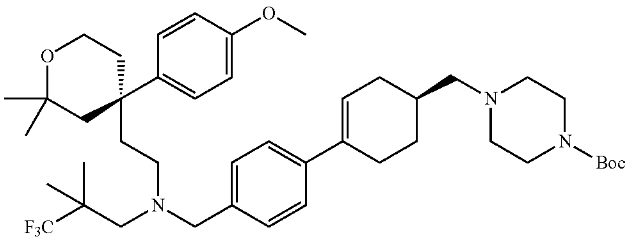 [SMILES: COc1ccc([C@]2(CCN(Cc3ccc(C4=CC[C@@H](CN5CCN(C(=O)OC(C)(C)C)CC5)CC4)cc3)CC(C)(C)C(F)(F)F)CCOC(C)(C)C2)cc1] |
| BZ5 | 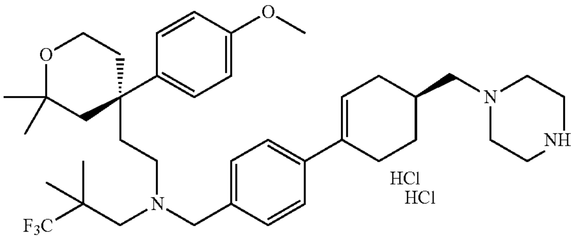 [SMILES: COc1ccc([C@]2(CCN(Cc3ccc(C4=CC[C@@H](CN5CCNCC5)CC4)cc3)CC(C)(C)C(F)(F)F)CCOC(C)(C)C2)cc1 ; Cl ; Cl] |
| BZ6 | 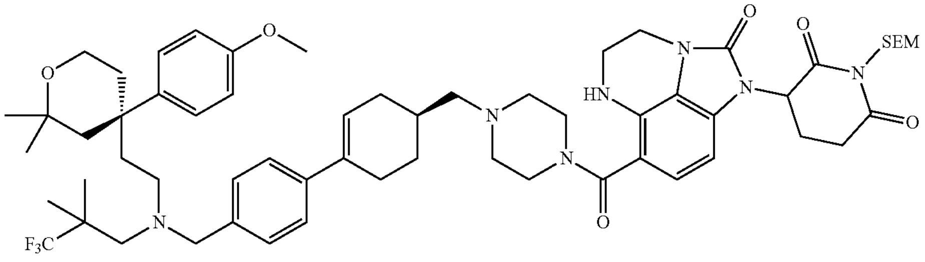 [SMILES: COc1ccc([C@]2(CCN(Cc3ccc(C4=CC[C@@H](CN5CCN(C(=O)c6ccc7c8c6NCCn8c(=O)n7C6CCC(=O)N(COCC[Si](C)(C)C)C6=O)CC5)CC4)cc3)CC(C)(C)C(F)(F)F)CCOC(C)(C)C2)cc1] |
| BZ7 | 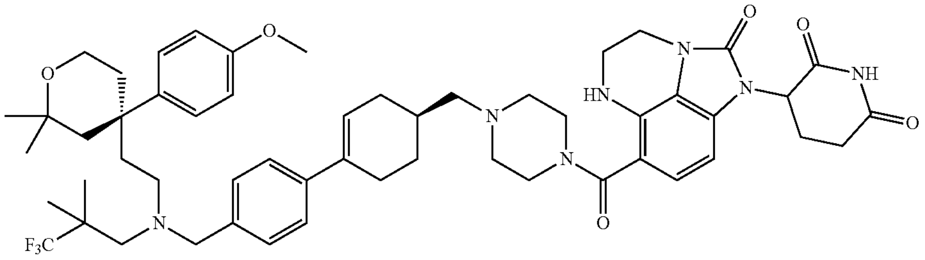 [SMILES: COc1ccc([C@]2(CCN(Cc3ccc(C4=CC[C@@H](CN5CCN(C(=O)c6ccc7c8c6NCCn8c(=O)n7C6CCC(=O)NC6=O)CC5)CC4)cc3)CC(C)(C)C(F)(F)F)CCOC(C)(C)C2)cc1] |

TABLE 91
| Ex | Structure |
|---|---|
| CA1 | 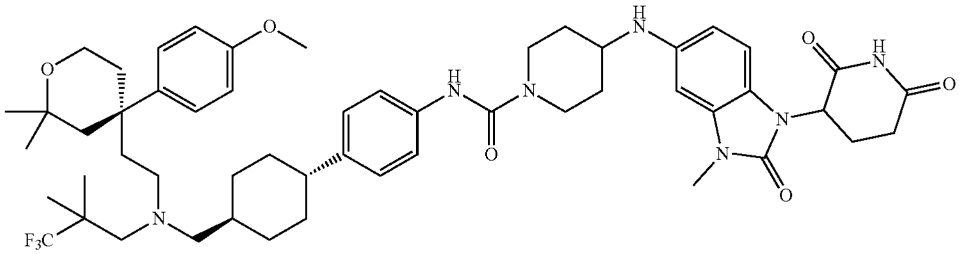 [SMILES: COc1ccc([C@]2(CCN(CC(C)(C)C(F)(F)F)C[C@H]3CC[C@H](c4ccc(NC(=O)N5CCC(Nc6ccc7c(c6)n(C)c(=O)n7C6CCC(=O)NC6=O)CC5)cc4)CC3)CCOC(C)(C)C2)cc1] |
| CB1 | 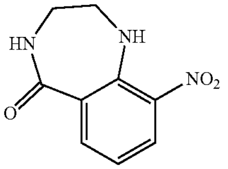 [SMILES: O=C1NCCNc2c1cccc2[N+](=O)[O-]] |
| CB2 | 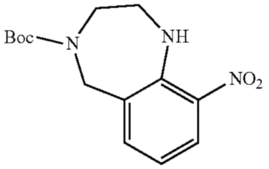 [SMILES: CC(C)(C)OC(=O)N1CCNc2c(cccc2[N+](=O)[O-])C1] |
| CB3 | 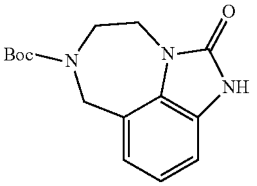 [SMILES: CC(C)(C)OC(=O)N1CCn2c(=O)[nH]c3cccc(c32)C1] |
| CB4 | 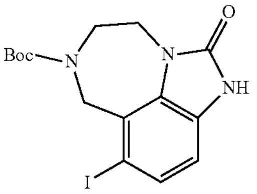 [SMILES: CC(C)(C)OC(=O)N1CCn2c(=O)[nH]c3ccc(I)c(c32)C1] |
| CB5 | 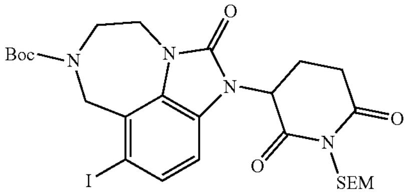 [SMILES: CC(C)(C)OC(=O)N1CCn2c(=O)n(C3CCC(=O)N(COCC[Si](C)(C)C)C3=O)c3ccc(I)c(c32)C1] |
| CB6 | 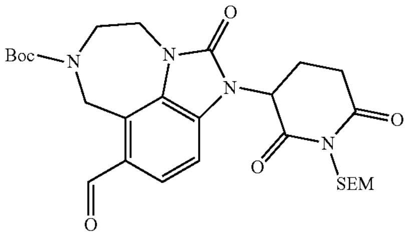 [SMILES: CC(C)(C)OC(=O)N1CCn2c(=O)n(C3CCC(=O)N(COCC[Si](C)(C)C)C3=O)c3ccc(C=O)c(c32)C1] |

TABLE 91-continued
| Ex | Structure |
| --- | --- |
| CB7 | 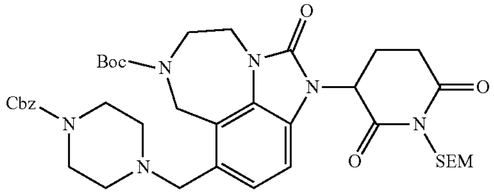 [SMILES: CC(C)(C)OC(=O)N1CCn2c(=O)n(C3CCC(=O)N(COCC[Si](C)(C)C)C3=O)c3ccc(CN4CCN(C(=O)OCc5ccccc5)CC4)c(c32)C1] |
| CB8 | 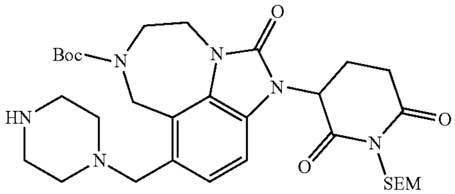 [SMILES: CC(C)(C)OC(=O)N1CCn2c(=O)n(C3CCC(=O)N(COCC[Si](C)(C)C)C3=O)c3ccc(CN4CCNCC4)c(c32)C1] |
| CB9 | 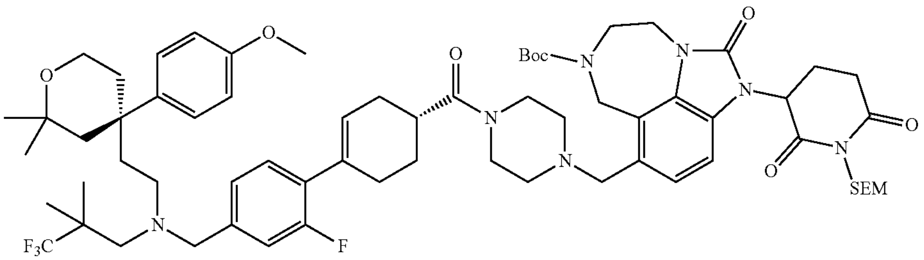 [SMILES: COc1ccc([C@]2(CCN(Cc3ccc(C4=CC[C@H](C(=O)N5CCN(Cc6ccc7c8c6CN(C(=O)OC(C)(C)C)CCn8c(=O)n7C6CCC(=O)N(COCC[Si](C)(C)C)C6=O)CC5)CC4)c(F)c3)CC(C)(C)C(F)(F)F)CCOC(C)(C)C2)cc1] |
| CB10 | 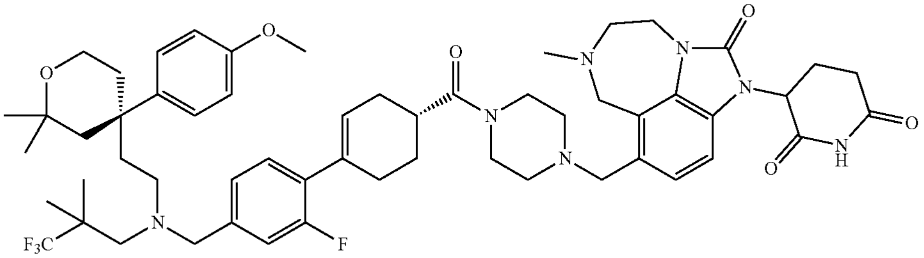 [SMILES: COc1ccc([C@]2(CCN(Cc3ccc(C4=CC[C@H](C(=O)N5CCN(Cc6ccc7c8c6CN(C)CCn8c(=O)n7C6CCC(=O)NC6=O)CC5)CC4)c(F)c3)CC(C)(C)C(F)(F)F)CCOC(C)(C)C2)cc1] |
| CC1 | 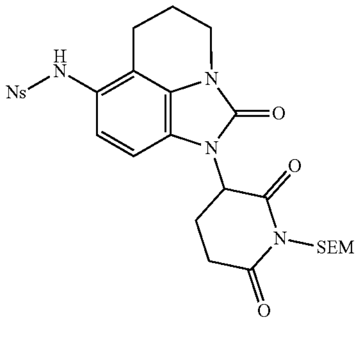 |

TABLE 92
| Ex | Structure |
| --- | --- |
| CC2 | 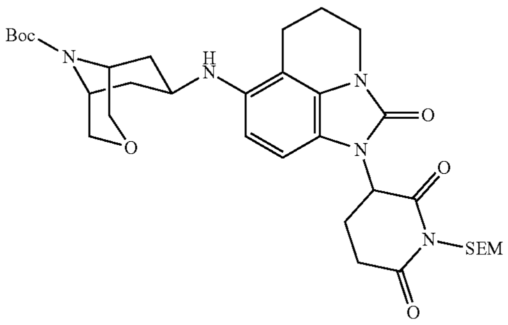 [SMILES: CC(C)(C)OC(=O)N1C2COCC1CC(Nc1ccc3c4c1CCCn4c(=O)n3C1CCC(=O)N(COCC[Si](C)(C)C)C1=O)C2] |
| CC3 | 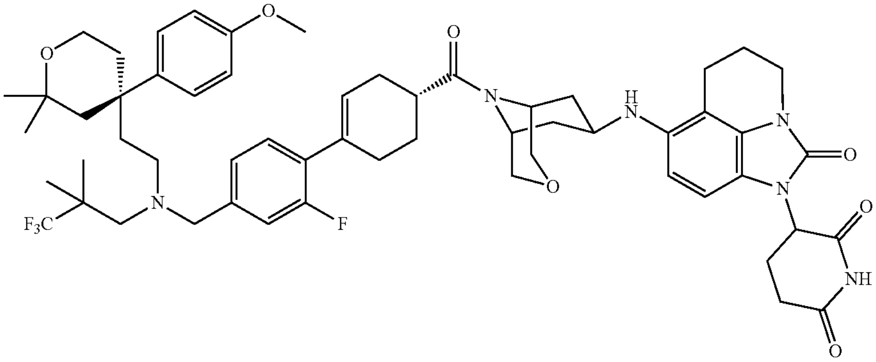 [SMILES: COc1ccc([C@]2(CCN(Cc3ccc(C4=CC[C@H](C(=O)N5C6COCC5CC(Nc5ccc7c8c5CCCn8c(=O)n7C5CCC(=O)NC5=O)C6)CC4)c(F)c3)CC(C)(C)C(F)(F)F)CCOC(C)(C)C2)cc1] |
| CD1 | 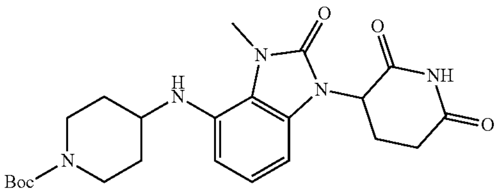 [SMILES: Cn1c(=O)n(C2CCC(=O)NC2=O)c2cccc(NC3CCN(C(=O)OC(C)(C)C)CC3)c21] |
| CD2 | 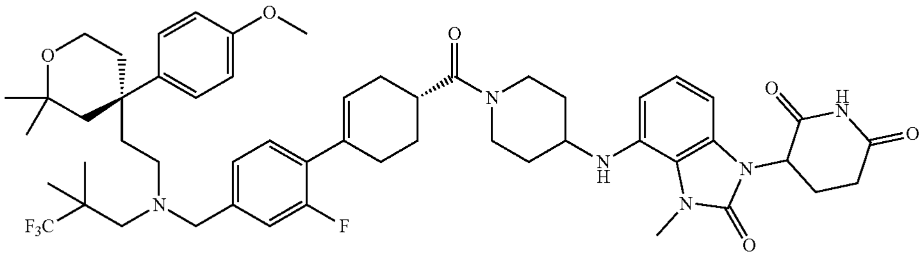 [SMILES: COc1ccc([C@]2(CCN(Cc3ccc(C4=CC[C@H](C(=O)N5CCC(Nc6cccc7c6n(C)c(=O)n7C6CCC(=O)NC6=O)CC5)CC4)c(F)c3)CC(C)(C)C(F)(F)F)CCOC(C)(C)C2)cc1] |
| CE1 | 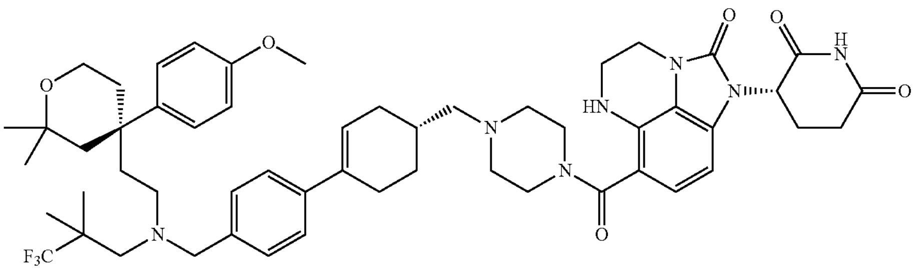 [SMILES: COc1ccc([C@]2(CCN(Cc3ccc(C4=CC[C@H](CN5CCN(C(=O)c6ccc7c8c6NCCn8c(=O)n7[C@H]6CCC(=O)NC6=O)CC5)CC4)cc3)CC(C)(C)C(F)(F)F)CCOC(C)(C)C2)cc1] |

TABLE 92-continued

| Ex | Structure |
|---|---|
| CF1 | 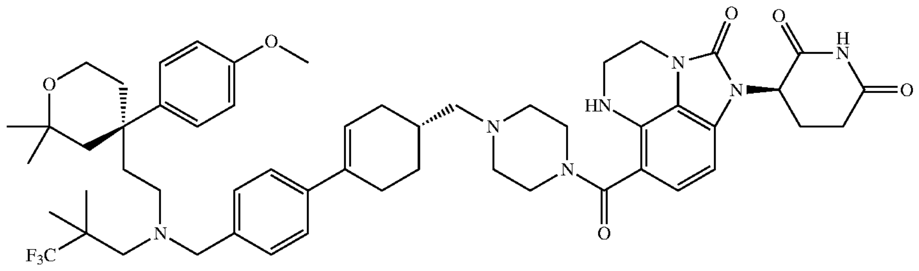 [SMILES: COc1ccc([C@]2(CCN(Cc3ccc(C4=CC[C@H](CN5CCN(C(=O)c6ccc7c8c6NCCn8c(=O)n7[C@@H]6CCC(=O)NC6=O)CC5)CC4)cc3)CC(C)(C)C(F)(F)F)CCOC(C)(C)C2)cc1] |
| CG1 | 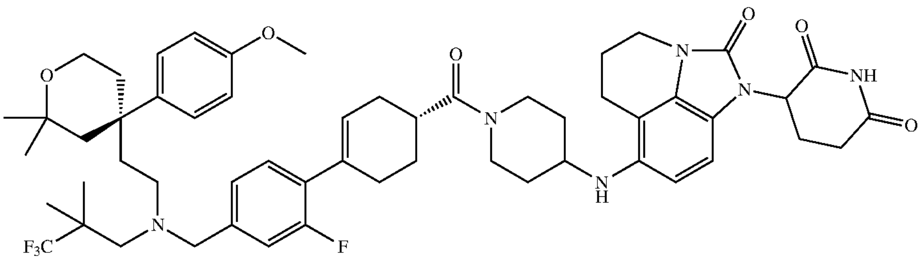 [SMILES: COc1ccc([C@]2(CCN(Cc3ccc(C4=CC[C@H](C(=O)N5CCC(Nc6ccc7c8c6CCCn8c(=O)n7C6CCC(=O)NC6=O)CC5)CC4)c(F)c3)CC(C)(C)C(F)(F)F)CCOC(C)(C)C2)cc1] |
| CH1 | 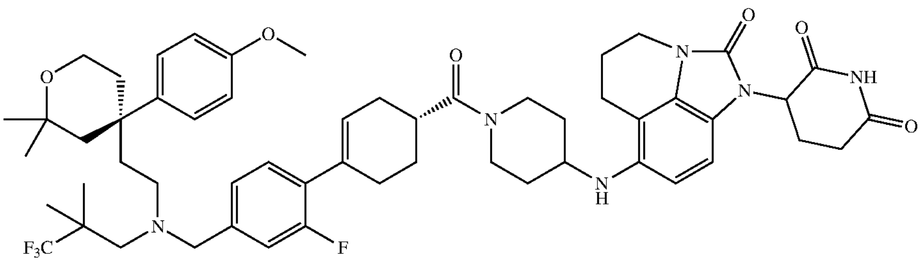 [SMILES: COc1ccc([C@]2(CCN(Cc3ccc(C4=CC[C@H](C(=O)N5CCC(Nc6ccc7c8c6CCCn8c(=O)n7C6CCC(=O)NC6=O)CC5)CC4)c(F)c3)CC(C)(C)C(F)(F)F)CCOC(C)(C)C2)cc1] |

<Experimental Example 1> Evaluation of Inhibitory Activity of Compound Against Binding of DAX1 to SF1-LBD The binding activity of each compound to the SF-1 ligand binding domain (LBD) was evaluated using the binding inhibitory activity of each compound against binding of DAX1 to SF1-LBD as an index. 100 nM His-SF1-LBD, 2 nM Biotin-DAX1 peptide (Biotin-MAGENHQWQGSI-LYNMLMSAKQT-$NH_2$) and each compound (8-point il dilution series with common ratio 2 from final concentration 2 μM) were mixed in assay buffer [25 mM HEPES (pH 7.5), 100 mM NaCl, 0.1% BSA, 0.01% CHAPS, 1 mM DTT] and reacted at room temperature for 30 min. Anti-6×His AlphaLISA Acceptor beads and Streptavidin-coated AlphaScreen Donor beads were mixed to a final concentrations of 5 μg/ml and 10 μg/ml, respectively, and reacted in the dark at room temperature for 60 min. AlphaLISA signals were detected using a multimode plate reader (EnVision Xcite, PerkinElmer). The binding rate of DAX1 peptide to SF1 was calculated from the luminescence amount (C) of the compound-free group and the luminescence amount (T) of the compound-added group, based on the following formula.

$$DAX1\text{ peptide binding rate (\%)} = 100 \times T/C \quad \text{[Math. 1]}$$

The DAX1 peptide binding rate at each concentration was analyzed using GraphPad Prism6 (GraphPad Software Inc.) to calculate the concentration ($IC_{50}$ value) of each compound that inhibits 50% of the binding of DAX1 to SF1-LBD. The $IC_{50}$ value (unit: nM) of the compound corresponding to each Example number is shown in Table 93.

TABLE 93

| Example No. | cell-free SF1 $IC_{50}$ |
|---|---|
| A6 | 19 |
| B5 | 20 |
| C8 | <16 |
| D3 | 29 |
| E2 | 19 |
| F4 | 31 |
| G3 | 54 |
| H1 | 32 |
| I2 | 47 |
| J4 | 39 |
| K5 | 29 |
| L2 | 32 |
| M5 | 18 |
| N2 | 41 |
| O2 | 36 |
| P3 | 30 |
| Q4 | 35 |
| R3 | 27 |
| S4 | 22 |
| T2 | 26 |
| U11 | 21 |

<Experimental Example 2> Evaluation of Changes in SF1 Target Gene Expression for NCI-H295R NCI-H295R cells were cultured in a 5% $CO_2$ incubator at 37° C. using DMEM/F12 medium (Thermo Fisher Scientific Inc.) containing 2.5% Nu-Serum (registered trademark) Growth Medium Supplement (Corning) and 1% Corning ITS+ Premix Universal Culture Supplement (Corning). The DMSO solution of each compound was serially diluted with DMSO using a D300e Digital Dispenser (TECAN), and the compounds were added to a 96-well plate (FALCON). NCI-H295R cells were seeded at $1\times10^4$ cells/50 μL/well on the 96-well plate containing the compounds added thereto, and cultured for 24 hr in a 5% $CO_2$ incubator at 37° C. The final DMSO concentration in the medium was adjusted to 0.1% (v/v) in all cases, and the concentration range of the compounds was set to 1000 nM to 0.32 nM with a common ratio of times. After the completion of culture, the medium was discarded, 50 μL/well of chilled D-PBS (Sigma Aldrich) was added to wash the cells, and D-PBS was discarded. After washing, 25 μL/well of Cells-to-CT (registered trademark) Bulk Lysis Reagents (Thermo Fisher Scientific, Inc.) was added to the wells, the mixture was stirred for 5 min with a plate mixer, and 2.5 μL/well of the reaction quenching liquid was added to prepare cell lysate. The cell lysate was dispensed into a 96-well plate (Corning) at 10 μL/well, and 40 μL/well of Cells-to-CT Bulk RT Reagents (Thermo Fisher Scientific, Inc.) was added. A reverse transcription reaction was performed at 37° C. for 50 min using a thermal cycler, and the reverse transcriptase was inactivated by heating at 95° C. for 5 min, and then stored at 10° C. PrimeTime (registered trademark) Gene Expression Master Mix (Integrated DNA Technologies), the target genes CYP11A1, CYP17A1, CYP21A2, or STAR, and the control gene ACTB PrimeTime (registered trademark) qPCR Probe Assays (Integrated DNA Technologies), and Nuclease free water were mixed at a ratio of 20:1:1:10 to prepare a PrimerProbe mix. The prepared PrimerProbe mix was added to a 384-well plate at 8 μL/well, and the cDNA obtained by reverse transcription was added at 2 μL/well. Real-Time PCR was performed under fast cycling conditions (95° C. for 3 min, followed by 40 cycles of 95° C. for 5 seconds and 62° C. for 30 seconds) to measure the fluorescent signal. The obtained data was analyzed using GraphPad Prism9 (GraphPad Software Inc.) to calculate the concentration ($IC_{50}$ value) that reduces the mRNA expression level by 50%. The $IC_{50}$ values (unit: nM) for CYP11A1, CYP17A1, CYP21A2, and STAR, of the compounds corresponding to each Example number are shown in Table 94.

TABLE 94

| Example No. | CYP11A1 | CYP17A1 | CYP21A2 | STAR |
|---|---|---|---|---|
| A6 | 102 | 283 | 142 | 159 |
| B5 | 10 | 56 | 17 | 24 |
| C8 | 7.8 | 70 | 13 | 26 |
| D3 | 53 | 144 | 78 | 76 |
| E2 | 17 | 189 | 33 | 65 |
| F4 | 14 | 166 | 23 | 69 |
| G3 | 32 | 73 | 42 | 35 |
| H1 | 25 | 80 | 39 | 37 |
| I2 | 29 | 117 | 52 | 55 |
| J4 | 4.1 | 70 | 8.1 | 14 |
| K5 | 12 | 141 | 28 | 47 |
| L2 | 17 | 238 | 46 | 83 |
| M5 | 2.8 | 13 | 4.3 | 3.9 |
| N2 | 19 | 113 | 30 | 39 |
| O2 | 35 | 211 | 82 | 75 |

TABLE 94-continued

| Example No. | CYP11A1 | CYP17A1 | CYP21A2 | STAR |
|---|---|---|---|---|
| P3 | 4.4 | 137 | 9.8 | 19 |
| Q4 | 8.5 | 189 | 19 | 44 |
| R3 | 3.3 | 28 | 4.3 | 6.2 |
| S4 | 1.2 | 12 | 2.2 | 3.2 |
| T2 | 1.2 | 24 | 2.4 | 4.1 |
| U11 | 10 | 140 | 24 | 54 |
| V5 | 9.8 | 71 | 21 | 18 |
| W5 | 90 | 372 | 138 | 131 |
| X2 | 511 | 1228 | 581 | 776 |

<Experimental Example 3> Evaluation of SF1 Degradation Induction Action on Human Adrenocortical Carcinoma Cell Line NCI-H295R Human adrenocortical carcinoma cell line NCI-H295R cells (ATCC, CRL-2128) were used as hosts, and NCI-H295R SF-1-HiBiT cells with HiBiT tag knocked in at the endogenous SF1 locus were cultured in a 5% $CO_2$ incubator at 37° C. using DMEM/F12 medium (Thermo Fisher Scientific Inc.) containing 2.5% Nu-Serum (registered trademark) Growth Medium Supplement (Corning) and 1% Corning ITS+ Premix Universal Culture Supplement (Corning). NCI-H295R SF-1-HiBiT cells were seeded in a 384-well plate (Thermo Fisher Scientific Inc.) at $1\times10^4$ cells/50 μL/well and cultured at 37° C. in a 5% $CO_2$ incubator for 24 hr. DMSO solutions of each compound were serially diluted with DMSO using a D300e Digital Dispenser (TECAN), added to a 384-well plate, and cultured in a 5% $CO_2$ incubator at 37° C. for 24 hr. The final DMSO concentration in the medium was adjusted to 0.1% (v/v) for all, and the concentration range of the compounds was set to 10000 nM to 4.6 nM or 1000 nM to 0.46 nM with a common ratio of 3. After completion of culture, the medium was discarded, and Nano-Glo (registered trade mark) HiBiT Lytic Detection System (Promega, Cat. No. N3040) was added at 20 μL/well and stirred with a plate mixer. Luminescence signals were then detected using a multimode plate reader (EnVision Xcite, PerkinElmer). The SF-1 protein degradation rate was calculated from the amount of luminescence (C) in the compound-free group and the amount of luminescence (T) in the compound-added group, based on the following formula.

$$SF\text{-}1 \text{ protein degradation rate } (\%) = 100\times(1-T/C) \quad \text{[Math. 2]}$$

The obtained data was analyzed using GraphPad Prism9 (GraphPad Software Inc.) or Genedata Screener (Genedata AG) to calculate the concentration that induces 50% degradation of SF-1 ($DC_{50}$ value). The HiBiT $DC_{50}$ values (unit: nM) of the compounds corresponding to each Example number are shown in Table 95 to Table 97.

<Experimental Example 4> Evaluation of Proliferation Inhibitory Action on NCI-H295R NCI-H295R cells were cultured in DMEM/F12 medium (Thermo Fisher Scientific, Inc.) containing 2.5% US Charcoal/Dextran Treated FBS (Hyclone) and 1% Corning ITS+ Premix Universal Culture Supplement (Corning). DMSO solutions of each compound were serially diluted with DMSO using a D300e Digital Dispenser (TECAN), and added to a 384-well plate (Thermo Fisher Scientific Inc.).

NCI-H295R cells were seeded in a 384-well plate at $2\times10^3$ cells/40 μL/well and cultured for 7 days in a 37° C., 5% $CO_2$ incubator. The final concentration of DMSO in the medium was adjusted to 0.1% (v/v) for all, and the concentration range of the compounds was set to 10000 nM to 0.038 nM with a common ratio of 4. On the first day of culture (day 0) and the seventh day of culture (day 7), 10 μL/well of CellTiter-Glo (registered trademark) 2.0 Assay (Promega) was added, and the luminescence signal was detected using a multimode plate reader (EnVision, PerkinElmer). The cell proliferation rate was calculated from the luminescence amount on the day of compound addition (CO), the luminescence amount of the compound-free group after 7 days of culture (C7), and the luminescence amount of the compound-added group (T7), based on the following formula.

$$\text{cell proliferation rate (\%)} = 100\times[(T7-C0)/(C7-C0)] \quad \text{[Math. 3]}$$

The concentration of each compound that inhibits the proliferation of NCI-H295R cells by 50% ($GI_{50}$ value) was calculated by a one-log plot of the cell survival rate and compound concentration at each concentration. The H295R $GI_{50}$ values (unit: nM) of the compounds corresponding to each Example No. are shown in Table 95 to Table 97.

TABLE 95

| Example No. | HiBiT $DC_{50}$ | H295R $GI_{50}$ |
|---|---|---|
| Y6 | 12 | 199 |
| Z8 | 10 | 43 |
| AA4 | 12 | 488 |
| AB6 | 29 | 165 |
| AC6 | 26 | 73 |
| AD1 | 6.9 | 47 |
| AE1 | 8.5 | 40 |
| AF1 | 6.9 | 121 |
| AG7 | 8.7 | 147 |
| AH4 | 5.7 | 123 |
| AI11 | 6.2 | 90 |
| AJ6 | 5.3 | 58 |
| AK10 | 4.9 | 82 |
| AL4 | 4.5 | 83 |
| AM10 | 7.3 | 106 |
| AN5 | 12 | 92 |
| AO7 | 5.4 | 39 |
| AP6 | 4.1 | 68 |
| AQ1 | 56 | 286 |
| AR7 | 6.5 | 82 |
| AS7 | 4.1 | 56 |
| AT3 | 7.7 | 45 |
| AU4 | 9.3 | 60 |
| AV2 | 7.4 | 61 |
| AW5 | 12 | 85 |
| AX3 | 7.1 | 61 |
| AY8 | 7.3 | 71 |
| AZ8 | 7.0 | 28 |
| BA6 | 4.9 | 23 |
| BB7 | 9.0 | 62 |

TABLE 96

| Example No. | HiBiT $DC_{50}$ | H295R $GI_{50}$ |
|---|---|---|
| BC6 | 6.2 | 48 |
| BD6 | 3.0 | 57 |
| BE5 | 2.6 | 124 |
| BF6 | 10 | 75 |
| BG5 | 9.2 | 84 |
| BH5 | 7.7 | 79 |
| BI2 | 11 | 79 |

TABLE 96-continued

| Example No. | HiBiT $DC_{50}$ | H295R $GI_{50}$ |
|---|---|---|
| BJ6 | 17 | 97 |
| BK9 | 3.2 | 24 |
| BL4 | 3.1 | 43 |
| BM10 | 2.2 | 22 |
| BN2 | 2.3 | 31 |
| BO4 | 15 | 129 |
| BP6 | 12 | 71 |
| BQ4 | 4.5 | 28 |
| BR3 | 2.2 | 23 |
| BS3 | 14 | 70 |
| BT6 | 3.5 | 48 |
| BU6 | 18 | 64 |
| BV10 | 14 | 123 |
| BW3 | 9.1 | 86 |
| BX6 | 7.1 | 52 |
| BY7 | 7.3 | 54 |
| BZ7 | 4.0 | 27 |
| CA1 | 5.5 | 48 |
| CB10 | 13 | 85 |
| CC3 | 4.9 | 36 |
| CD2 | 7.0 | 33 |

TABLE 97

| Example No. | HiBiT $DC_{50}$ | H295R $GI_{50}$ |
|---|---|---|
| CE1 | 4.3 | 70 |
| CF1 | 5.1 | 84 |
| CG1 | 1.8 | 18 |
| CH1 | 2.8 | 25 |

<Experimental Example 5> Evaluation of Antitumor Activity Against NCI-H295R Cell Subcutaneous Transplant Model (Adrenocortical Carcinoma)

NCI-H295R cells were subcutaneously transplanted at 1.0 to $2.0\times10^7$ cells/head into the right flank of female NSG mice and, when the estimated tumor volume (major axis× minor axis×minor axis/2) reached 100 to 300 $mm^3$, the mice were divided into groups of 4 to 5 mice each such that no difference was present between groups. Female NSG mice were purchased from Charles River Japan Co., Ltd. From the day of grouping, each compound was orally administered at a dose of 30 mg/kg/day once a day for 10 to 11 consecutive days (QD×10 to 11). Individual estimated tumor volumes were measured from the day of grouping until 11 to 12 days after grouping (the day the test was terminated). To the vehicle-control group was administered 0.5% methylcellulose containing 6.2-6.4 mM mesylic acid.

The antitumor activity against the NCI-H295R cell subcutaneous transplant model in Experimental Example 5 was calculated by the following formula on the day the test was terminated.

$$\text{tumor growth inhibition rate (\%)} = (1 - TVCt/TVCc)\times 100 \quad \text{[Math. 4]}$$

$$TVC = \text{(individual tumor volume on test termination day)} - \text{(individual tumor volume on grouping day)}$$

$$TVCt = TVC \text{ average value of administered group}$$

$$TVCc = TVC \text{ average value of administration-free group}$$

The tumor growth inhibition rate (unit: %) of the compound corresponding to each Example No. is shown in Table 98.

TABLE 98

| Example No. | tumor growth inhibition rate (%) |
|---|---|
| AW5 | 109 |
| BK9 | 131 |
| BY7 | 118 |

<Experimental Example 6> Evaluation of Antitumor Activity in Human Prostate Cancer Cell Subcutaneous Transplant Model (Prostate Cancer)

A xenograft model derived from a prostate cancer patient (obtained from the National Institute of Biomedical Innovation (NIBIO)) was used for antitumor evaluation. Tumors excised from seed mice were cut into about 4-5 mm squares and subcutaneously transplanted into the right flank of male NSG mice. On the fourth day after transplantation, the mice were divided into groups of 8 to 10 mice each to ensure uniformity of the seed mice. From the day of grouping, each compound was orally administered once a day at a dose of 100 mg/kg/day for 28 to 32 consecutive days (QD x 28 to 32). Individual estimated tumor volumes were measured from the day of grouping until the day after the final administration (the day of completion of test). To the vehicle-control group was administered 0.5% methylcellulose containing 21.3 mM mesylic acid.

The antitumor activity in the human prostate cancer cell subcutaneous transplant model was calculated by the following formula on the day of completion of each test.

$$\text{tumor growth inhibition rate (\%)} = (1 - TVCt/TVCc) \times 100 \quad \text{[Math. 5]}$$

$$TVC = \text{(individual tumor volume on test termination day)} - \text{(individual tumor volume on grouping day)}$$

$$TVCt = TVC \text{ average value of administered group}$$

$$TVCc = TVC \text{ average value of administration-free group}$$

The tumor growth inhibition rate (unit: %) of the compound corresponding to each Example No. is shown in Table 99.

TABLE 99

| Example No. | tumor growth inhibition rate (%) |
|---|---|
| AW5 | 10 |
| BK9 | 43 |
| BY7 | 38 |

<Experimental Example 7> Inhibitory Activity on Normal Mouse Uterine Weight (Inhibitory Action on Estrogen Activity)

Female NSG mice were purchased from Charles River Japan, Inc. From the day of grouping, each compound was orally administered at a dose of 100 mg/kg/day once a day for 8 consecutive days (QD×8). To the vehicle-control group was administered 0.5% methylcellulose. 24 hr after the final administration, the wet weight of the mouse uterus was measured, and the relative uterine weight (%) to the vehicle control group was calculated by the following formula.

$$\text{relative uterine weight (\%)} = \text{(average uterine weight of administered group/average uterine weight of administration-free group)} \times 100 \quad \text{[Math. 6]}$$

The relative uterine weight (unit: %) of the compound corresponding to each Example No. to the vehicle control group is shown in Table 100.

TABLE 100

| Example No. | relative uterine weight (%) |
|---|---|
| AW5 | 74 |
| BK9 | 56 |
| BY7 | 42 |

<Experimental Example 8> Evaluation of Binding Activity to CRBN

The binding activity of each compound to CRBN can be evaluated as follows using, for example, the competition with HTRF Thalidomide-Red ligand for the CRBN partial protein as an index.

150 nM His-Avi-3C-hCRBN (318-426, C366S), 80 nM HTRF Thalidomide-Red ligand, 0.8 μg/mL MAb Anti 6His-Eu cryptate, and each test compound (8-point dilution series with common ratio 3 from final concentration 50 μM) are mixed in HTRF PROTAC Binding Buffer 1, and reacted for 3 hr at room temperature. HTRF signals are measured using a plate reader (Biotek SynergyNEO2, Agilent). The ratio value for each well is calculated by the following formula.

$$\text{ratio value} = \text{(fluorescence intensity at 665 nm)/(fluorescence intensity at 620 nm)} \times 10^4 \quad \text{[Math. 7]}$$

Then, T/C for each test compound treatment is calculated using the following formula.

$$T/C = \text{(ratio value of test compound-added group} - \text{Min)/(Max} - \text{Min)} \quad \text{[Math. 8]}$$

Max: ratio value of well containing His-CRBN, Thalidomide-Red and Anti-His Eu and not containing evaluation sample Min: ratio value of well containing Thalidomide-Red and Anti-His Eu and not containing evaluation sample The T/C at each concentration is analyzed using GraphPad Prism9 for Windows 64-bit (GraphPad Software Inc. Version 9.1.0) to calculate the concentration ($IC_{50}$ value) of each test compound that inhibits 50% of the binding of HTRF Thalidomide-Red ligand to CRBN.

One embodiment of the compound or a pharmaceutically acceptable salt thereof of the present invention showed an $IC_{50}$ value of the order of μM or less.

INDUSTRIAL APPLICABILITY

Since a compound represented by the formula (1) or a pharmaceutically acceptable salt thereof of the present invention has an SF-1 antagonist activity, it can be used as an SF-1 antagonist or SF-1 inhibitor. In addition, since SF-1 is known to be involved in the development or progression of various diseases such as adrenocortical carcinoma and castration-resistant prostate cancer, the compound represented by the formula (1) or a pharmaceutically acceptable salt thereof of the present invention can be used in the treatment of such diseases. In addition, since the compound represented by the formula (1) or a pharmaceutically acceptable salt thereof of the present invention has SF-1 antagonist activity, it can be used as a partial structure in a larger molecule (e.g., polyfunctional molecule) by combining a moiety corresponding to the compound represented by the formula (1) or a pharmaceutically acceptable salt thereof of the present invention with other functional moieties.

Furthermore, since the compound represented by the formula (1) or a pharmaceutically acceptable salt thereof of the present invention specifically binds to SF-1, it can also be used as an SF-1 binder, and further can be used as an SF-1-binding moiety in a larger molecule (e.g., polyfunctional molecule) by combining a moiety corresponding to the compound represented by the formula (1) or a pharmaceutically acceptable salt thereof of the present invention with other functional moieties. Among these, a polyfunctional molecule containing a moiety corresponding to the compound represented by the formula (1) or a pharmaceutically acceptable salt thereof of the present invention and an E3 ligase-binding moiety, particularly, a compound represented by the formula (2) or a pharmaceutically acceptable salt thereof of the present invention, or a crystal thereof, can degrade SF-1 protein and inhibit the proliferation of tumor cells, and thus can be used as an SF-1 inhibitor and an SF-1 degrader, as well as for the treatment of SF-1-related diseases such as adrenocortical carcinoma, castration-resistant prostate cancer, and the like.

This application is based on a patent application No. 2023-169833 filed in Japan (filing date: Sep. 29, 2023), the contents of which are incorporated in full herein.

The invention claimed is:

1. A compound selected from the group consisting of:

(3RS)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3R)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3S)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3R)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3S)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3R)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3S)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, (3R)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, and (3S)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, or a pharmaceutically acceptable salt thereof.

2. The compound according to claim 1, selected from the group consisting of:

(3RS)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, (3R)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, and (3S)-3-[5-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-3-methyl-2-oxo-2,3-dihydro-1H-benzimidazol-1-yl]piperidine-2,6-dione, or a pharmaceutically acceptable salt thereof.

3. The compound according to claim 1, selected from the group consisting of:

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, (3R)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, and (3S)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione, or a pharmaceutically acceptable salt thereof.

4. The compound according to claim 1, selected from the group consisting of:

(3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, (3R)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, and (3S)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione, or a pharmaceutically acceptable salt thereof.

5. The compound according to claim 1, selected from the group consisting of:

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, (3R)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, and (3S)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione, or a pharmaceutically acceptable salt thereof.

6. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate.

7. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione monobenzenesulfonate.

8. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate.

9. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione monoethanesulfonate.

10. The compound or pharmaceutically acceptable salt thereof according to claim 1, which is (3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate.

11. The compound or pharmaceutically acceptable salt thereof according to claim 1, which is (3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione mono-10-camphorsulfonate.

12. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione ethanesulfonate.

13. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione monoethanesulfonate.

14. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-

2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione salicylate.

15. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione monosalicylate.

16. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione benzenesulfonate.

17. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione monobenzenesulfonate.

18. The compound or pharmaceutically acceptable salt thereof according to claim 1, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate.

19. The compound or pharmaceutically acceptable salt thereof according to claim 1$, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione mono-10-camphorsulfonate.

20. A crystal of a compound selected from the group consisting of:

(3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate, (3RS)-3-[7-({1-[(4R)-2'-fluoro-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione ethanesulfonate, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione salicylate, (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione benzenesulfonate, and (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate.

21. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione benzenesulfonate, having peaks at diffraction angles (2θ) of 2.15±0.2, 8.30±0.2, 10.29±0.2, 14.75±0.2, 17.19±0.2, 20.00±0.2, 21.34±0.2, 22.68±0.2, 23.77±0.2, and 25.23±0.2 in a powder X-ray diffraction pattern obtained by irradiation with copper Kα ray (λ=1.54 angstroms).

22. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[4,5,1-ij]quinolin-1(2H)-yl]piperidine-2,6-dione ethanesulfonate, having peaks at diffraction angles (2θ) of 2.21±0.2, 12.04±0.2, 14.87±0.2, 17.69±0.2, 18.93±0.2, 20.41±0.2, 22.42±0.2, 23.19±0.2, 24.13±0.2, and 27.98±0.2 in a powder X-ray diffraction pattern obtained by irradiation with copper Kα ray (λ=1.54 angstroms).

23. The crystal according to claim 20, which is (3RS)-3-[7-({1-[(4R)-2'-Fluoro-4'-{[{2-[(4R)-4-(4-methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-carbonyl]piperidin-4-yl}amino)-2-oxo-5,6-dihydro-4H-imidazo[4,5,1-ij]quinolin-1(2H)-yl]piperidine-2,6-dione 10-camphorsulfonate, having peaks at diffraction angles (2θ) of 3.89±0.2, 6.81±0.2, 7.68±0.2, 8.20±0.2, 10.28±0.2, 13.15±0.2, 15.97±0.2, 16.81±0.2, 18.58±0.2, and 23.56±0.2 in a powder X-ray diffraction pattern obtained by irradiation with copper Kα ray (λ=1.54 angstroms).

24. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione ethanesulfonate, having peaks at diffraction angles (2θ) of 2.27±0.2, 8.18±0.2, 9.88±0.2, 13.09±0.2, 14.57±0.2, 15.80±0.2, 16.91±0.2, 17.77±0.2, 18.87±0.2, and 20.14±0.2 in a powder X-ray diffraction pattern obtained by irradiation with copper Kα ray (λ=1.54 angstroms).

25. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)

amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione salicylate, having peaks at diffraction angles (2θ) of 2.20±0.2, 4.34±0.2, 9.45±0.2, 10.97±0.2, 13.23±0.2, 16.98±0.2, 18.09±0.2, 20.20±0.2, 21.32±0.2, and 25.19±0.2 in a powder X-ray diffraction pattern obtained by irradiation with copper Kα ray (λ=1.54 angstroms).

26. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione benzenesulfonate, having peaks at diffraction angles (2θ) of 2.19±0.2, 8.87±0.2, 10.86±0.2, 12.55±0.2, 13.05±0.2, 14.99±0.2, 17.84±0.2, 20.62±0.2, 21.43±0.2, and 25.27±0.2 in a powder X-ray diffraction pattern obtained by irradiation with copper Kα ray (λ=1.54 angstroms).

27. The crystal according to claim 20, which is (3RS)-3-[7-(4-{[(4R)-4'-{[{2-[(4R)-4-(4-Methoxyphenyl)-2,2-dimethyloxan-4-yl]ethyl}(3,3,3-trifluoro-2,2-dimethylpropyl)

amino]methyl}-2,3,4,5-tetrahydro[1,1'-biphenyl]-4-yl]methyl}piperazine-1-carbonyl)-2-oxo-5,6-dihydro-4H-imidazo[1,5,4-de]quinoxalin-1(2H)-yl]piperidine-2,6-dione 10-camphorsulfonate, having peaks at diffraction angles (2θ) of 2.20±0.2, 7.82±0.2, 11.05±0.2, 12.42±0.2, 13.34±0.2, 15.23±0.2, 16.49±0.2, 17.86±0.2, 20.15±0.2, and 24.36±0.2 in a powder X-ray diffraction pattern obtained by irradiation with copper Kα ray (λ=1.54 angstroms) crystal.

28. A pharmaceutical composition comprising the compound or a pharmaceutically acceptable salt thereof according to claim 1 and a pharmaceutically acceptable carrier.

29. A method for treating castration-resistant prostate cancer, adrenocortical carcinoma, Leydig cell tumor, hormone-sensitive prostate cancer, breast cancer, Cushing's syndrome, or primary aldosteronism, comprising administering an effective amount of the compound or a pharmaceutically acceptable salt thereof according to claim 1 to a subject in need of a treatment of castration-resistant prostate cancer, adrenocortical carcinoma, Leydig cell tumor, hormone-sensitive prostate cancer, breast cancer, Cushing's syndrome, or primary aldosteronism.

* * * * *